US006475807B1

(12) United States Patent
Geysen et al.

(10) Patent No.: US 6,475,807 B1
(45) Date of Patent: Nov. 5, 2002

(54) MASS-BASED ENCODING AND QUALITATIVE ANALYSIS OF COMBINATORIAL LIBRARIES

(75) Inventors: Hendrik Mario Geysen, Chapell Hill; Daniel Stuart Kinder, Cary; Craig Daniel Wagner, Chapel Hill, all of NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/091,954

(22) PCT Filed: Apr. 8, 1997

(86) PCT No.: PCT/US97/05701

§ 371 (c)(1),
(2), (4) Date: Jun. 26, 1998

(87) PCT Pub. No.: WO97/37953

PCT Pub. Date: Oct. 16, 1997

Related U.S. Application Data

(60) Provisional application No. 60/014,970, filed on Apr. 8, 1996.

(51) Int. Cl.[7] .................... G01N 33/566; G01N 33/543; C12Q 1/00; C12M 1/00
(52) U.S. Cl. ...................... 436/518; 436/501; 436/528; 435/4; 435/DIG. 1; 435/DIG. 40; 435/DIG. 41; 435/289.1
(58) Field of Search ............................ 435/4, DIG. 46, 435/DIG. 1, DIG. 40, DIG. 41, 289.1; 436/518, 536, 528

(56) References Cited

U.S. PATENT DOCUMENTS

| 5,549,974 A | * | 8/1996 | Holmes |
| 5,574,656 A | * | 11/1996 | Agraflotls et al. |
| 5,635,598 A | * | 6/1997 | Lebl et al. |
| 5,639,603 A | * | 6/1997 | Dower et al. |
| 5,770,358 A | * | 6/1998 | Dower et al. |
| 5,846,839 A | * | 12/1998 | Gallop et al. |
| 5,968,736 A | * | 10/1999 | Still et al. |
| 6,001,579 A | * | 12/1999 | Still et al. |

FOREIGN PATENT DOCUMENTS

| GB | 2 304 410 | | 3/1997 |
| WO | 95/04160 | * | 2/1995 |
| WO | WO95/28640 | | 10/1995 |
| WO | WO96/30392 | | 10/1996 |
| WO | WO97/08190 | | 3/1997 |
| WO | WO97/14814 | | 4/1997 |

OTHER PUBLICATIONS

Geysen, H.M., *Chemistry and Biology*, vol. 3, No. 8, Aug. 1996, pp. 679–688, "Isotope or mass encoding of combinatorial libraries".

* cited by examiner

*Primary Examiner*—Padmashri Ponnaluri
(74) *Attorney, Agent, or Firm*—Frank P. Grassler

(57) ABSTRACT

The insertion of isotopically labeled portions into solid state combinatorial synthesis constructs followed by mass spectrometer, mass-based nuclear magnetic resonance spectrometry or mass-based infrared spectrometry analysis allows for the physical, non-chemical encoding of large numbers of combinatorial synthesis products.

22 Claims, 287 Drawing Sheets

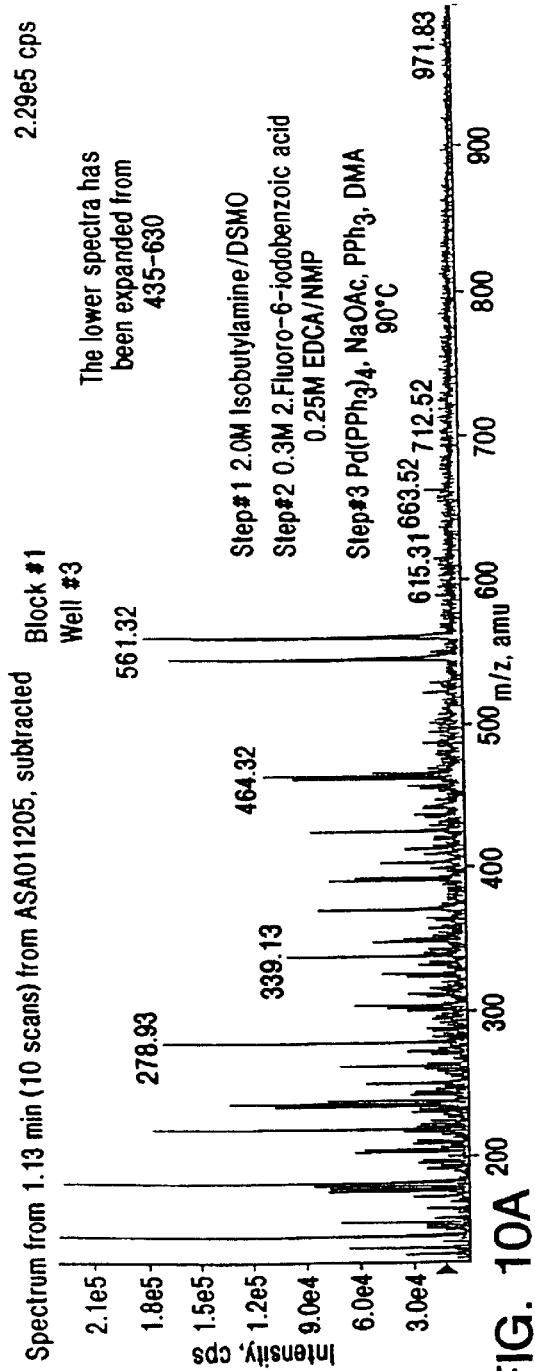
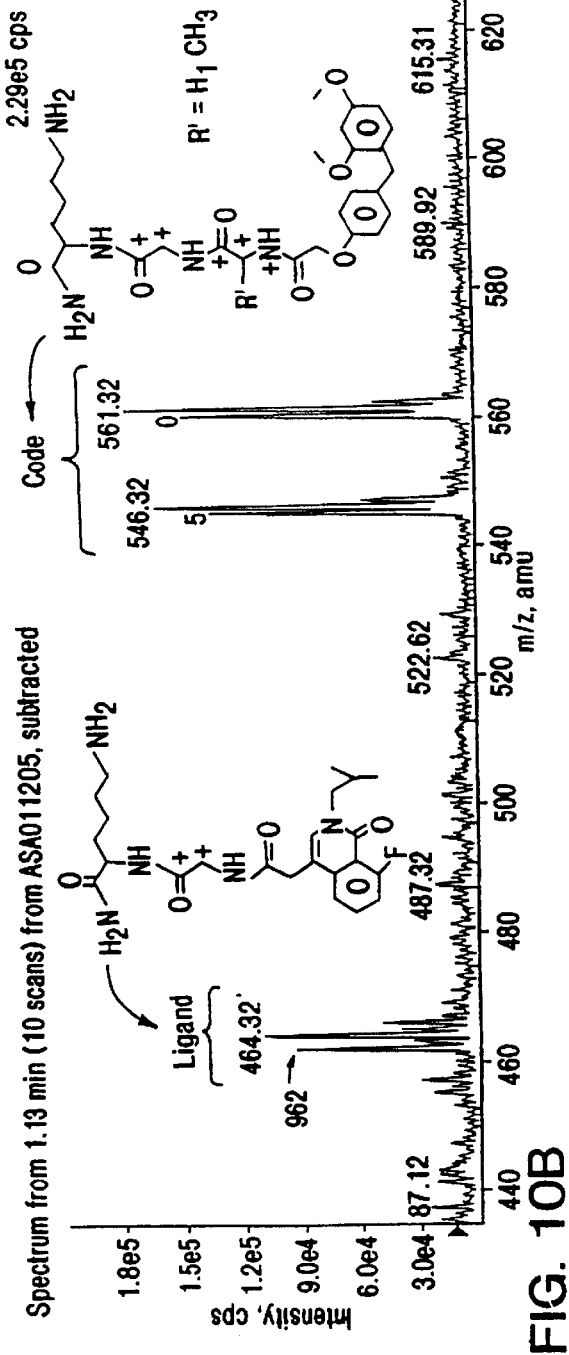
FIG. 10A
FIG. 10B

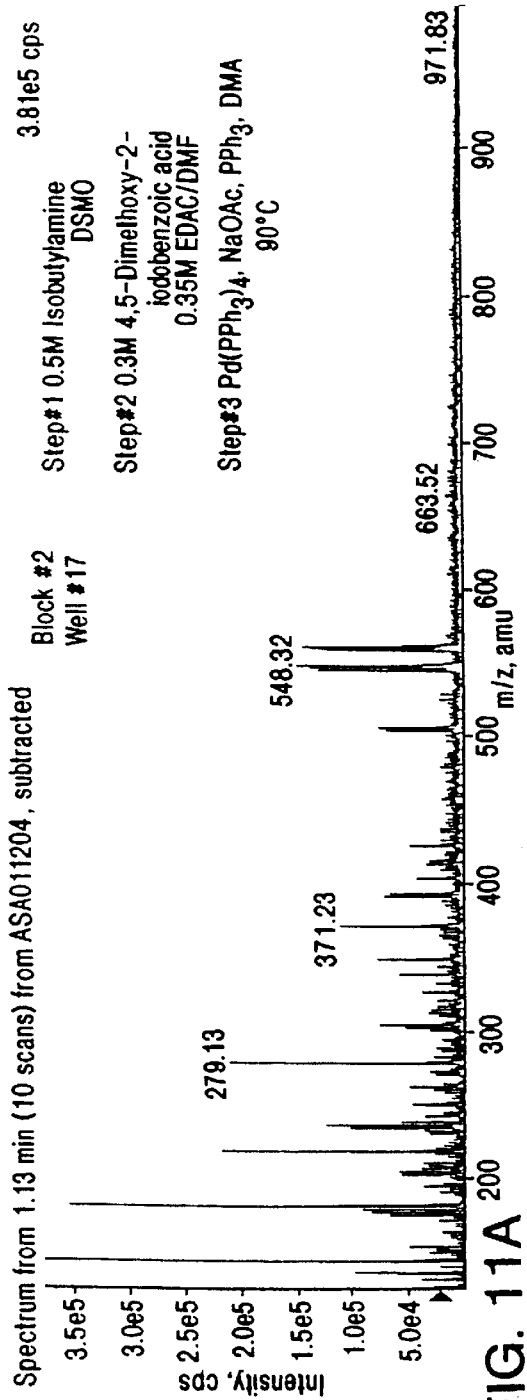
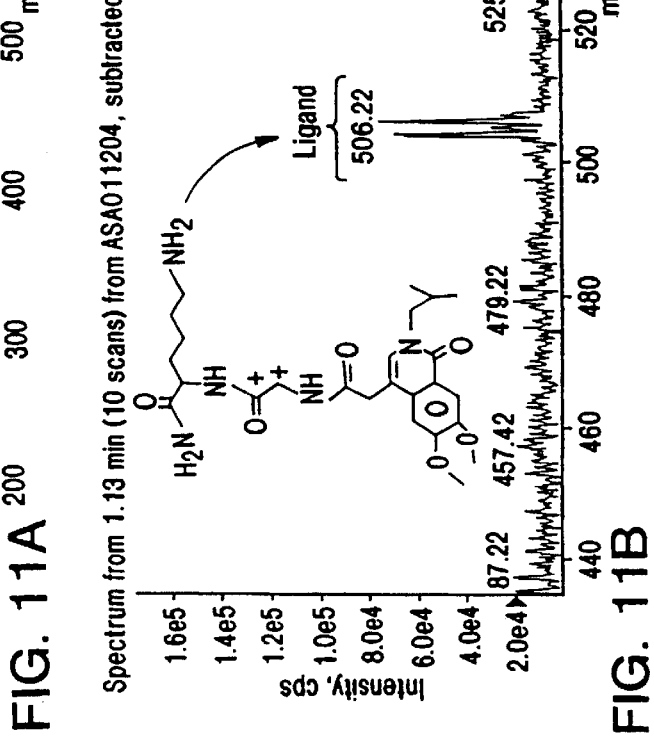
FIG. 11A
FIG. 11B

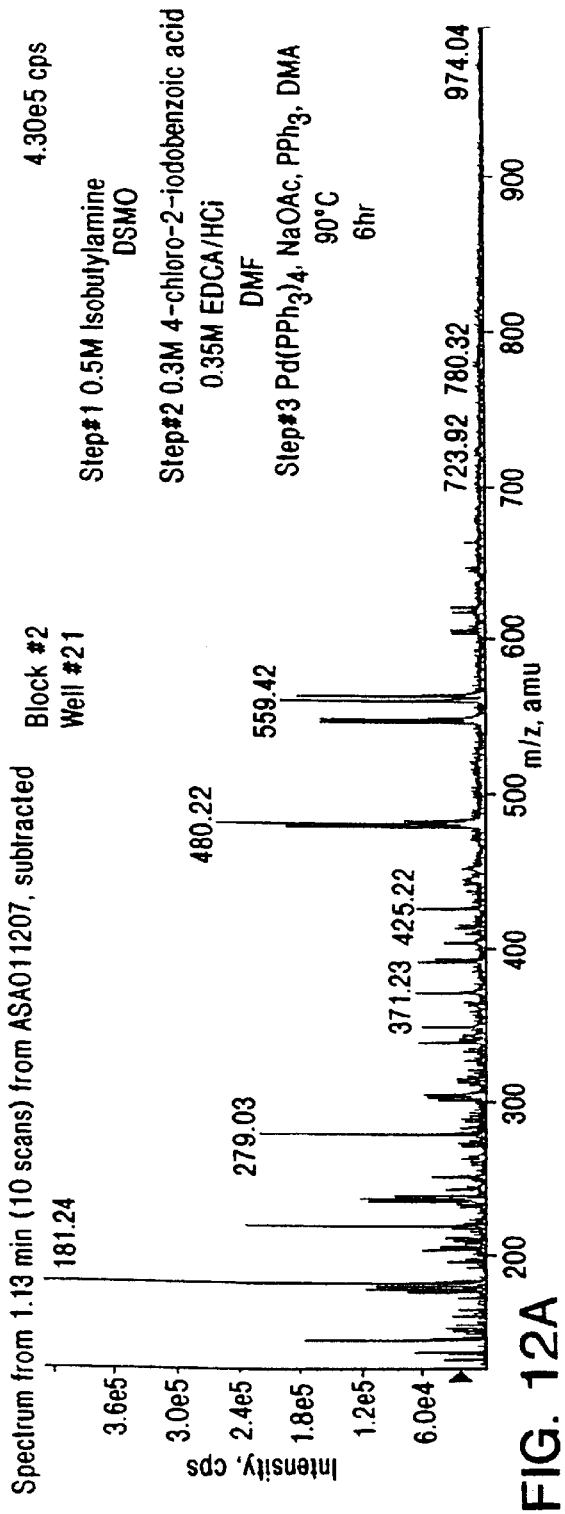
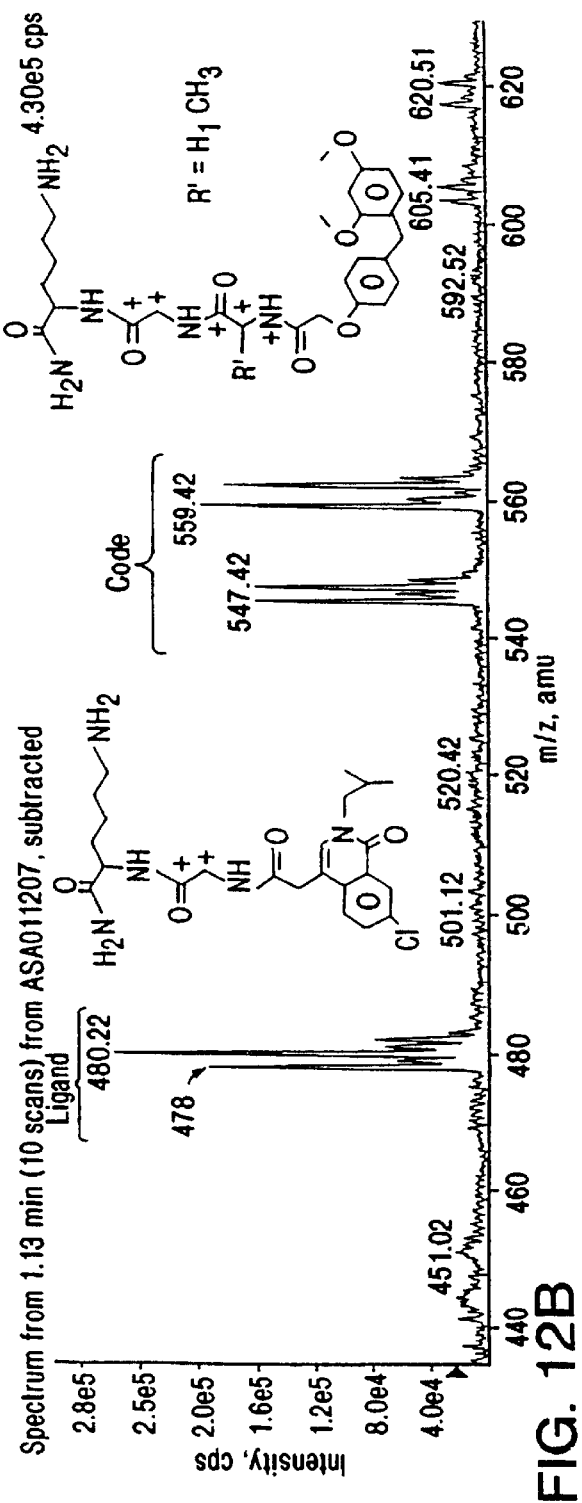
FIG. 12A
FIG. 12B

I. Systhesis of serially encoded tentagel resin.

II. Reaction Screening of 1(2H)-Isoquinolinones with serially encoded tentagel resin.

P(S-co-MS)
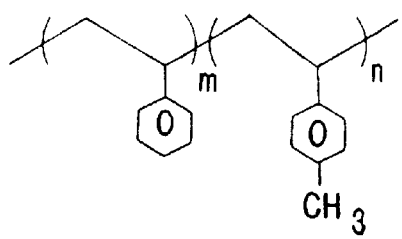
P(S-co-MS)-Rf$_1$
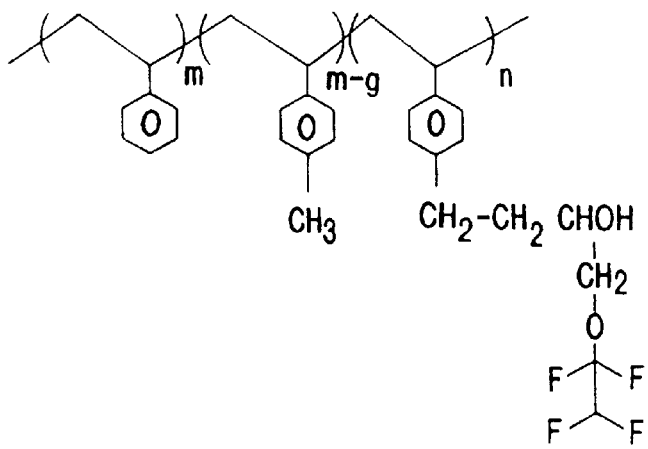
PS-BOH-Rf$_1$-Rf$_2$
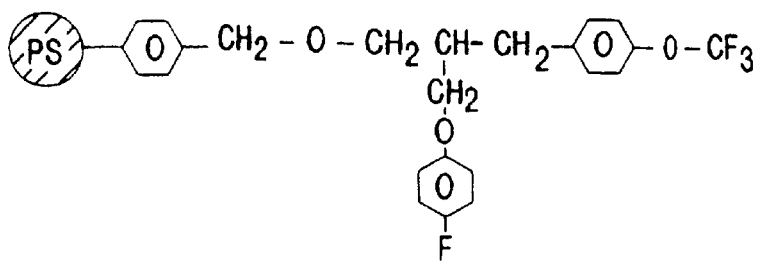
PS-PEG-Rf$_1$
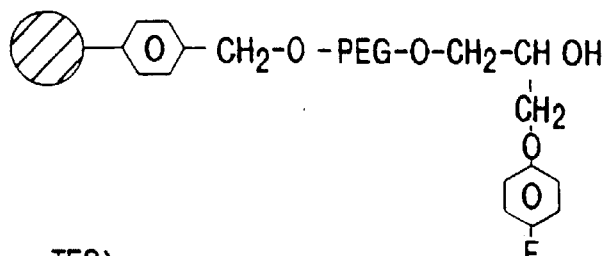
Poly(S-co-FS-co-TFS)
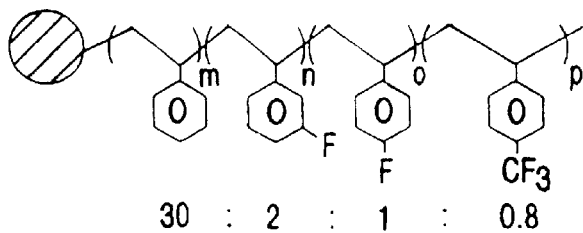
30 : 2 : 1 : 0.8
FIG. 107

MASS-BASED ENCODING AND QUALITATIVE ANALYSIS OF COMBINATORIAL LIBRARIES

BACKGROUND OF THE INVENTION

This application is filed pursuant to 35 U.S.C. §371 as a United States National Phase Application of International Application No. PCT/US97/05701 filed Apr. 8, 1997, which claims priority from 60/014,970 filed Apr. 8, 1996.

A portion of the disclosure of this patent document contains material which is subject to copyright protection. The copyright owner has no objection to the facsimile reproduction by anyone of the patent document or the patent disclosure, as it appears in the Patent and Trademark Office patent files or records, but otherwise reserves all copyrights whatsoever.

The present invention generally relates to the field of combinatorial chemistry and in particular relates to encoding the library products of combinatorial synthesis.

Recent trends in the area of research for novel chemical and especially pharmacological agents have been concentrated on the preparation of so-called "chemical libraries" as potential sources of new leads for drug discovery. Chemical libraries are intentionally created collections of differing molecules which can be prepared either synthetically or biosynthetically and screened for biological activity in a variety of different formats. One can have libraries of soluble molecules; libraries of compounds tethered to resin beads, silica chips or other solid supports; or recombinant peptide libraries displayed on bacteriaphage or other biological display vectors. Chemical libraries are advantageously made by using techniques from the field of combinatorial chemistry. The field of combinatorial chemistry is a synthetic strategy which leads to large chemical libraries. Combinatorial chemistry can be defined as the systematic and repetitive covalent connection of a set of different building blocks of varying structures to each other to yield a large array of diverse molecular entitites.

Traditionally, new medicinal chemical lead structures have originated from the isolation of natural products from microbiological fermentations, plant extracts, and animal sources; from screening of pharmaceutical company compound databases; and more recently through the application of both mechanism-based and structure-based approaches to rational drug design. All of these methods are relatively expensive. Recent cost studies suggest that the average cost of creating a new molecular entity in a major pharmaceutical company is around $7,500 per compound, using the traditional chemical synthesis technology that requires more or less constant hands-on manipulation of reagents and apparatus and the attention of a chemist. Furthermore, the advent of high throughput automated techniques has made possible the robotized screening of in excess of hundreds of thousands of individual compounds per year, per drug target. The availability of this capability, combined with the relatively high cost of more traditional hand crafted chemistry has caused a global shift in emphasis toward the concept of mass production, which is an industrial concept that can be put into being using the approach of combinatorial chemistry.

The inefficiencies of hand crafted chemistry are thus largely addressed by a switch to the concept of using combinatorial chemical technologies for rapidly synthesizing compound collections. Thus, by employing a building block approach and by systematically assembling these blocks in many combinations using chemical procedures it is possible to create chemical libraries as vast populations of molecules. An essential starting point for the generation of molecular diversity is an assortment of small, reactive molecules which may be considered chemical building blocks. The universe of structural diversity accessible through assembly of even a small set of building-block elements is potentially very large, and unleashing the power inherent in the building block approach is crucial to the success of the combinatorial method. The building block argument is easily illustrated as follows. Theoretically, the number of possible different individual compounds, N prepared by an ideal combinatorial synthesis is determined by two factors; the number of blocks available for each step "B" and the number of synthetic steps in the reaction scheme, s. If an equal number of building blocks are used in each reaction step, then $N=B^s$. If the number of blocks that one desires for each step varies (e.g. b, c, d in a three-step synthesis), then $N=bcd$.

From the above, it can be seen that a relatively conservative combinatorial synthesis procedure involving 20 blocks in a three step synthesis process will produce $20^3=8000$ compounds. This relatively generous production output then raises the next question, which is, how will the compounds be identified? For example, a typical combinatorial synthesis technique is that of the split synthesis. As an example of split synthesis in the solid state synthesis of peptides, a batch of resin support (typically small resin beads) is divided into n fractions, coupling a single monomer amino acid to each aliquot in a separate reaction, and then throroughly mixing all the resin particles together. Repeating this protocol for a total of x cycles can produce a stochastic collection of up to $n^x$ different molecules, as governed by a hypergeometric distribution. To ensure representation of the majority of possible ligands one needs to begin with a multiplicity of beads. A typical value would be ten times as many beads as the desired number of ligands. Theoretically a set of every possible combination of the building blocks exists in the aliquots. In order to determine the composition of a particular compound which is found to be of interest, one could proceed with direct ligand structural analysis, preferably on a mass spectrometer, on a species-by-species basis. A typical combinatorial synthesis now typically takes place on a reaction plate having from 96 to 2,304 reaction wells. One identifies the product compounds of true interest by a positive response in an appropriate assay. However, even after assays are run that will greatly reduce the number of compounds as having been non-active in the assay, the problem with a conventional mass spectrometer analytical approach is that many individual analysis trials are required, there may only be very small quantities of material available after running a combinatorial synthesis, and overall turn around time may be quite lengthy. A need exists, then to somehow label compounds as they are going through their combinatorial steps. Where compounds are, for example, tethered to resin beads, prior art solutions to the problem have included attaching chemical identifier tags to the beads coincident with each block coupling step in the synthesis. The different chemical properties of each tag would then convey which building block was coupled in a particular step of the synthesis, and the overall structure of a ligand on any bead could be deduced by "reading" the set of tags on that bead, in effect having encoded the bead.

Tags should ideally have a highly discrete information content, be amenable to very high sensitivity detection and decoding, and must be stable to reagents used in the ligand synthesis. Prior art tags attached onto beads have included nucleotides, peptides, or a combined series of hydrocarbon homologs and polychlorinated aromatics. Single stranded oligonucleotides are built on resin beads upon which peptide synthesis is being performed and which are subsequently amplified through polymerase chain reaction and sequenced. Another technique is one where orthogonally differentiated diamine linkers are used in the construction of soluble chimeric peptides comprising a "binding" strand and a "coding" strand. As amino acid monomer building blocks are coupled to the binding strand, this is recorded by building an amino acid code onto the "coding" strand. The sequence of the coding strand is then resolved by Edman degradation. One problem with this approach is that it requires an extra chemical step for every step taken in the construction of the library. Another problem with this approach is that it requires requires orthogonal synthetic procedures for building up a tag in conjunction with synthesis of ligands, i.e., it requires the addition of like moieties, whereas there is very great interest in discovering methods for producing compounds which are not limited to sequential addition of like moieties. Such methods would find application, for example in the modification of steroids, antibiotics, sugars, coenzymes, enzyme inhibitors, ligands, and the like, which frequently involve a multi-stage synthesis in which one would wish to vary the reagents and/or reactions conditions to provide a variety of compounds. In such methods the reagents may be organic or inorganic reagents, where functionalities may be introduced or modified, side groups attached or removed, rings opened or closed, stereochemistry changed, and the like. For such a method to be viable, however, there needs to be a convenient way to identify the structures of the large number of compounds which result from a wide variety of different modifications.

A technique that is useful for the screening of nonsequenceable organic molecules prepared by multistep combinatorial synthesis uses a series of gas chromatographically resolvable halocarbon derivatives as molecular tags which, when appended to reactive groups on the bead surface, can constitute a binary code that reflects the chemical history of any member of a library. Instead of the oligonucleotide or peptide coding approaches where the order of assembly of the chemical building blocks for any library member is preserved in the sequence of a single cognate tagging molecule, the binary strategy uses a uniquely defined mixture of tags to represent each building block at each particular step of the synthesis. Thus a set of N tags can be used to encode the combinatorial synthesis of a library of $2^N$ different members. After assembly, the tags are photolysed and analyzed by electron capture capillary gas chromatography.

In all cases, the use of reporter tags complicates synthetic strategies, increases the risk of side reactions and by-products, and yields only indirect evidence of structure. Thus, there is a need to find a way whereby a compound's reaction history may be recorded, and the structure of the resulting compound identified.

The use of $^{13}C$ site-specific labels on the ligand itself has also been used, in connection with $^{13}C$ NMR spectroscopy as a method of monitoring progress in solid state combinatorial synthesis.

Yet another method is that of using a chip which allows for separate analysis at physically separate sites on the surface of the chip. By knowing what reactant is added sequentially at each such site, one can record the sequence of events and thus the series of reactions. If one then subjects the chip to a screening method for a particular desired characteristic and detects the characteristic one can readily determine the compound synthesized at the site which demonstrates that characteristic.

A discrete sample-by-sample analysis will yield a great deal of extraneous information, as everything in the sample will be analyzed. However, in analyzing the results of a combinatorial synthesis, it is desirable to be able to track in linear terms, since all that is being tracked by a linear method is what is being added to the construct of interest in the synthesis, which will omit the presence of solvents, resin bits, side reactions and impurities.

In view of the above needs and shortcomings of the prior art, it is a primary object of the present invention to reduce the amount of time needed to read and de-code the products of a combinatorial synthesis. It is another object of the present invention to provide a method of encoding combinatorial constructs that does not require orthogonal chemistry, that is, chemistry that has been carefully selected so as not to be interfering with the chemistry that is being executed as part of the combinatorial synthesis itself. Another object of the invention is to minimize the amount of capital investment needed to develop a coding strategy that requires no more than what is needed to initially develop a set of appropriate solid support links.

Unlike the methods of the prior art, the present invention embodies a method of isotopically rather than chemically encoding a monomer to read a synthetic history. Readable differences in the encoding moieties therefore rely on physical differentiation, rather than chemical differentiation. The isotopically encoded monomer is, however, chemically bonded to the ligand of interest during synthesis, in contrast to prior art identification methods in which differentiable isotopes are physically mixed into and interspersed with bulk chemicals or commodities to identify their manufacturing source. The invention likewise does not rely on tagging a molecule, like other prior art approaches.

DESCRIPTION OF THE FIGS.

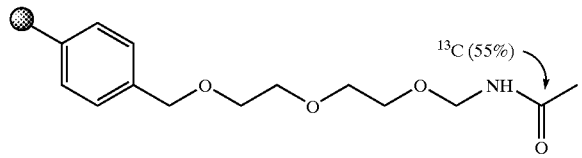

denoting that 55% of the carbon at the penultimate position was doped with $C^{13}$.

Figure 6:
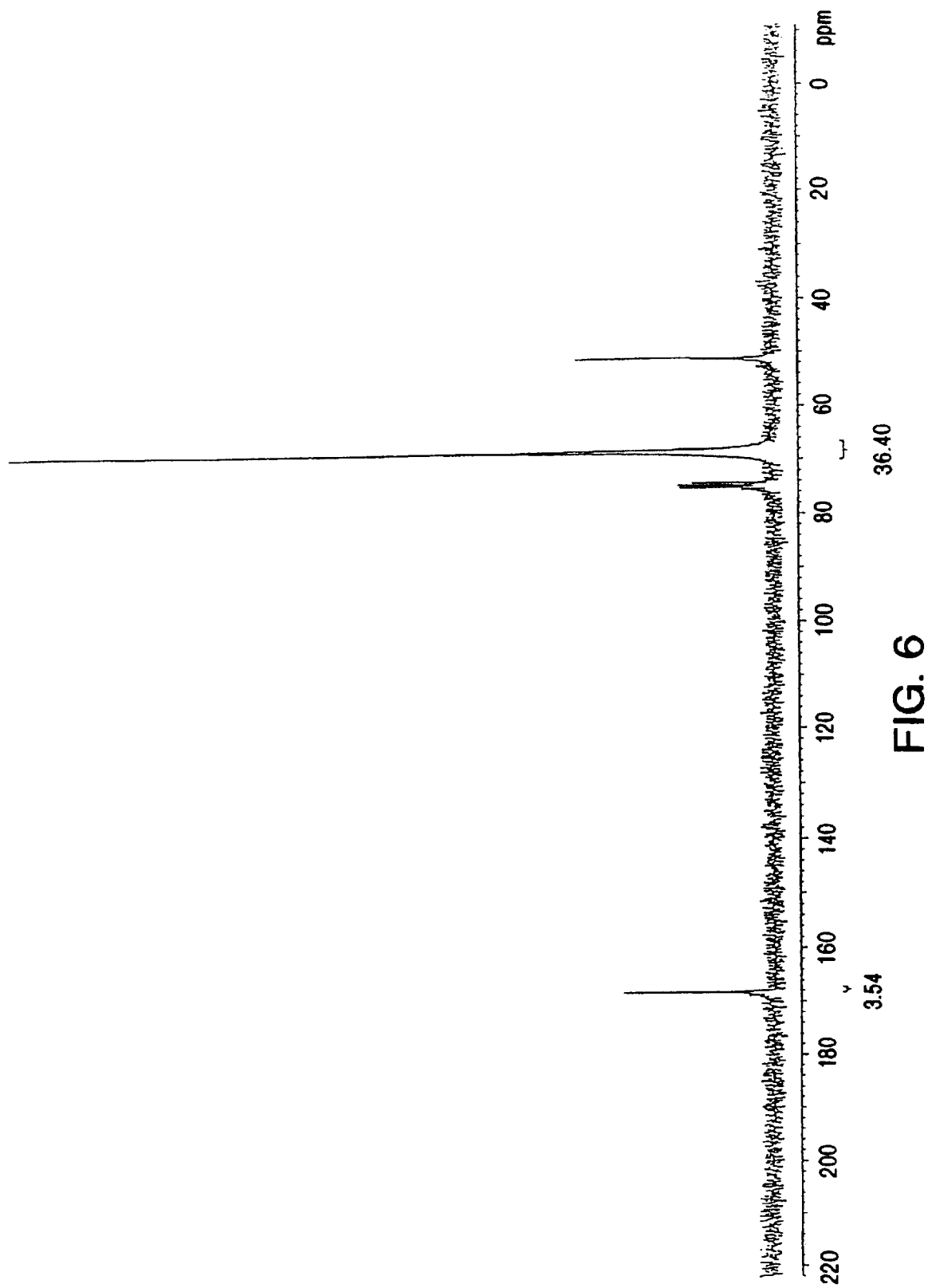

FIG. 6 is an NMR peak pattern for the compound:

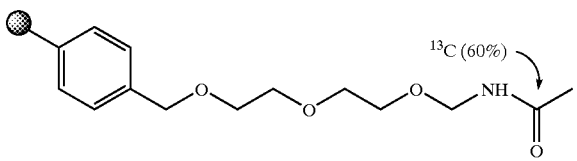

denoting that 60% of the carbon at the penultimate position was doped with $C^{13}$.

Figure 7:
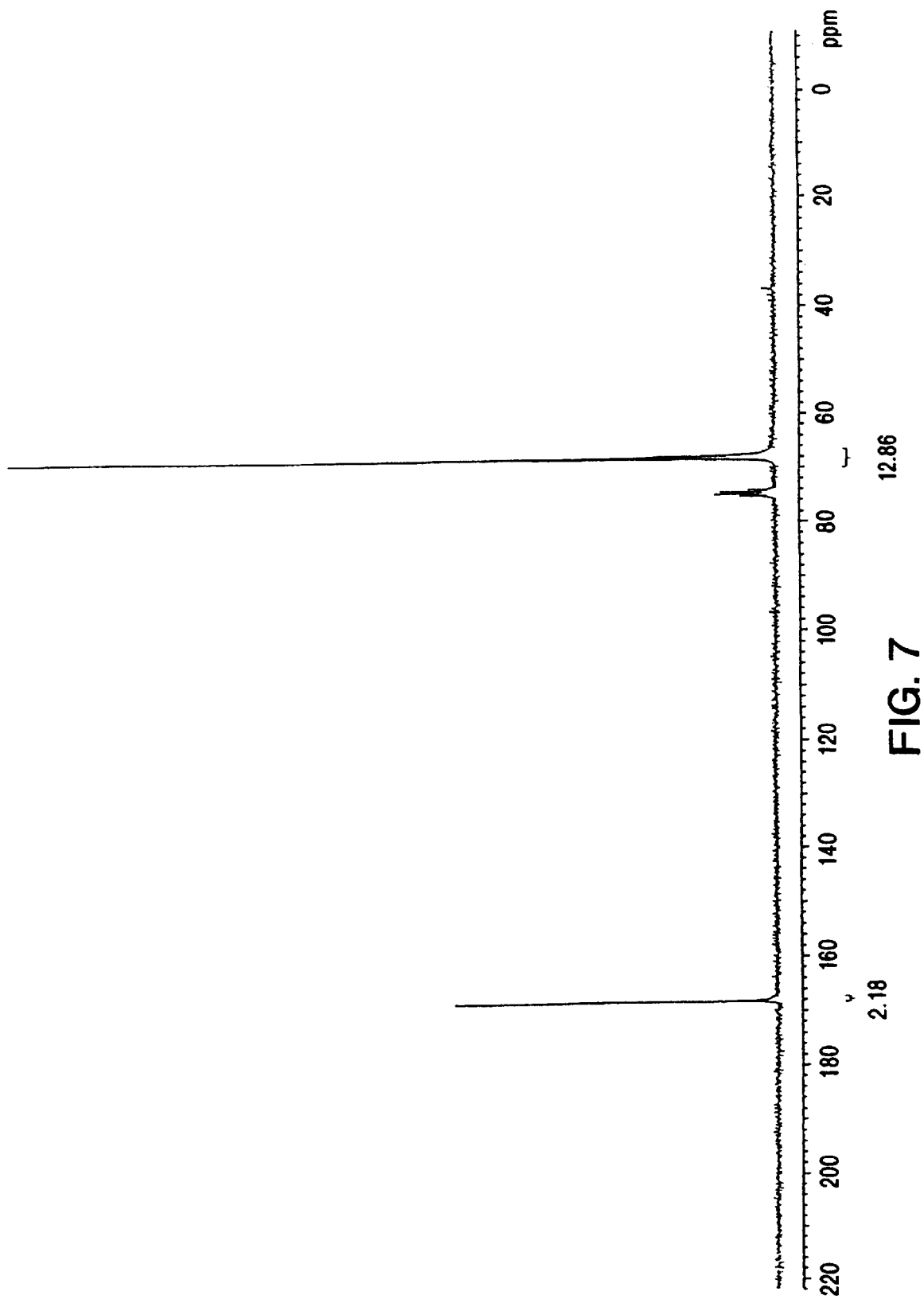

FIG. 7 is an NMR peak pattern for the compound:

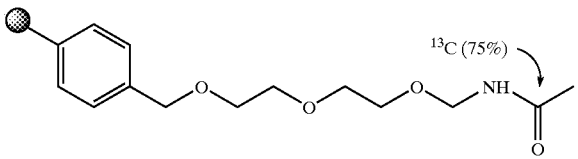

denoting that 75% of the carbon at the penultimate position was doped with $C^{13}$.

Figure 8:
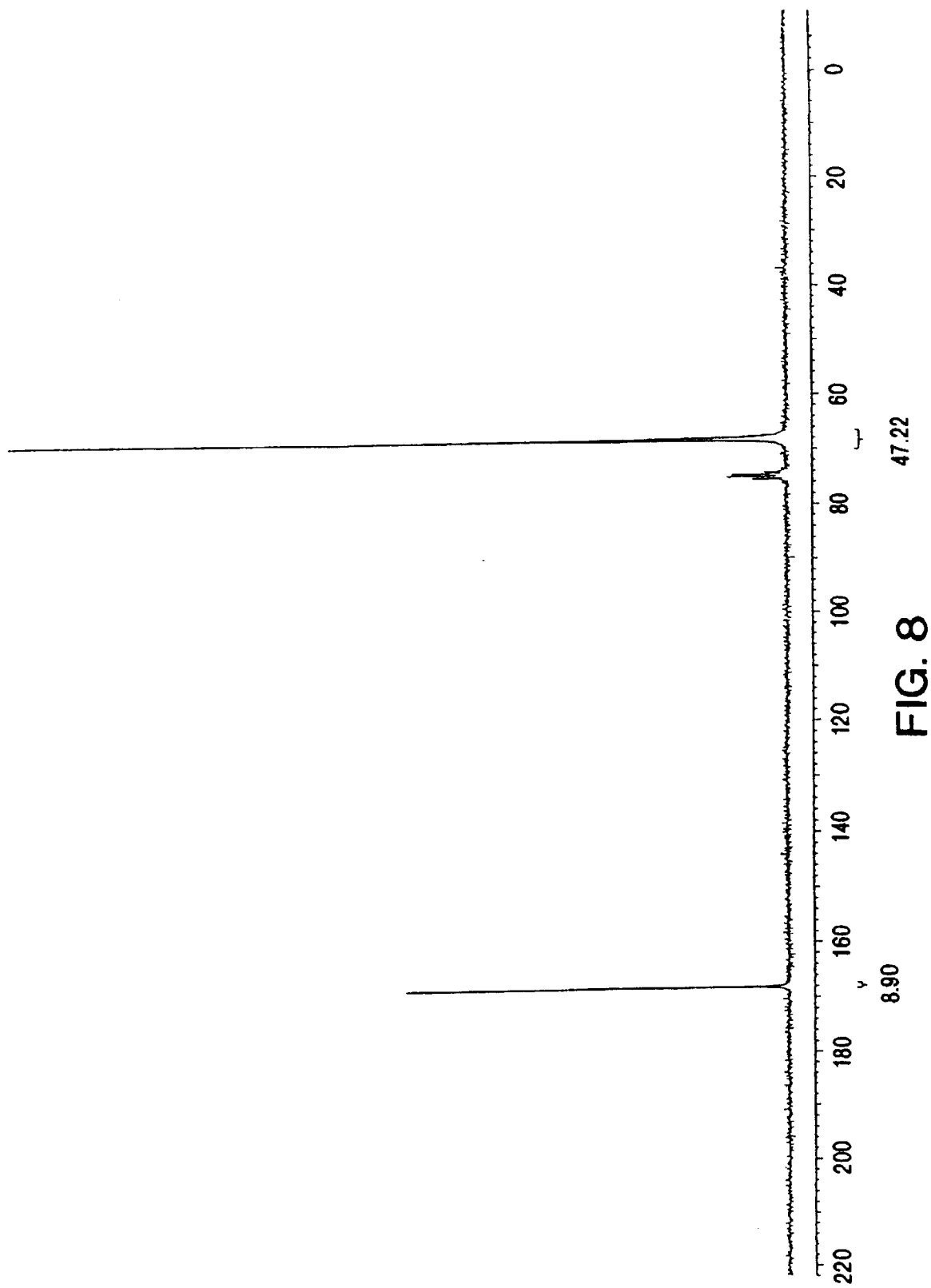

FIG. 8 is an NMR peak pattern for the compound:

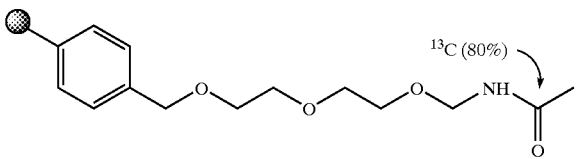

denoting that 80% of the carbon at the penultimate position was doped with $C^{13}$.

Figure 9:
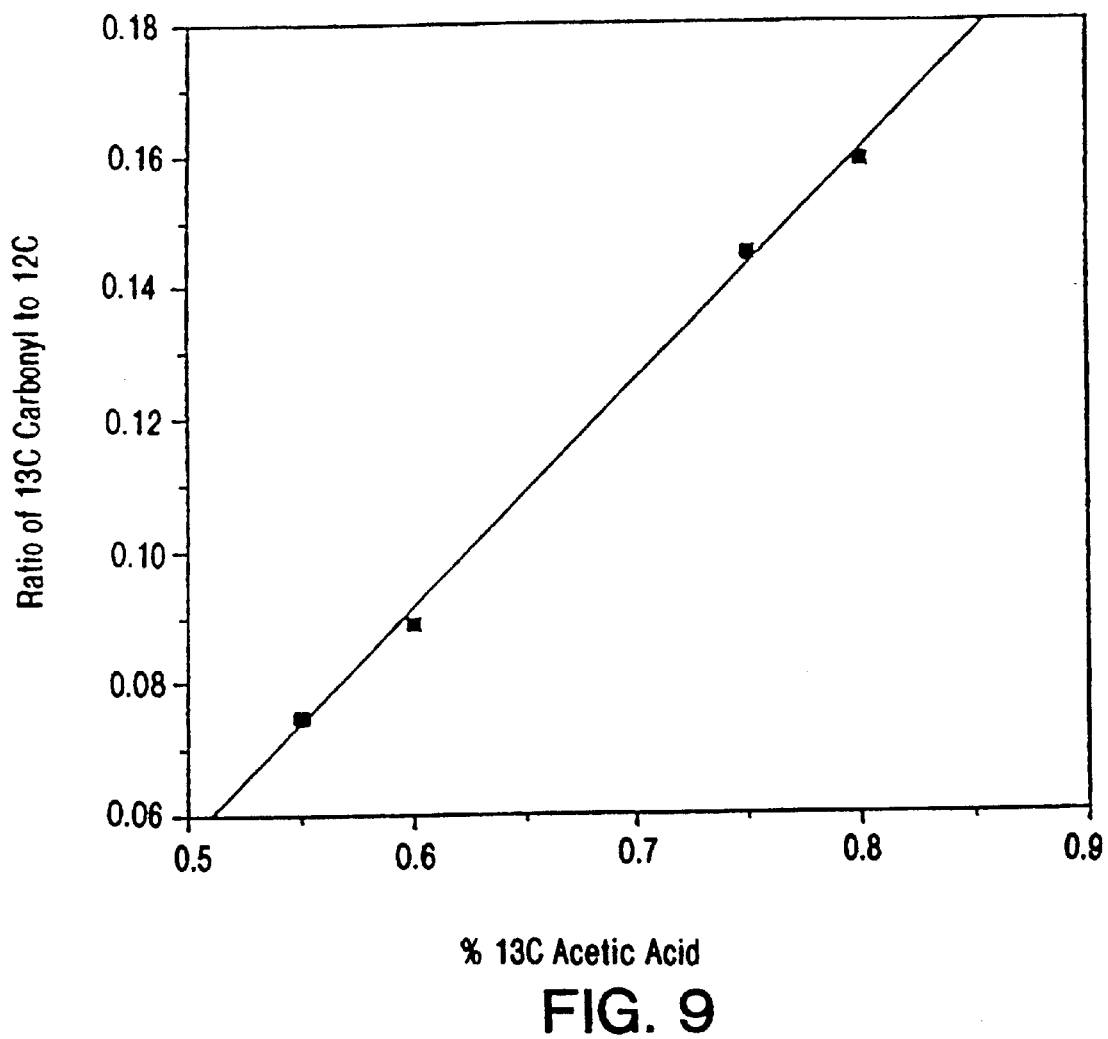
Figure 13:
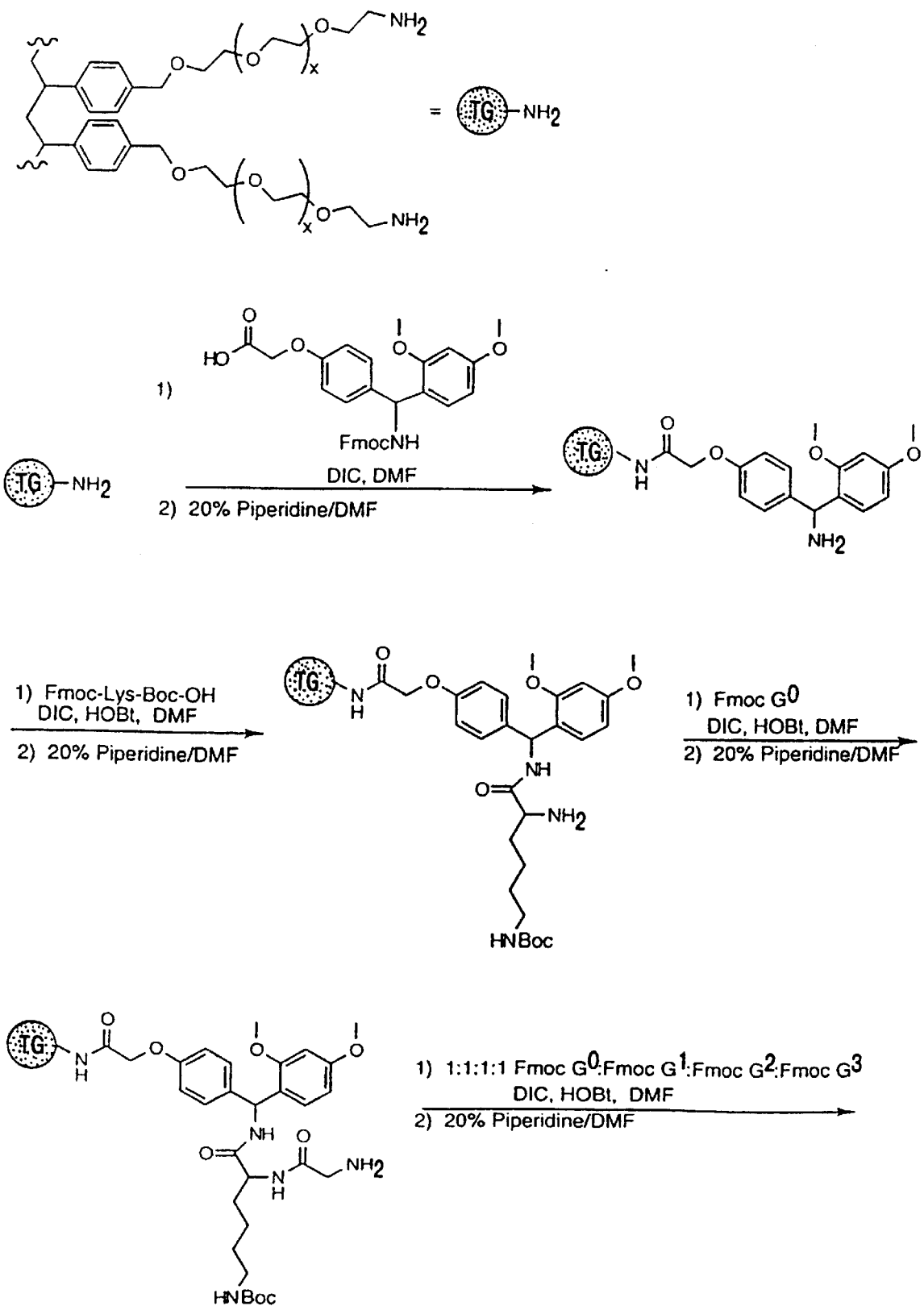
Figure 14:
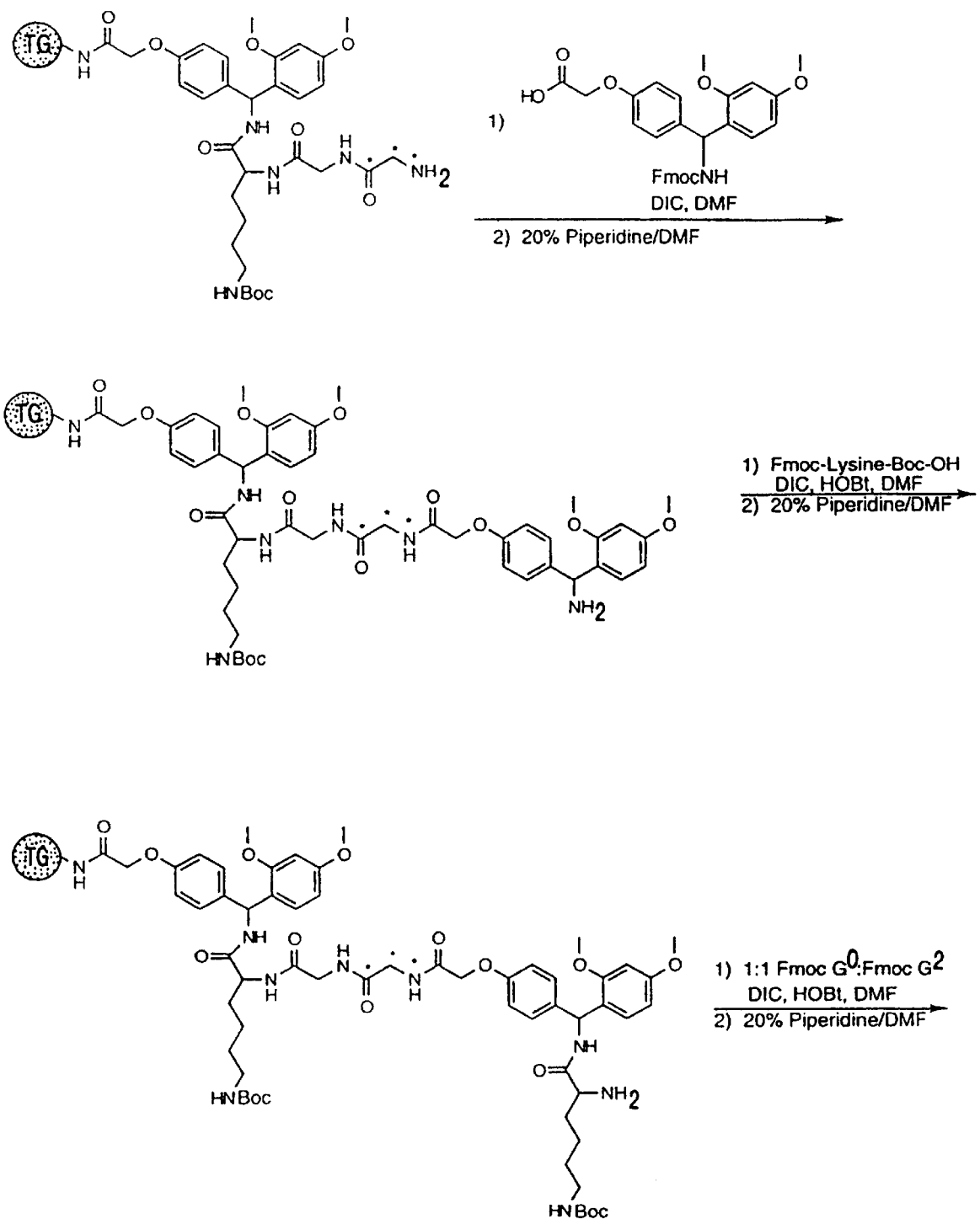
Figure 15:
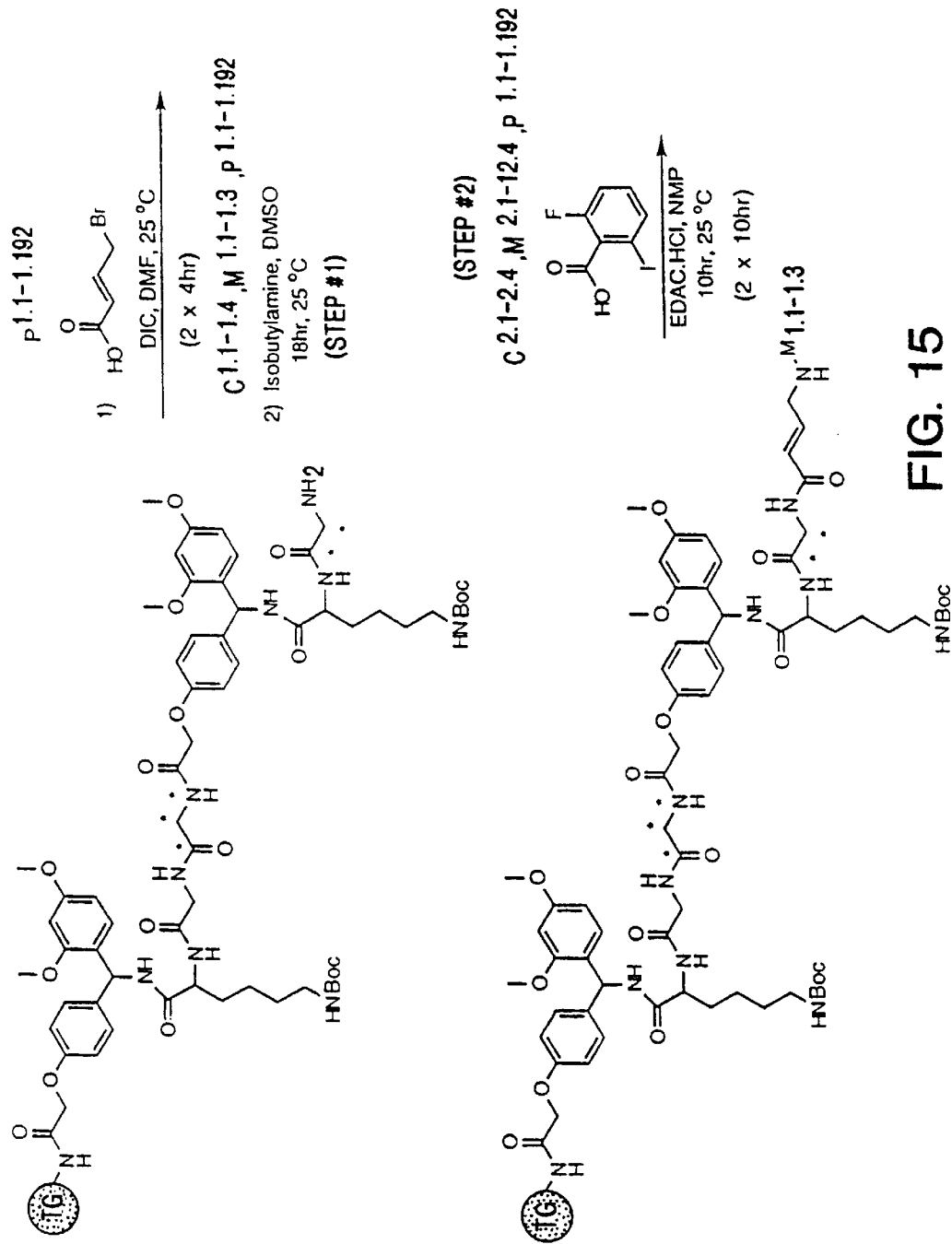
Figure 16:
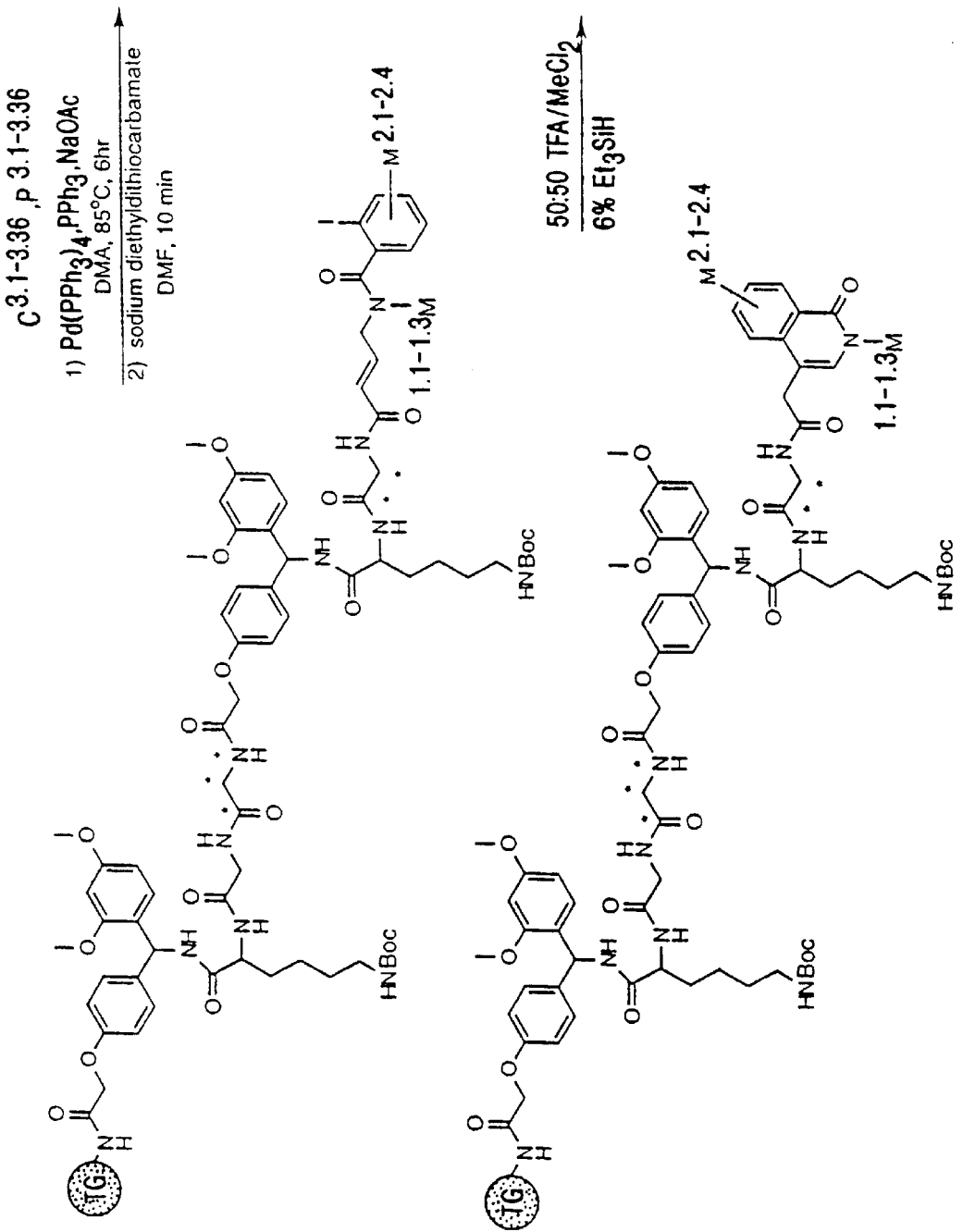
Figure 17:
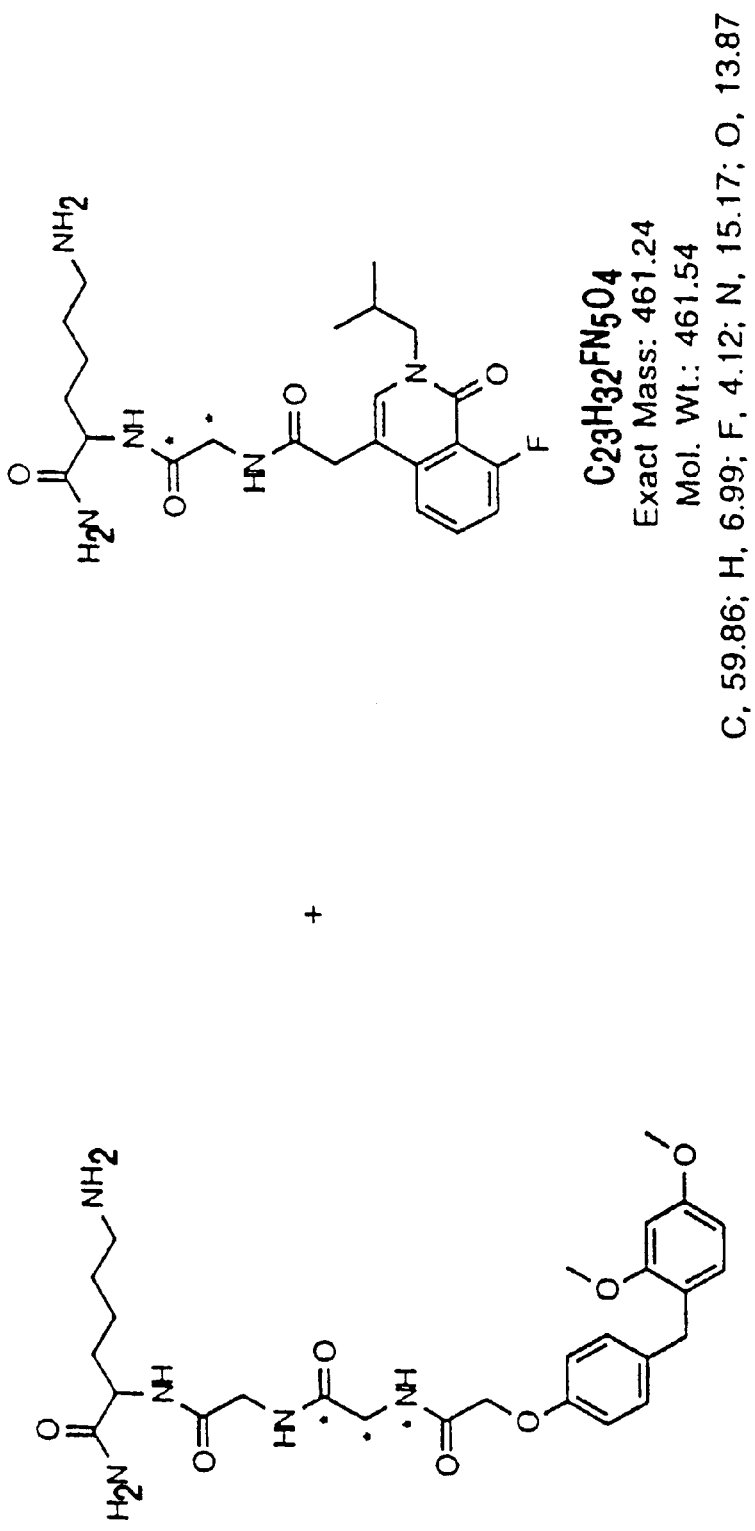
Figure 18:
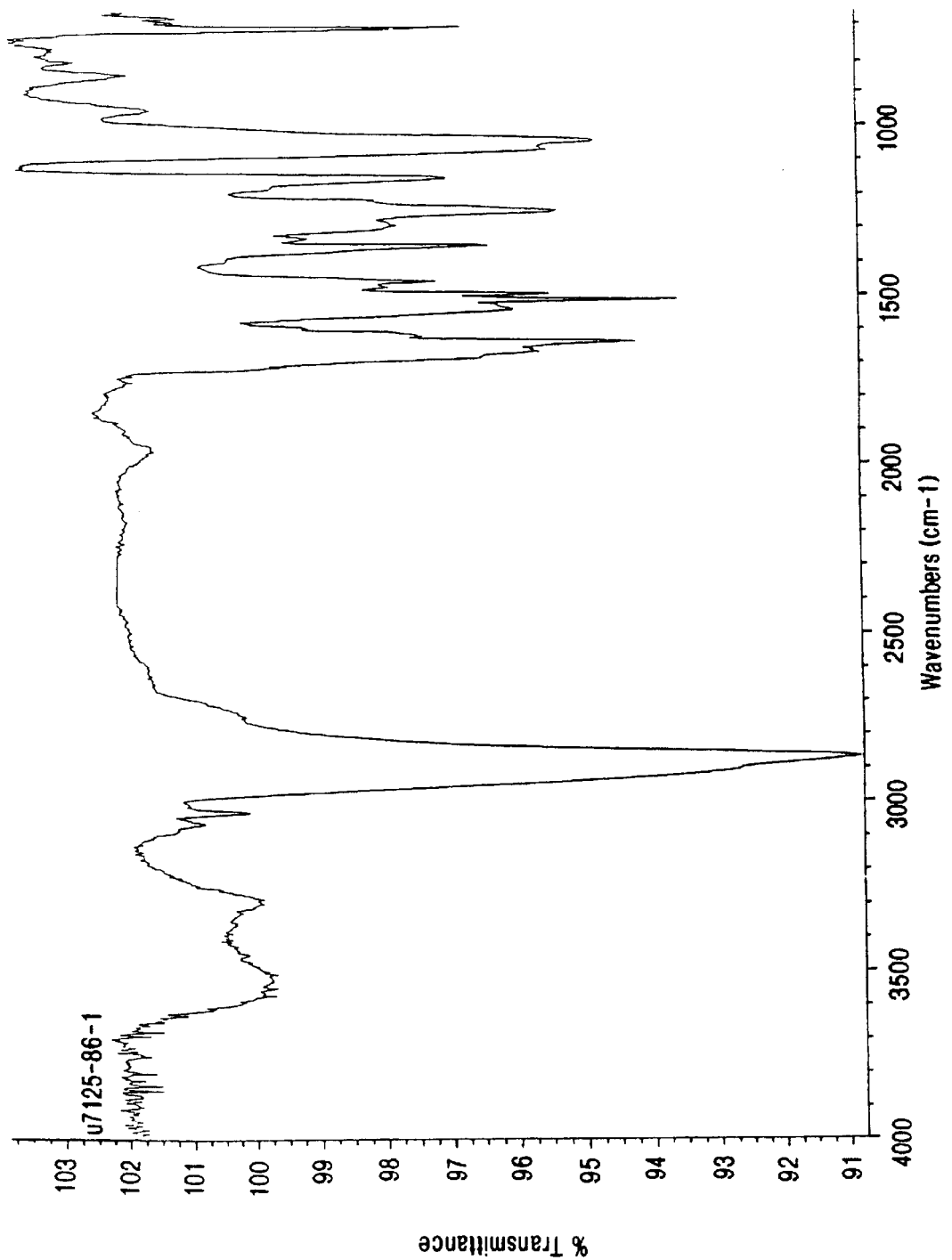
Figure 19:
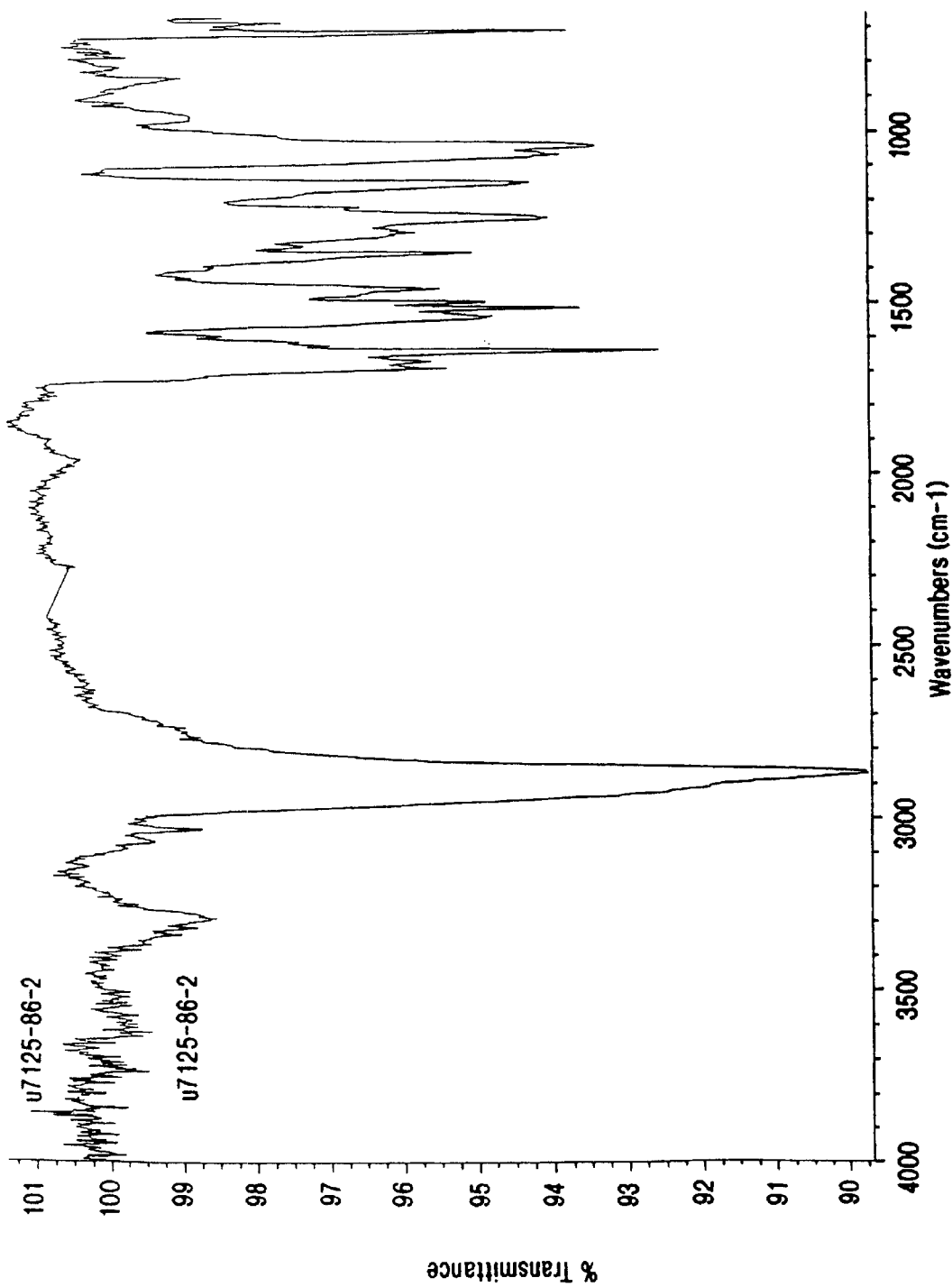
Figure 20:
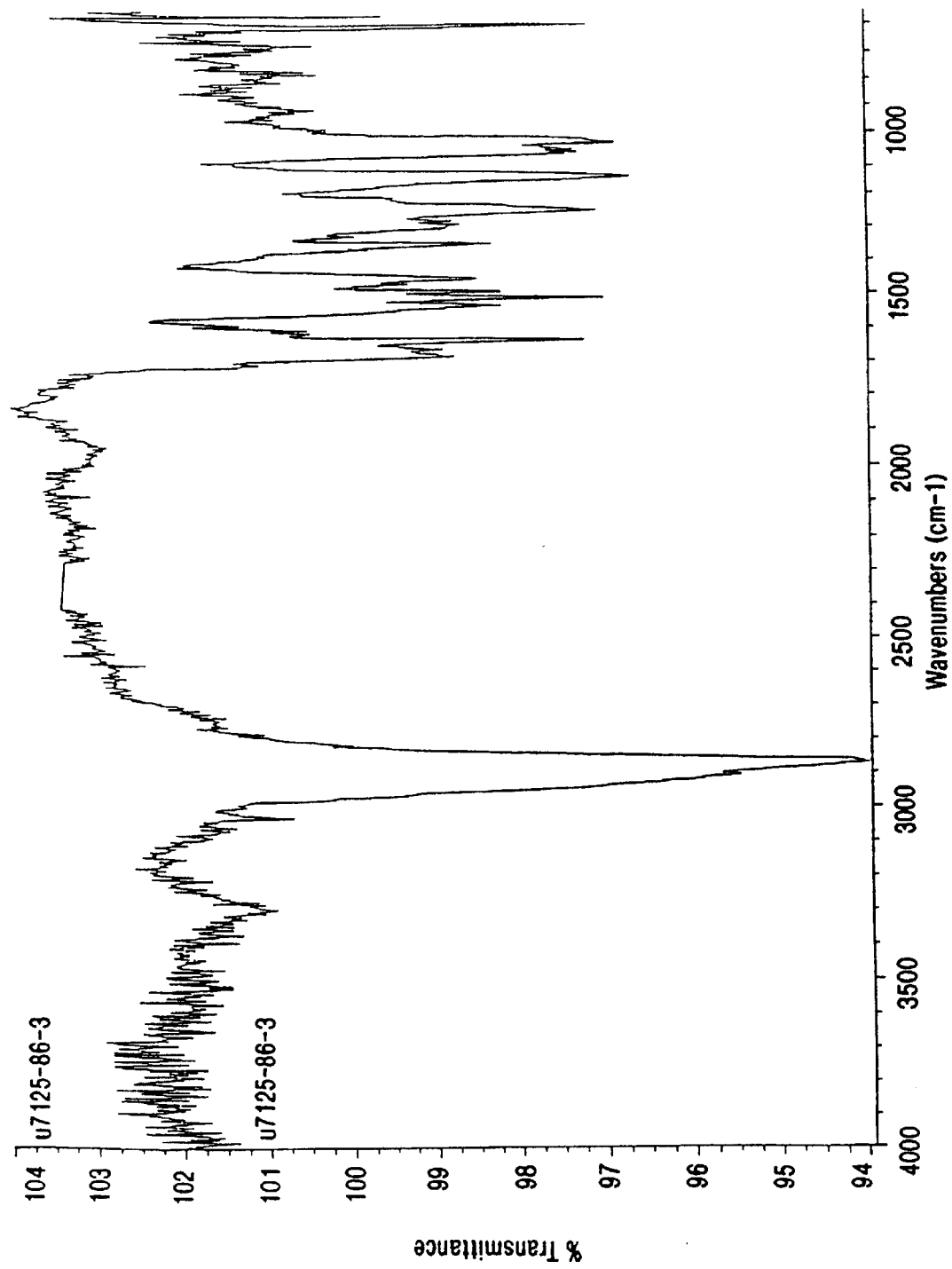
Figure 21:
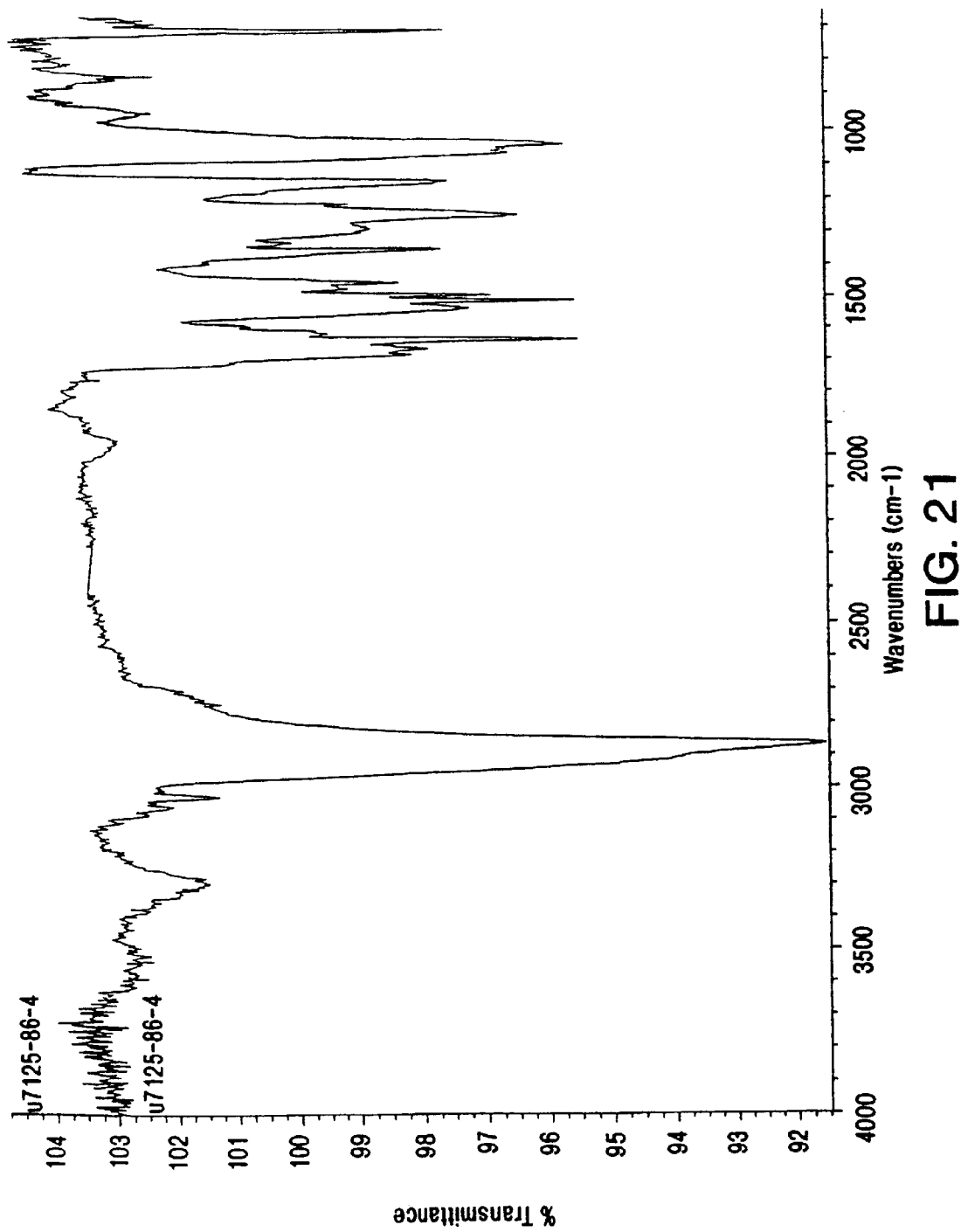
Figure 22:
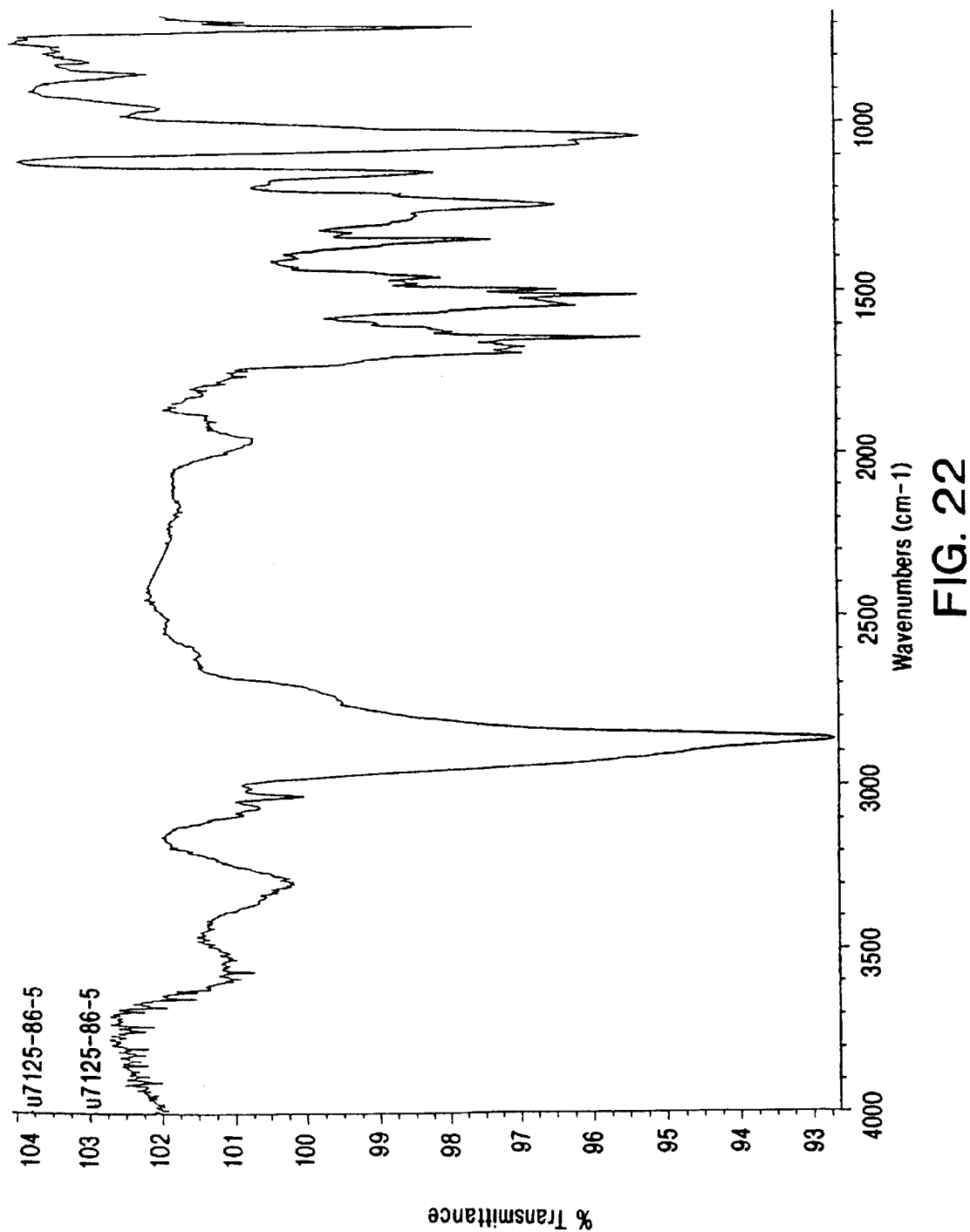
Figure 23:
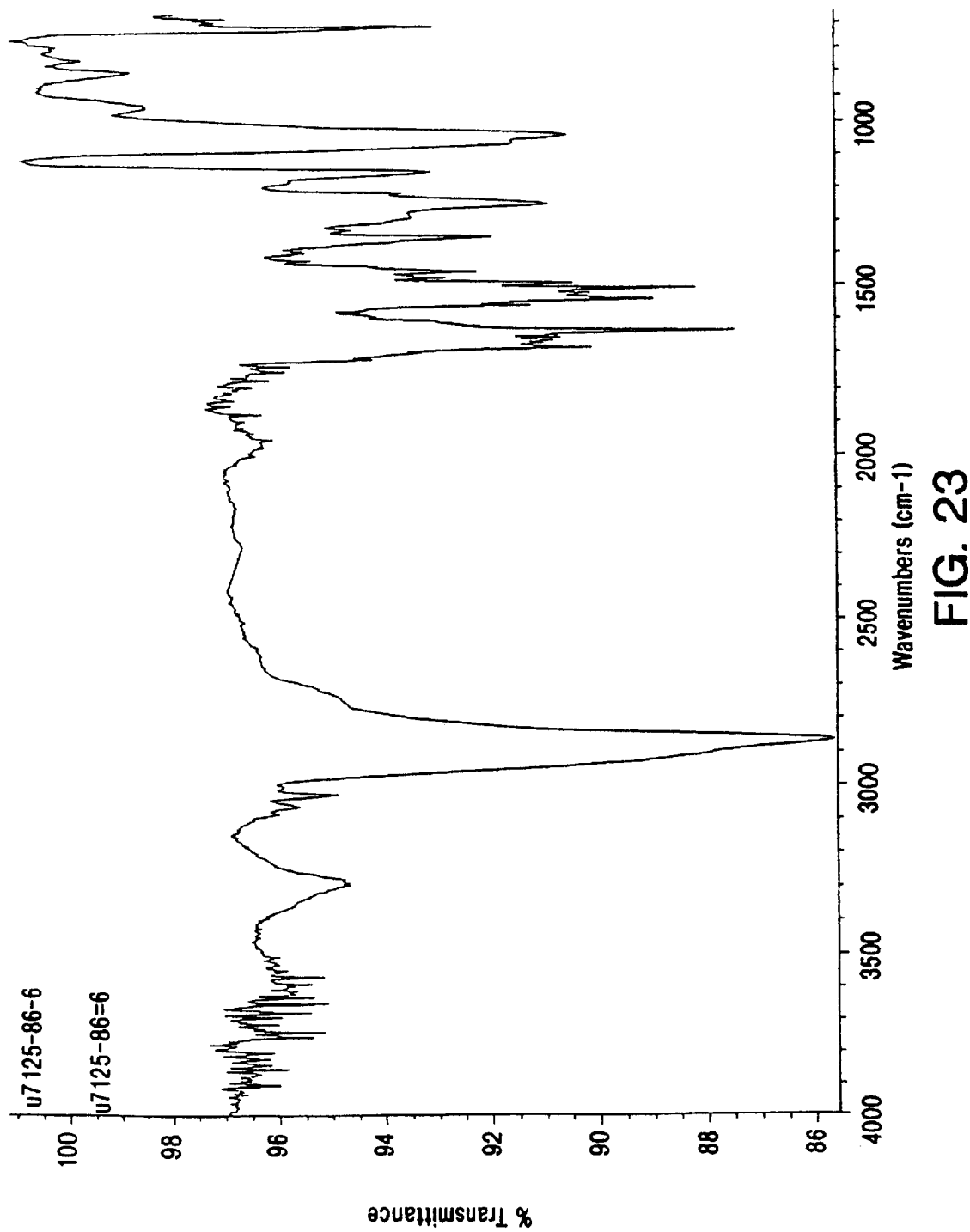
Figure 24:
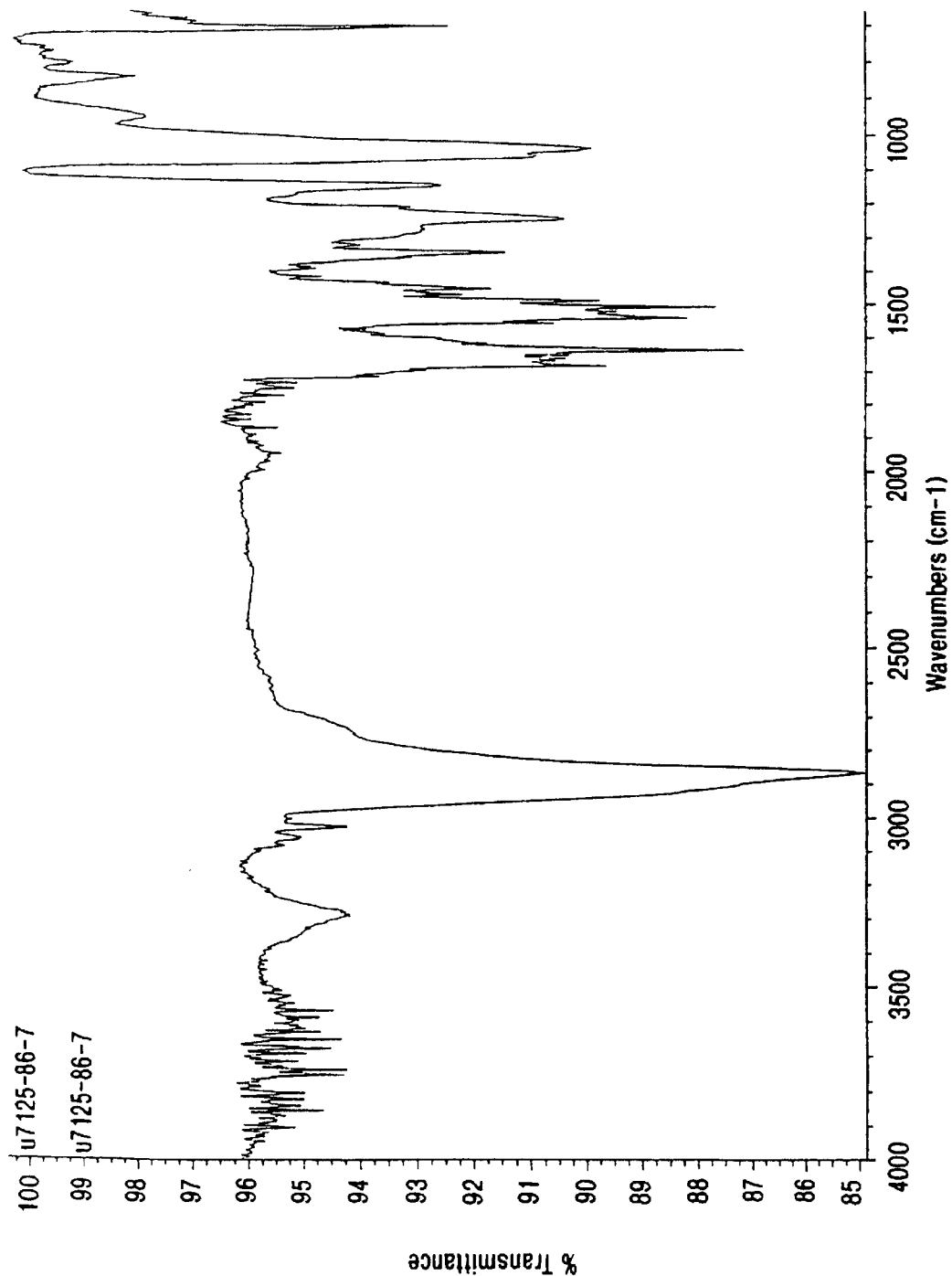
Figure 25:
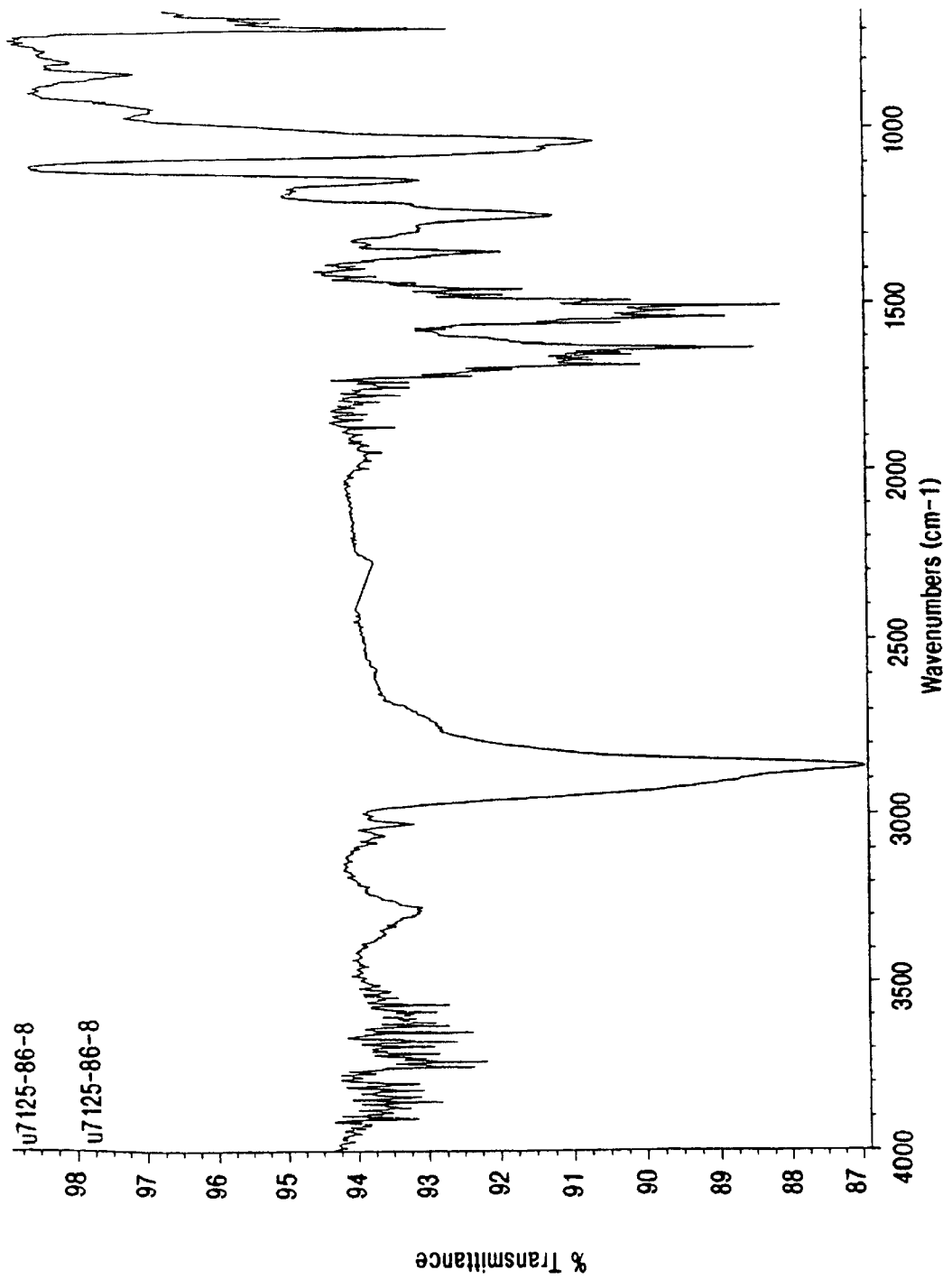
Figure 26:
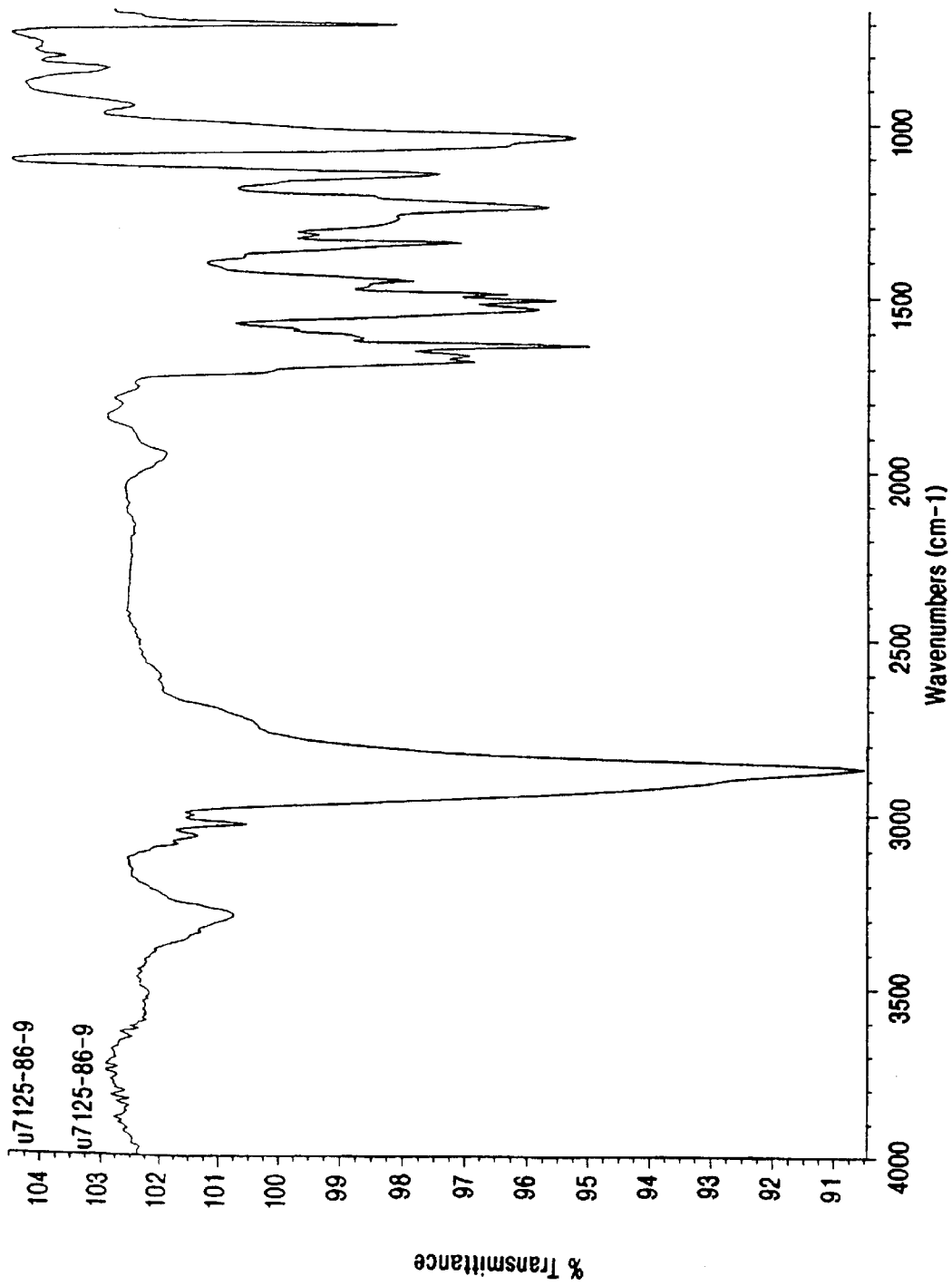
Figure 27:
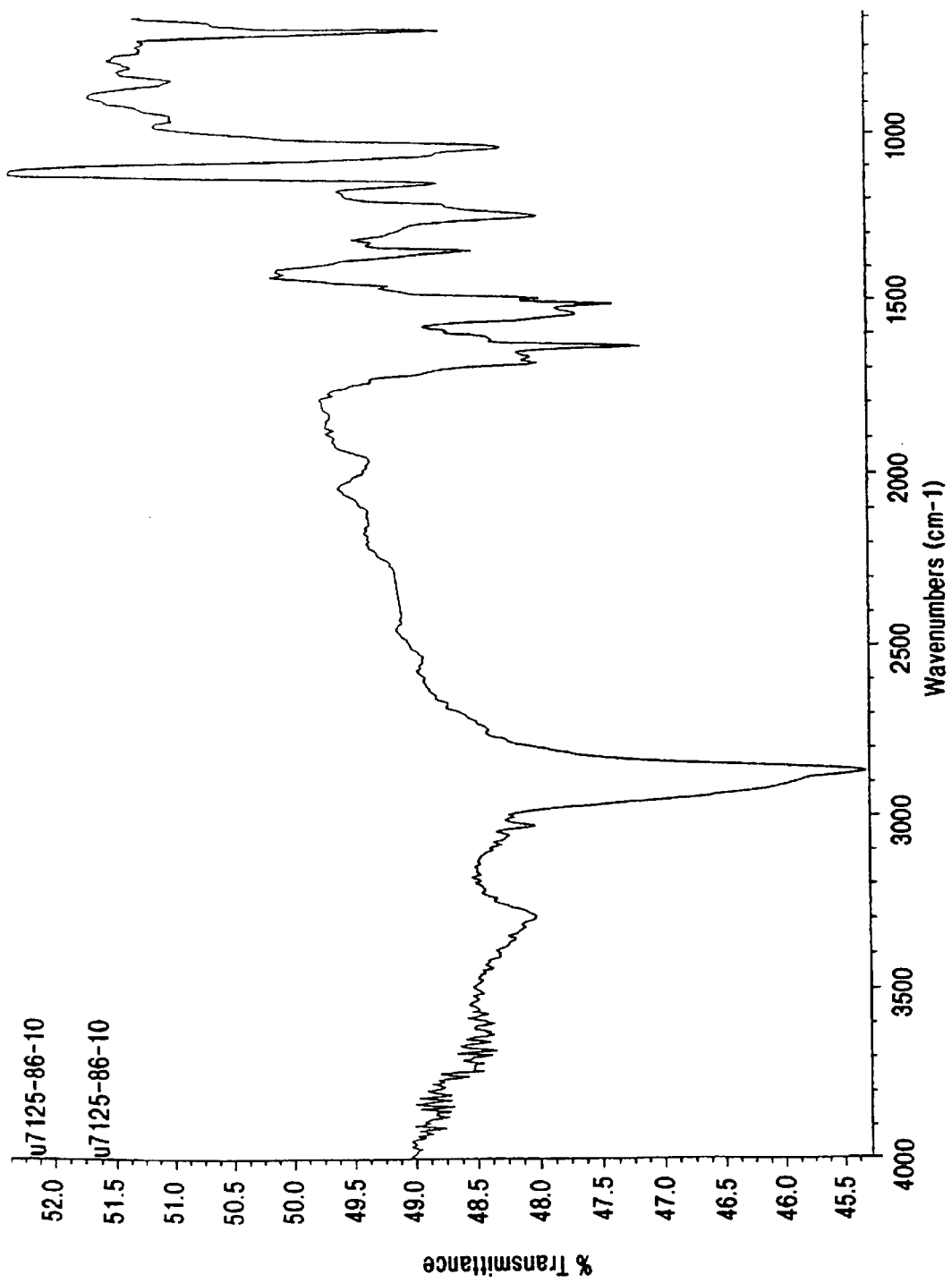
Figure 28:
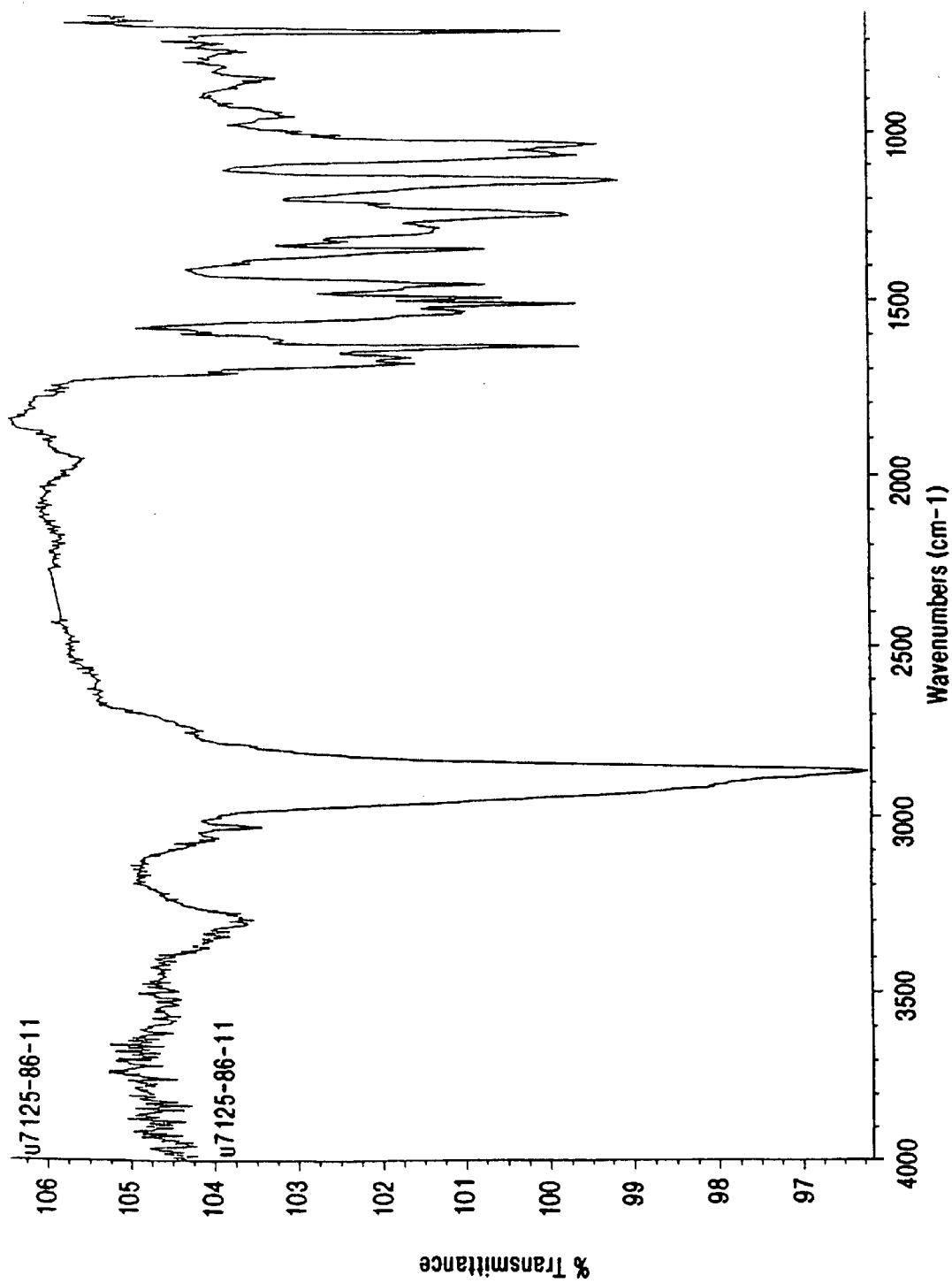
Figure 29:
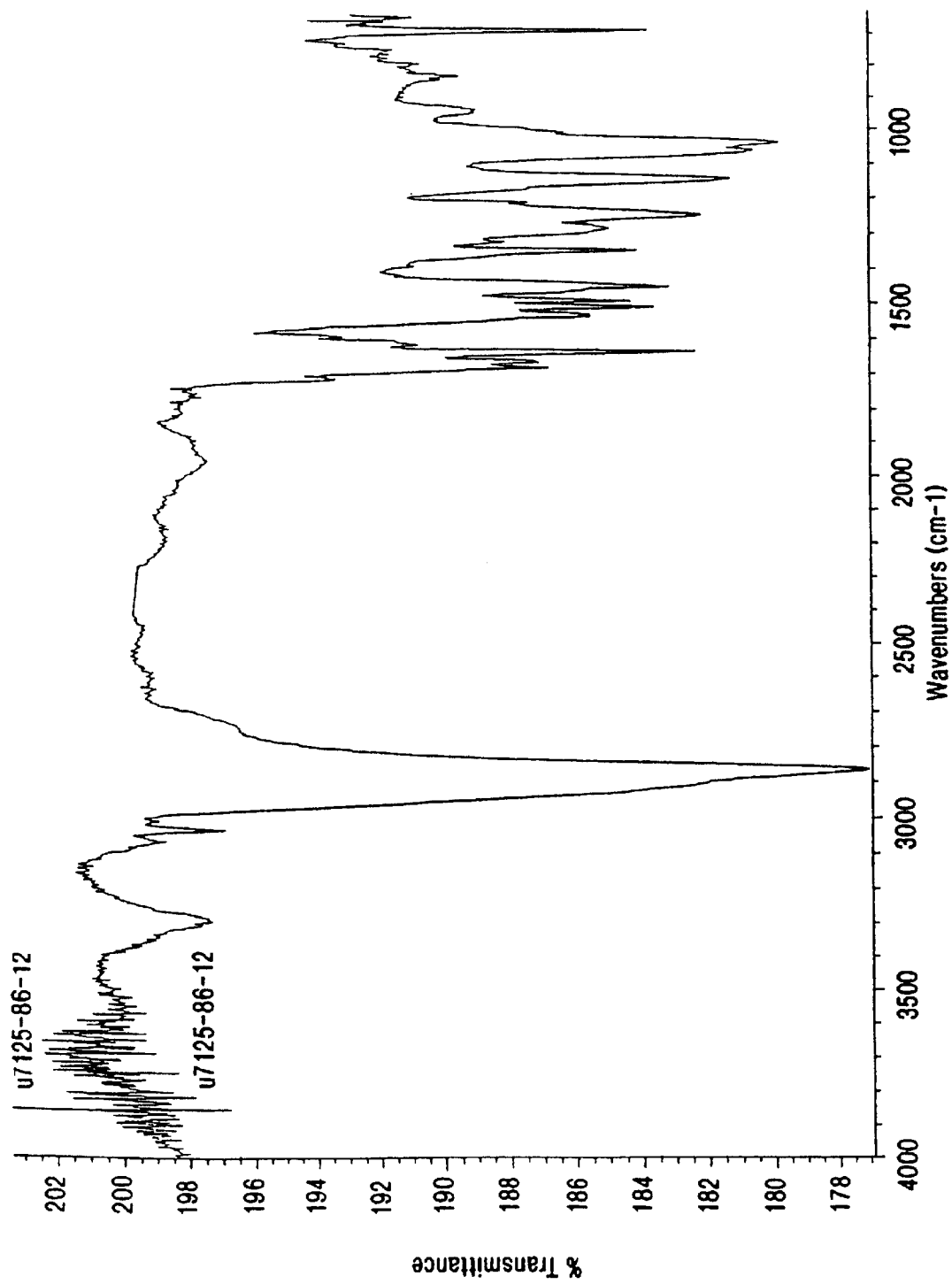
Figure 30:
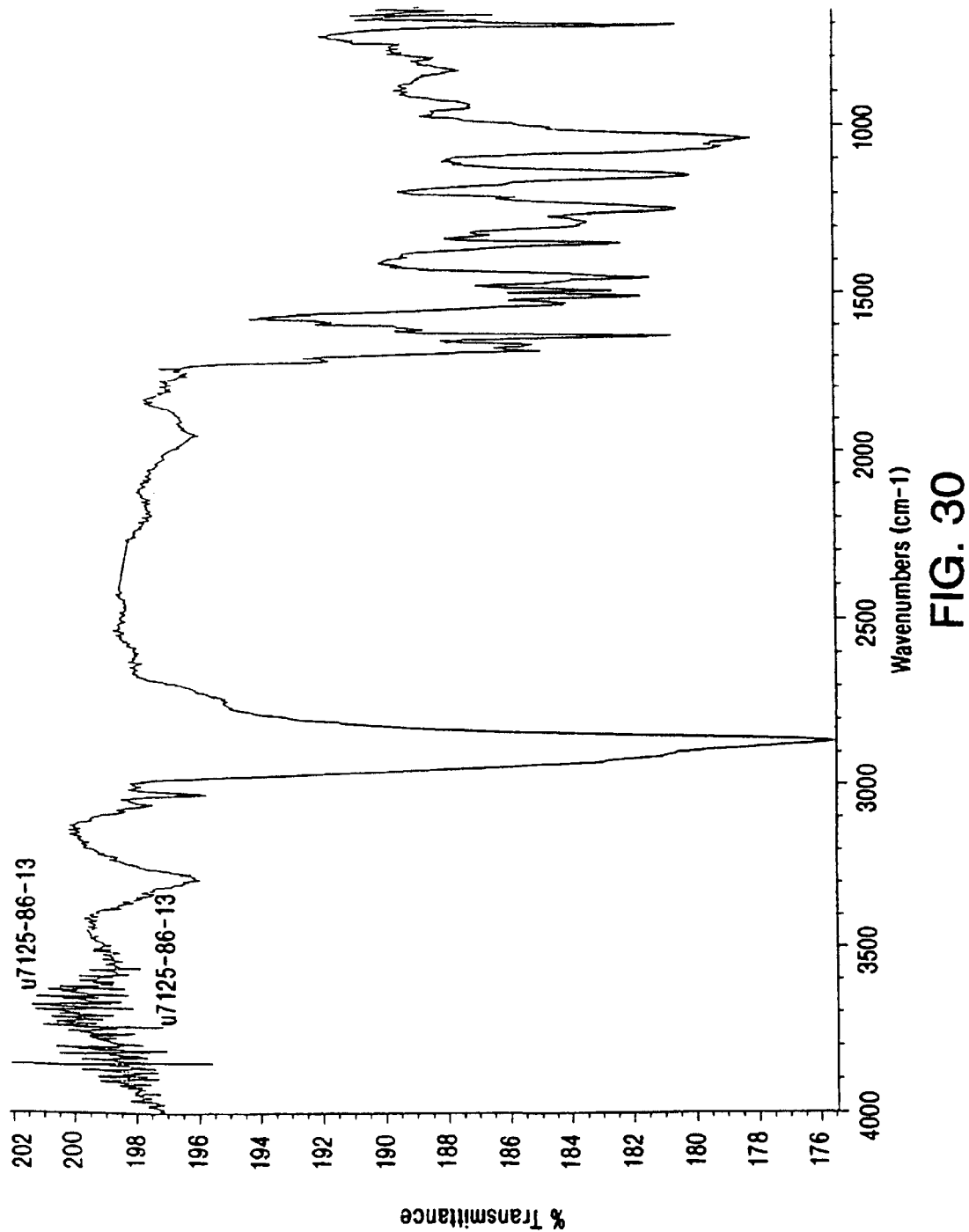
Figure 31:
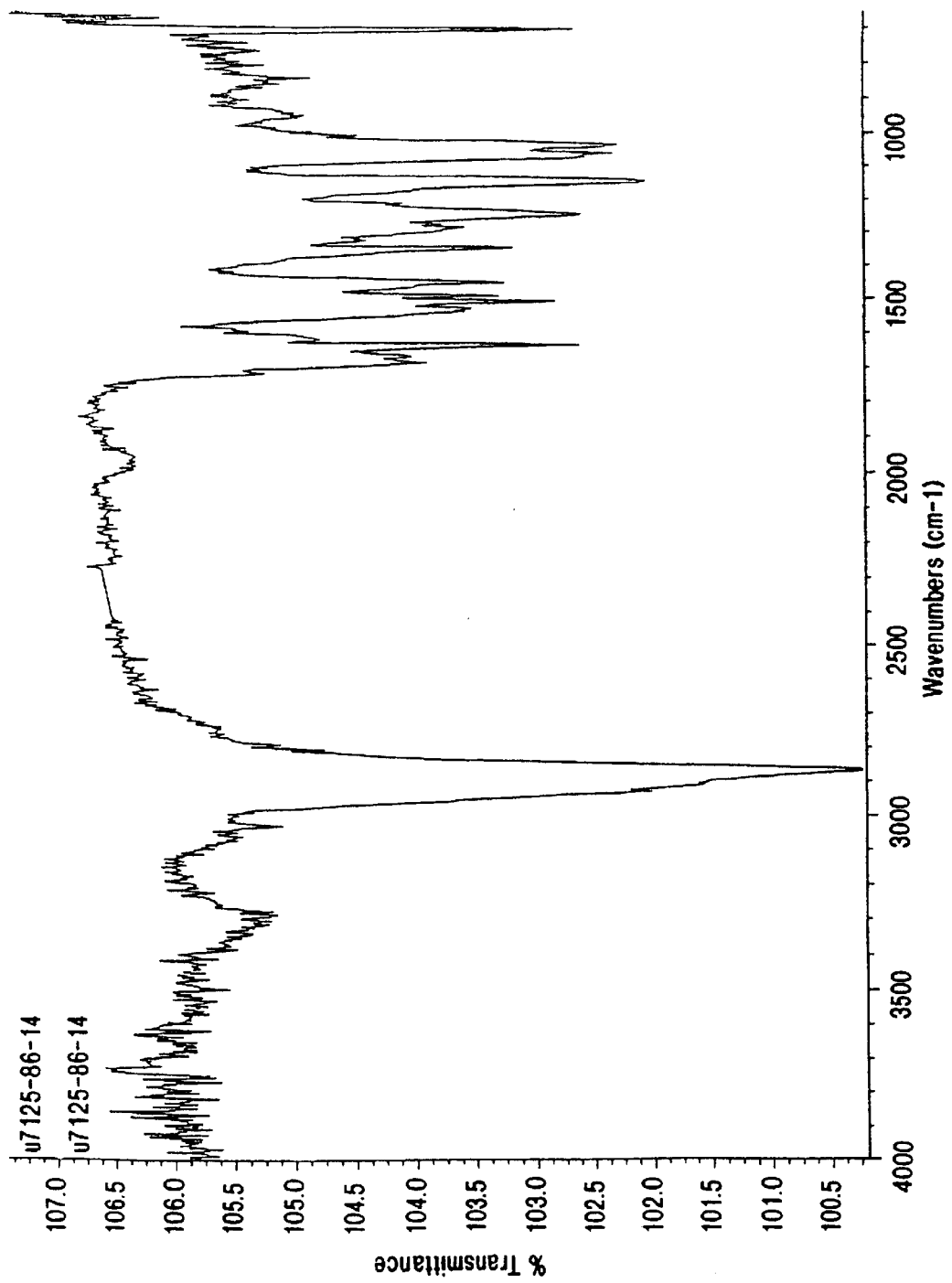
Figure 32:
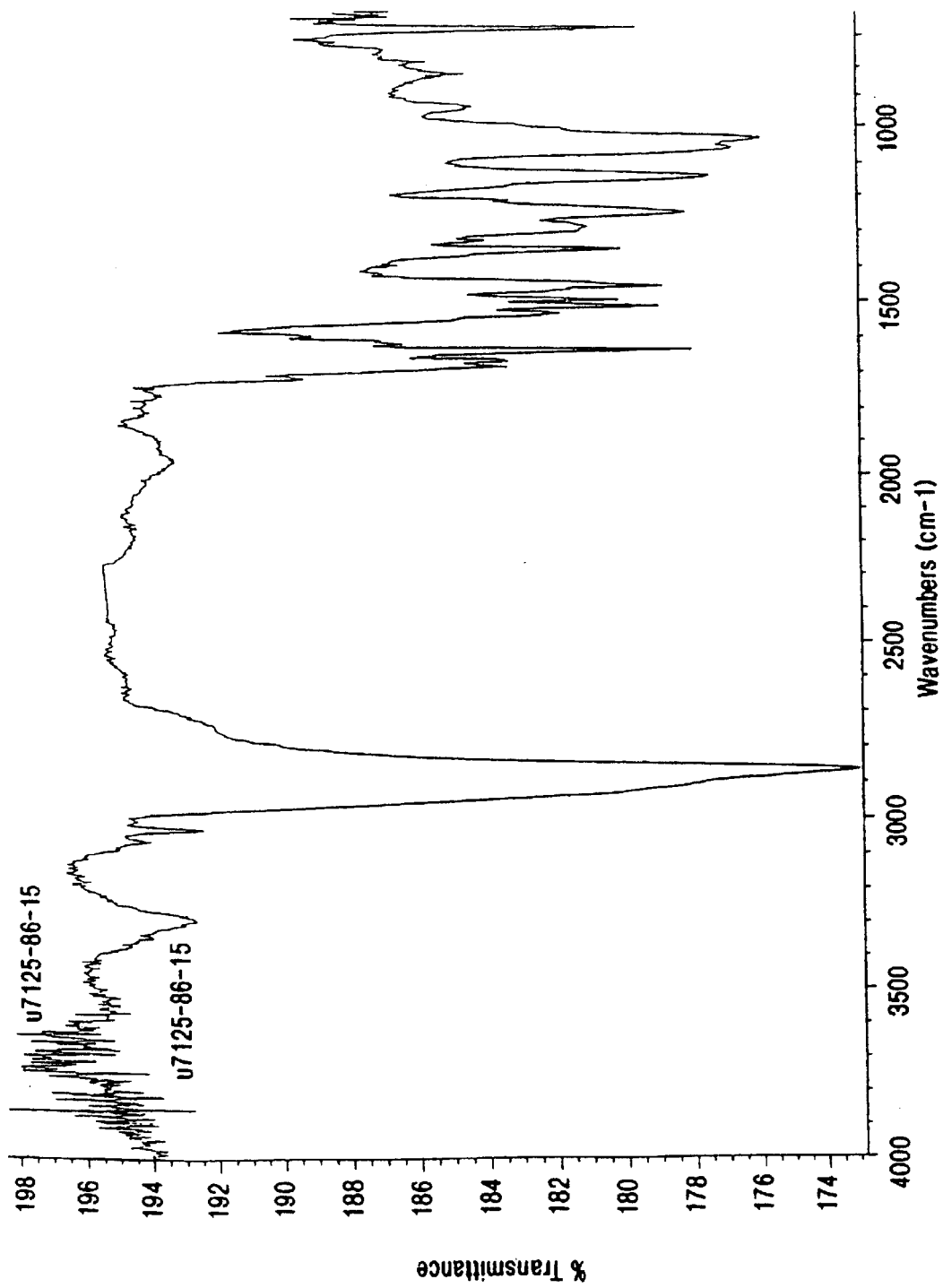
Figure 33:
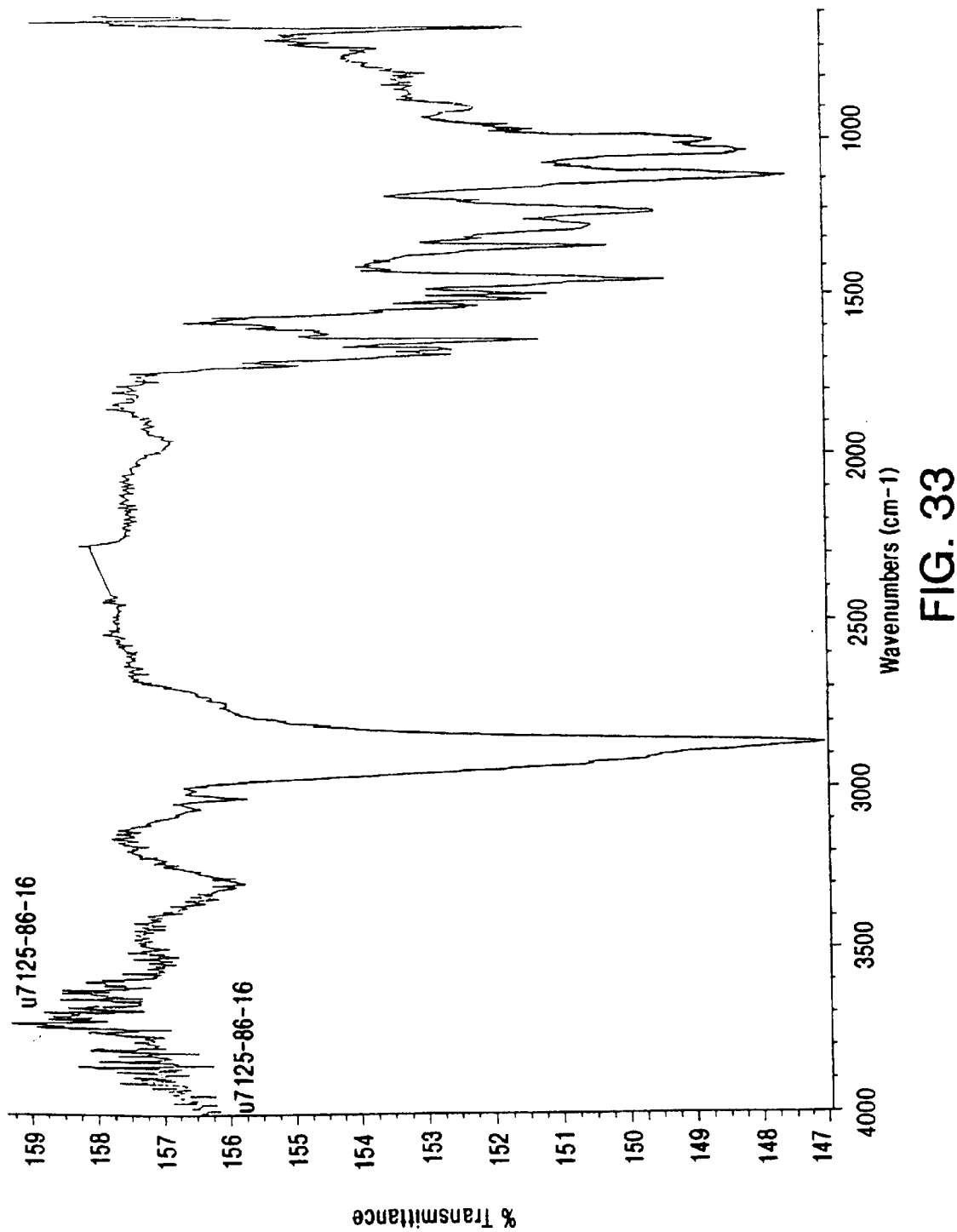
Figure 34:

Figure 35:
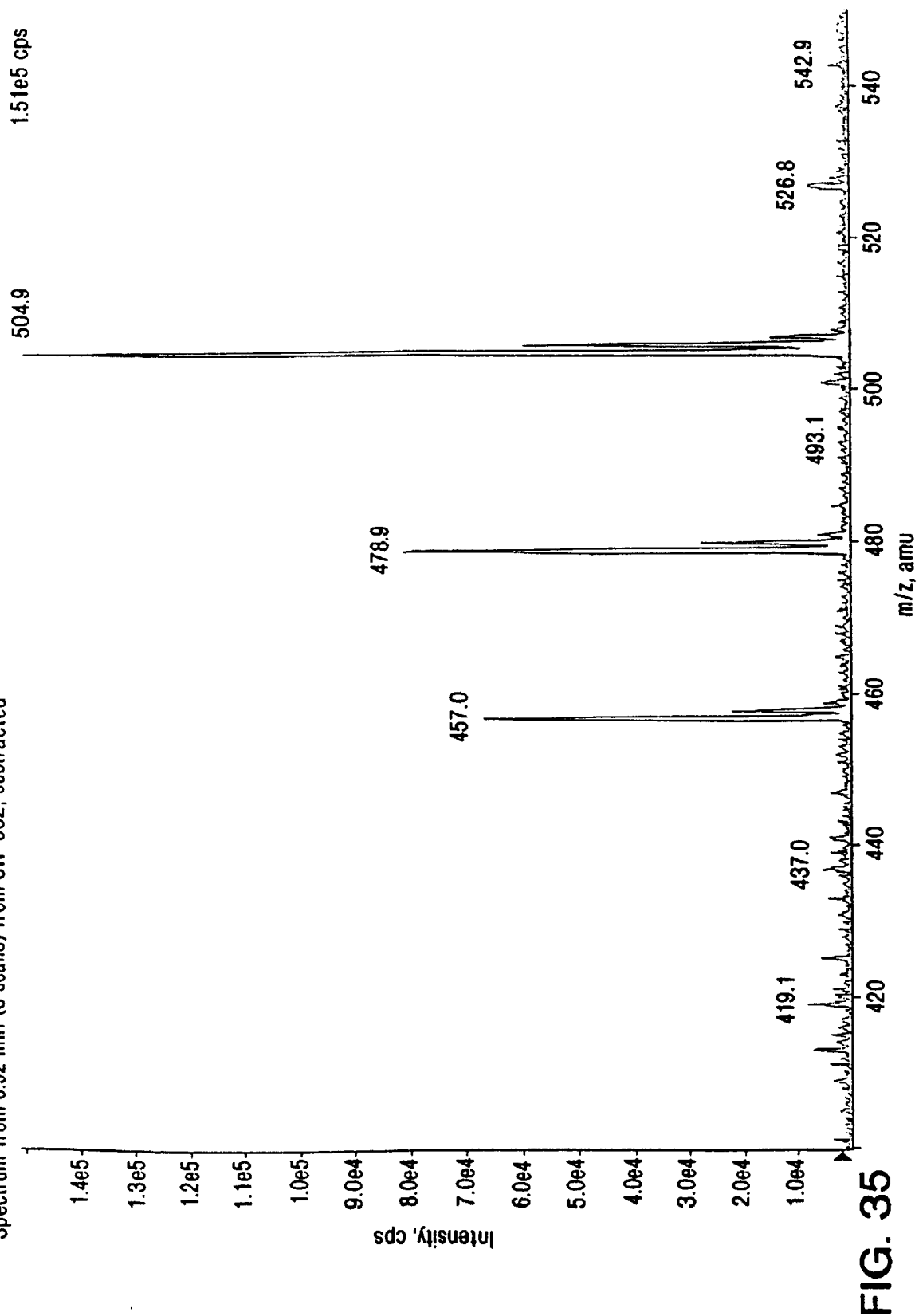
Figure 36:
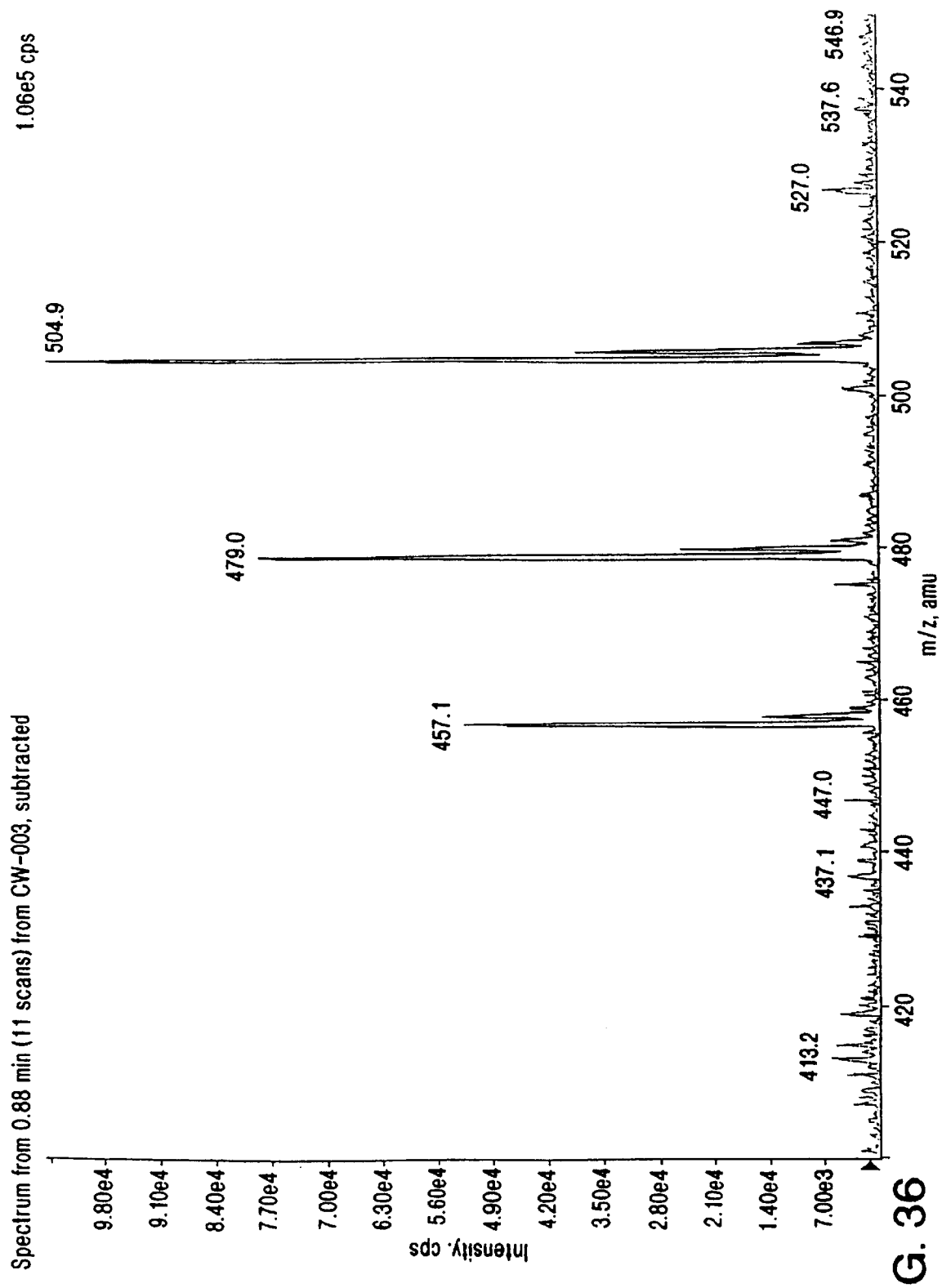
Figure 37:
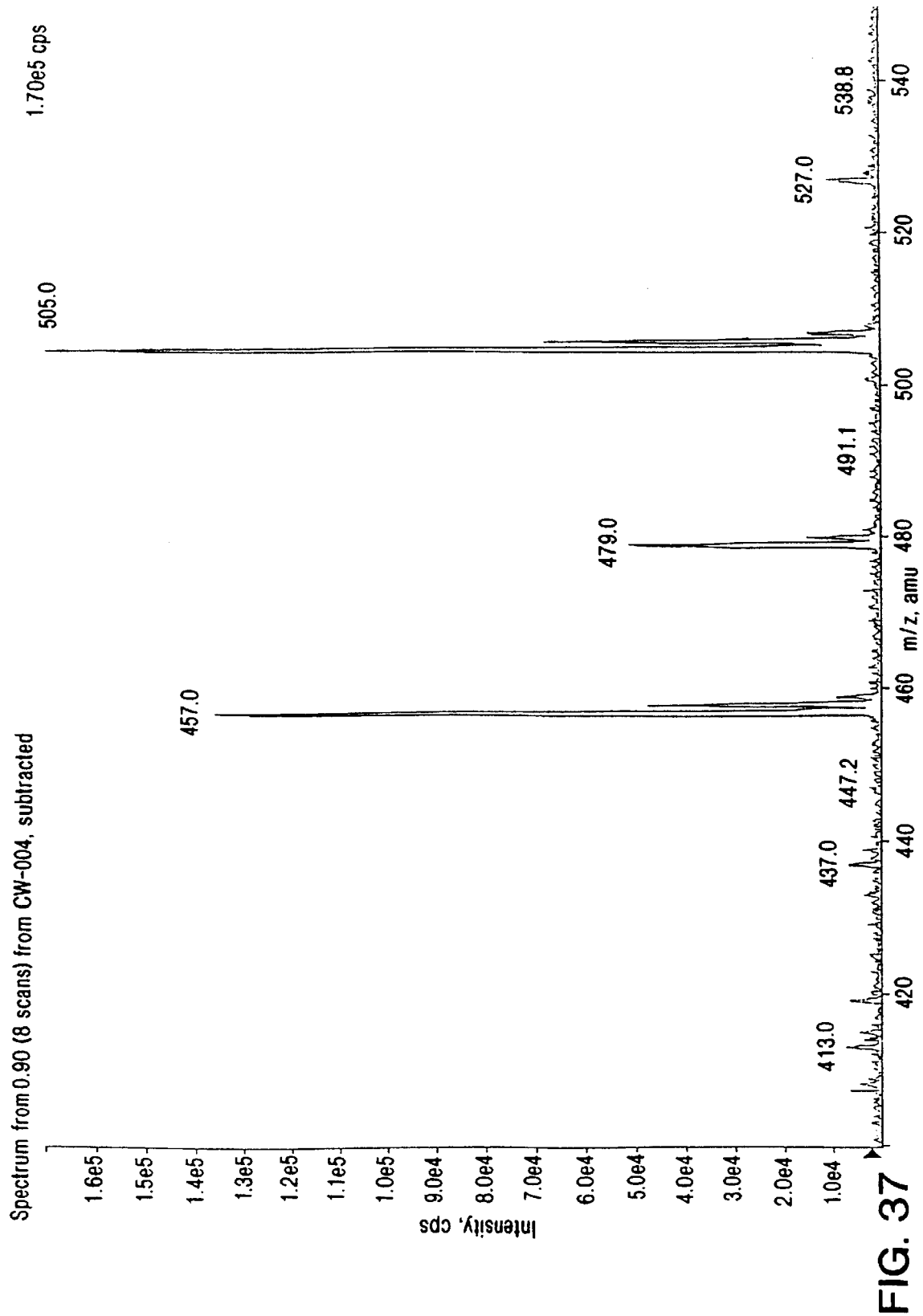
Figure 38:
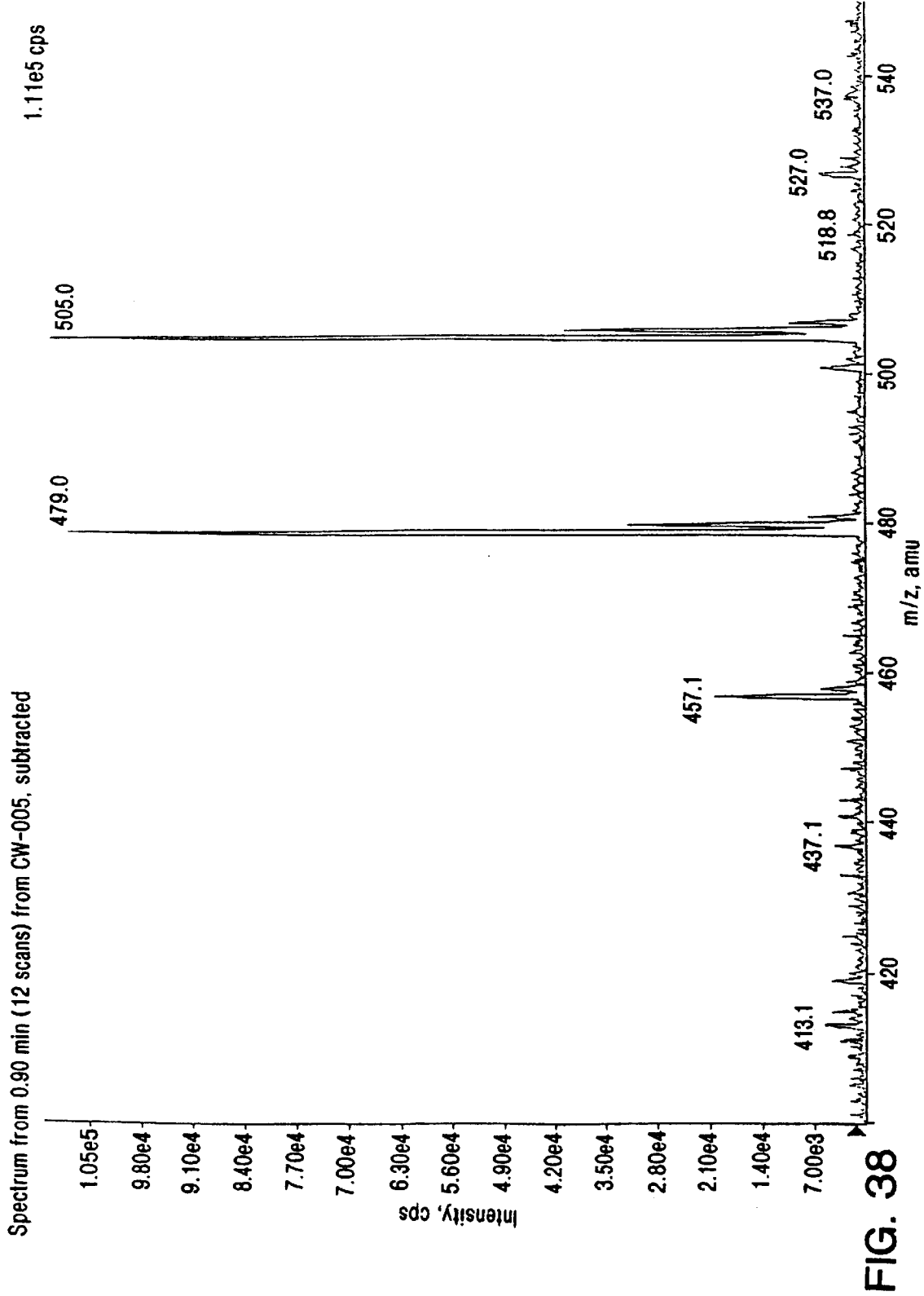
Figure 39:
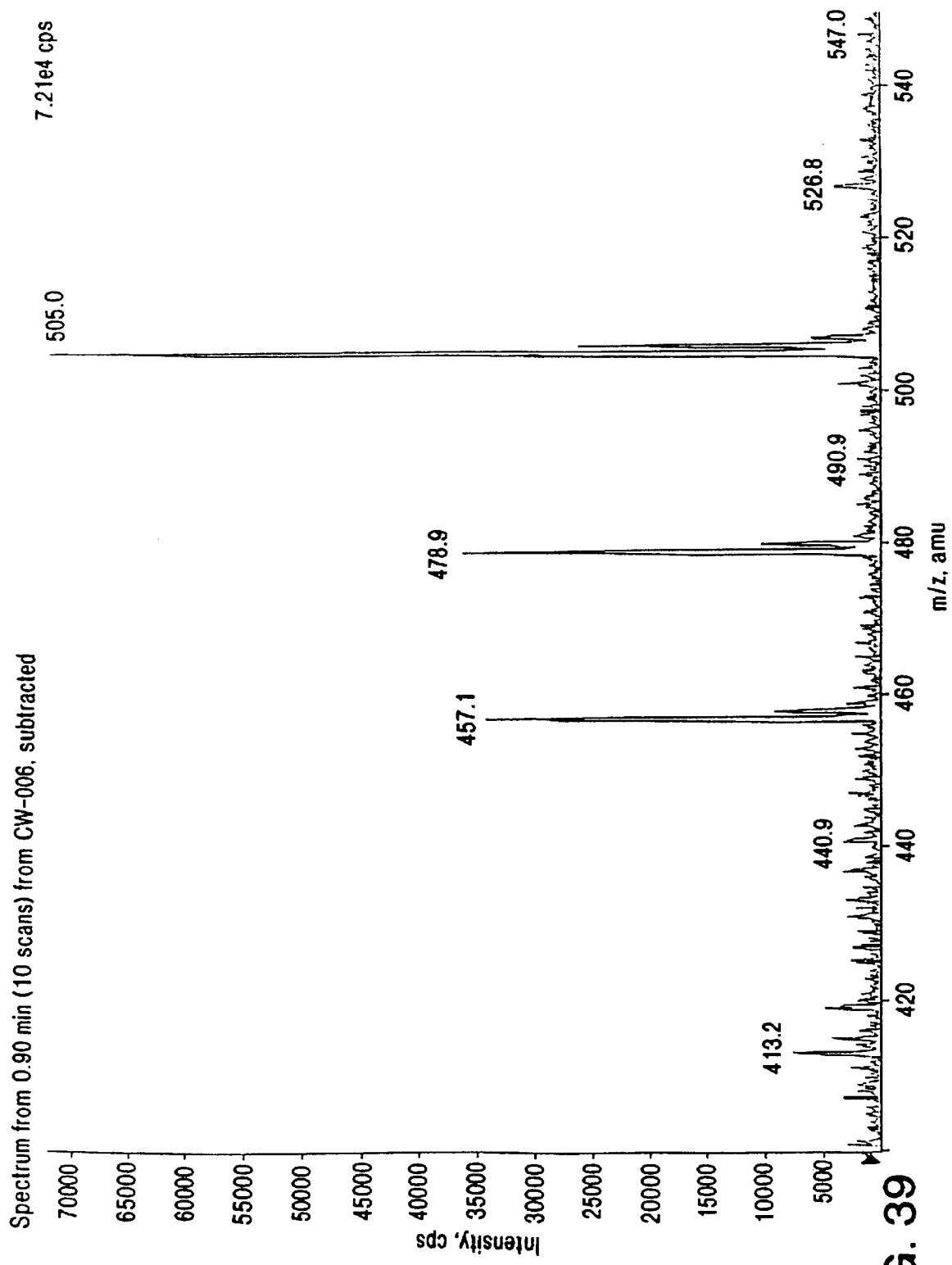
Figure 40:
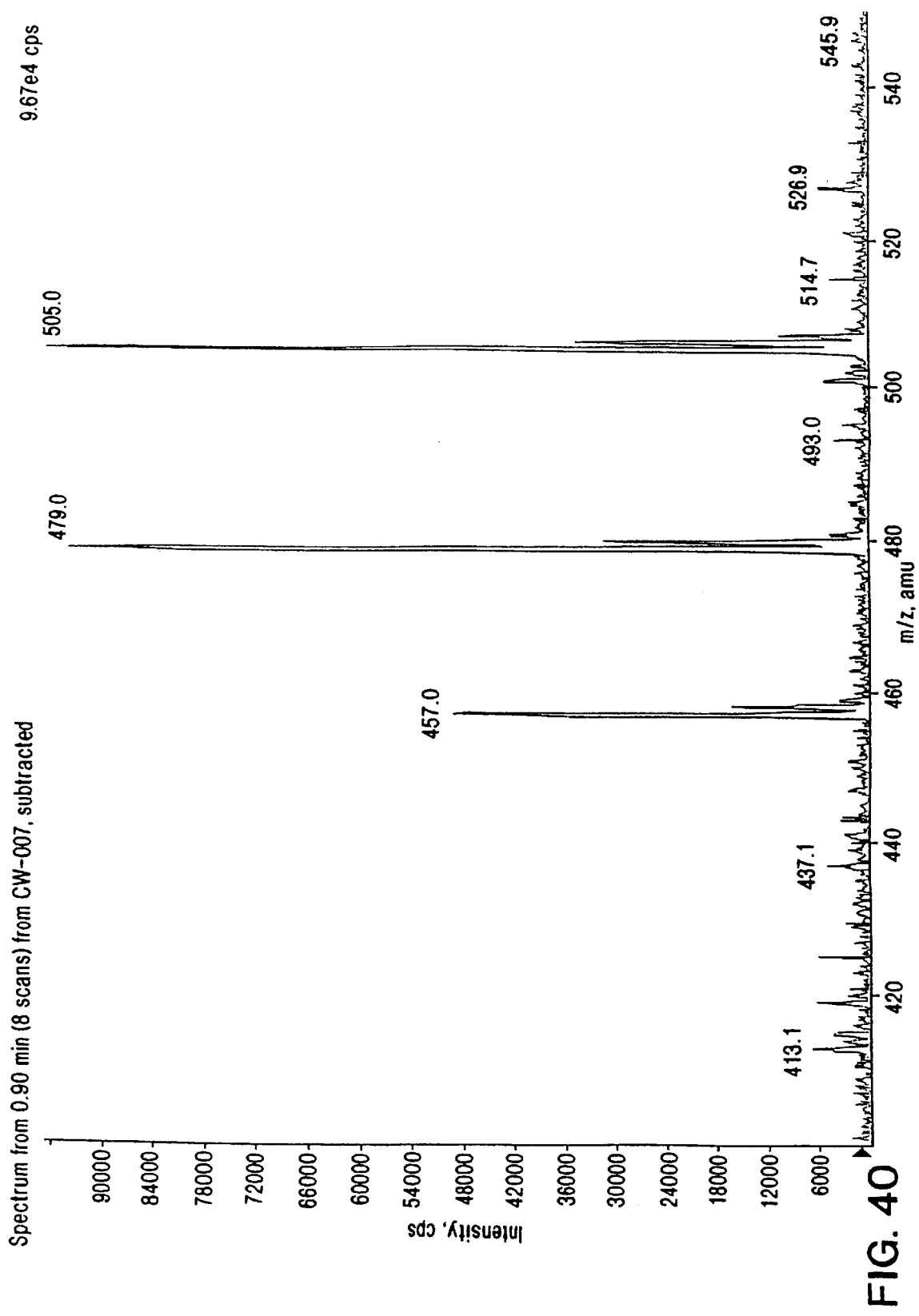
Figure 41:
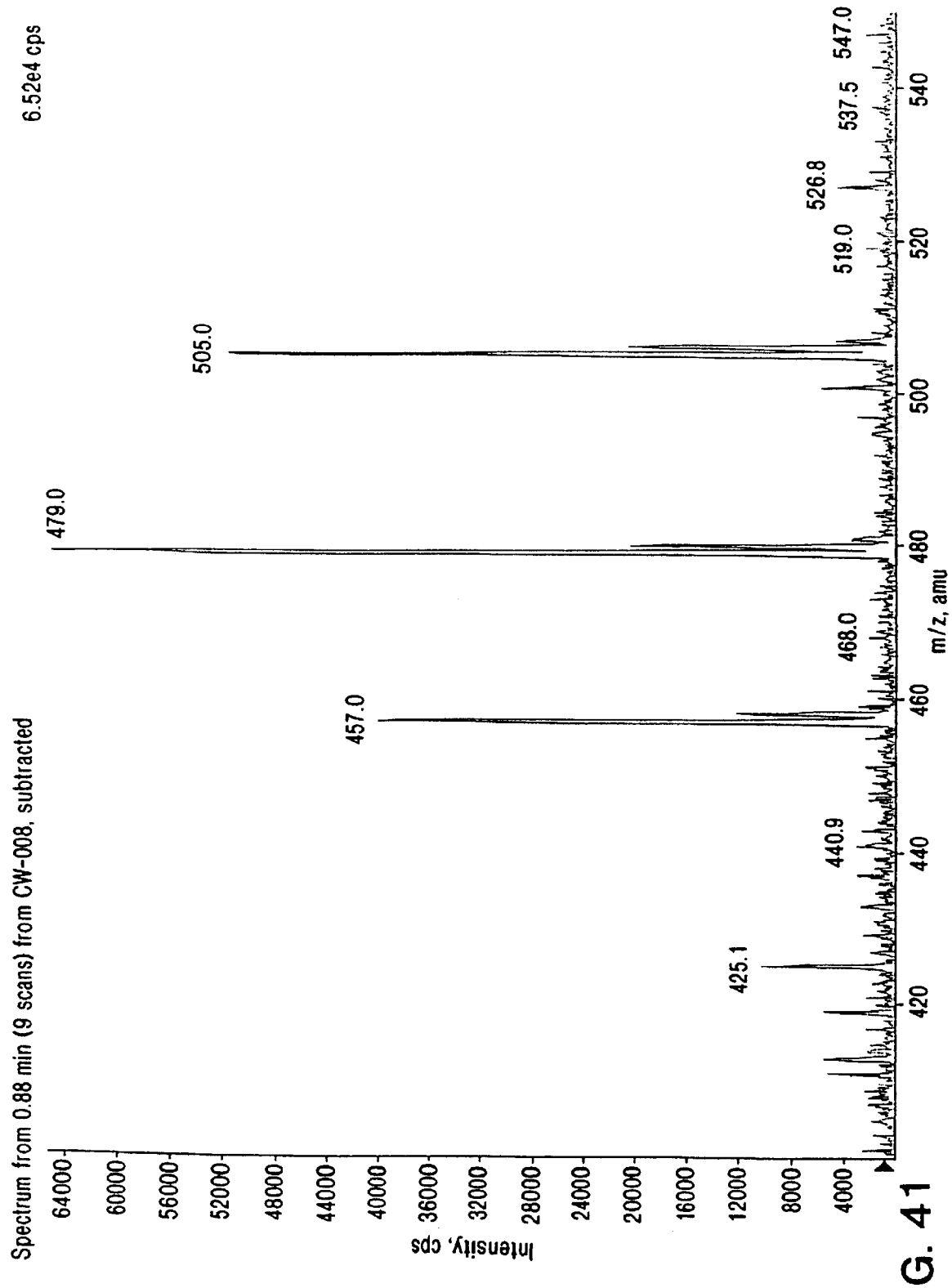
Figure 42:
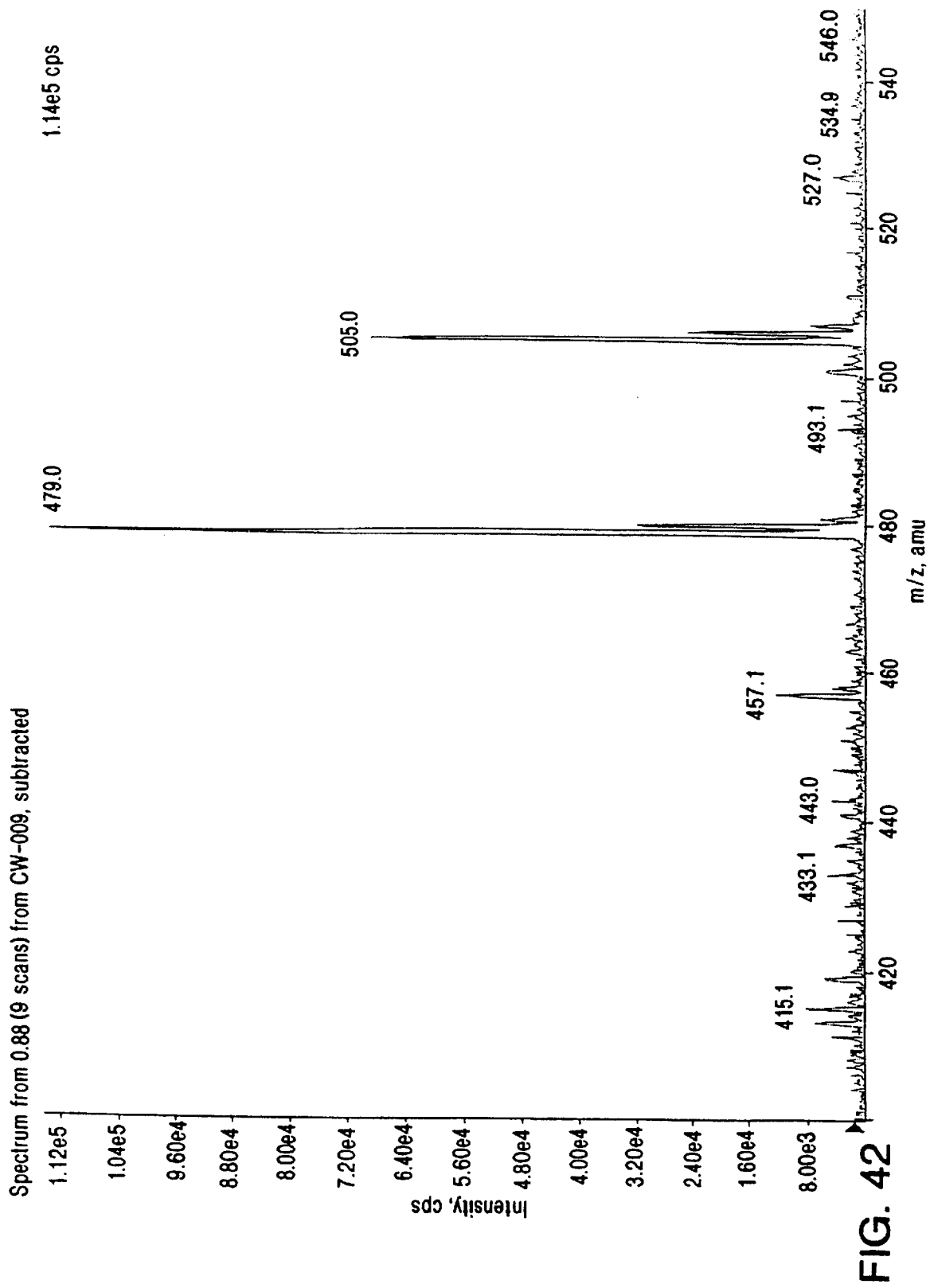
Figure 43:
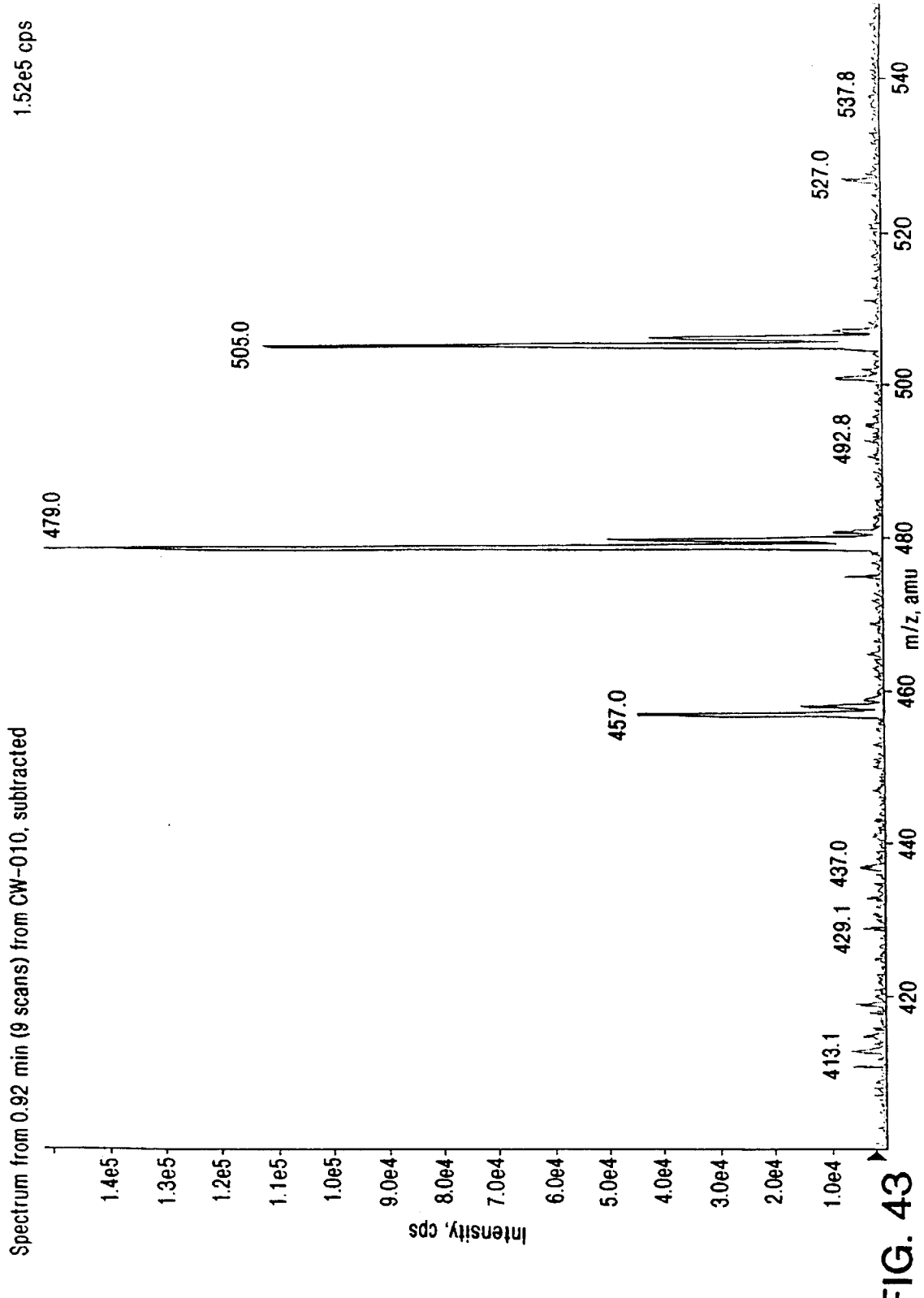
Figure 44:
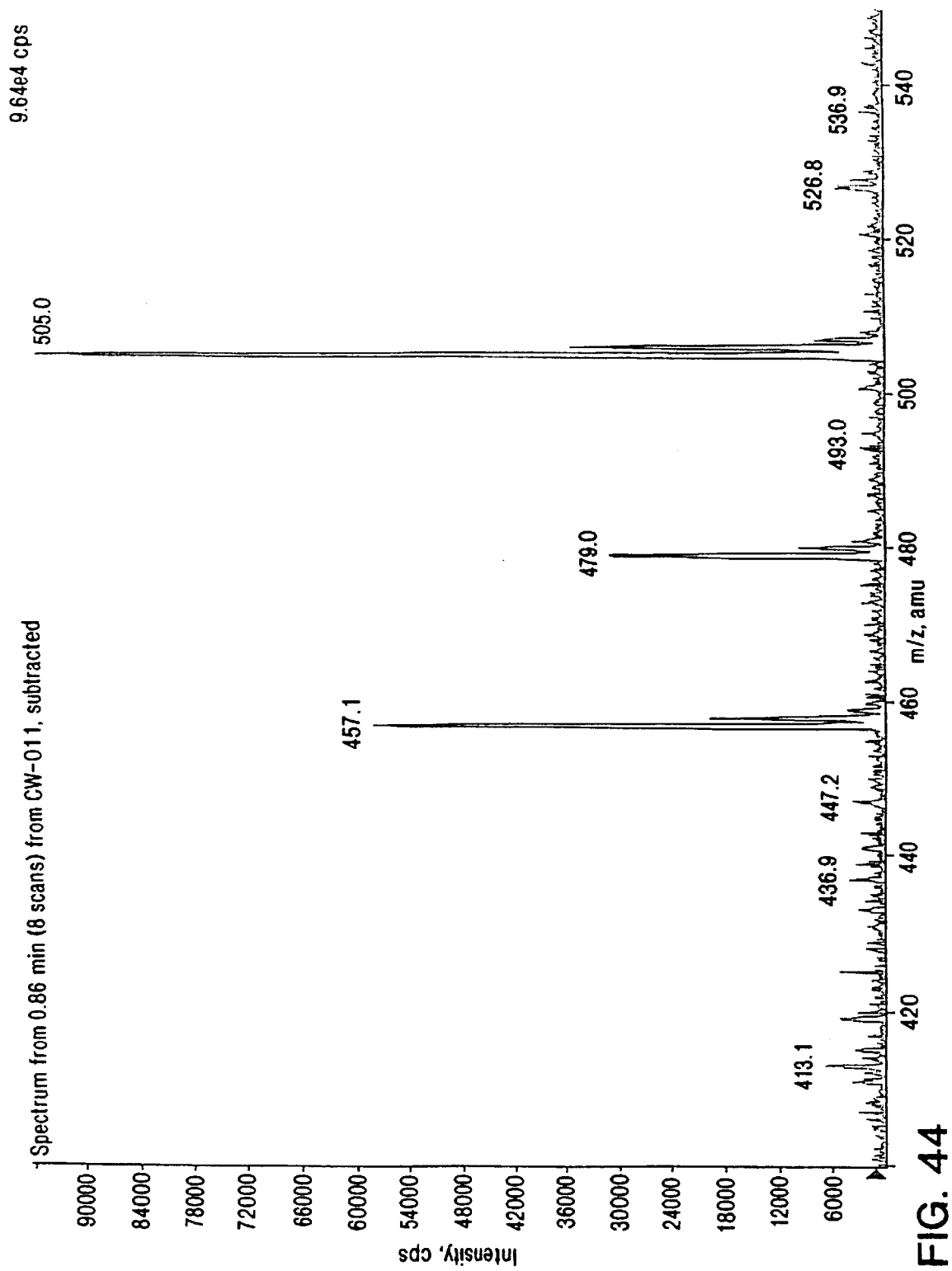
Figure 45:
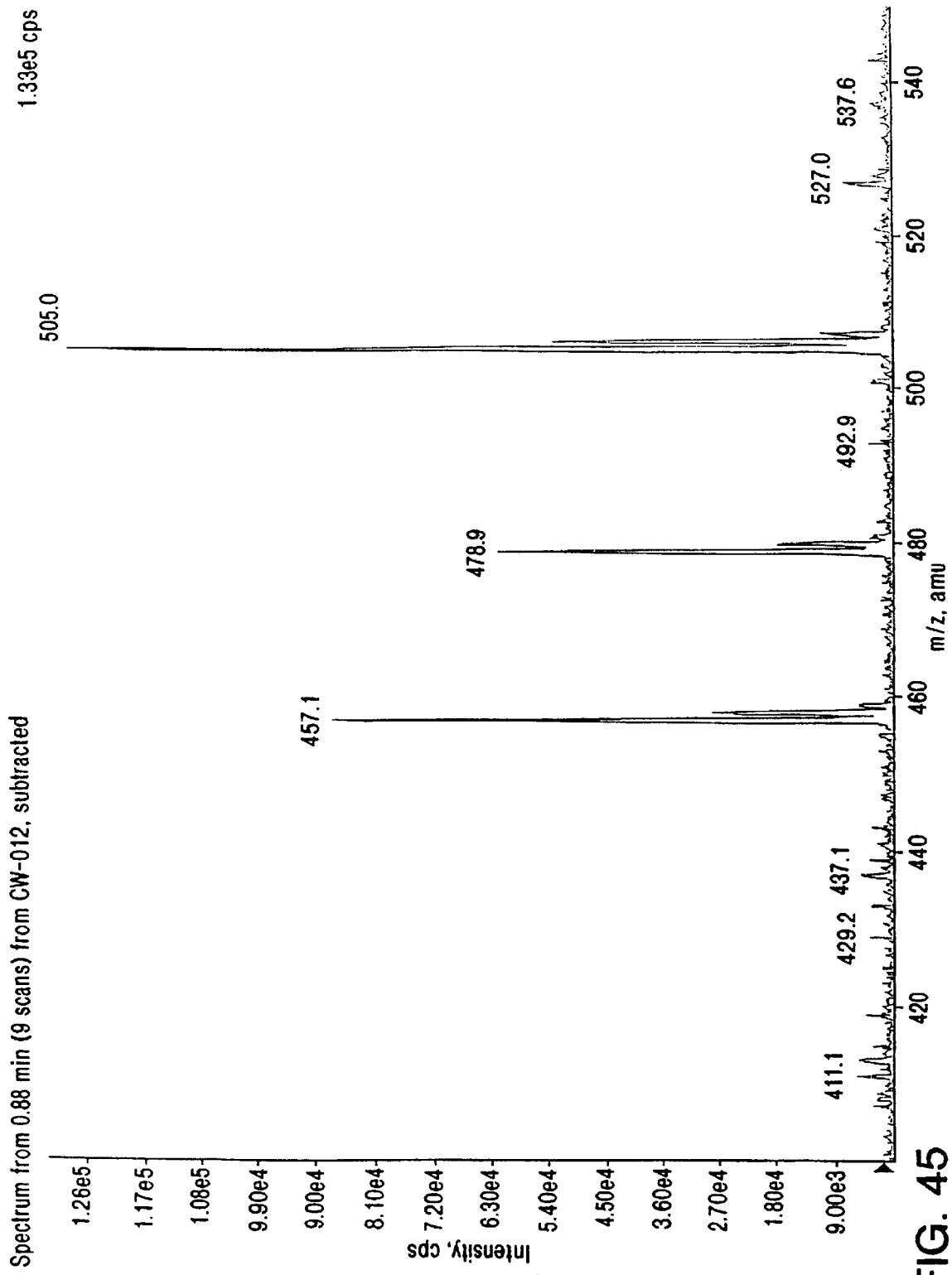
Figure 46:
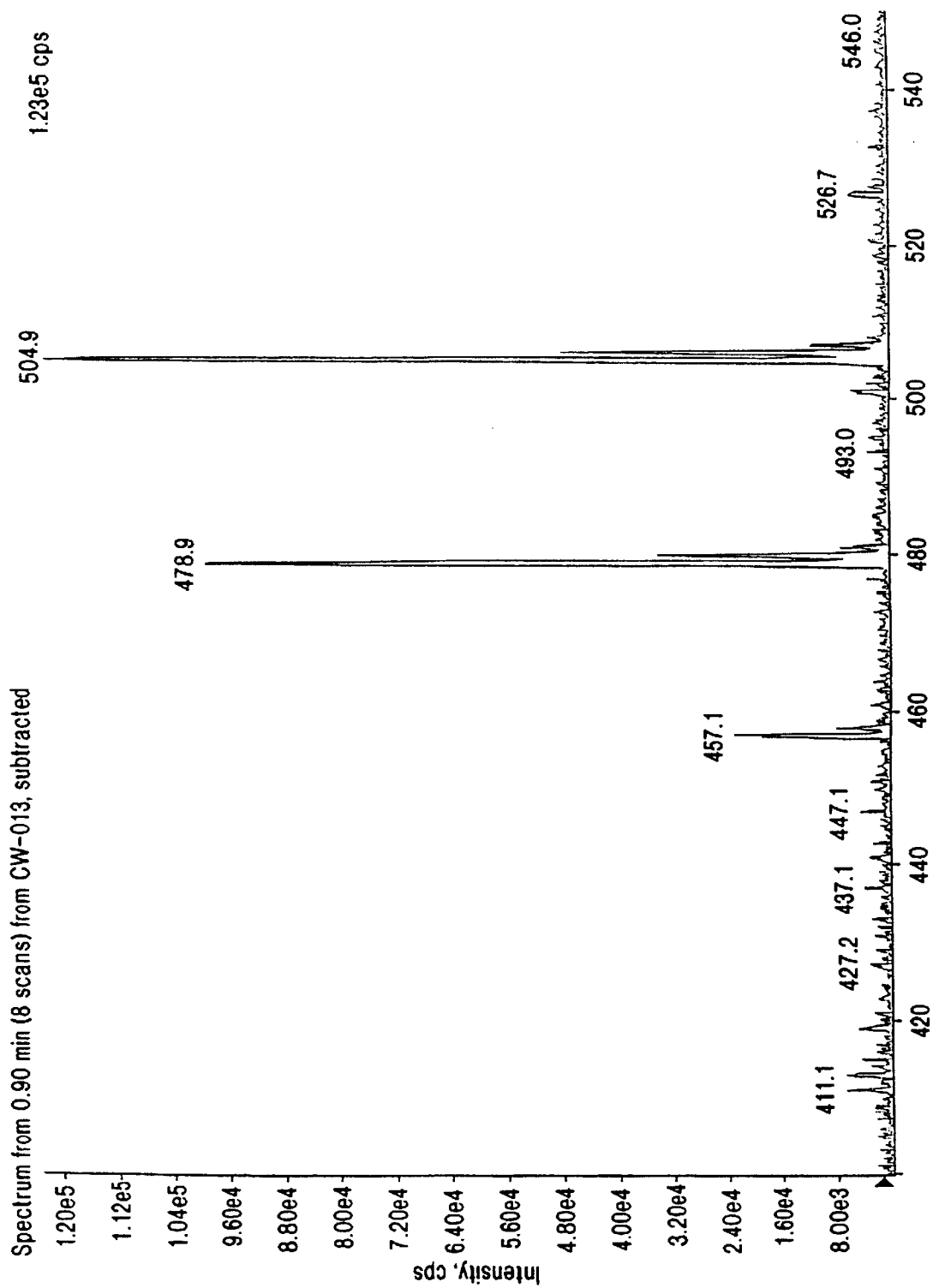
Figure 47:
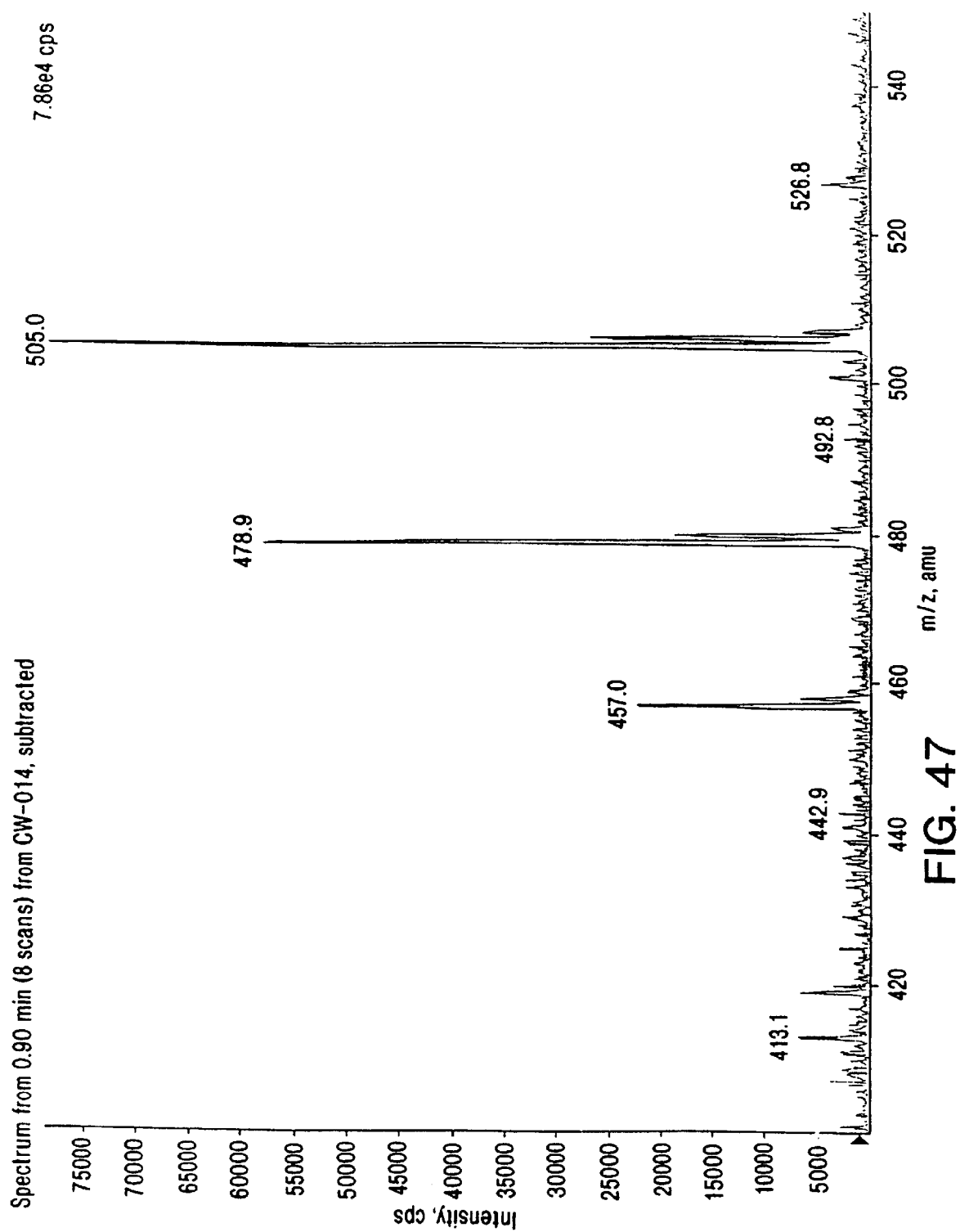
Figure 48:
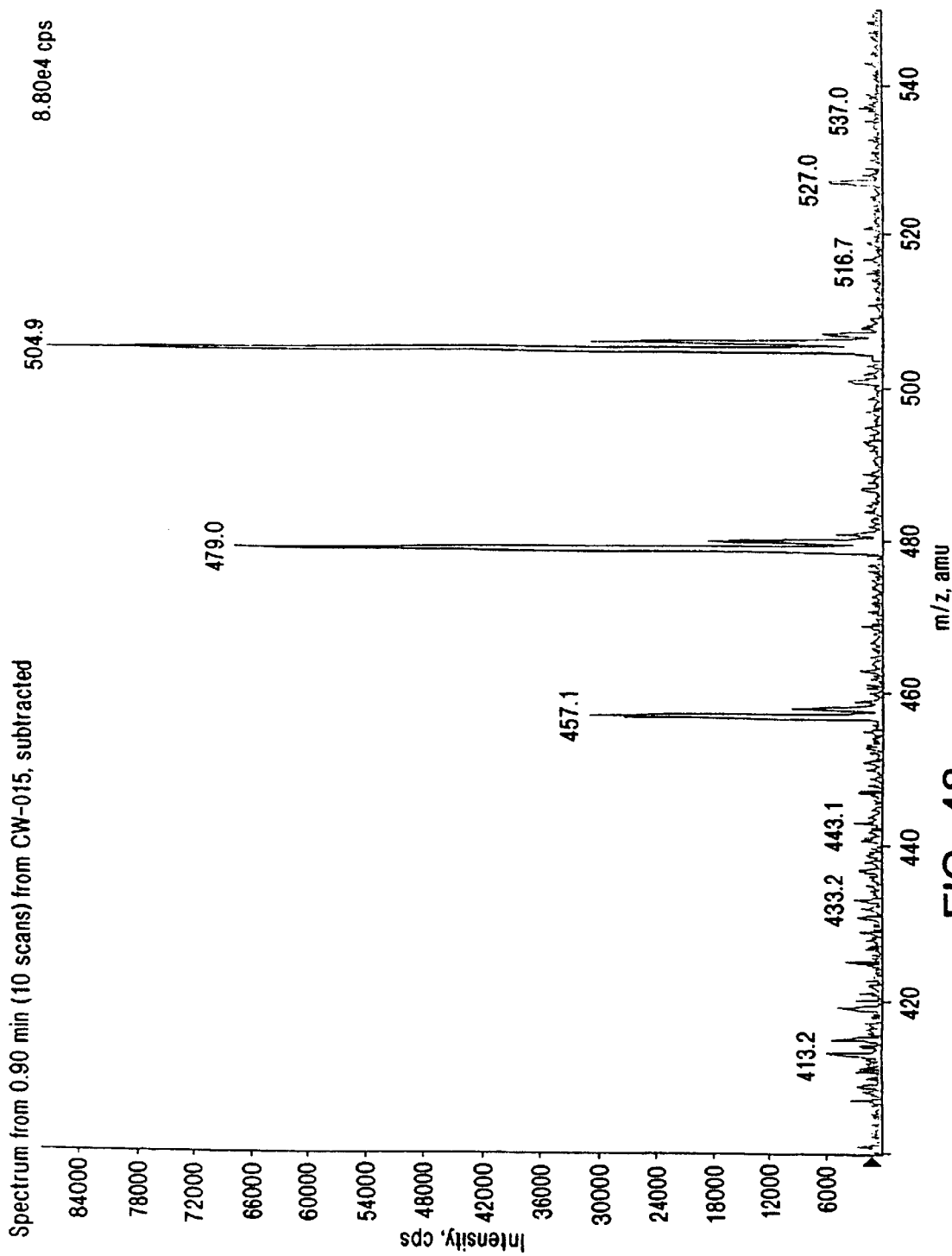
Figure 49:
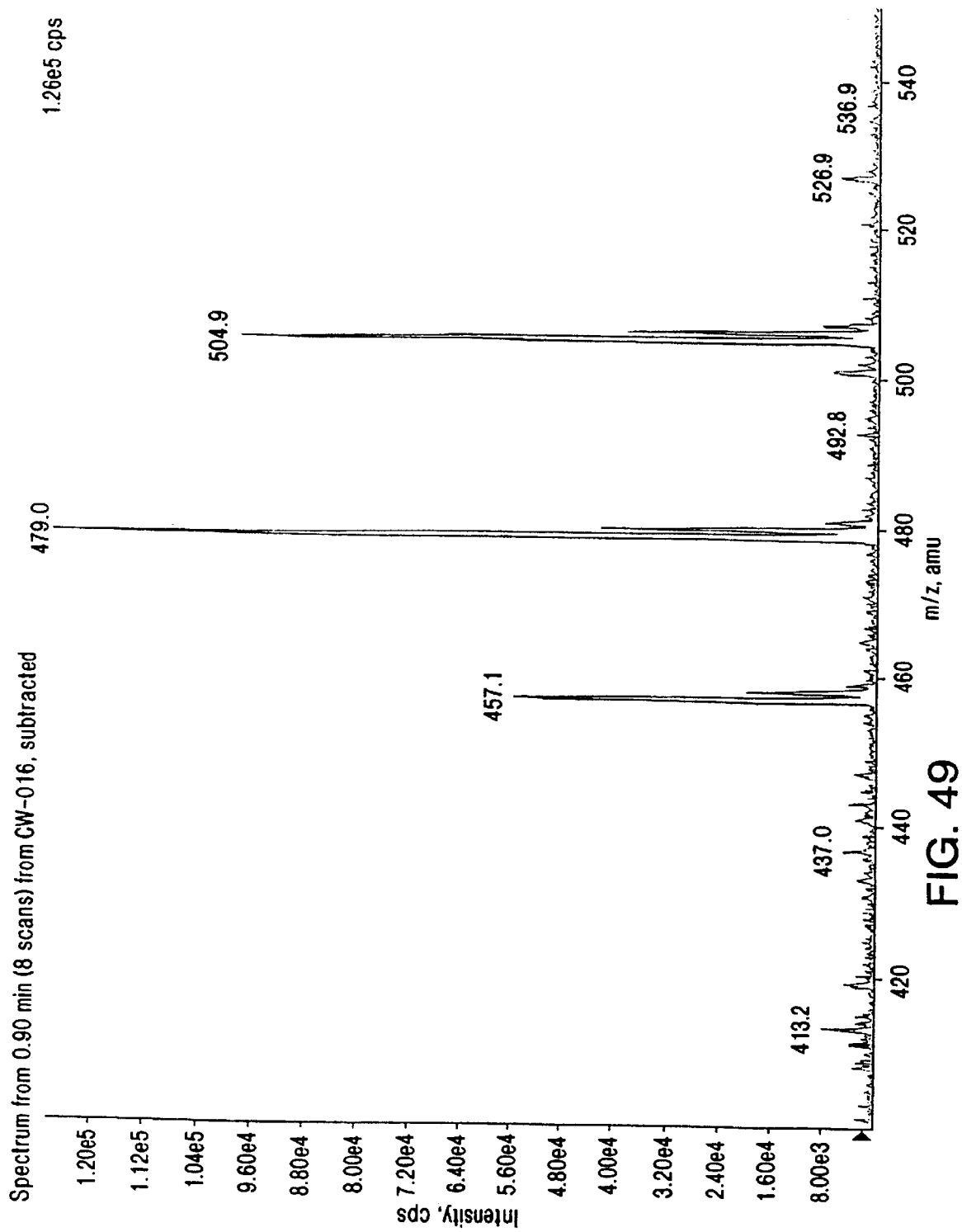
Figure 50:
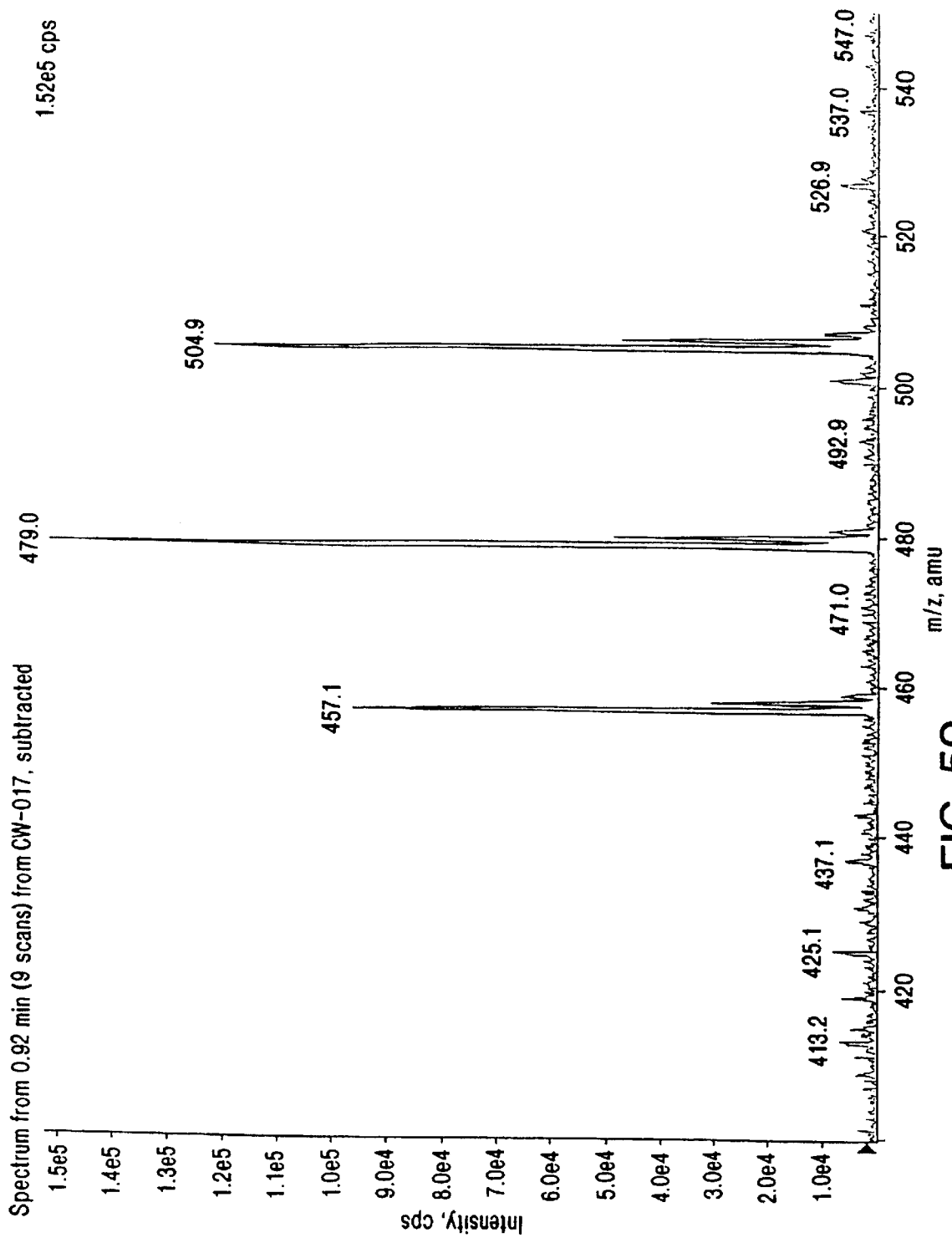
Figure 51:
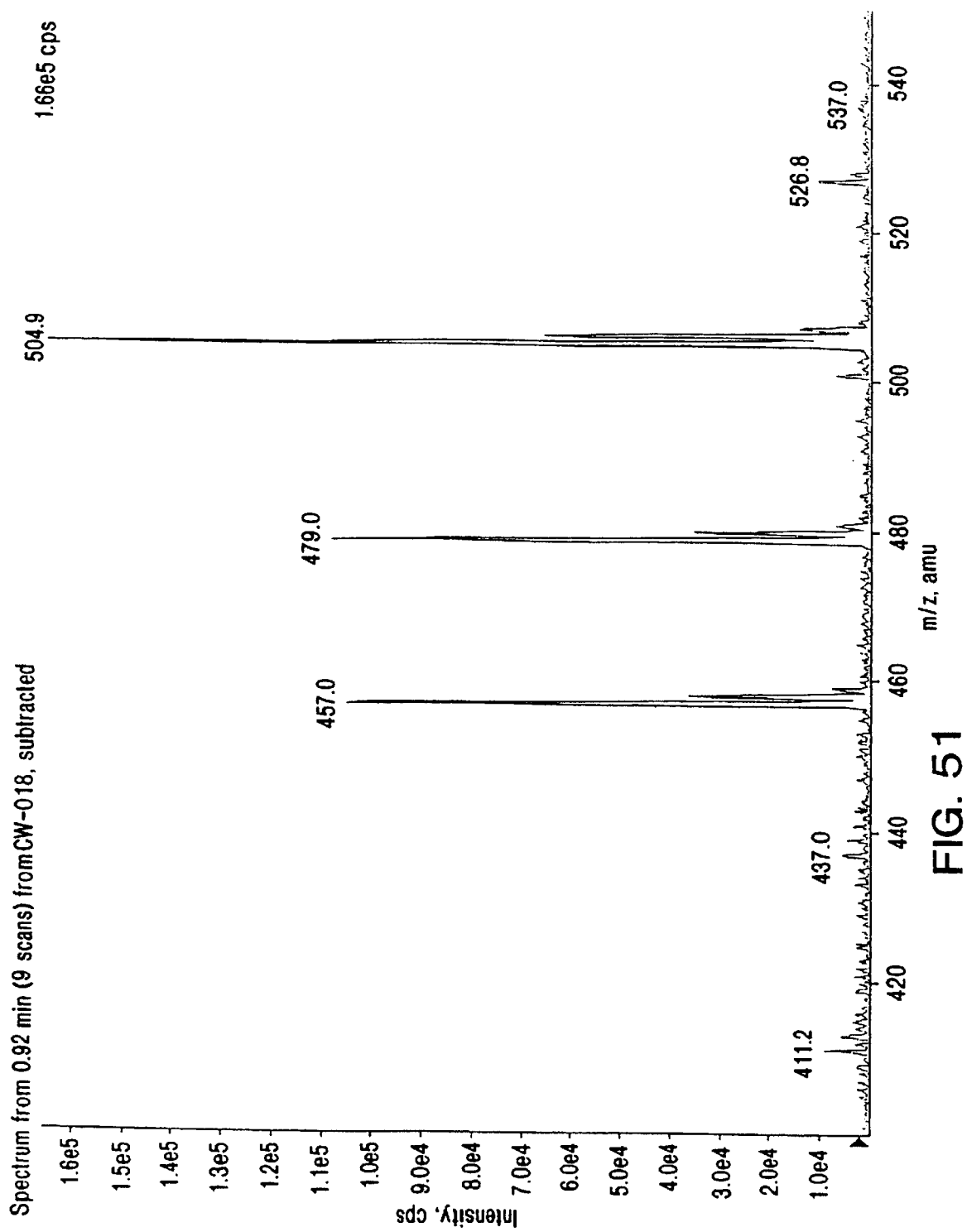

FIG. 9 is a chart that correlates the observed ratio of $C^{13}$ to $C^{12}$ in the NMR spectra of FIGS. 5 through 8 with the % of $C^{13}$ present in each.

FIGS. 10 through 12 show spectra observed in conjunction with the Example 23 procedure on the Reaction Screening embodiment of the invention.

FIGS. 13 through 17 show synthesis flow diagrams used in the Example 23 disclosure on the Reaction Screening embodiment of the invention.

FIGS. 18 through 51 show spectra observed in conjunction with the Example 24 disclosure of the Ratio Coding embodiment of the invention.

Figure 52:
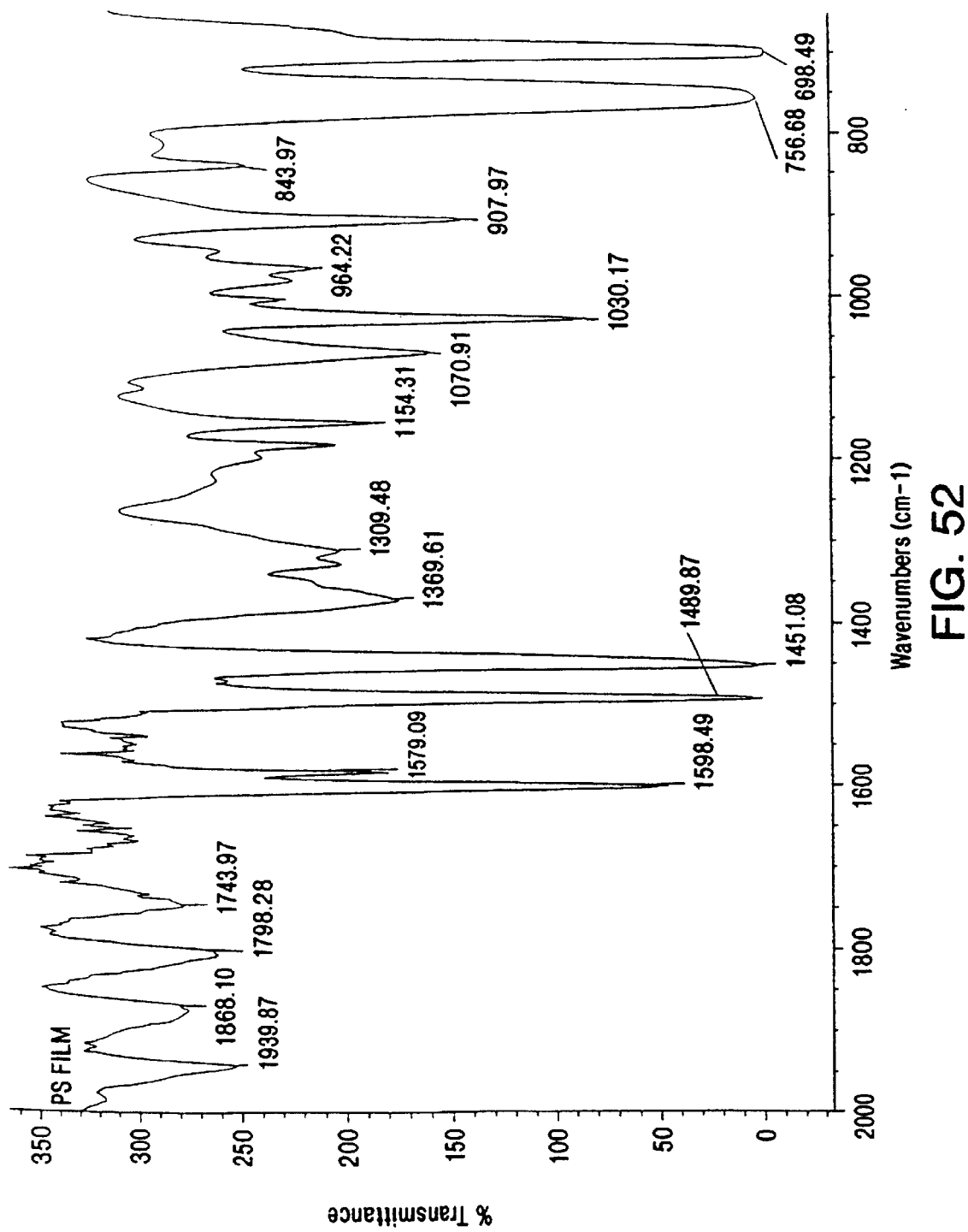
Figure 53:
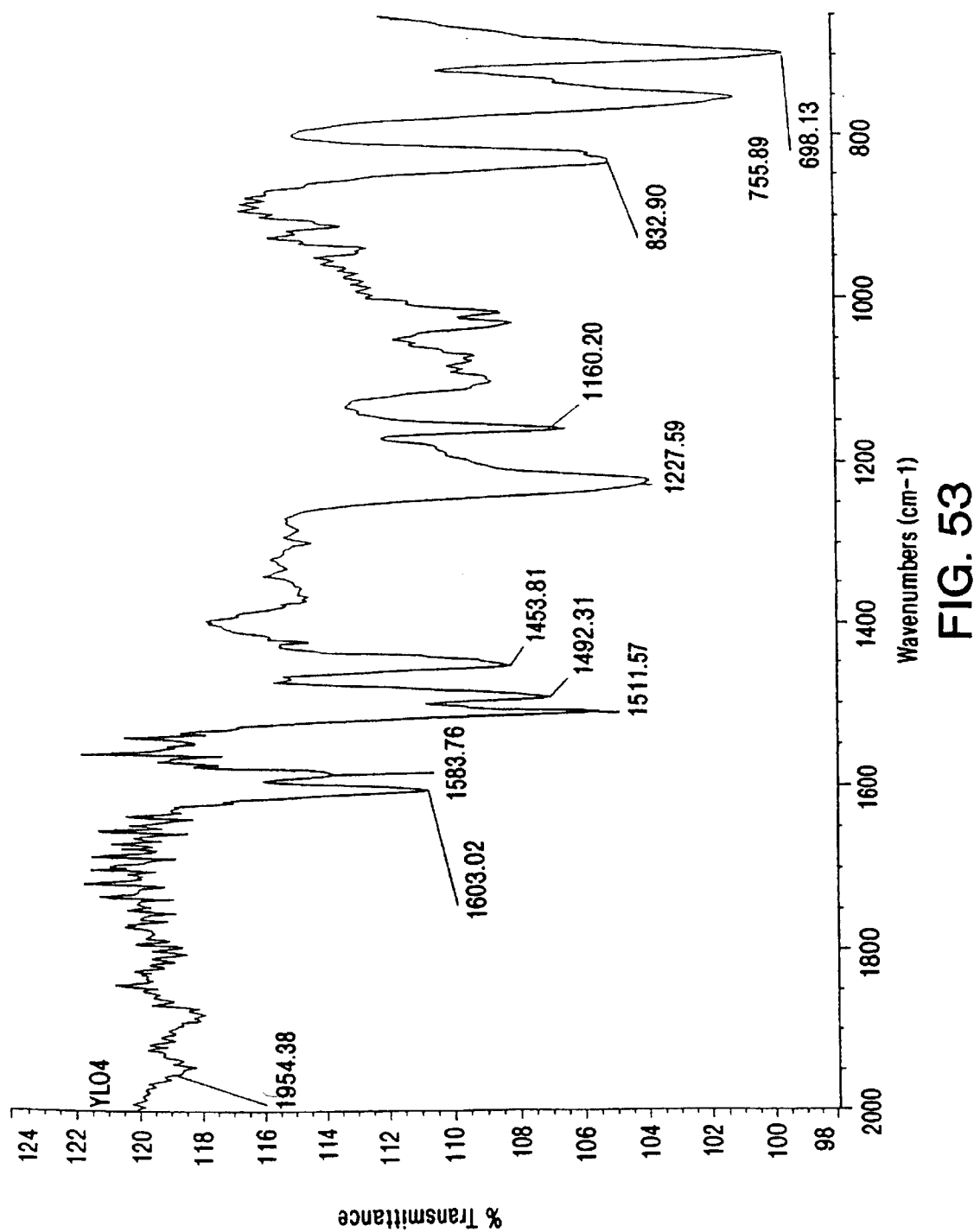
Figure 54:
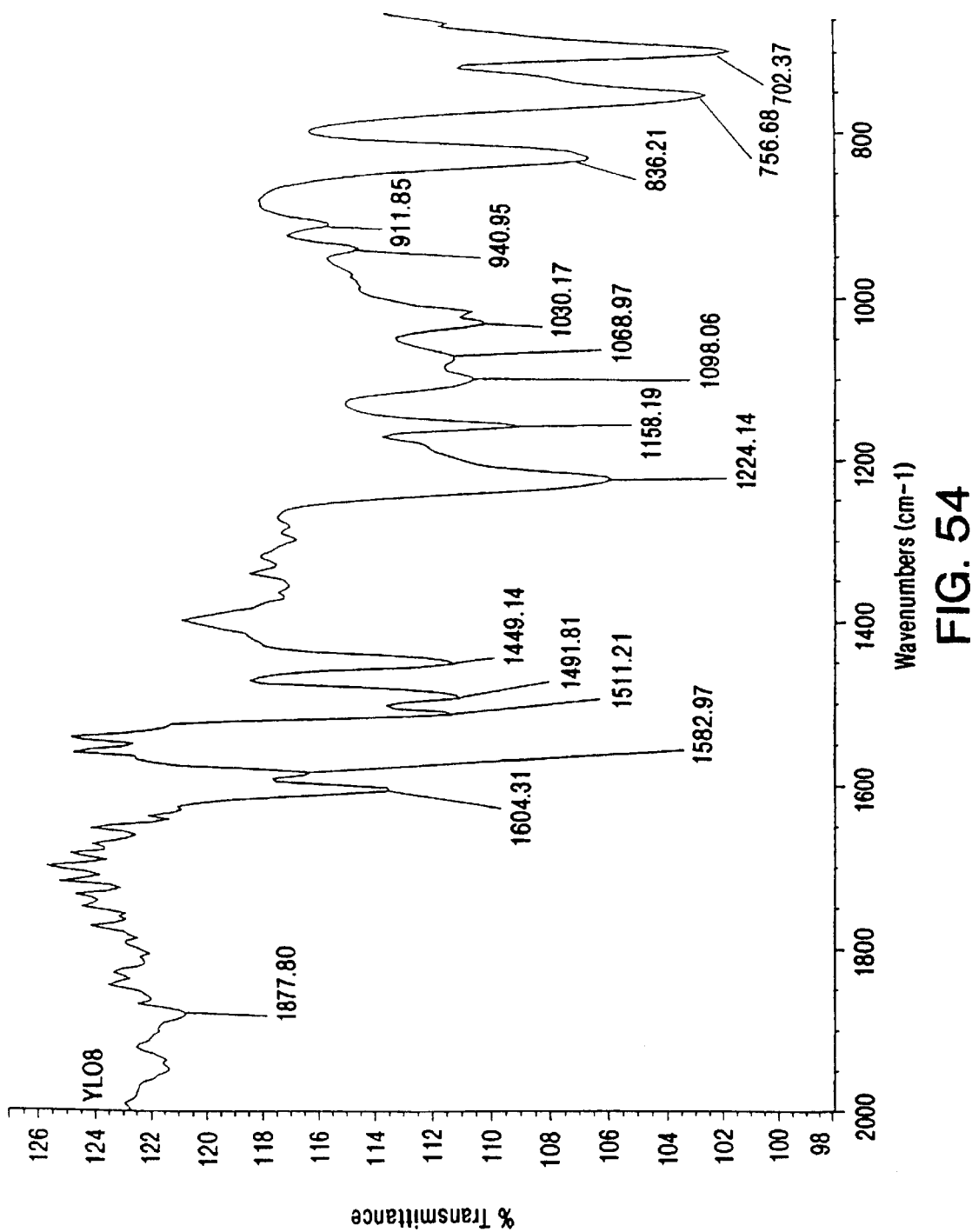
Figure 55:
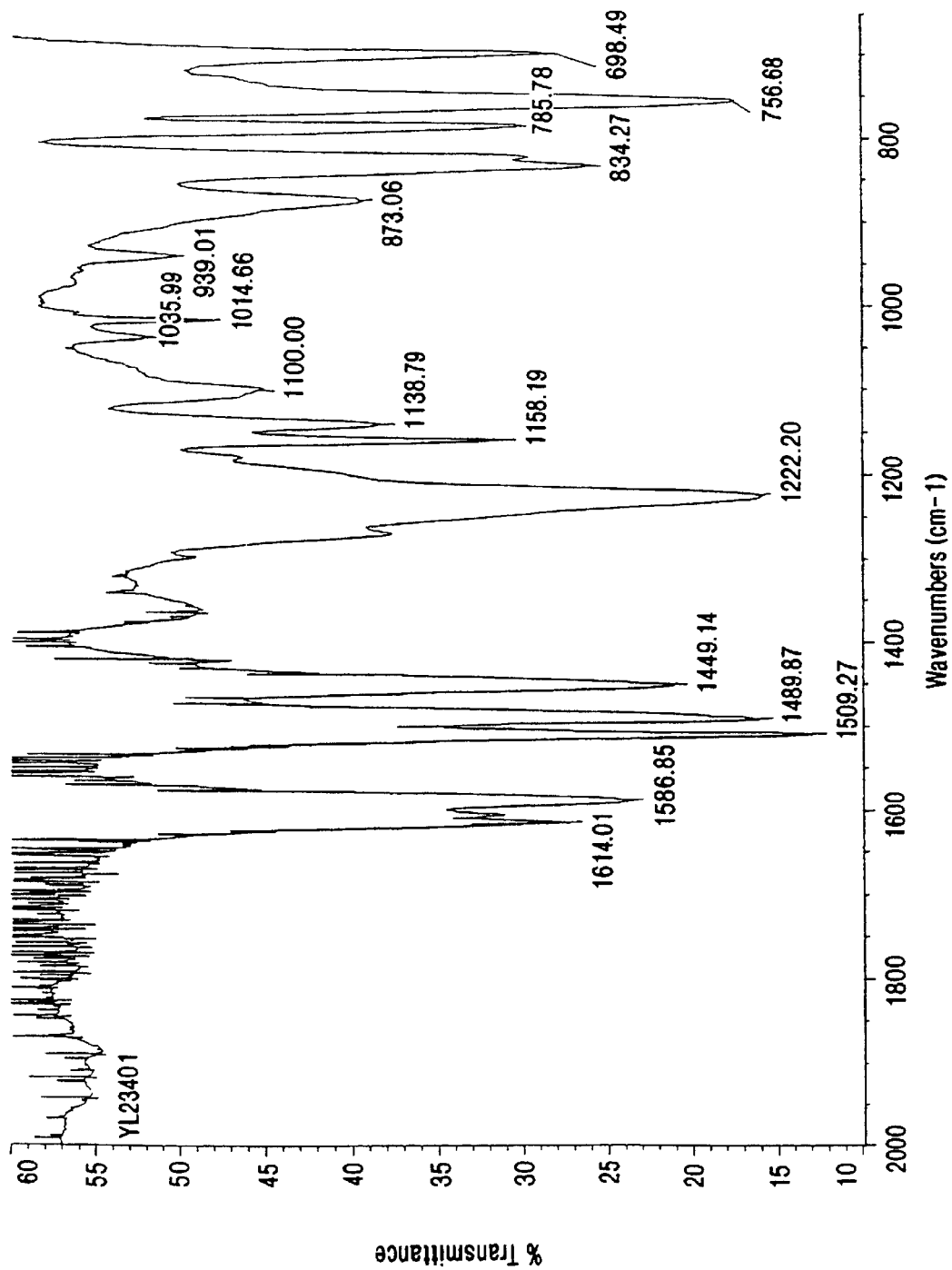
Figure 56:
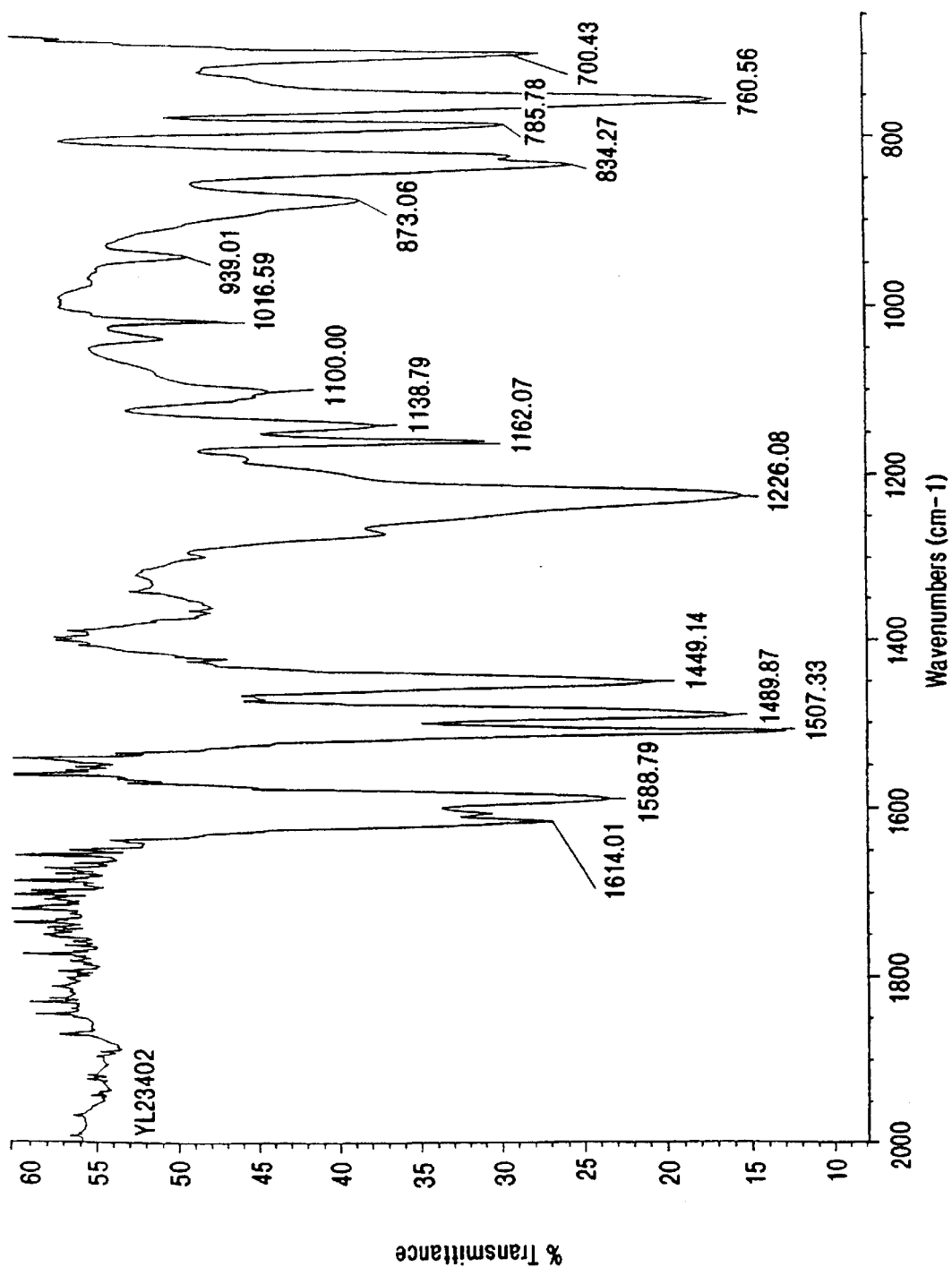
Figure 57:
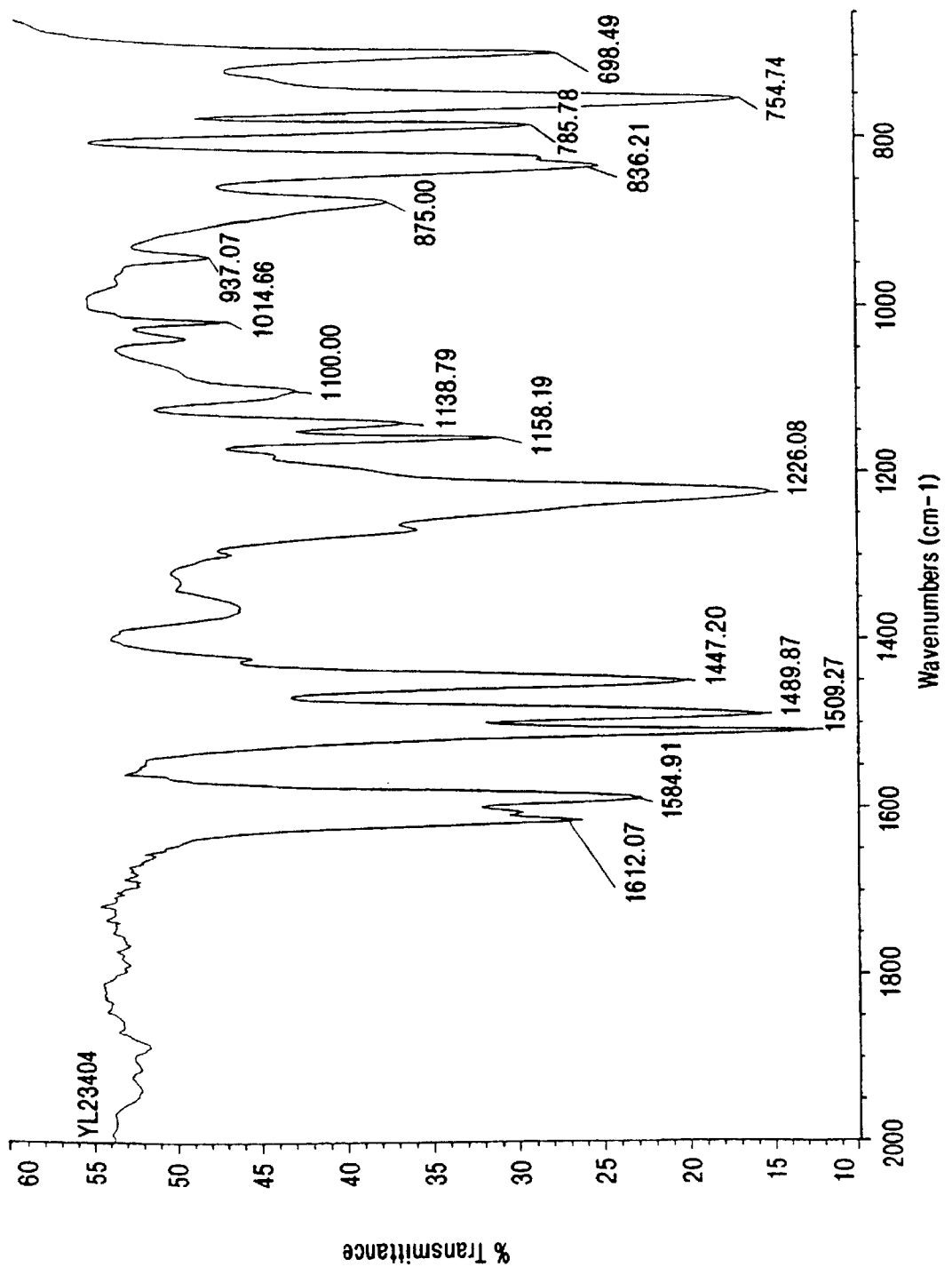
Figure 58:
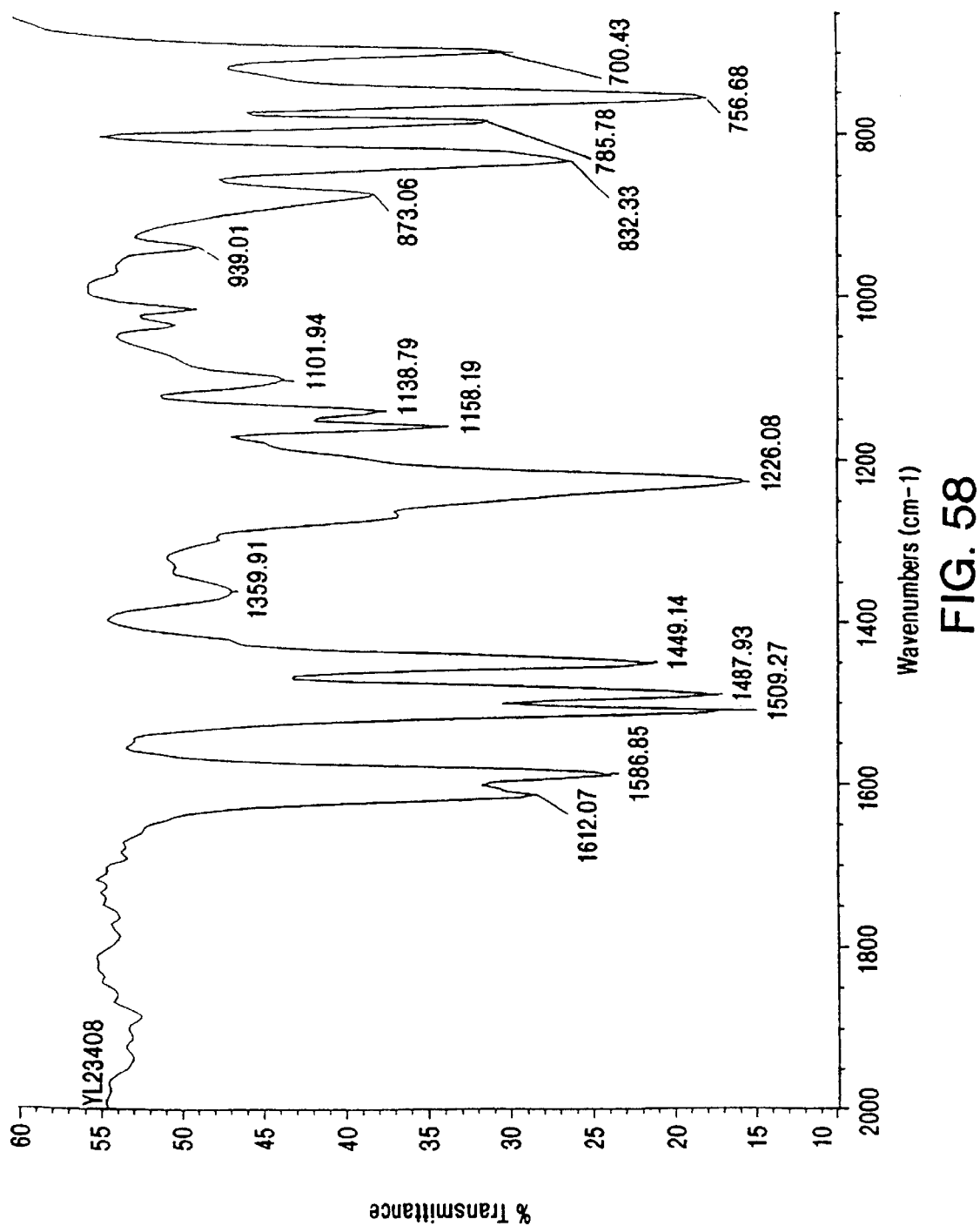
Figure 59:
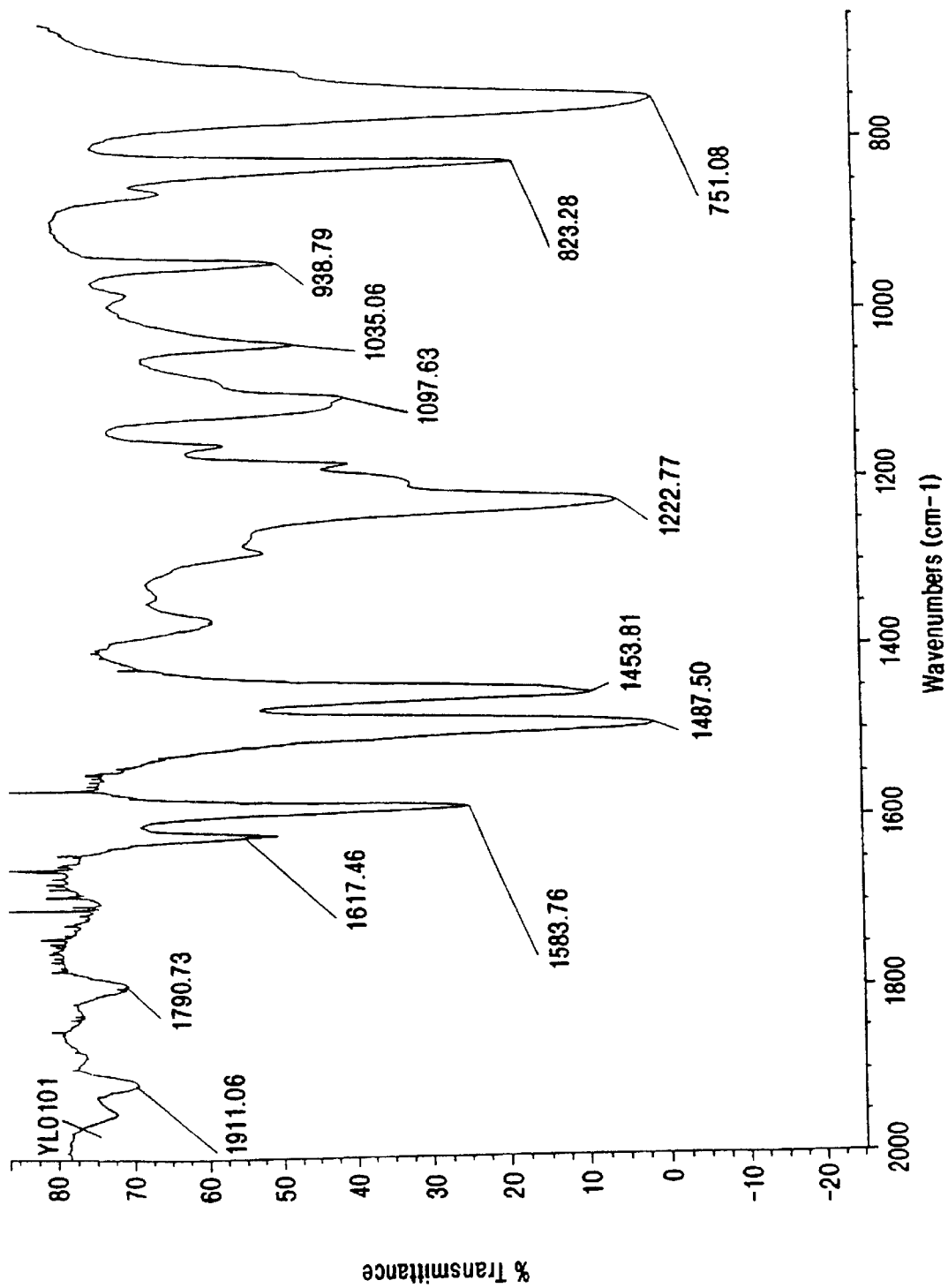
Figure 60:
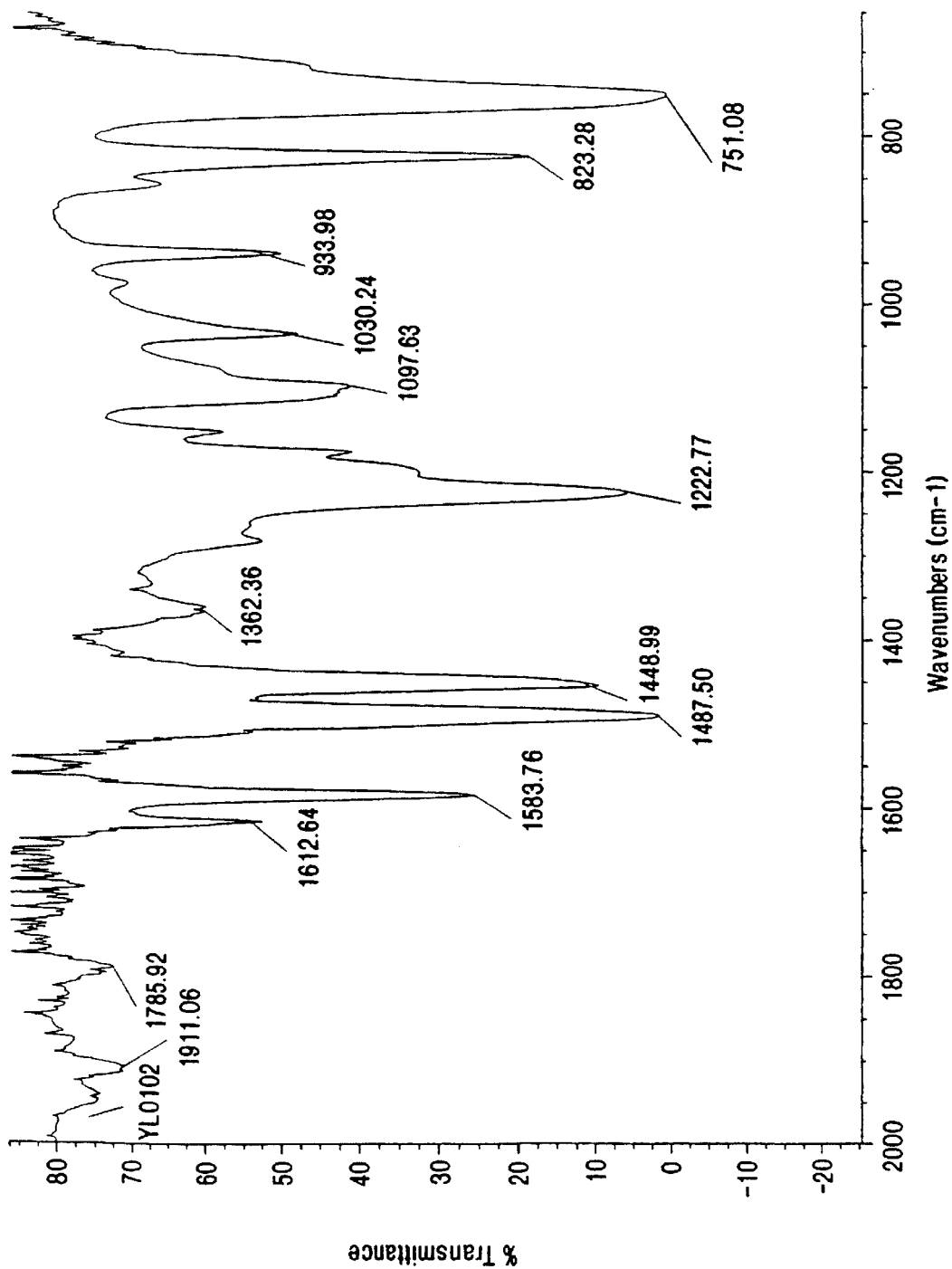
Figure 61:
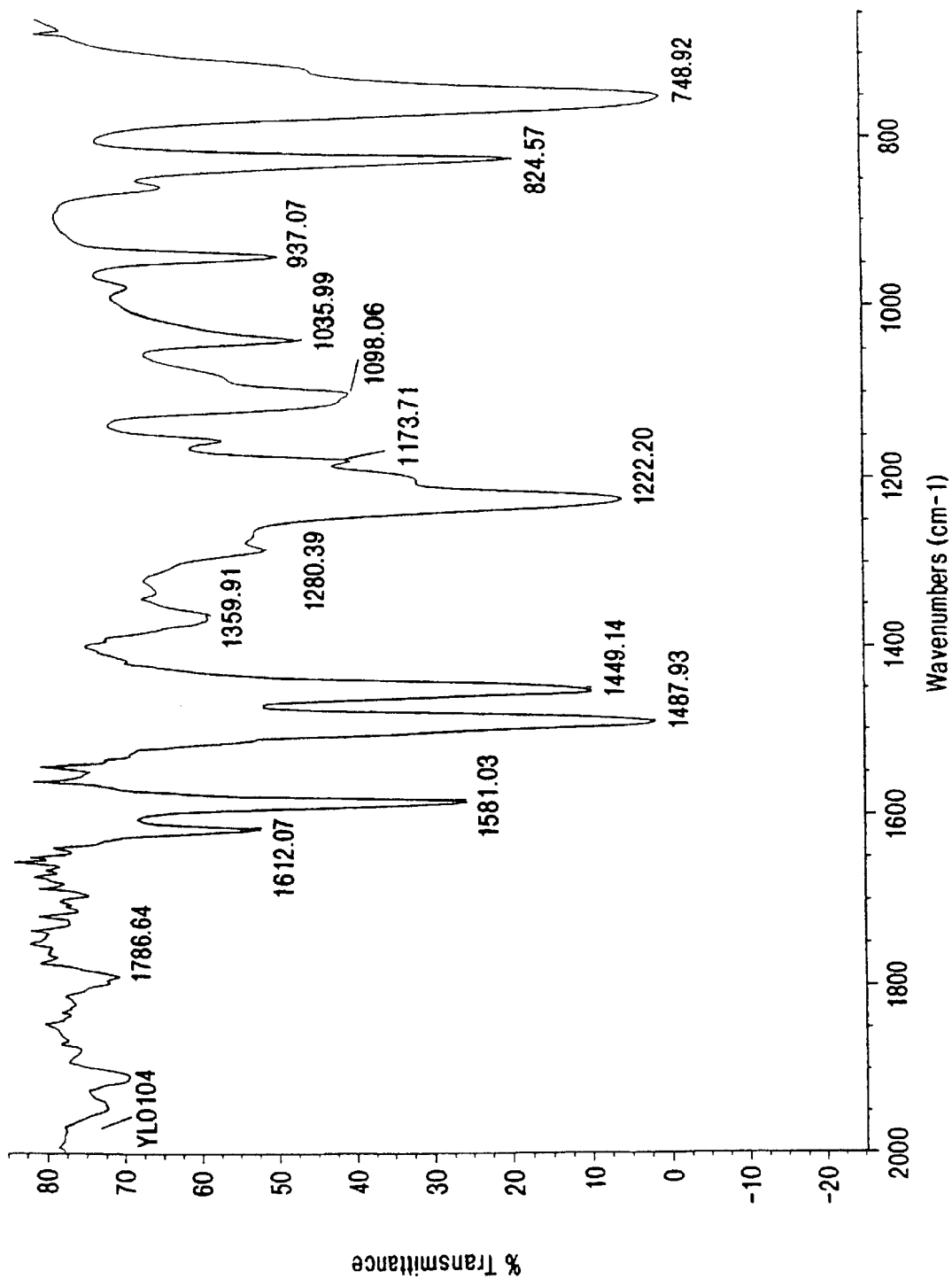
Figure 62:
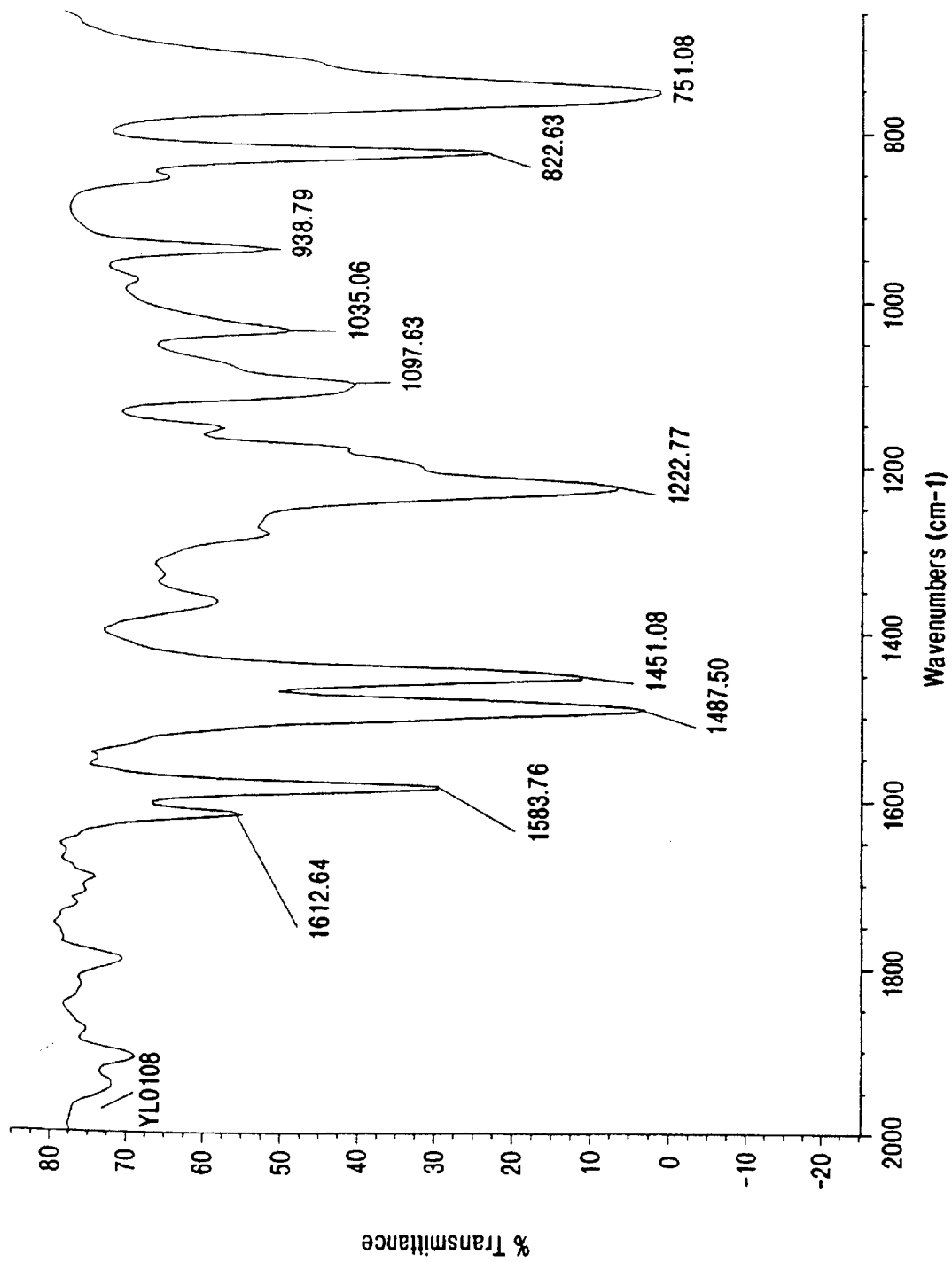
Figure 63:
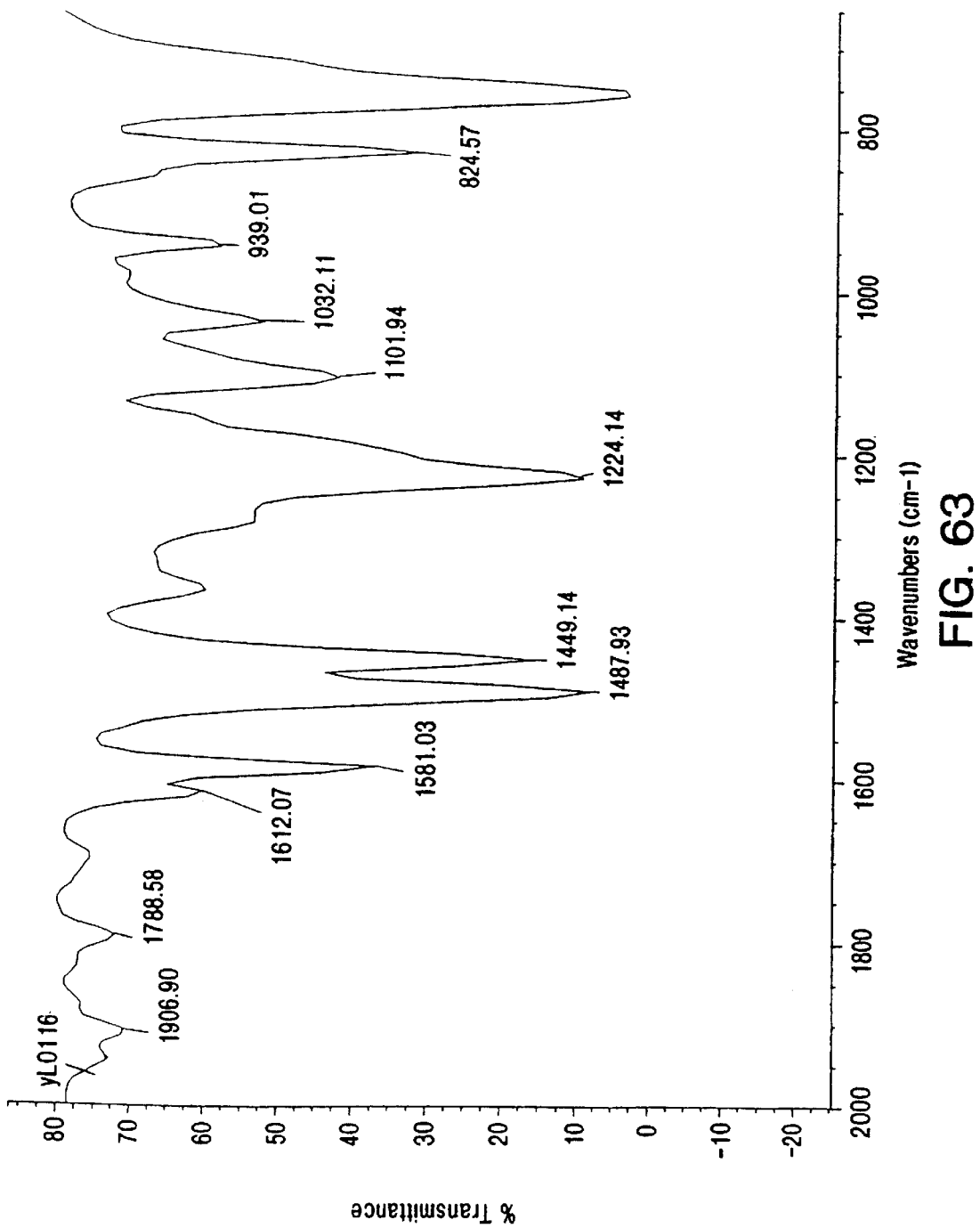
Figure 64:
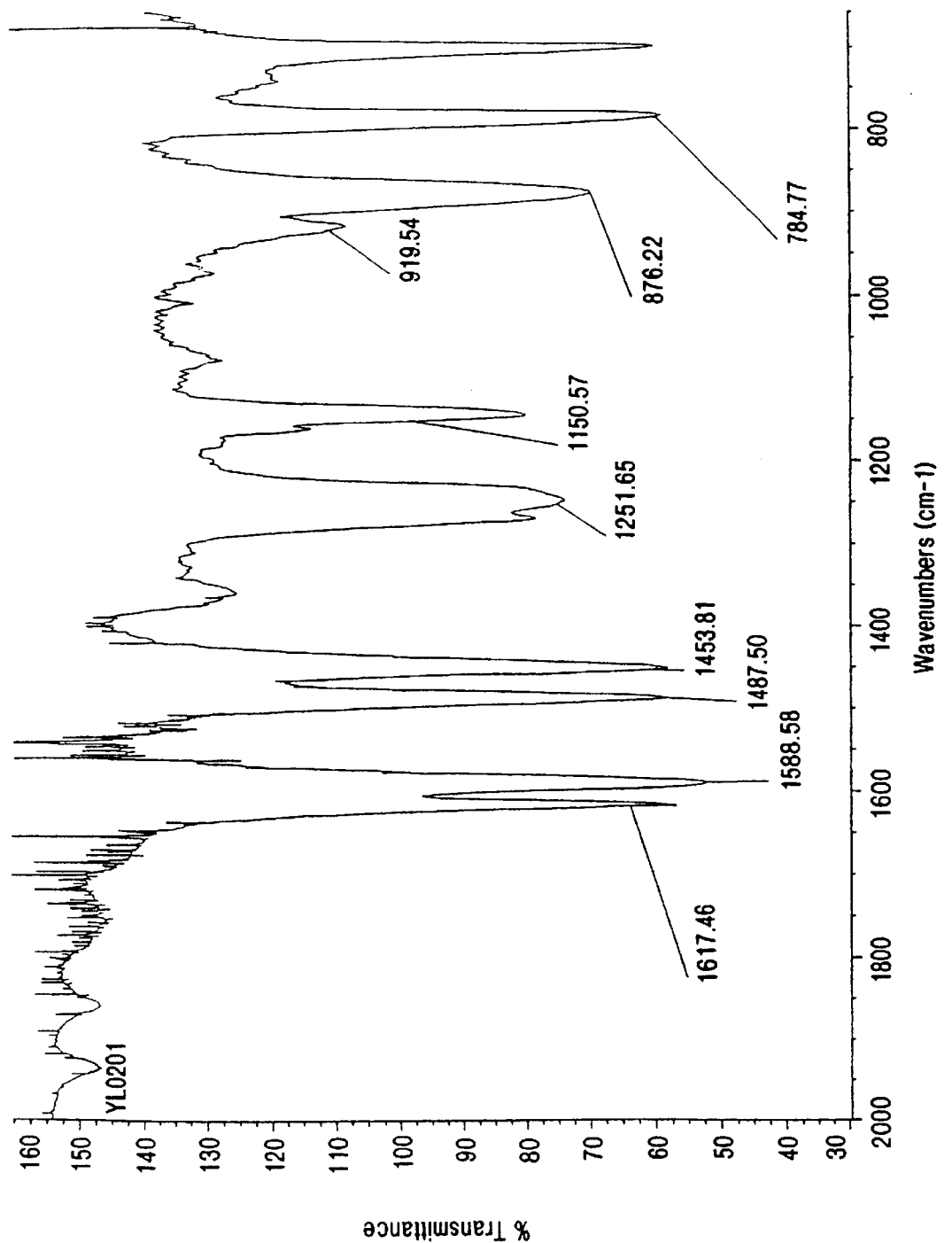
Figure 65:
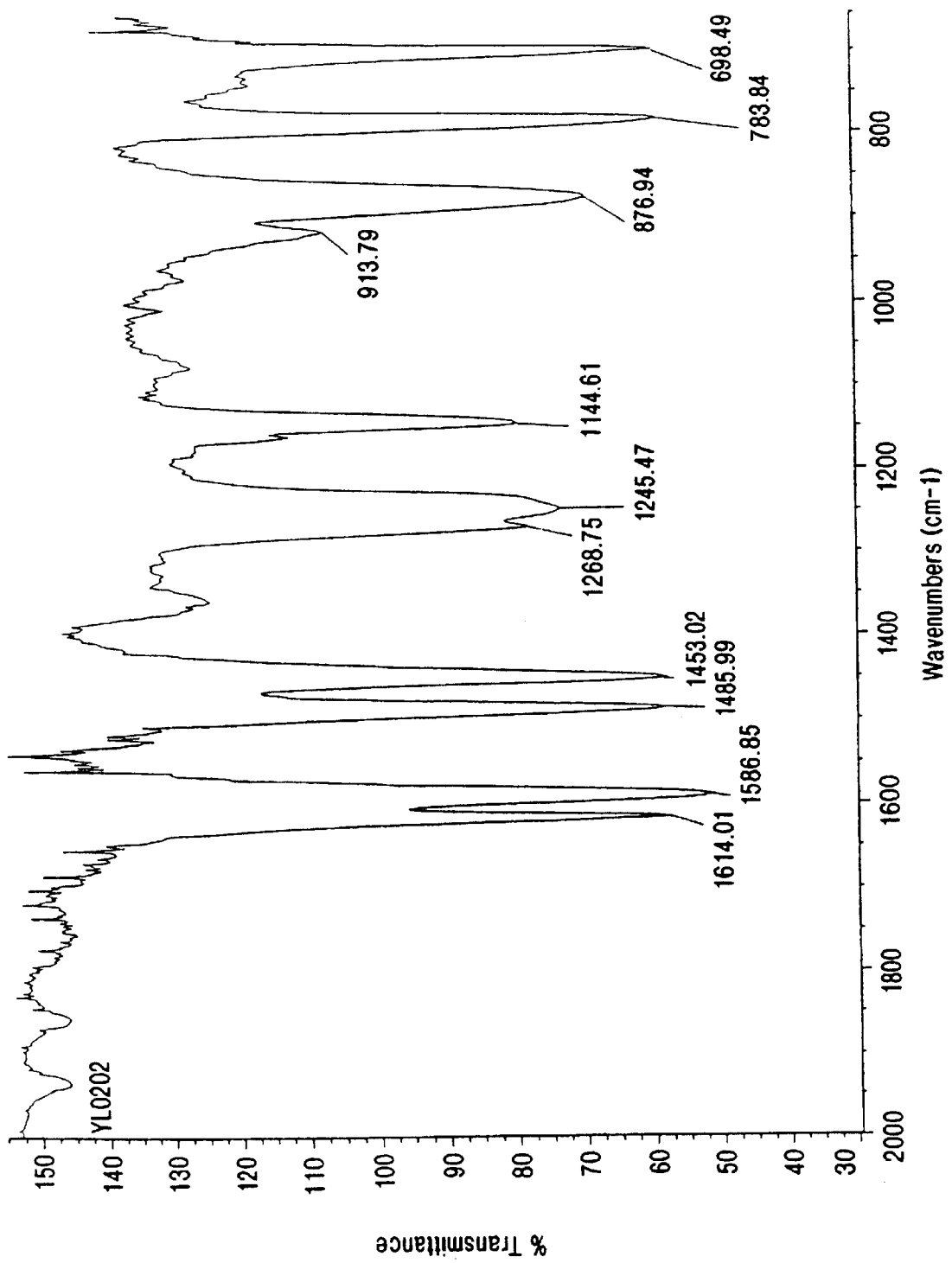
Figure 66:
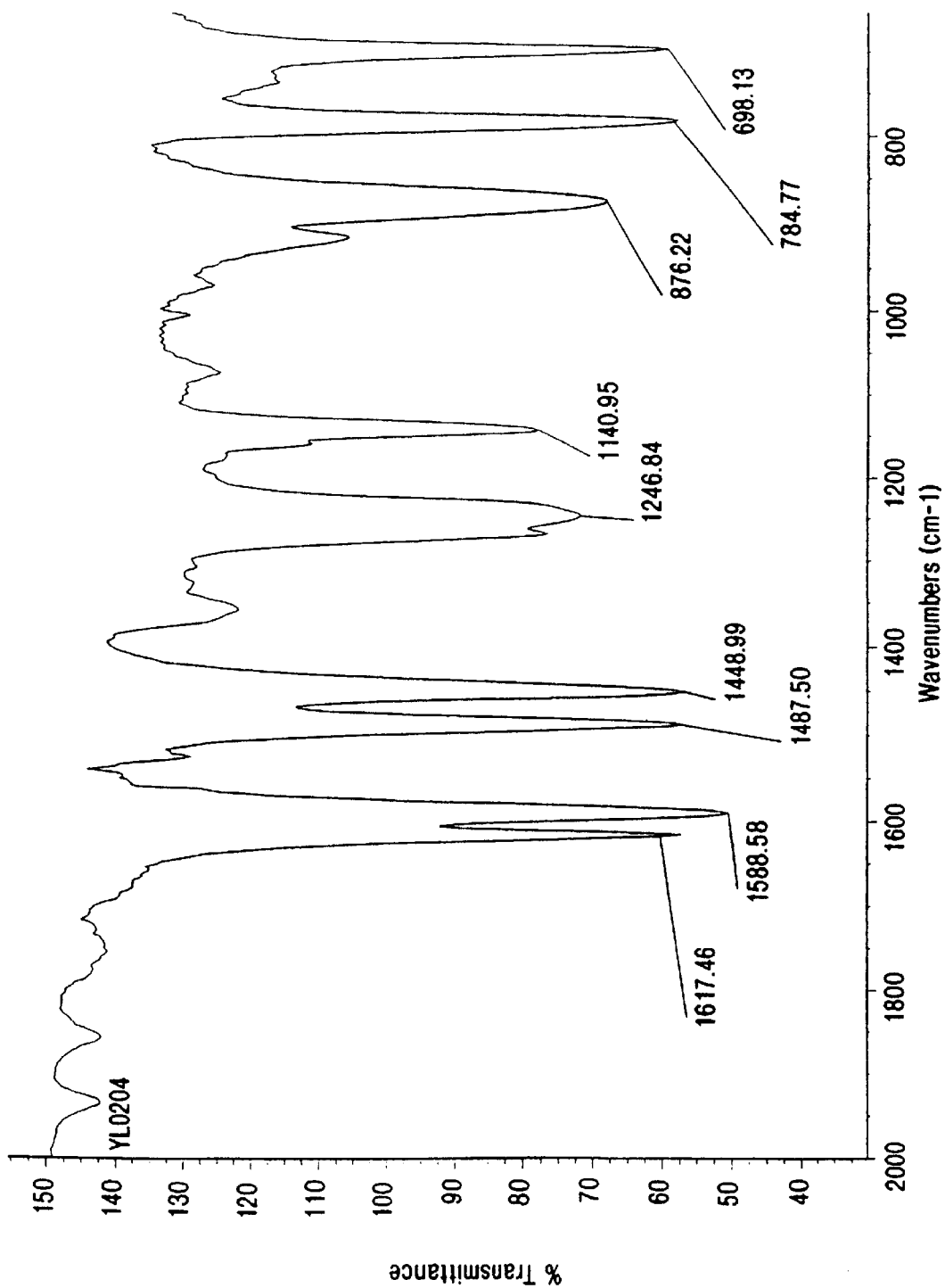
Figure 67:
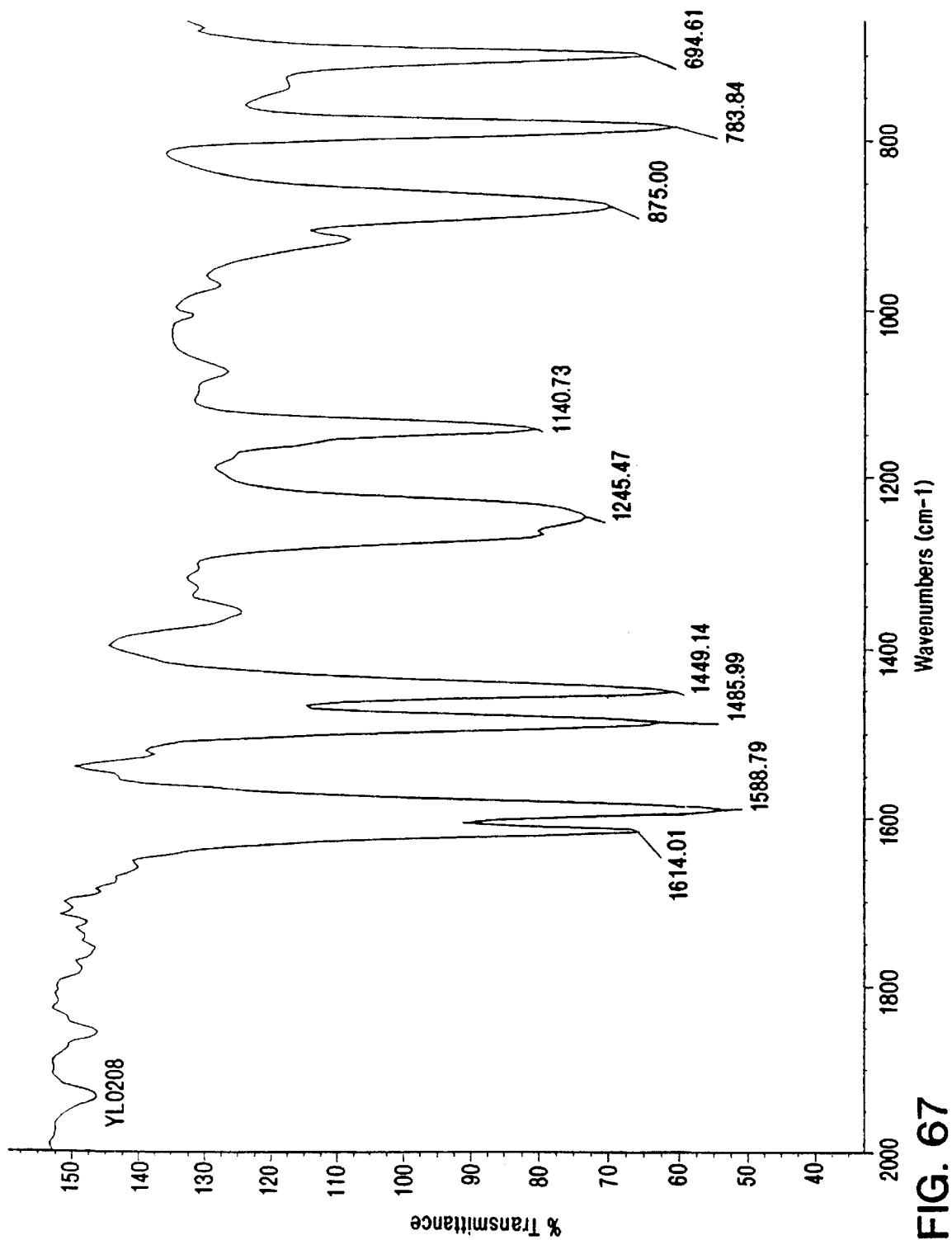
Figure 68:
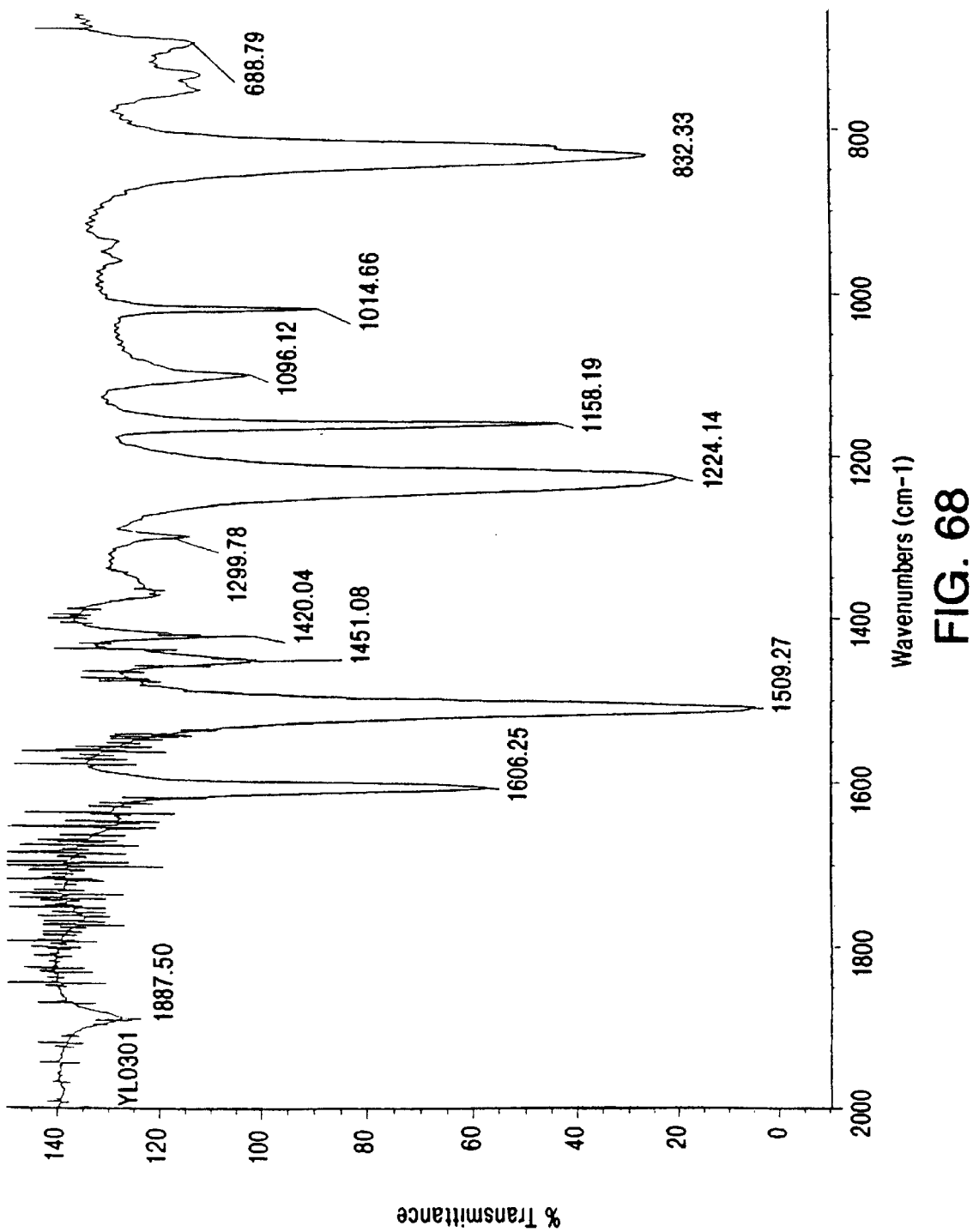
Figure 69:
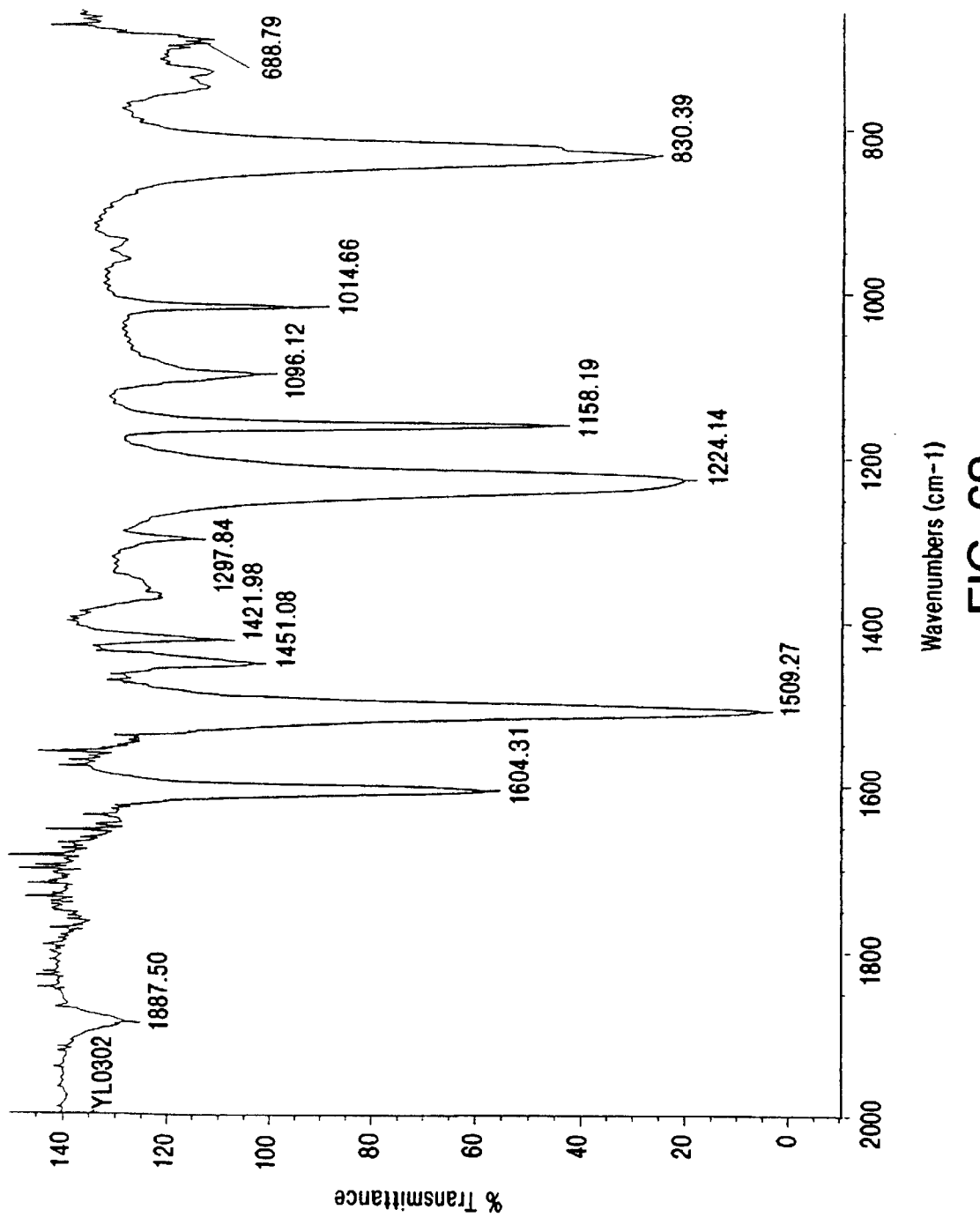
Figure 70:
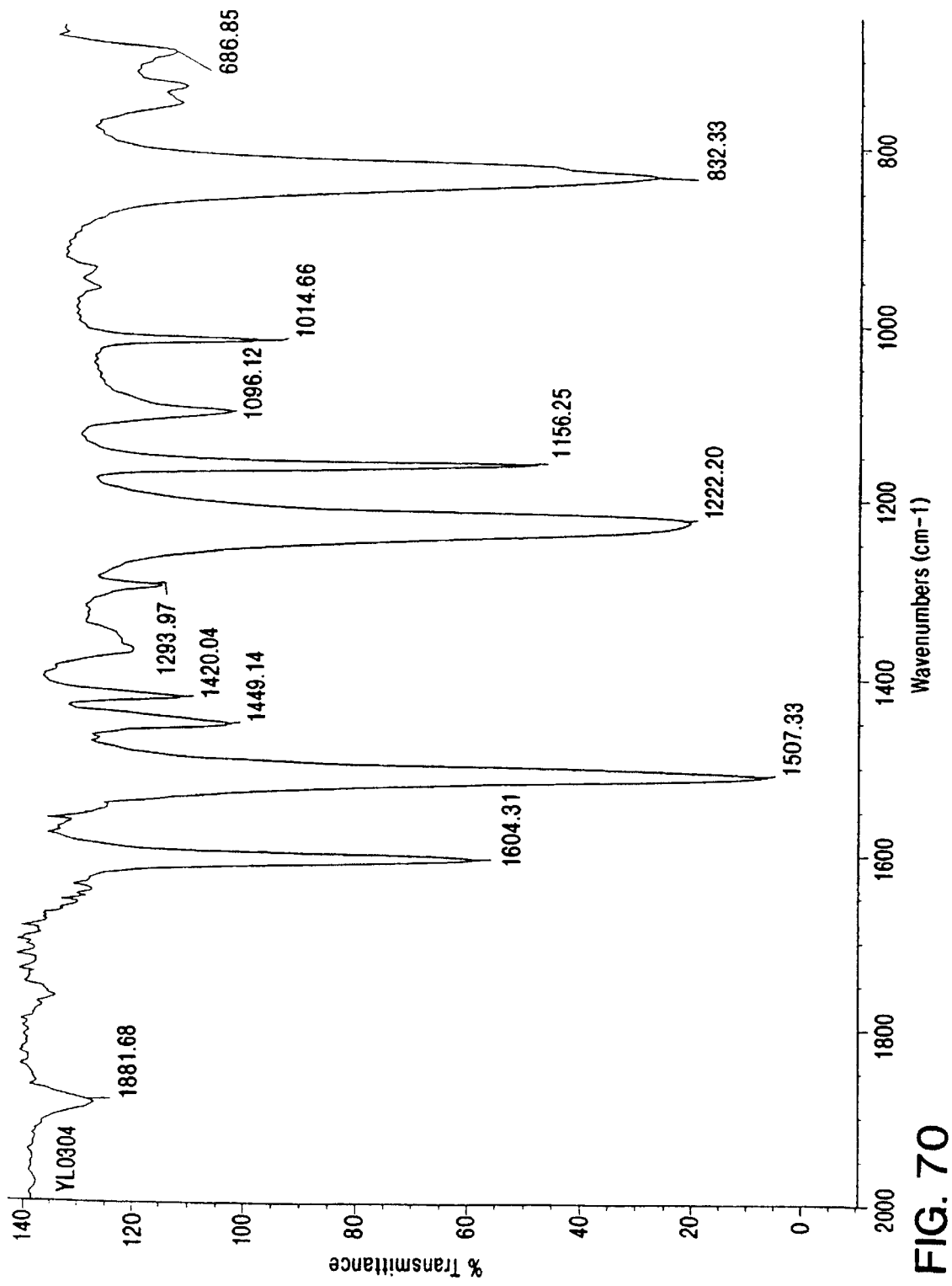
Figure 71:
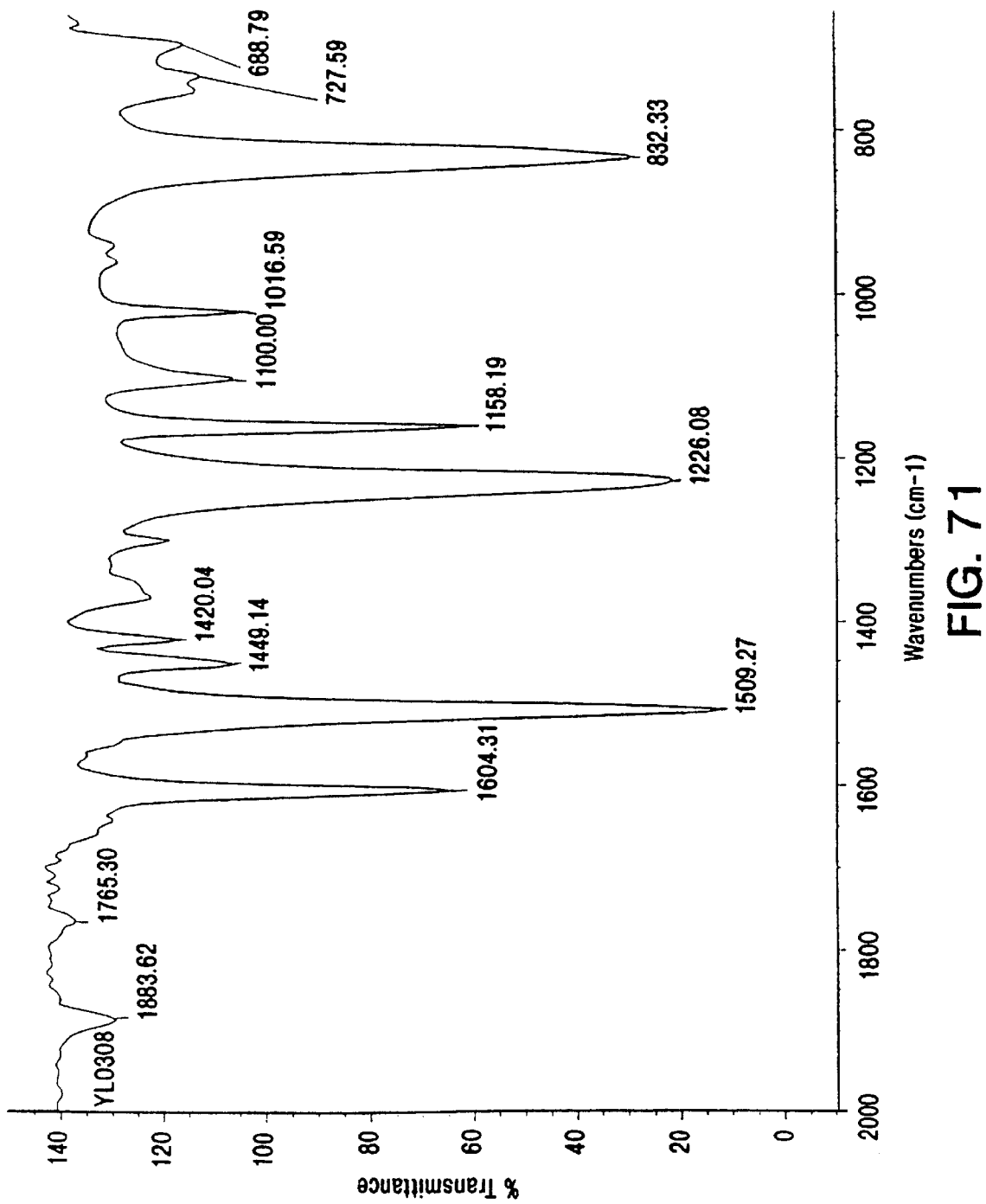
Figure 72:
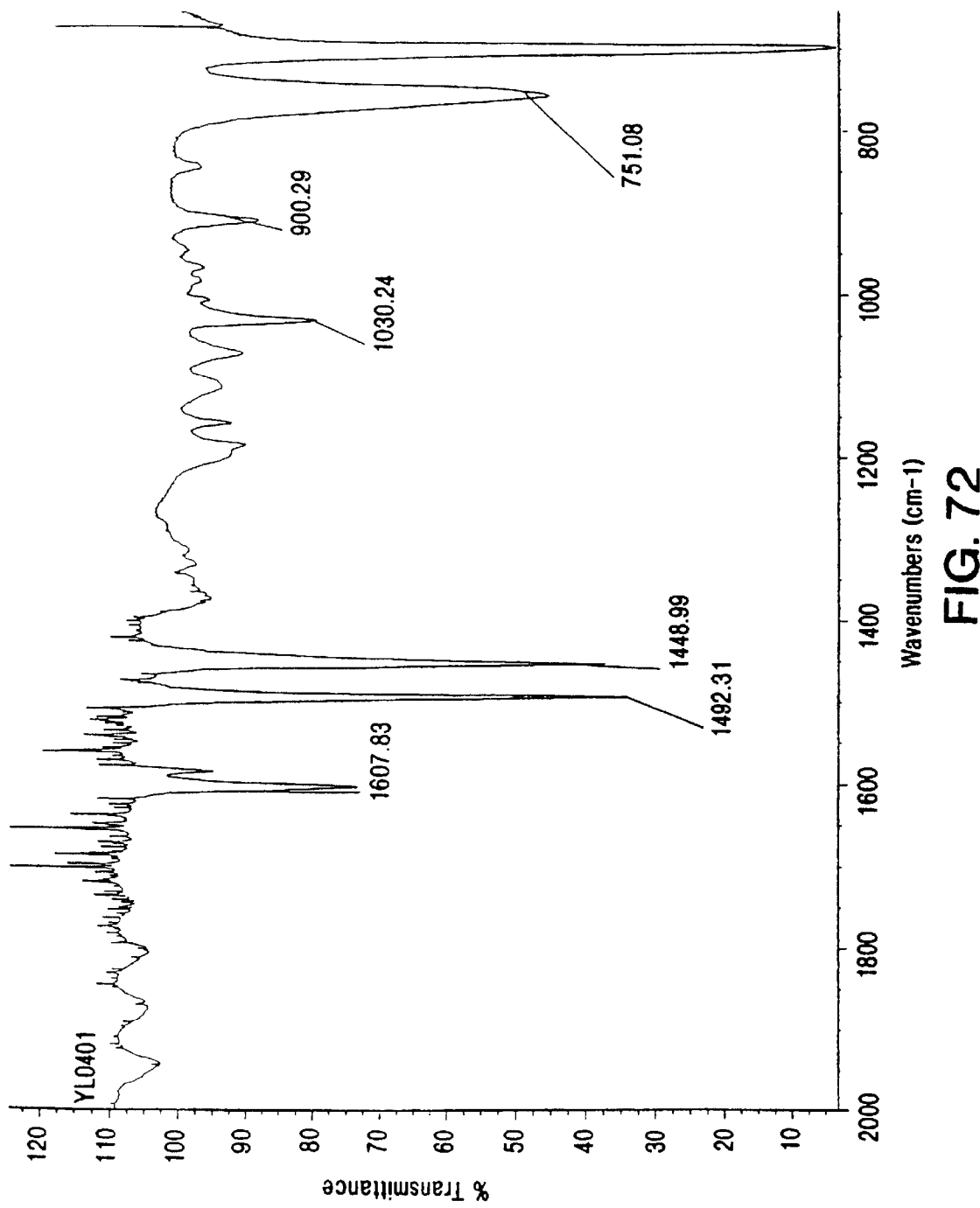
Figure 73:
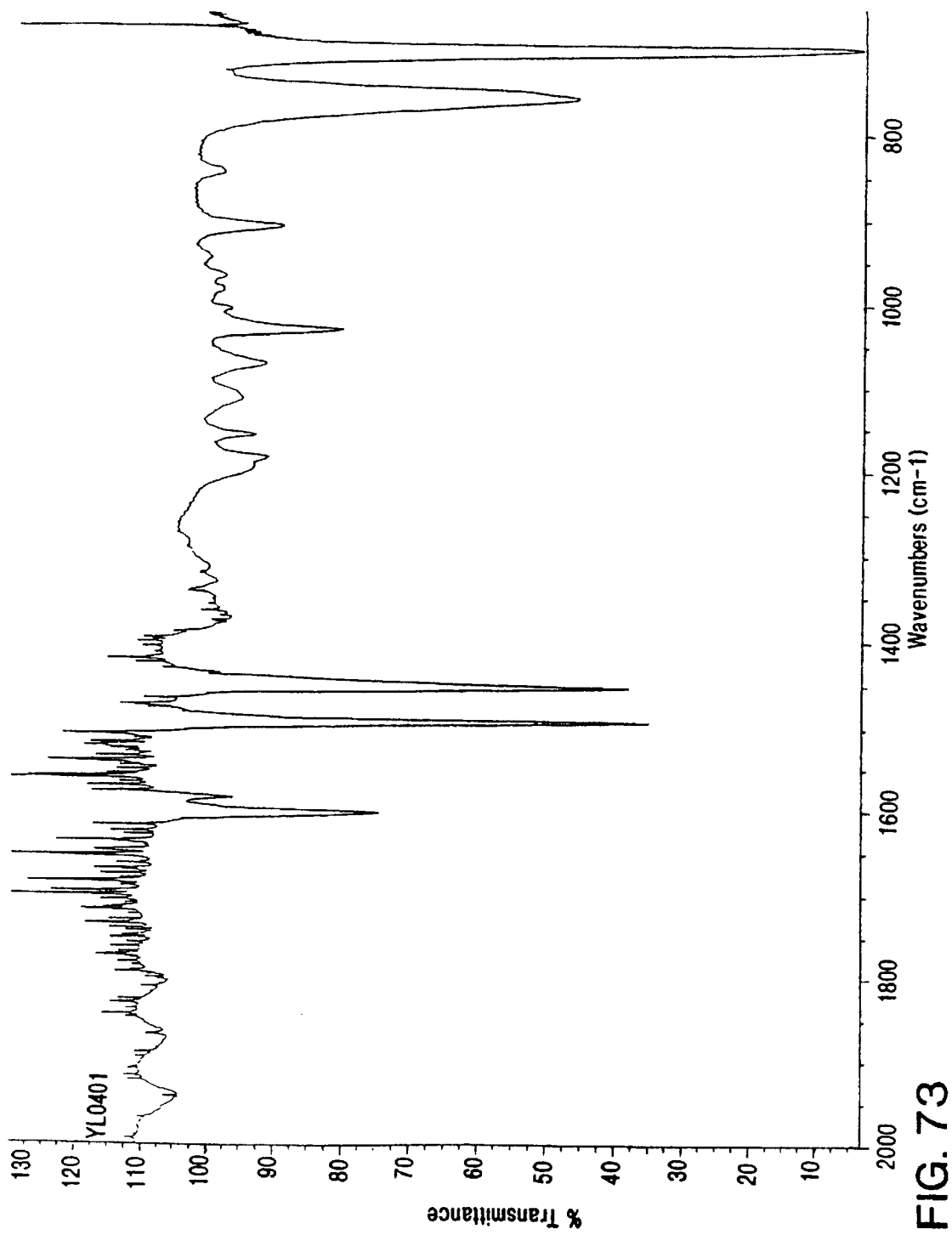
Figure 74:
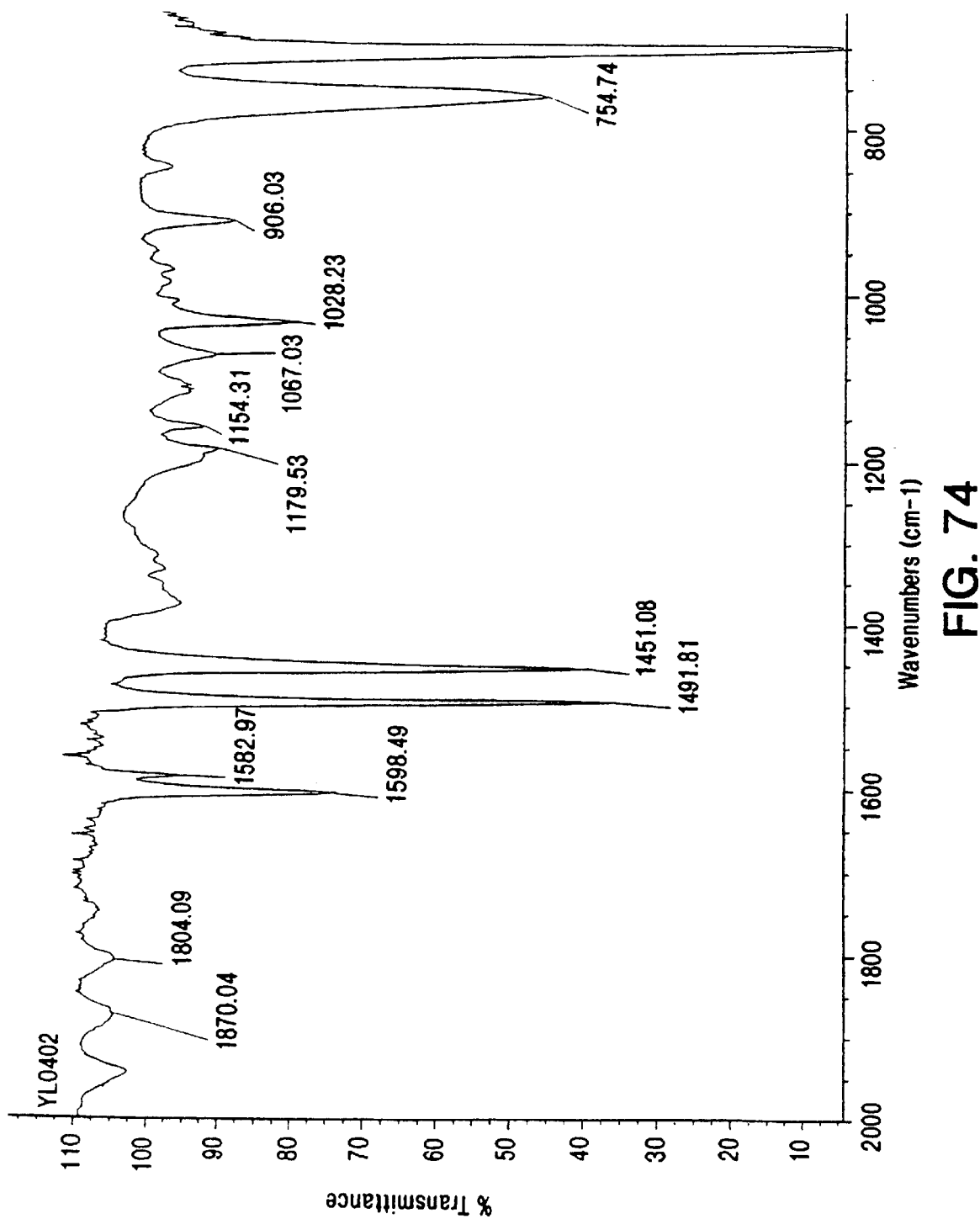
Figure 75:
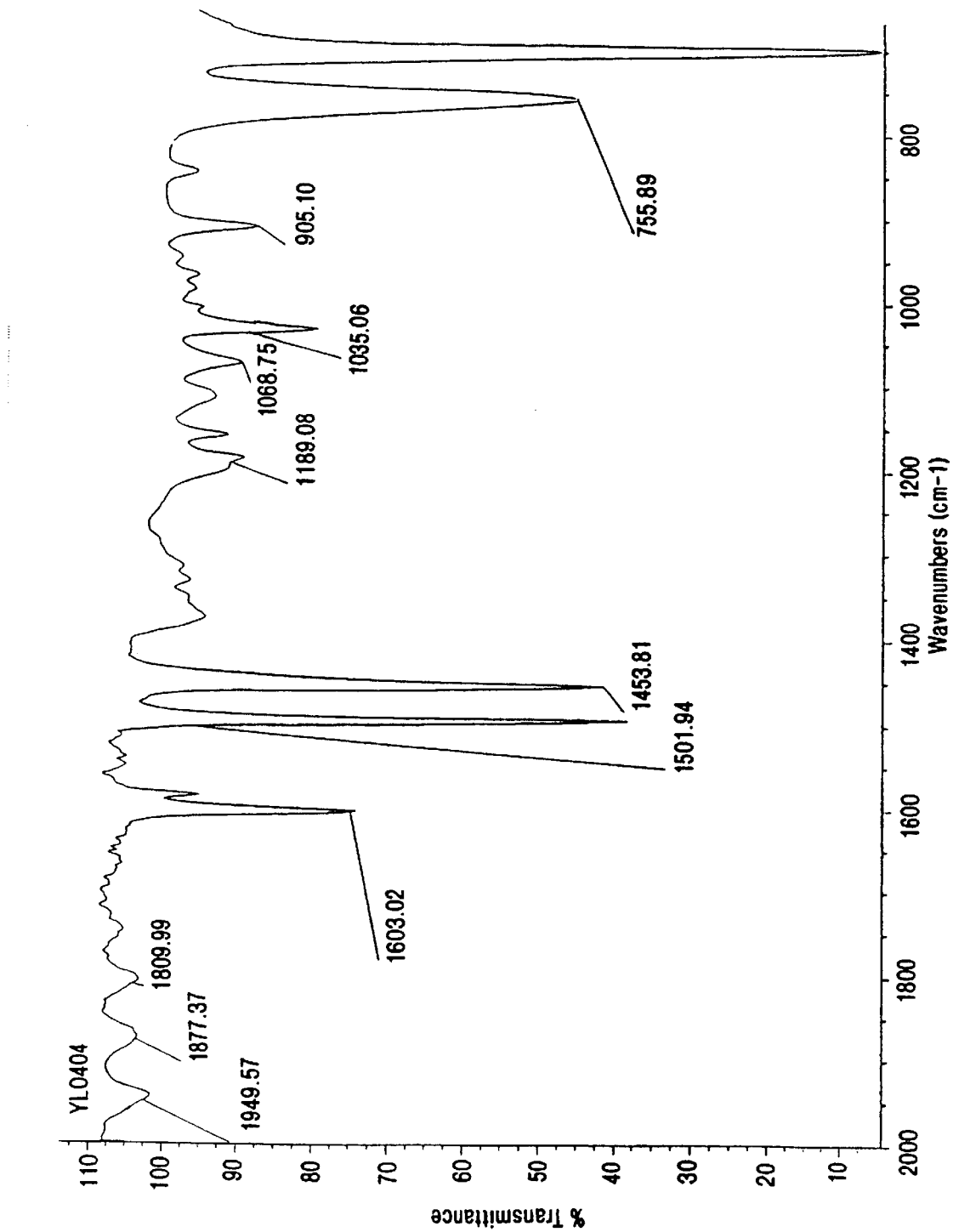
Figure 76:
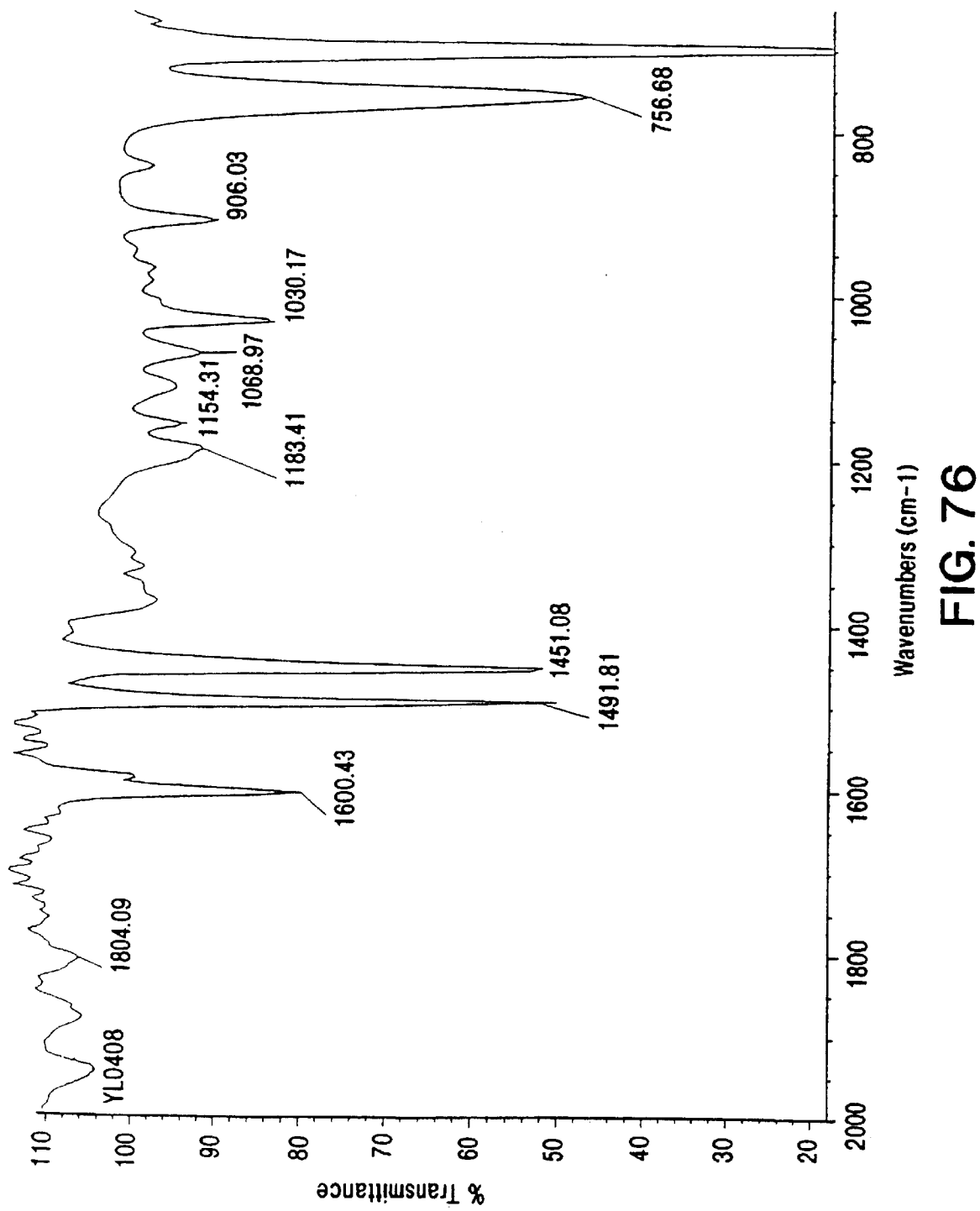
Figure 77:
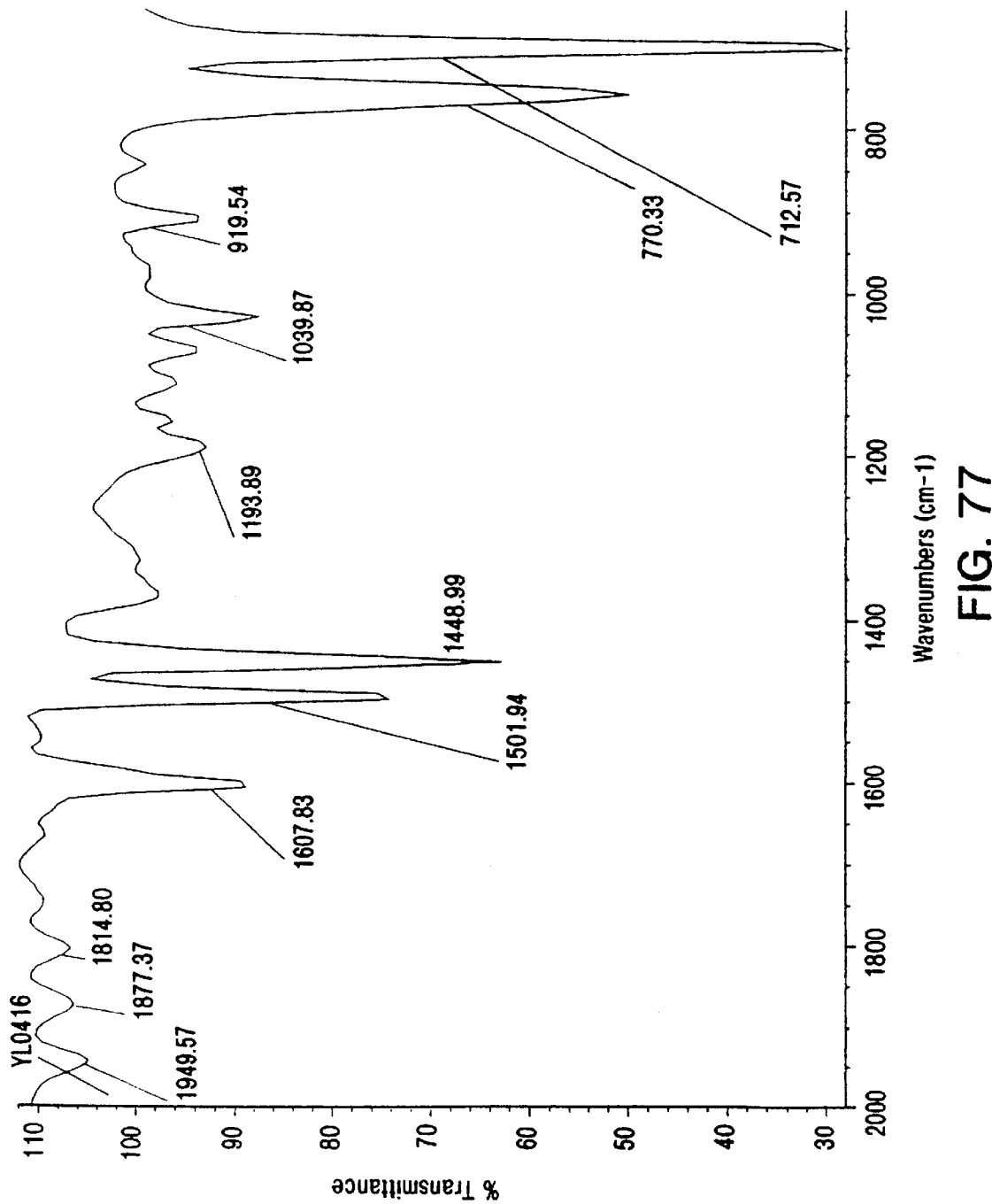
Figure 78:
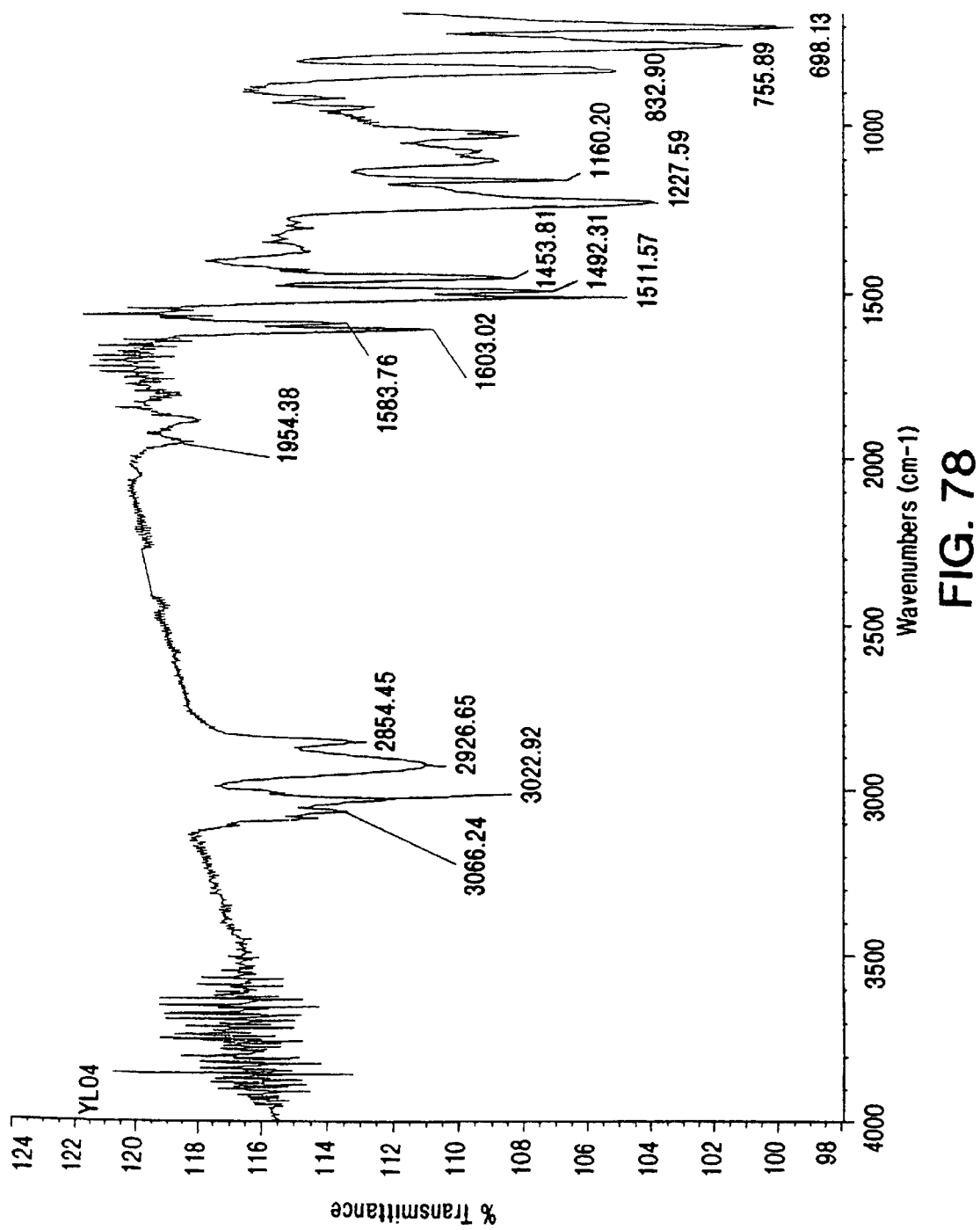
Figure 79:
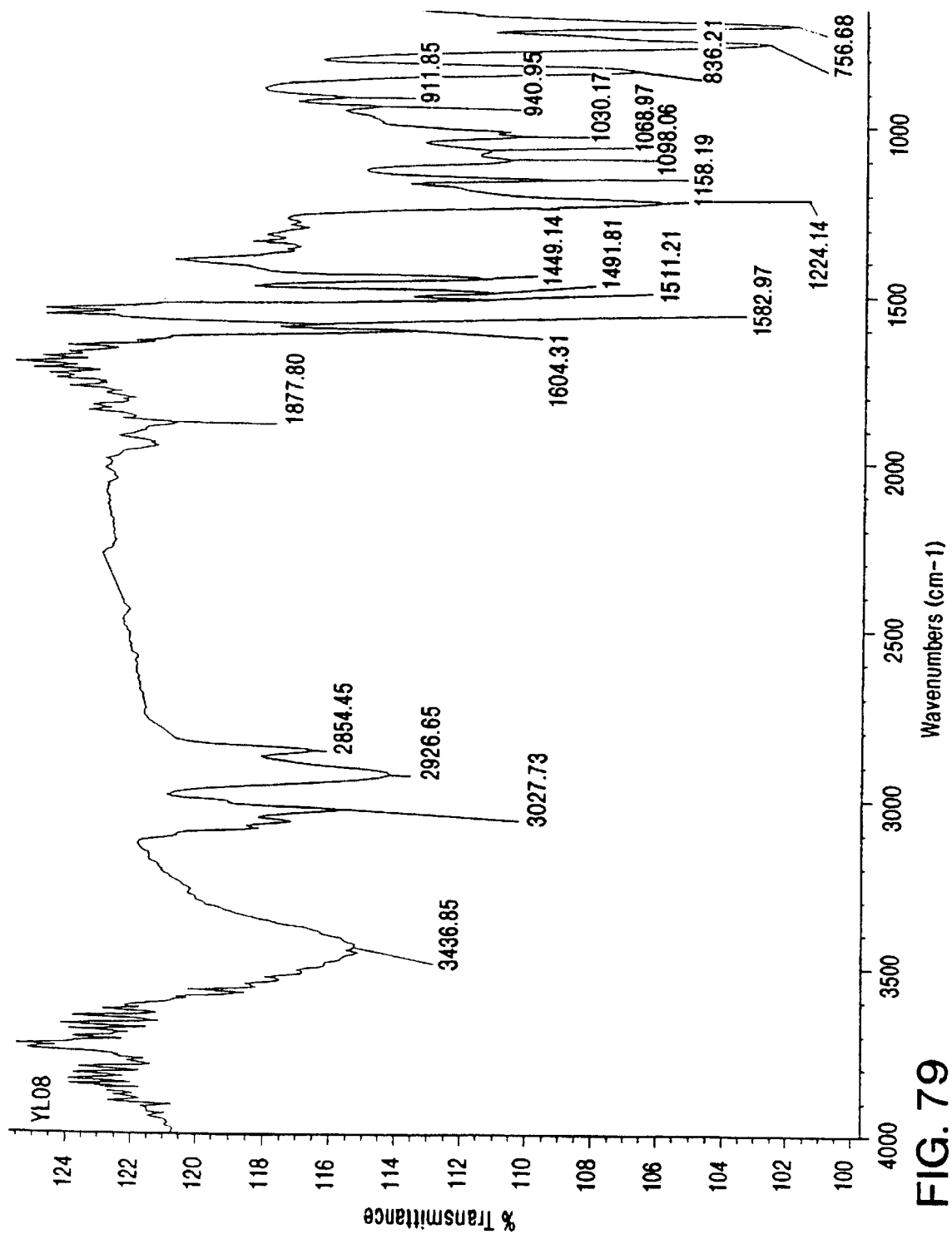
Figure 80:
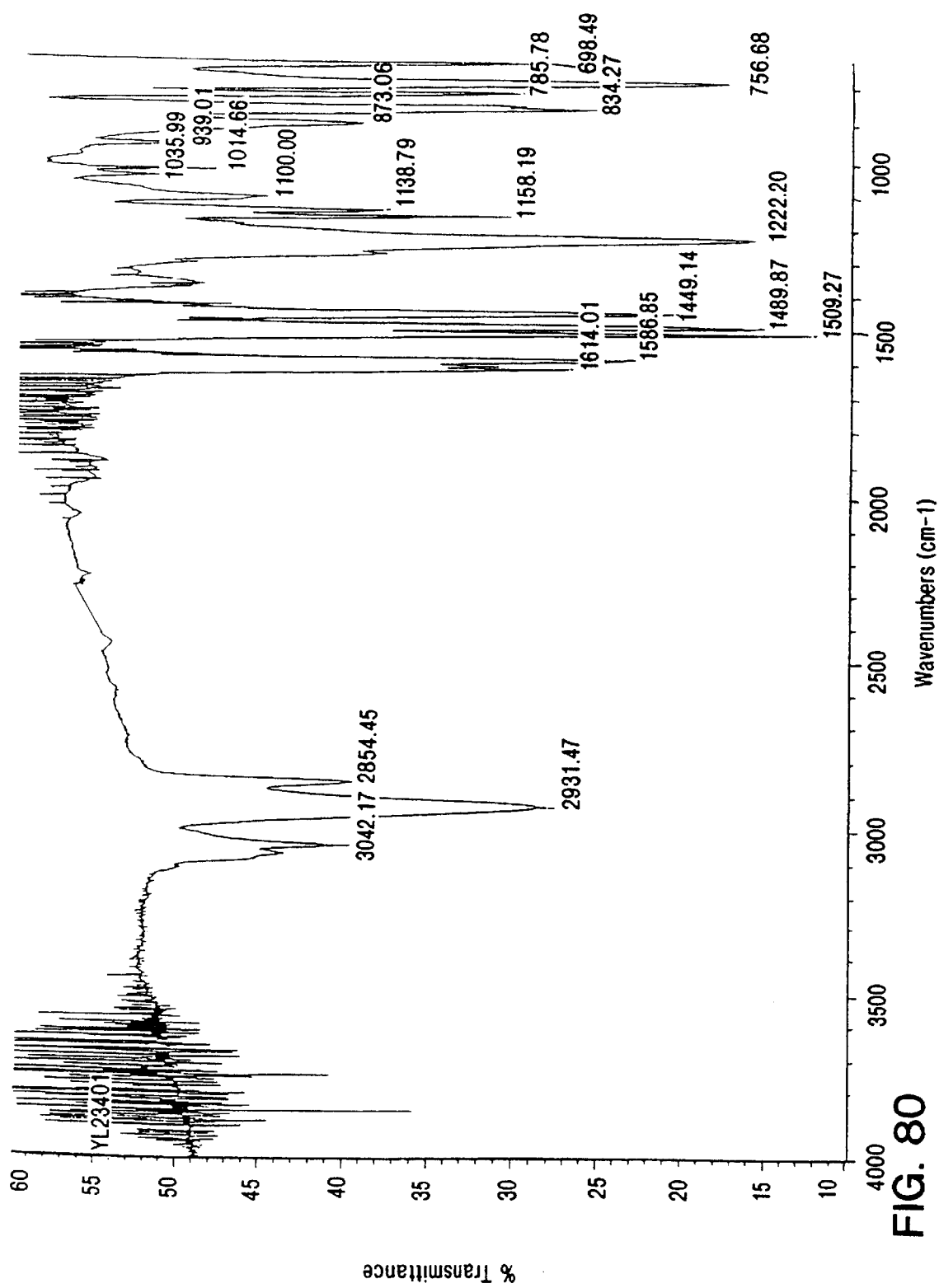
Figure 81:
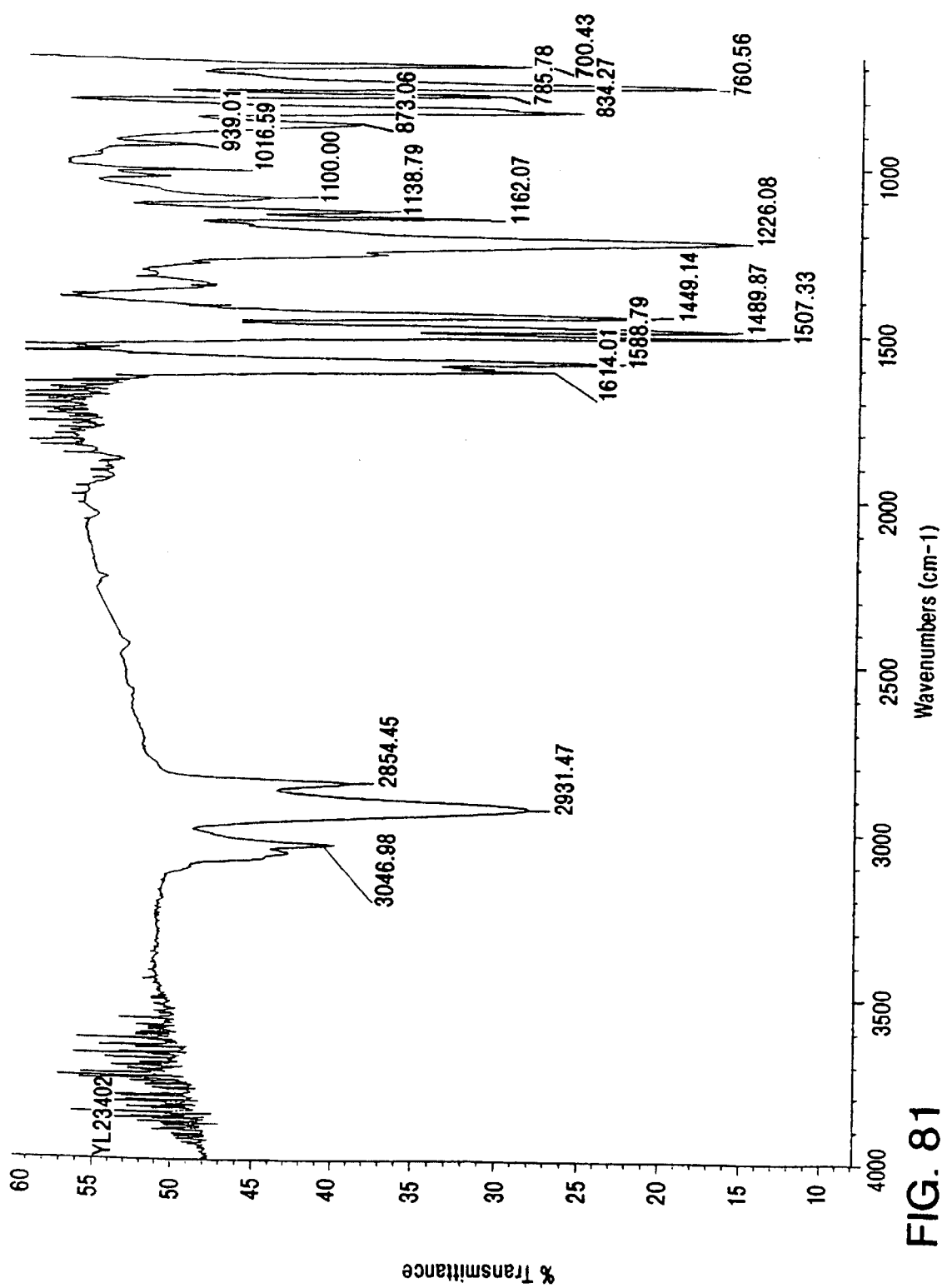
Figure 82:
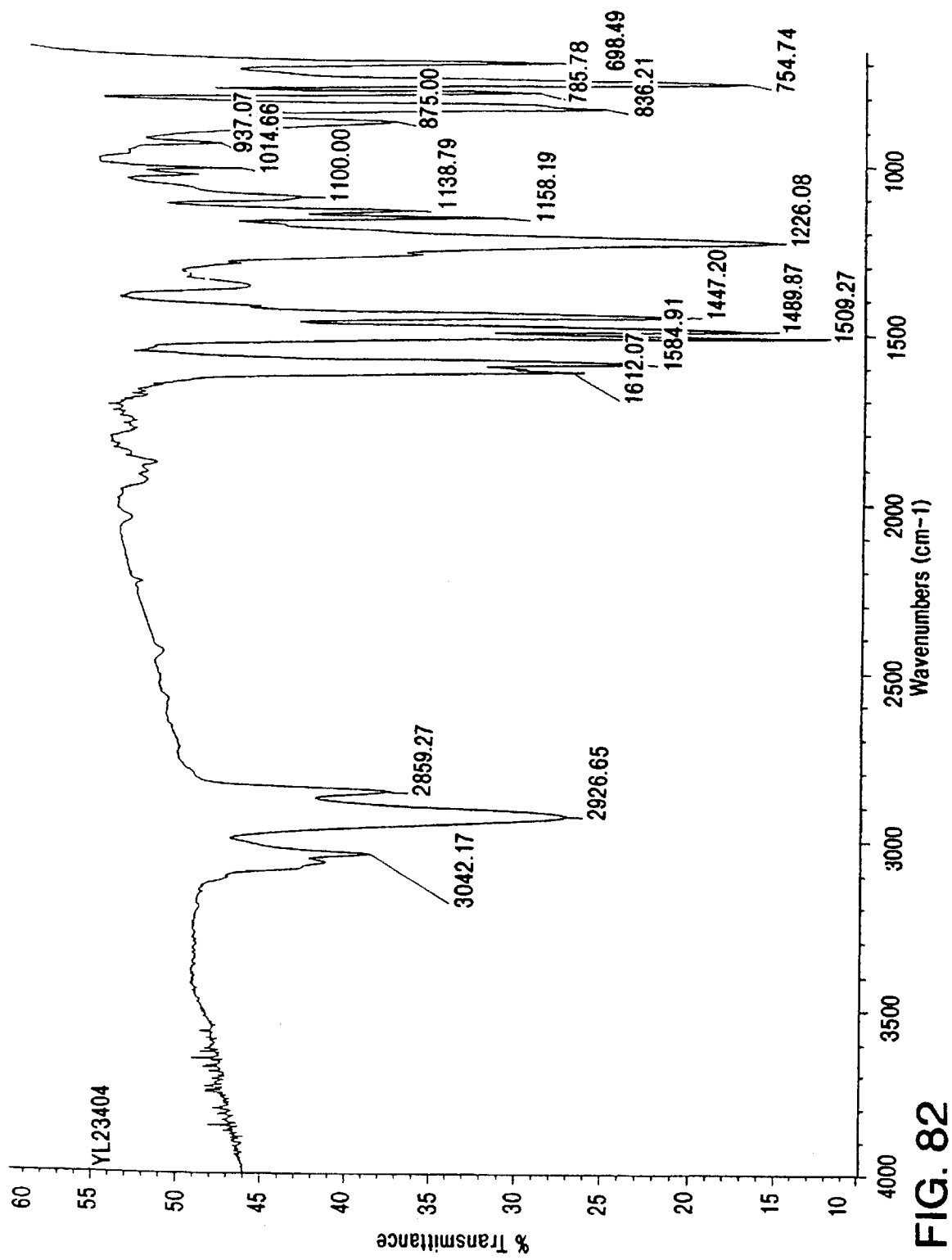
Figure 83:
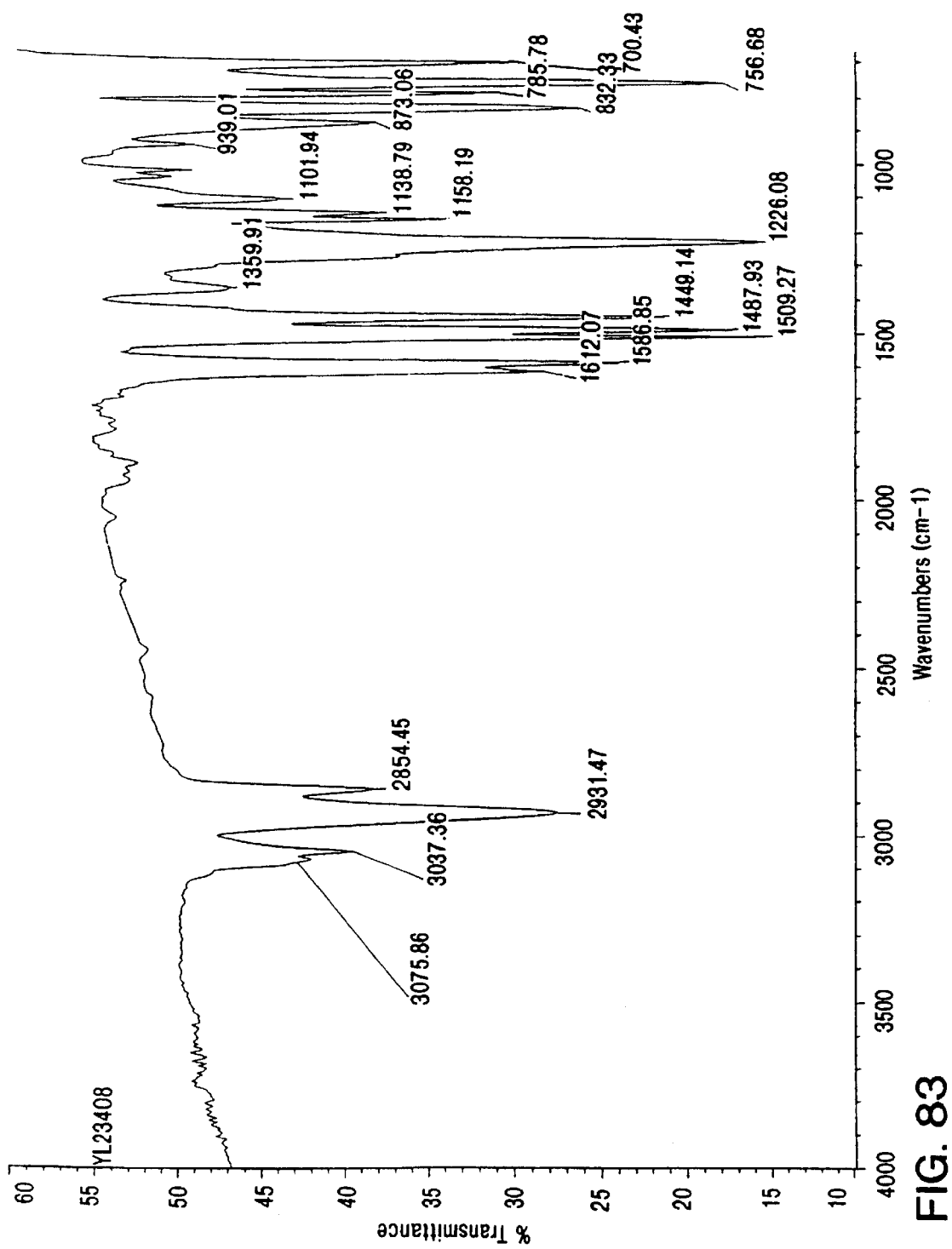
Figure 84:
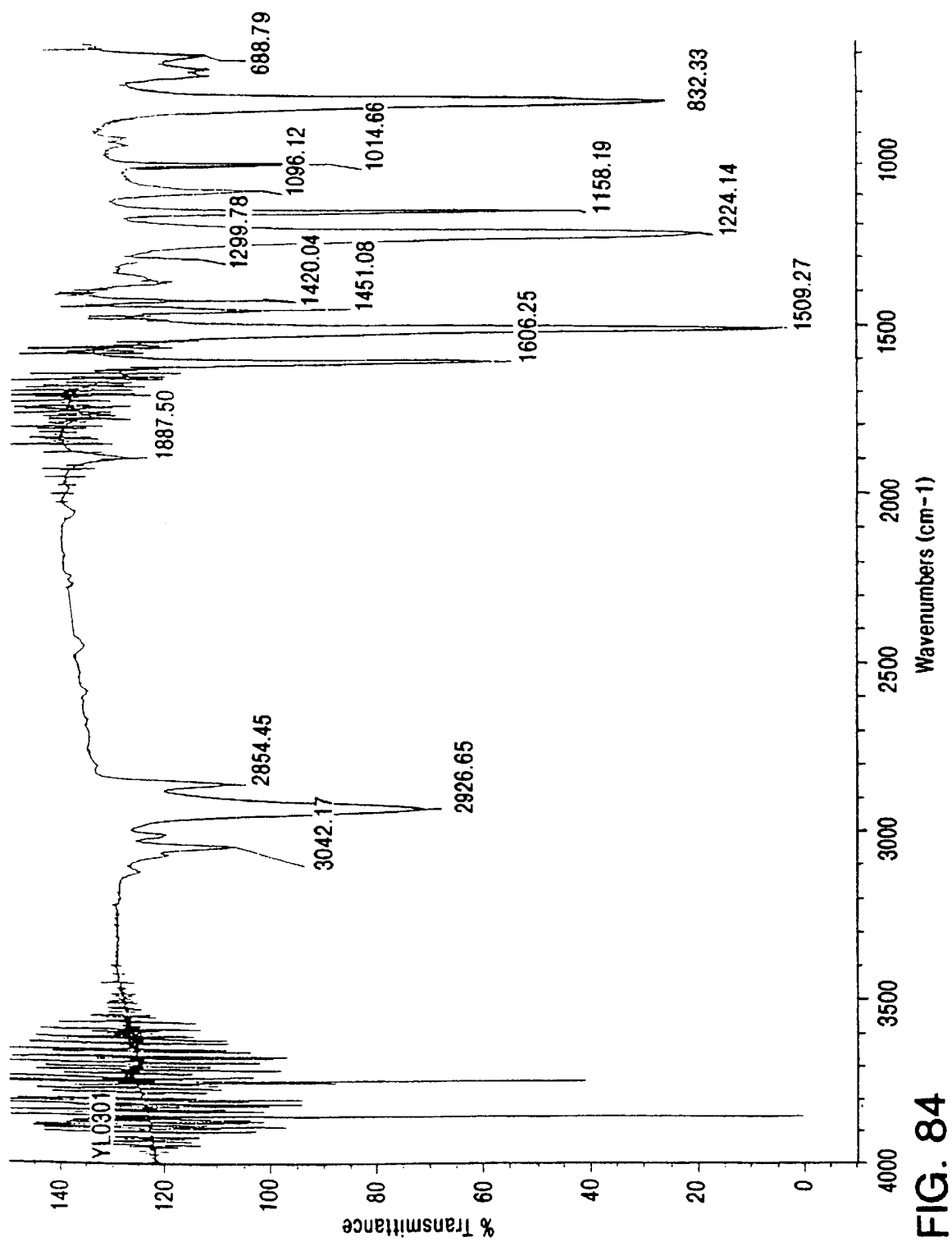
Figure 85:
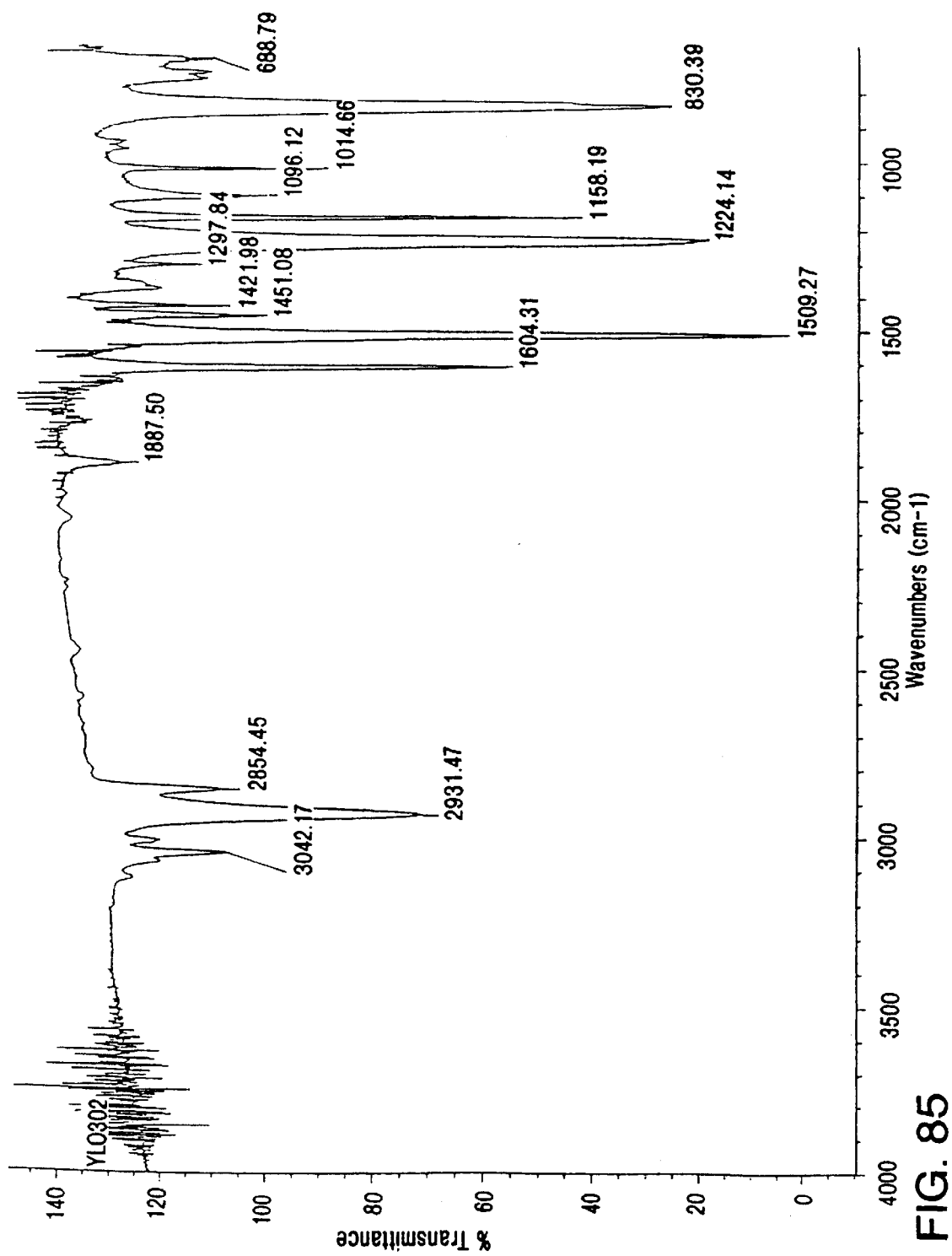
Figure 86:
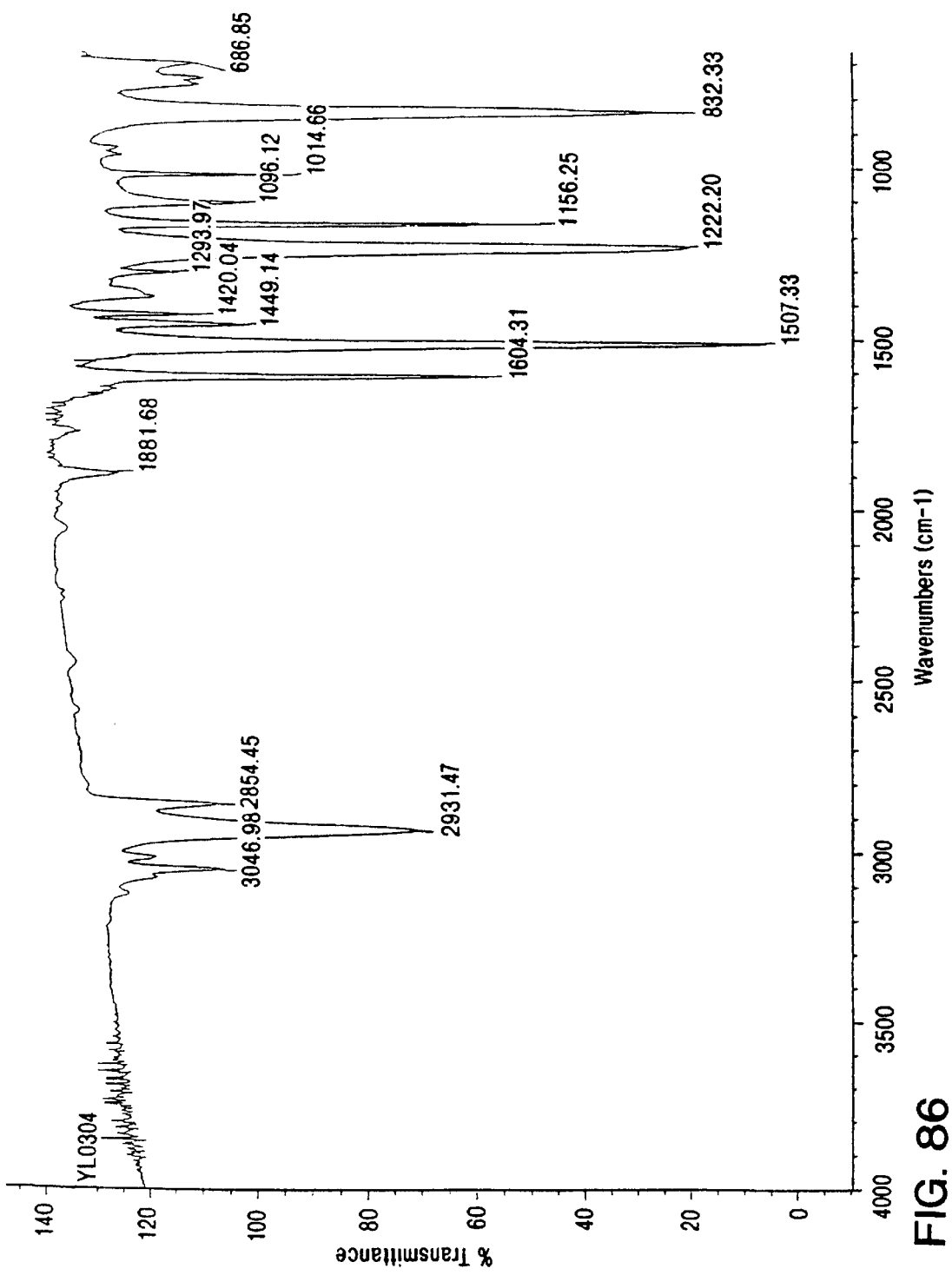
Figure 87:
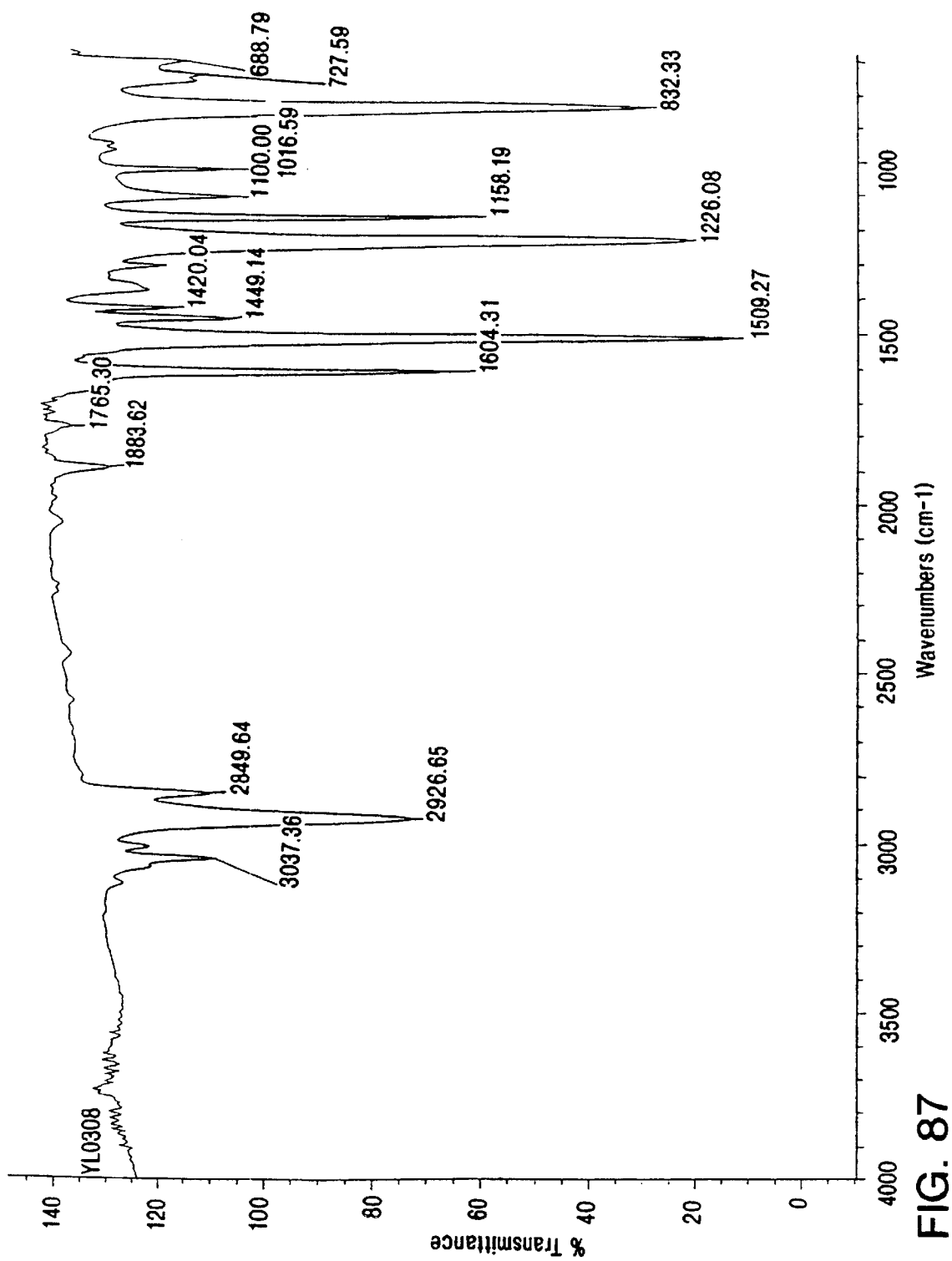
Figure 88:
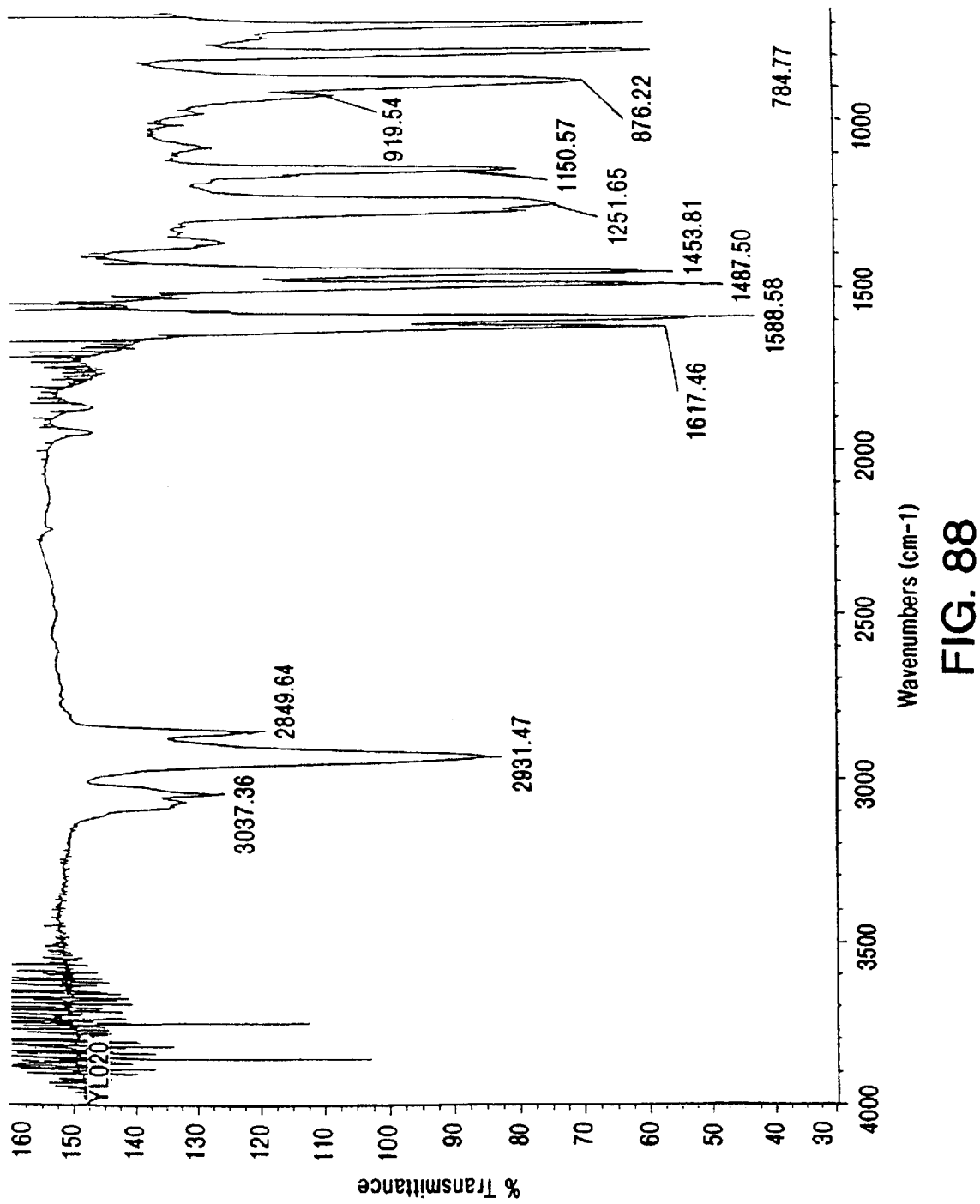
Figure 89:
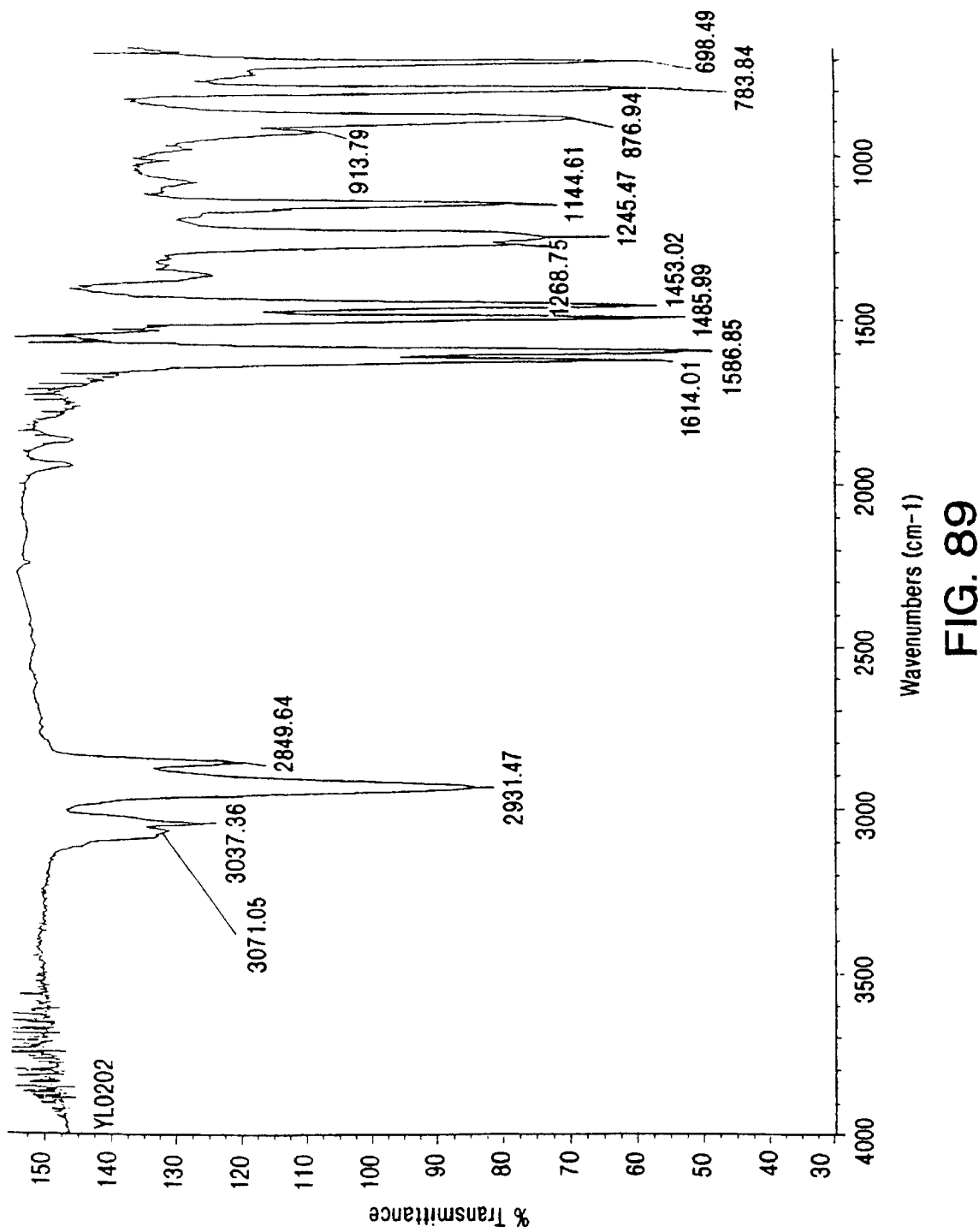
Figure 90:
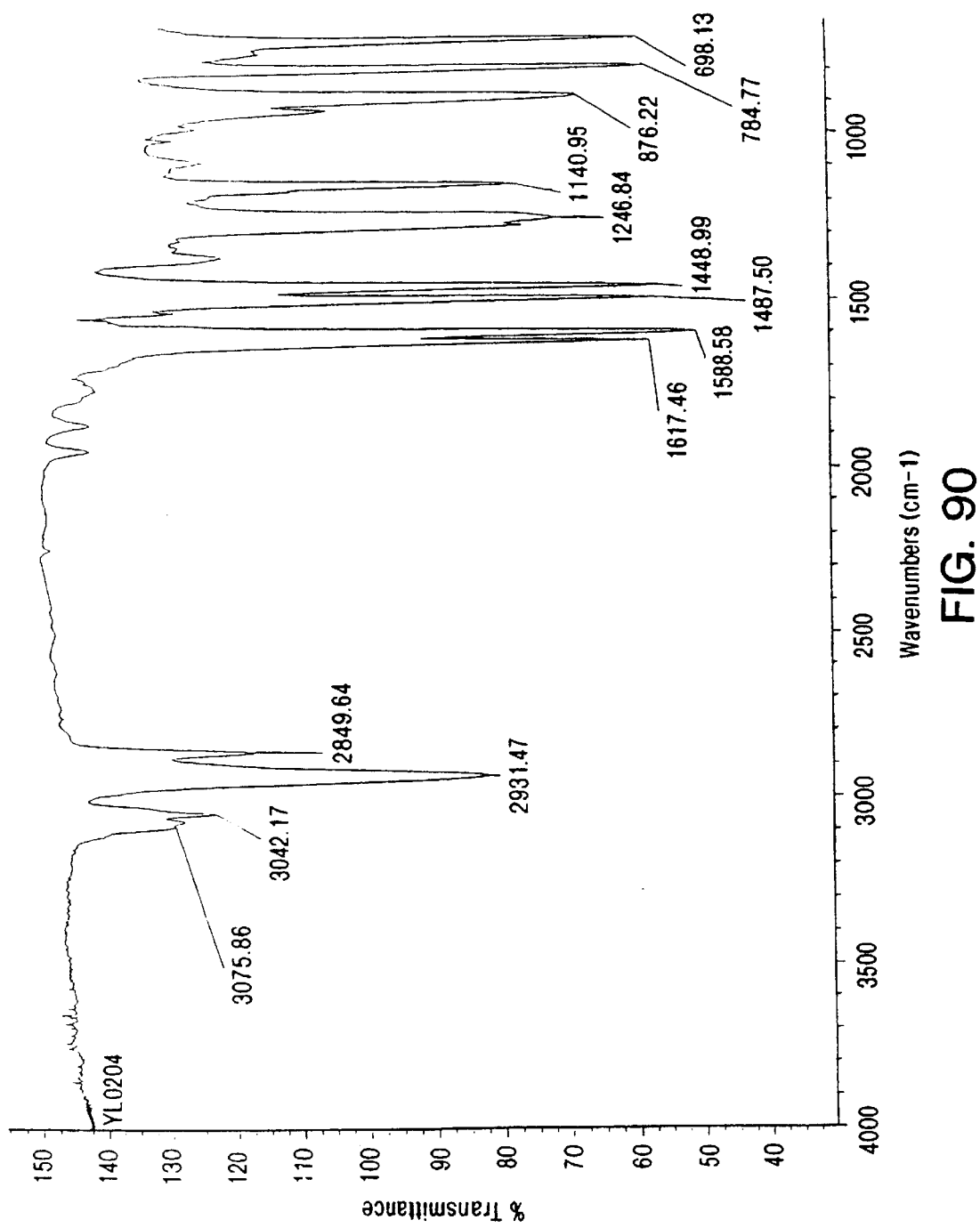
Figure 91:
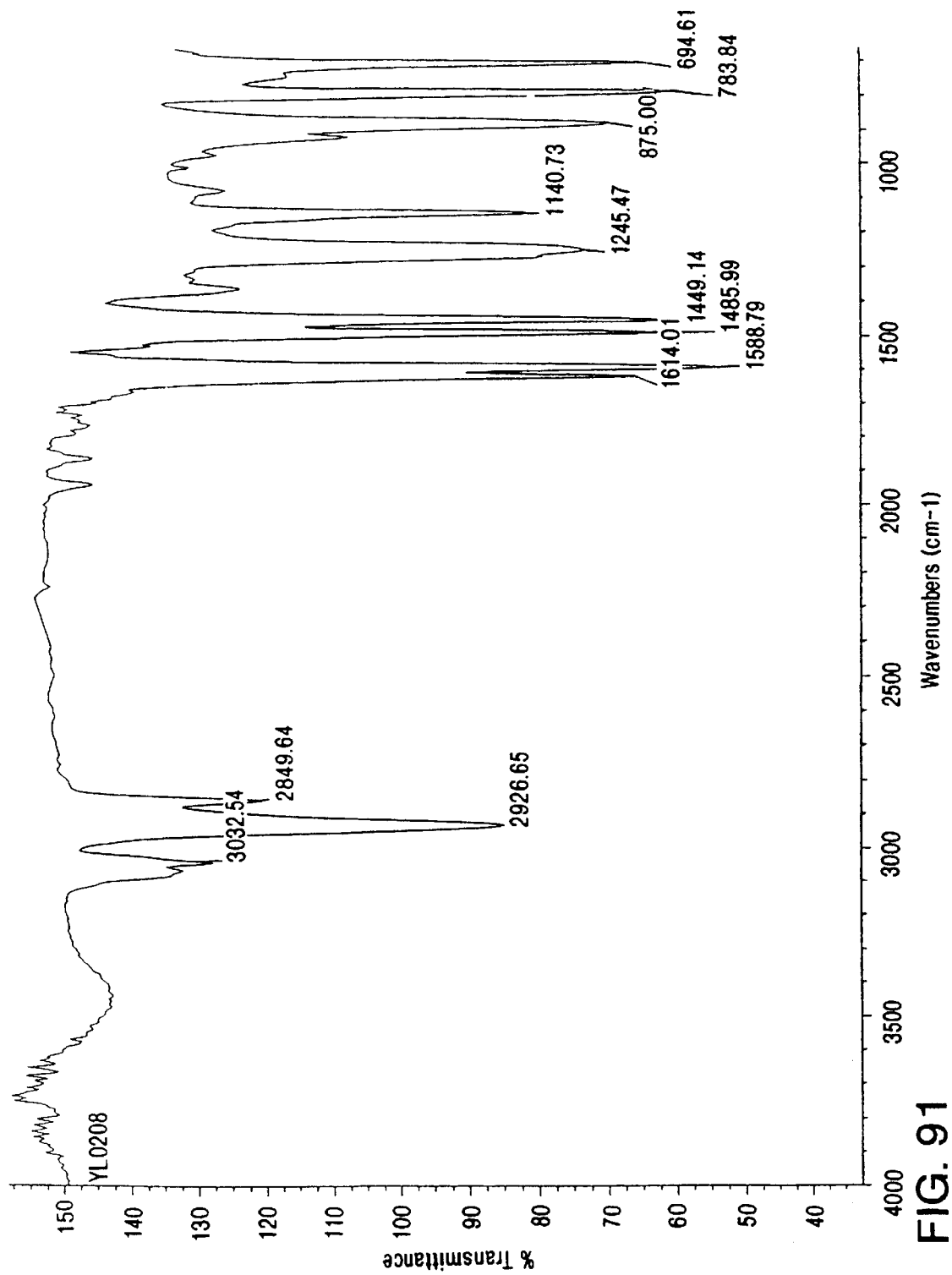
Figure 92:
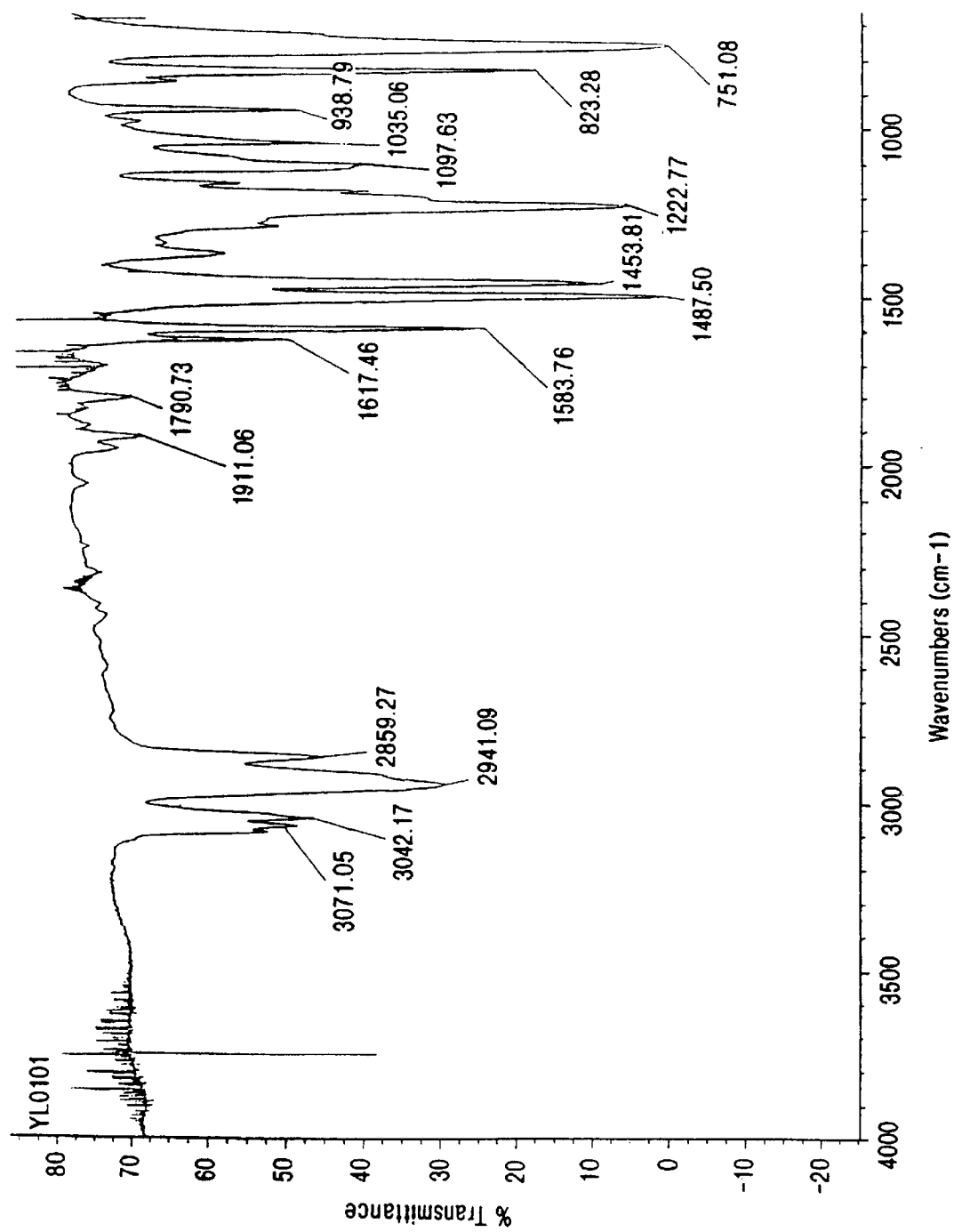
Figure 93:
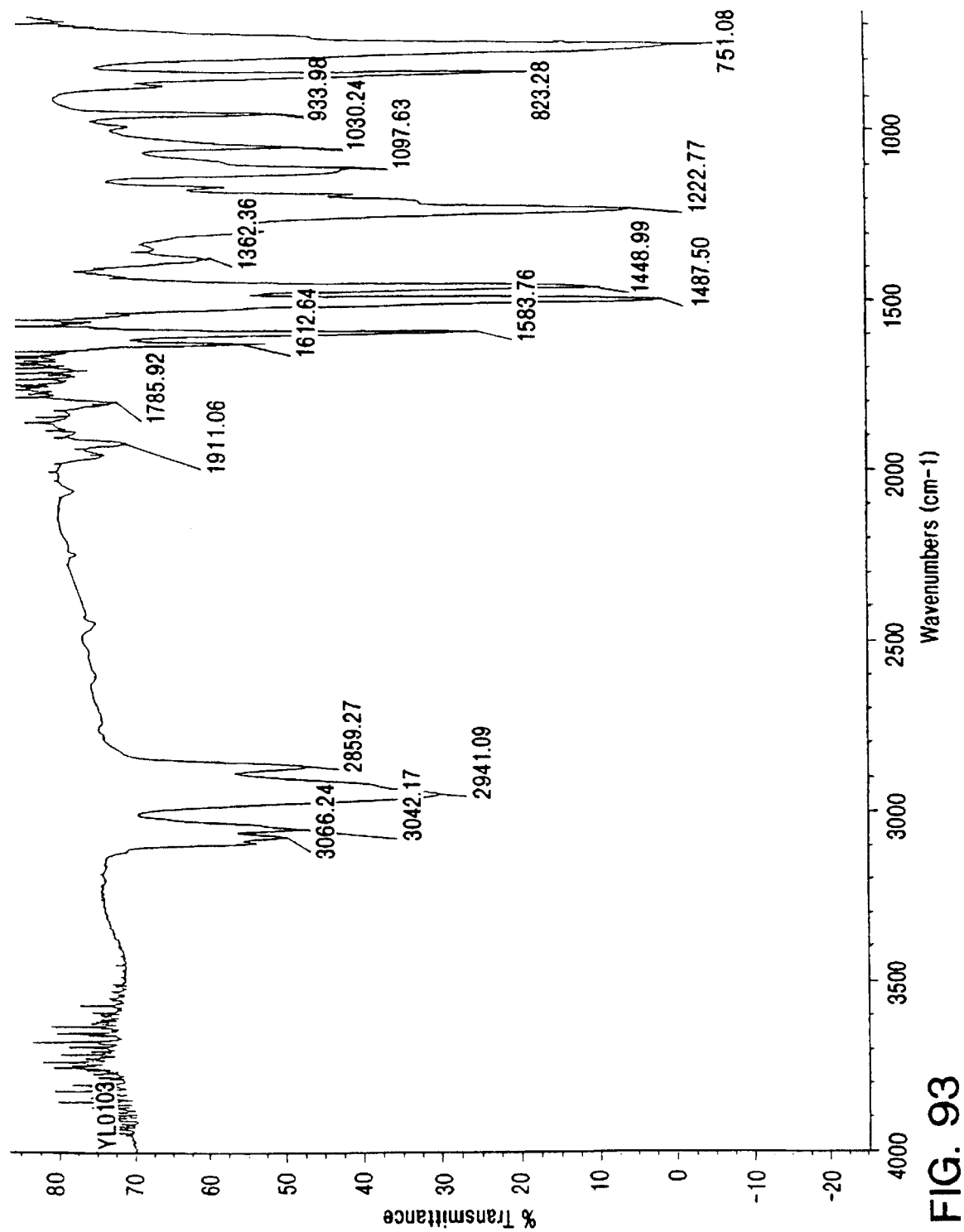
Figure 94:
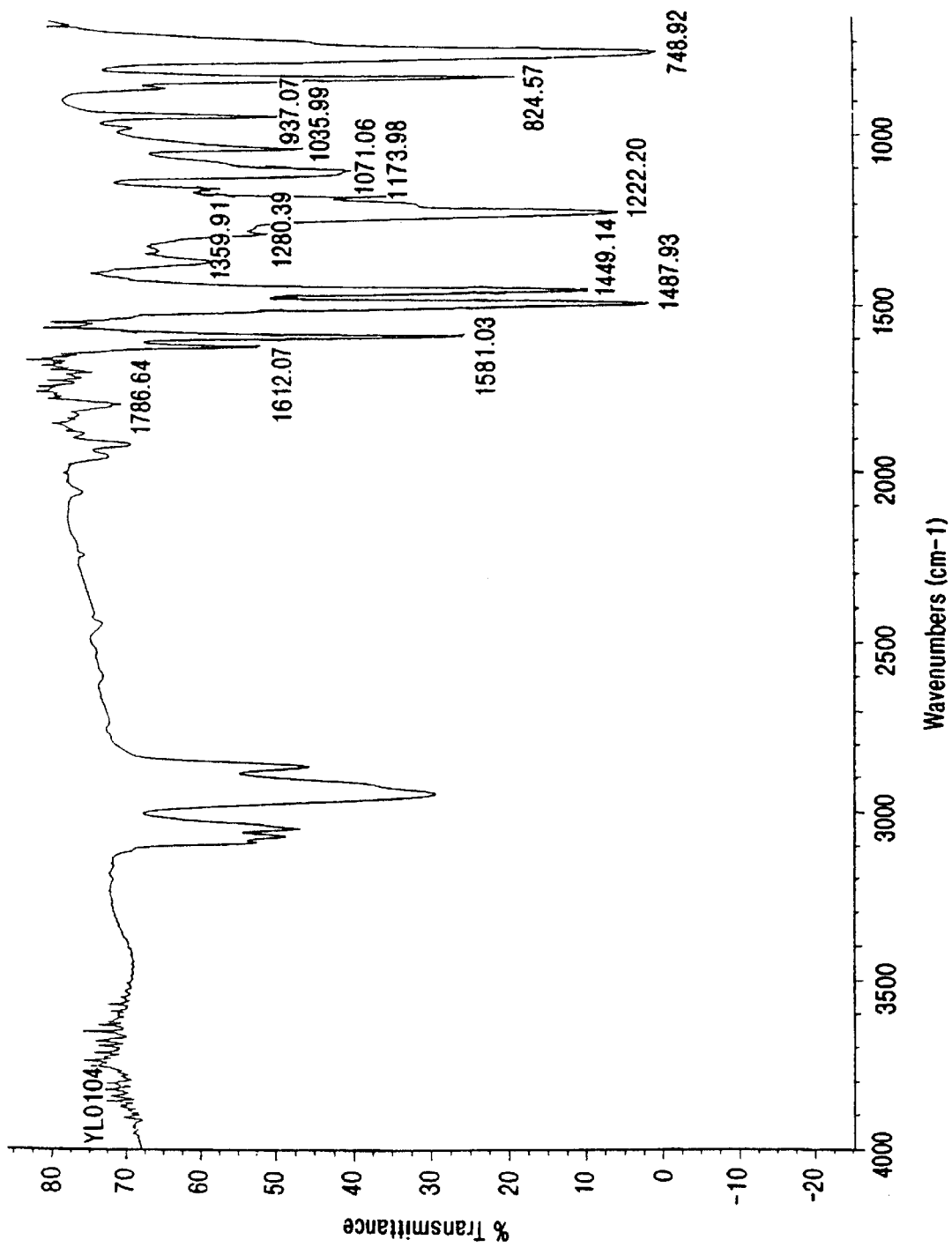
Figure 95:
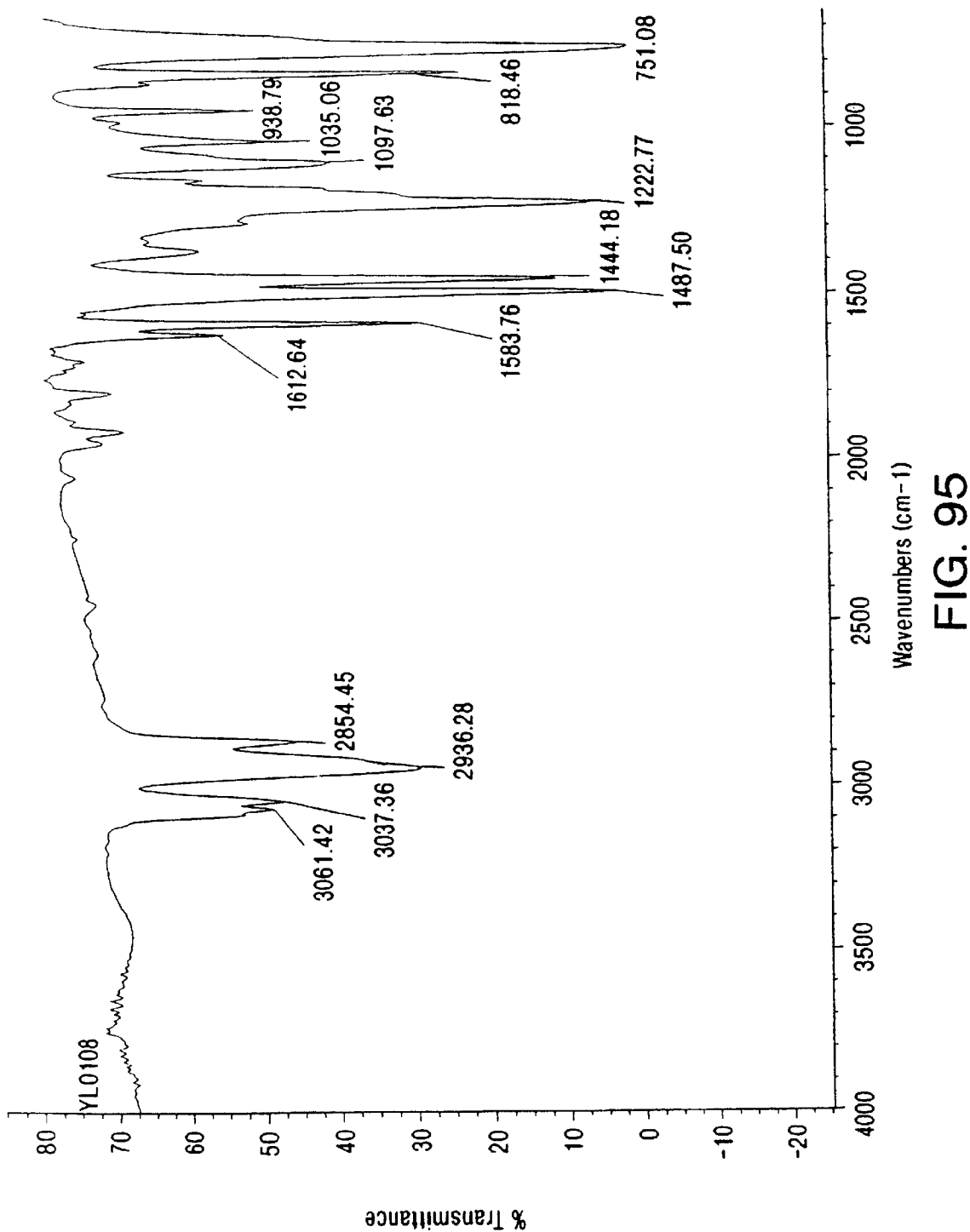
Figure 96:
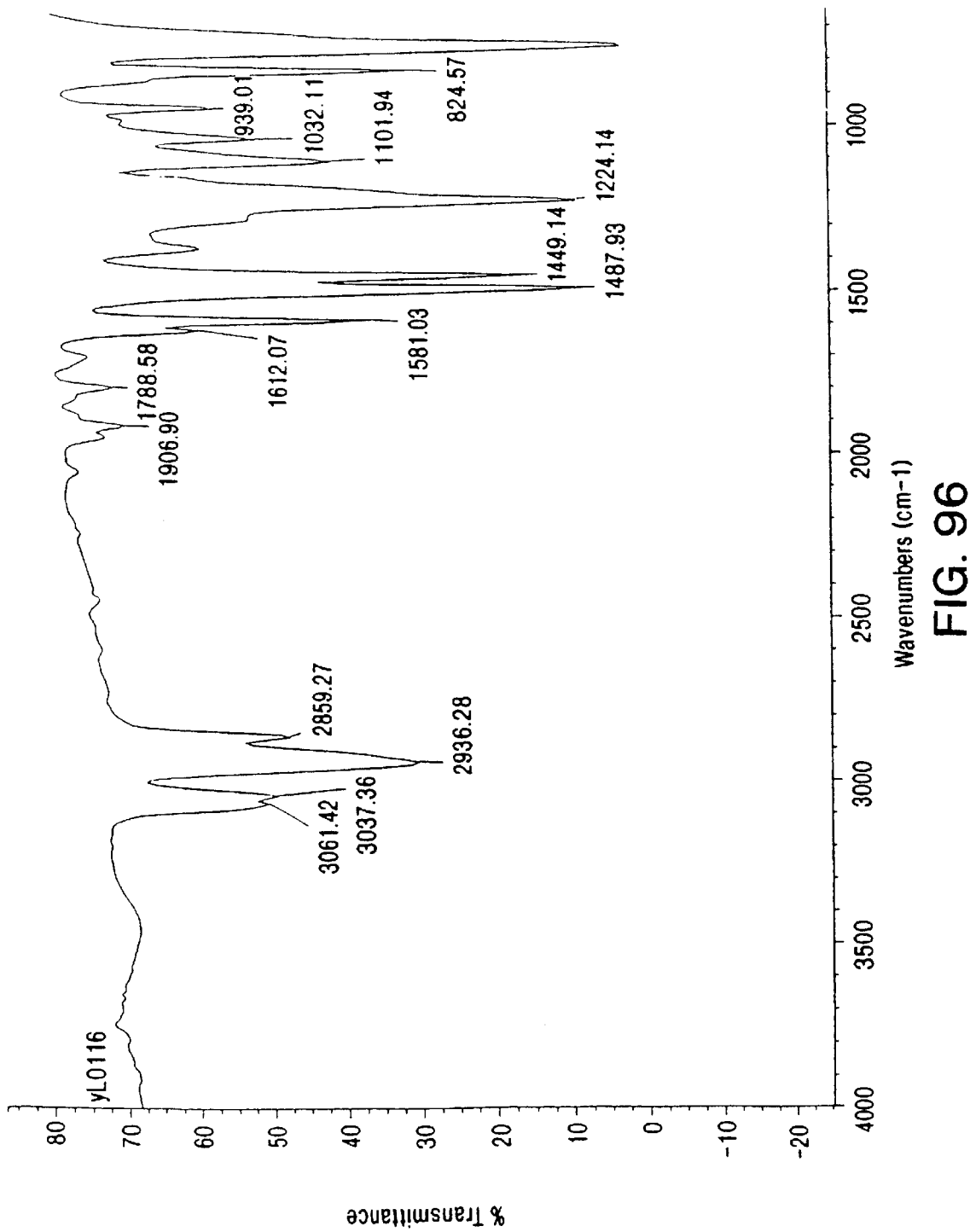
Figure 97:
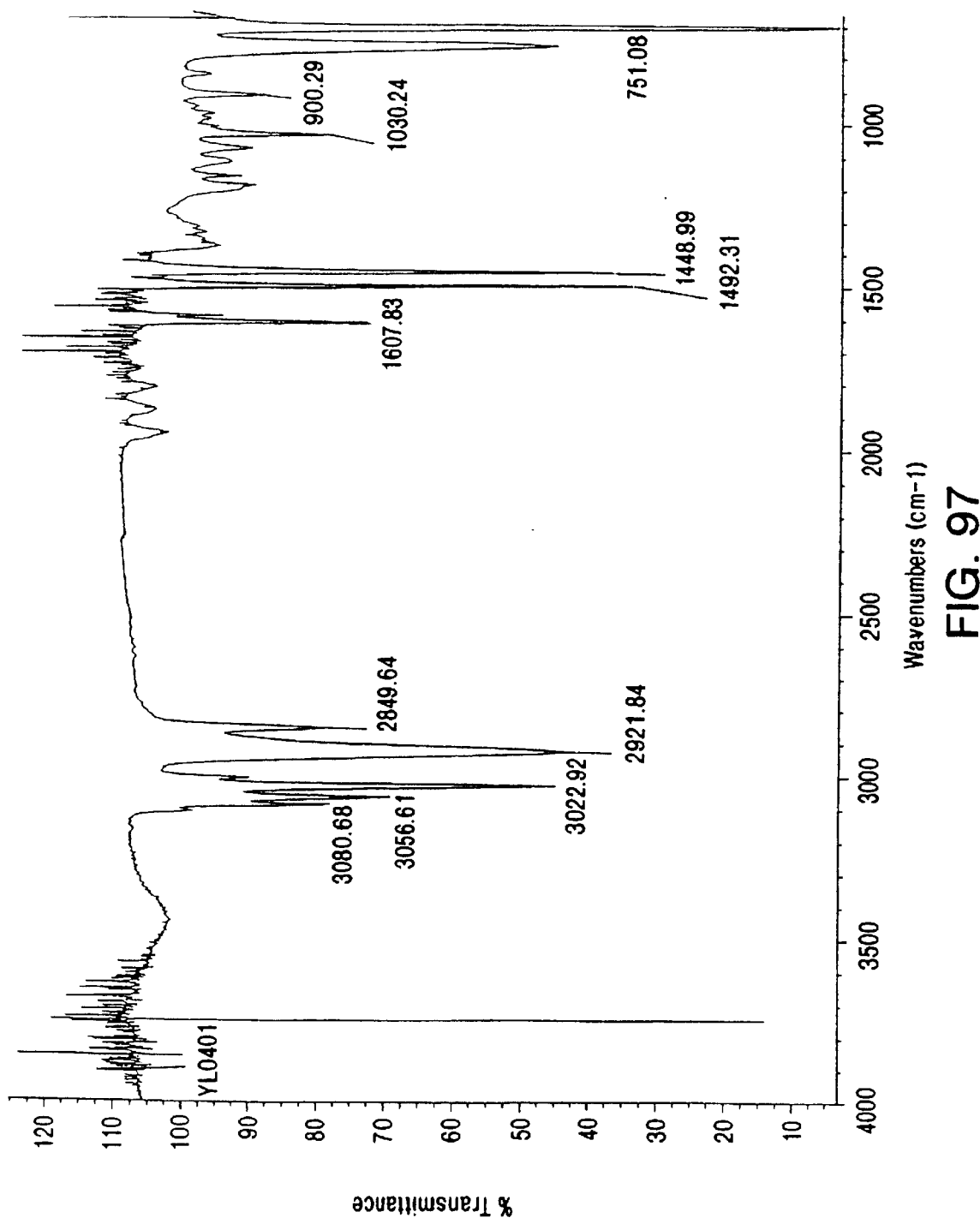
Figure 98:
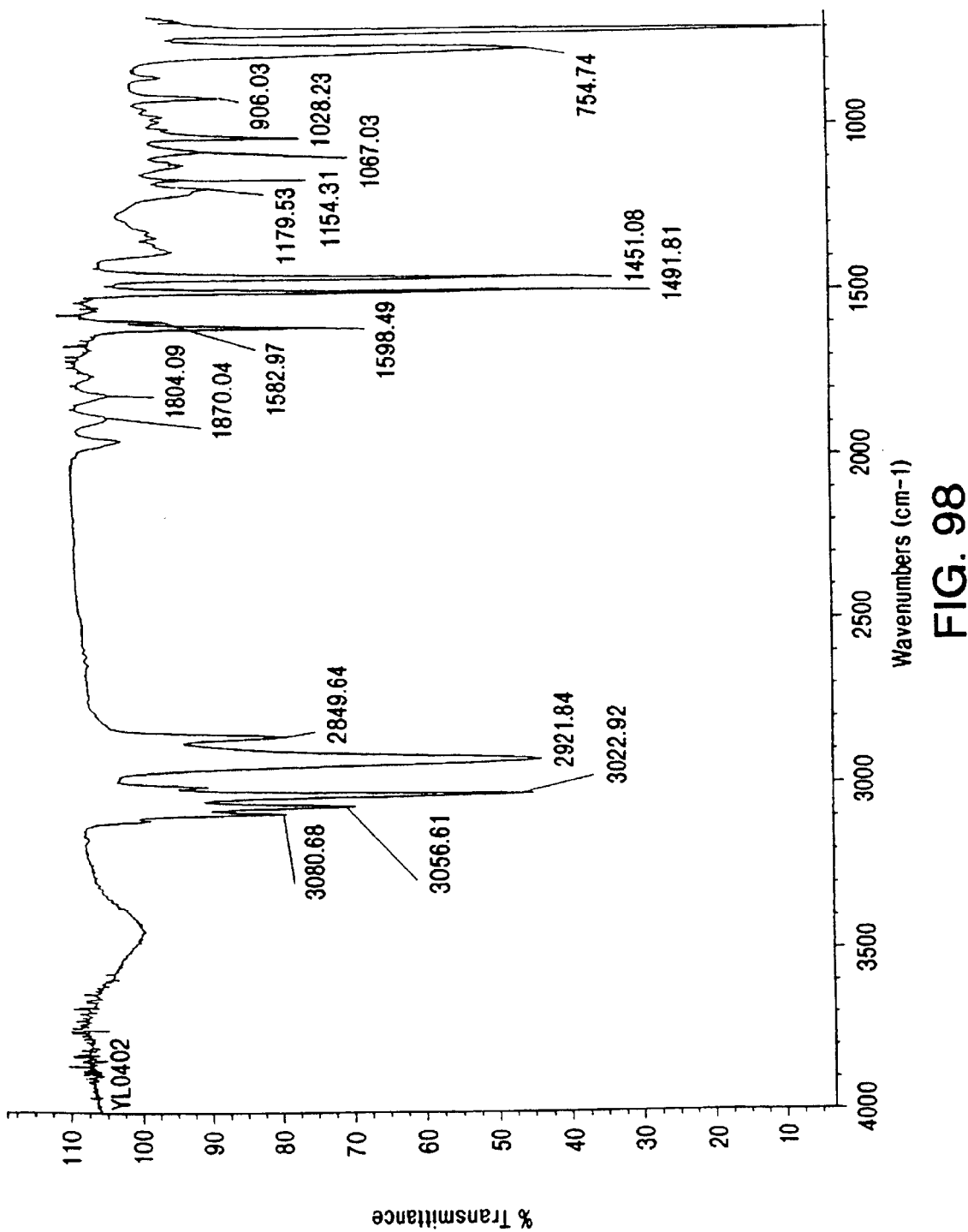
Figure 99:
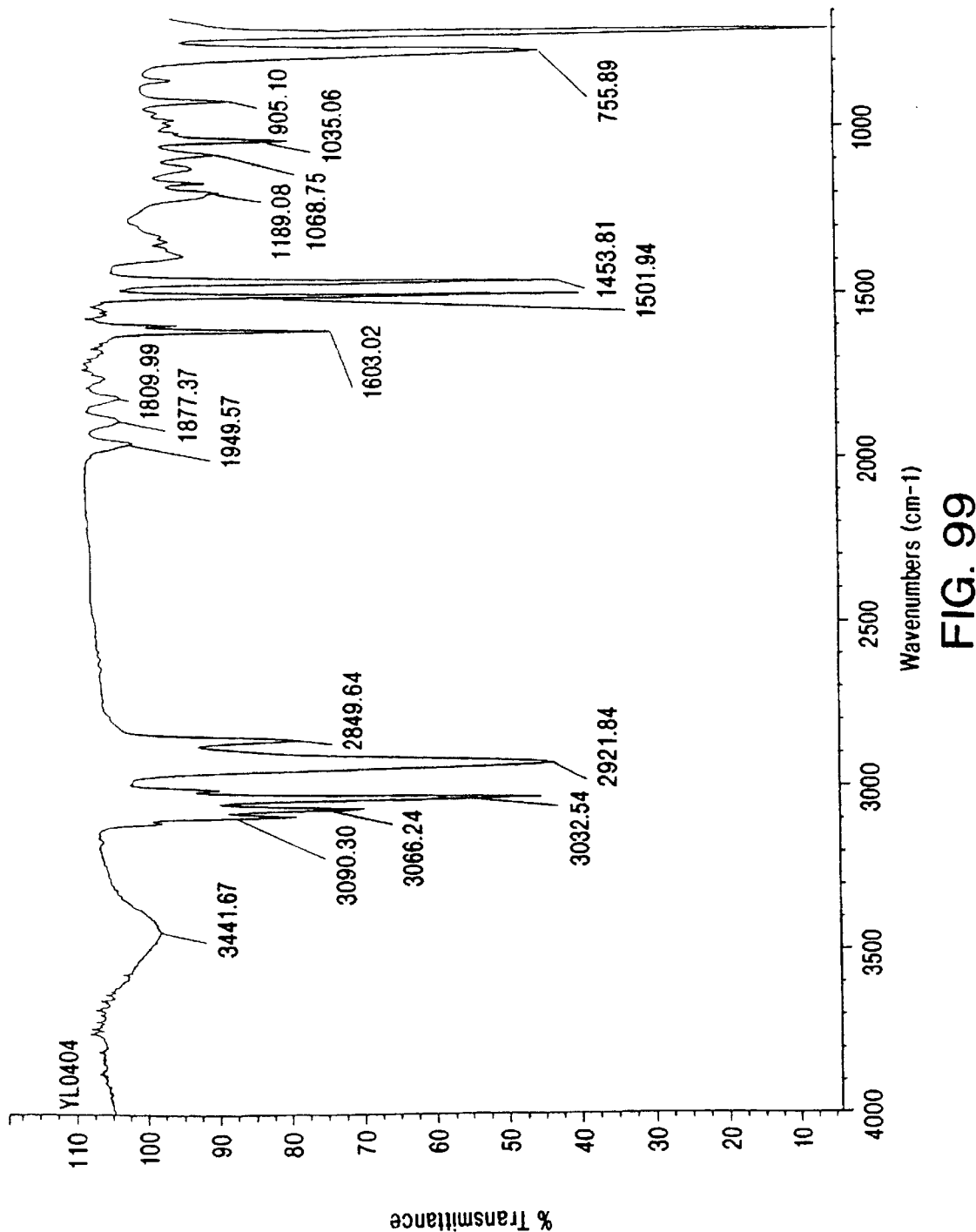
Figure 100:
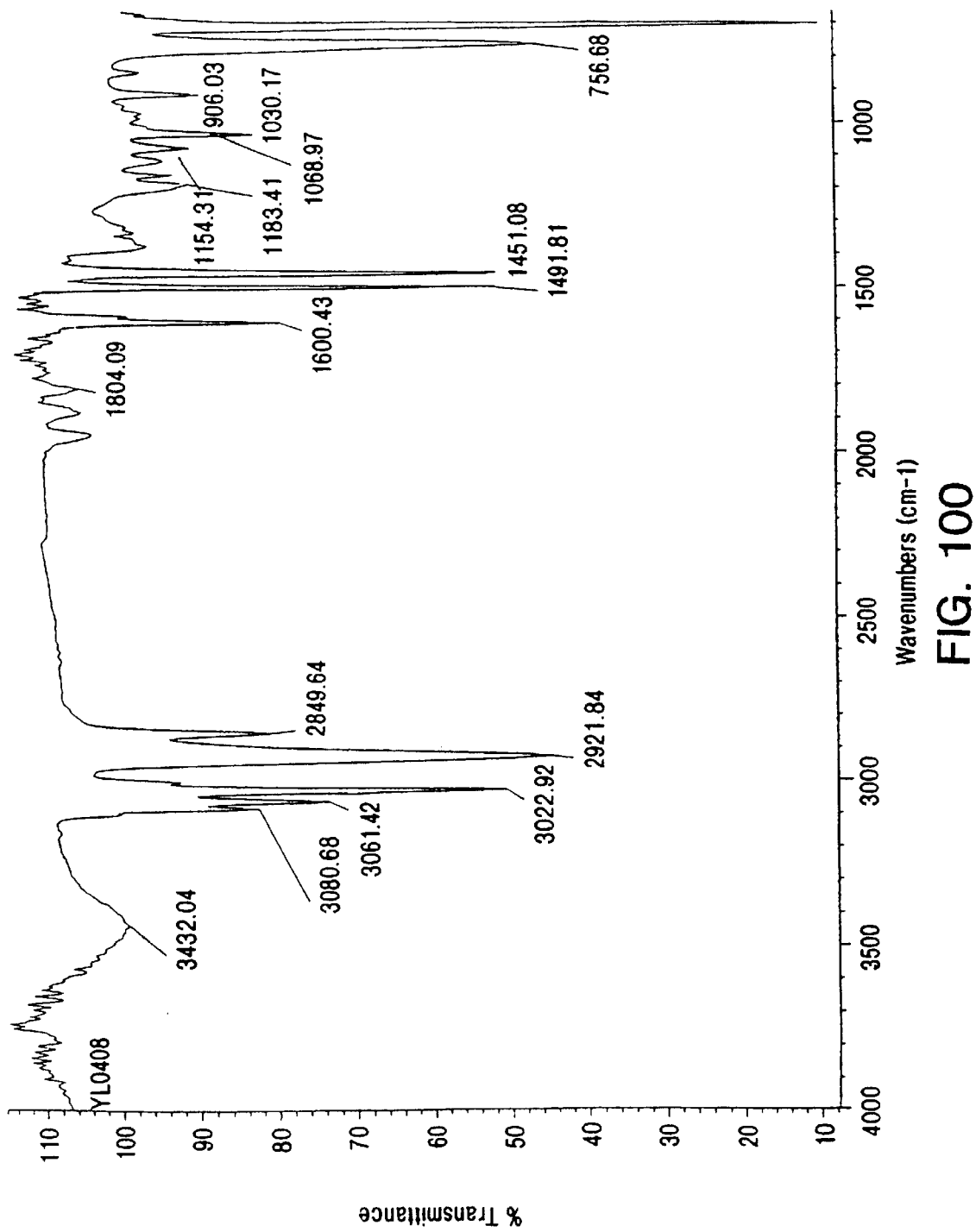
Figure 101:
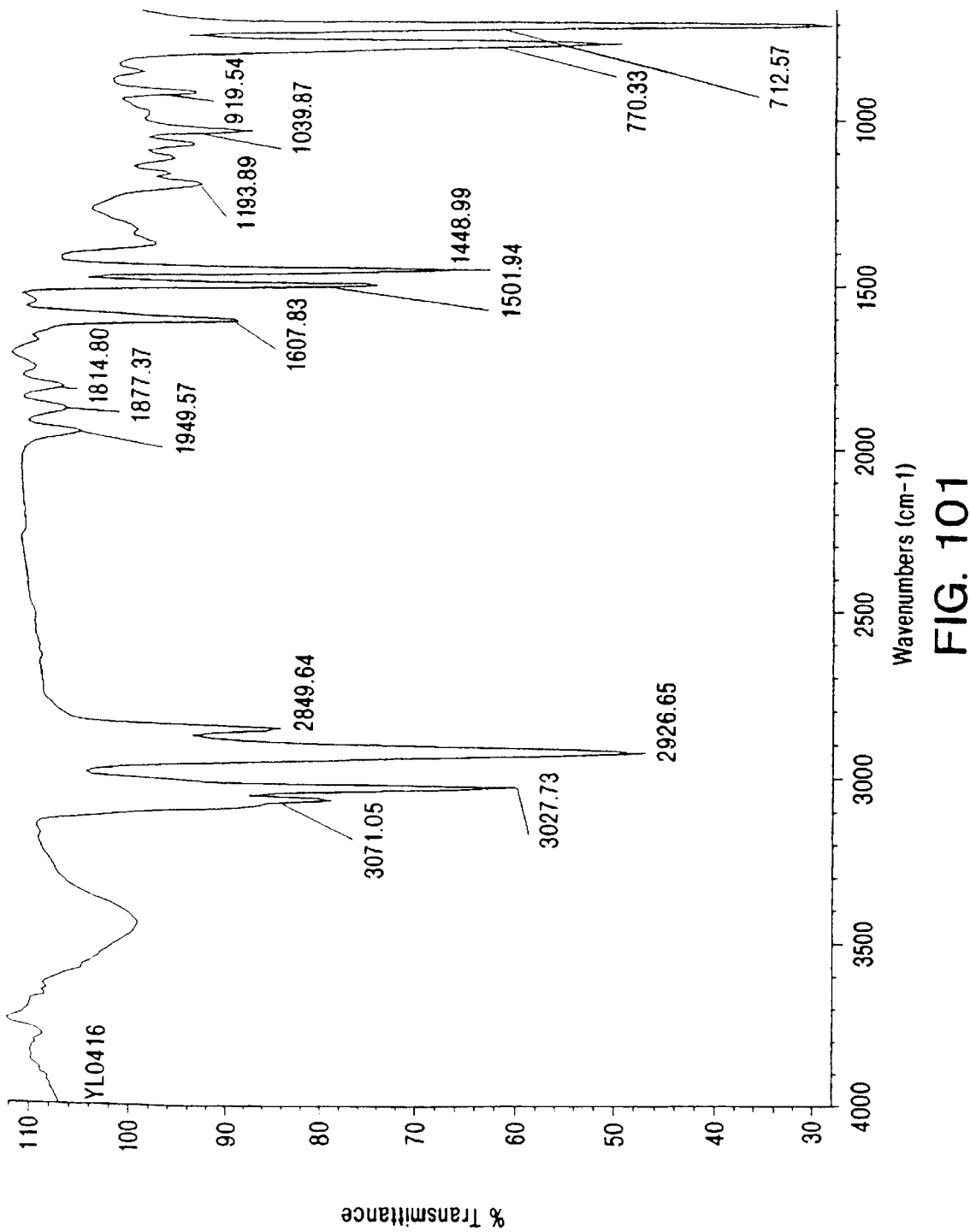
Figure 102:
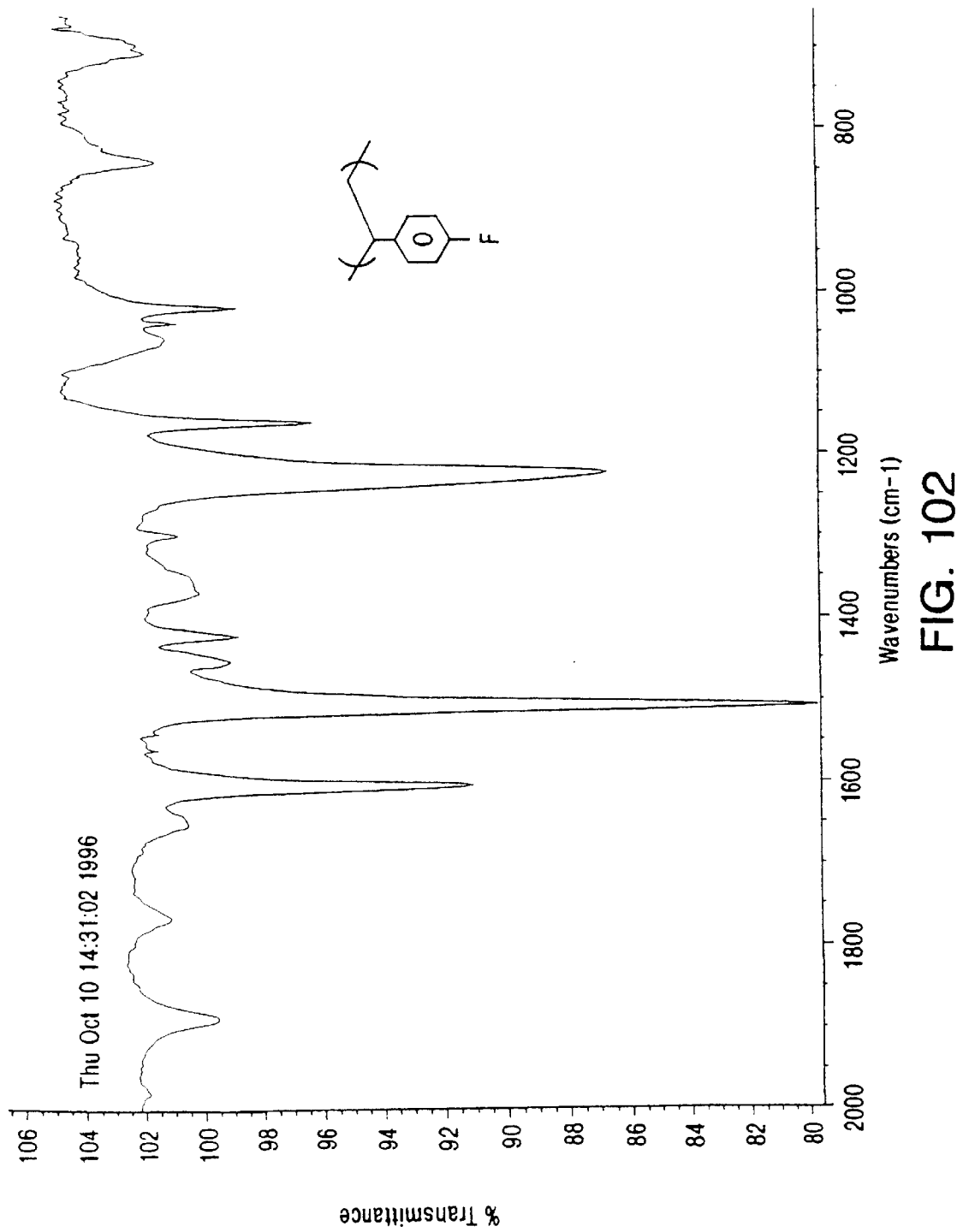
Figure 103:
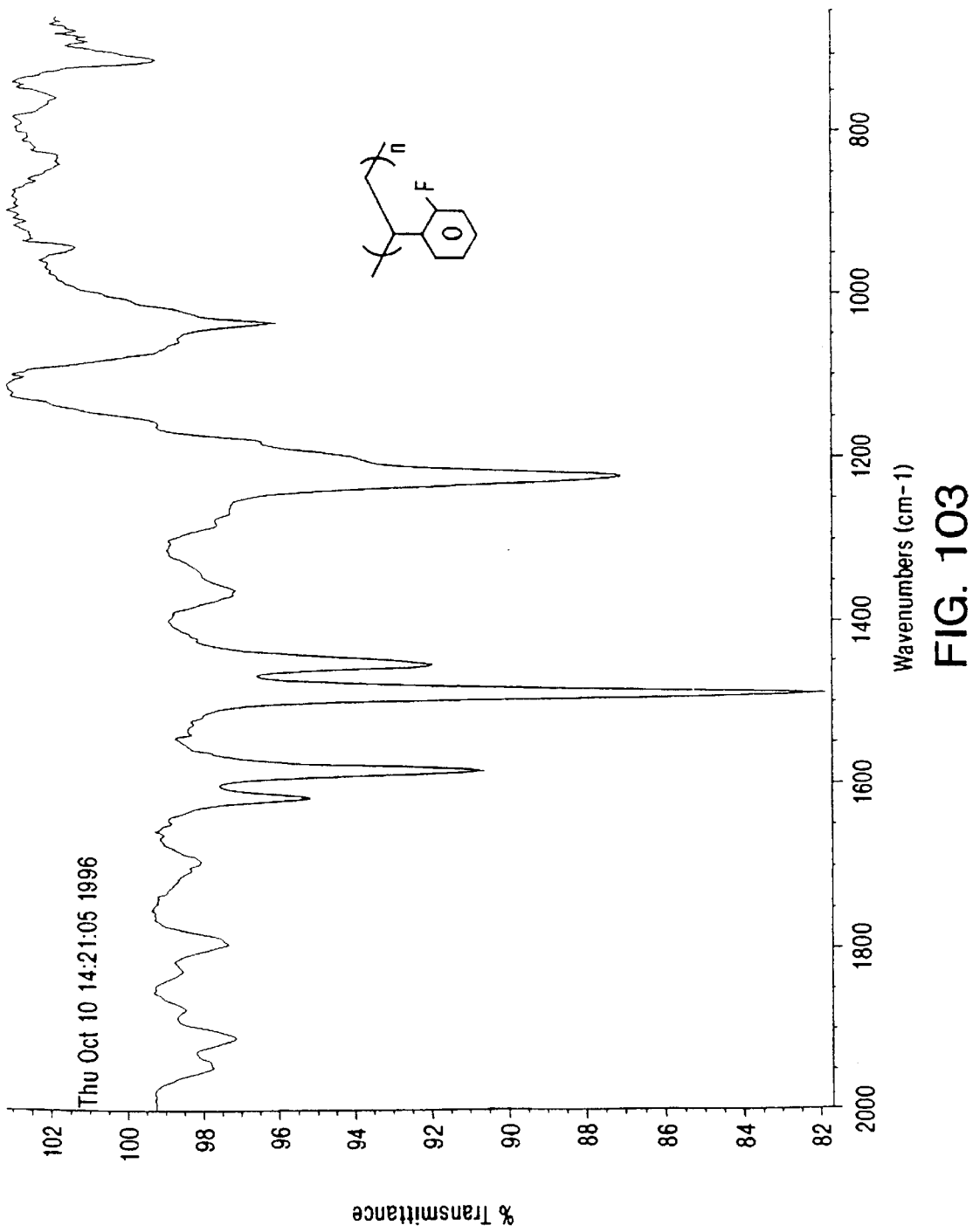
Figure 104:
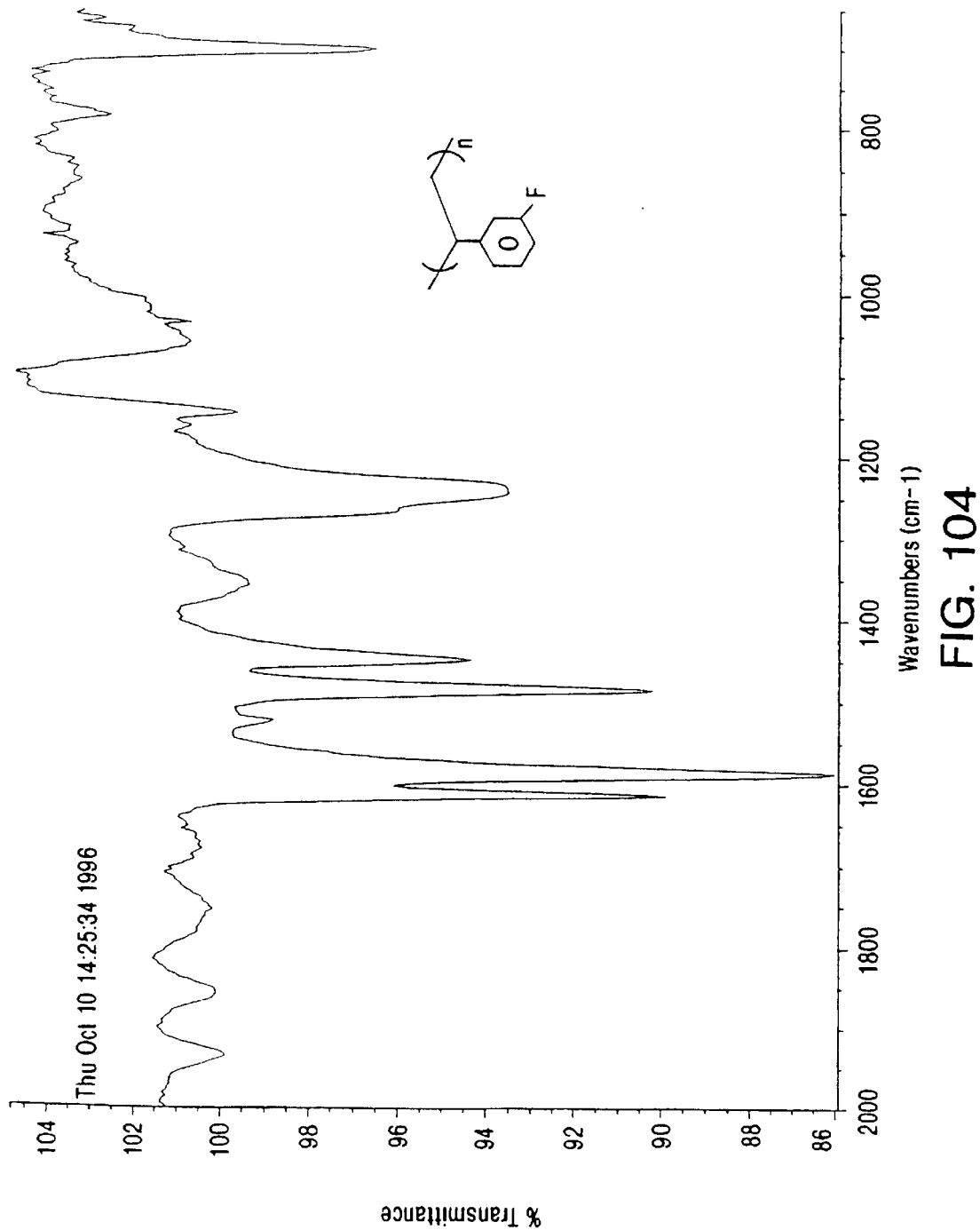
Figure 105:
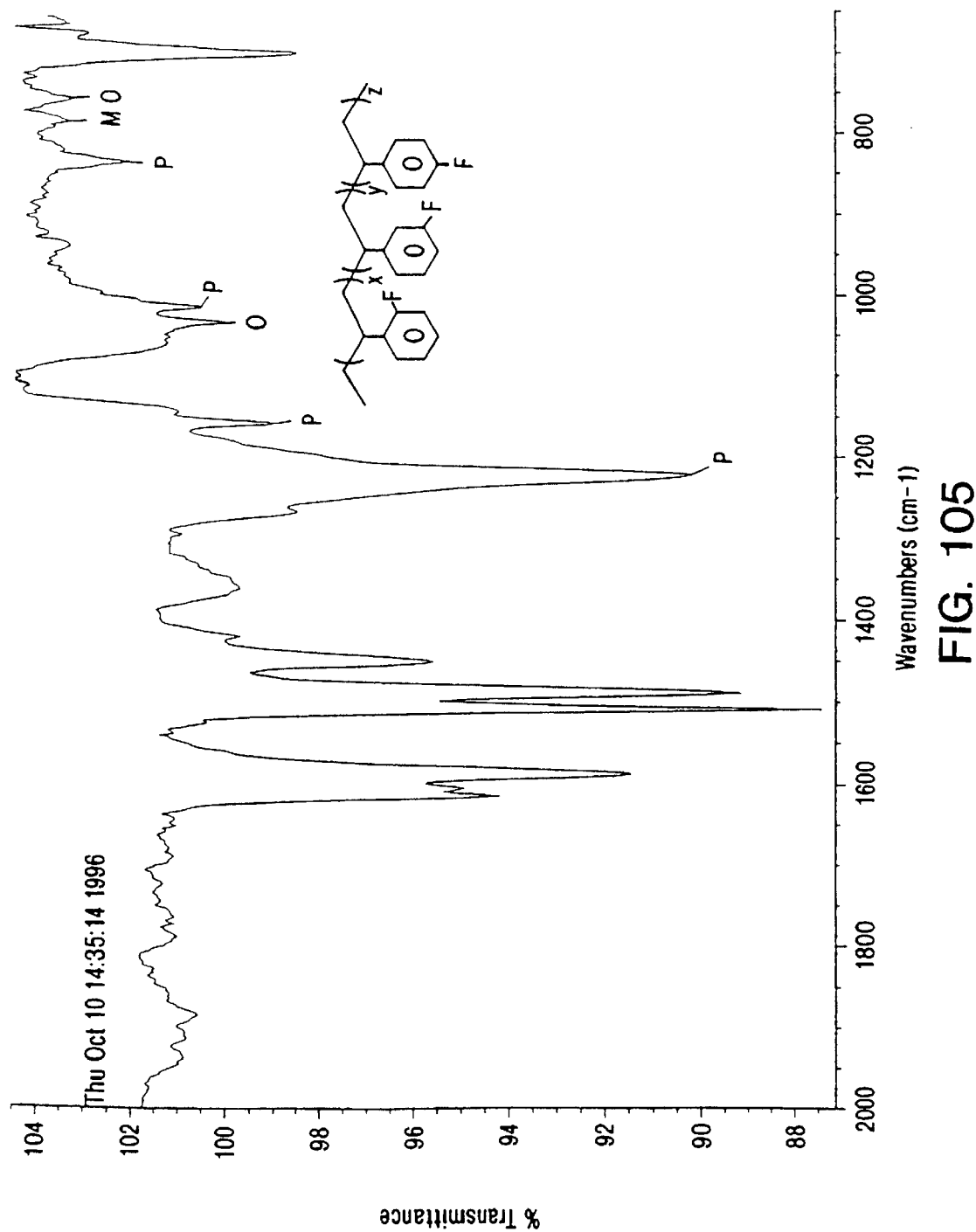
Figure 106:
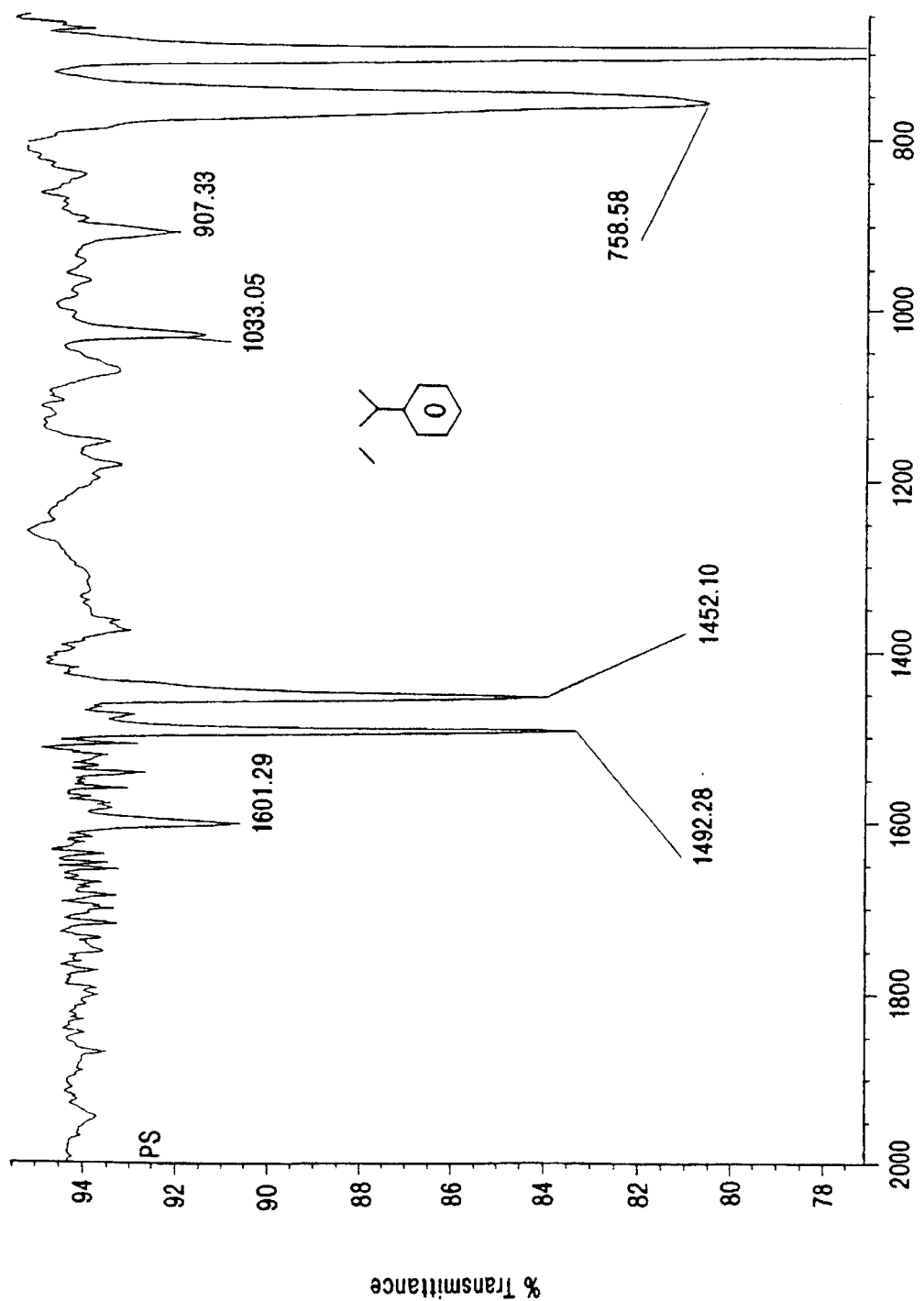
Figure 108:
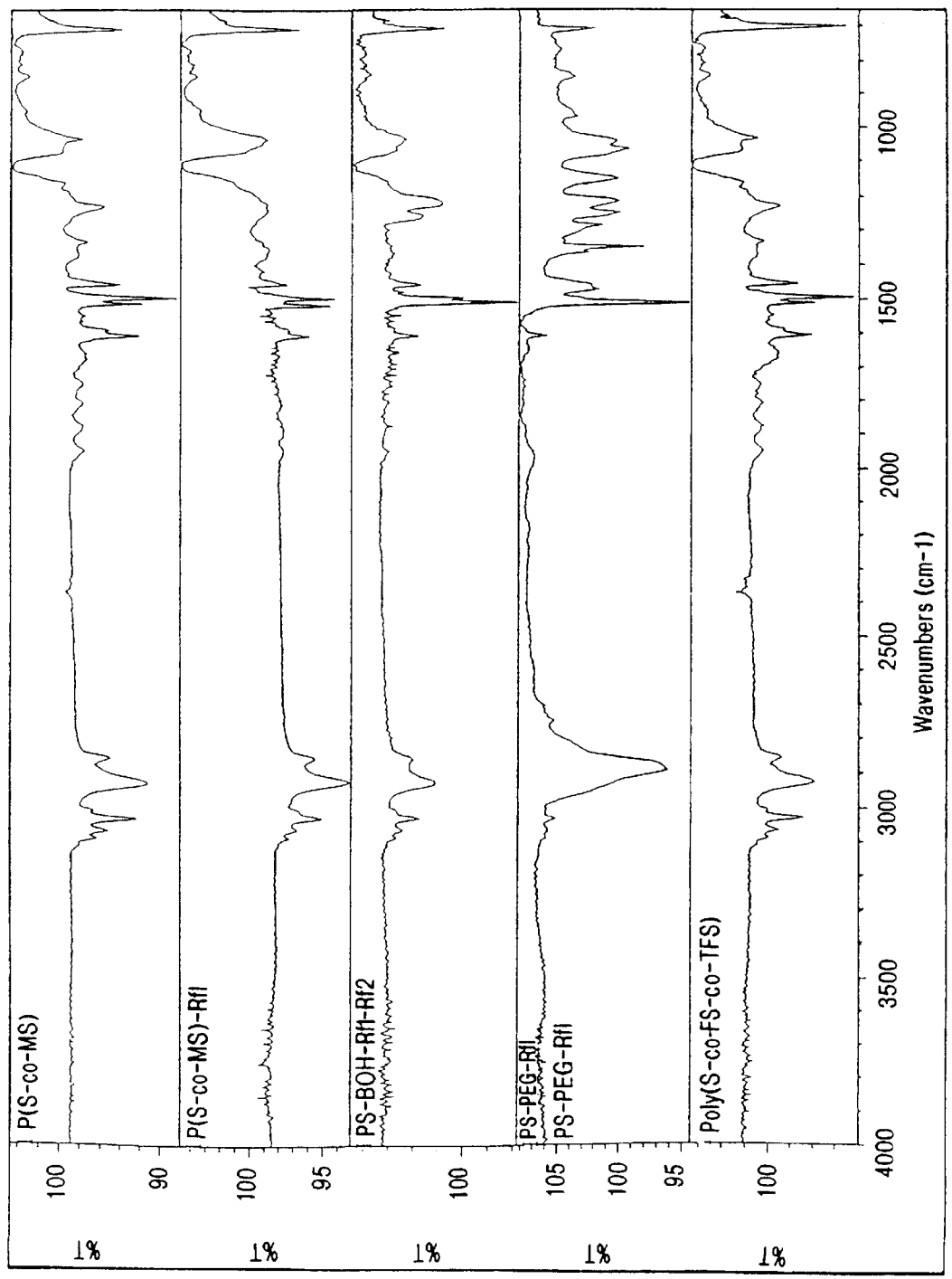
Figure 109:
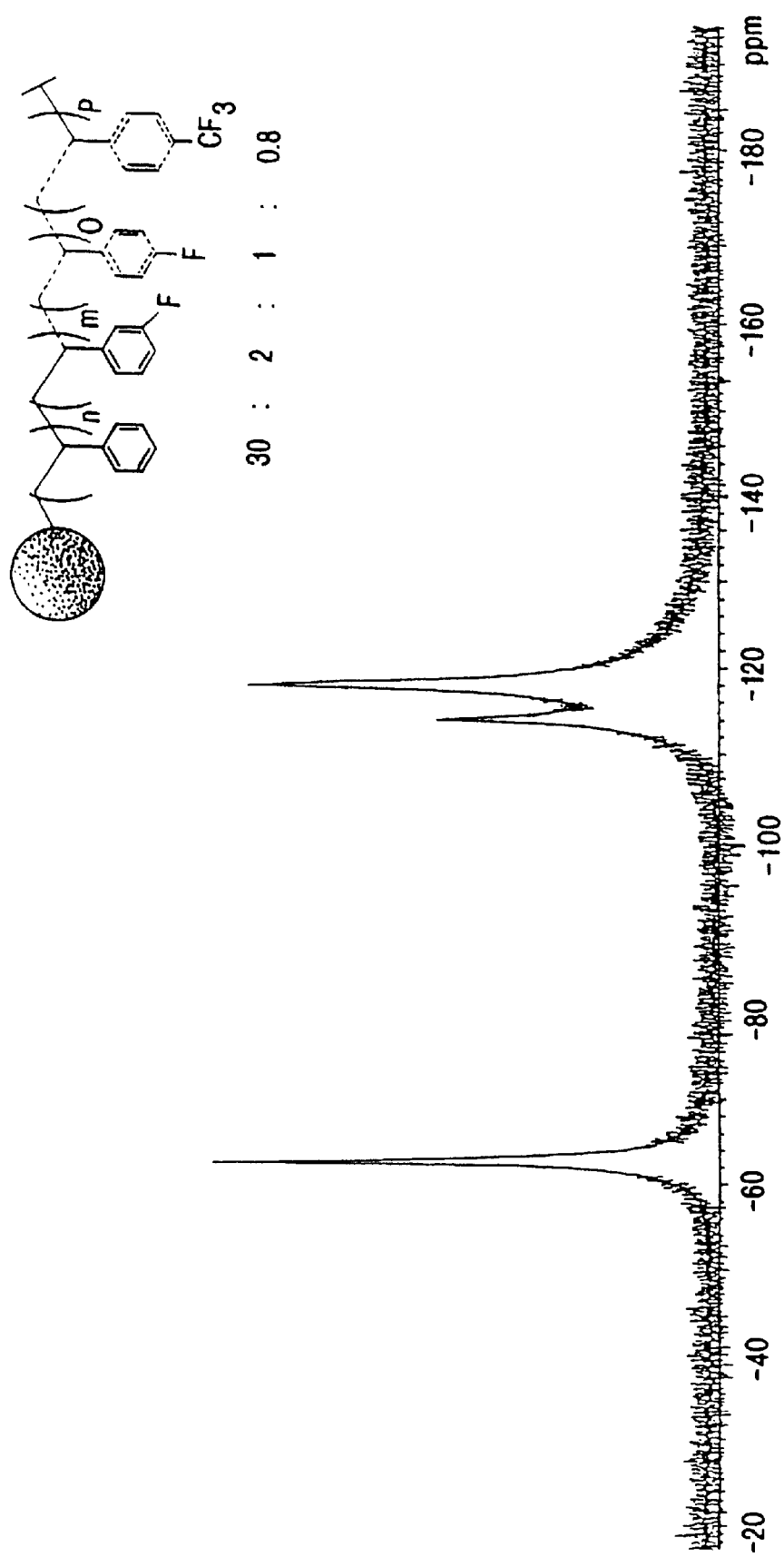
Figure 110:
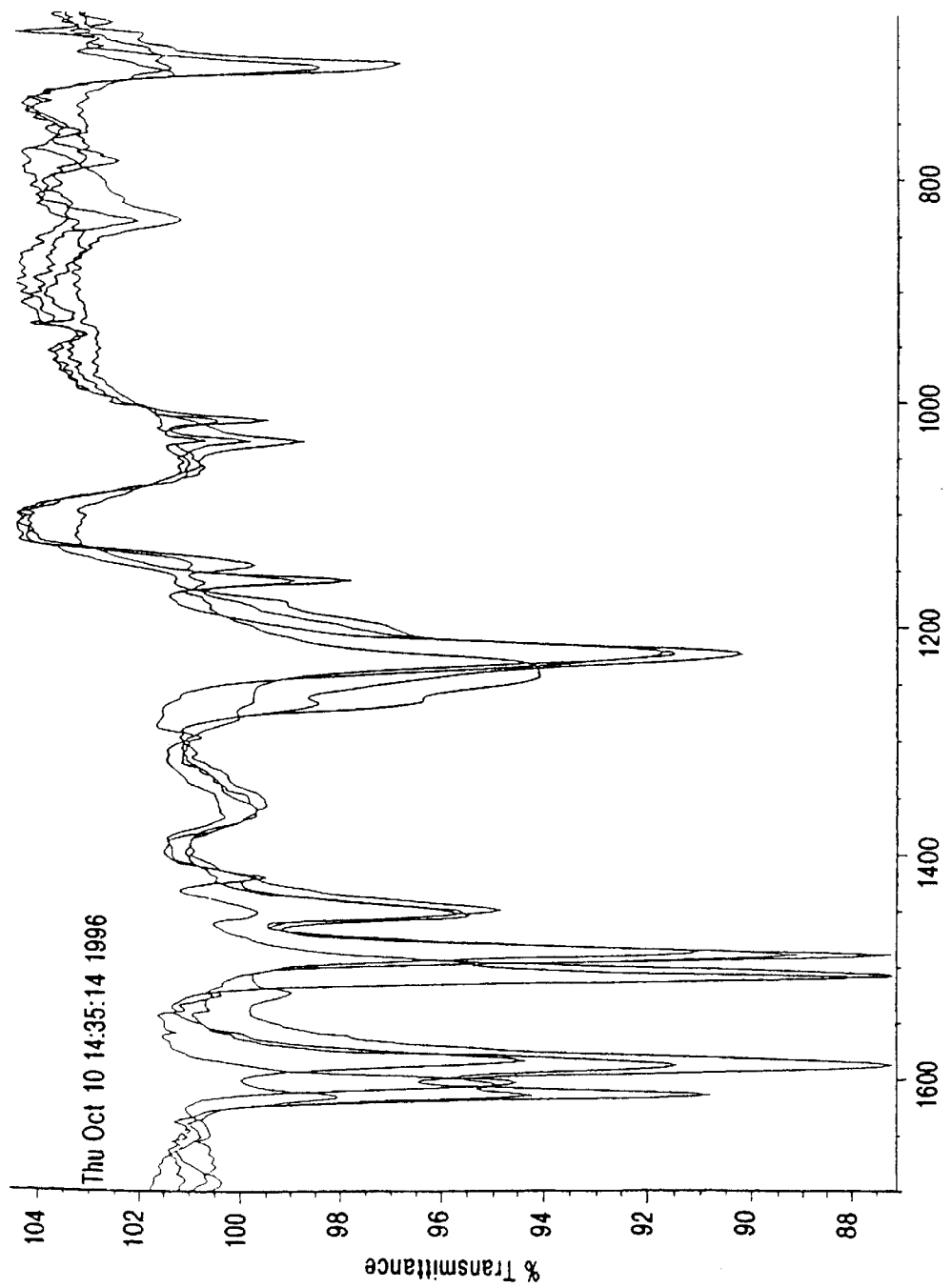
Figure 111:
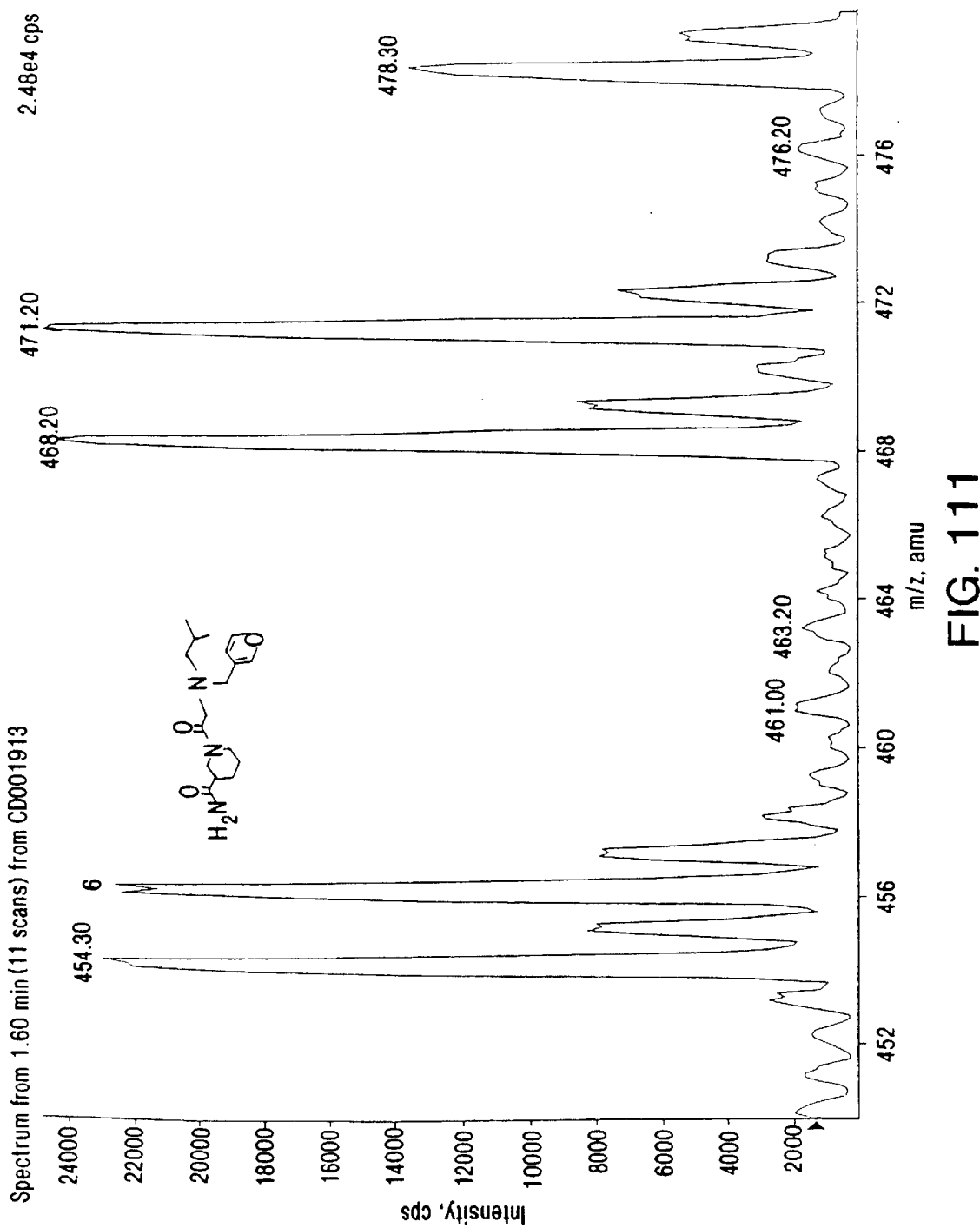
Figure 112:
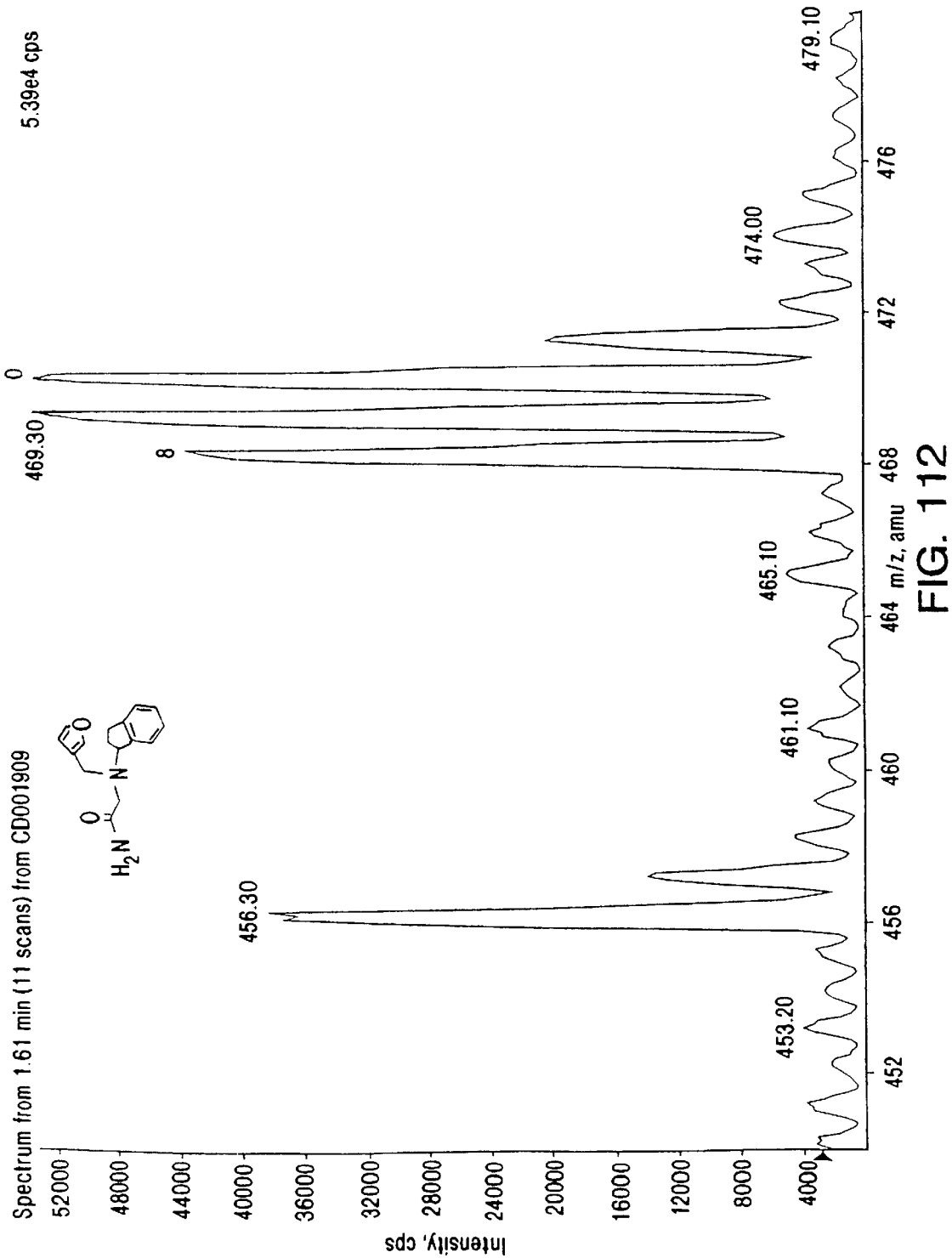
Figure 113:
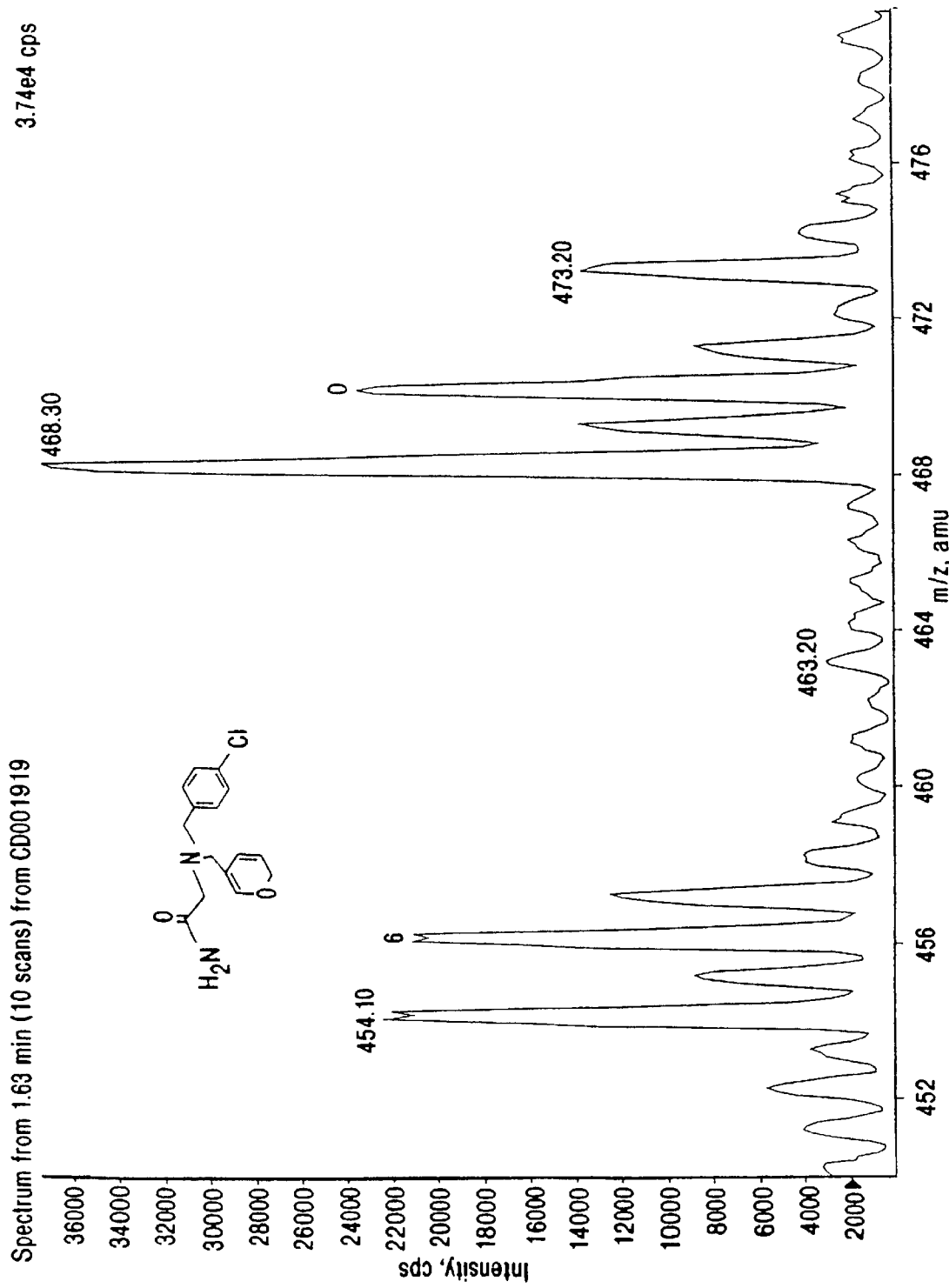
Figure 114:
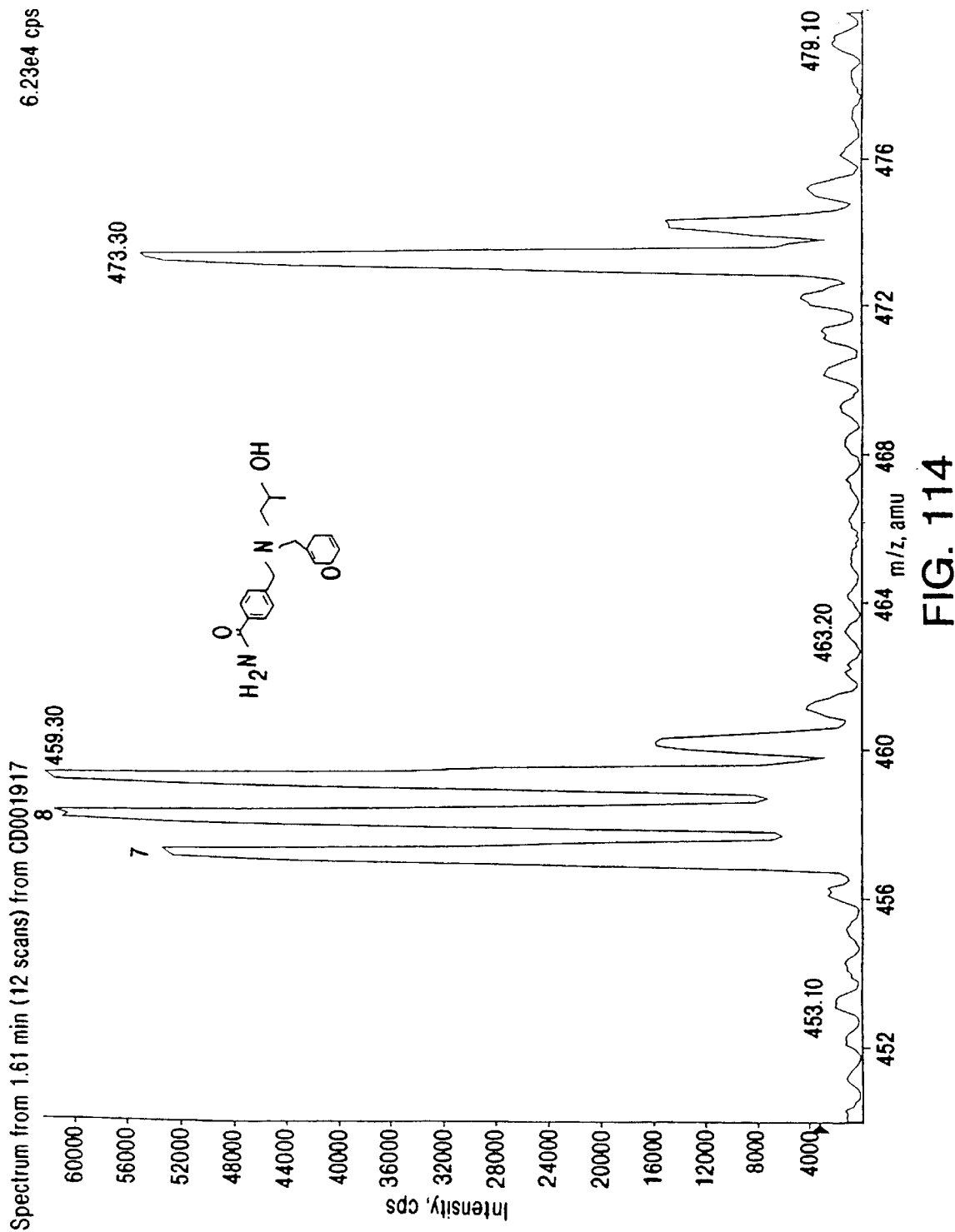
Figure 115:
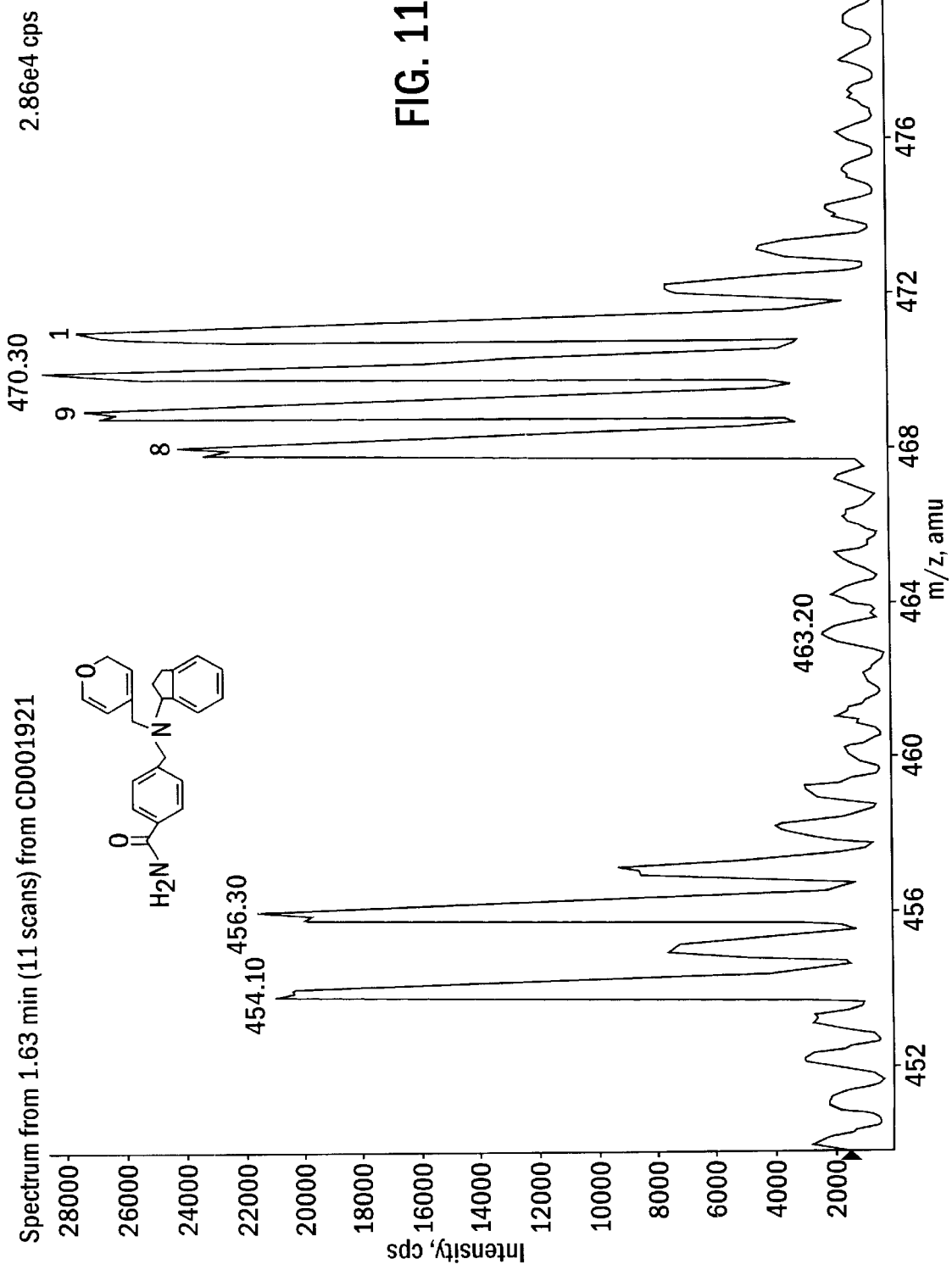
Figure 116:
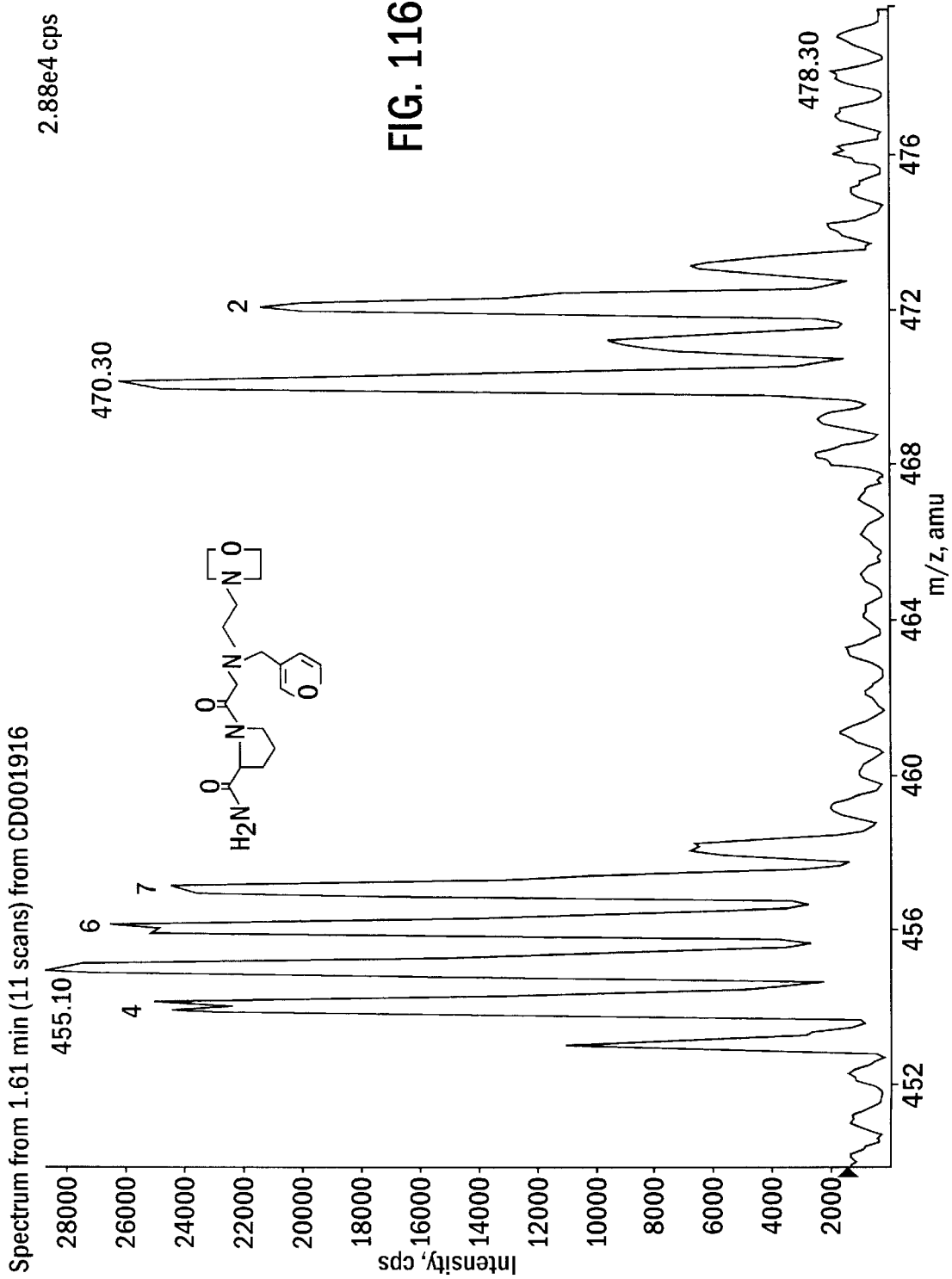
Figure 117:
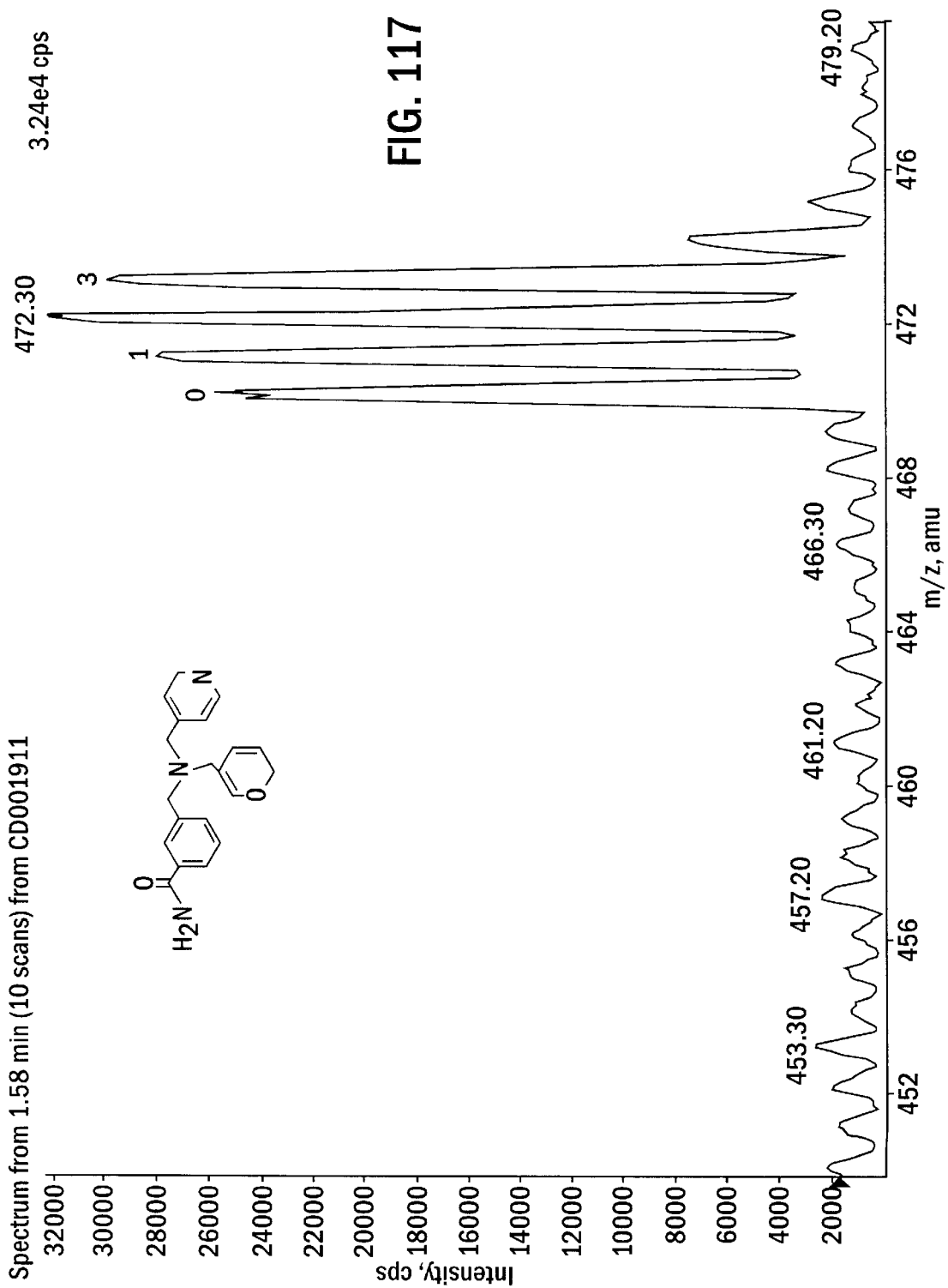
Figure 118:
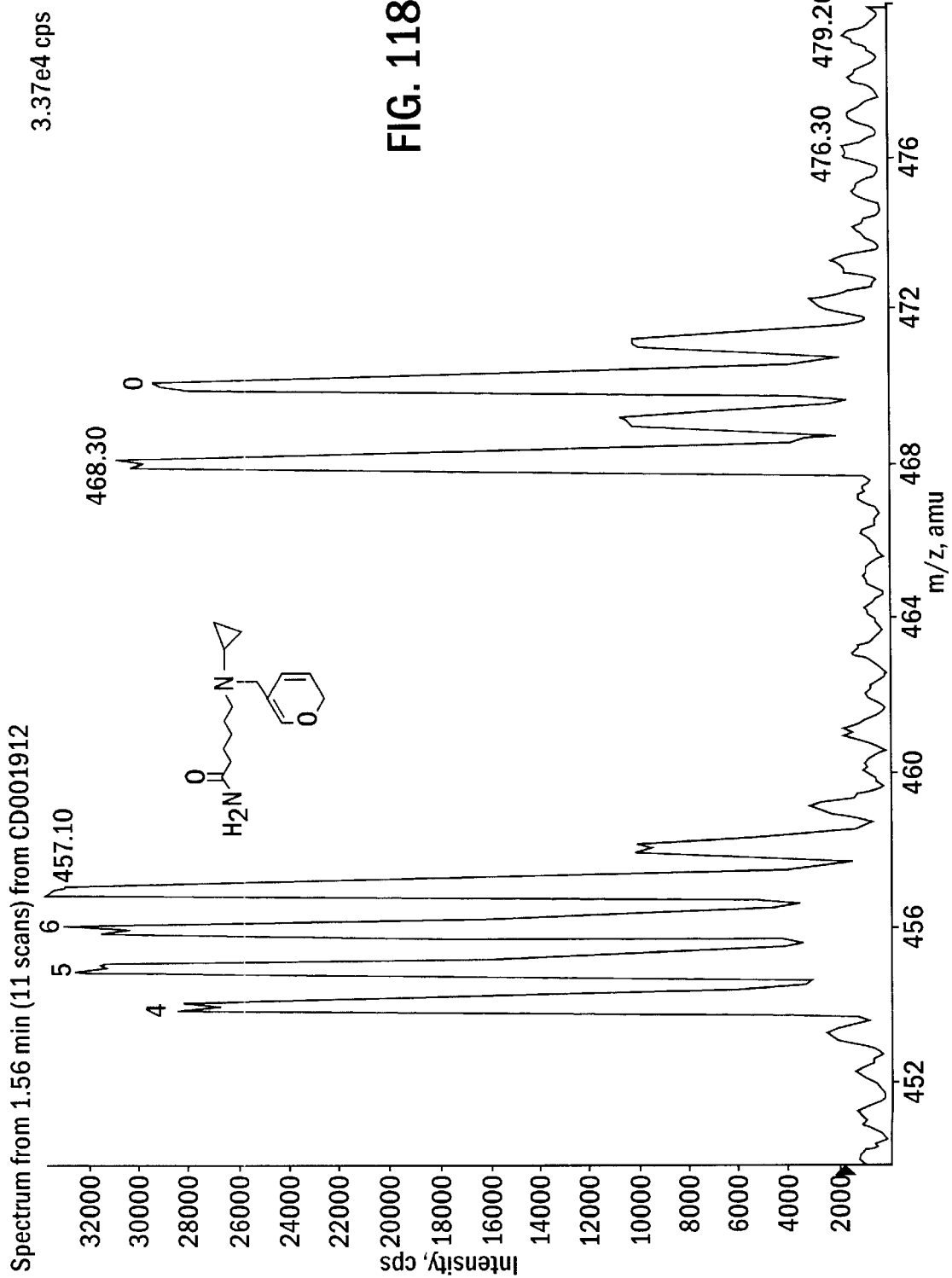
Figure 119:
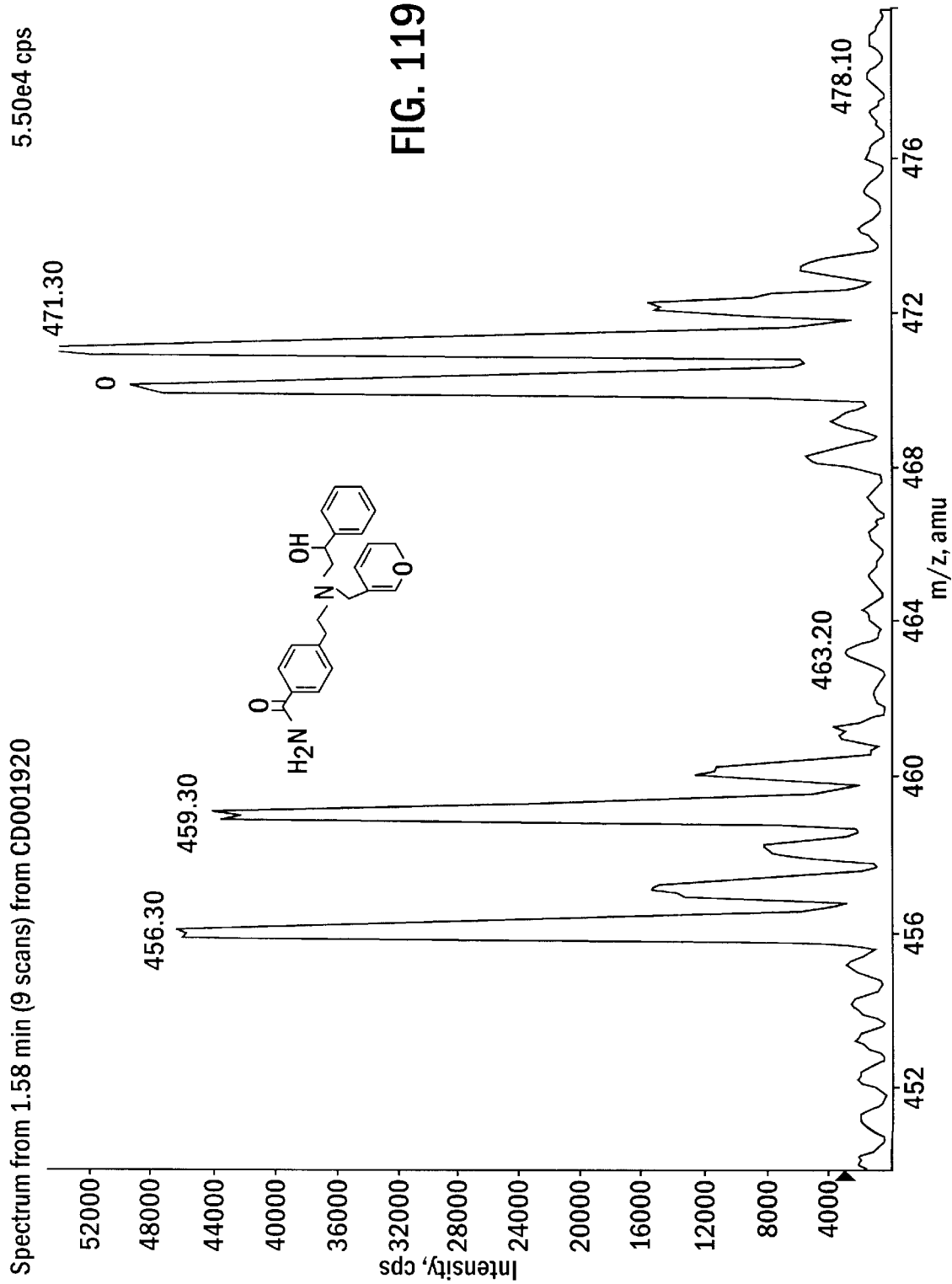
Figure 120:
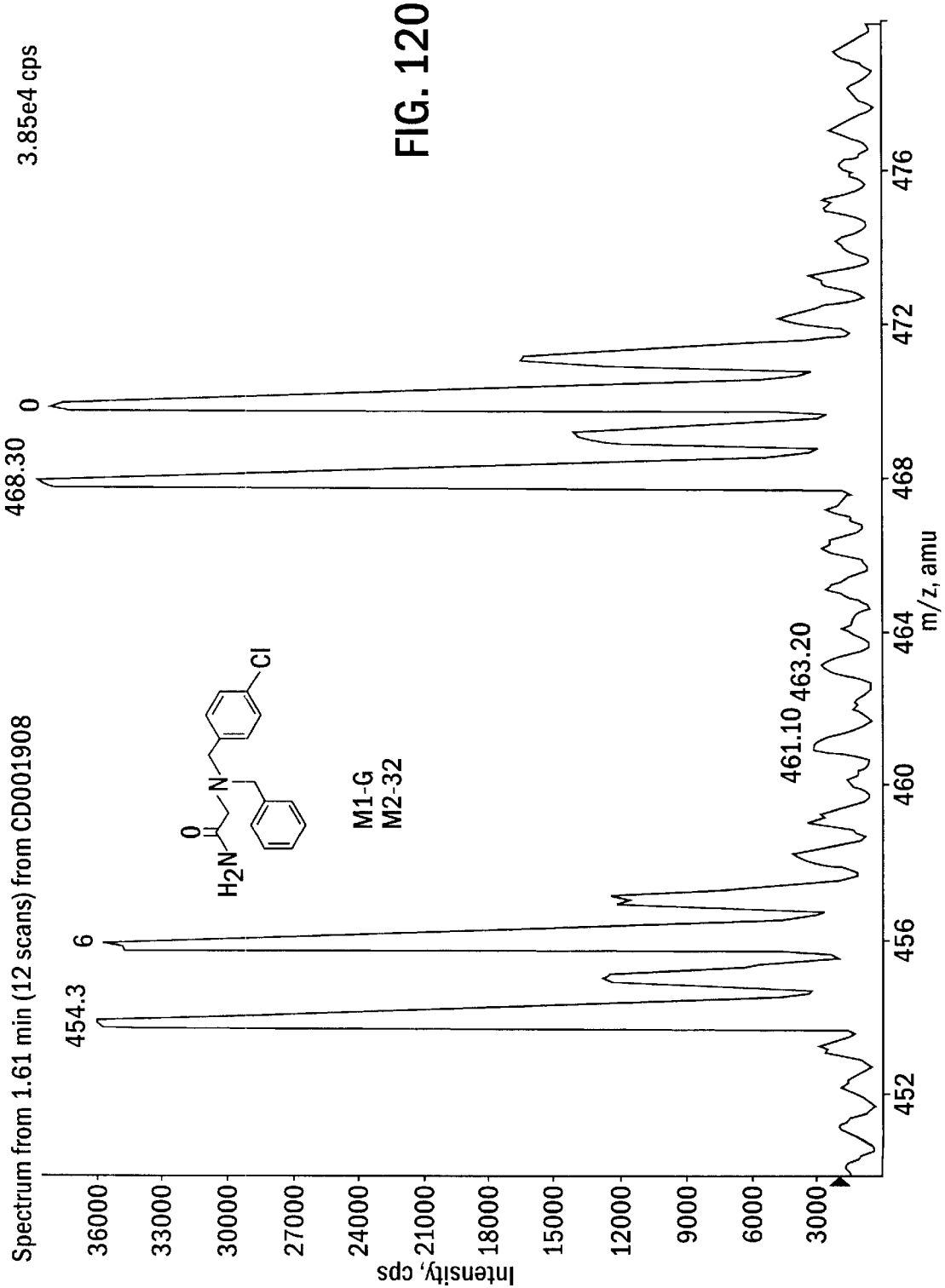
Figure 121:
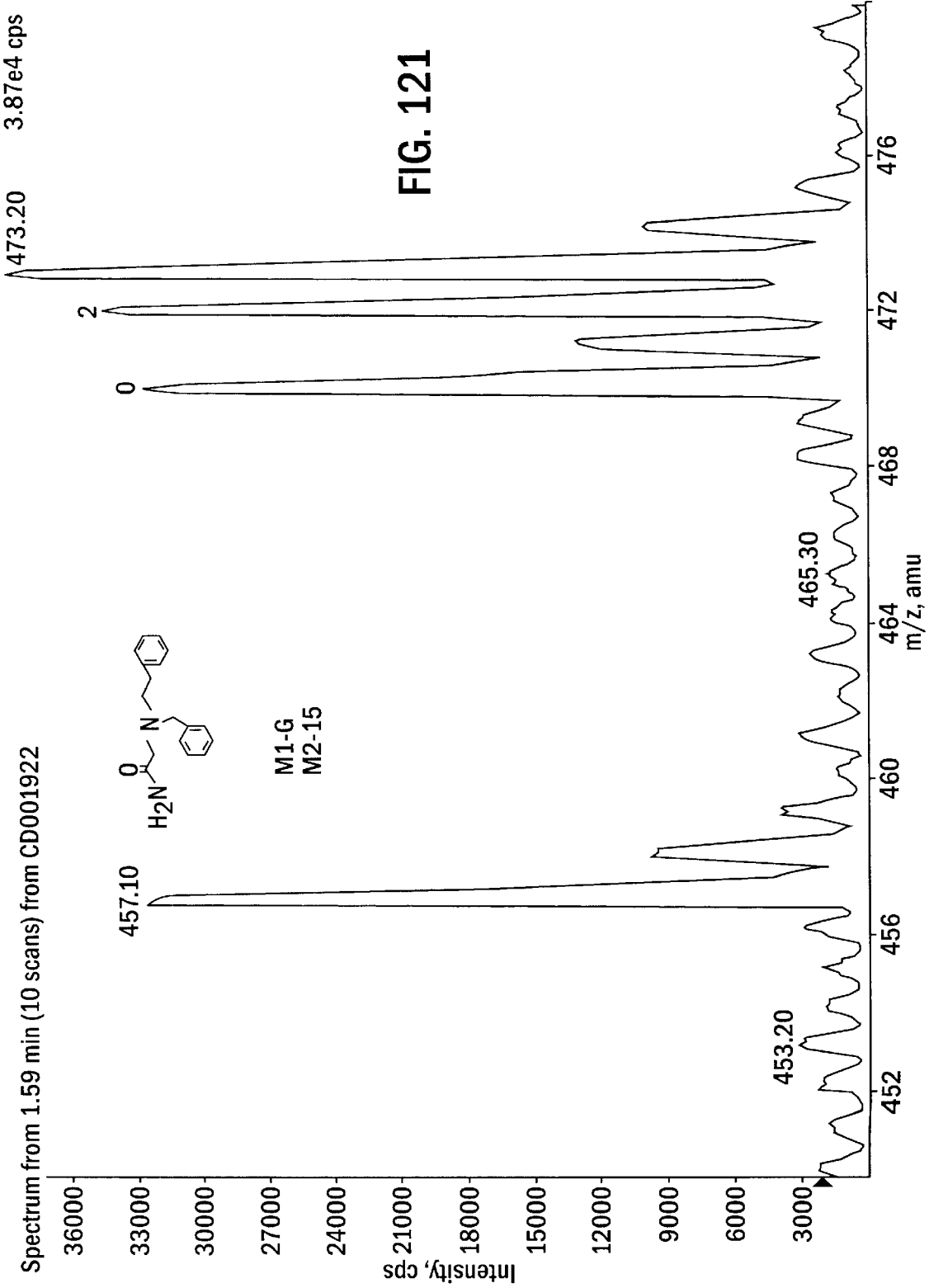
Figure 122:
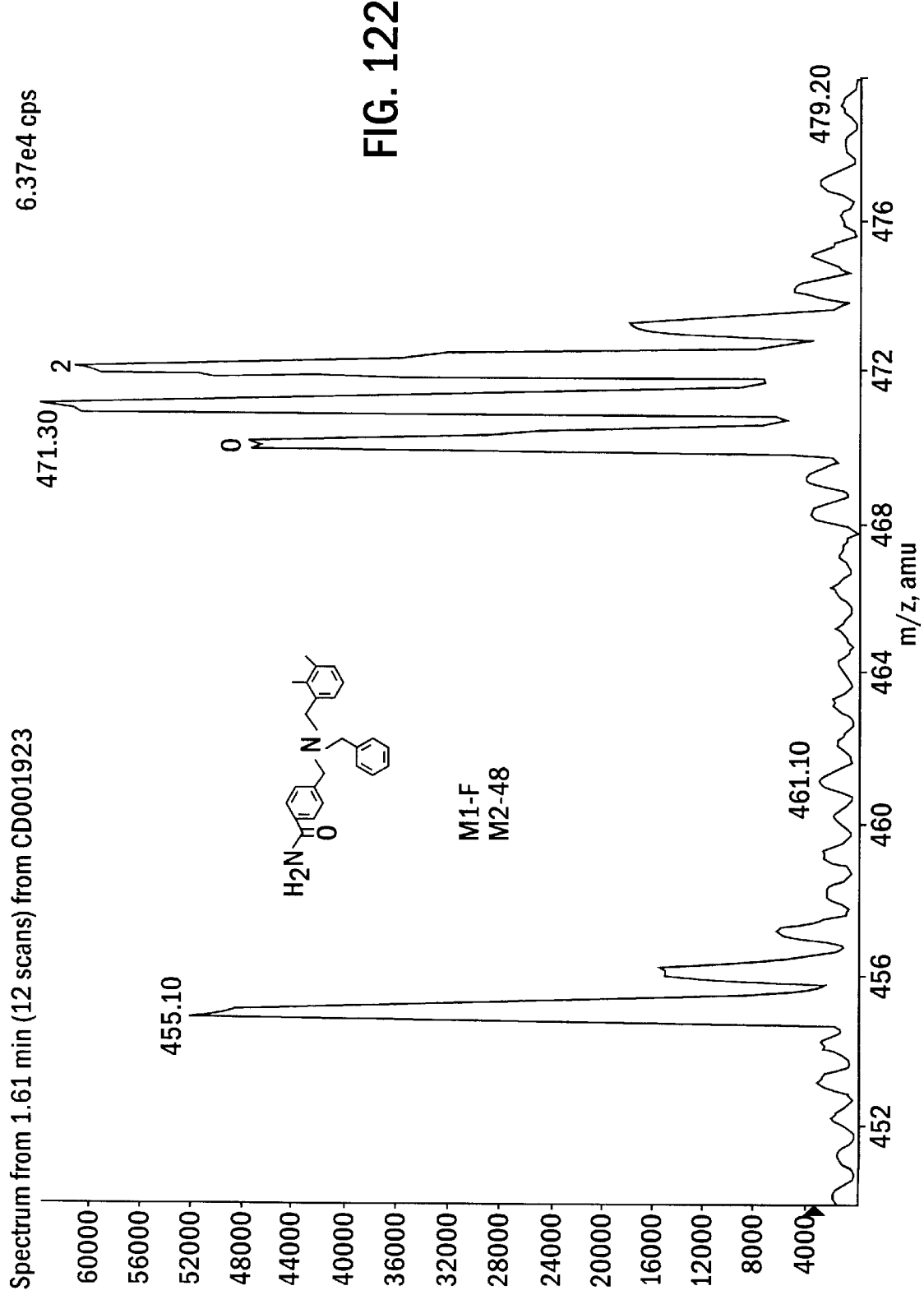
Figure 123:
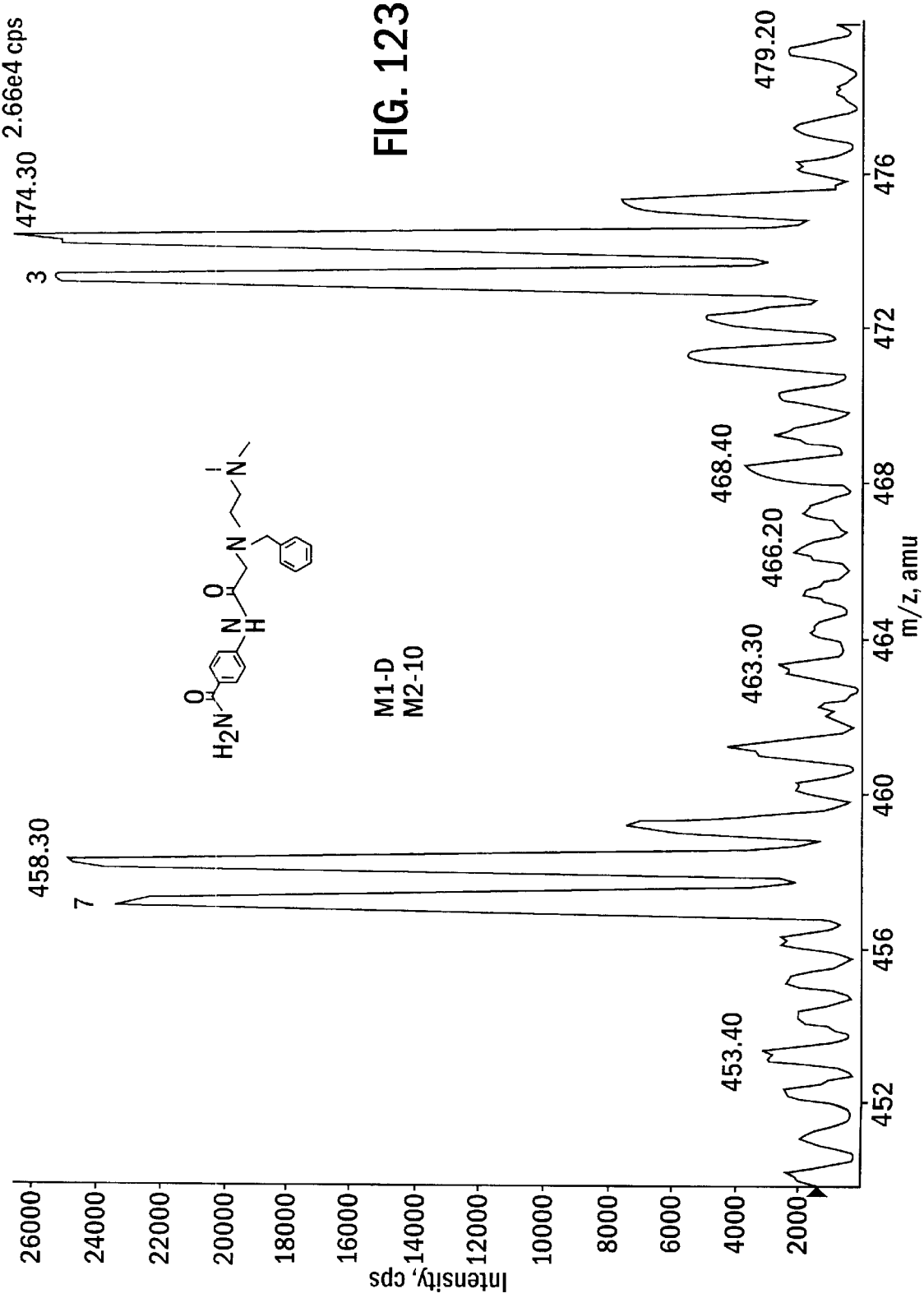
Figure 124:
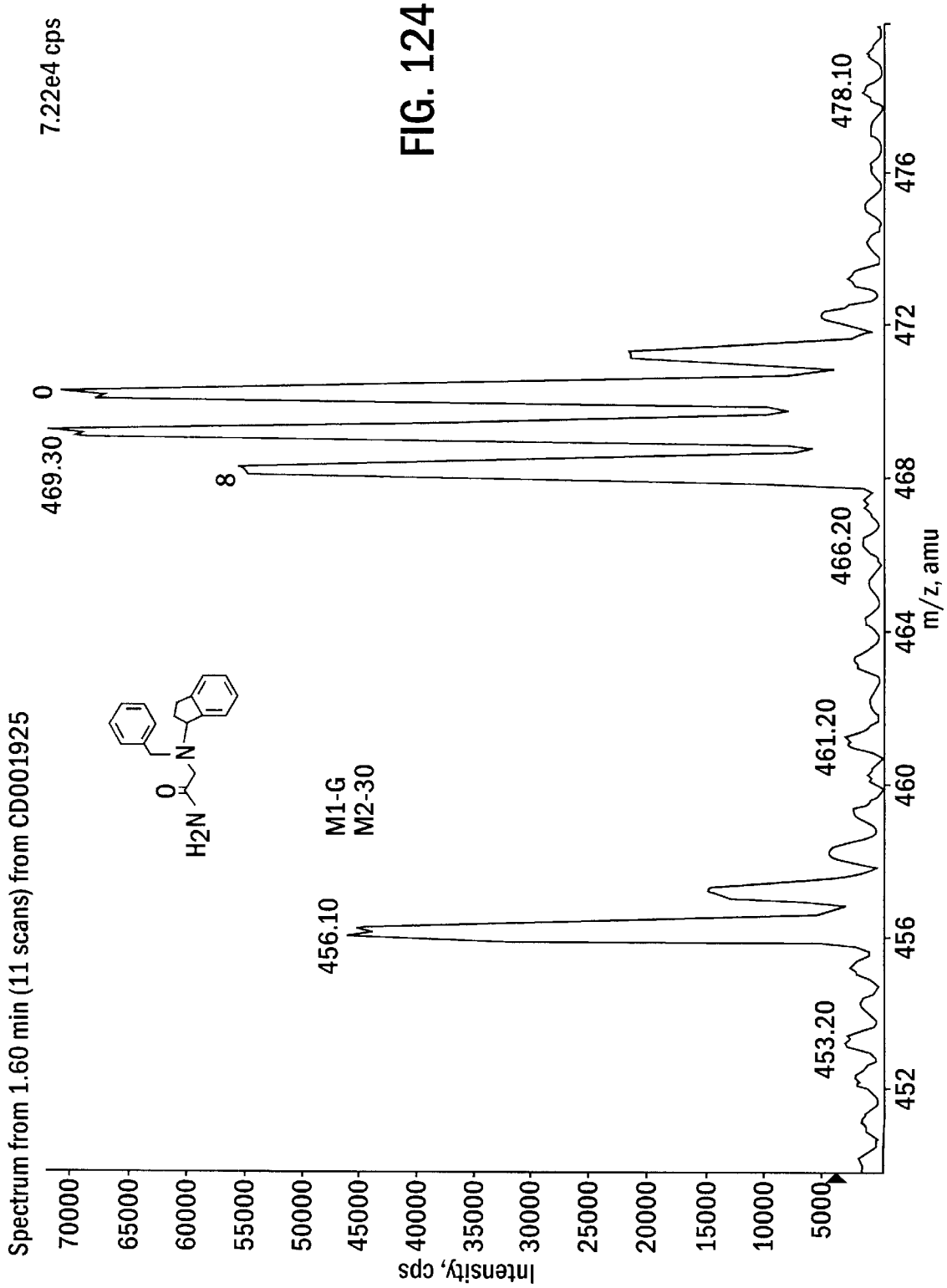
Figure 125:
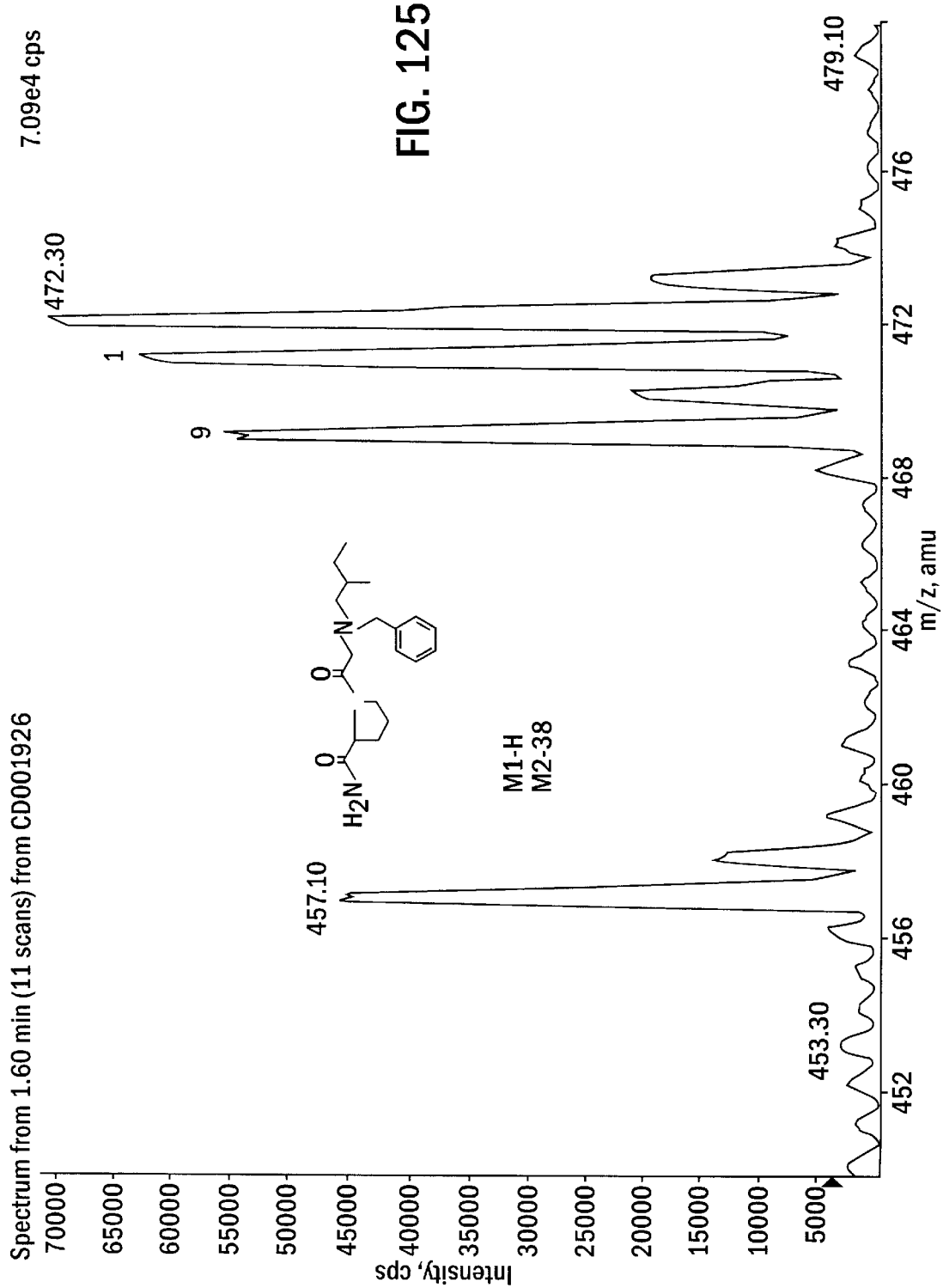
Figure 126:
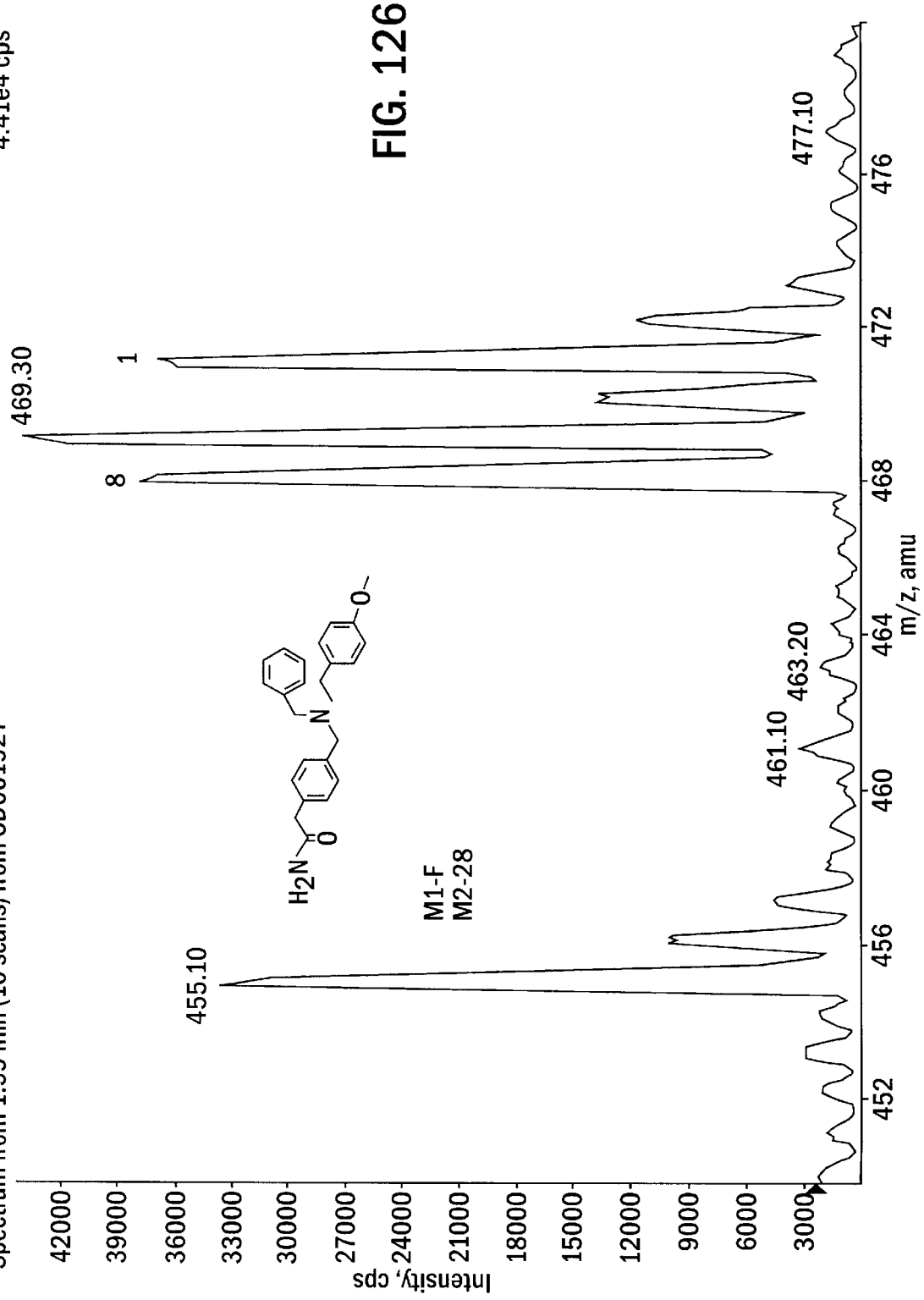
Figure 127:
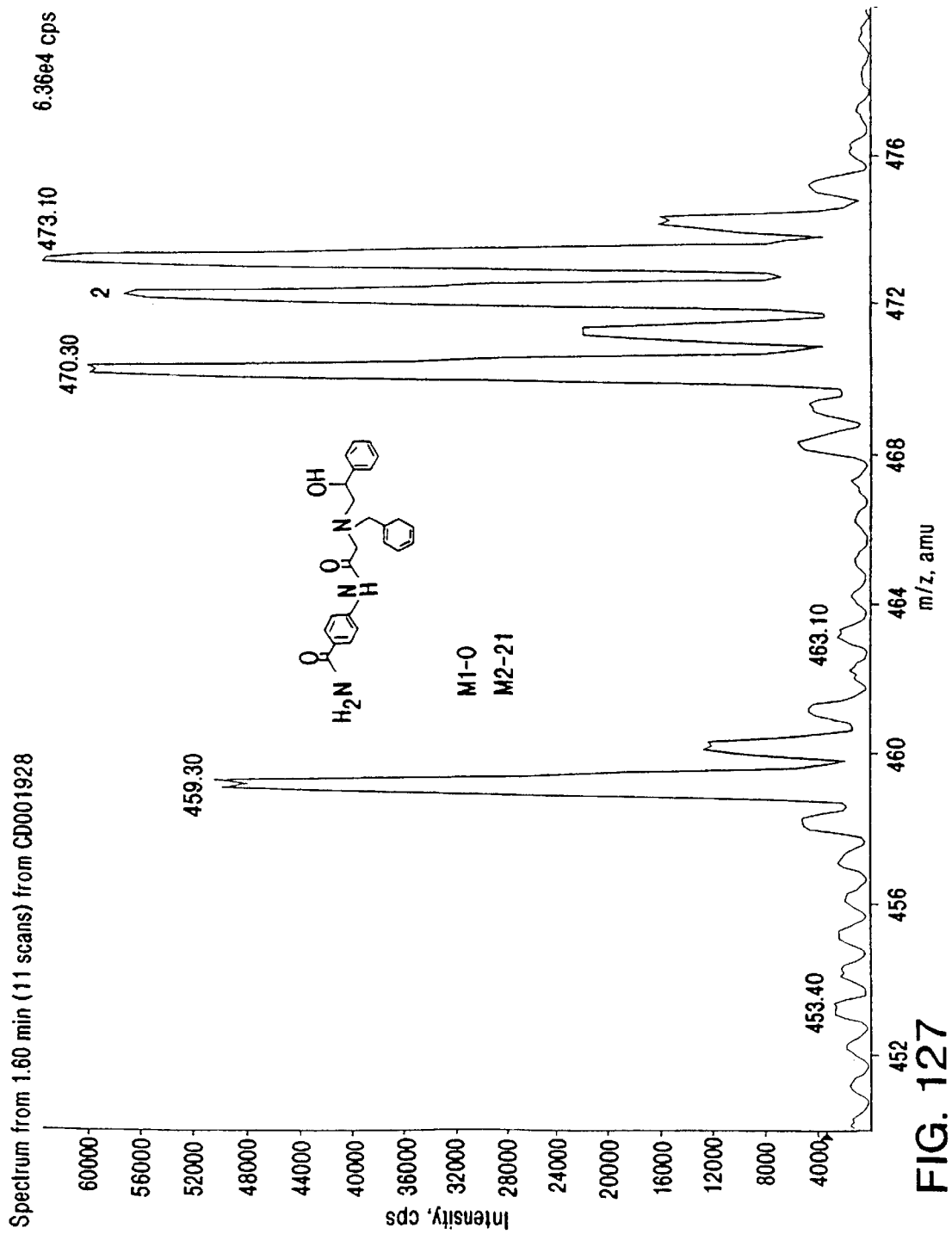
Figure 128:
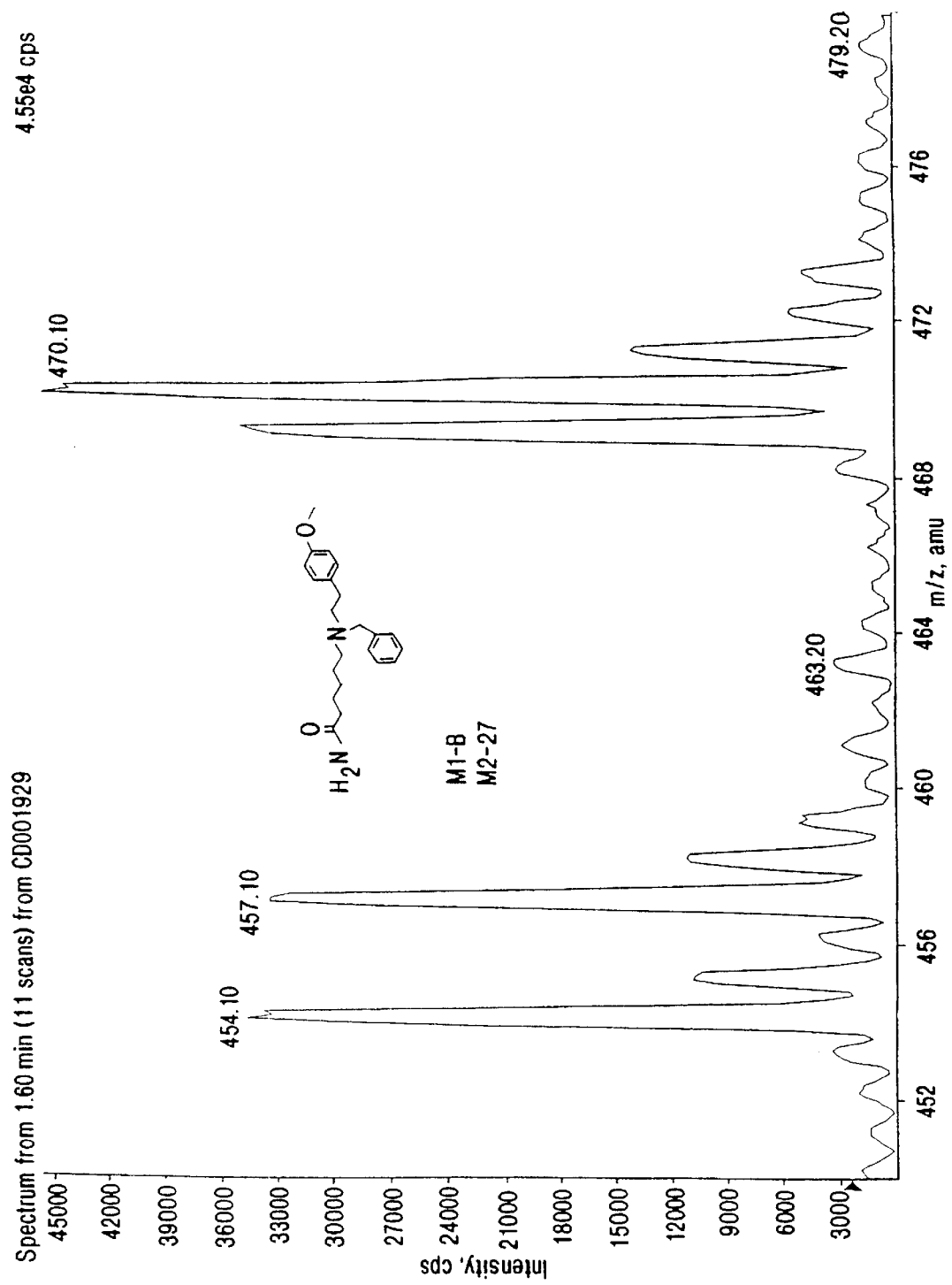
Figure 129:
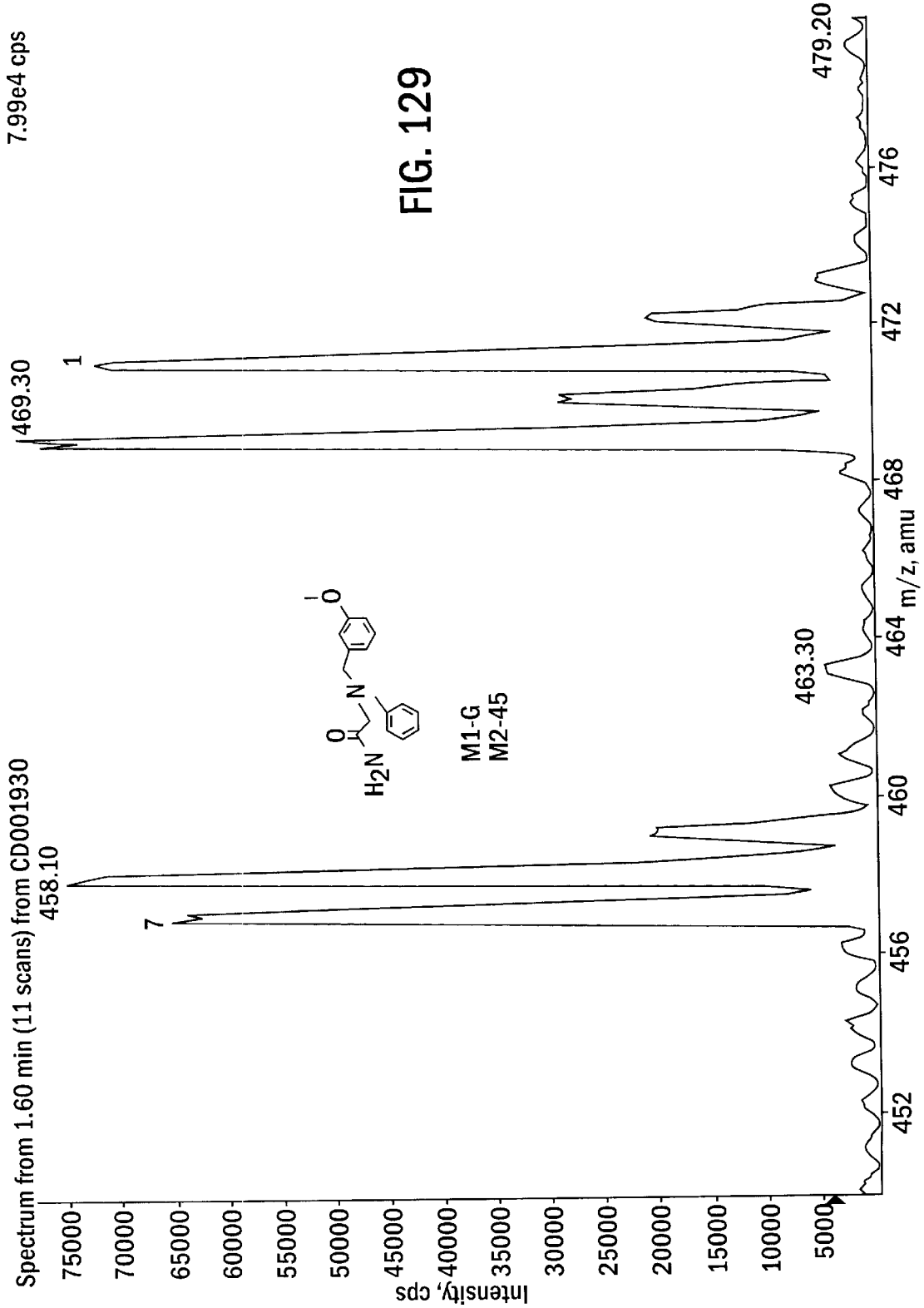
Figure 130:
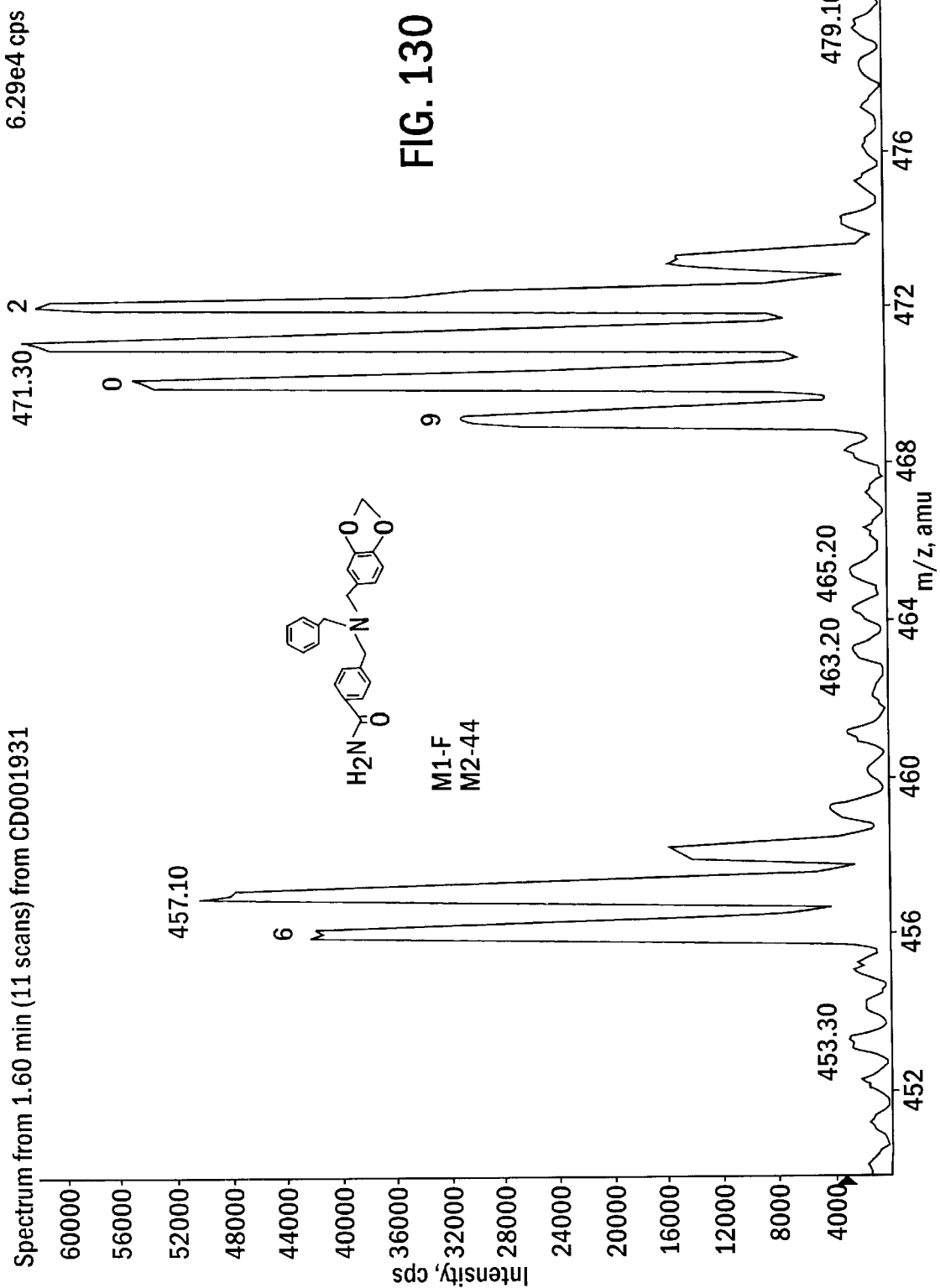
Figure 131:
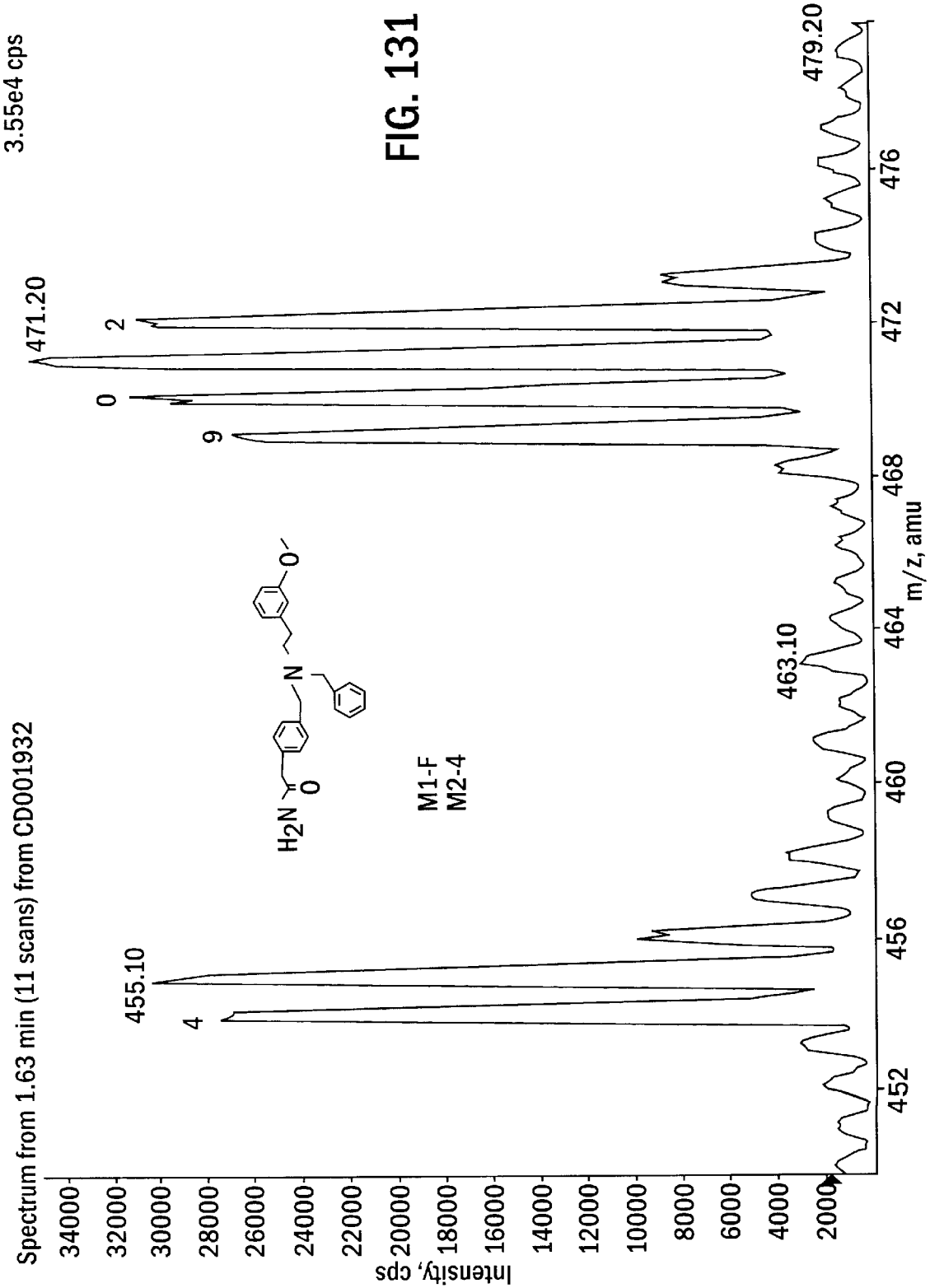
Figure 132:
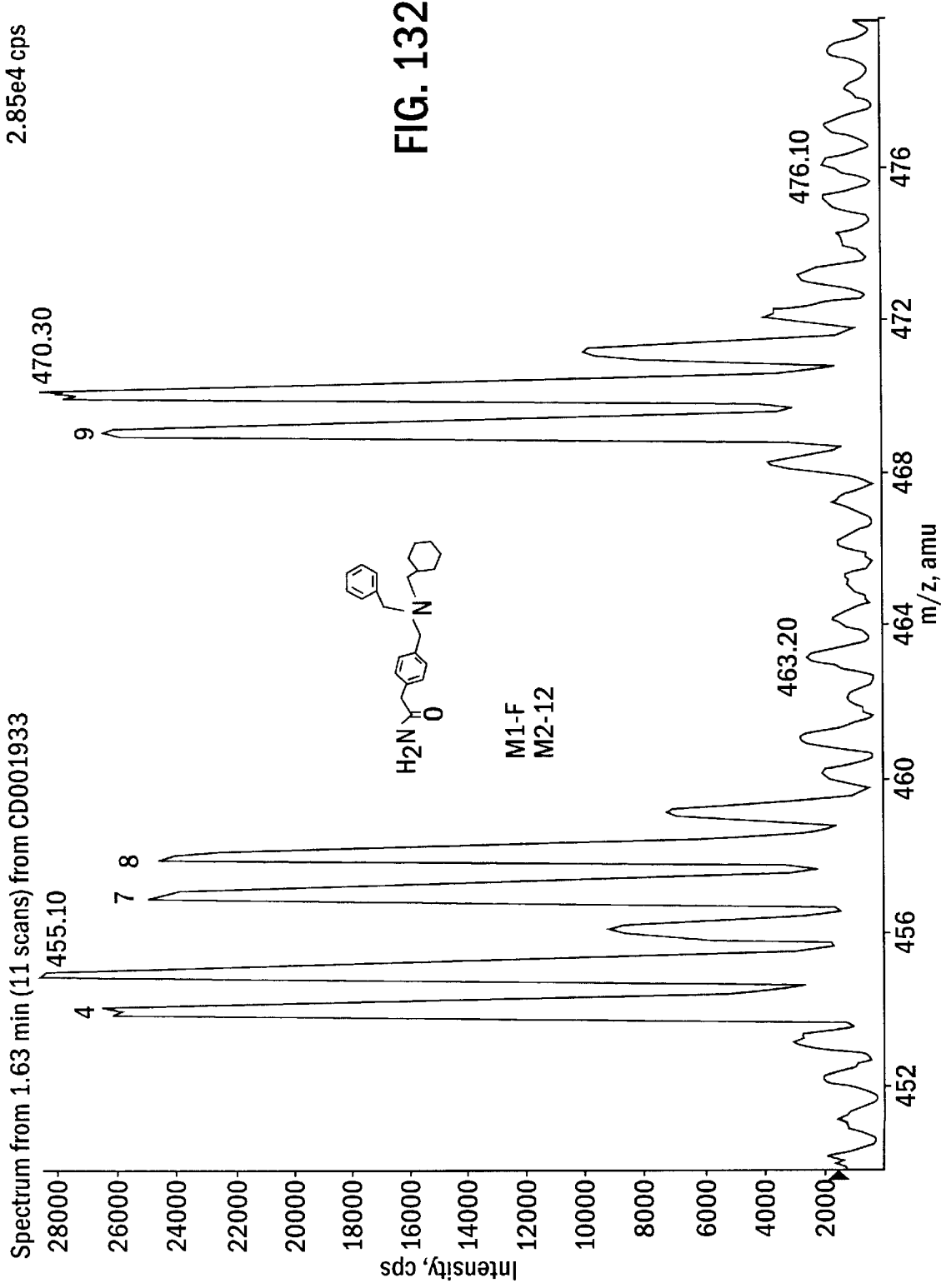

FIGS. 52 through 110 show spectra that are produced in conjunction the disclosure of Example 25 of encoding styrene and Example 26 disclosing copolymerization of styrene and F-styrene.

FIGS. 111 through 132 show spectra representing the decoding of a parallel synthesis of a library on encoded resin beads, using a dual linker approach in which a first linker was a photocleavable linker and a second linker was a Knorr linker.

Figure 133:
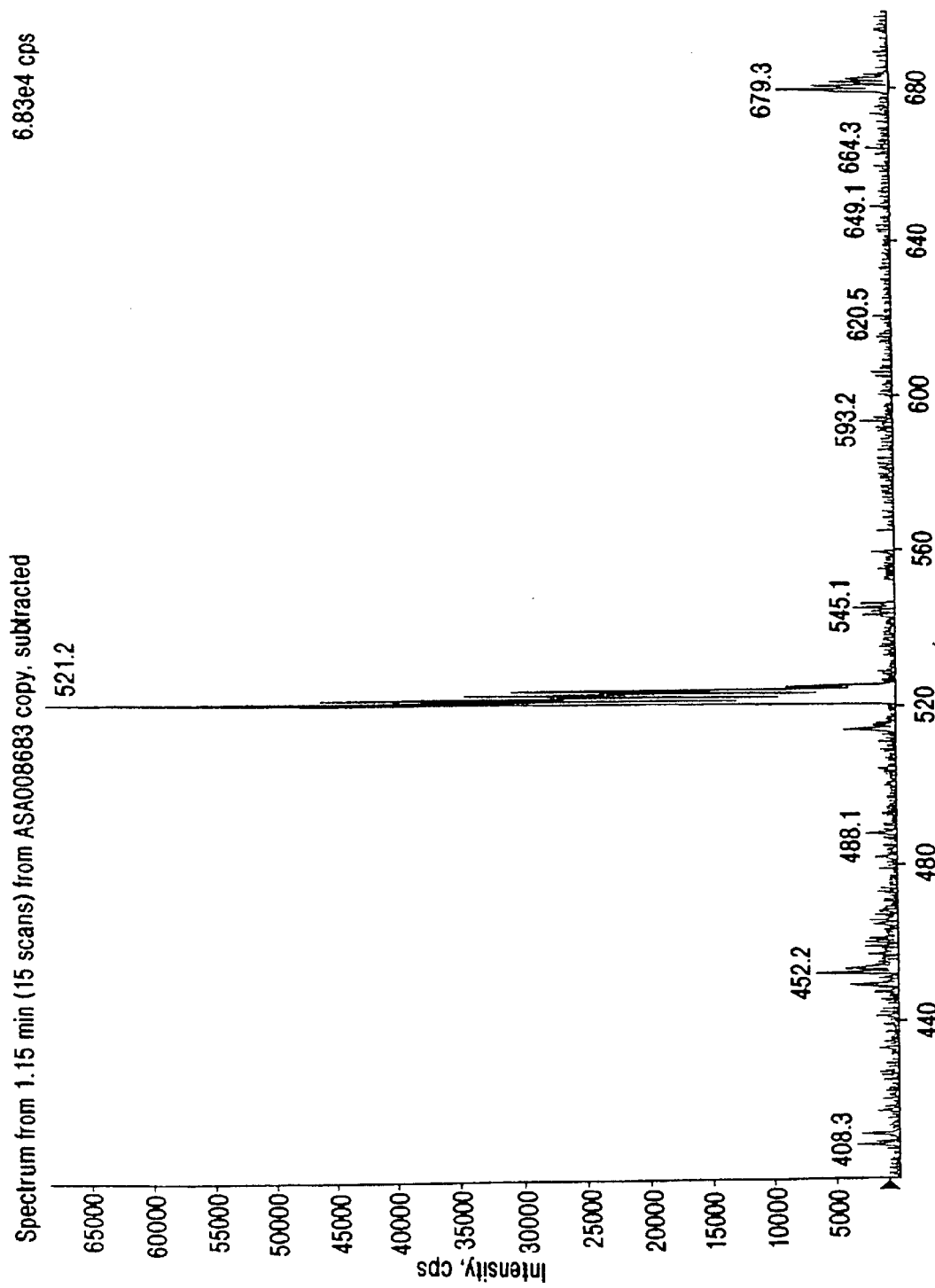
Figure 134:

Figure 135:
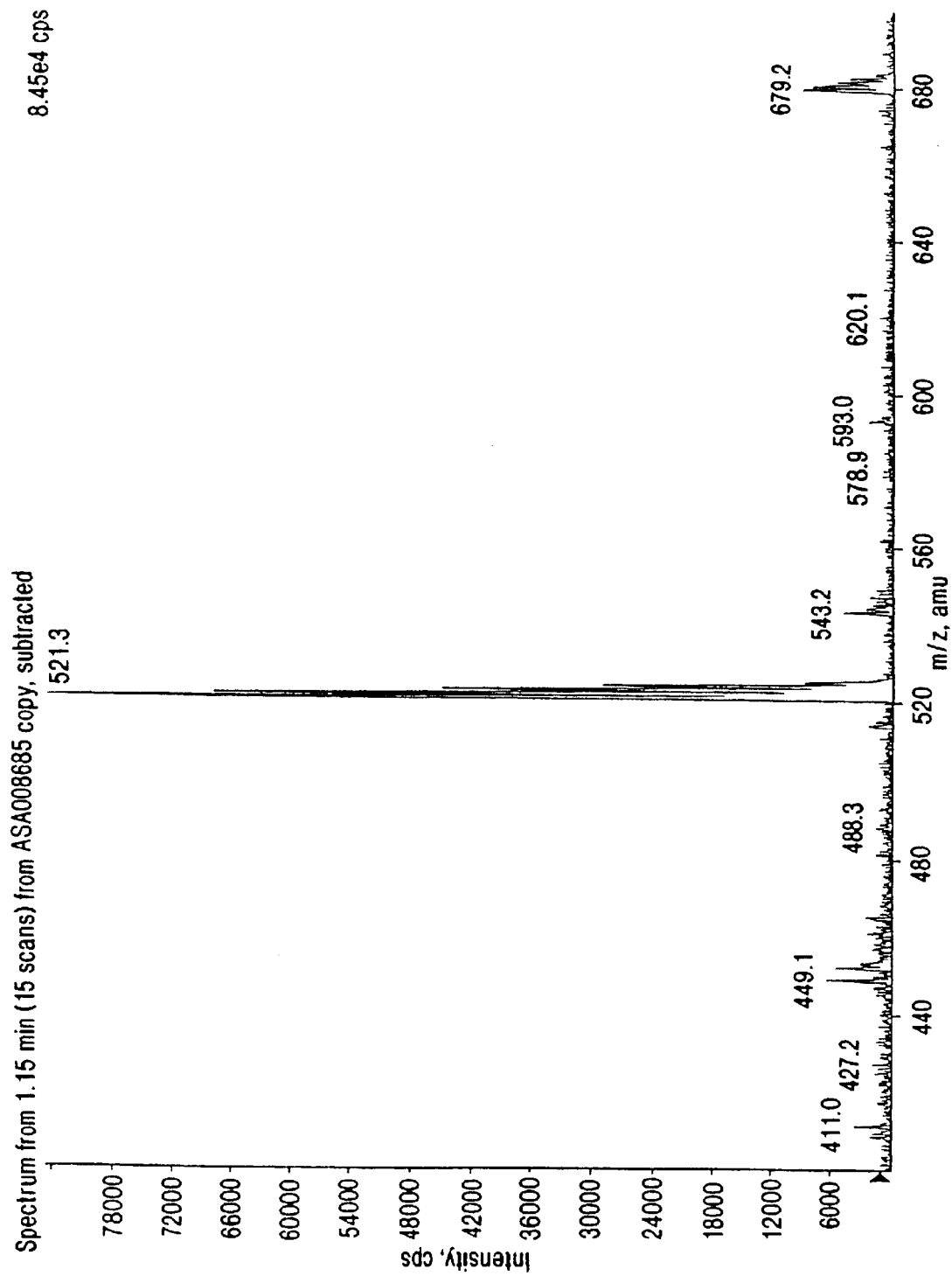
Figure 136:
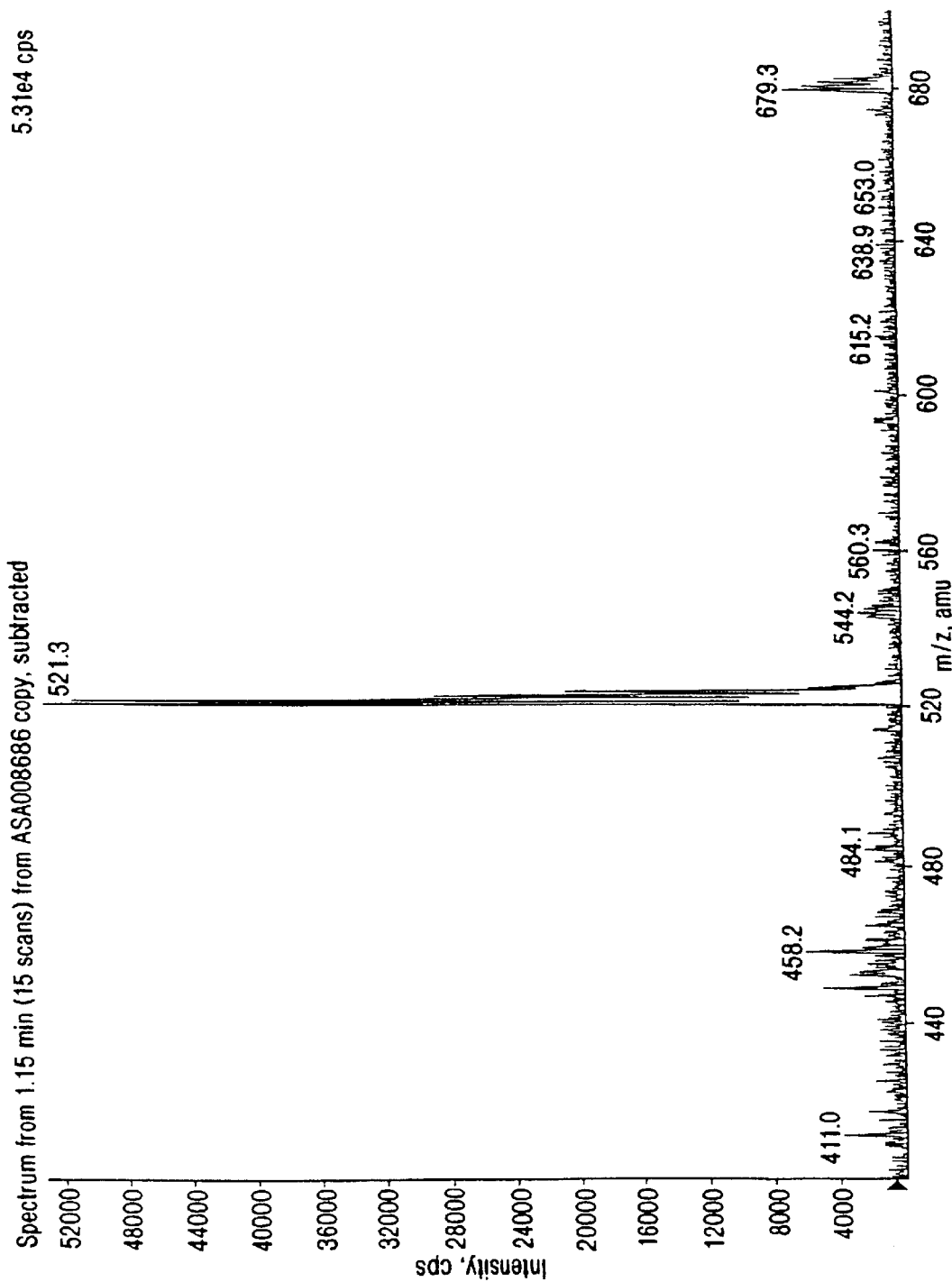
Figure 137:
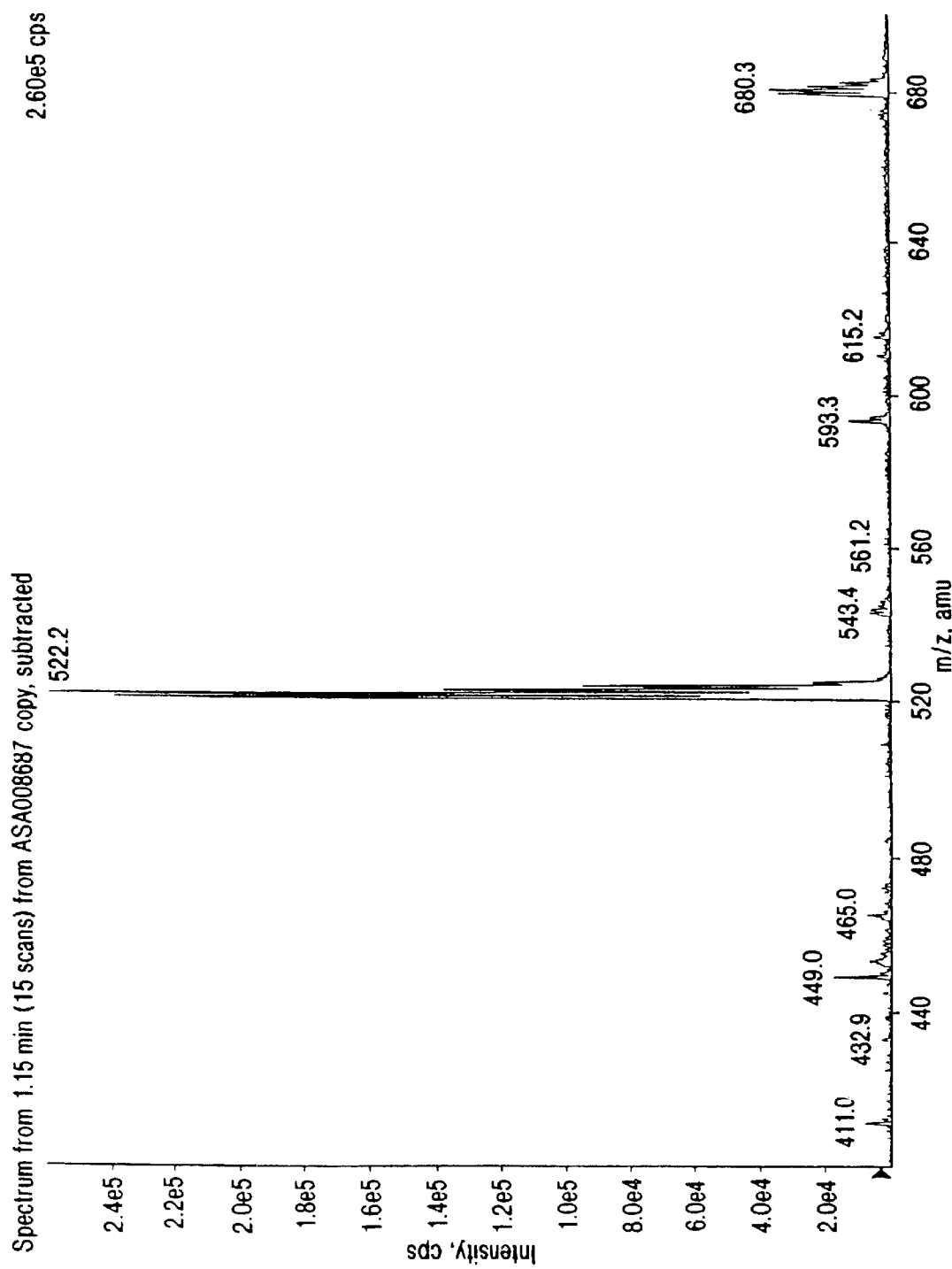
Figure 138:
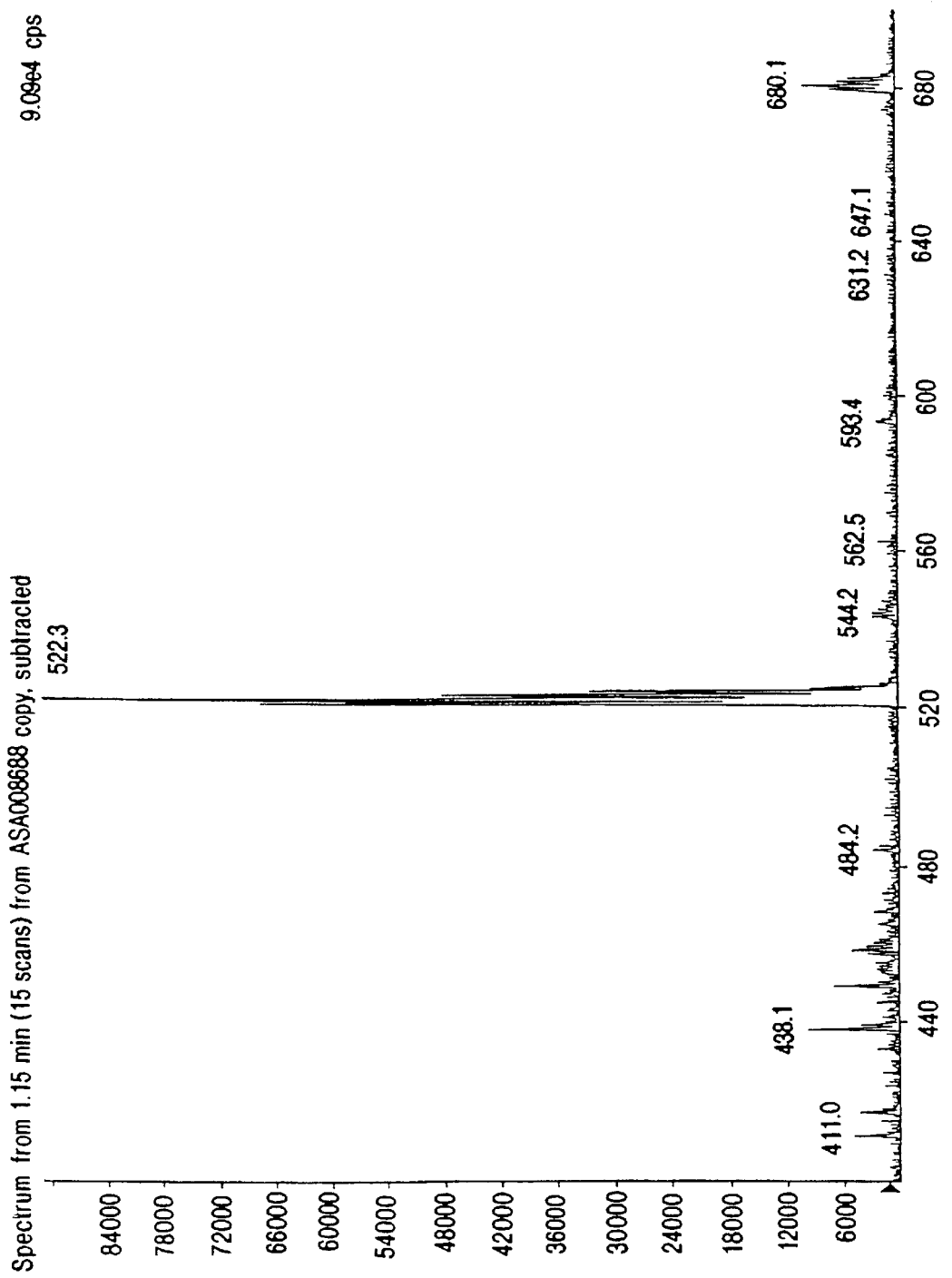
Figure 139:
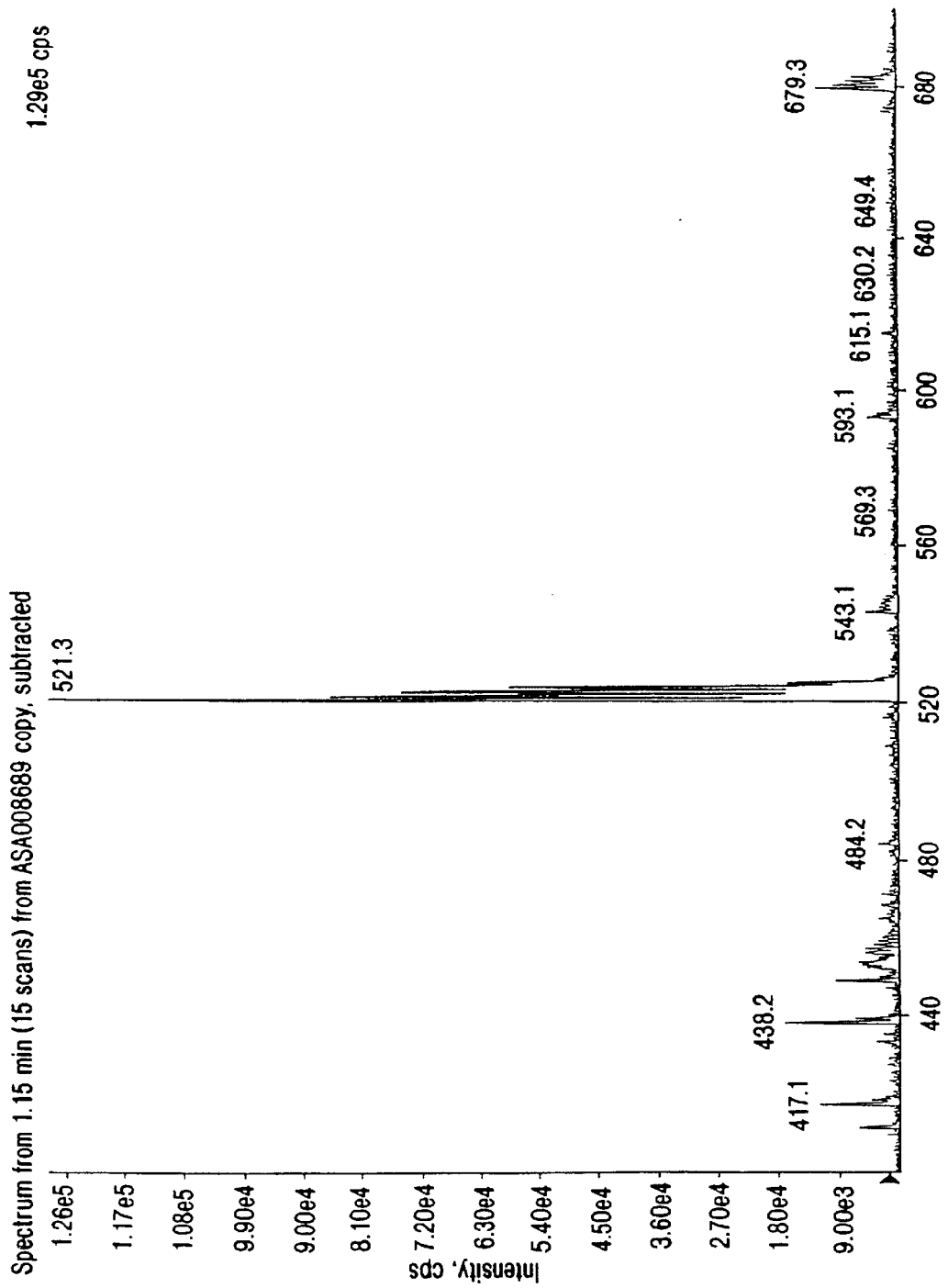
Figure 140:
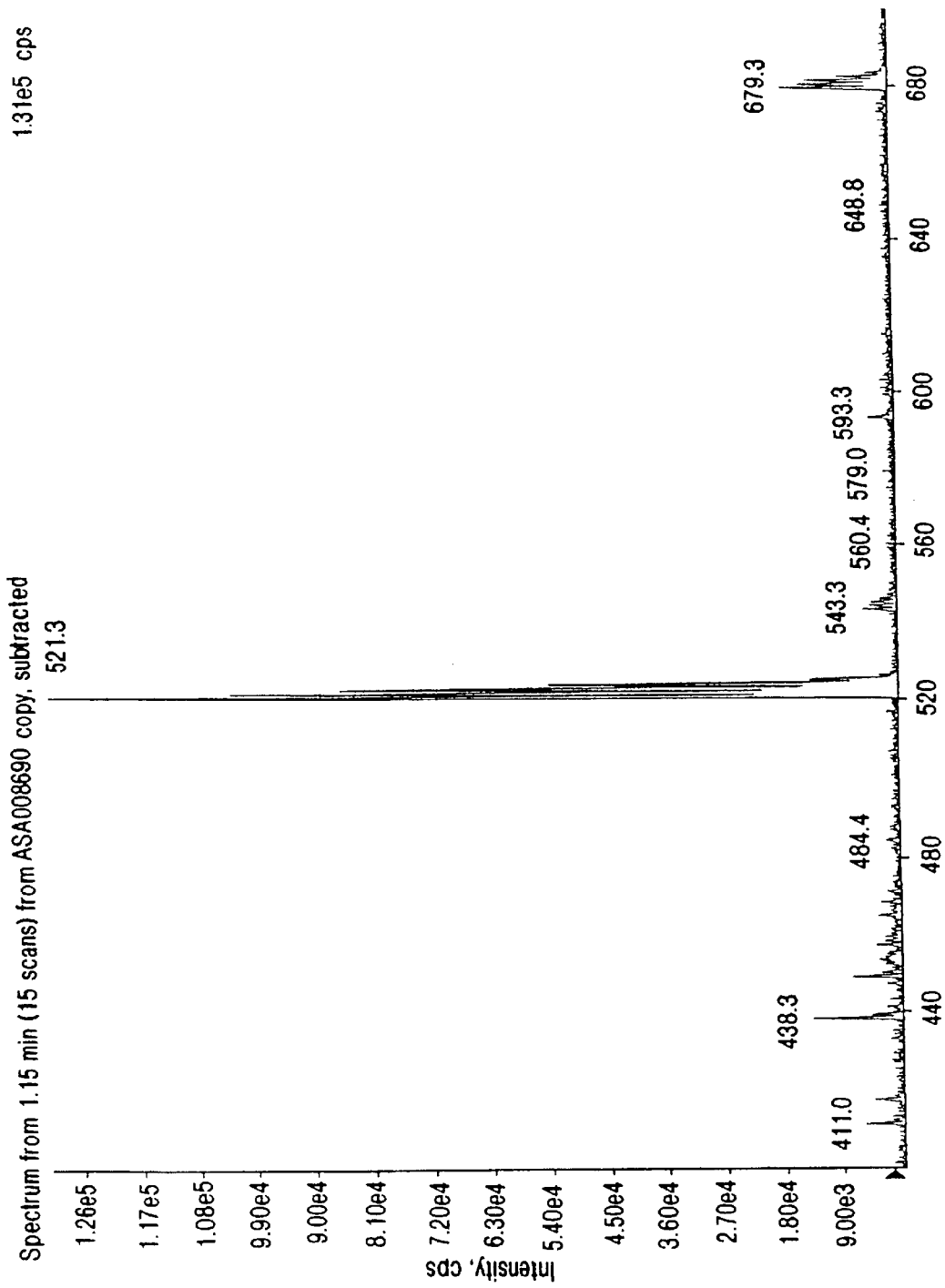
Figure 141:
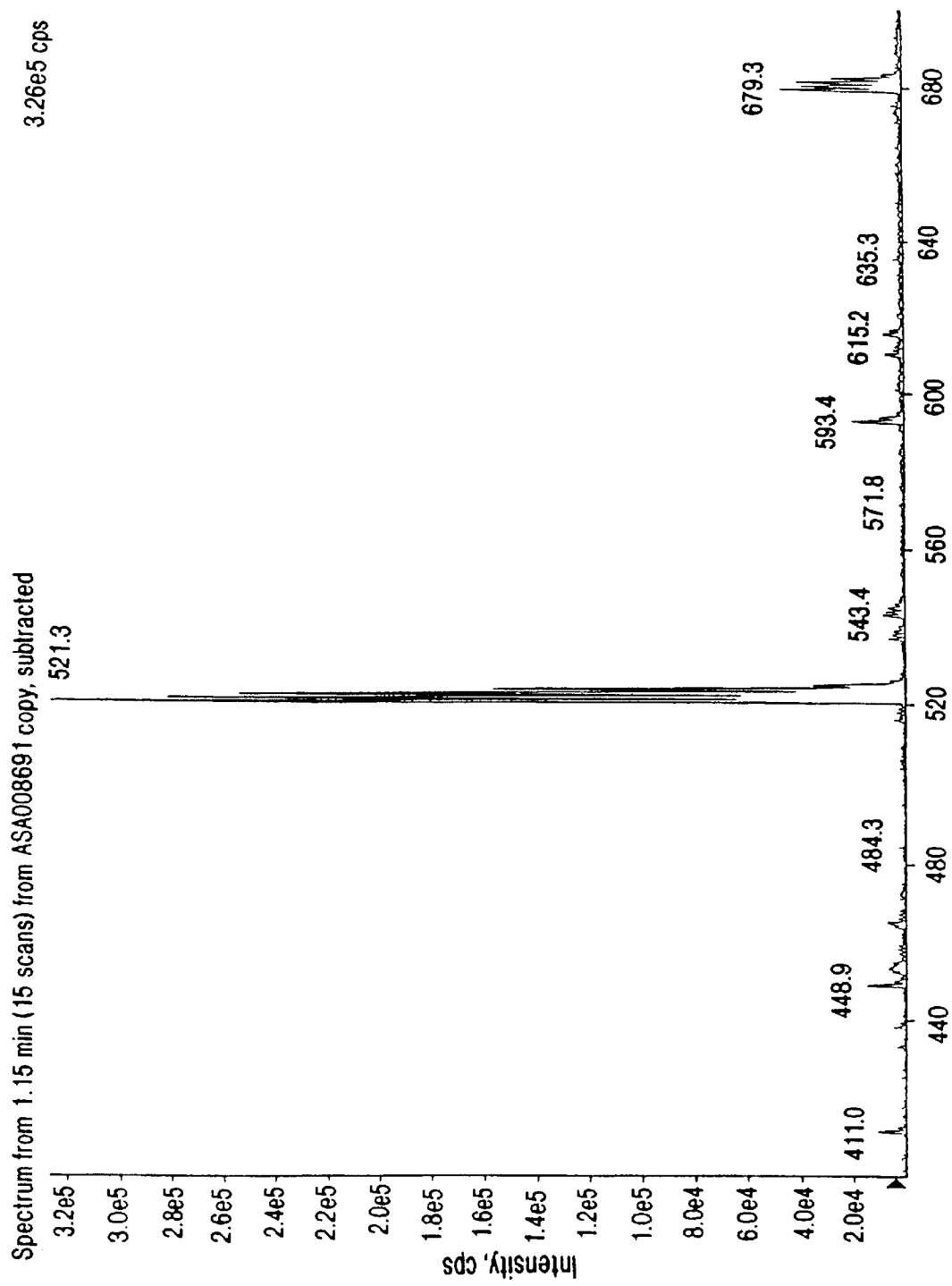
Figure 142:
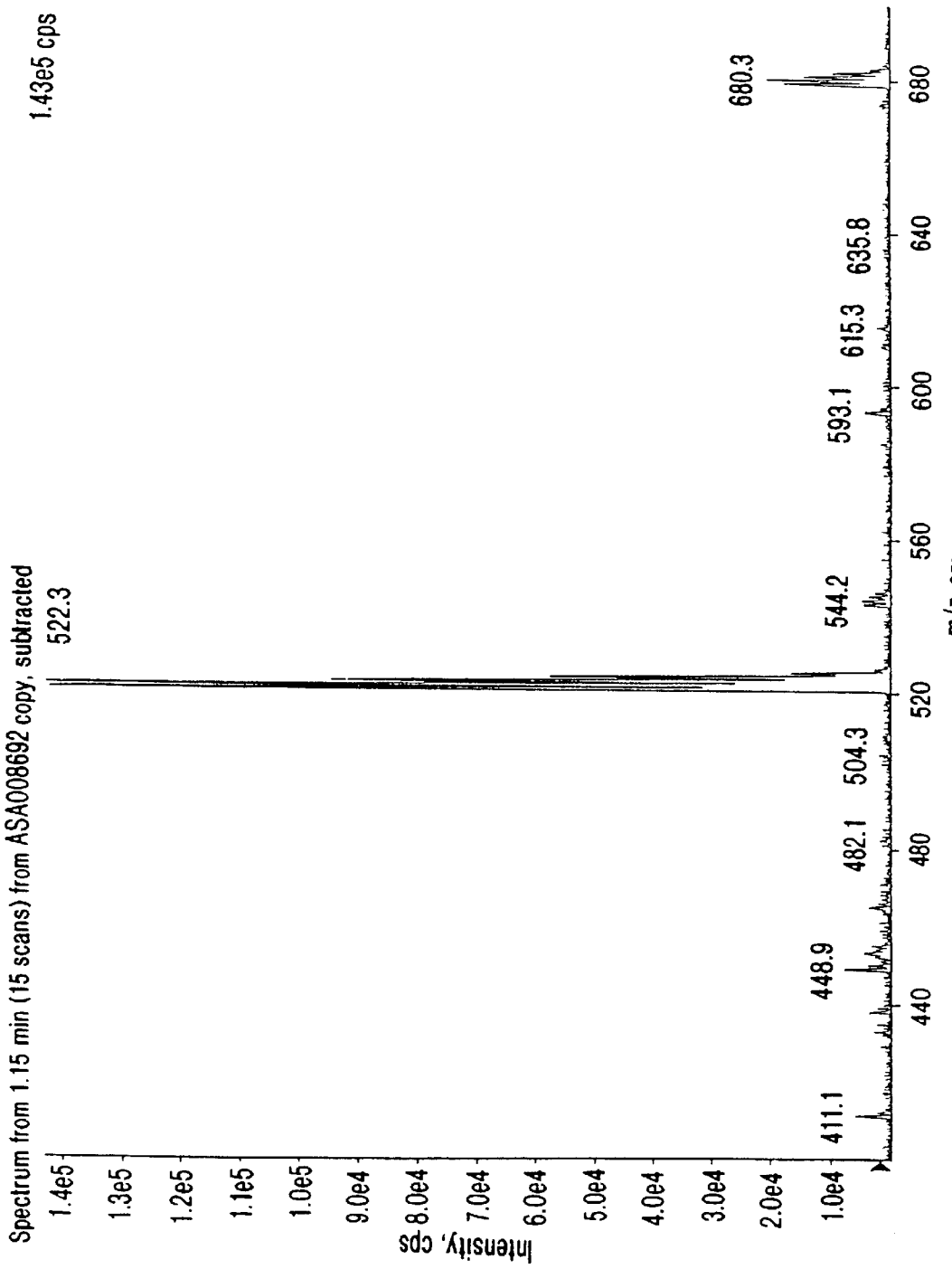
Figure 143:
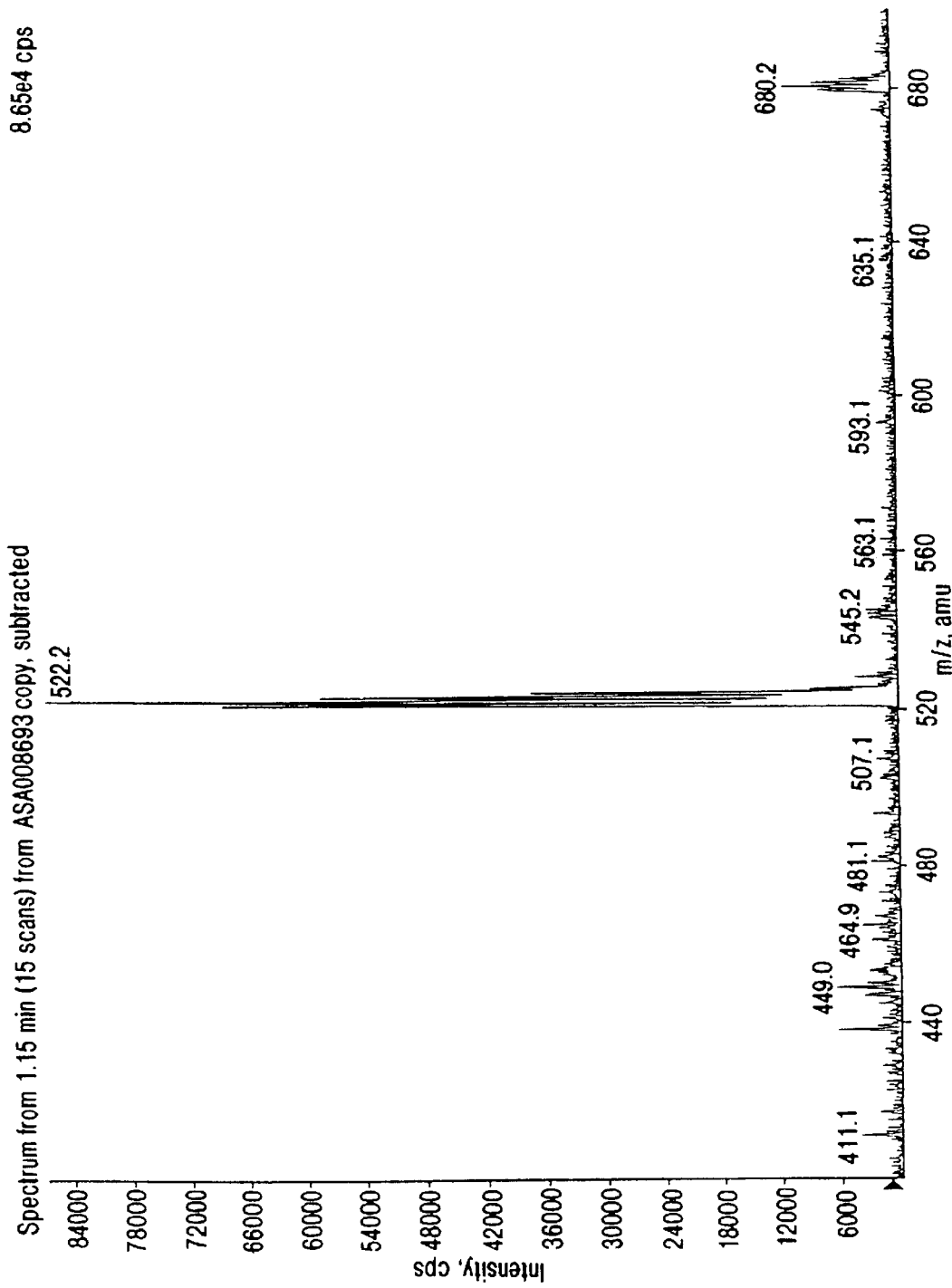
Figure 144:
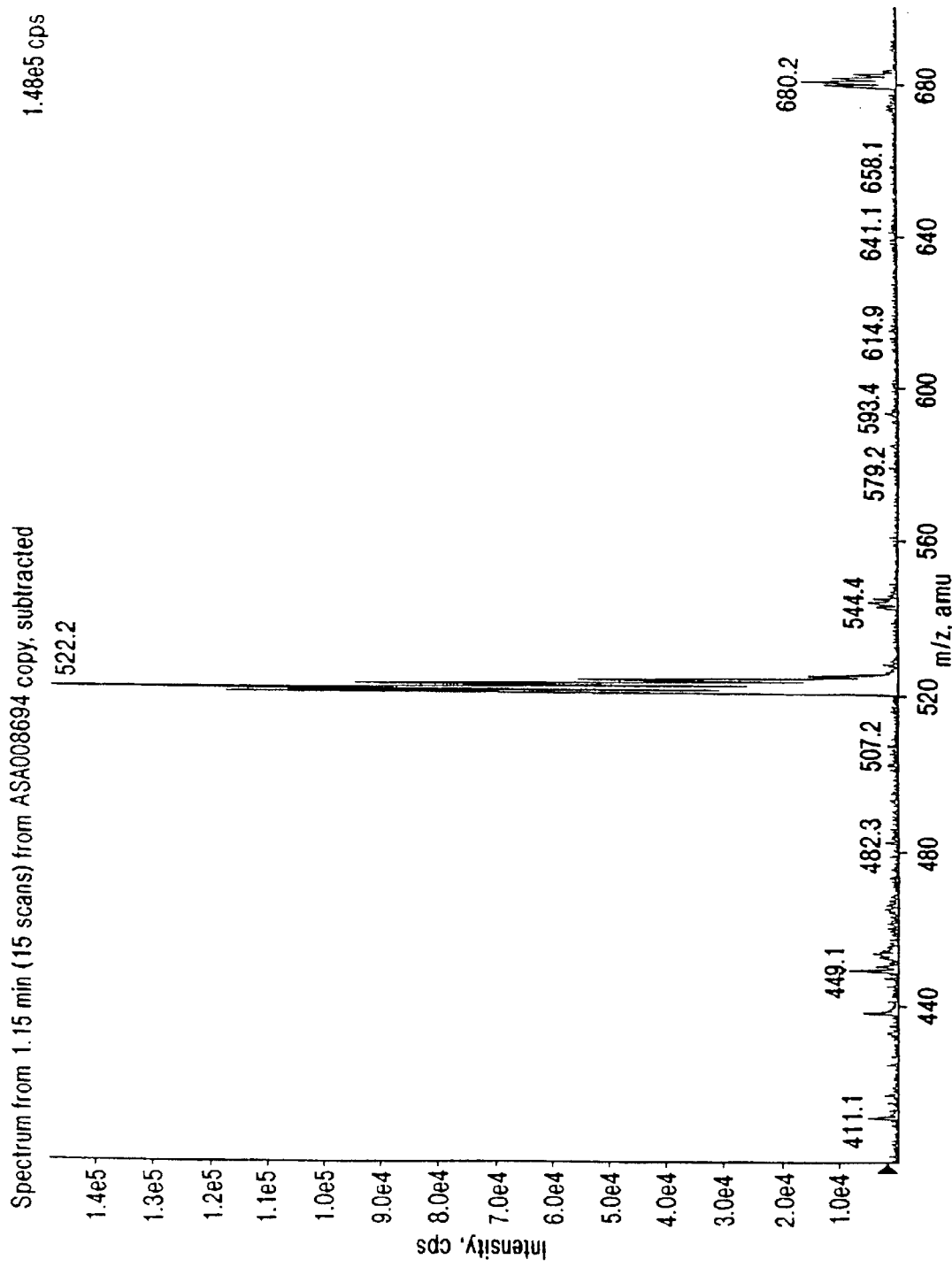
Figure 145:
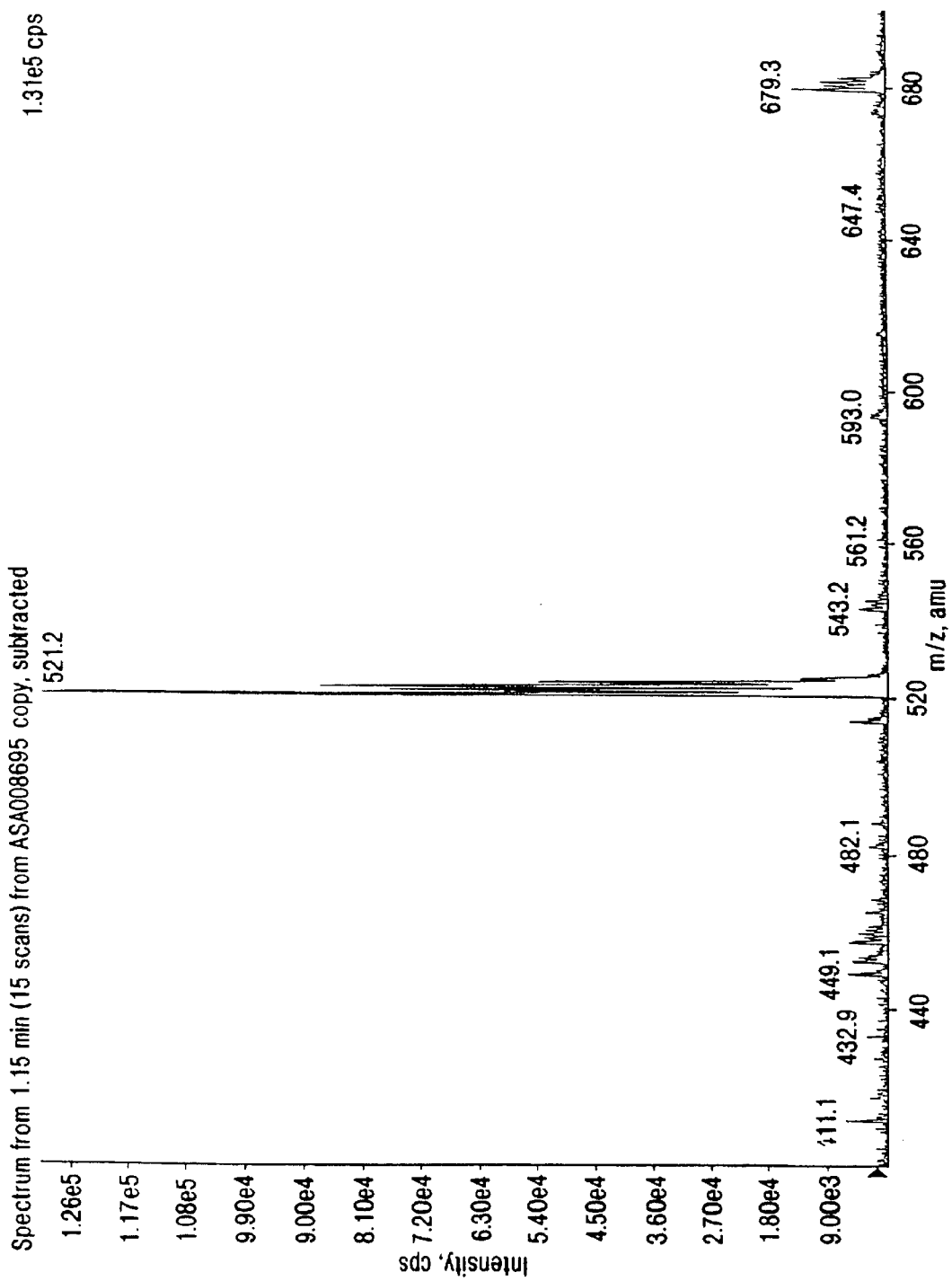
Figure 146:
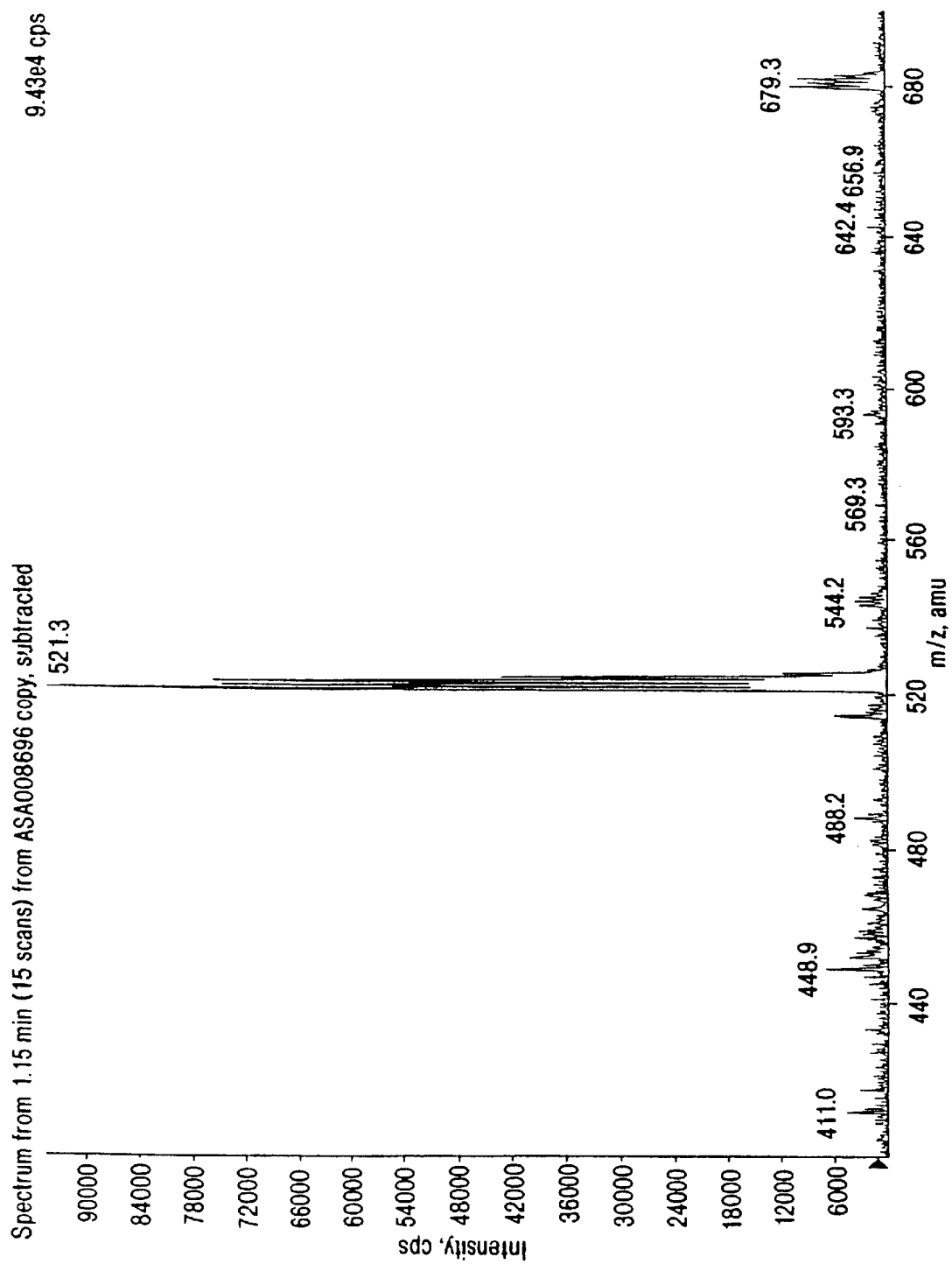
Figure 147:
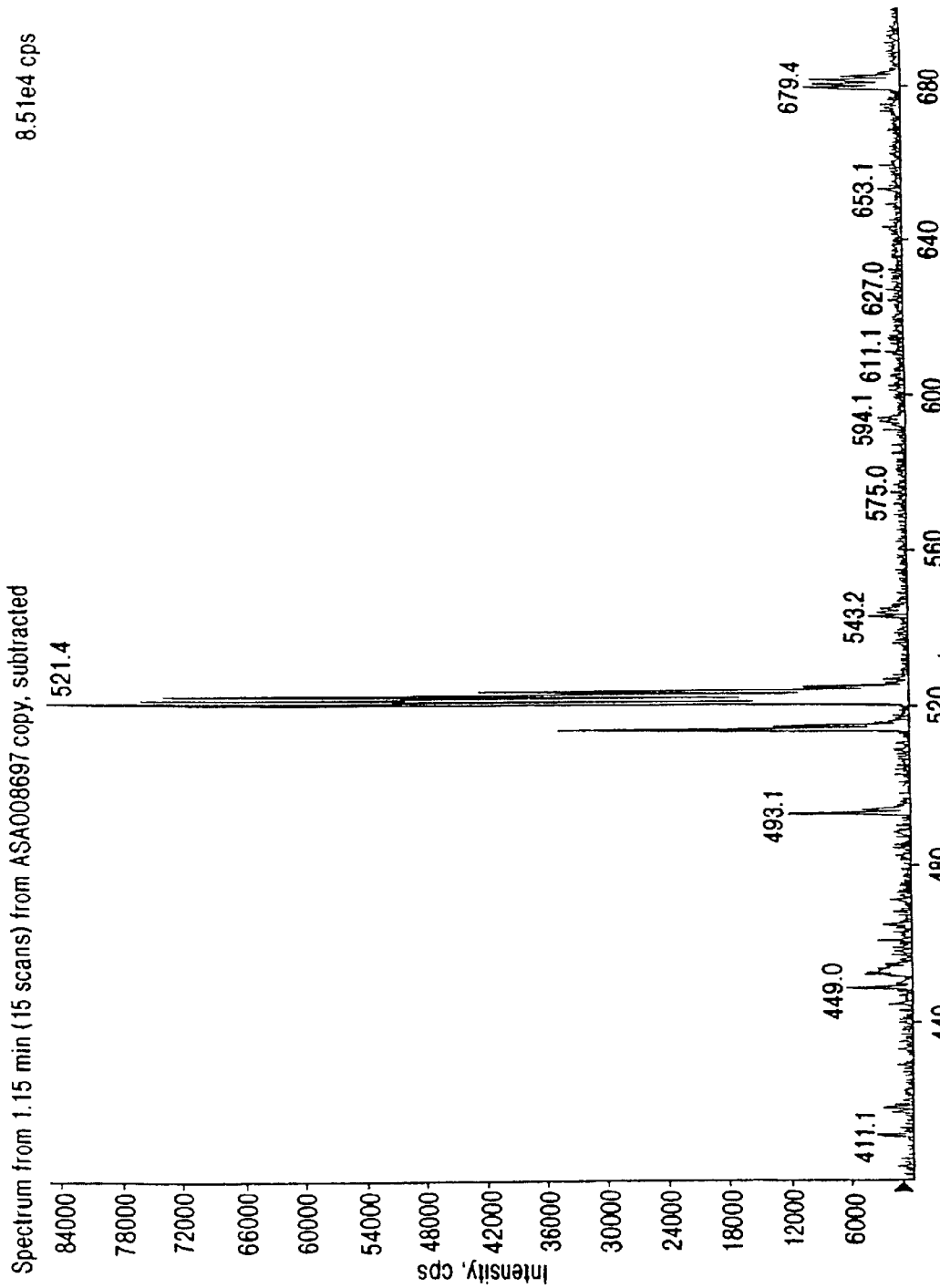
Figure 148:
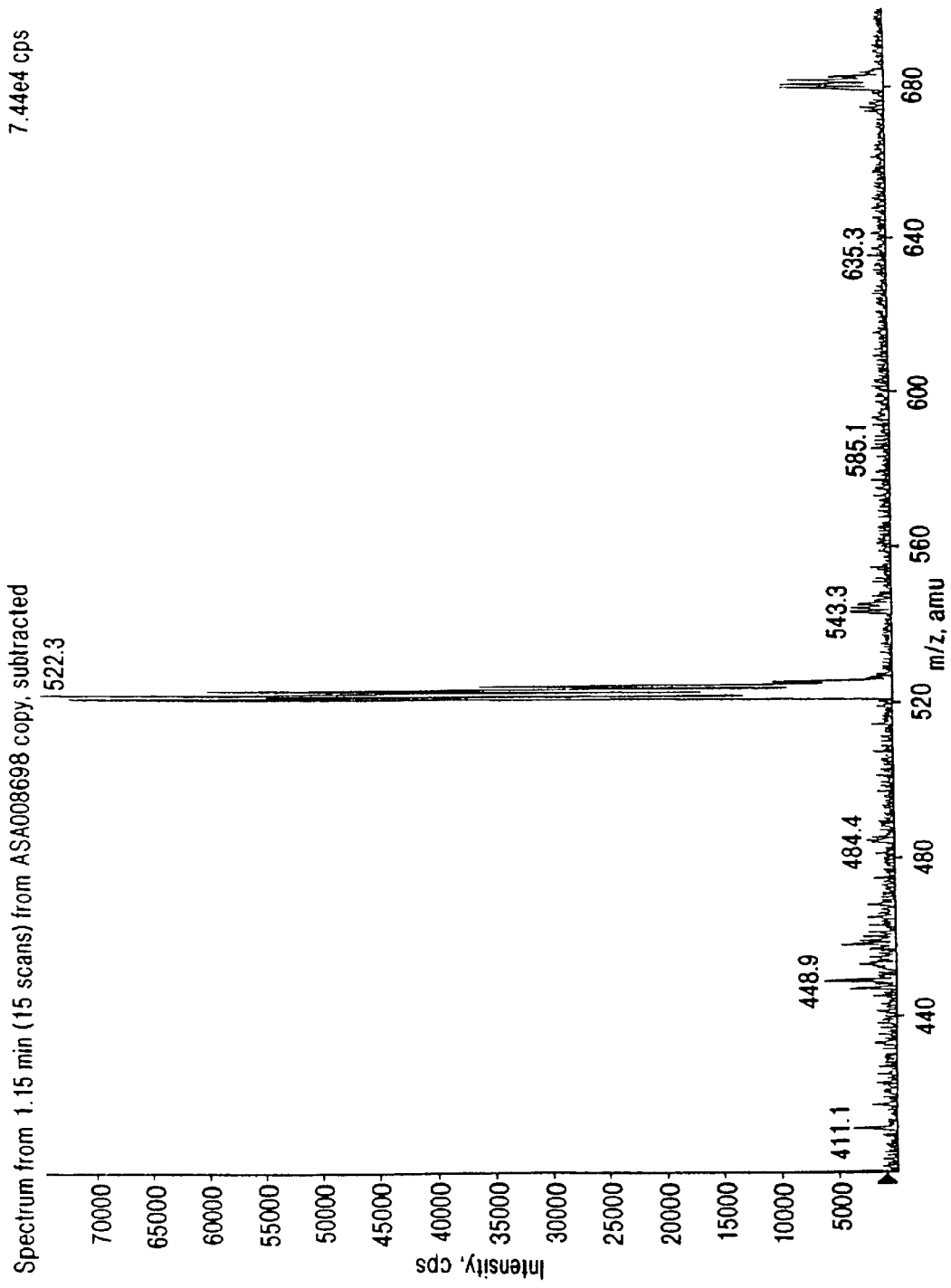
Figure 149:
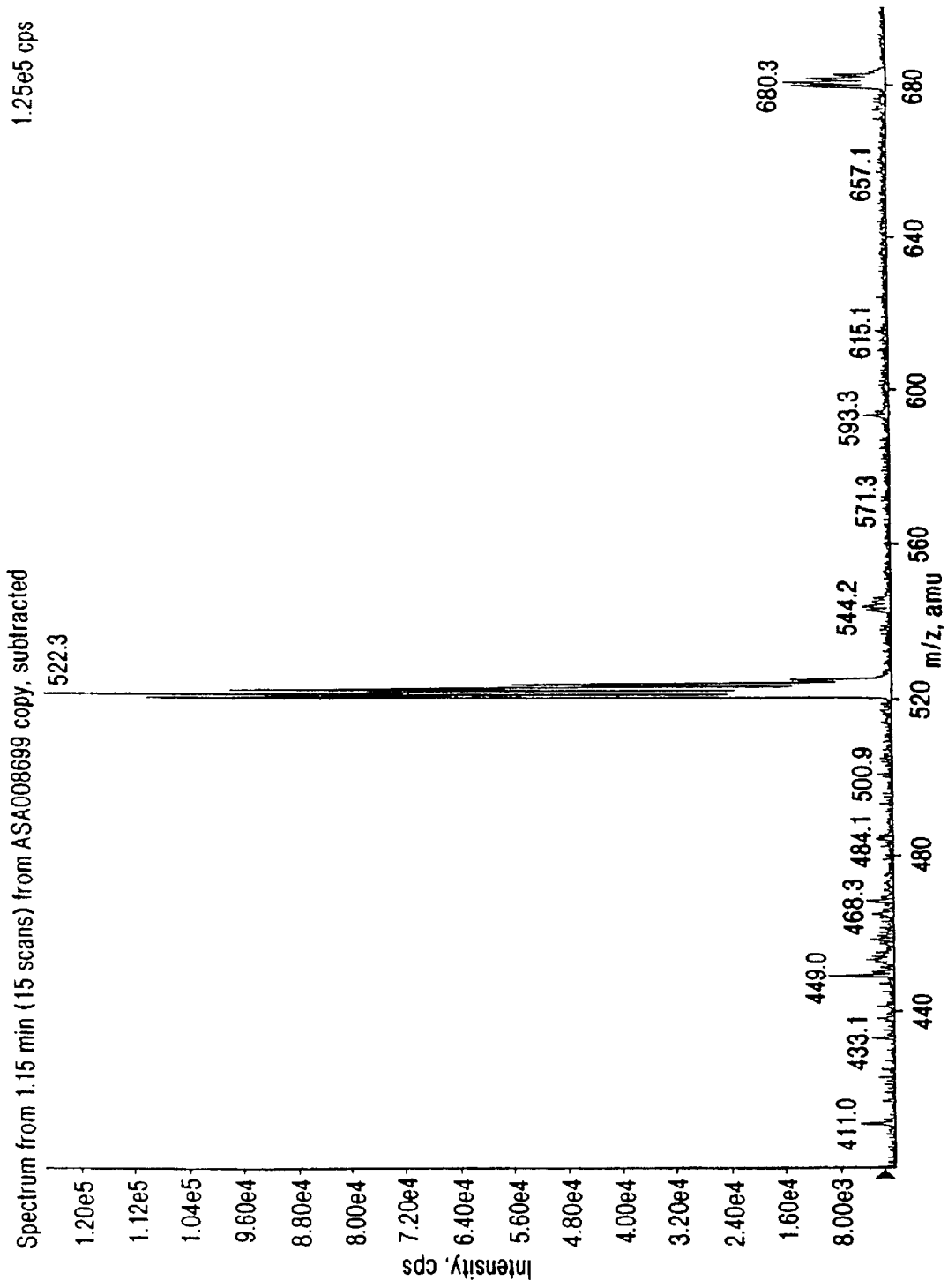
Figure 150:
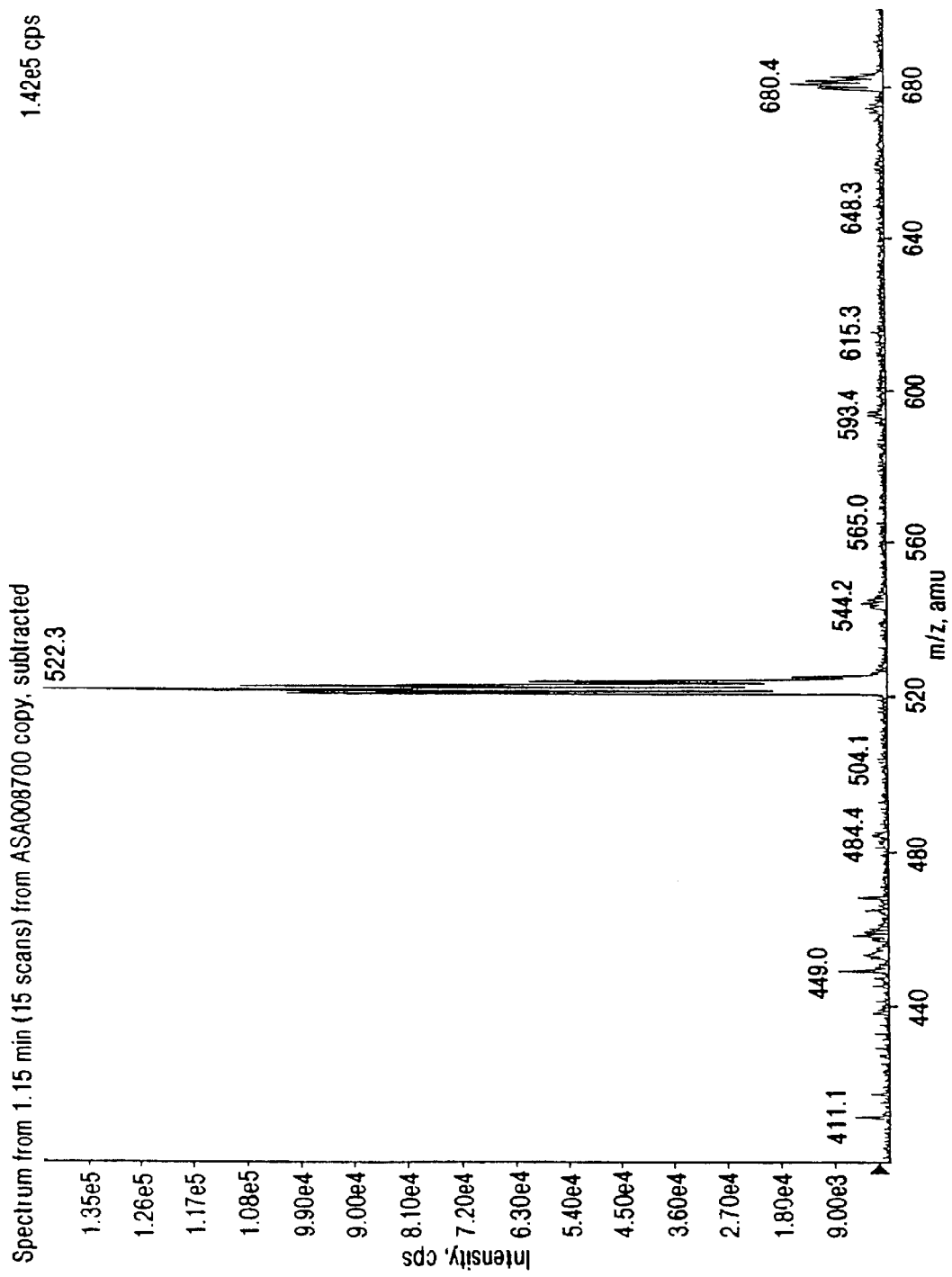
Figure 151:
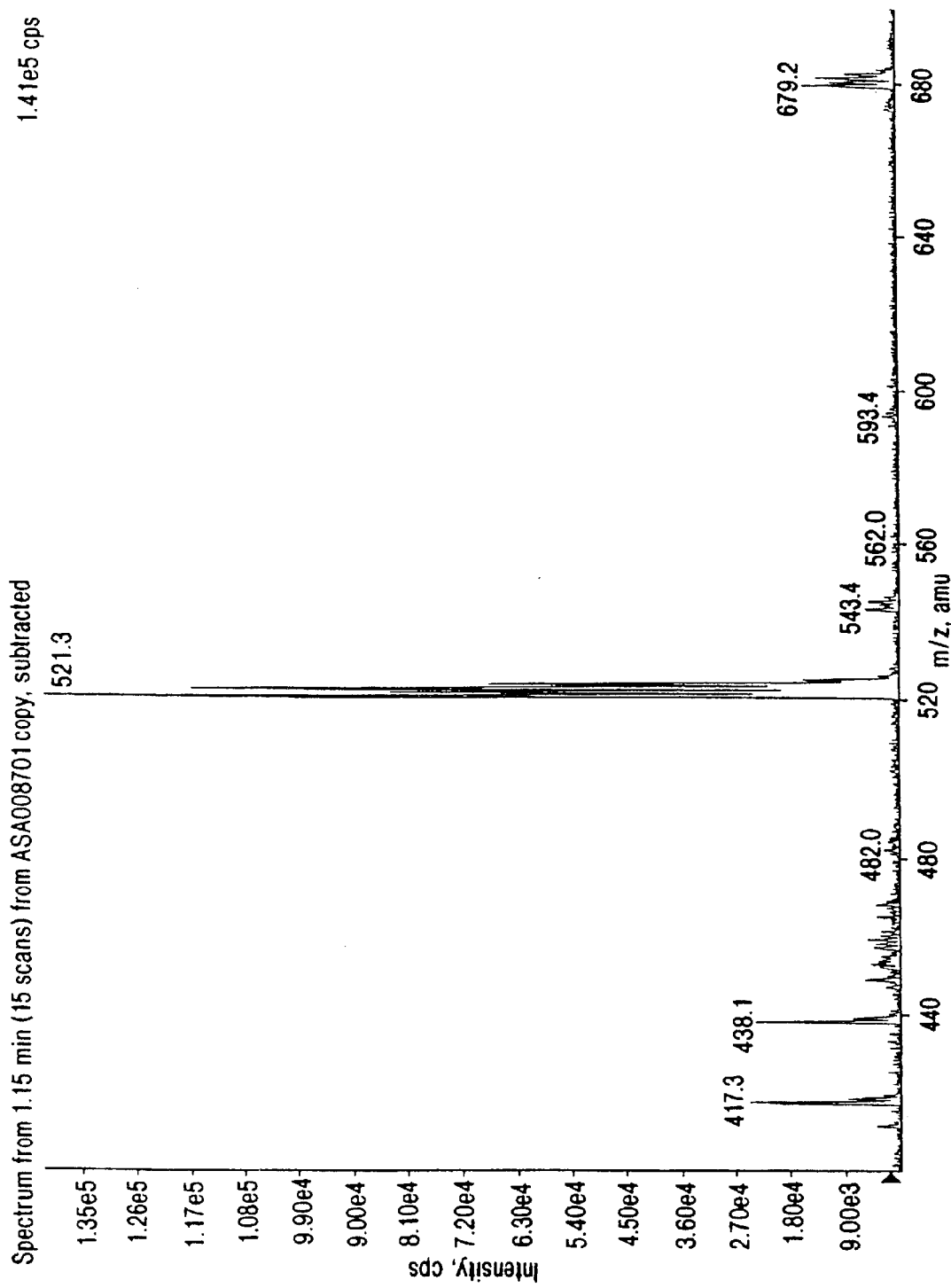
Figure 152:
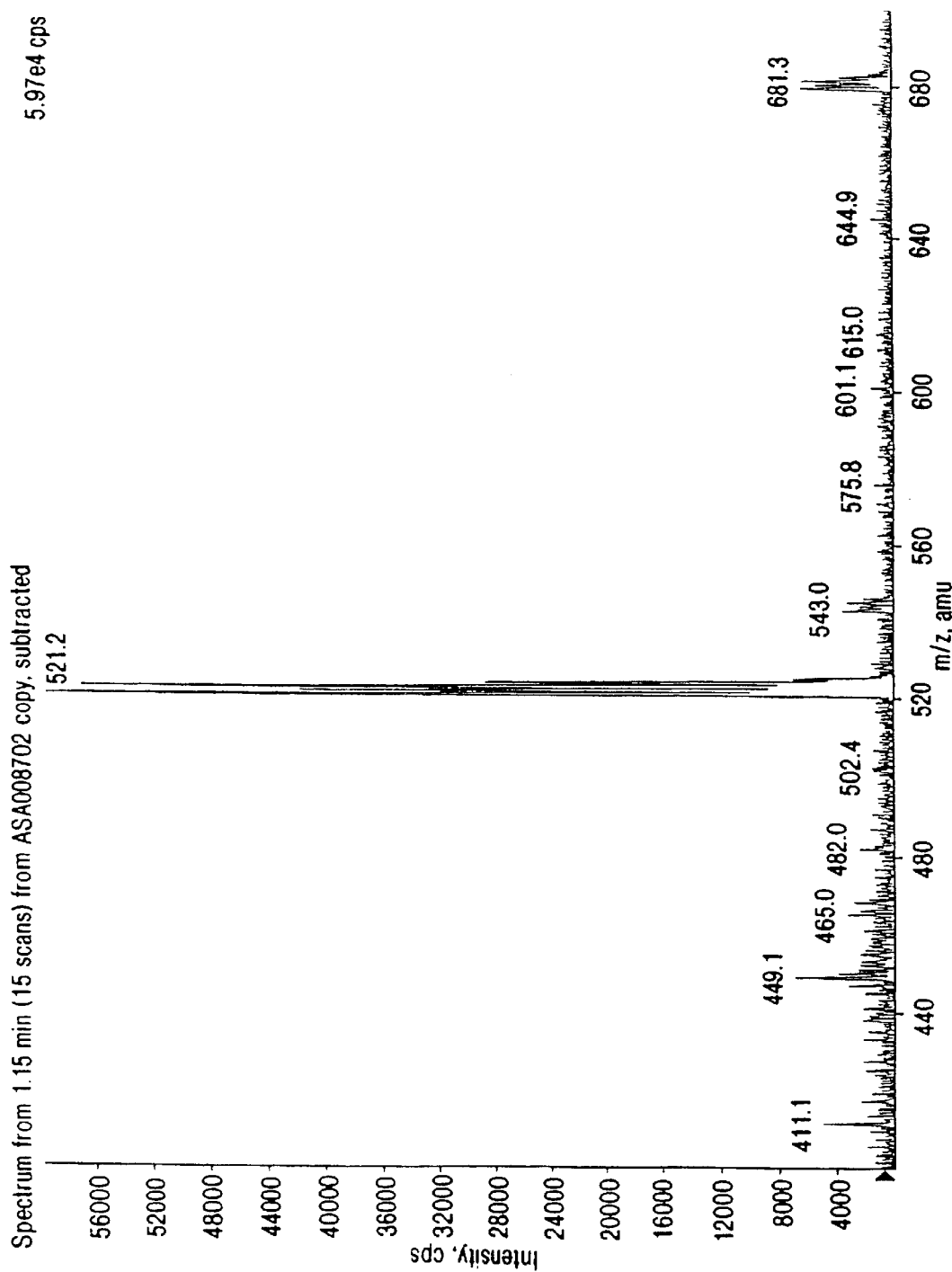
Figure 153:
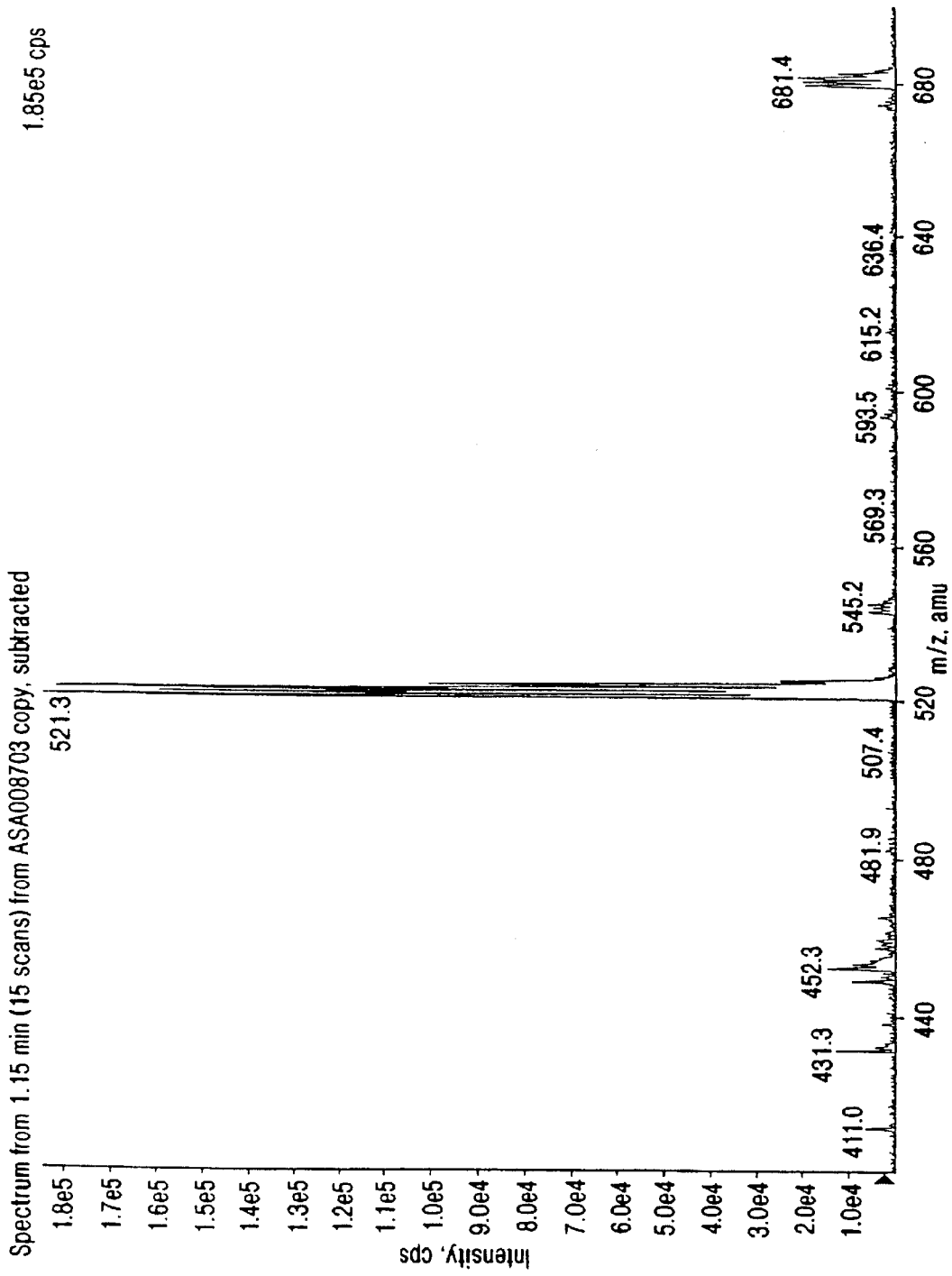
Figure 154:
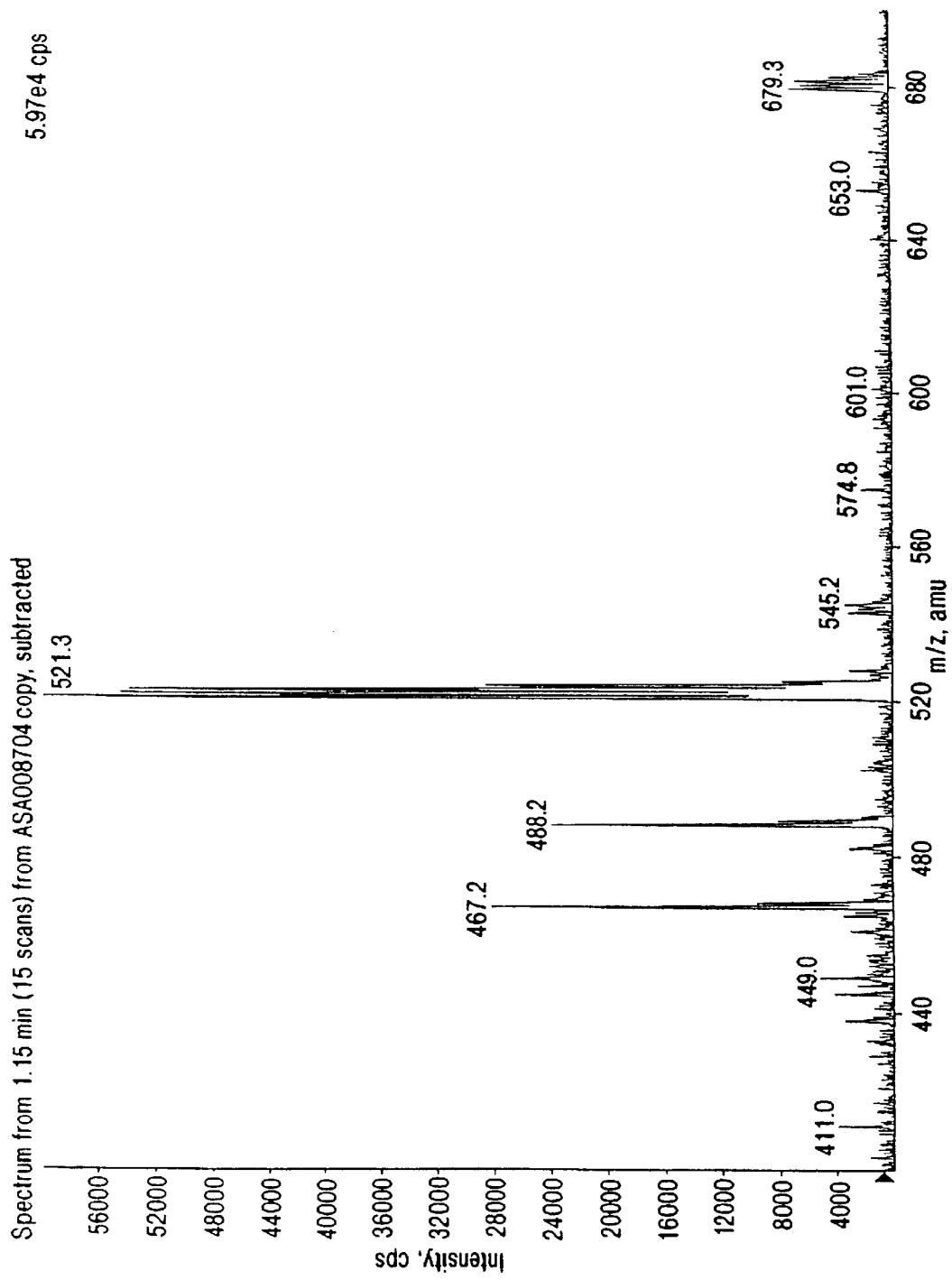
Figure 155:
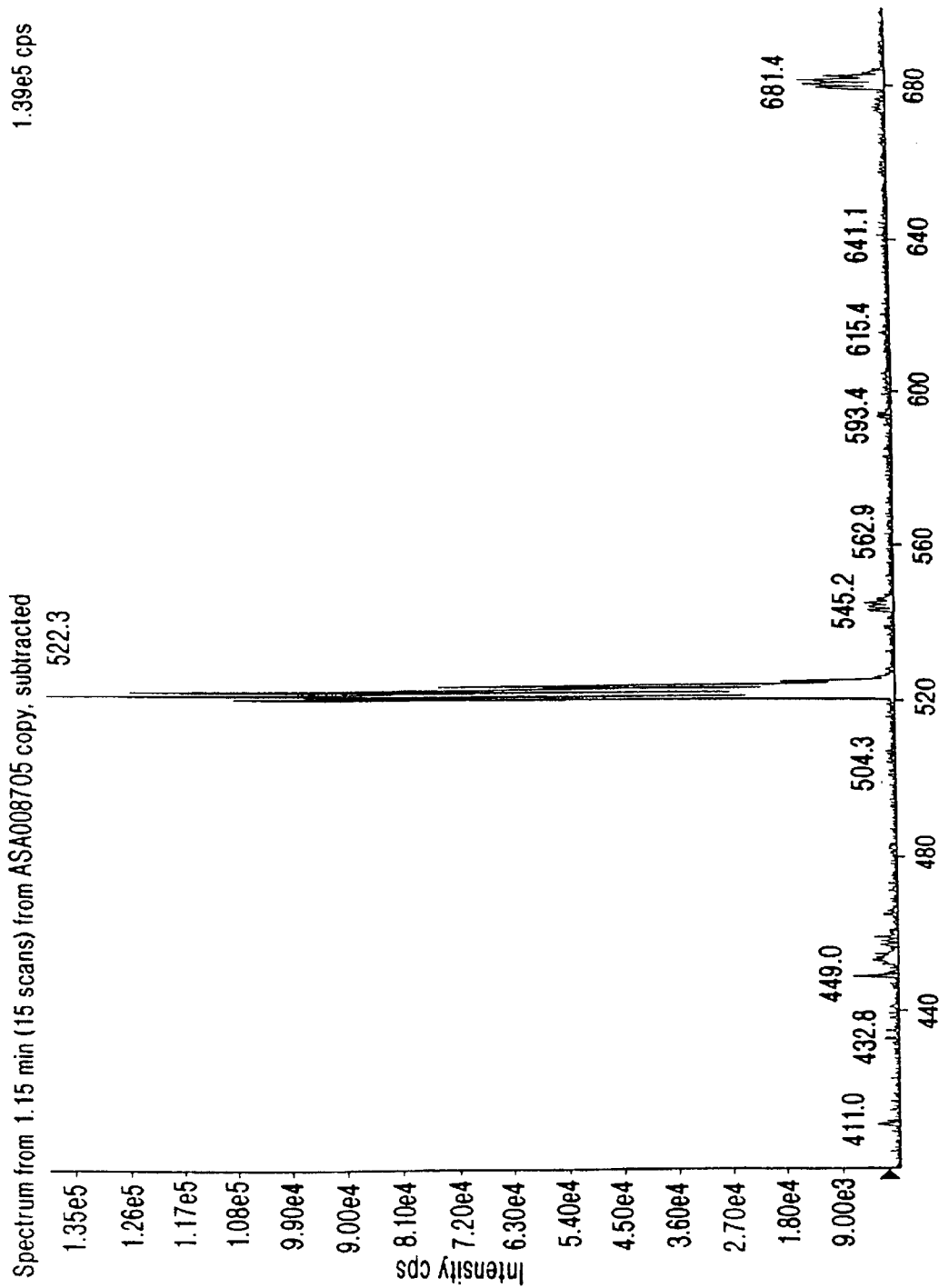
Figure 156:
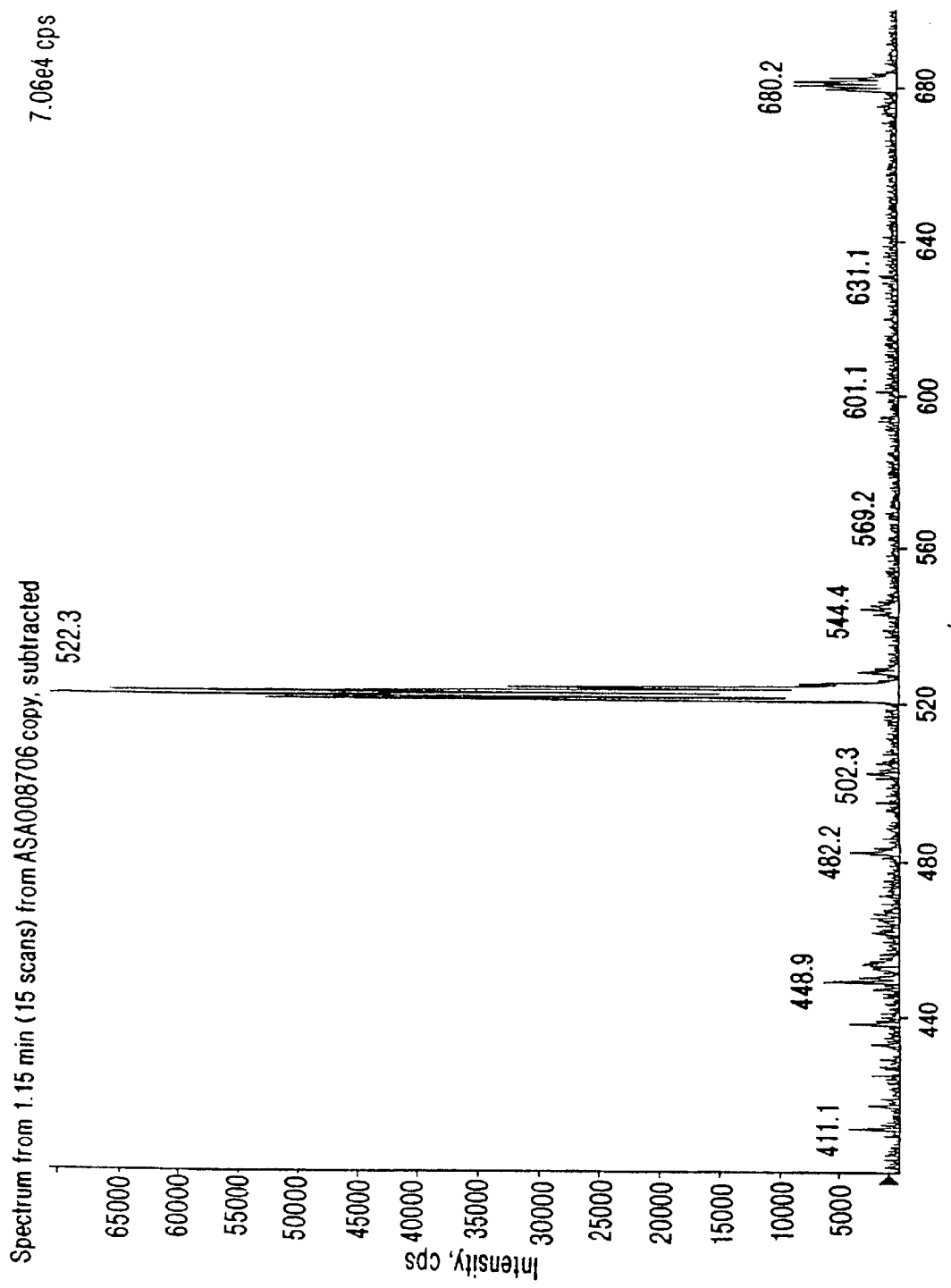
Figure 157:
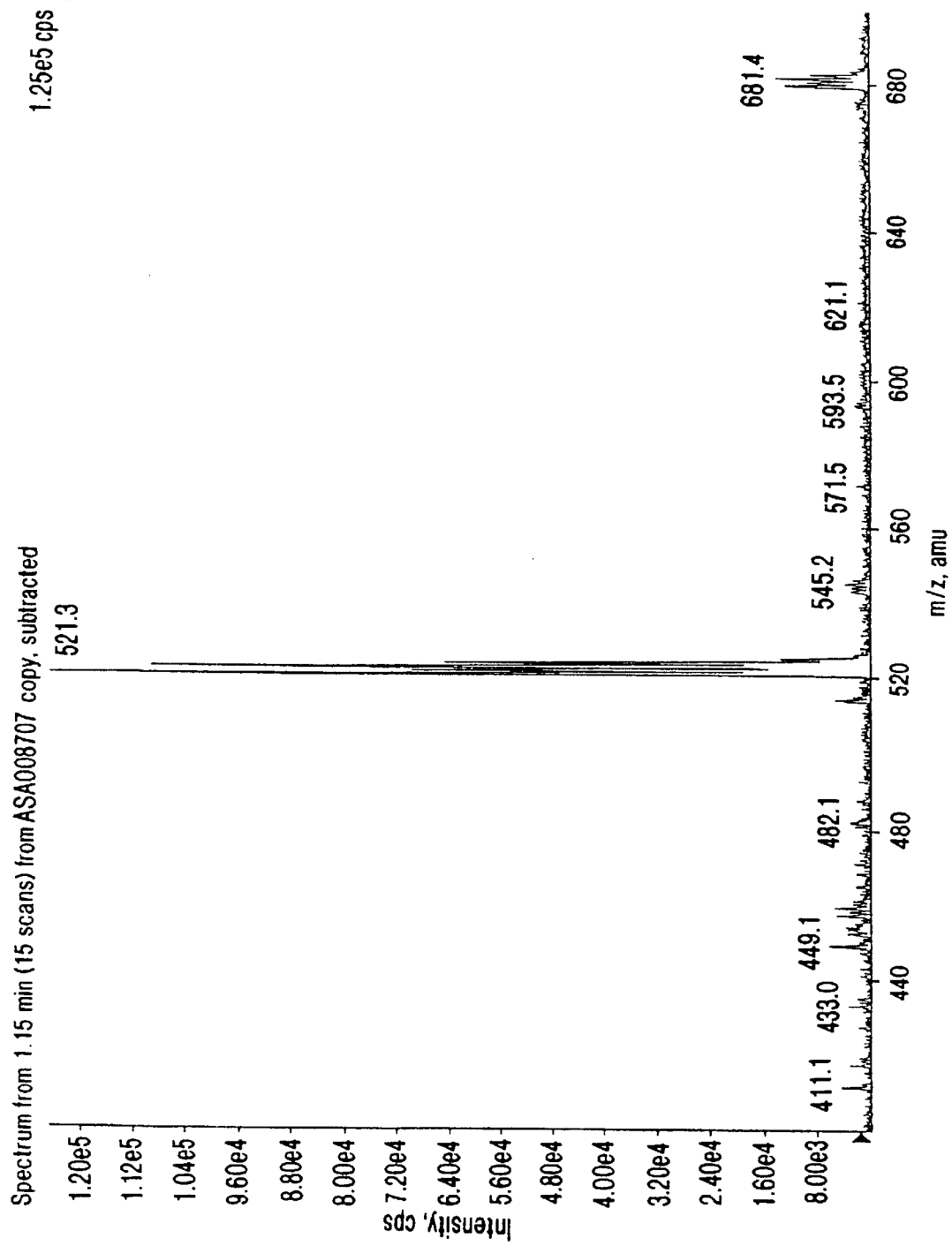
Figure 158:
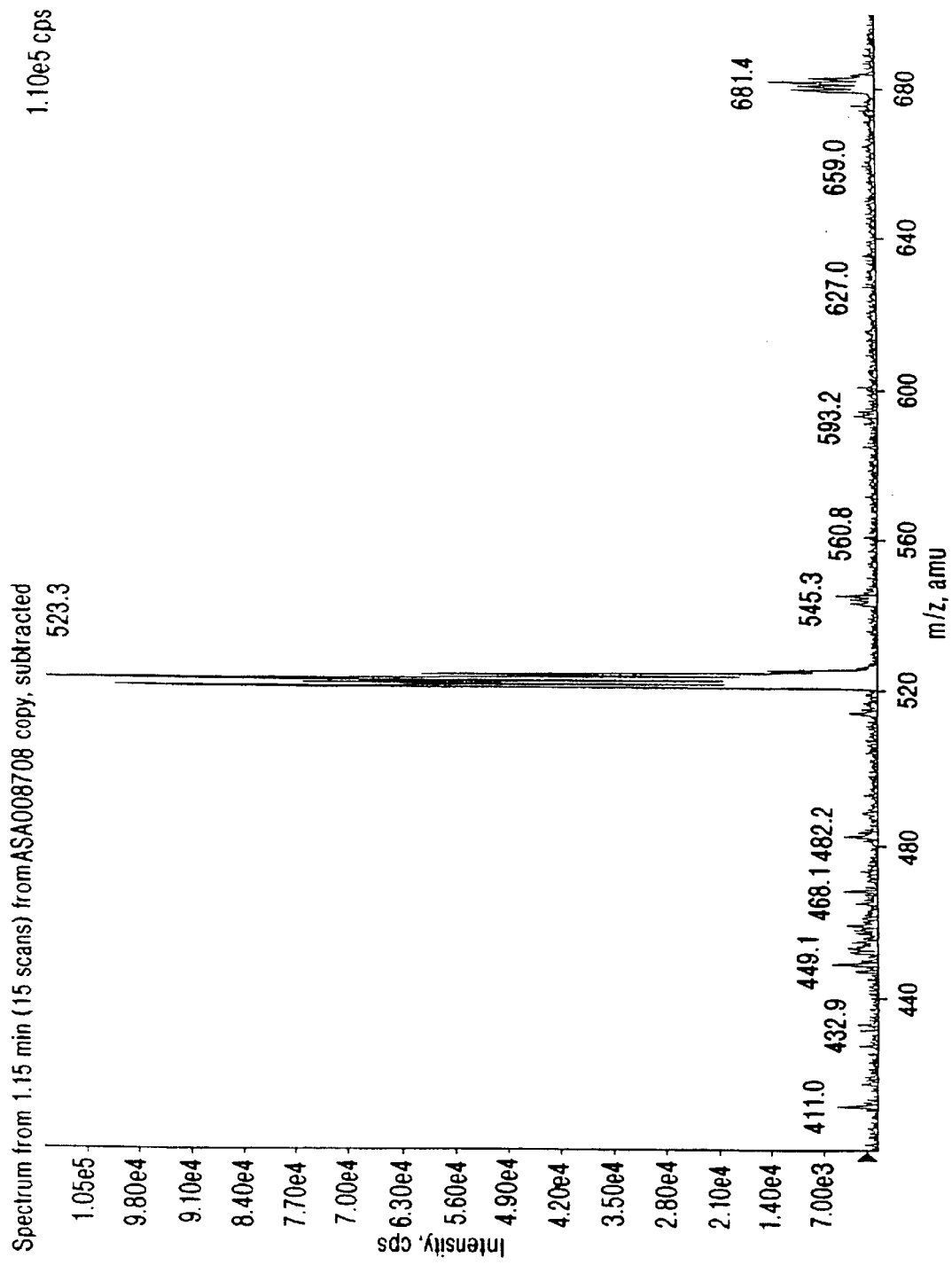
Figure 159:
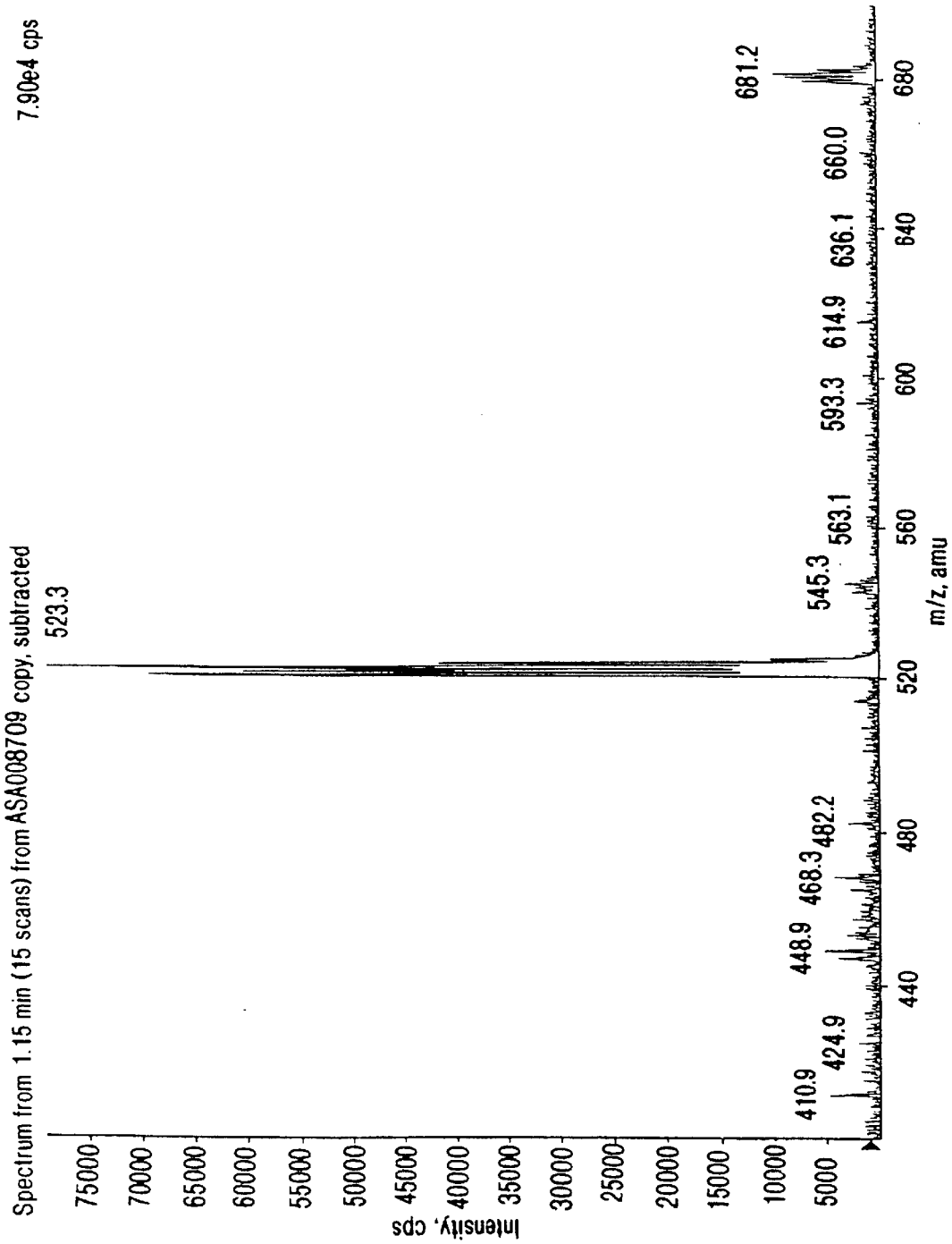
Figure 160:
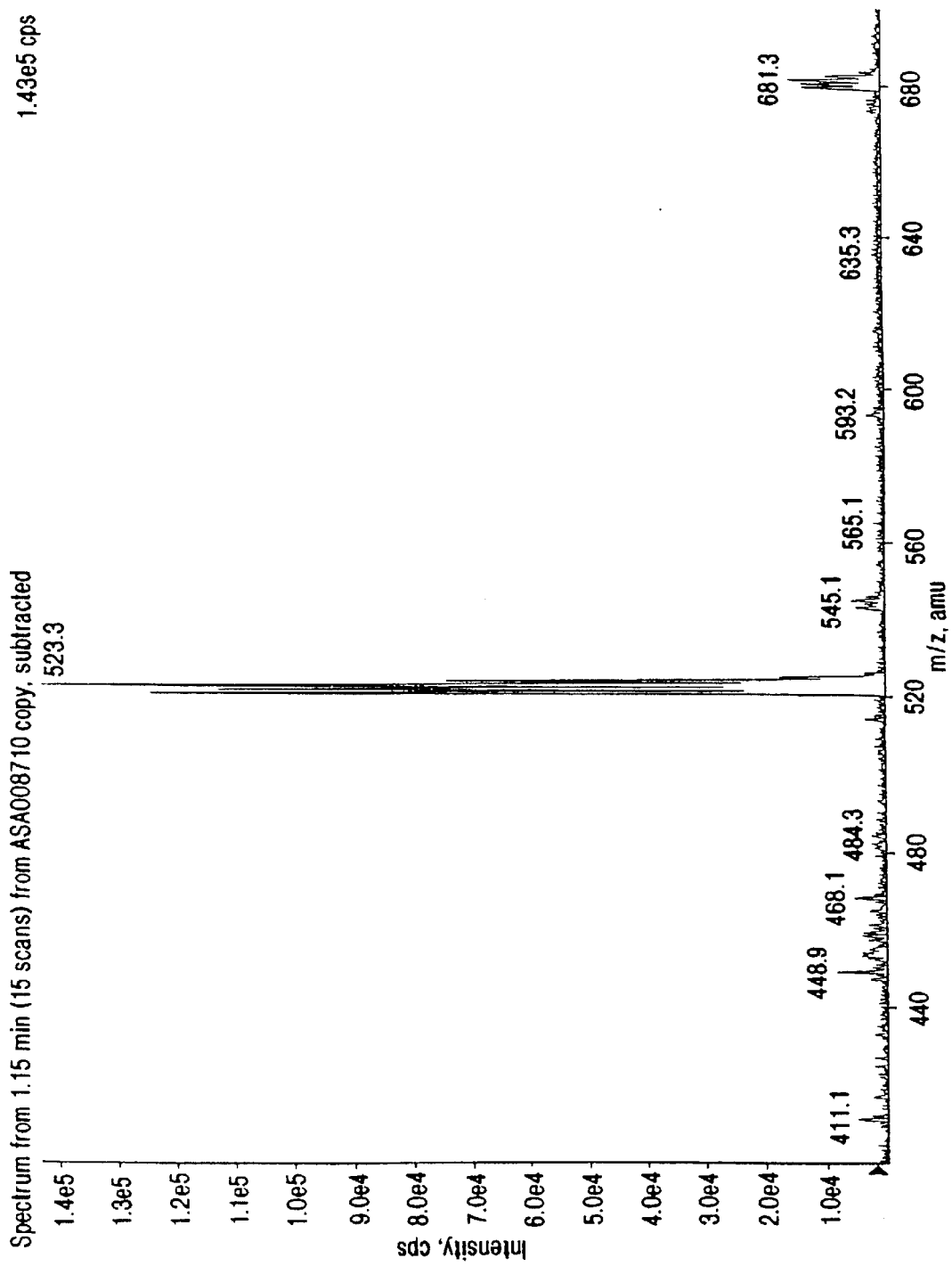
Figure 161:
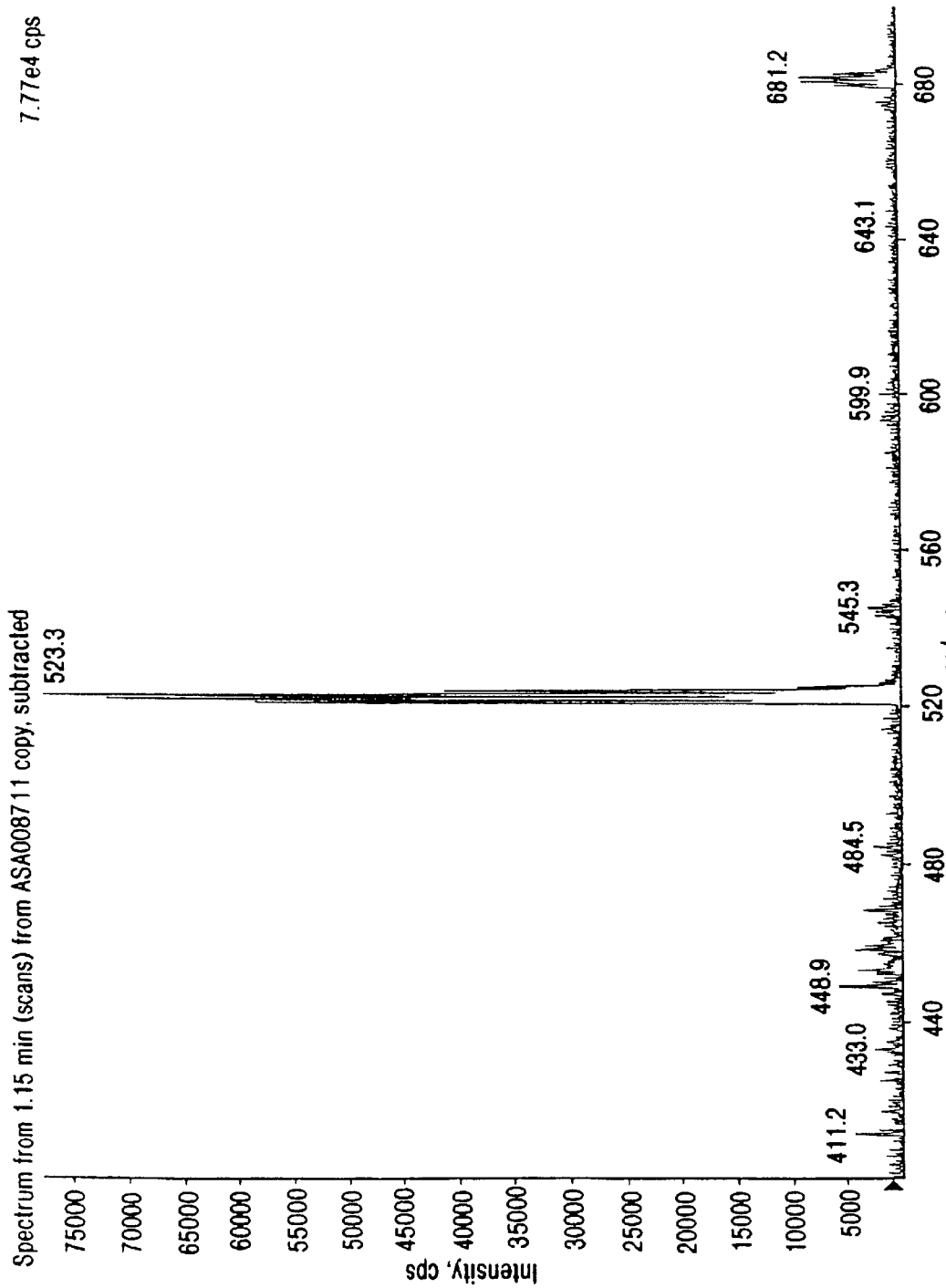
Figure 162:
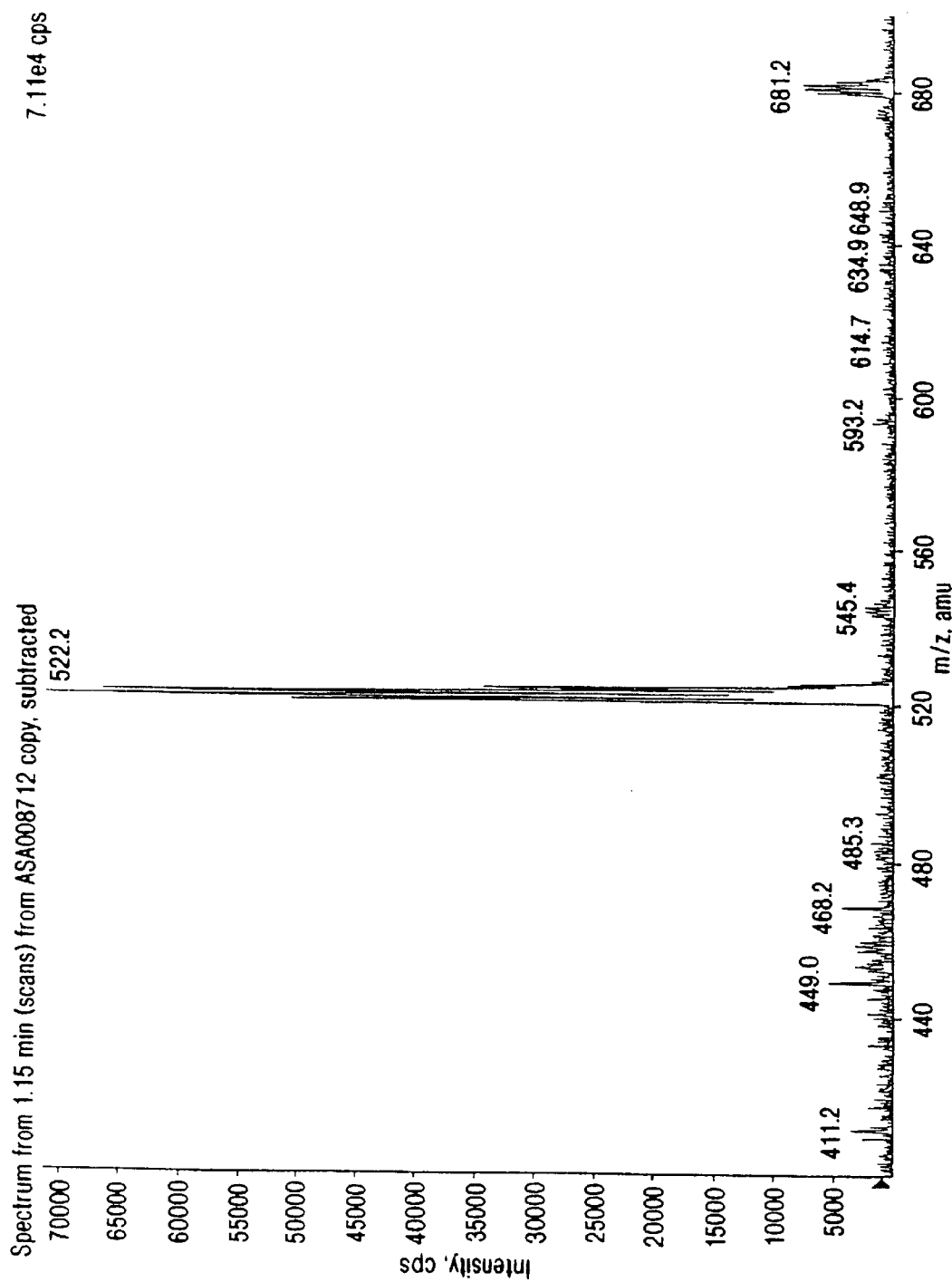
Figure 163:
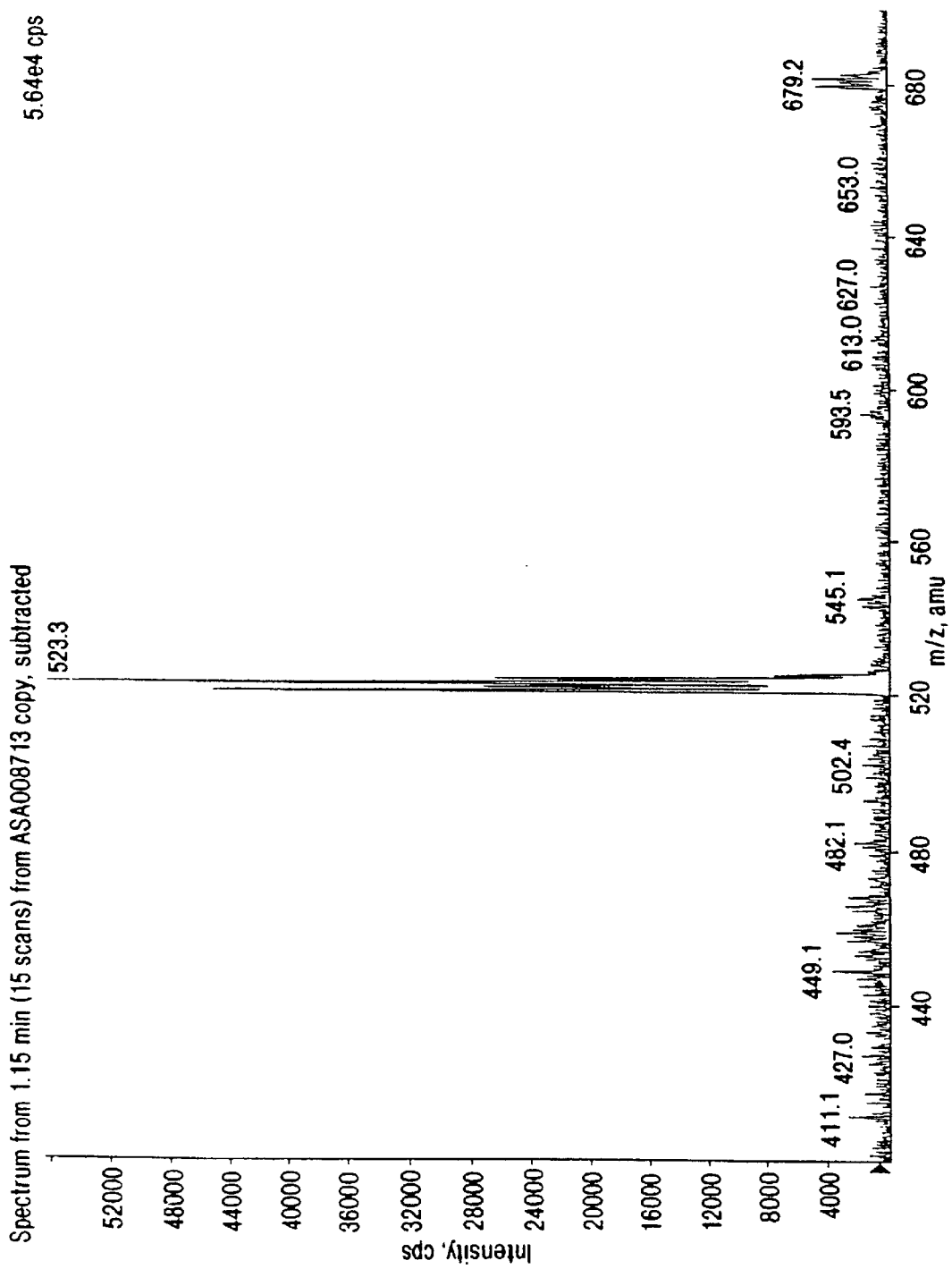
Figure 164:
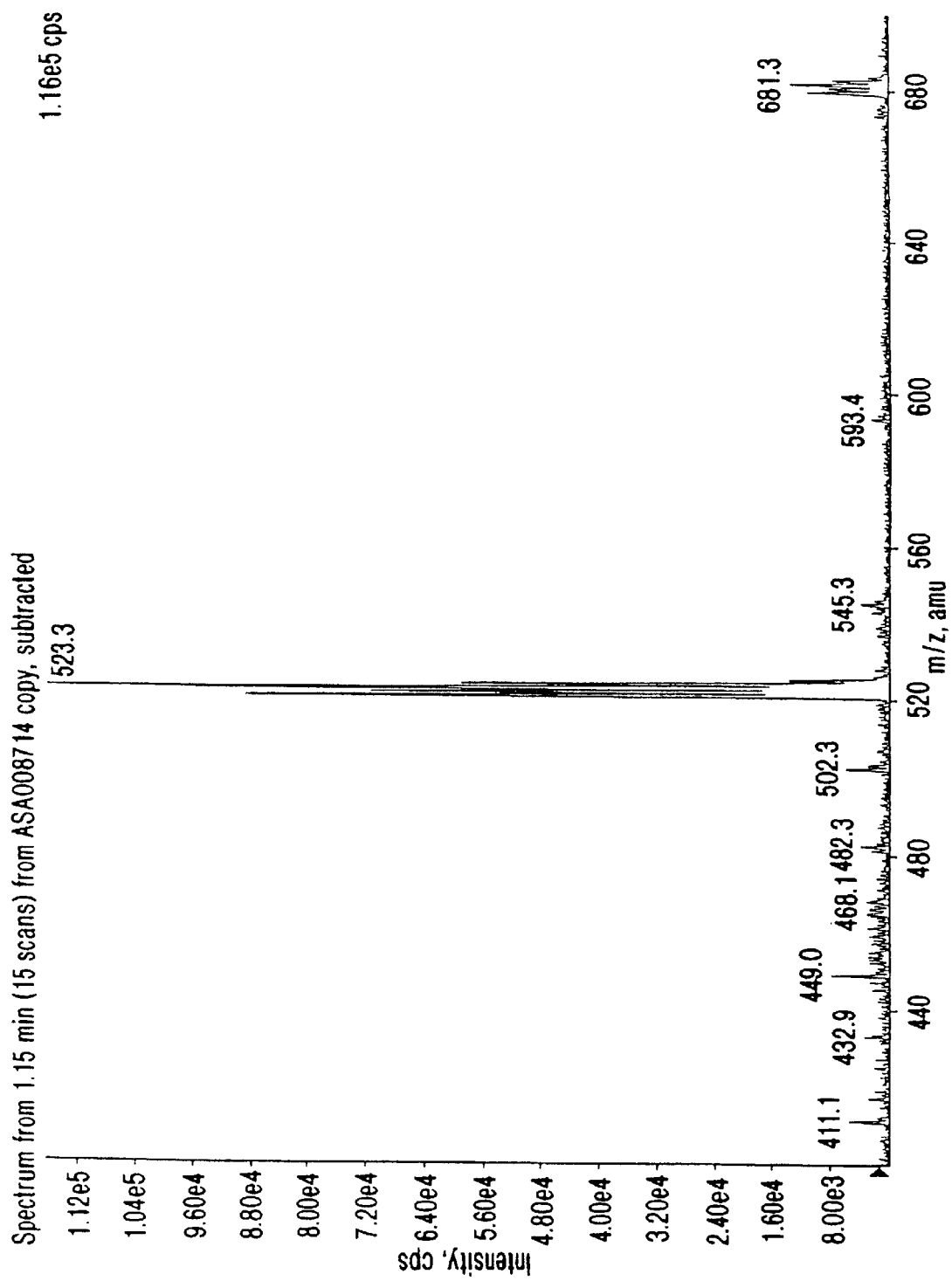
Figure 165:
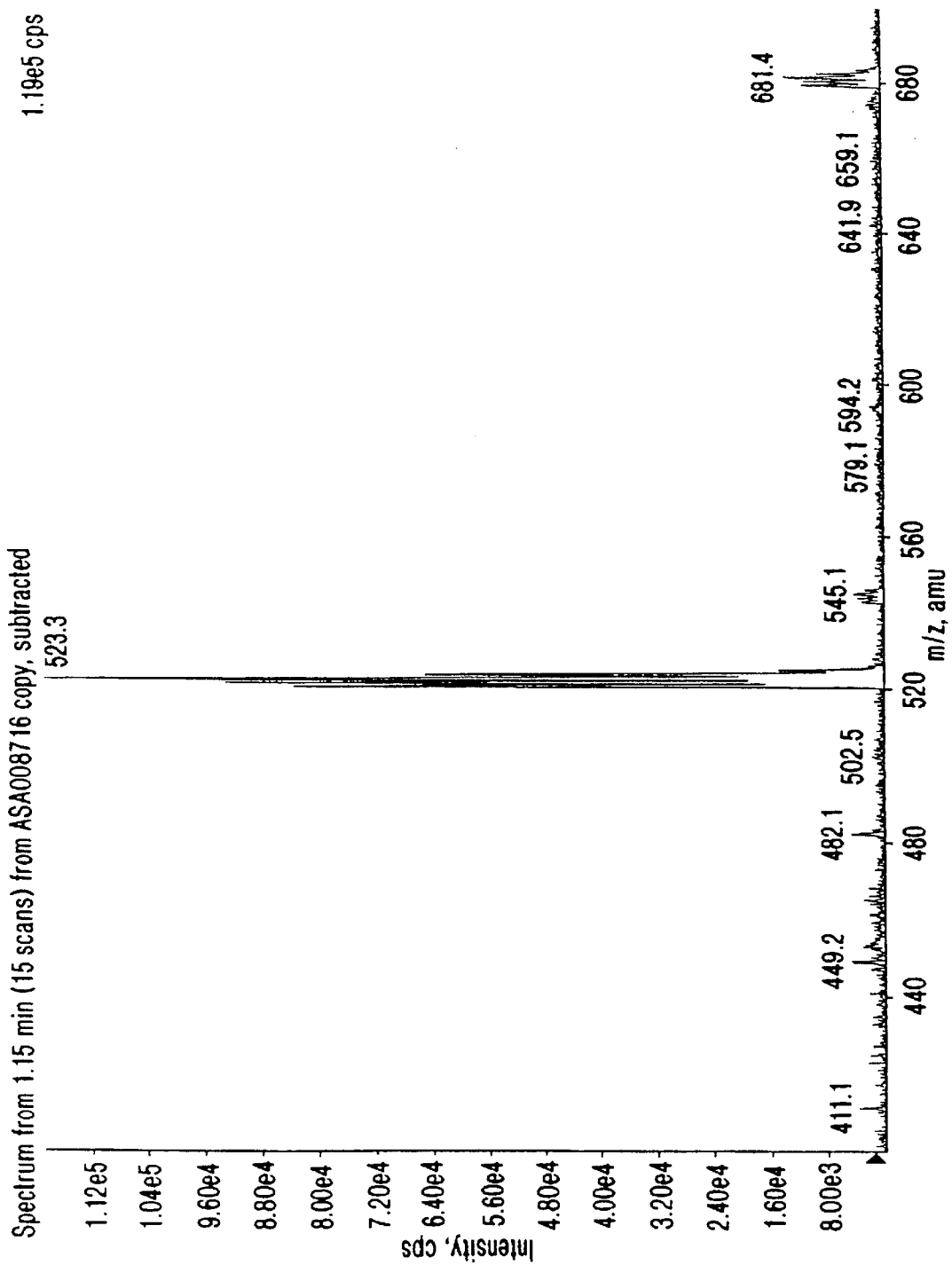
Figure 166:
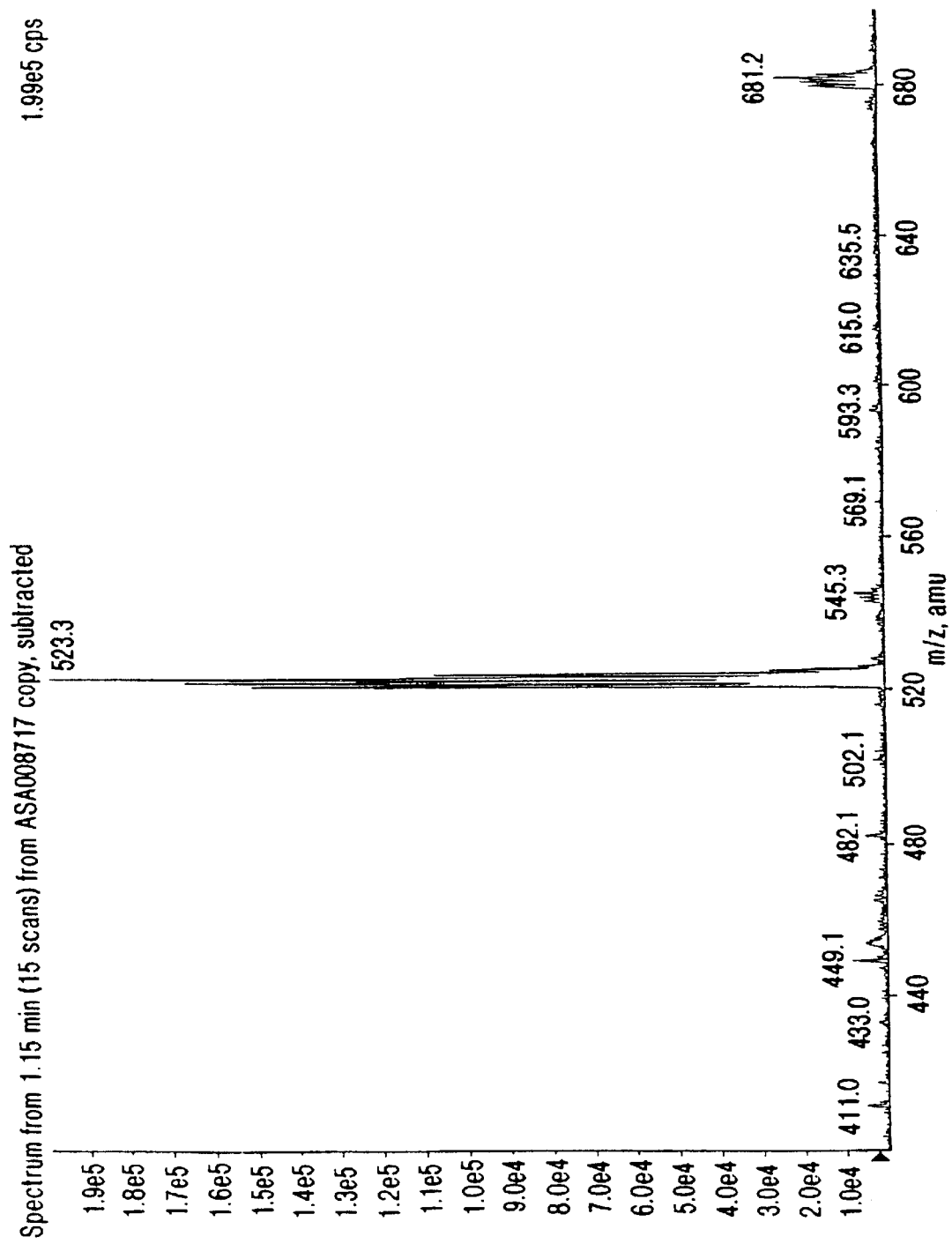
Figure 167:
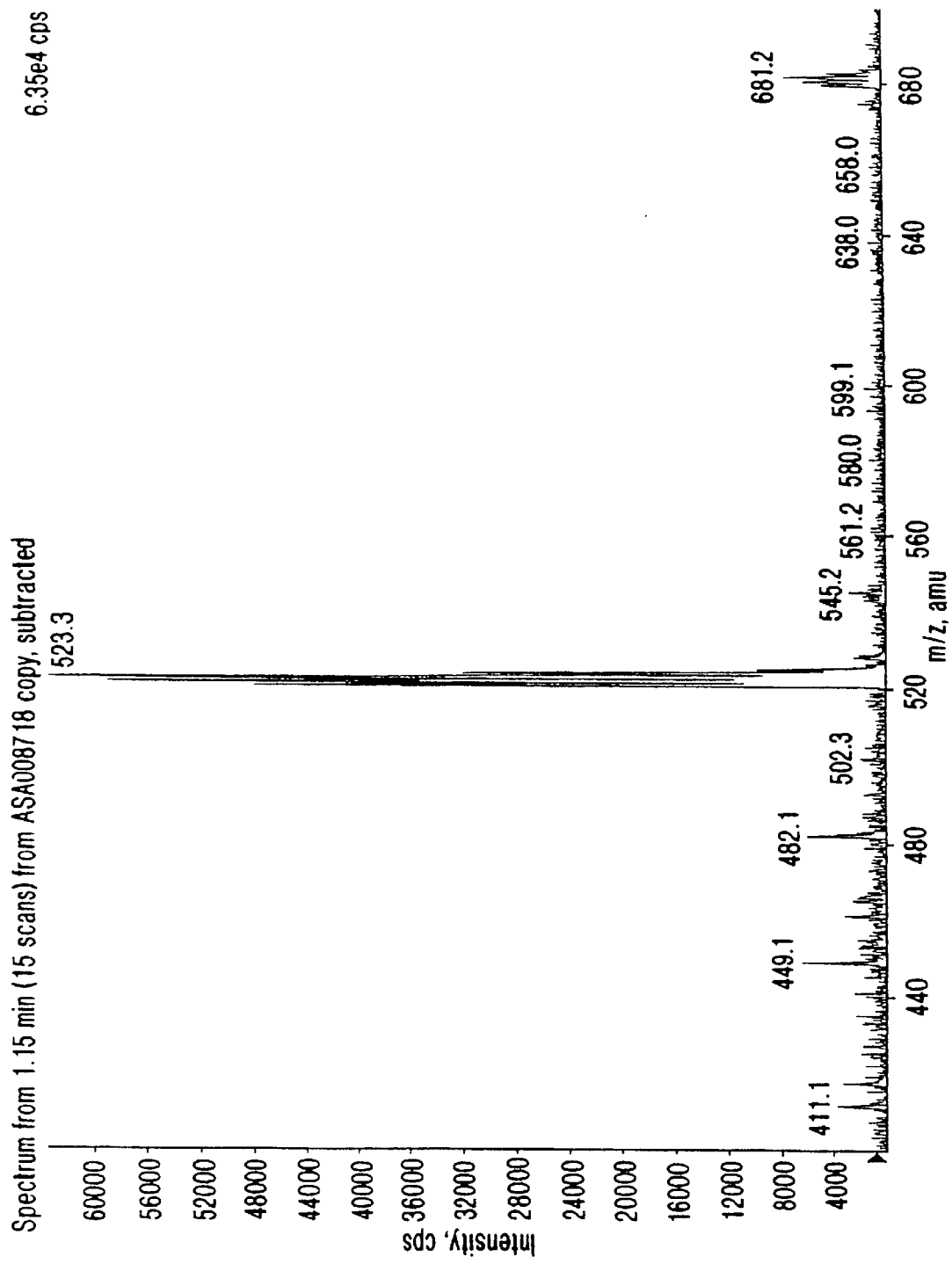
Figure 168:
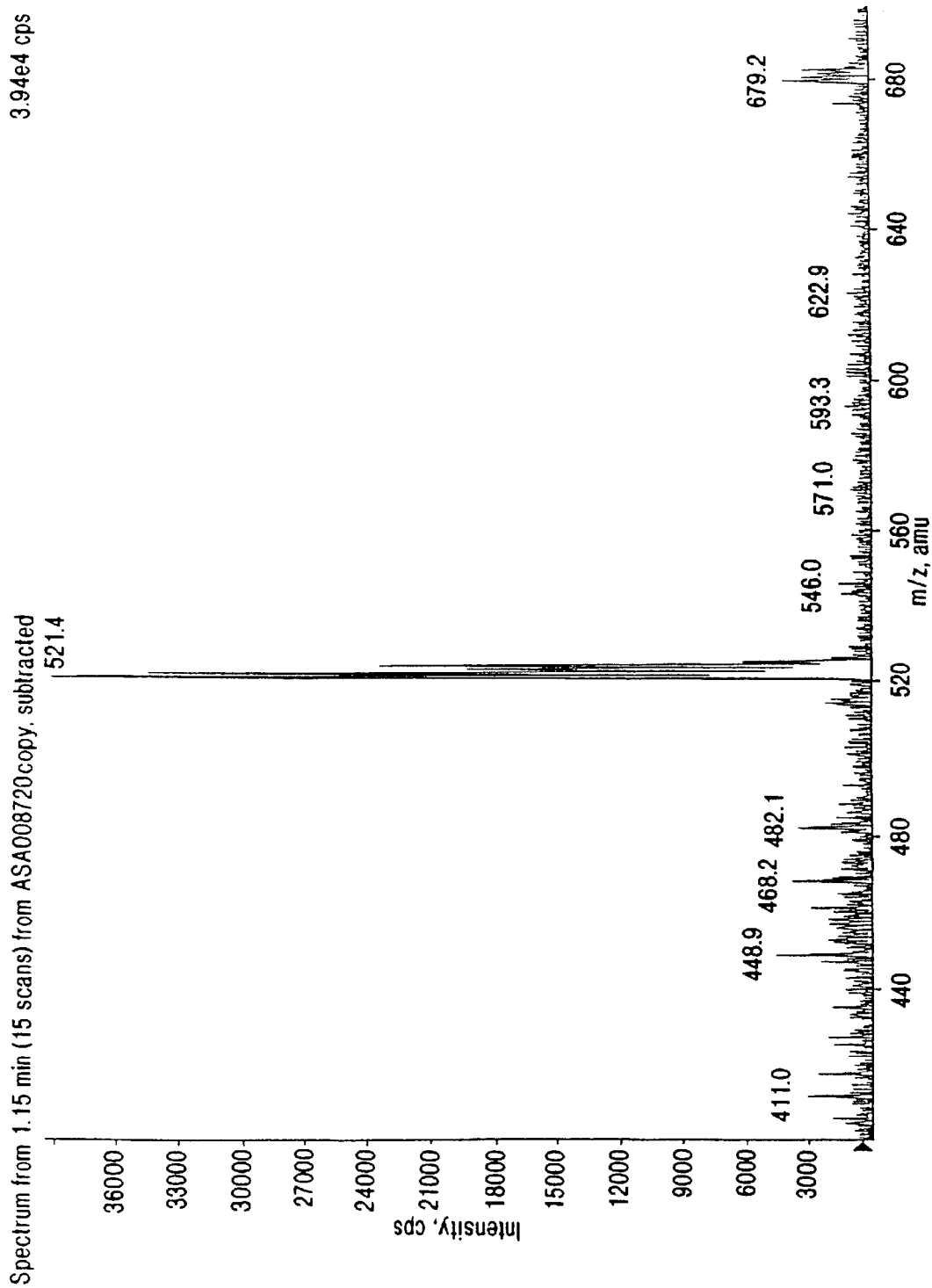
Figure 169:
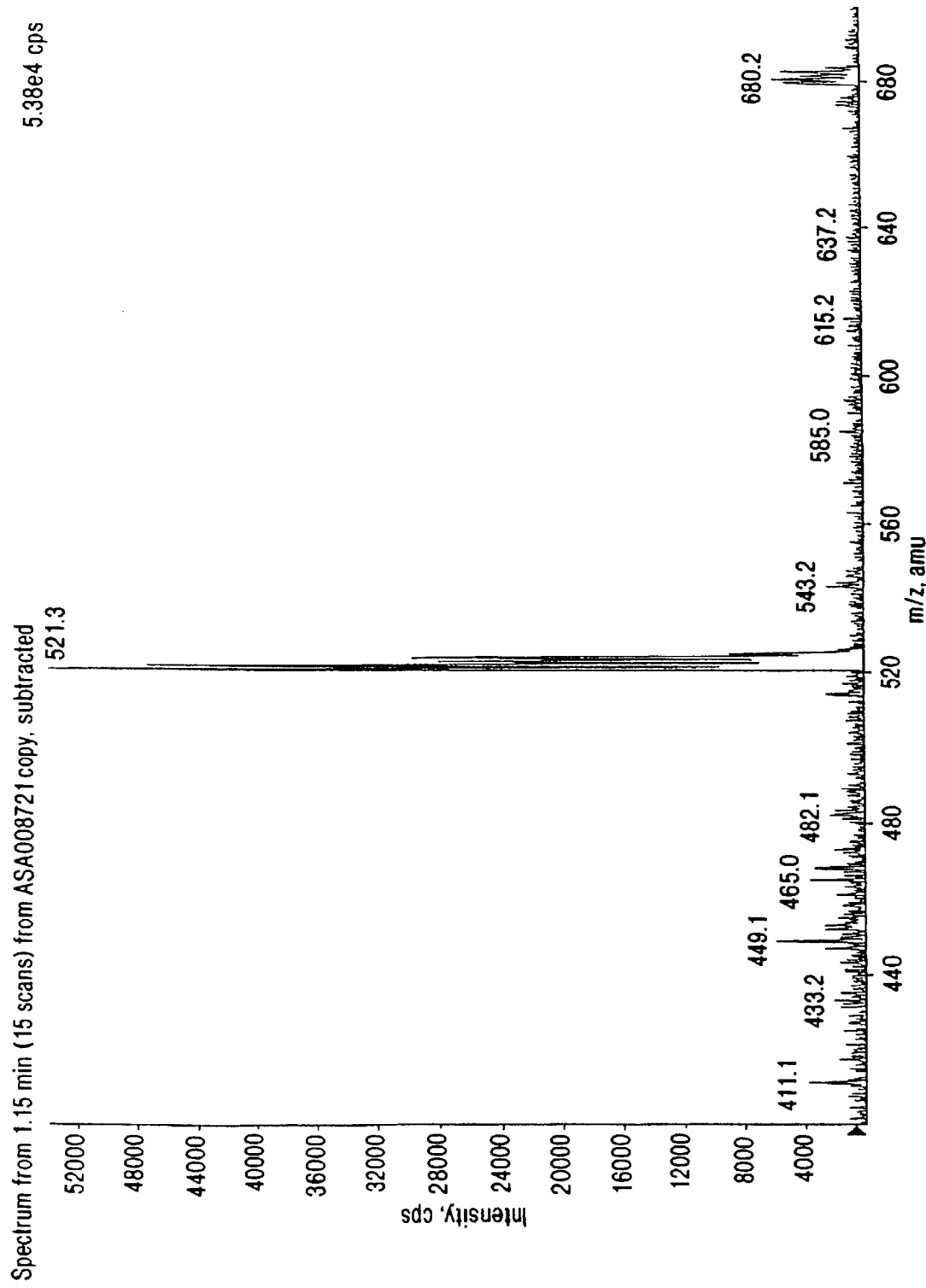
Figure 170:
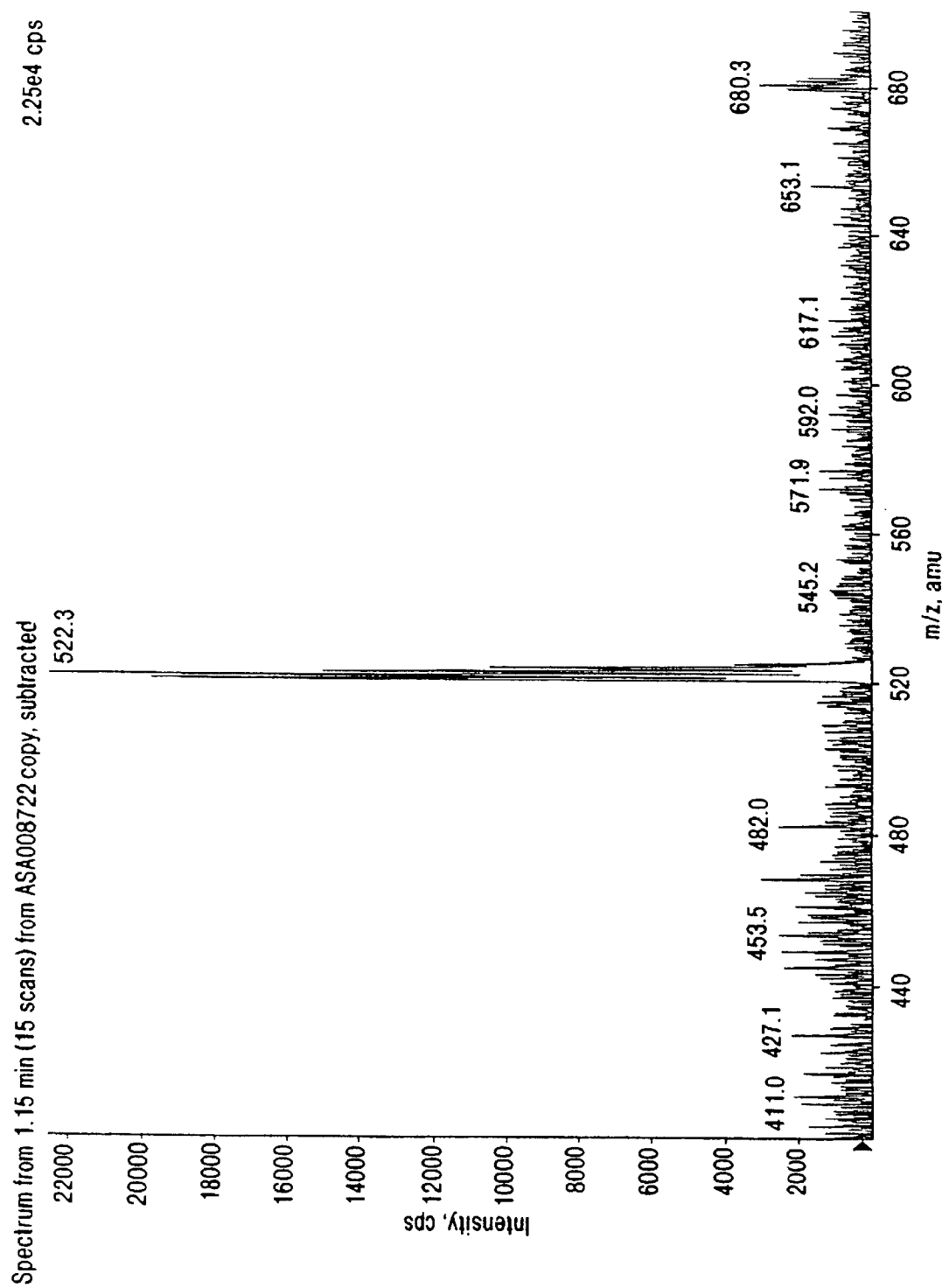
Figure 171:
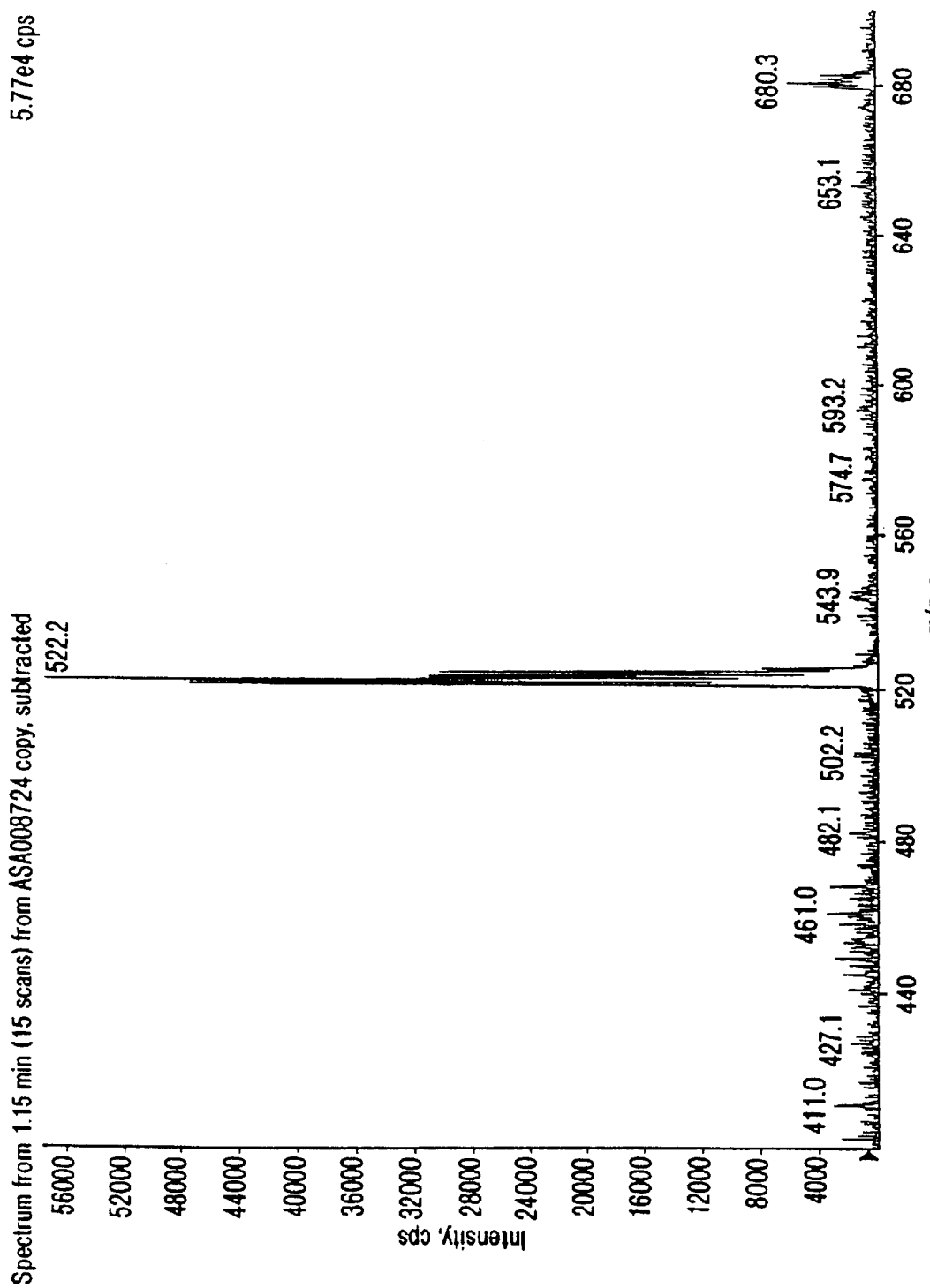
Figure 172:
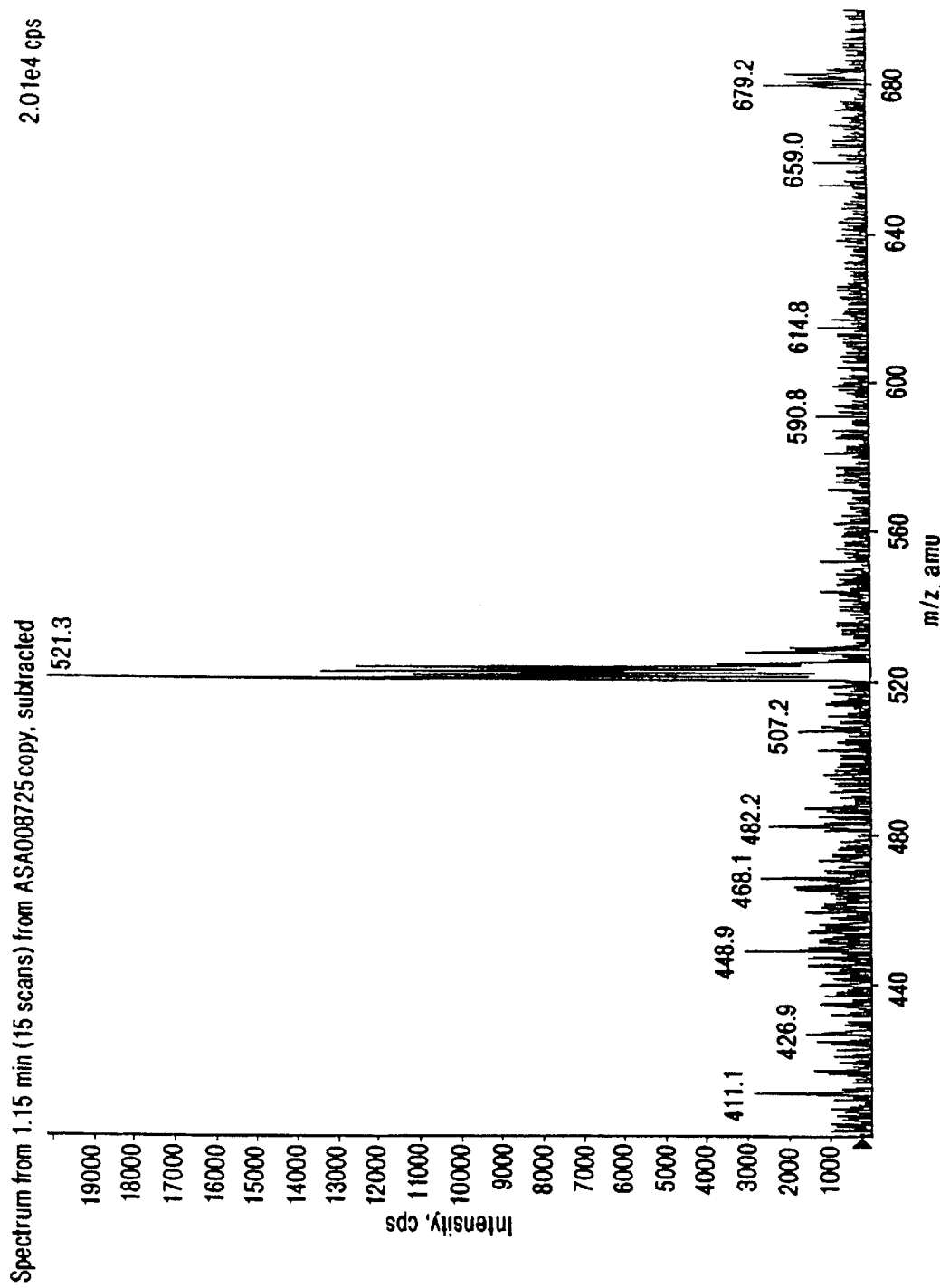
Figure 173:
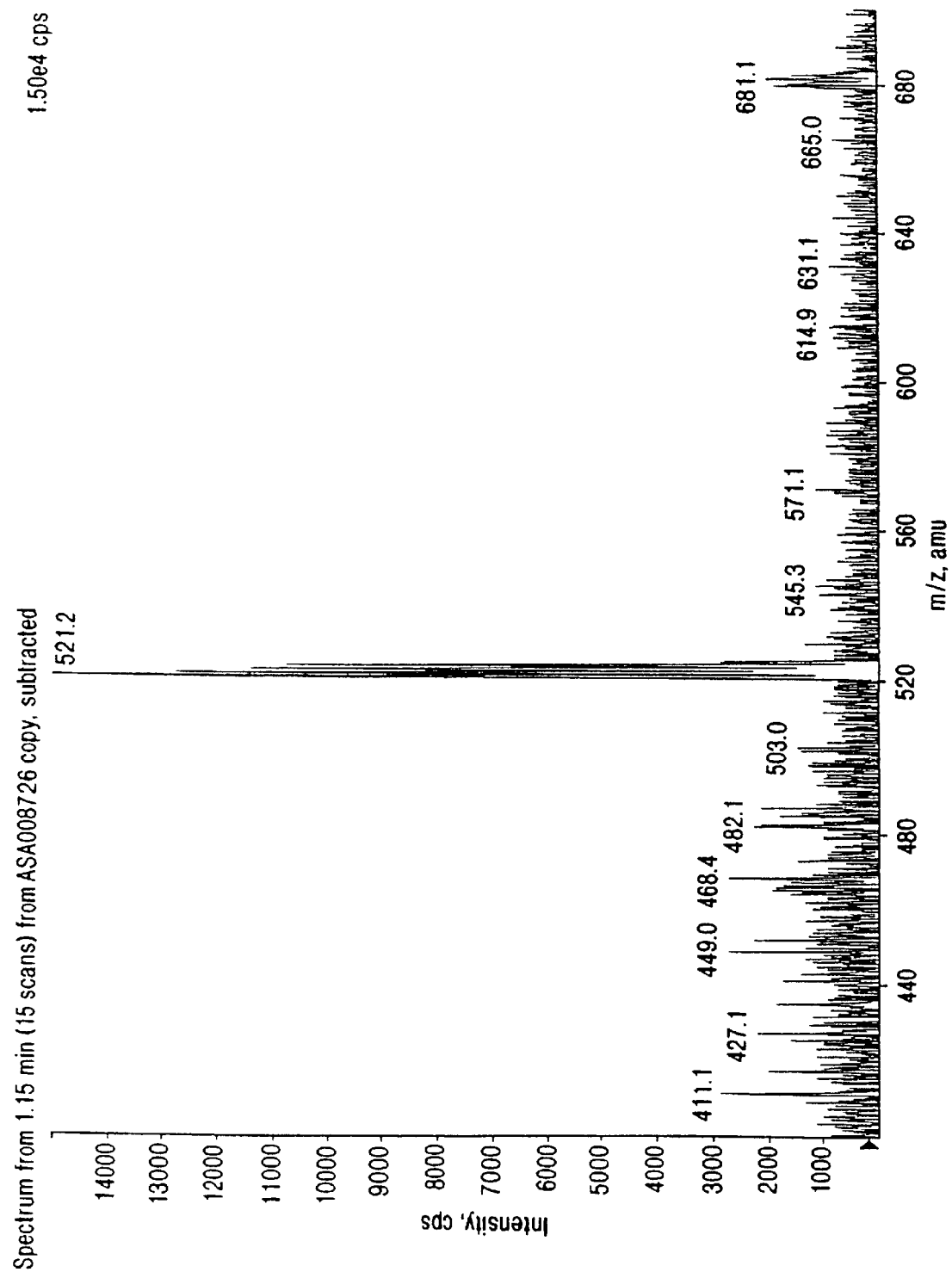
Figure 174:
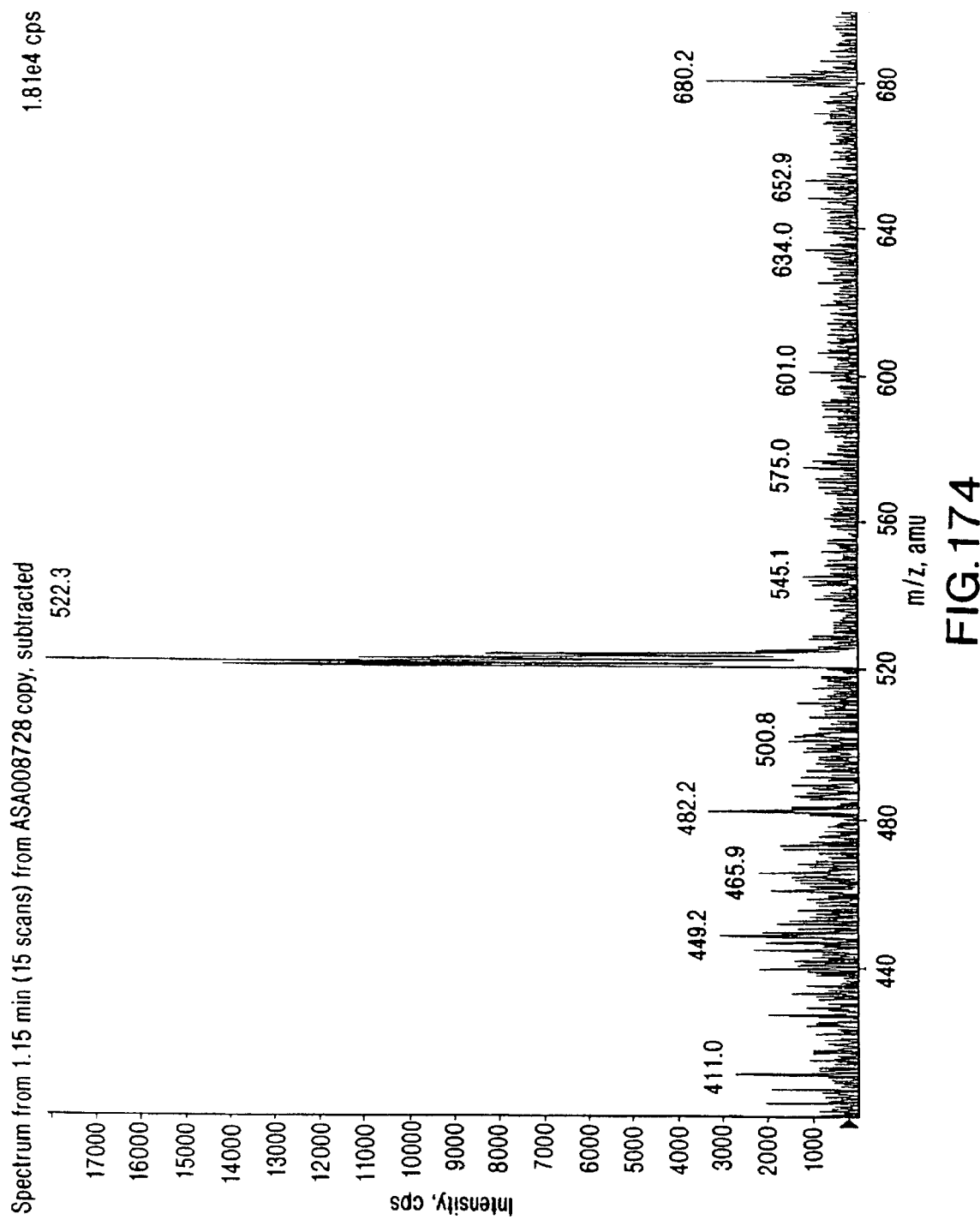
Figure 175:
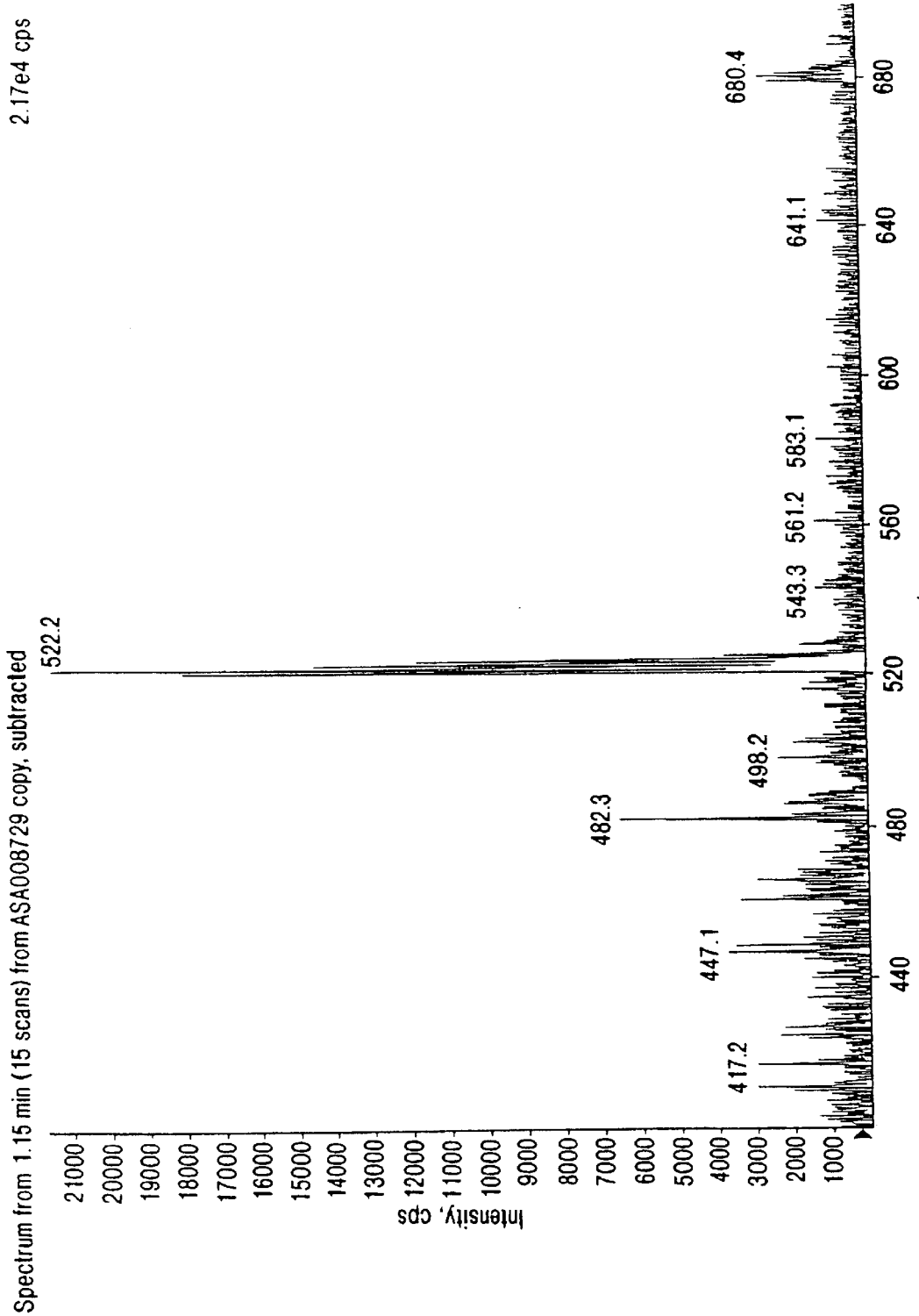
Figure 176:
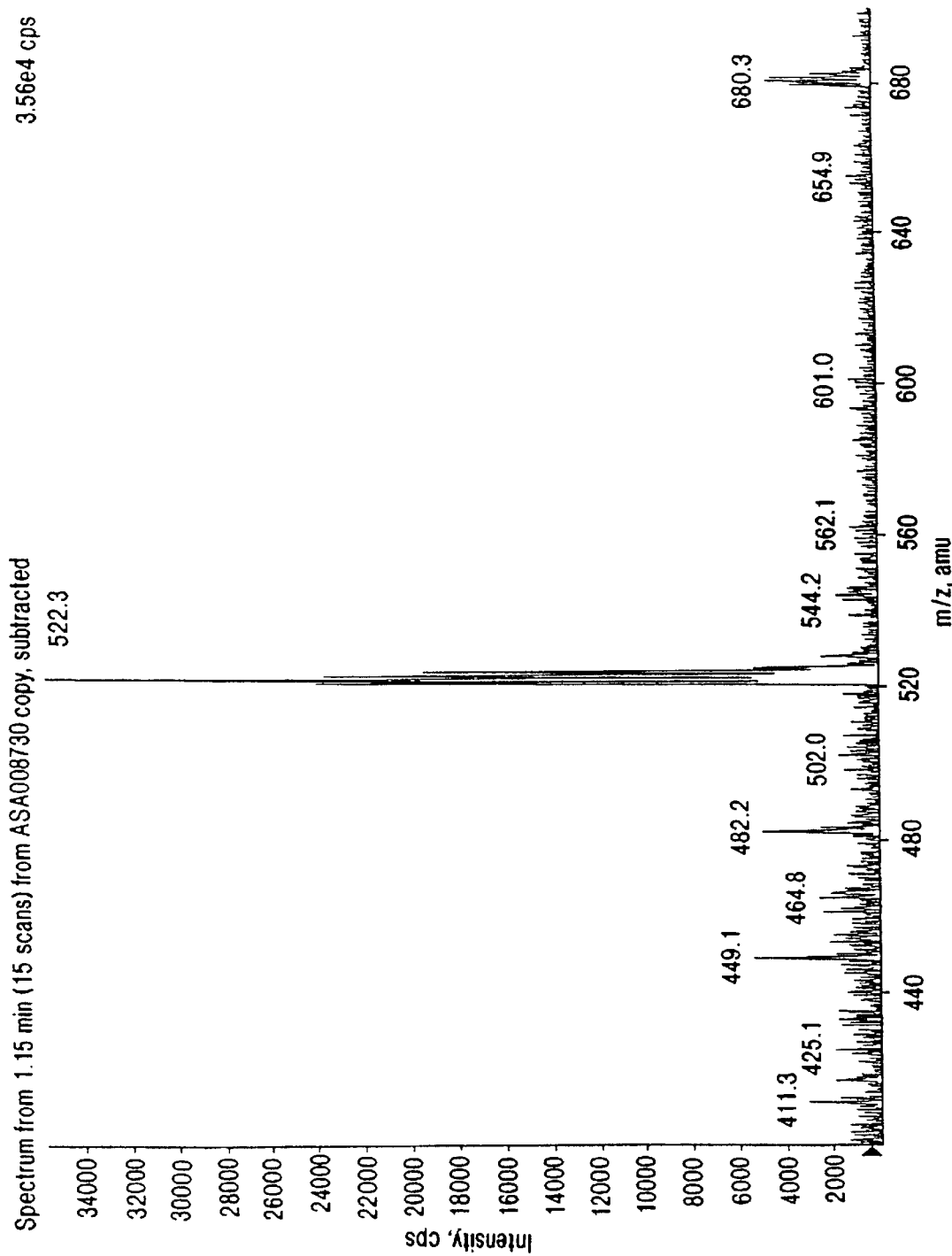
Figure 177:
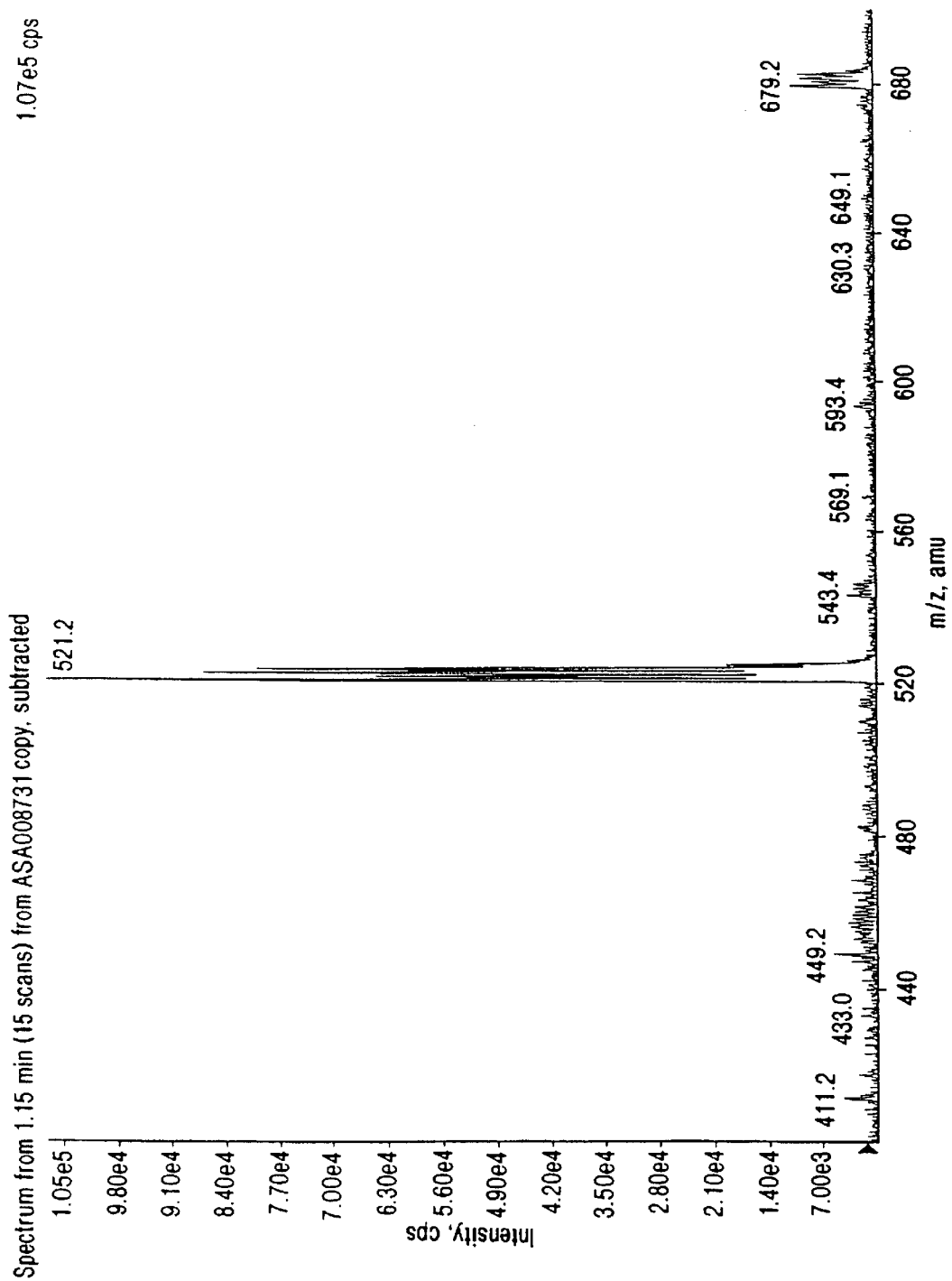
Figure 178:
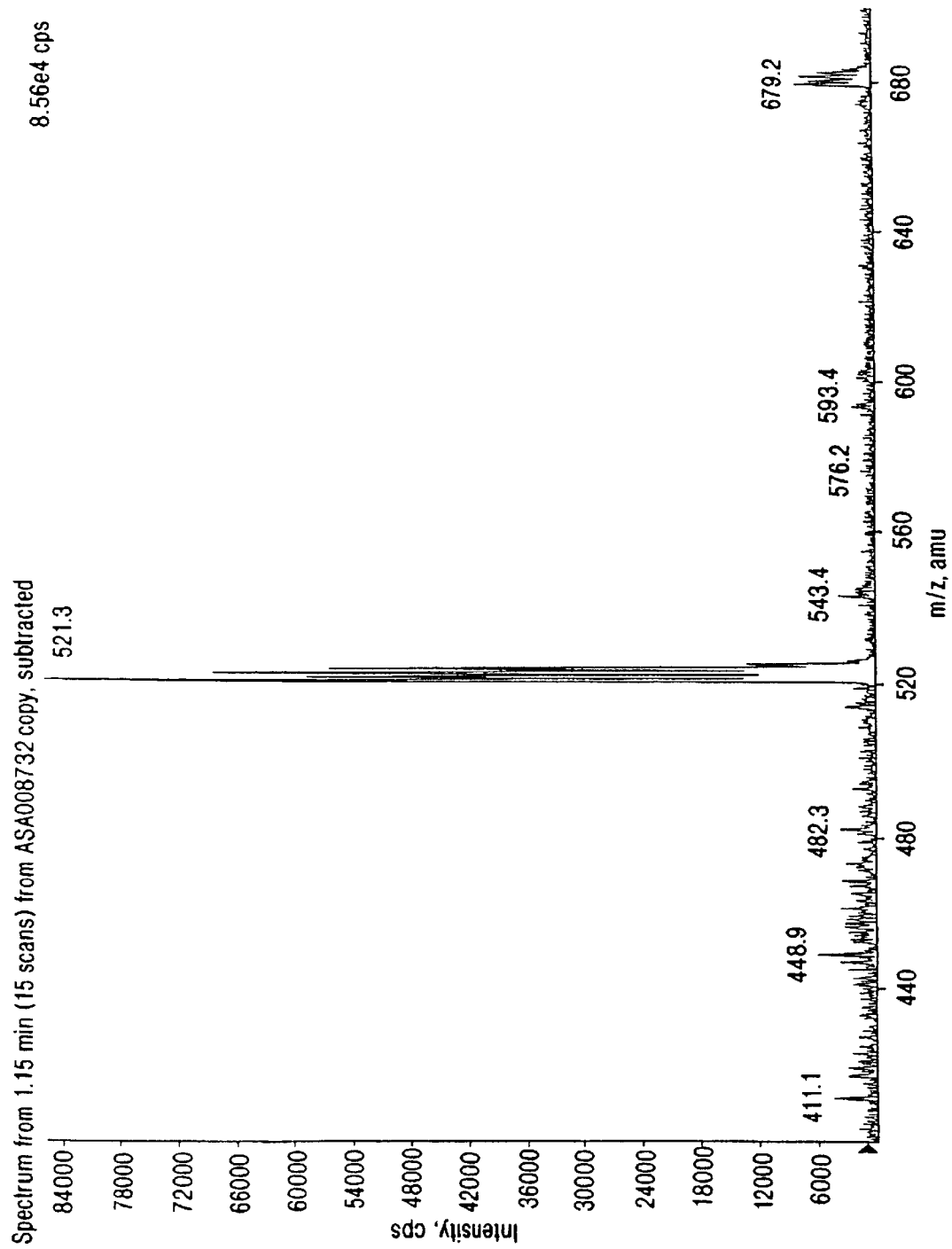
Figure 179:
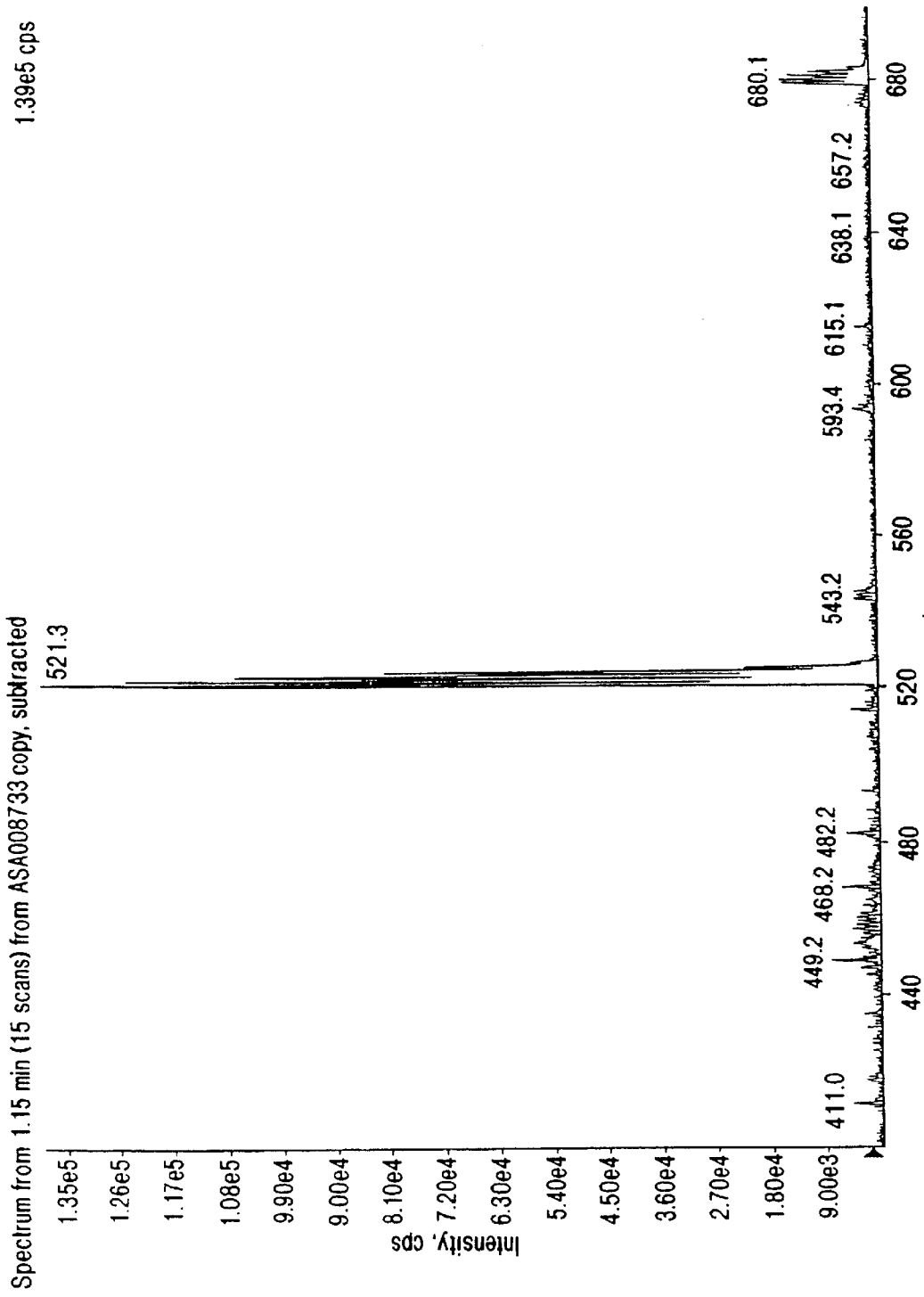
Figure 180:
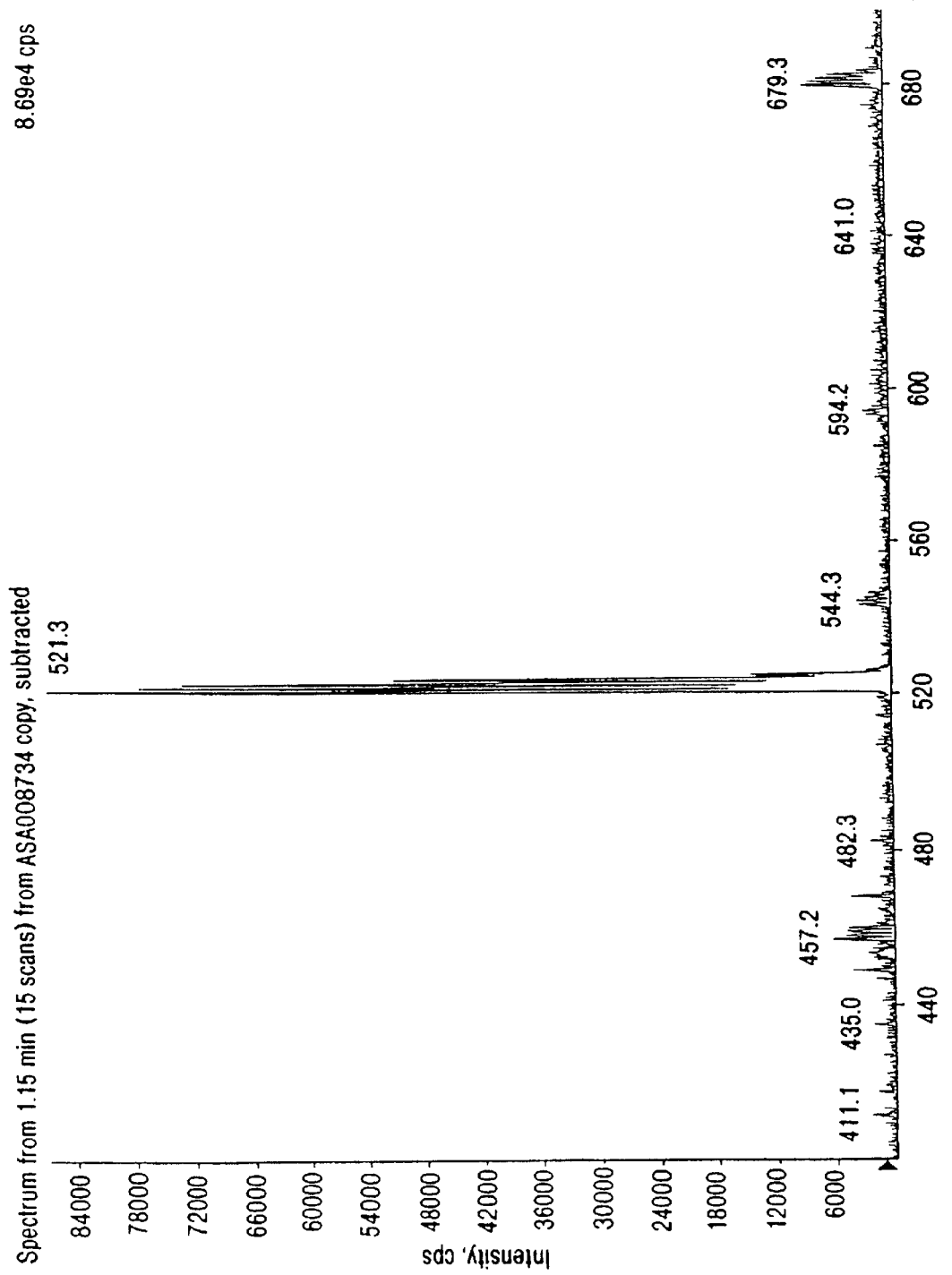
Figure 181:
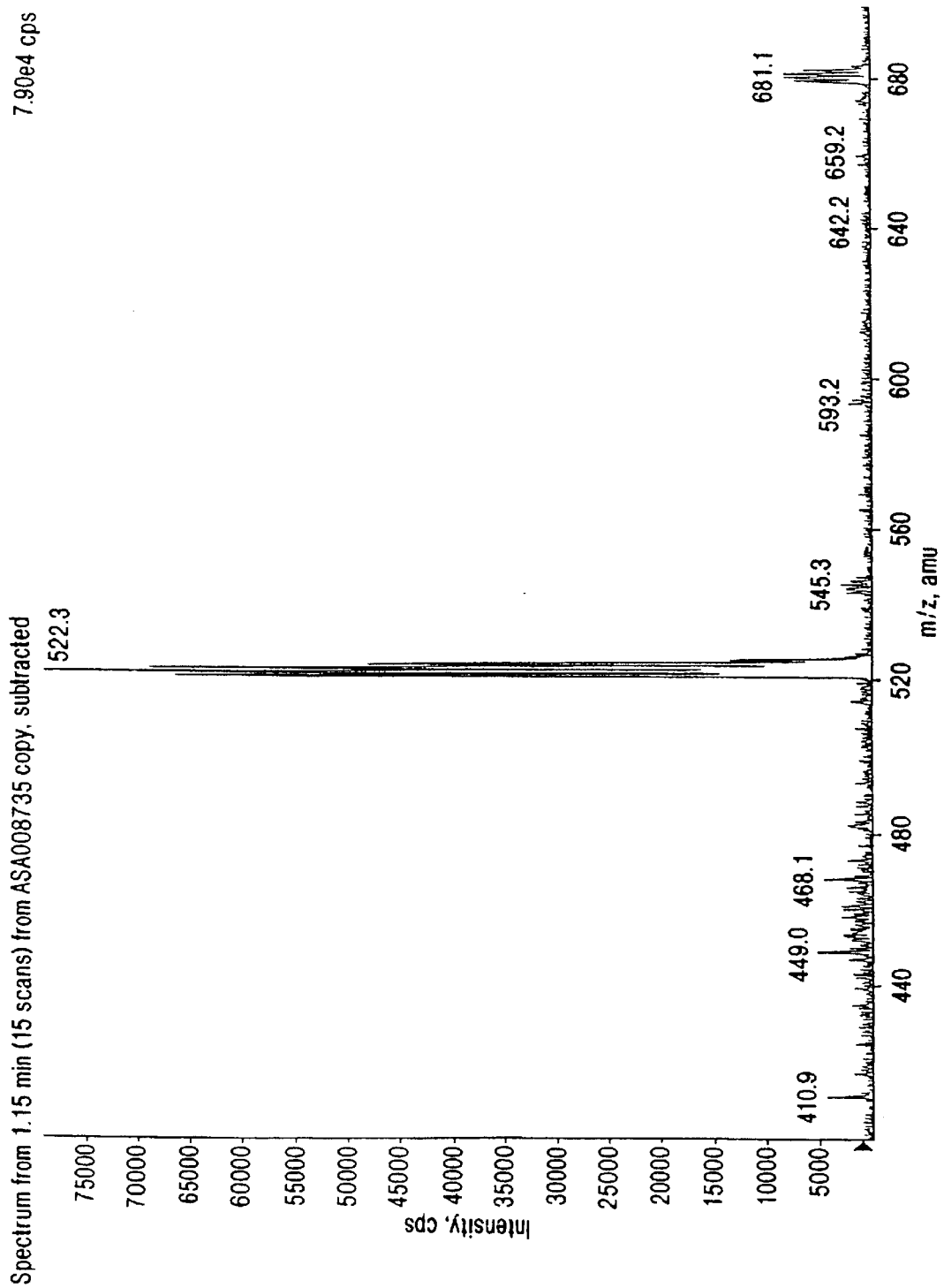
Figure 182:
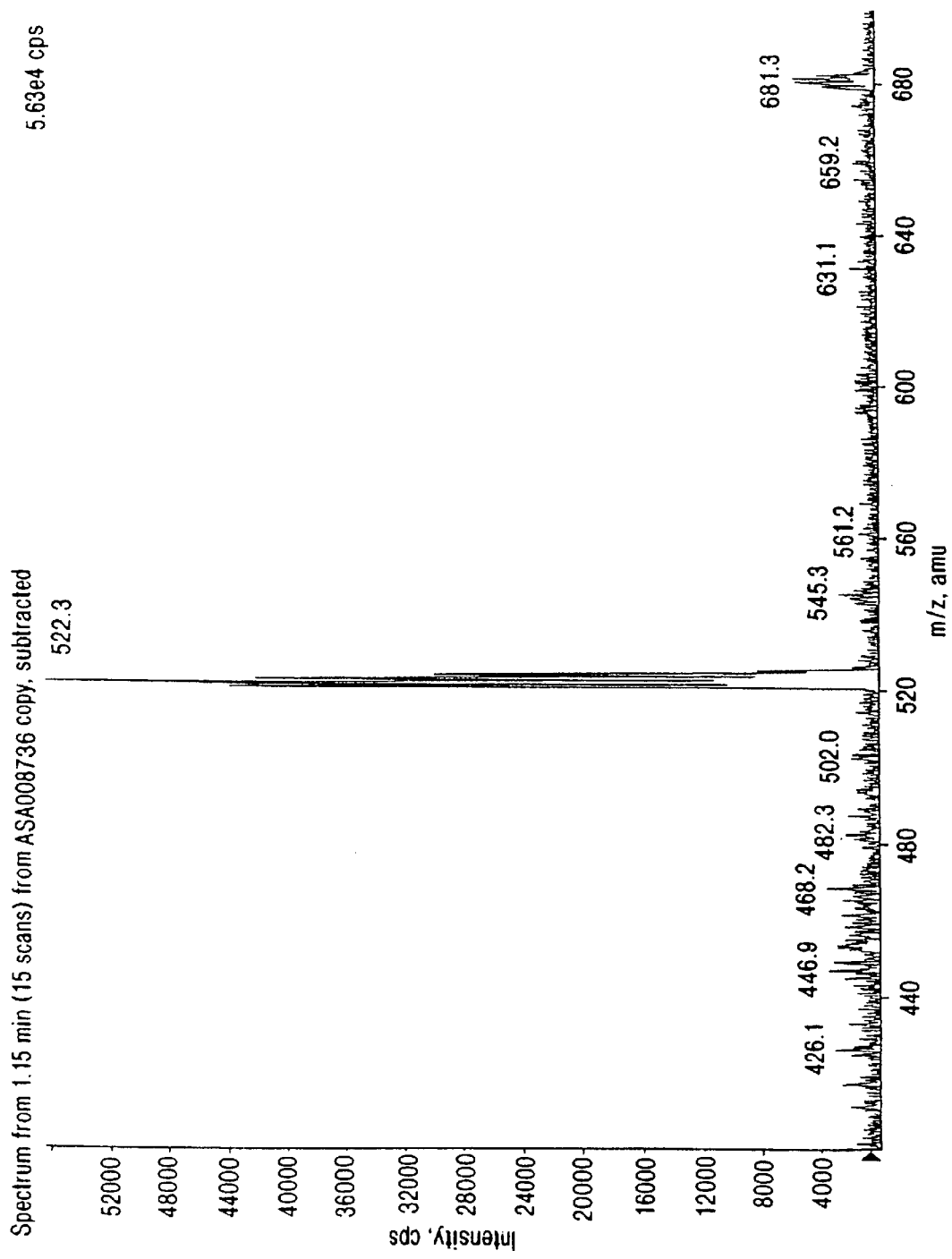
Figure 183:
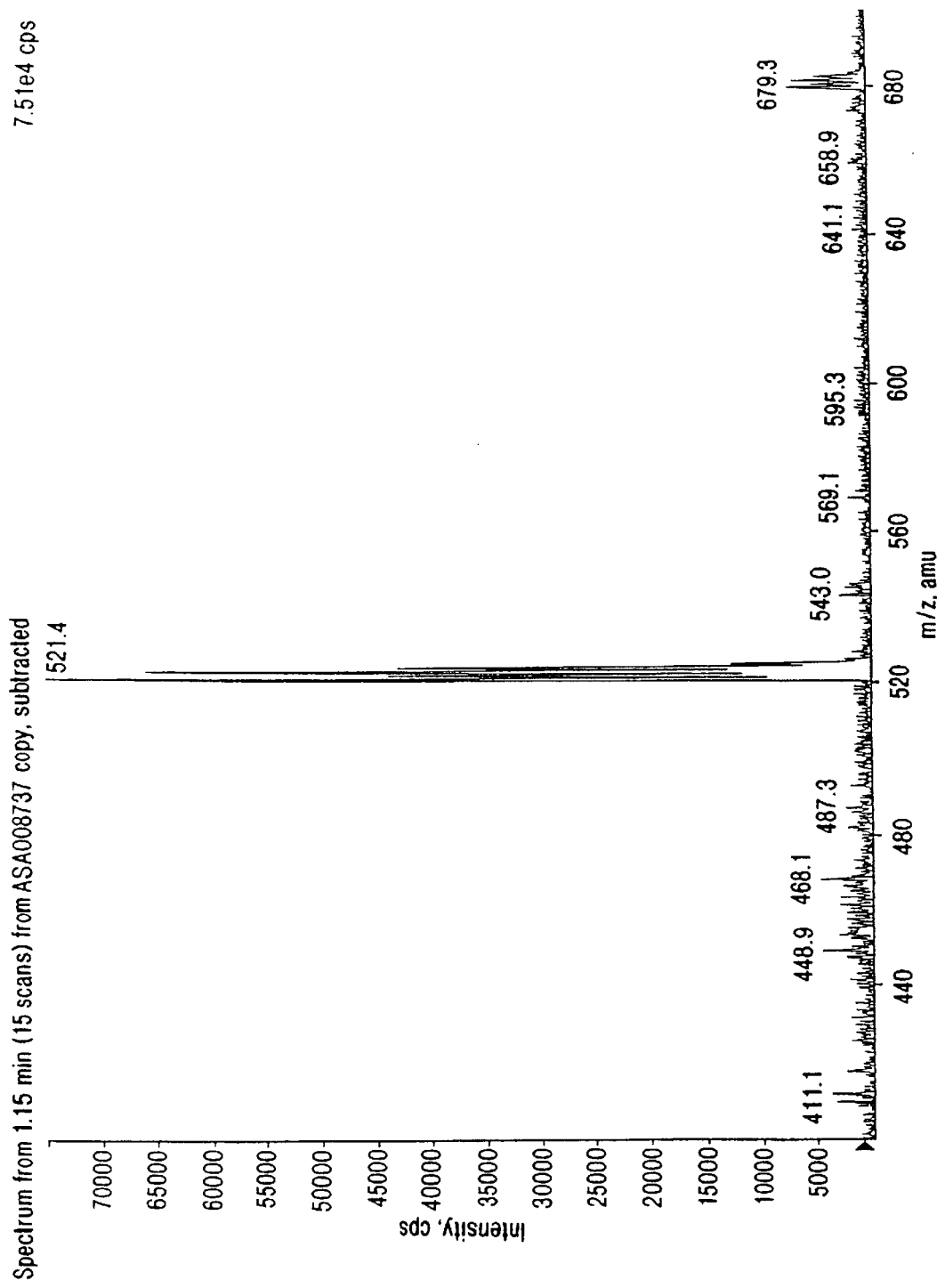
Figure 184:
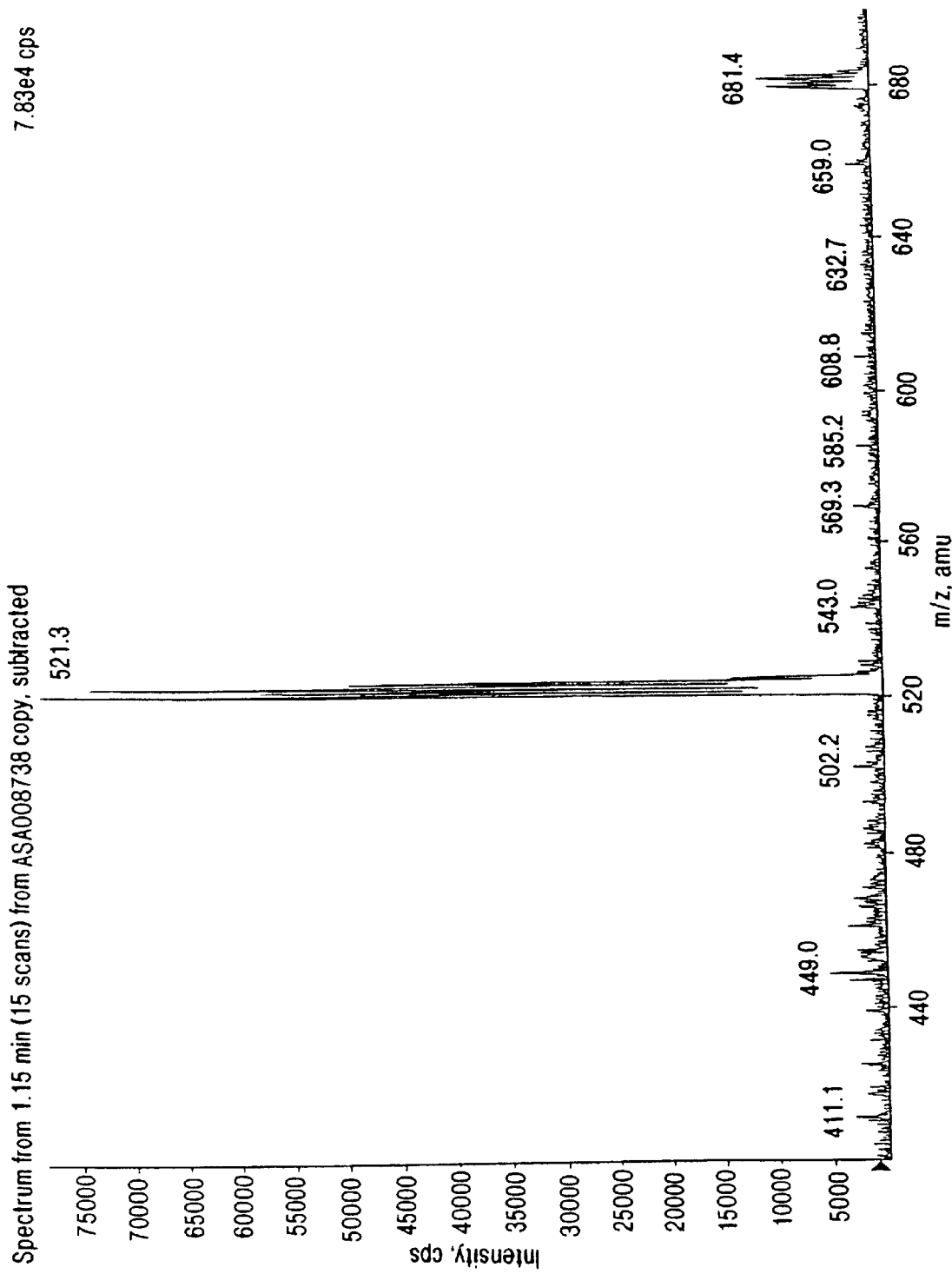
Figure 185:
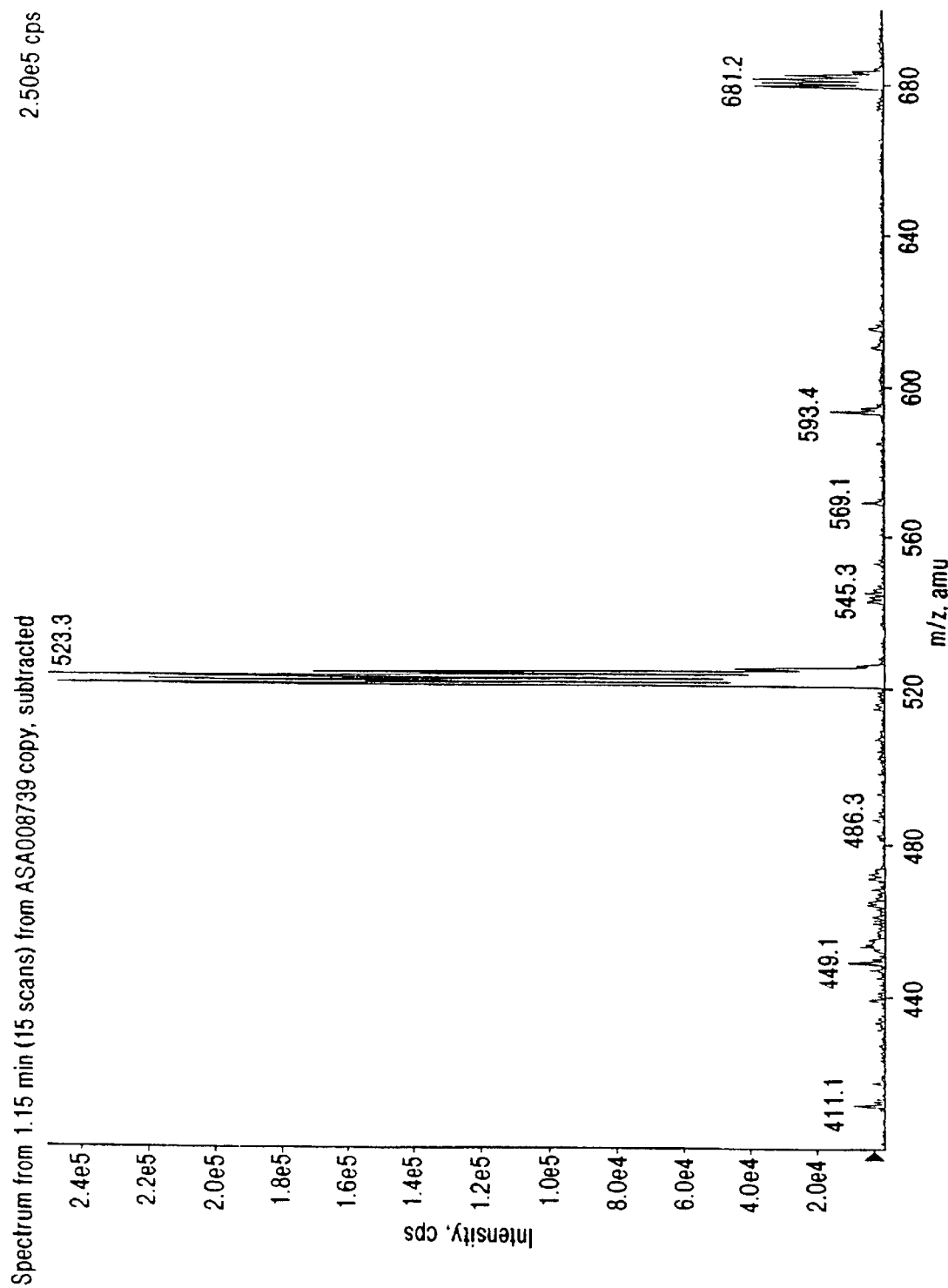
Figure 186:
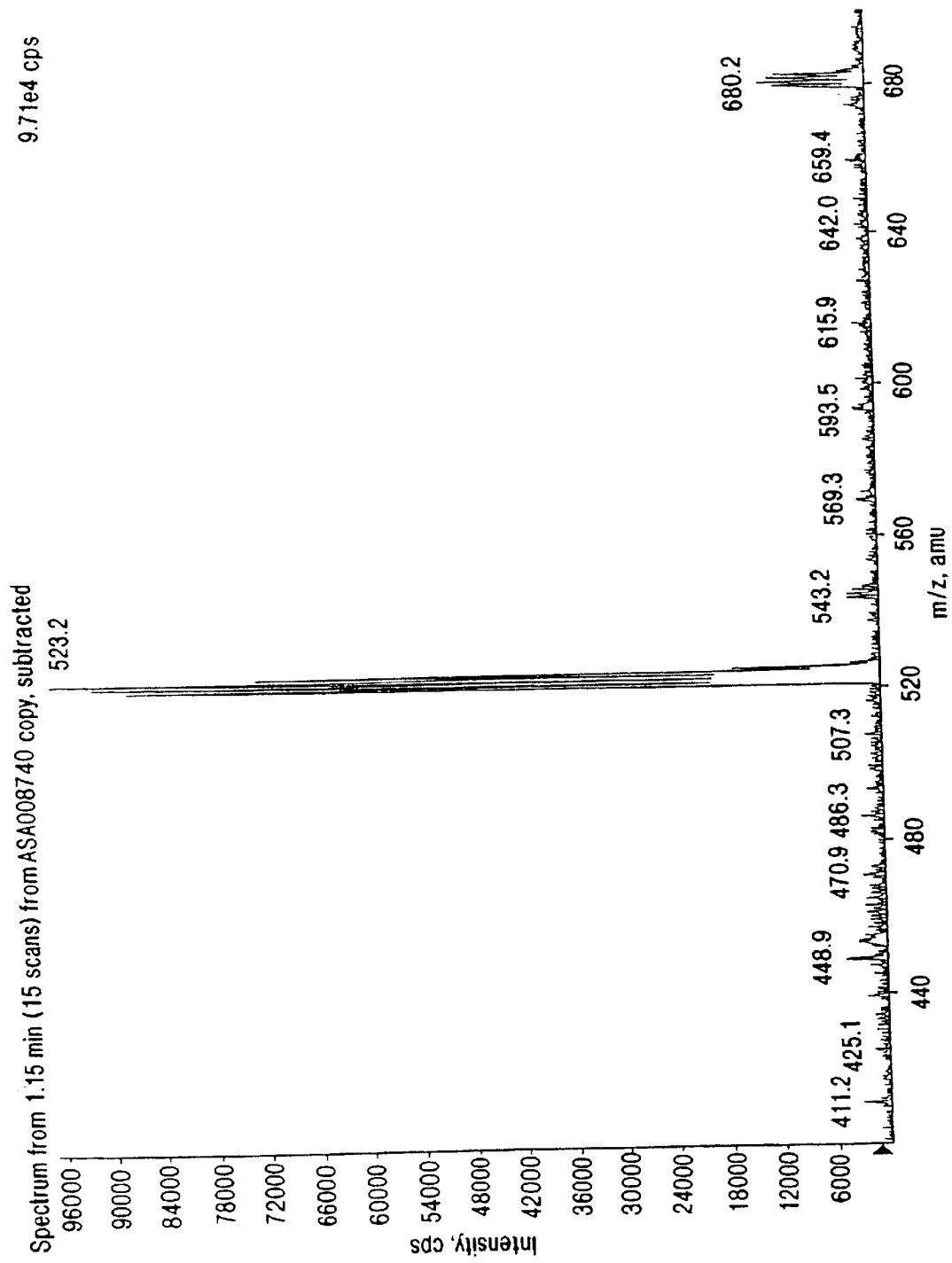
Figure 187:
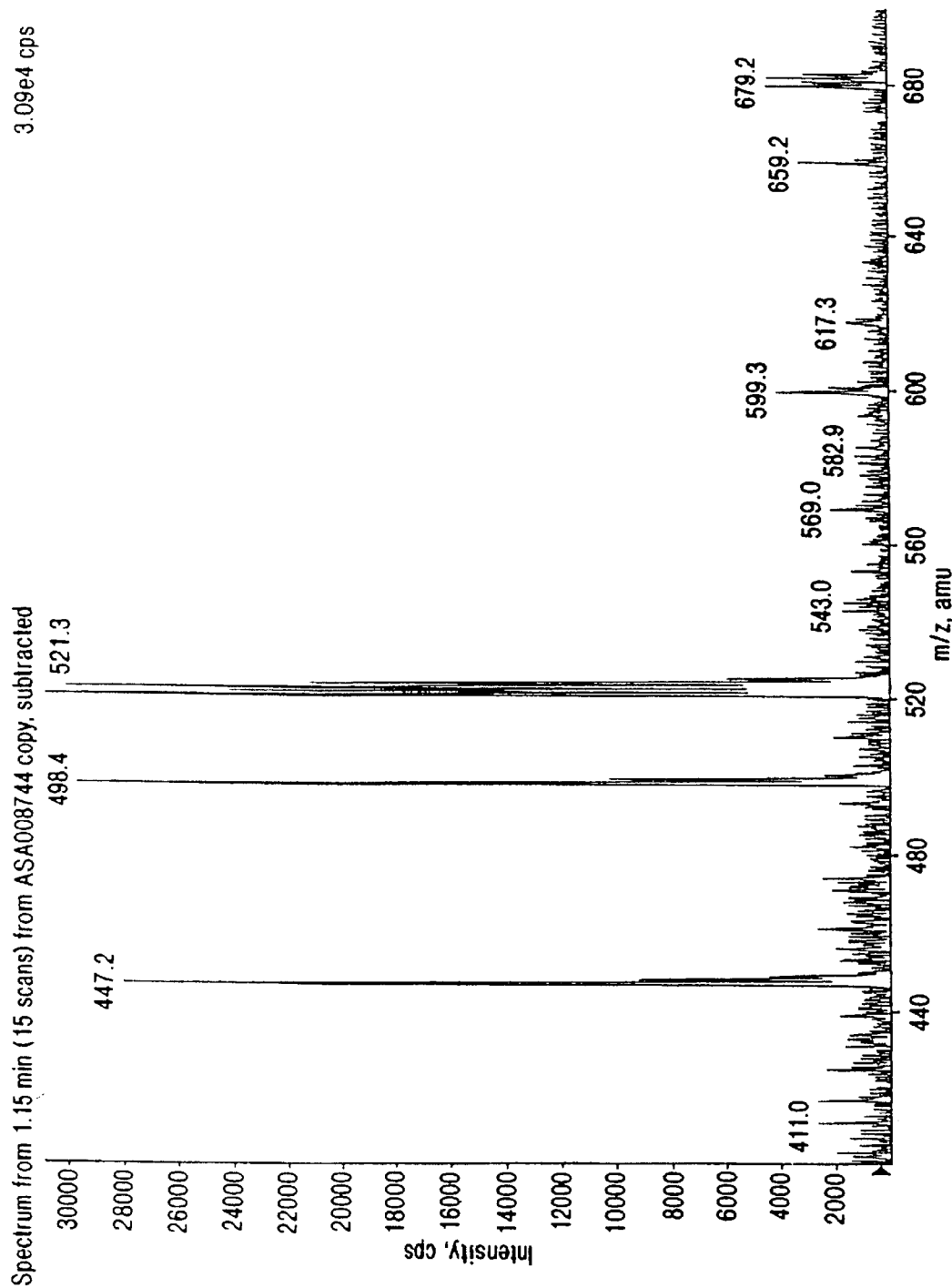
Figure 188:
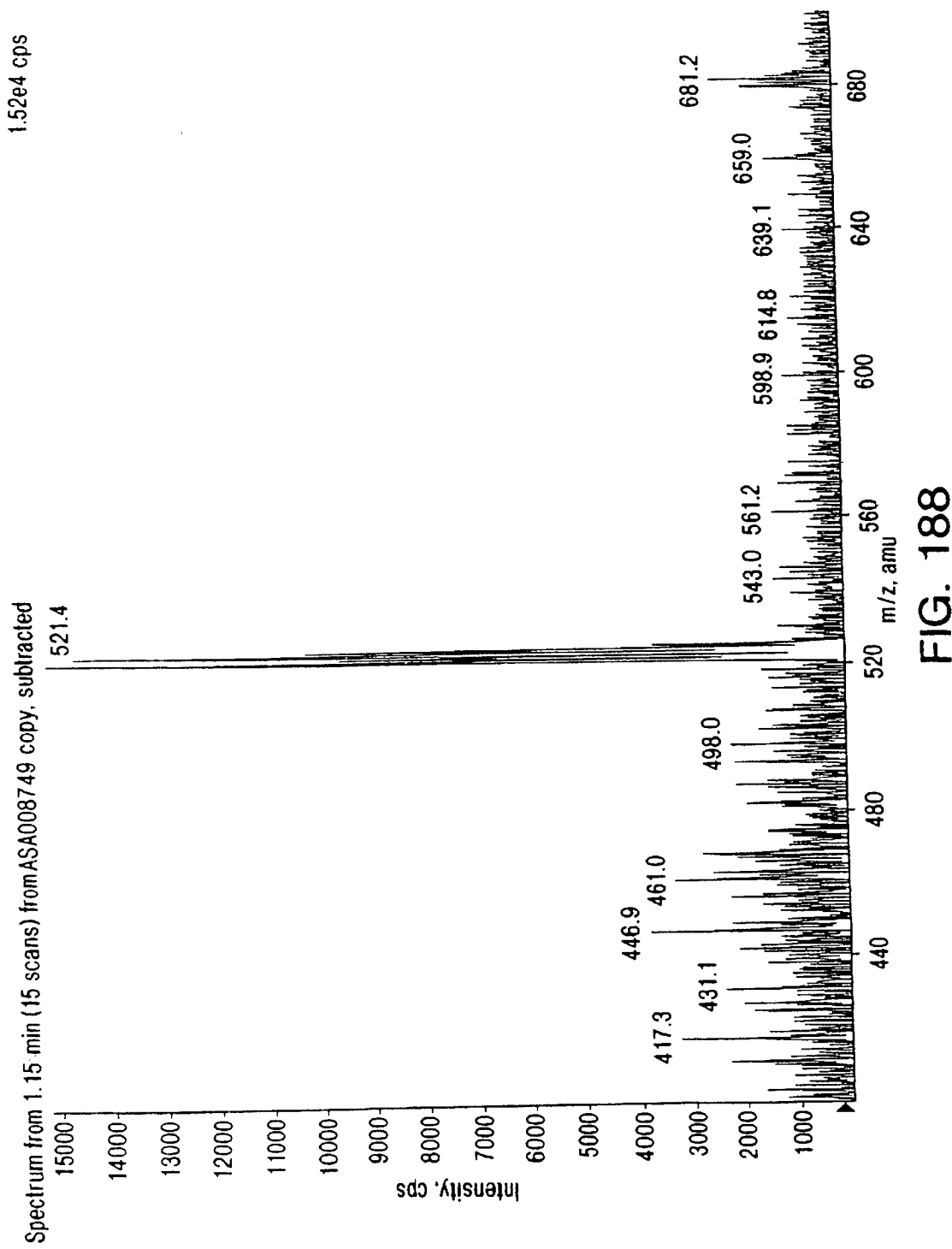
Figure 189:
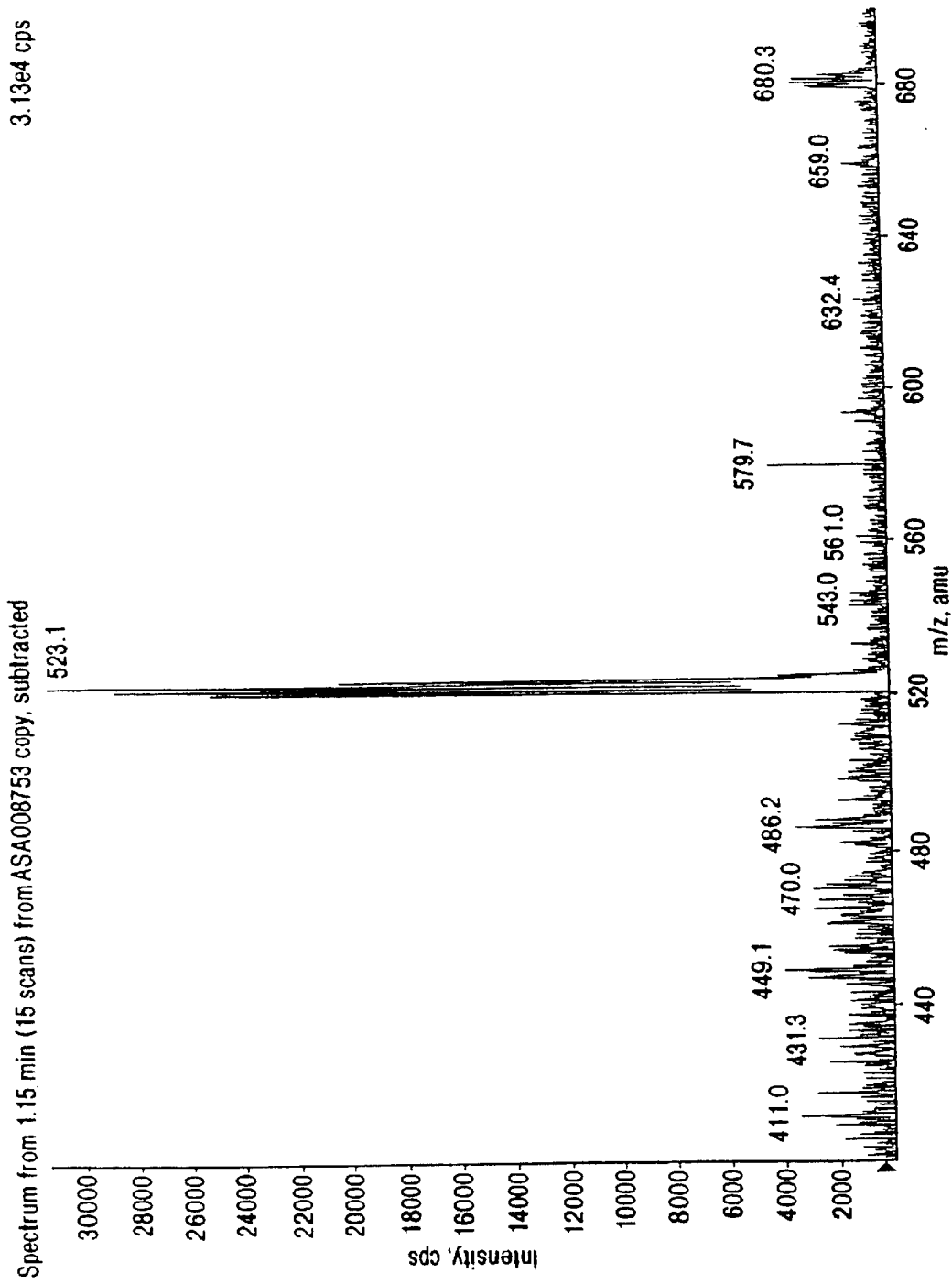
Figure 190:
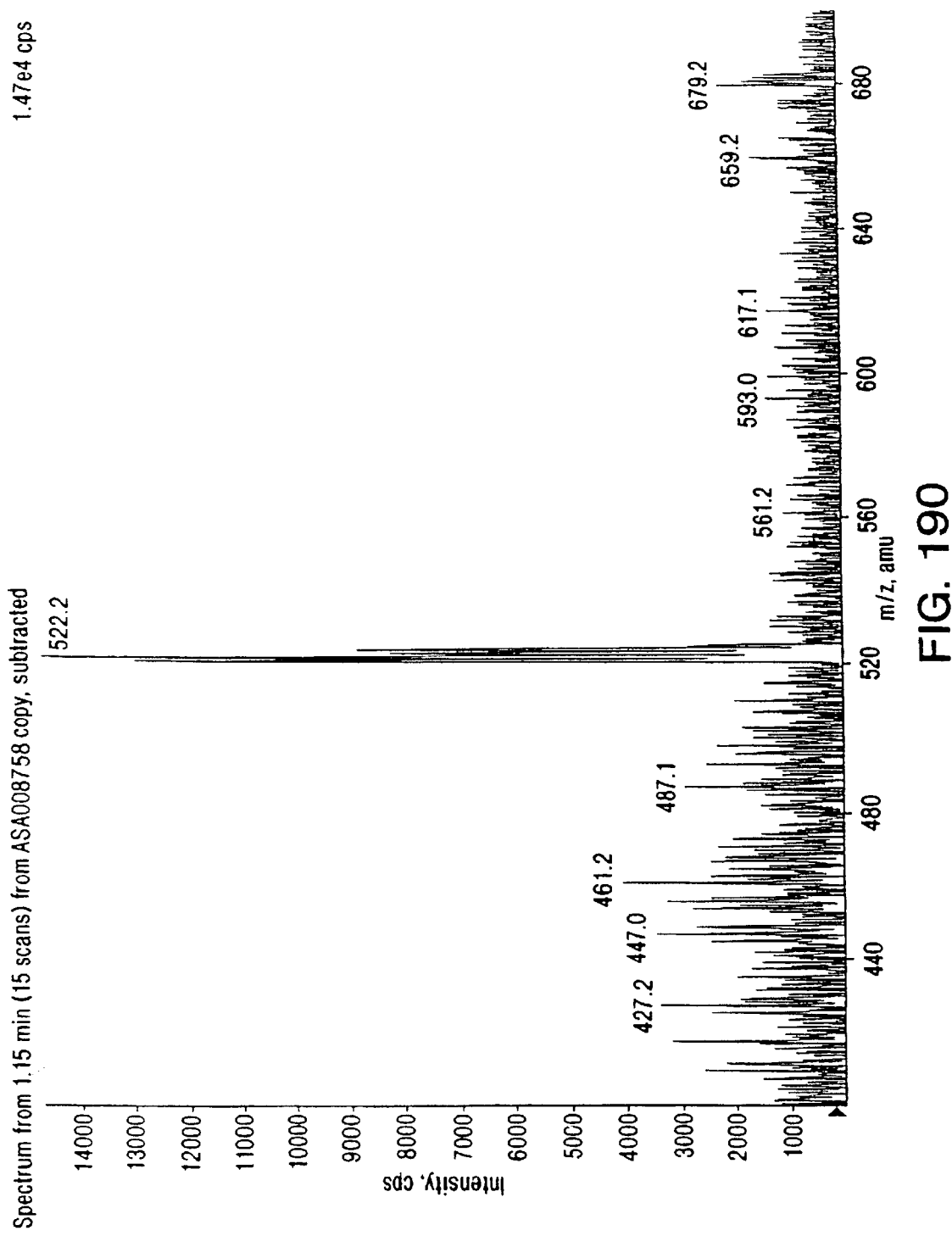
Figure 191:
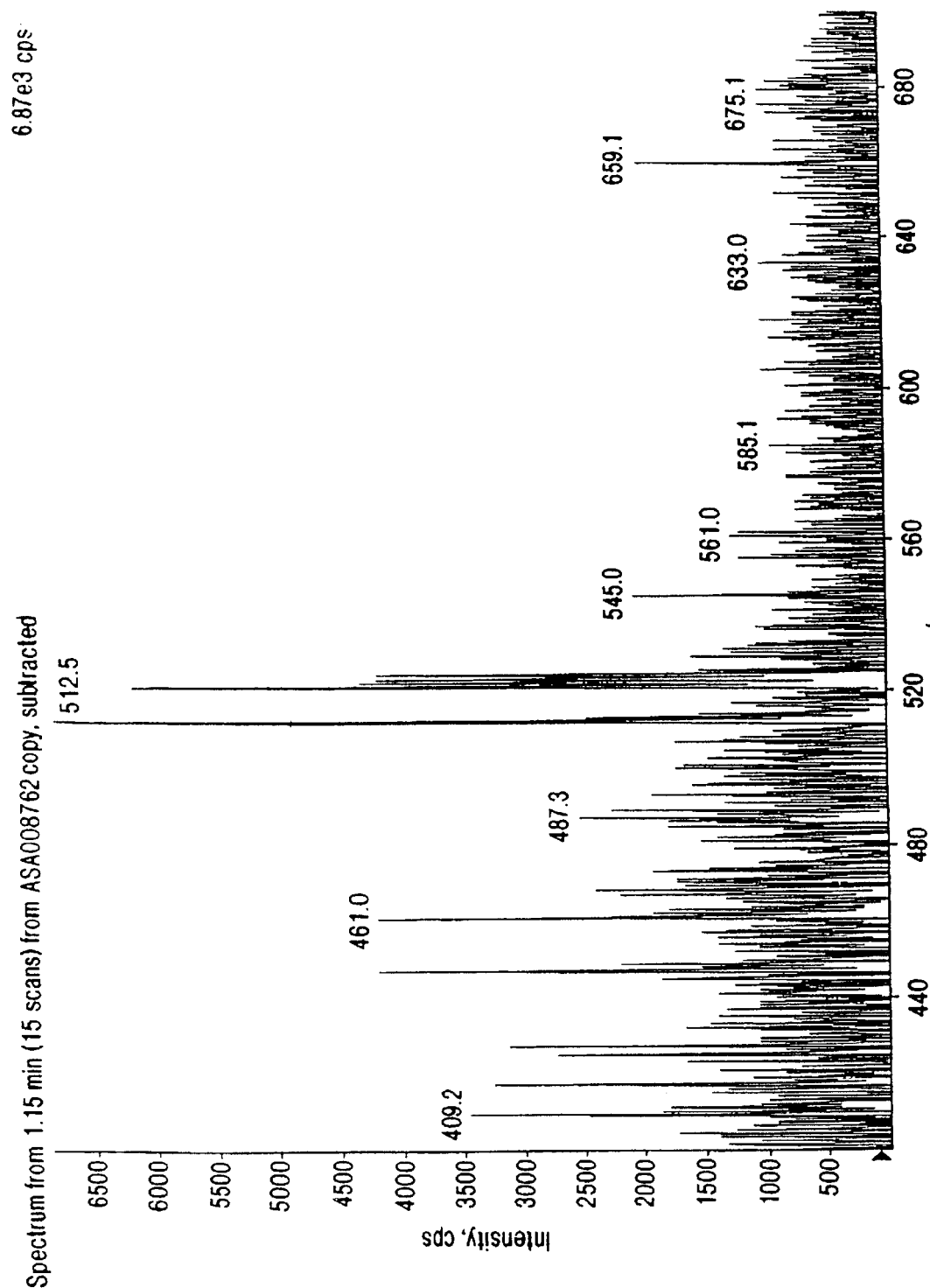
Figure 192:
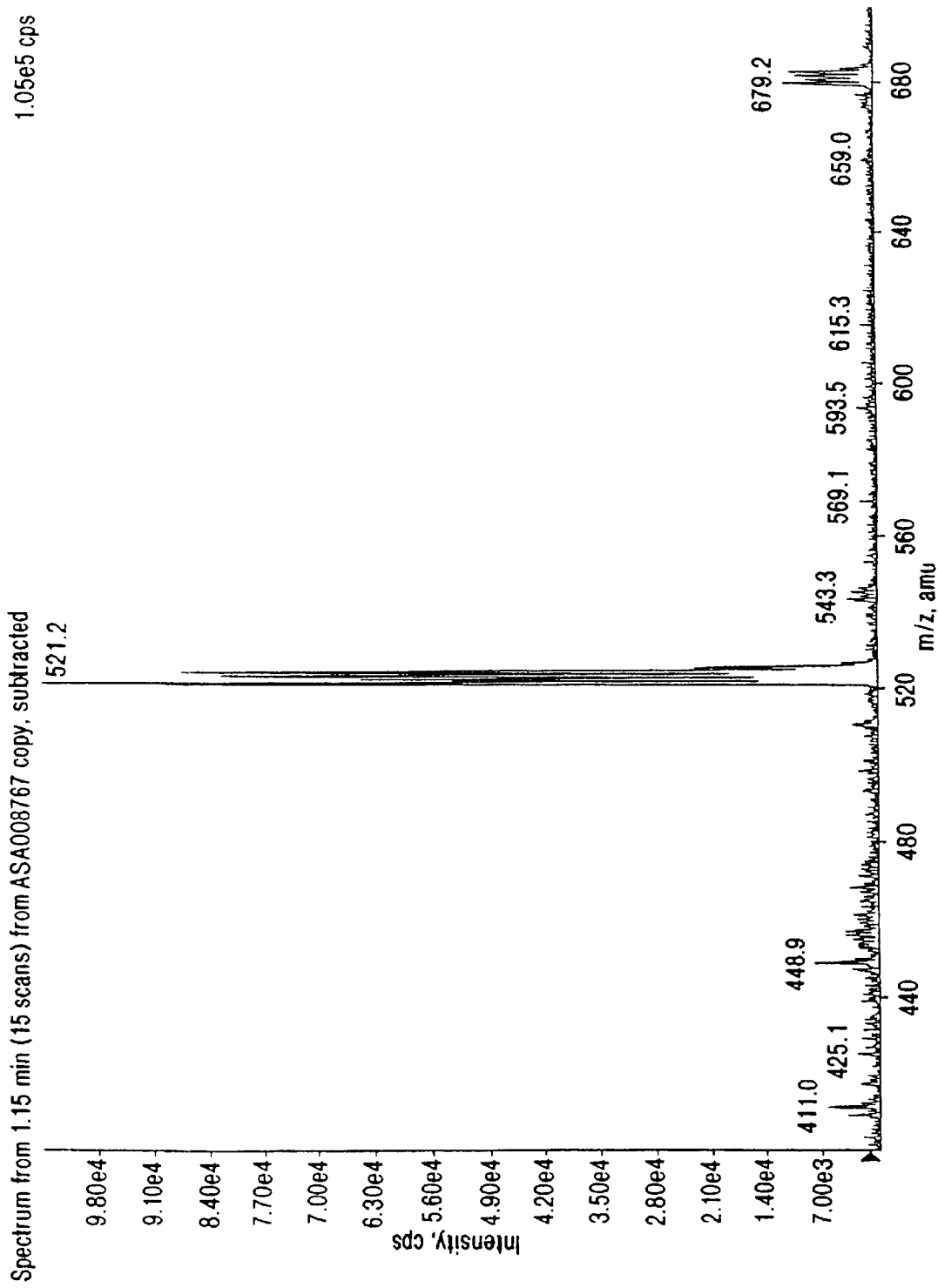
Figure 193:
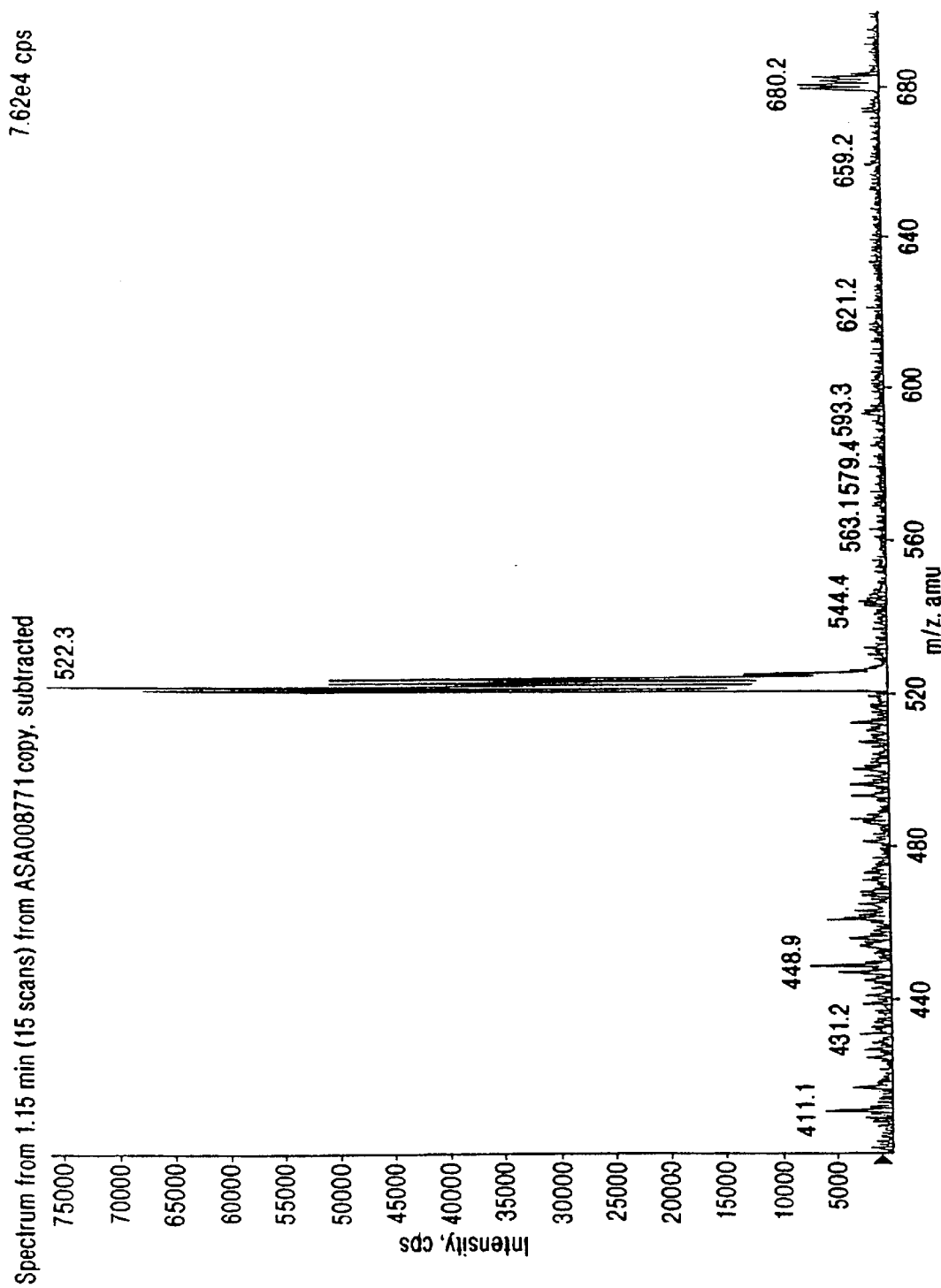
Figure 194:
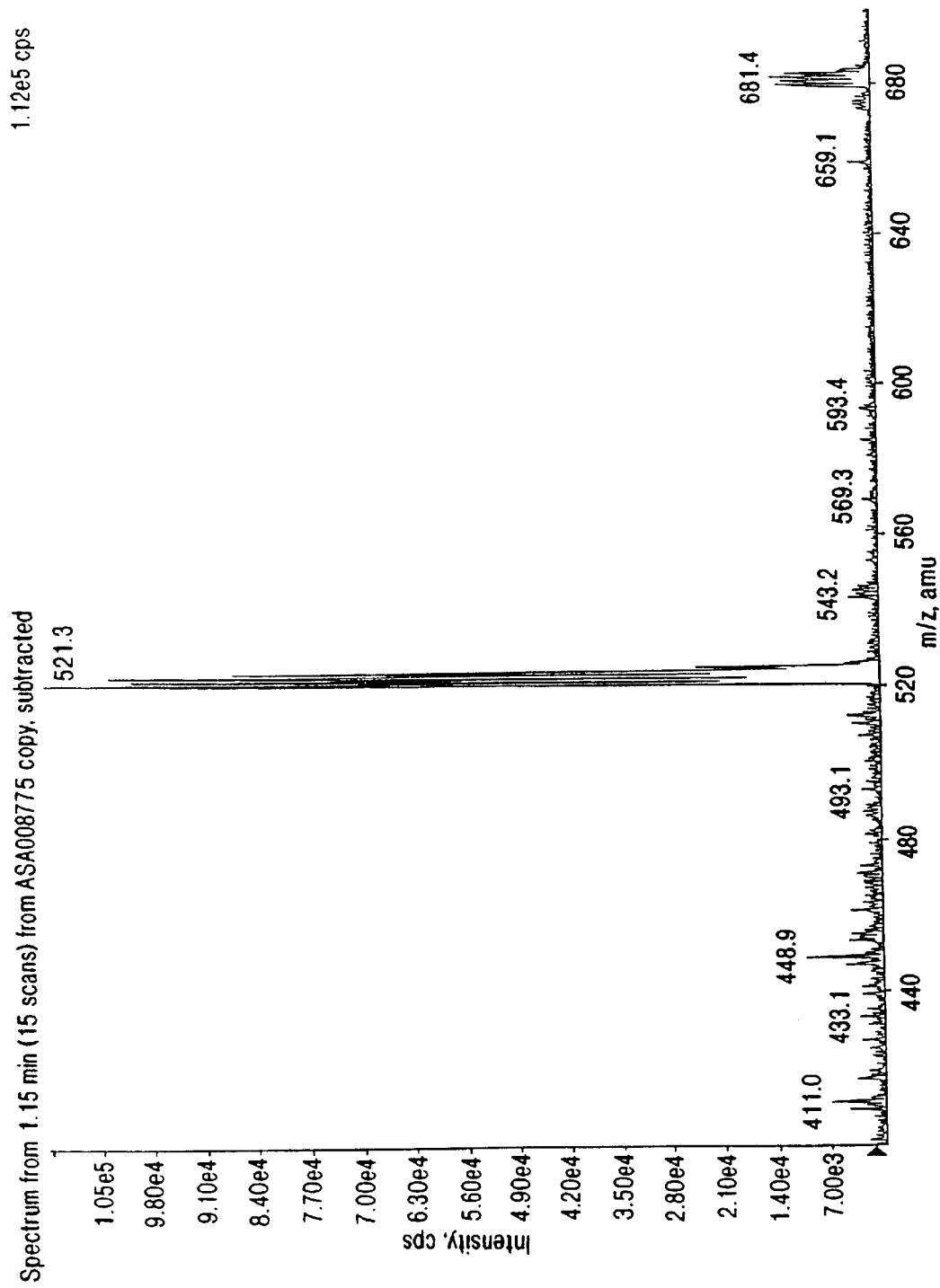
Figure 195:
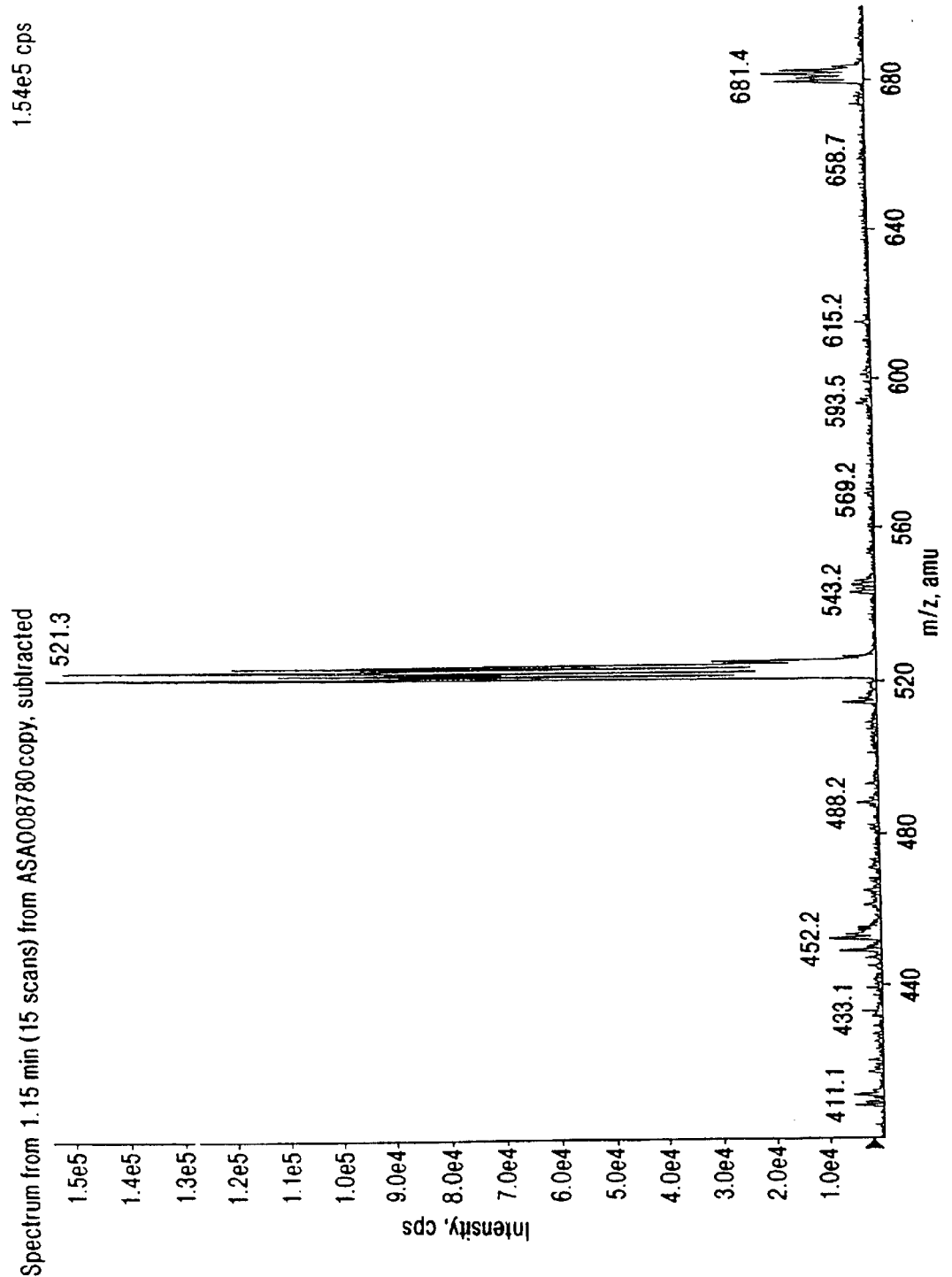
Figure 196:
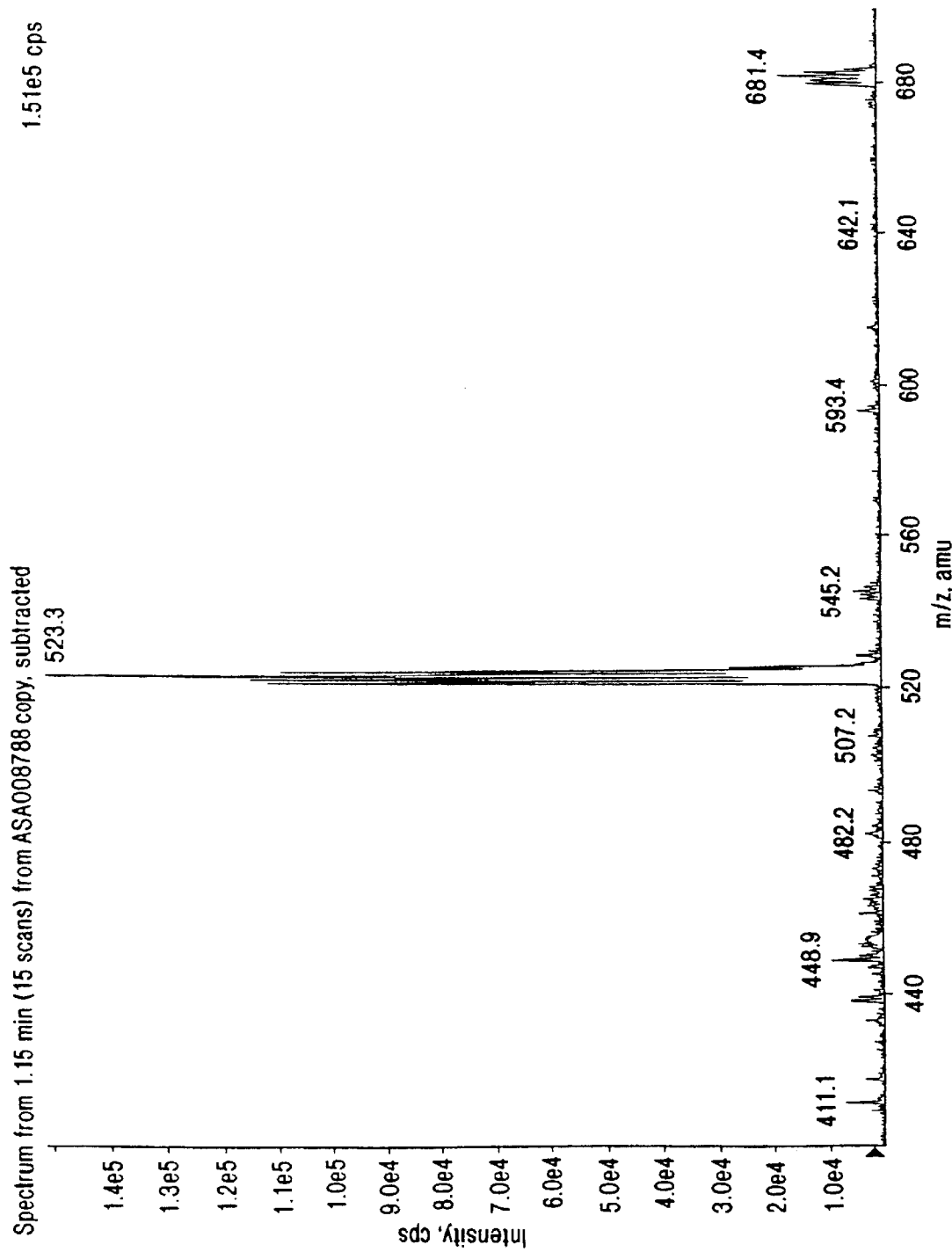
Figure 197:
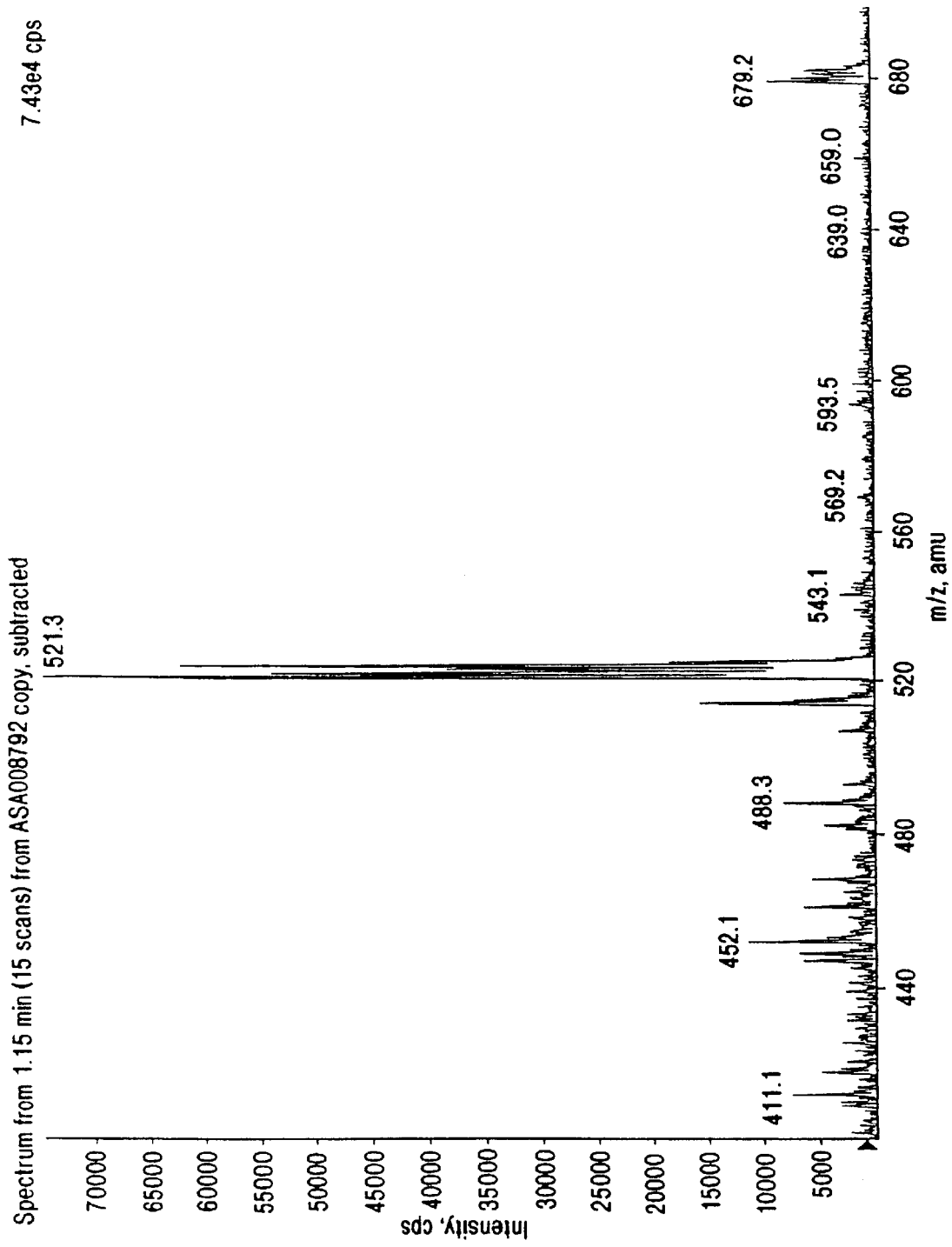
Figure 198:
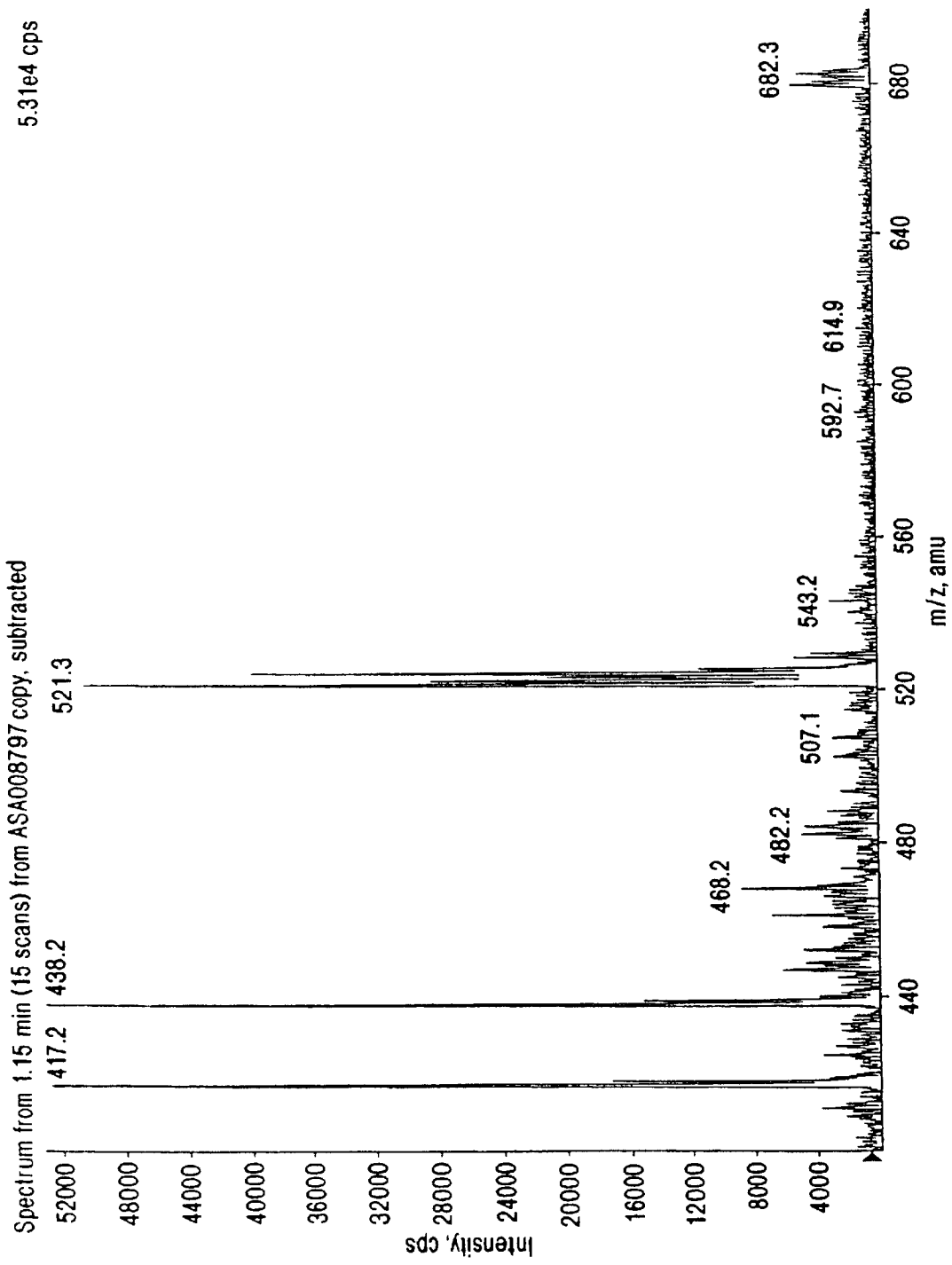
Figure 199:
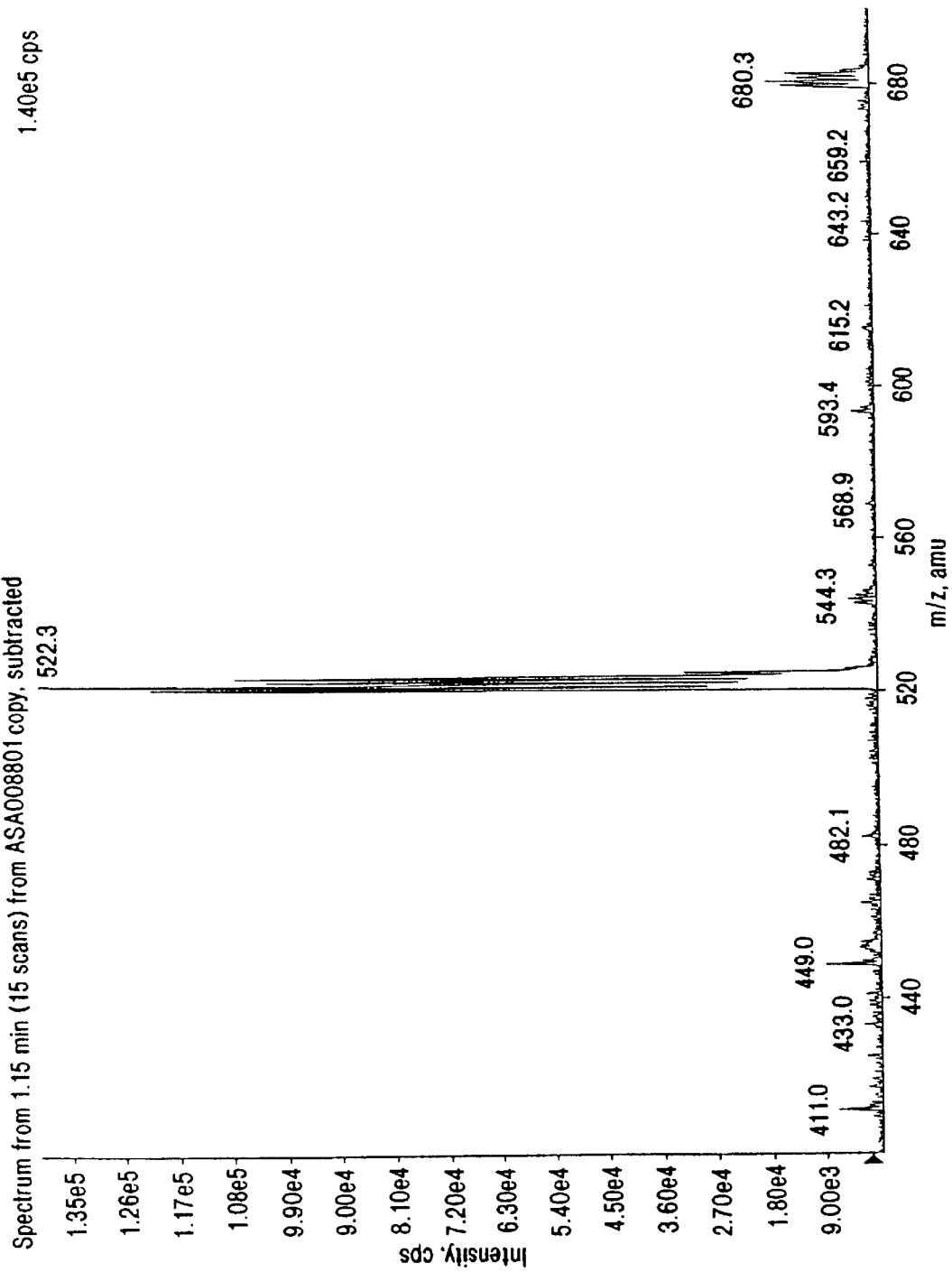
Figure 200:
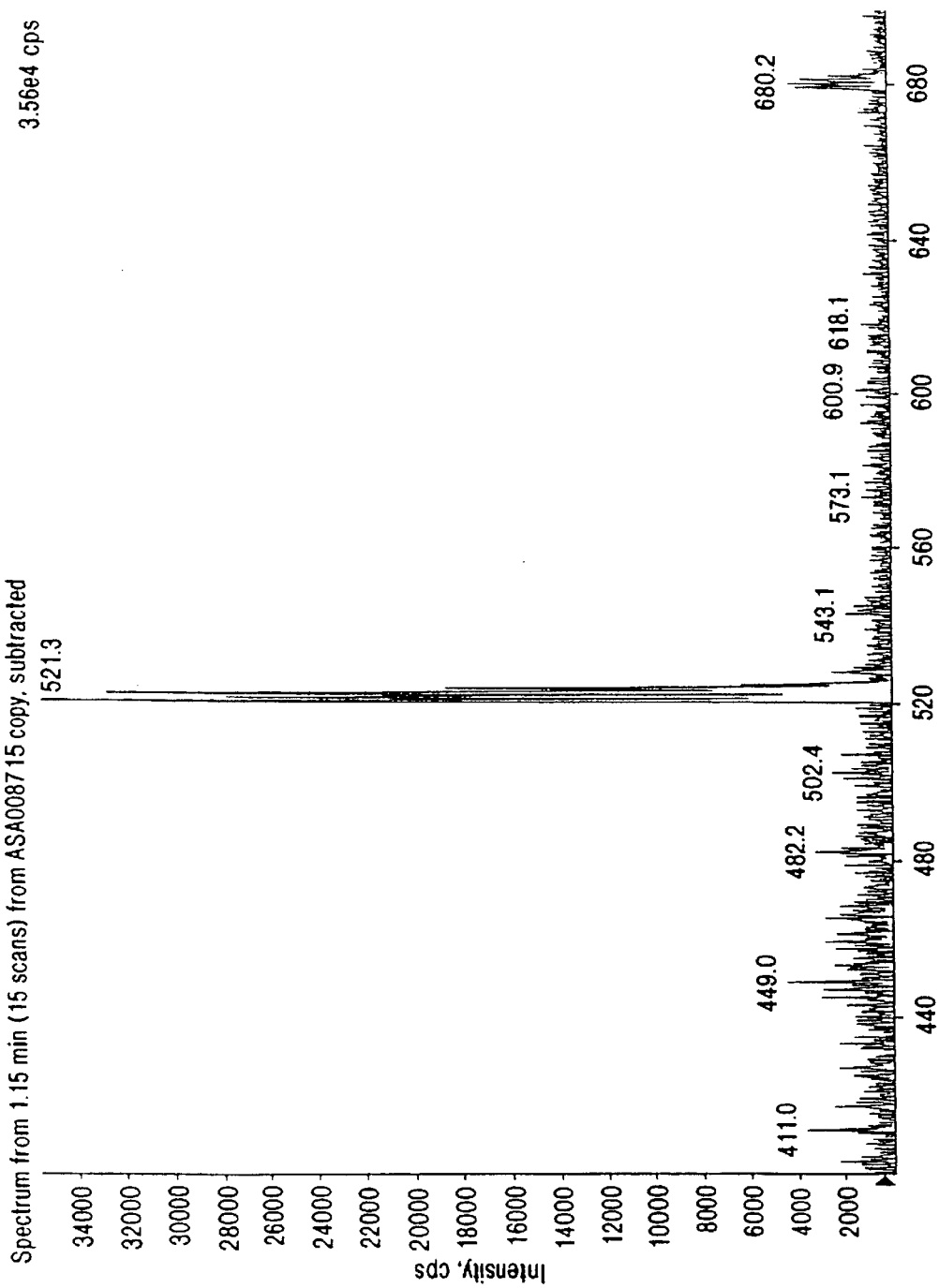
Figure 201:
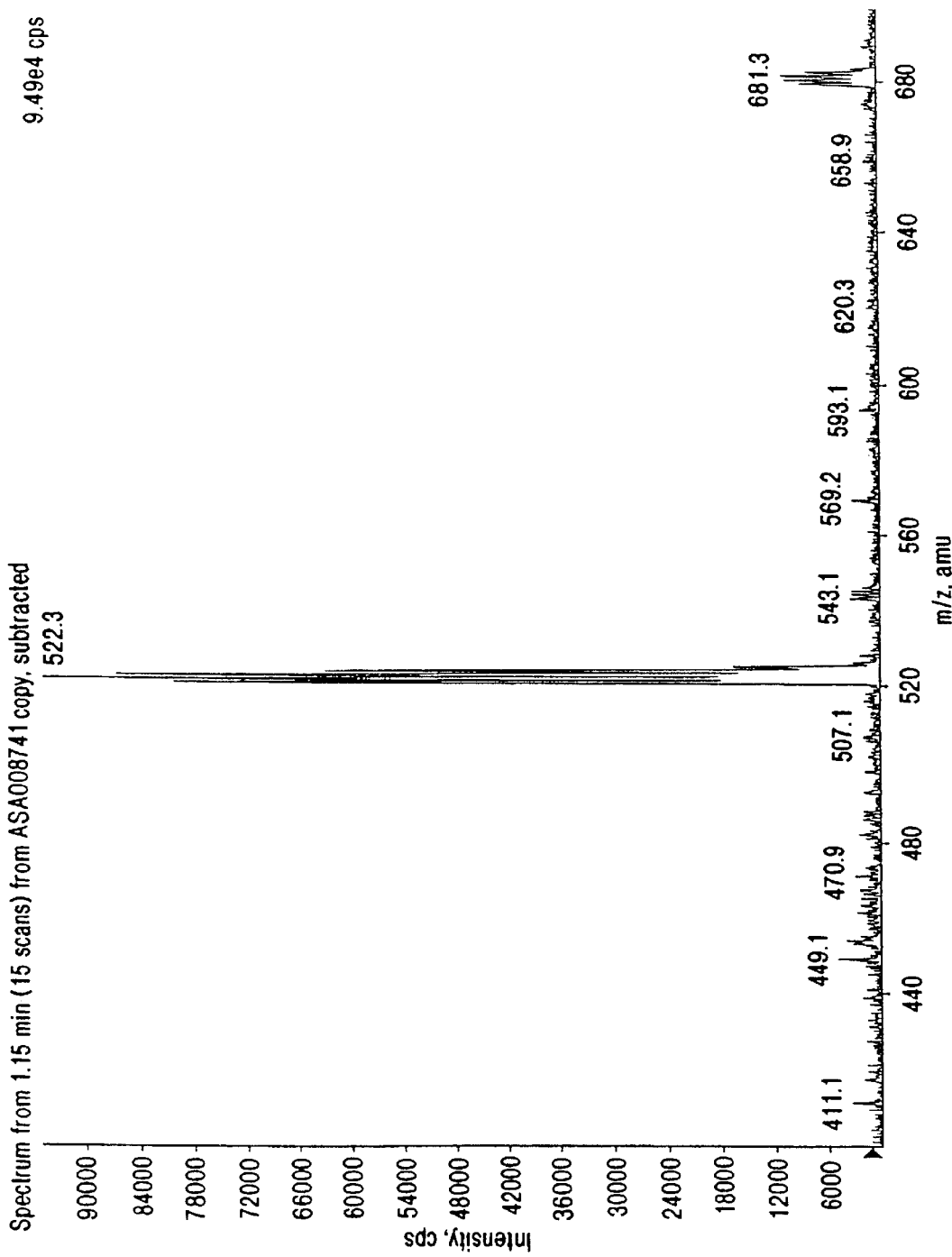
Figure 202:
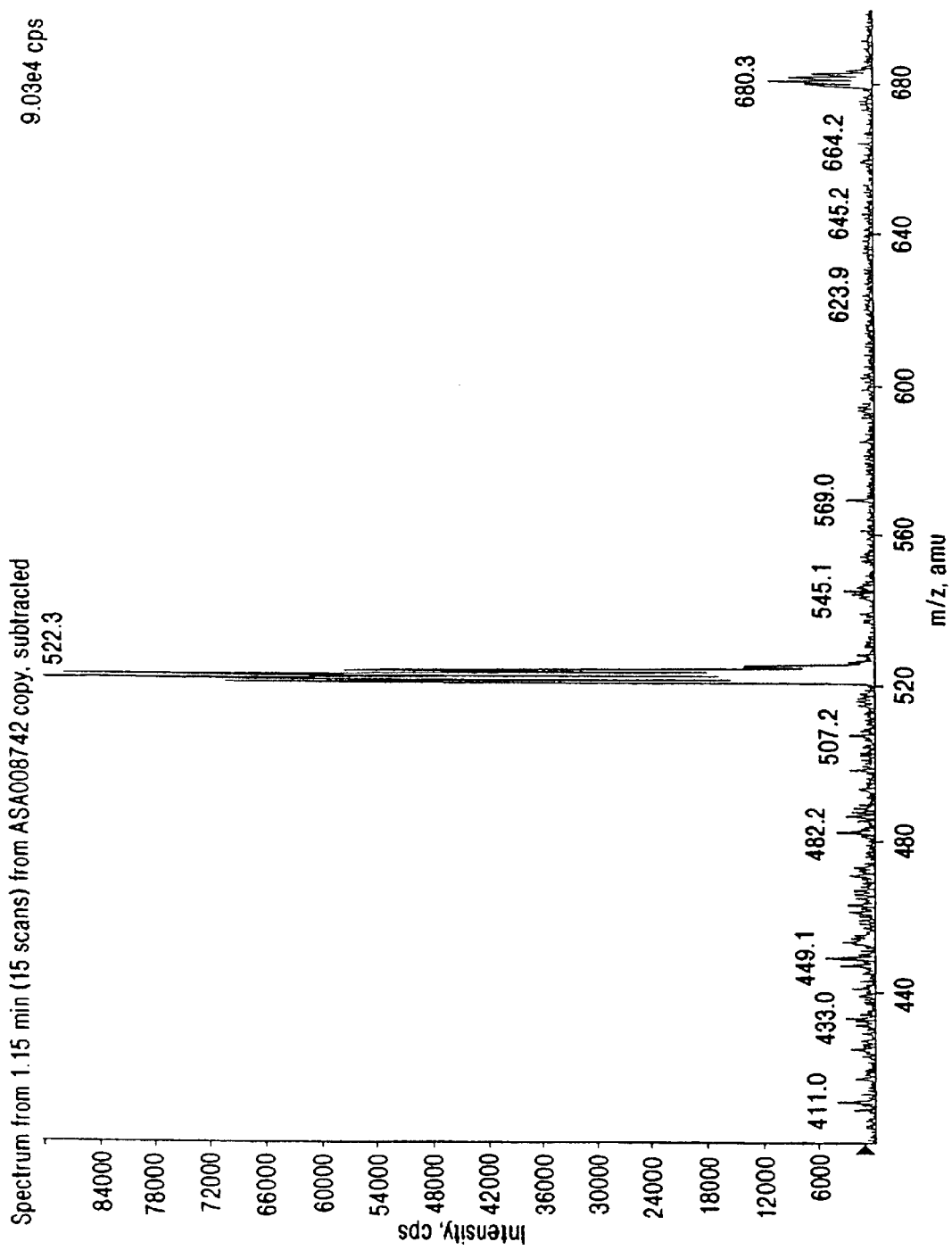
Figure 203:
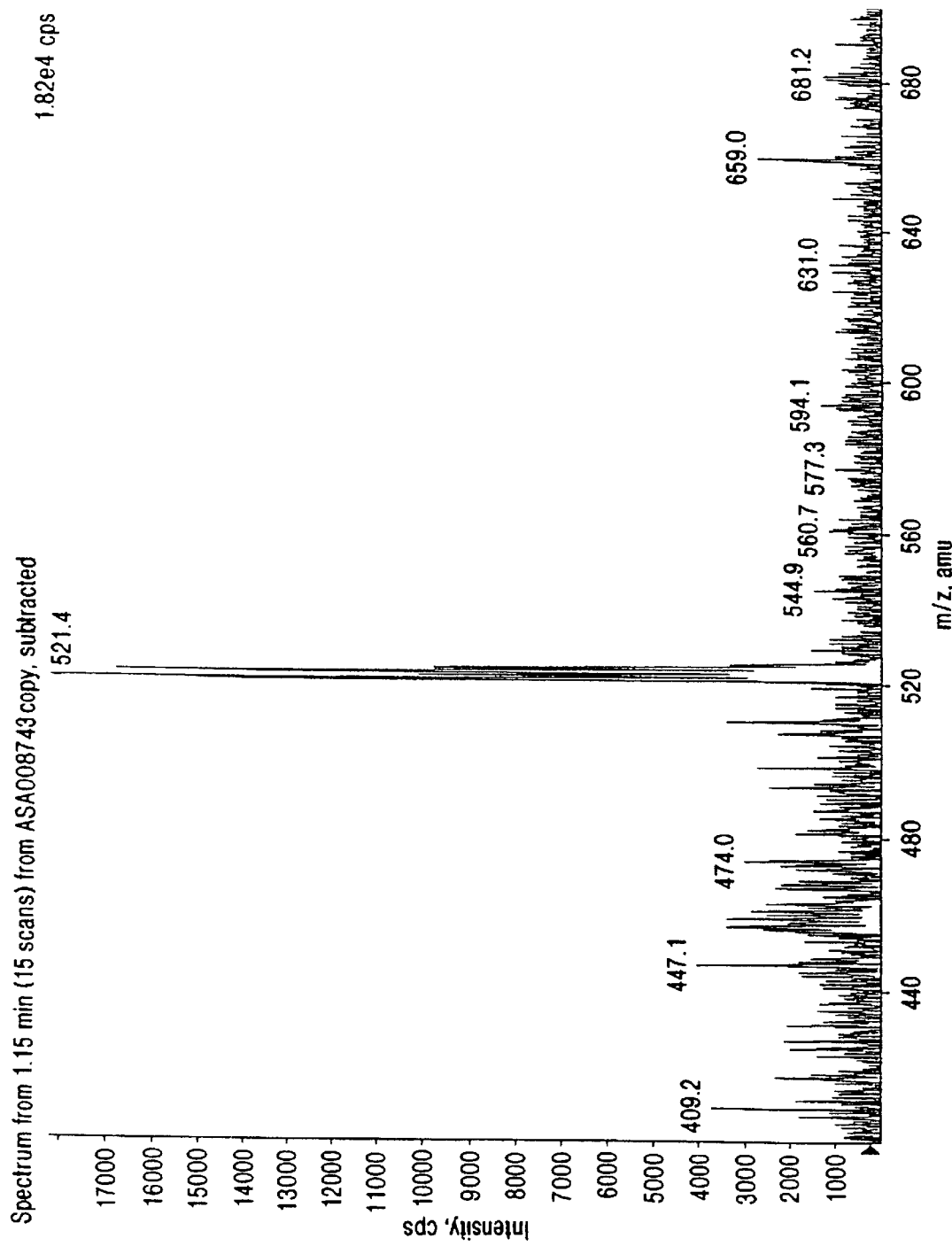
Figure 204:
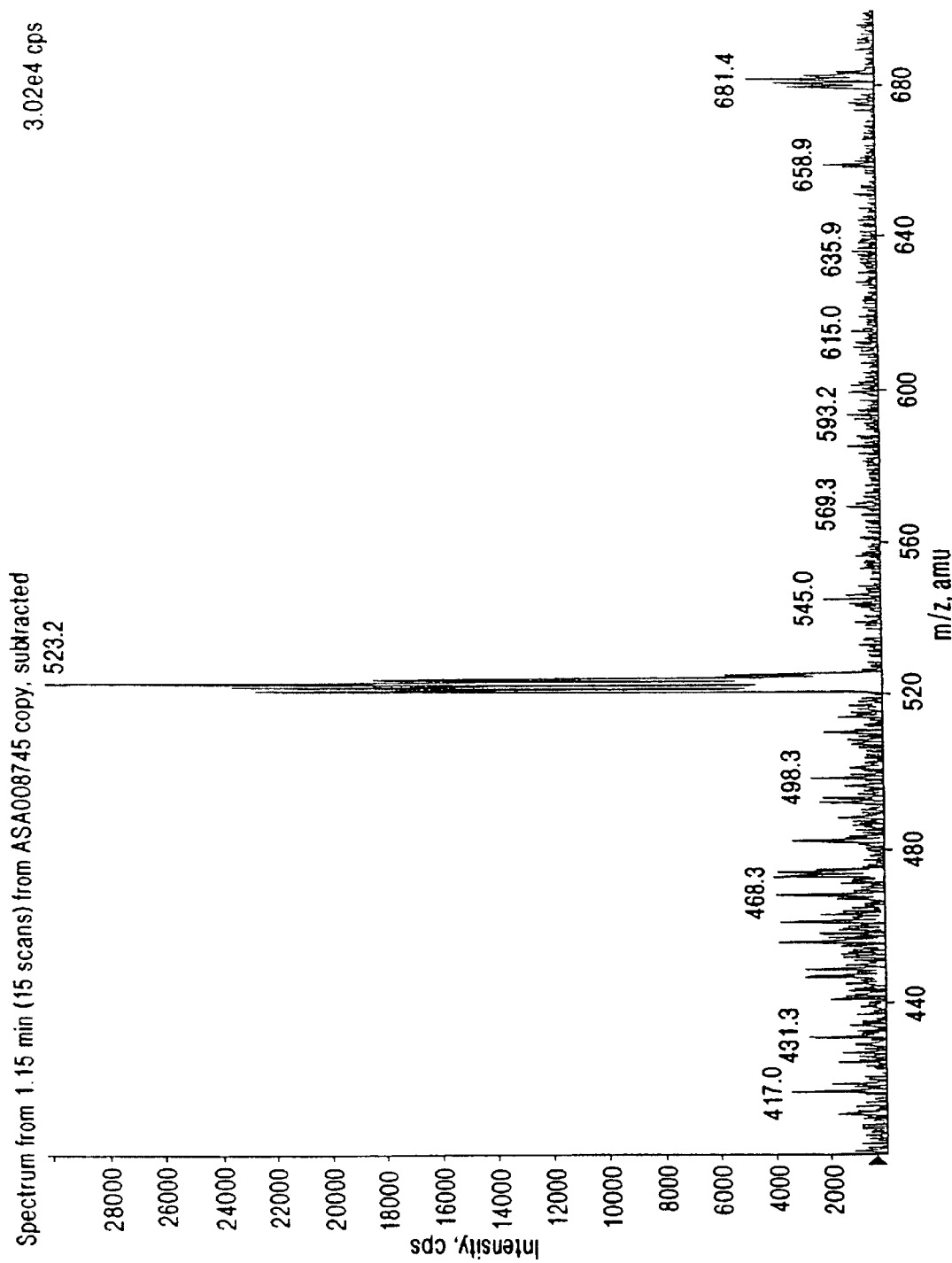
Figure 205:
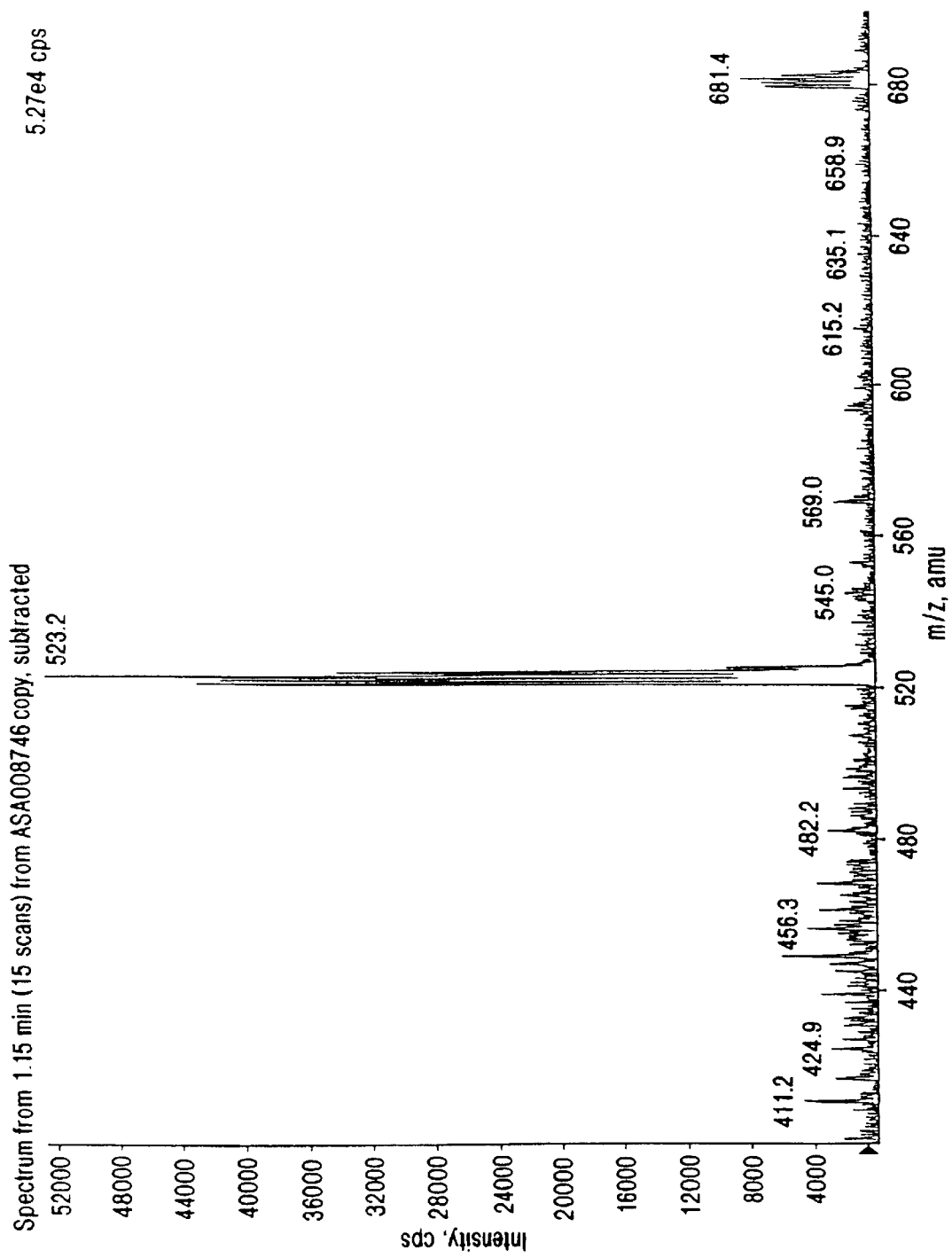
Figure 206:
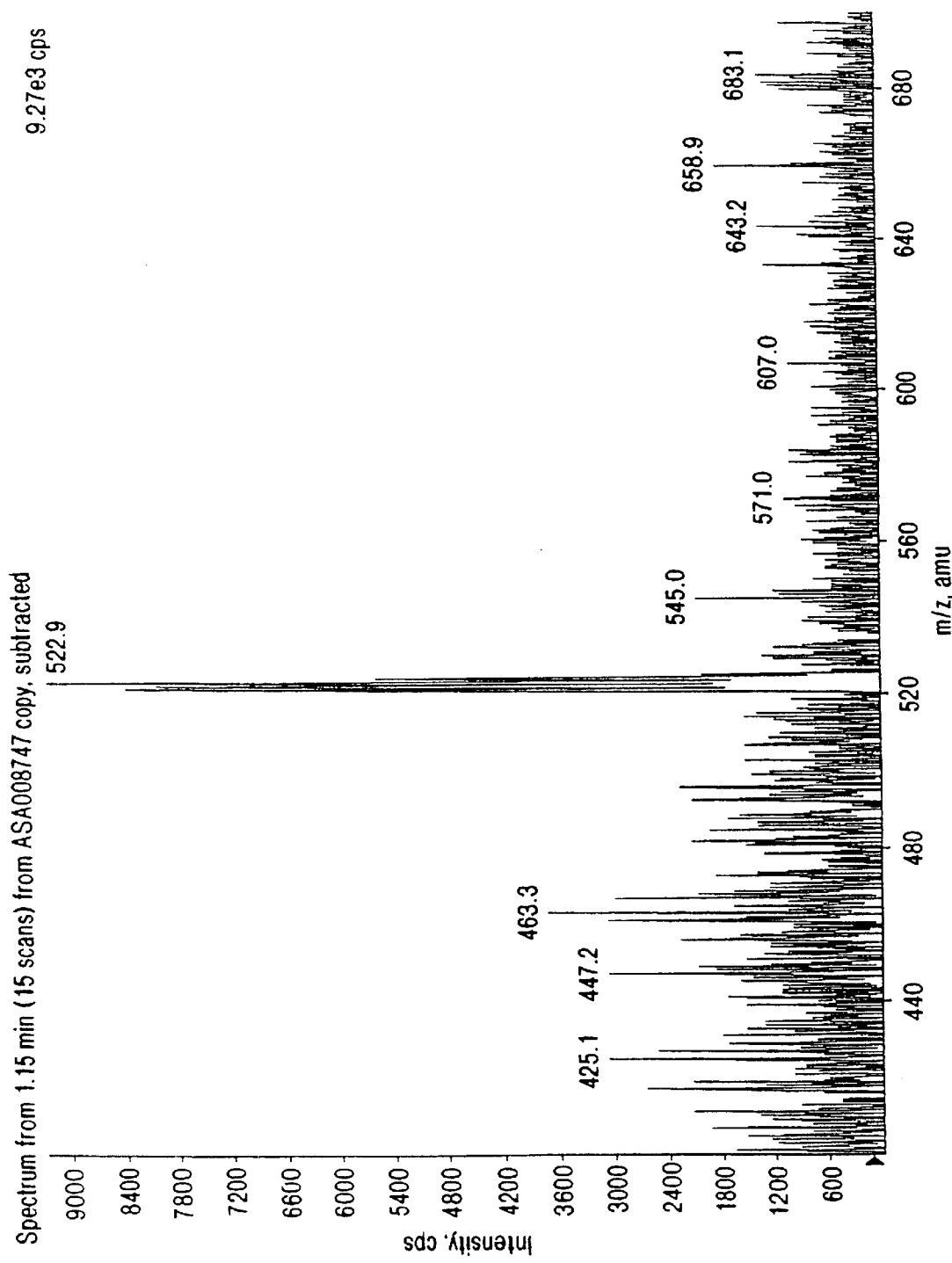
Figure 207:
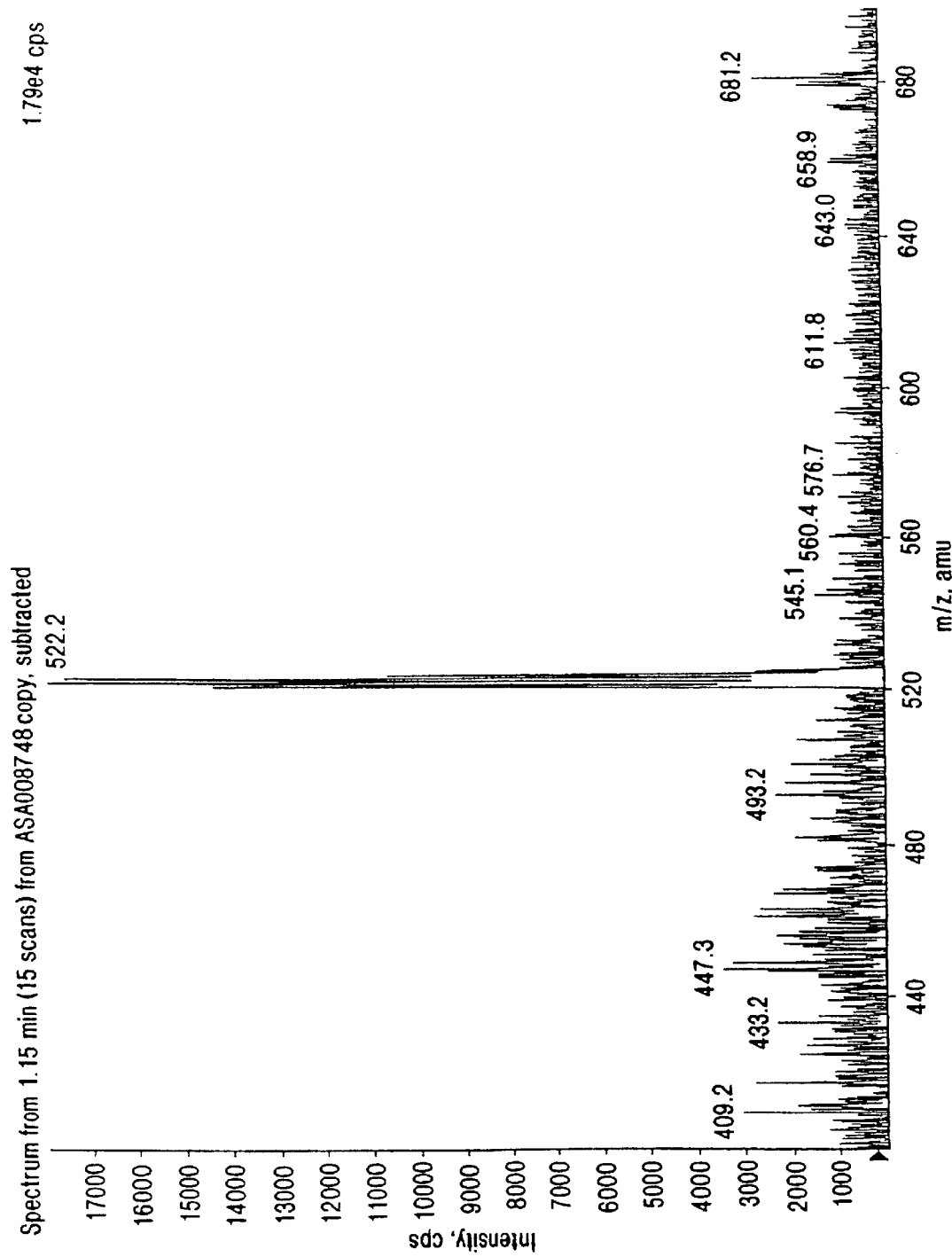
Figure 208:
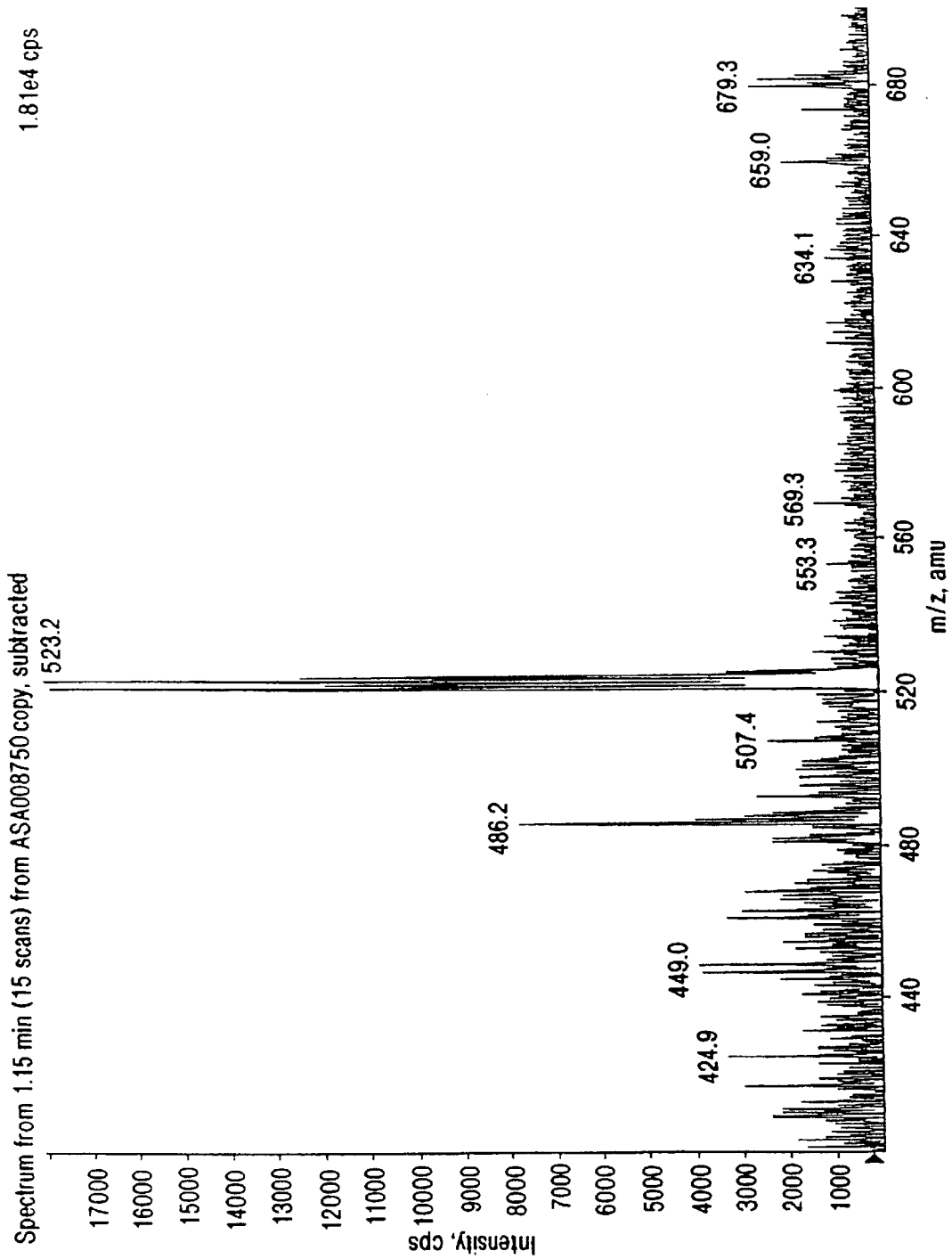
Figure 209:
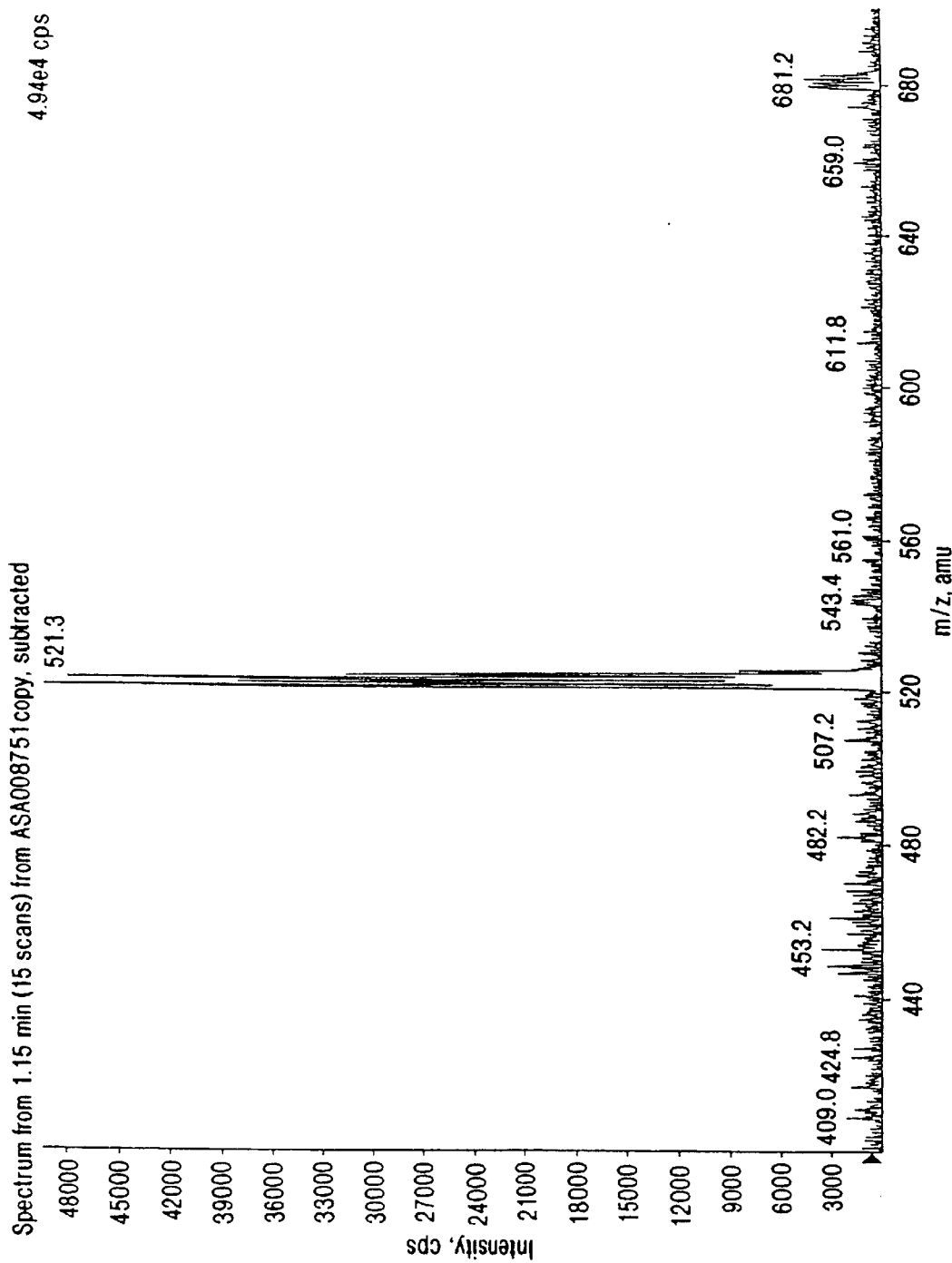
Figure 210:
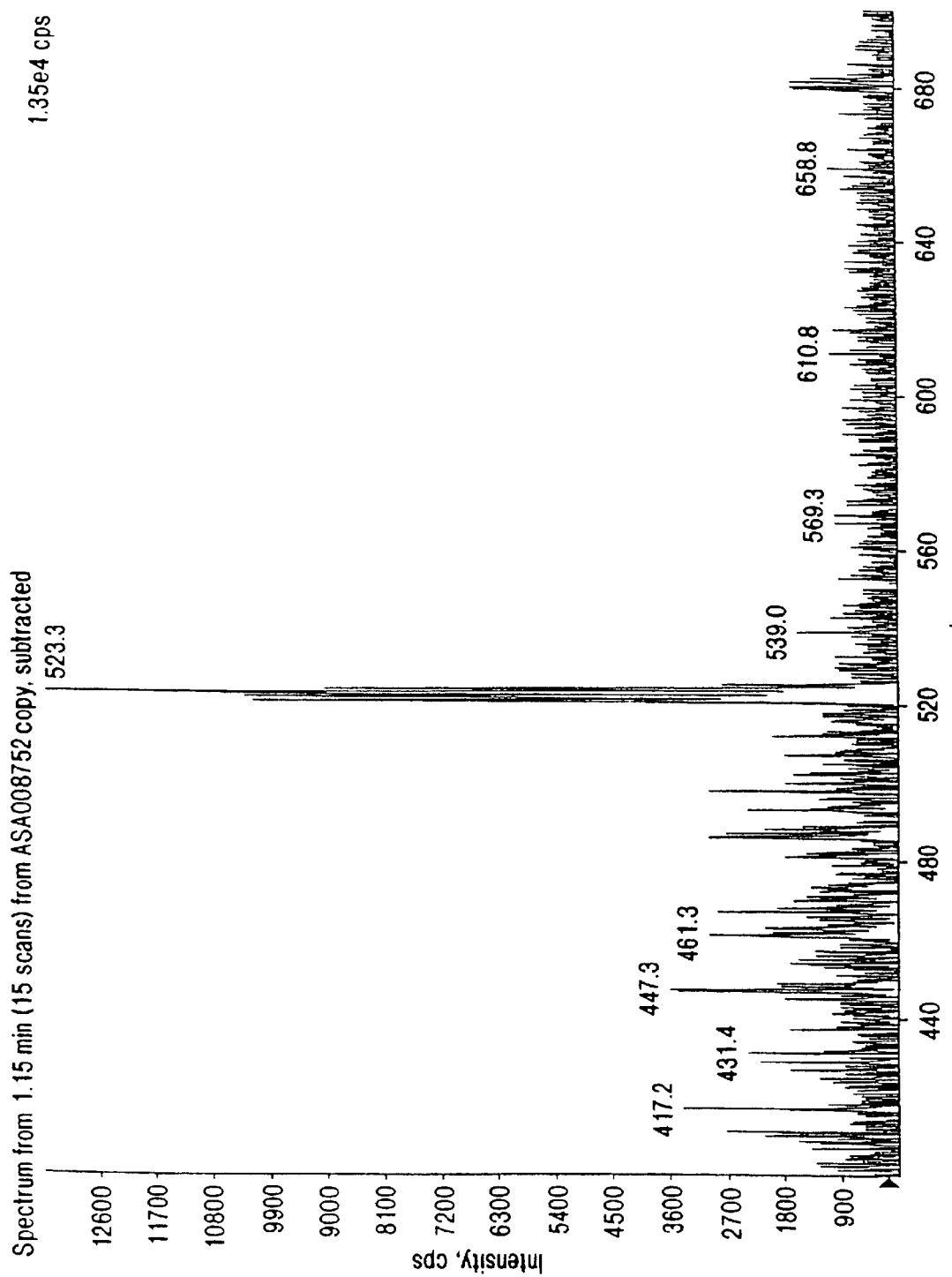
Figure 211:
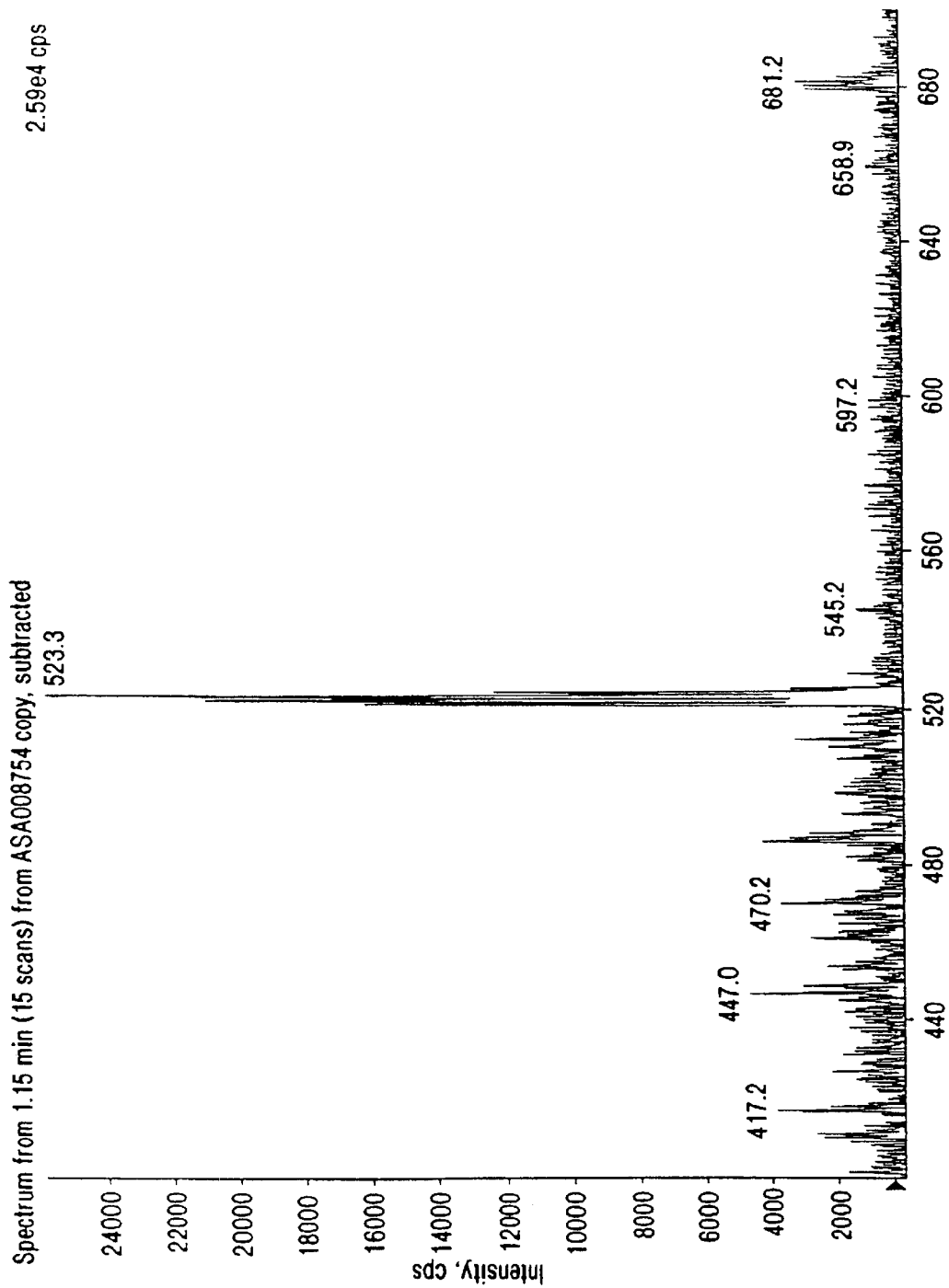
Figure 212:
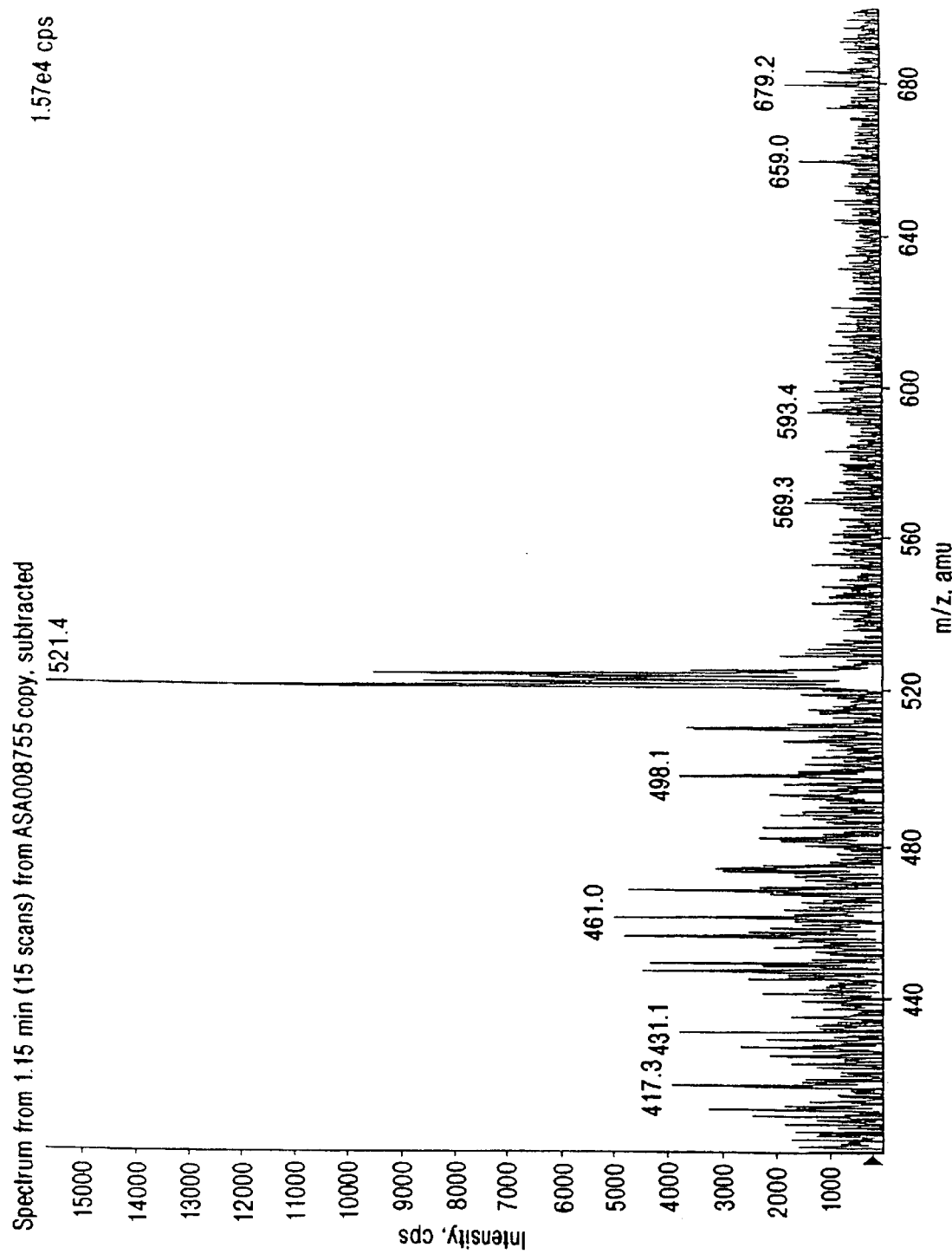
Figure 213:
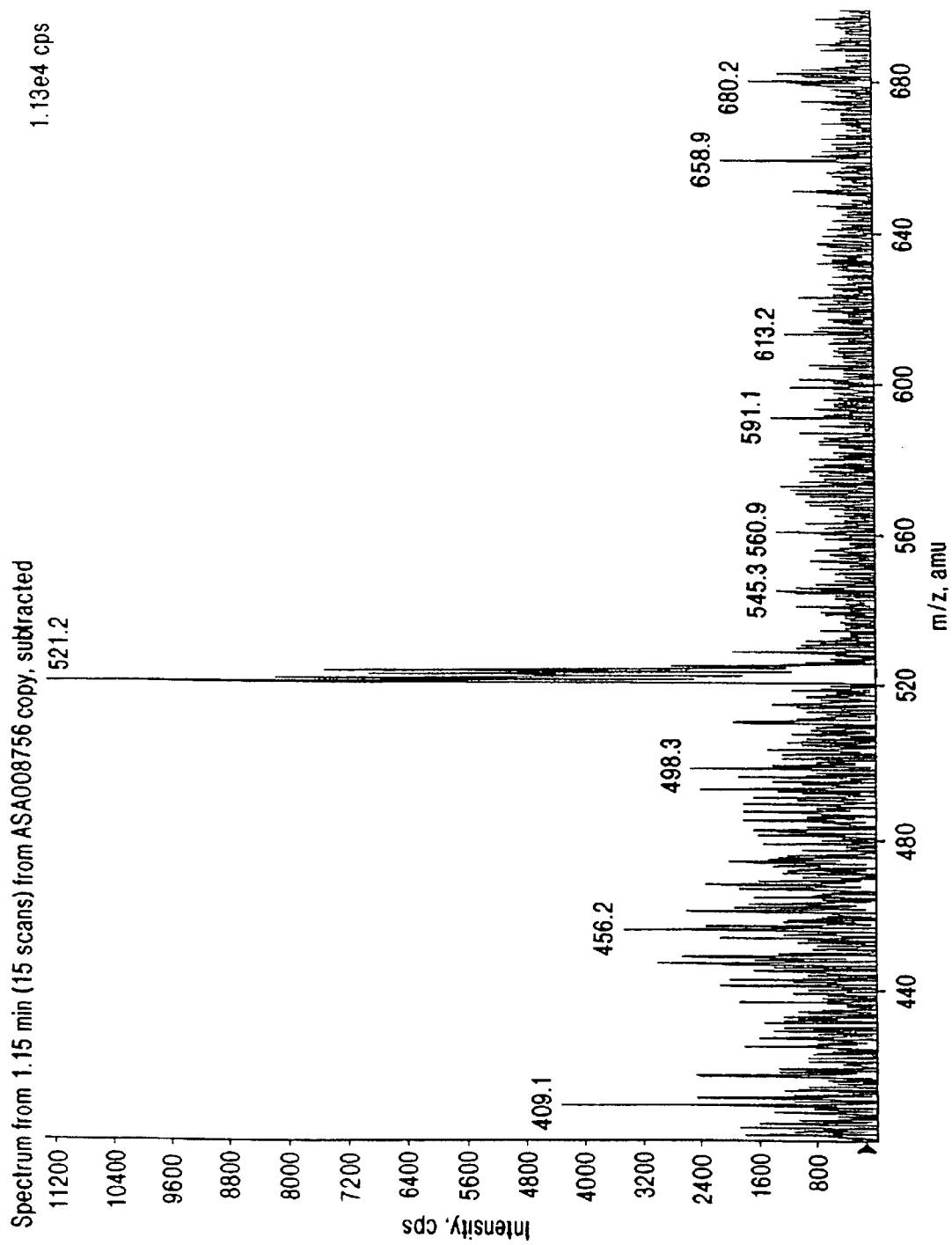
Figure 214:
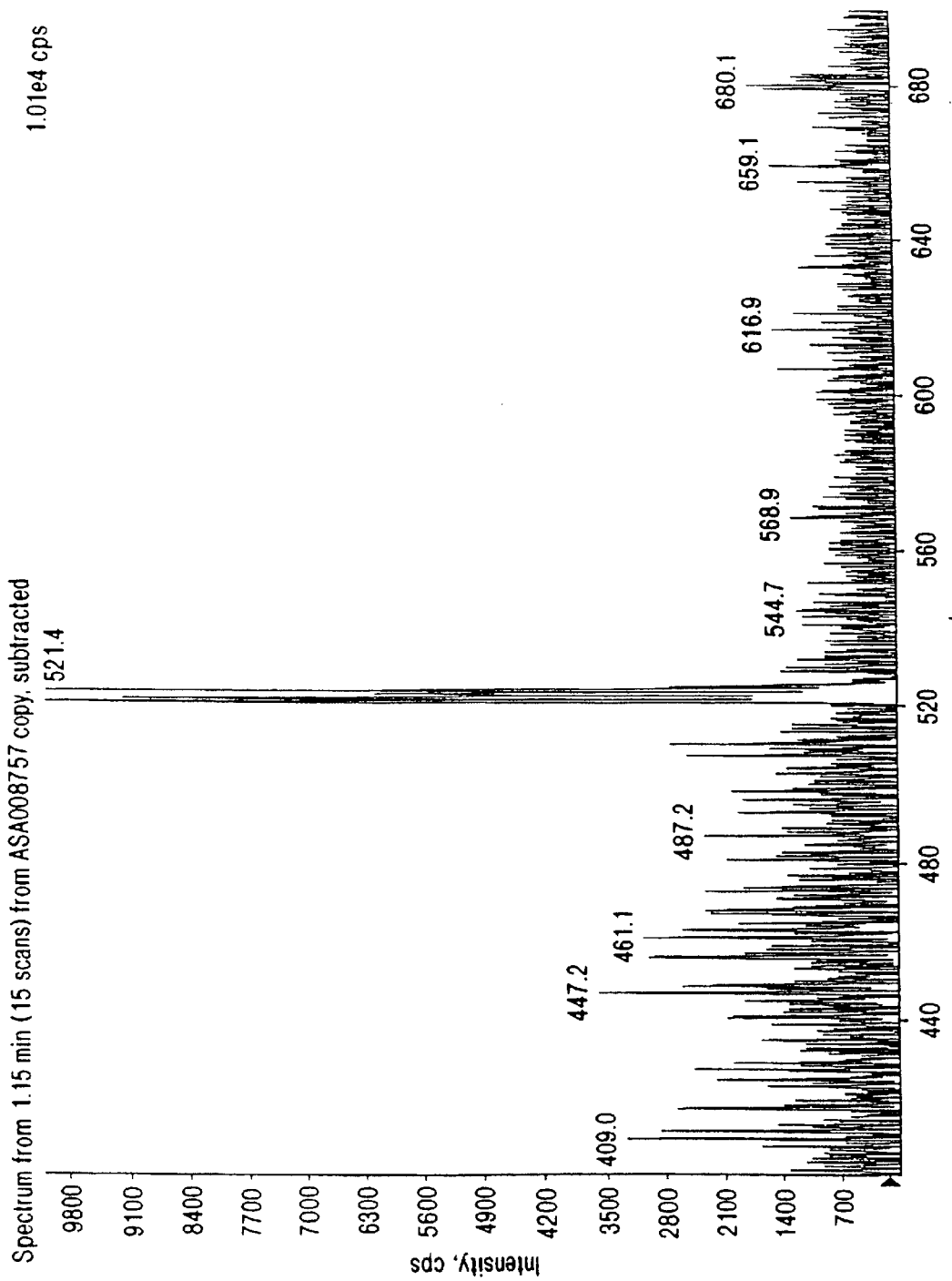
Figure 215:
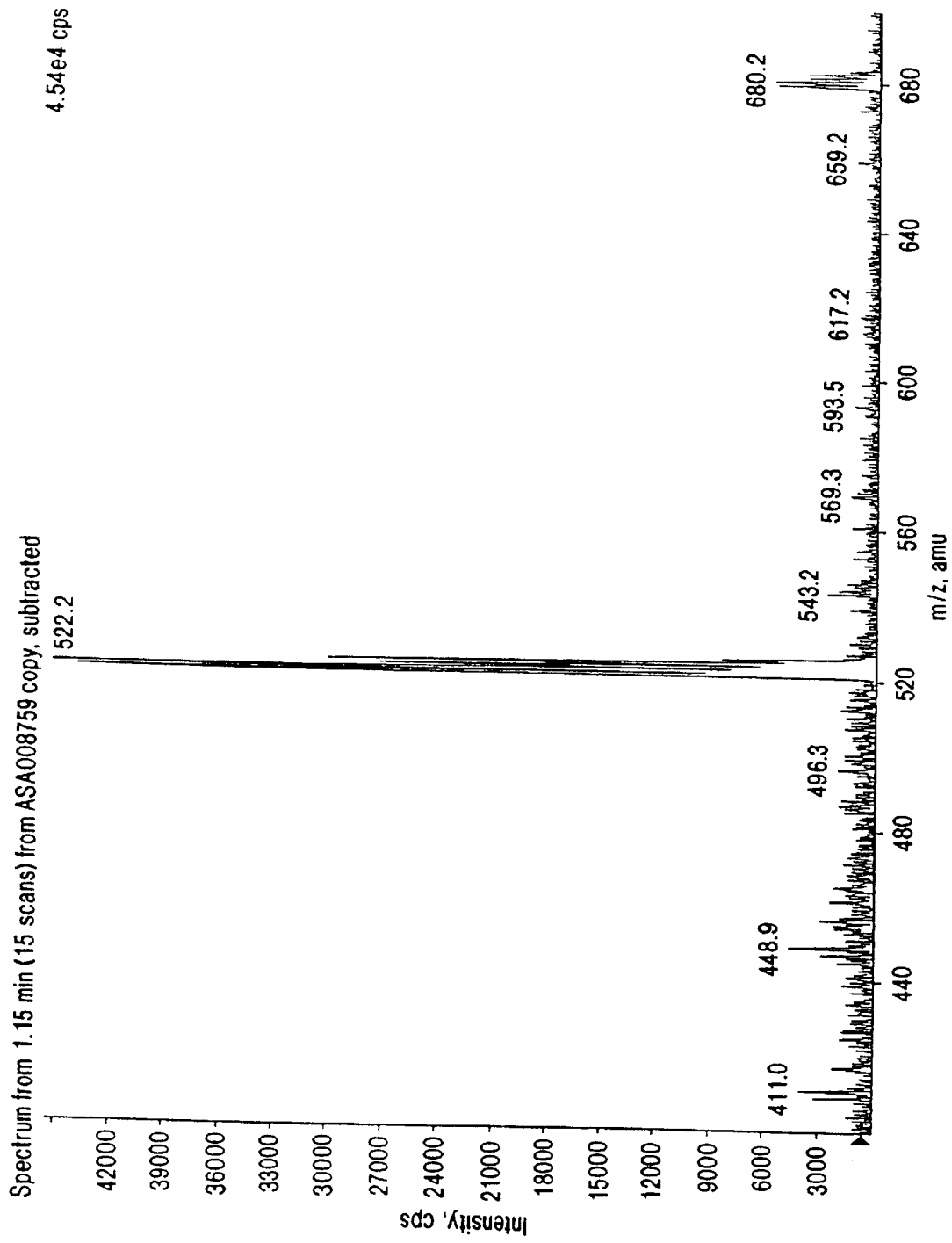
Figure 216:
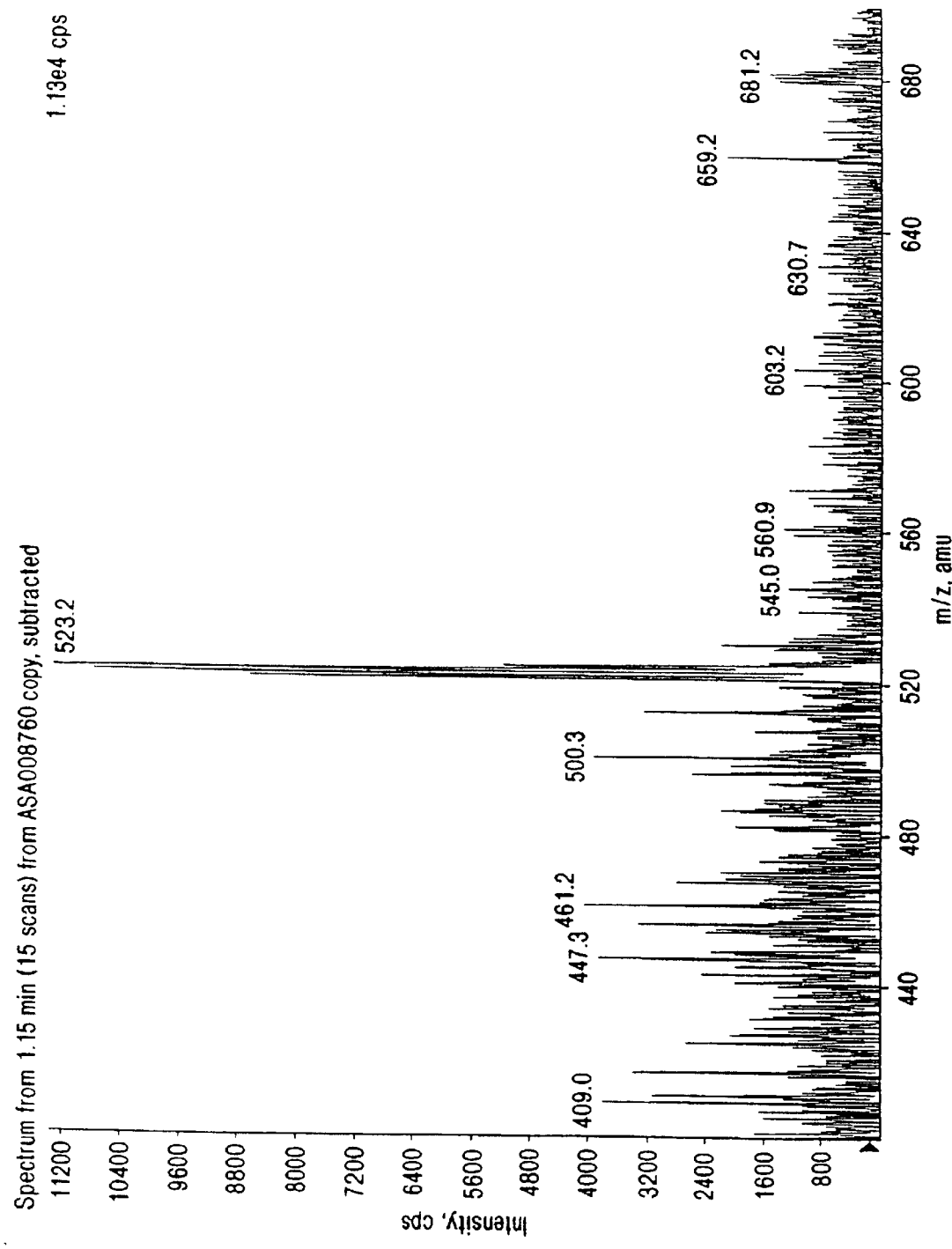
Figure 217:
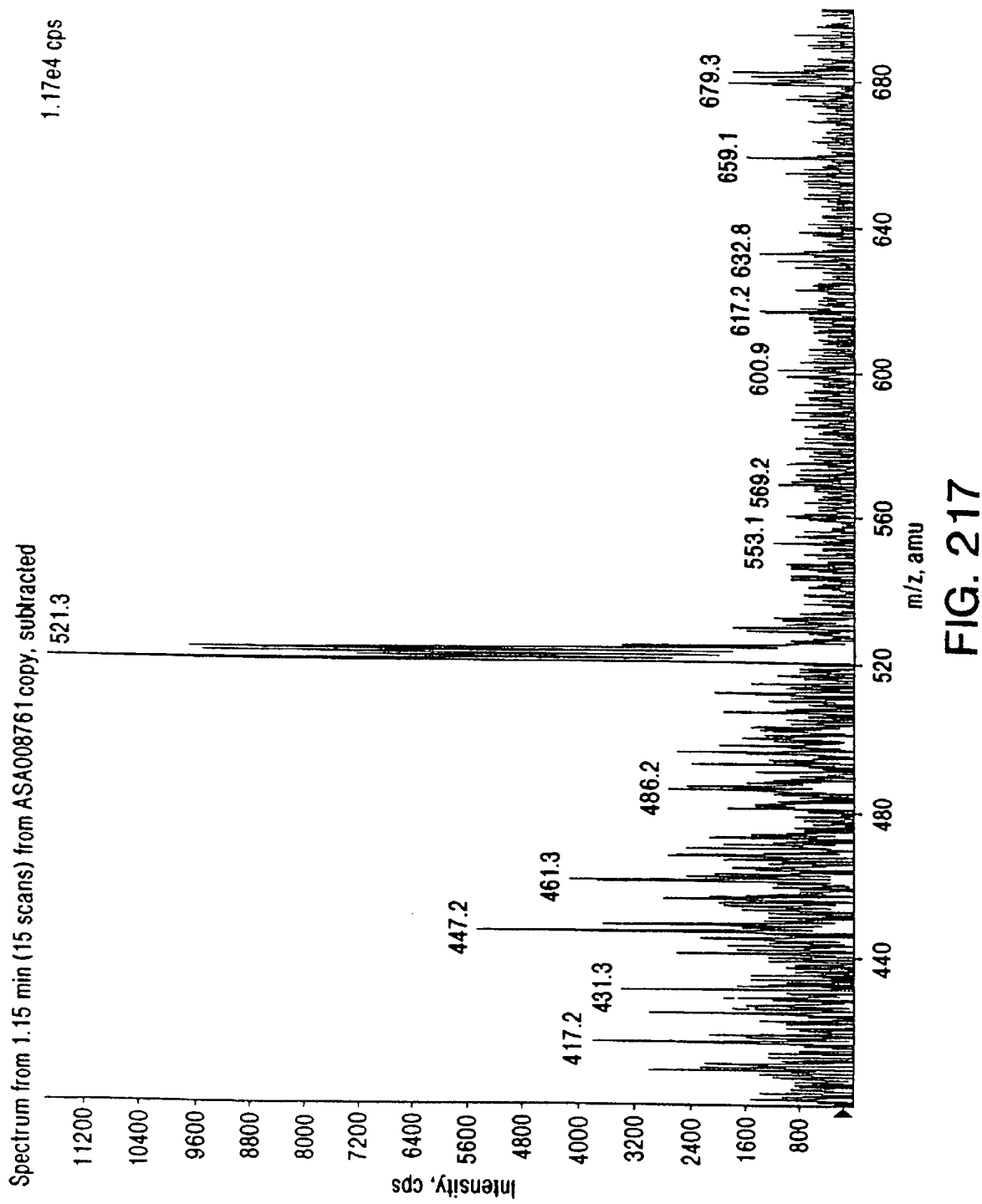
Figure 218:
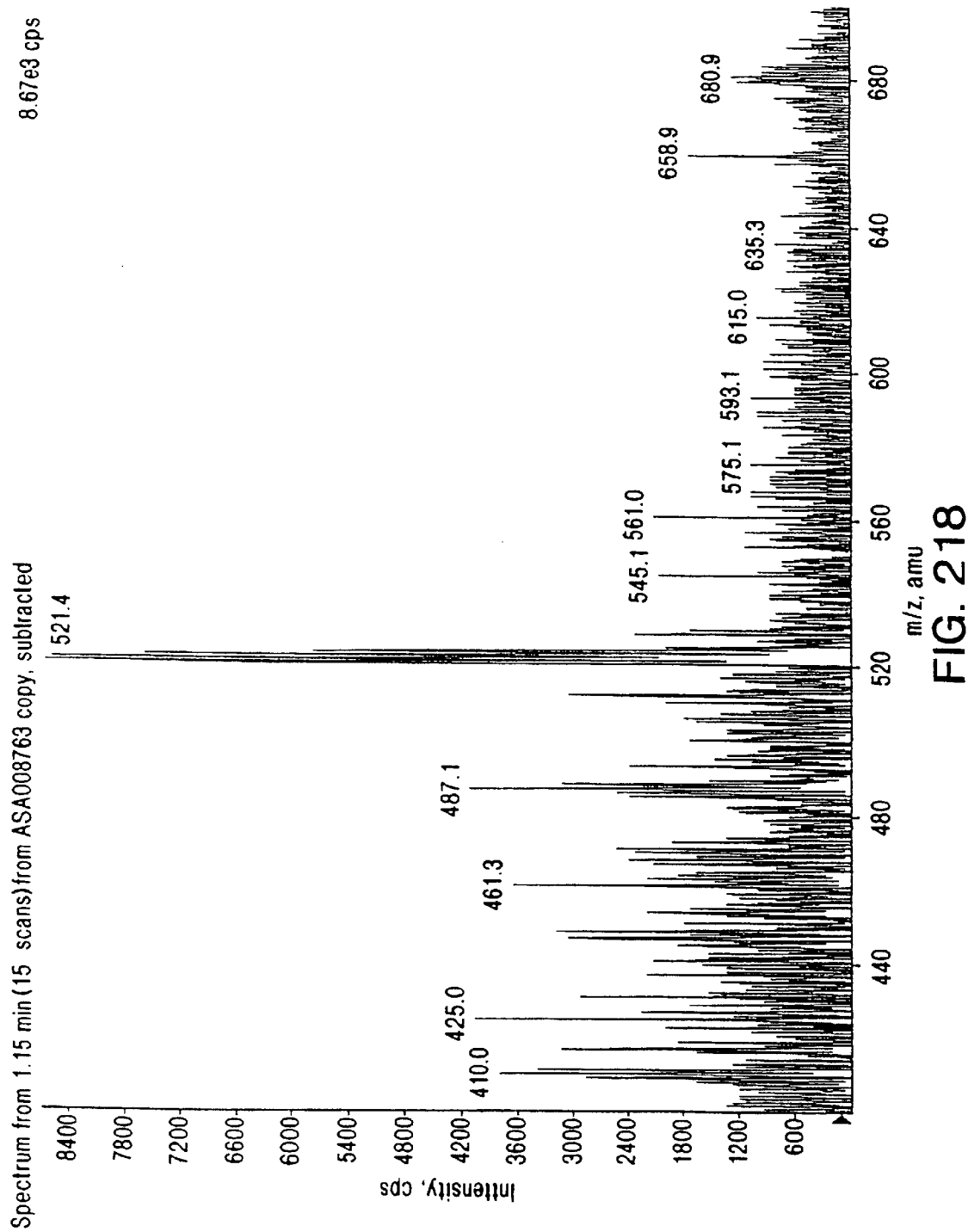
Figure 219:
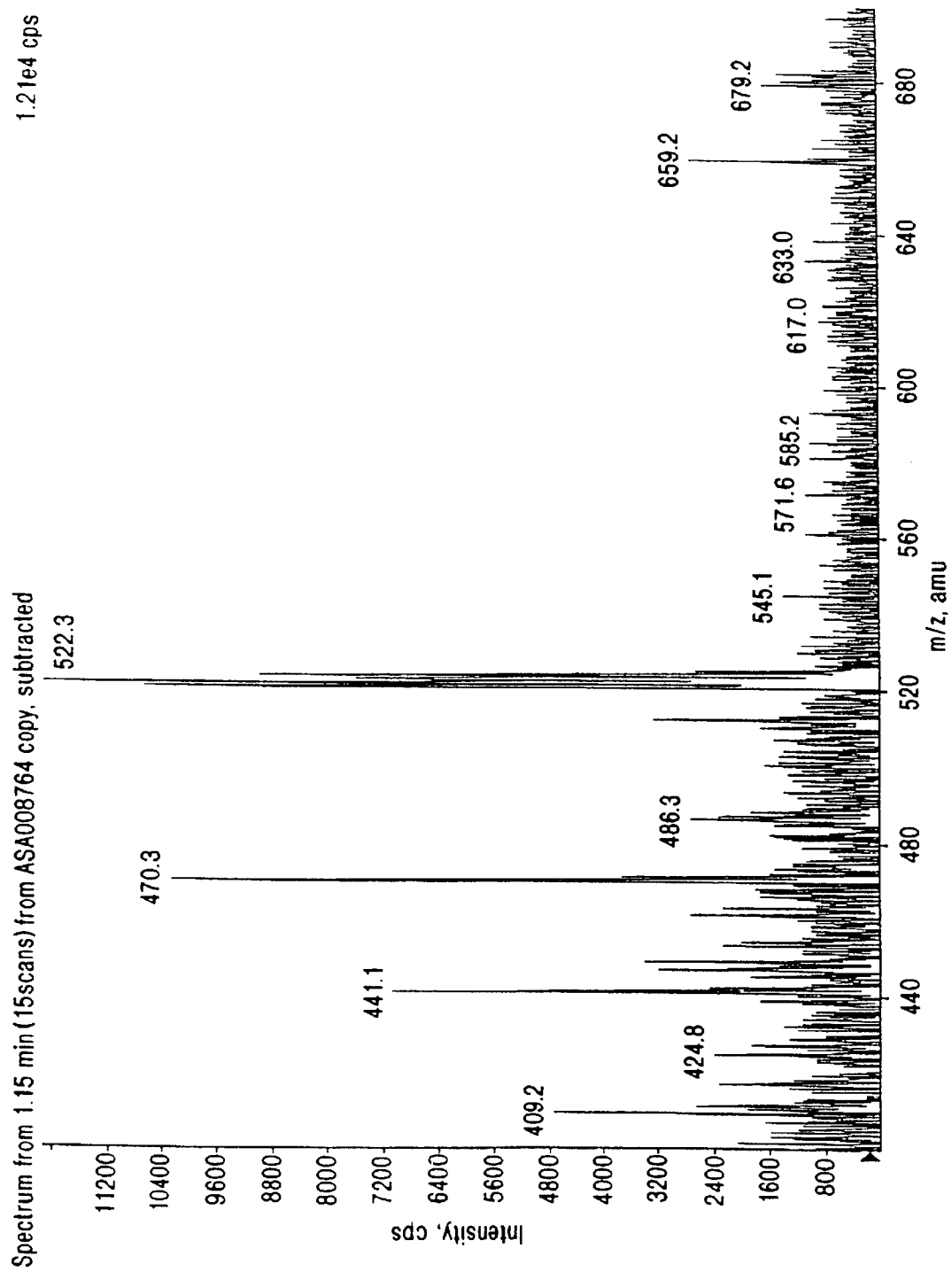
Figure 220:
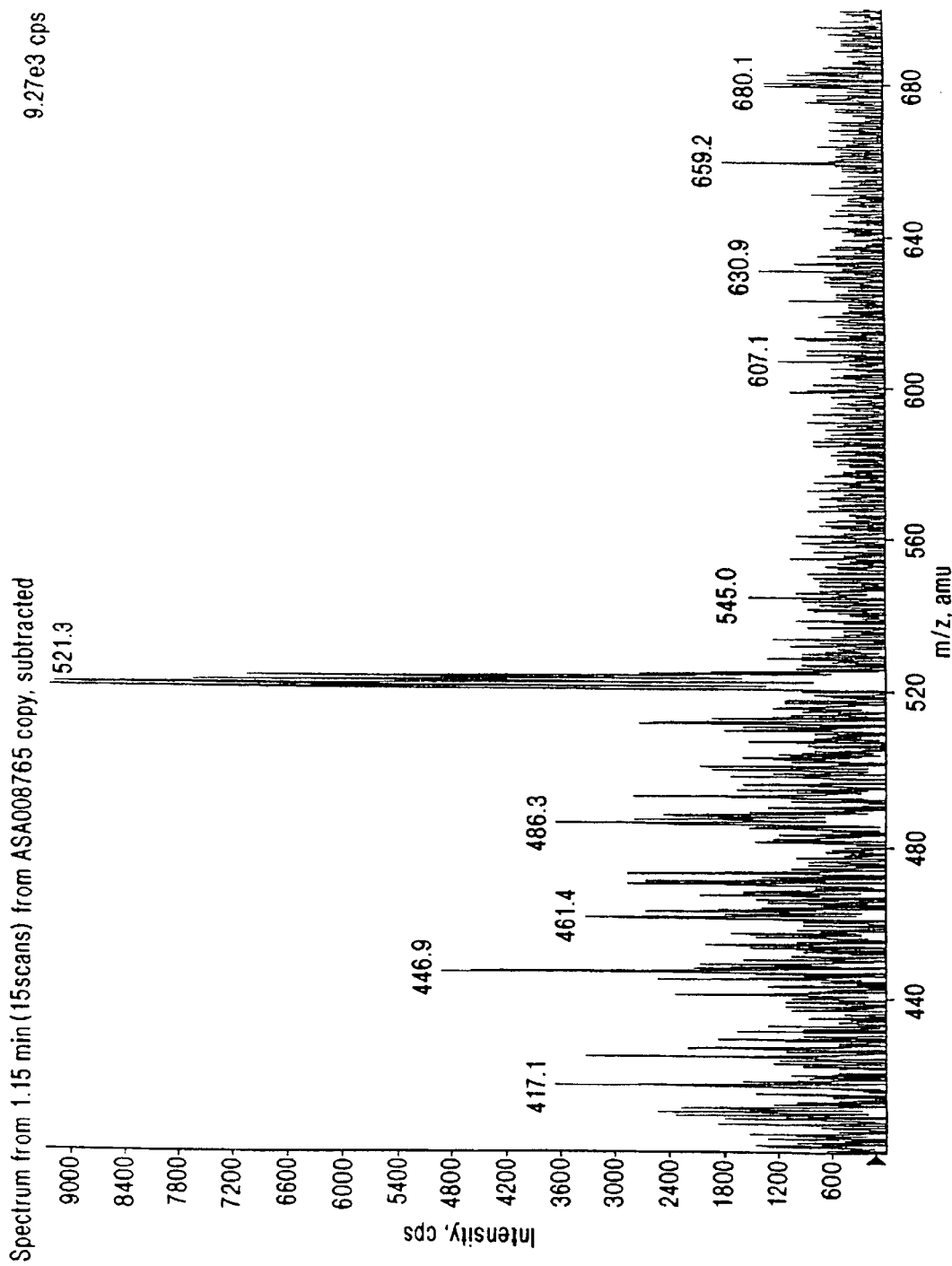
Figure 221:
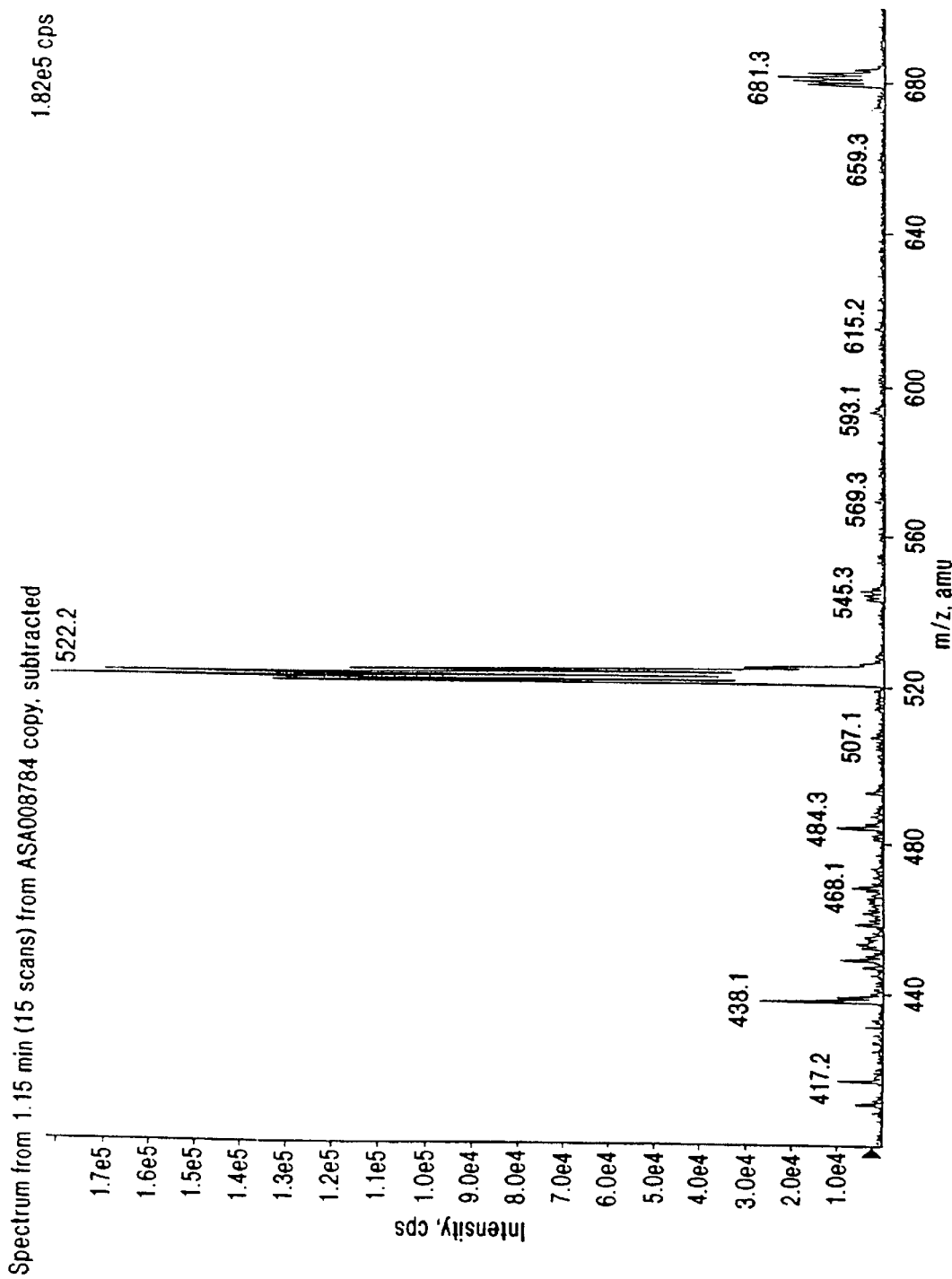
Figure 222:
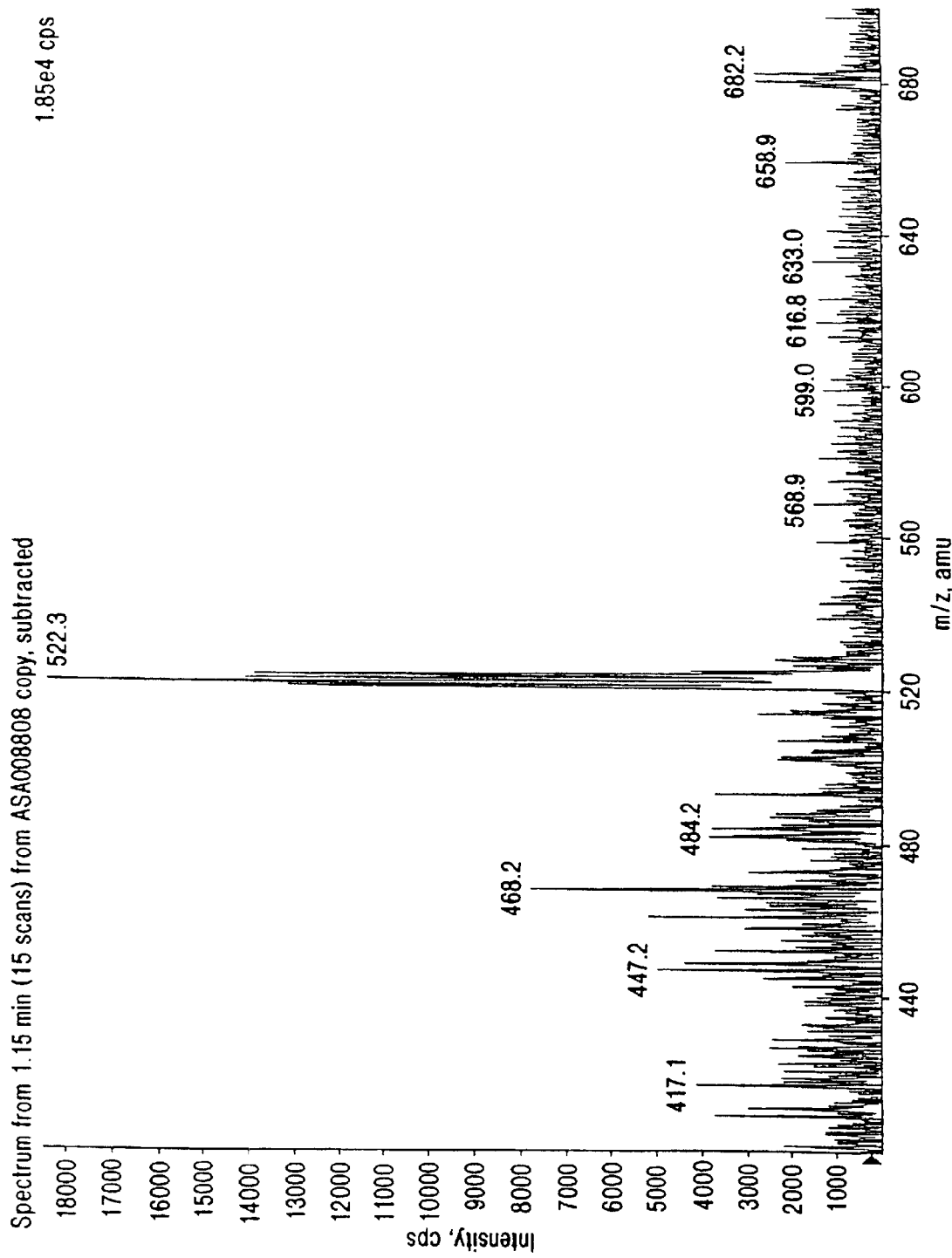
Figure 223:
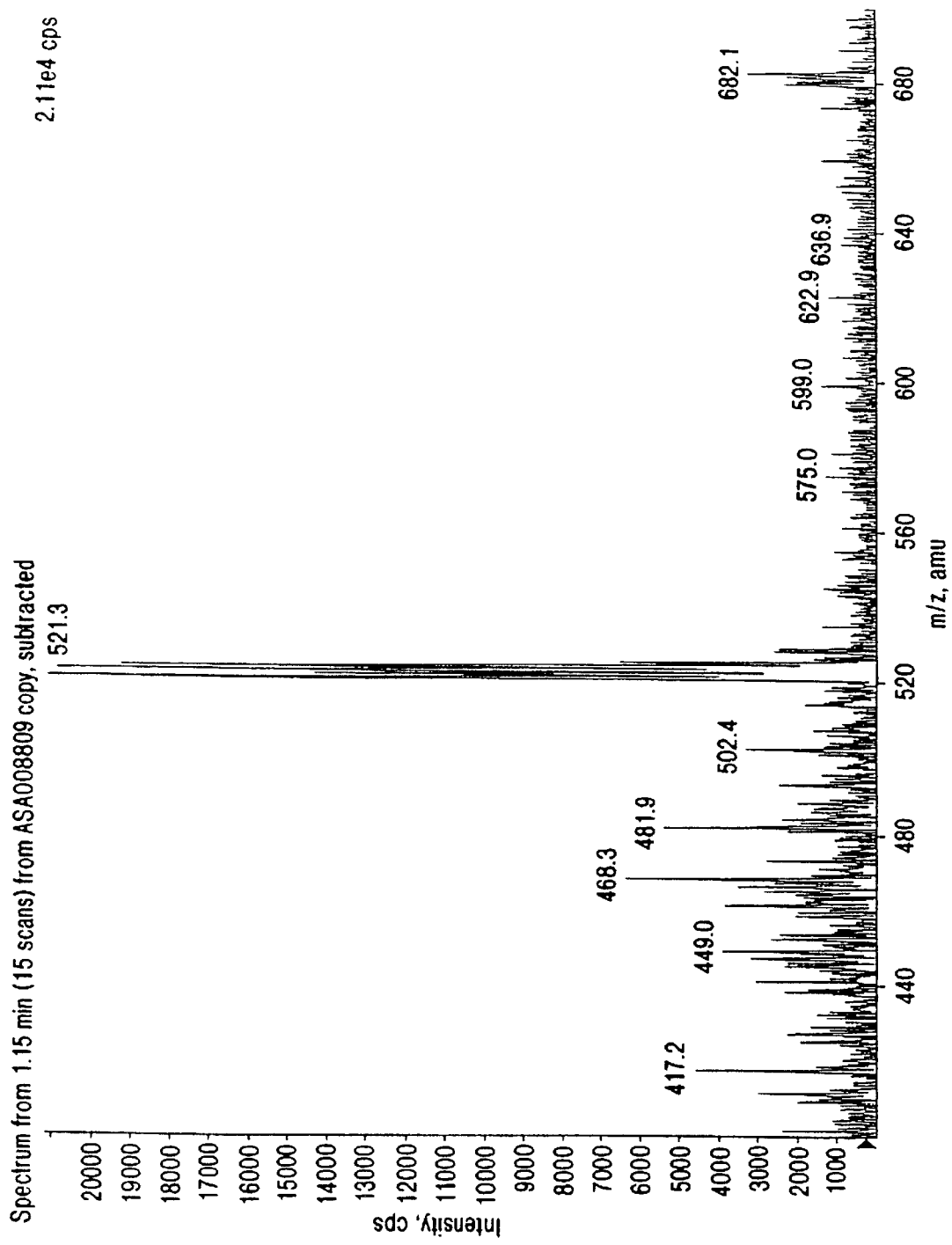
Figure 224:
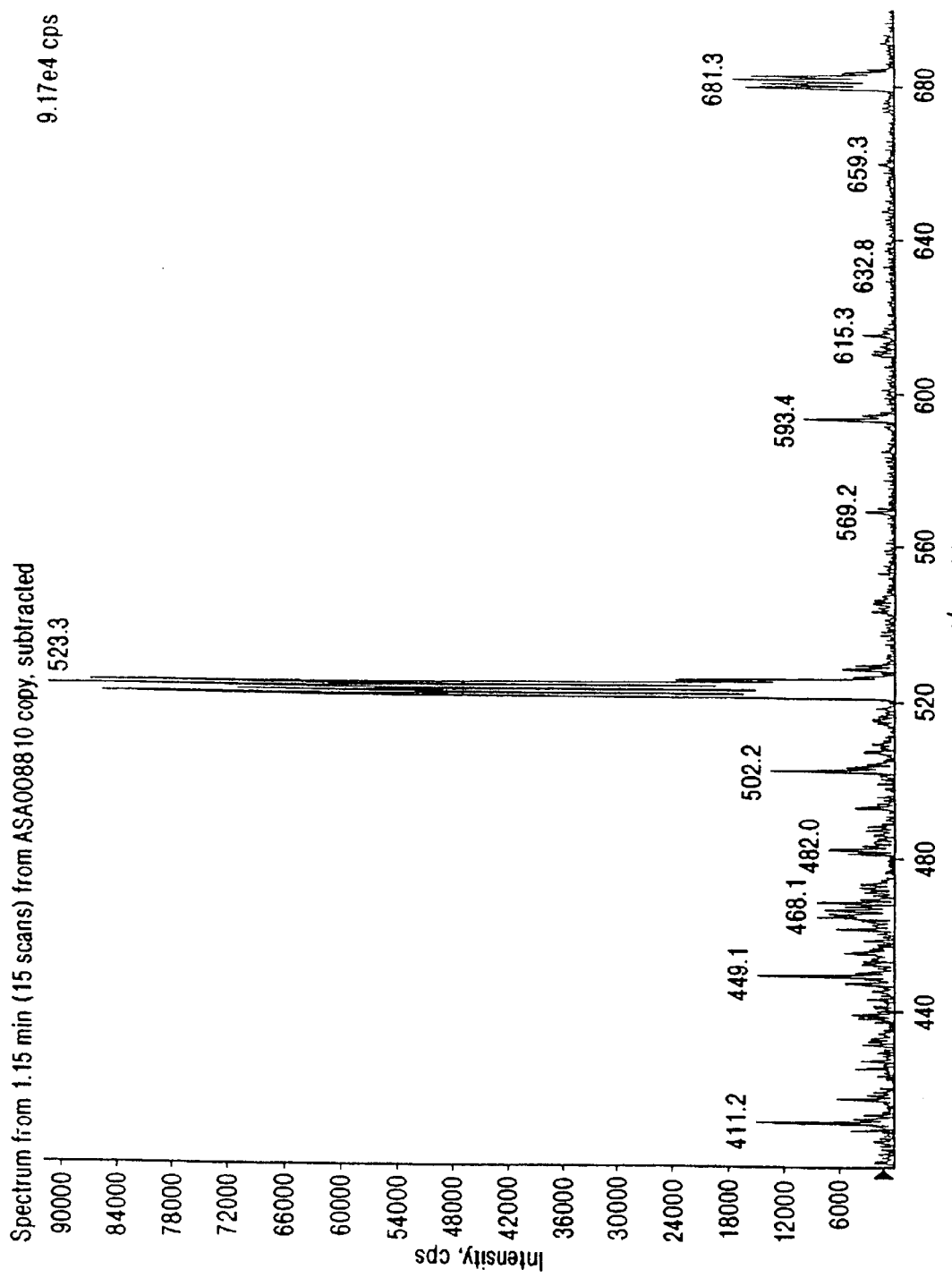
Figure 225:
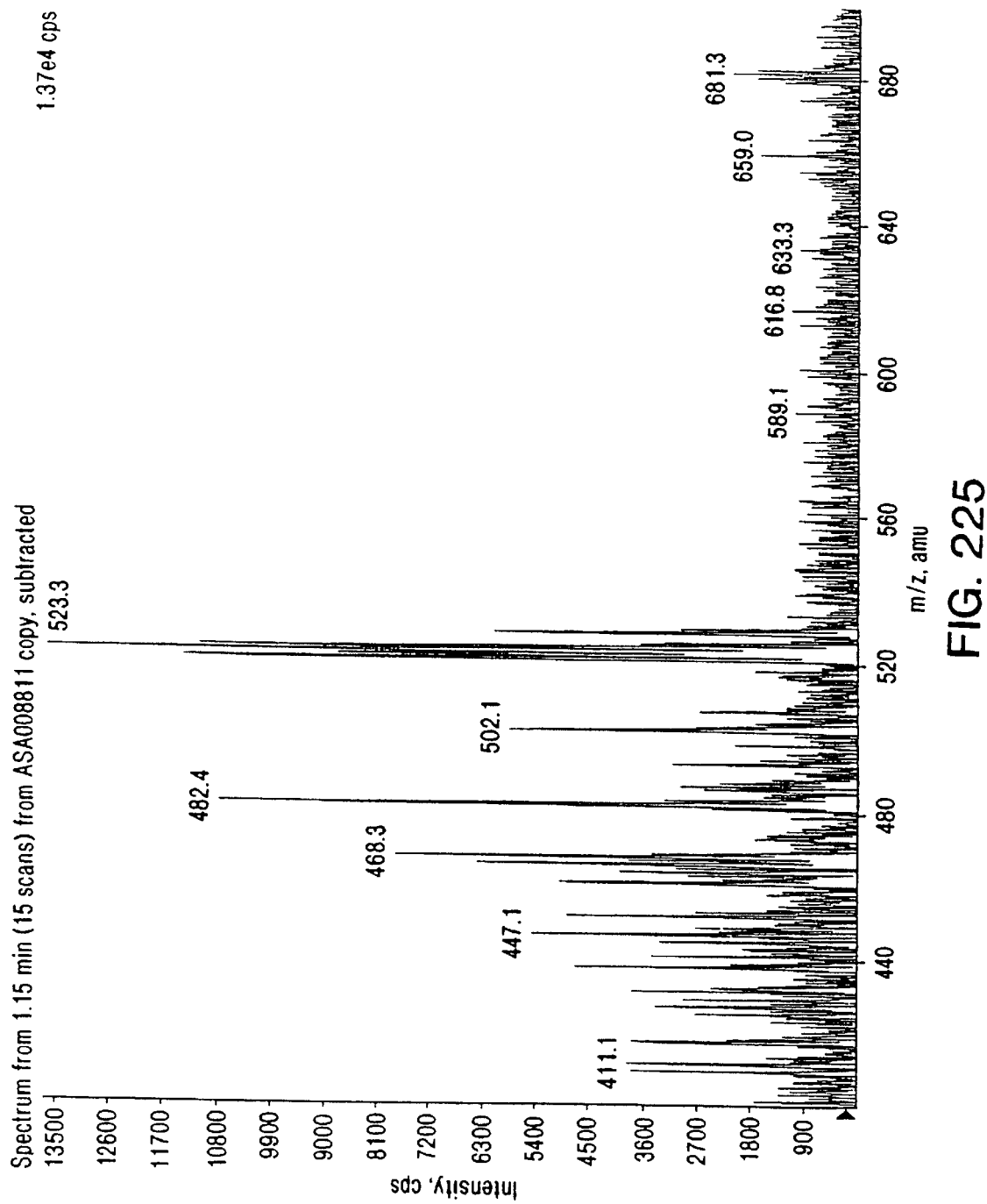
Figure 226:
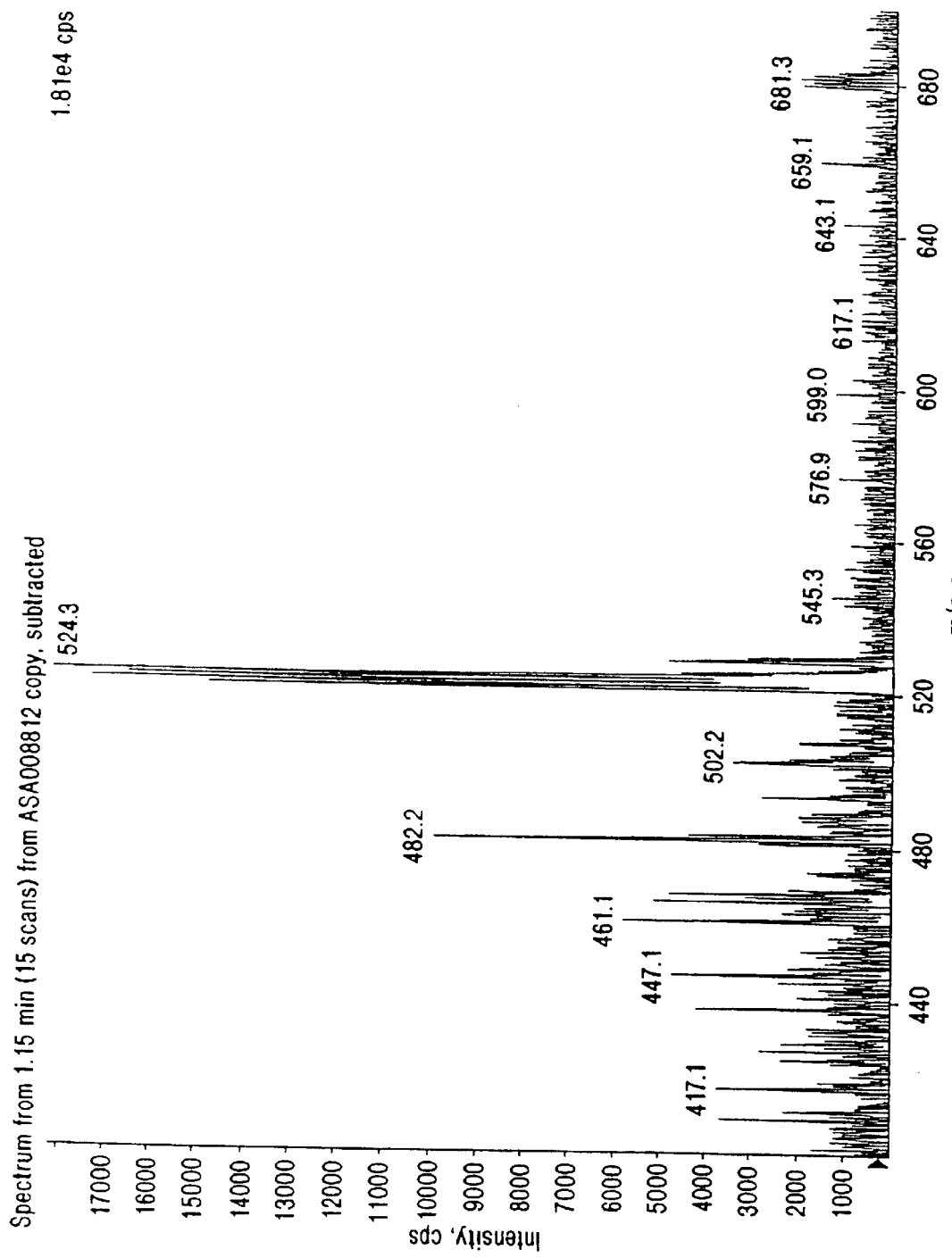
Figure 227:
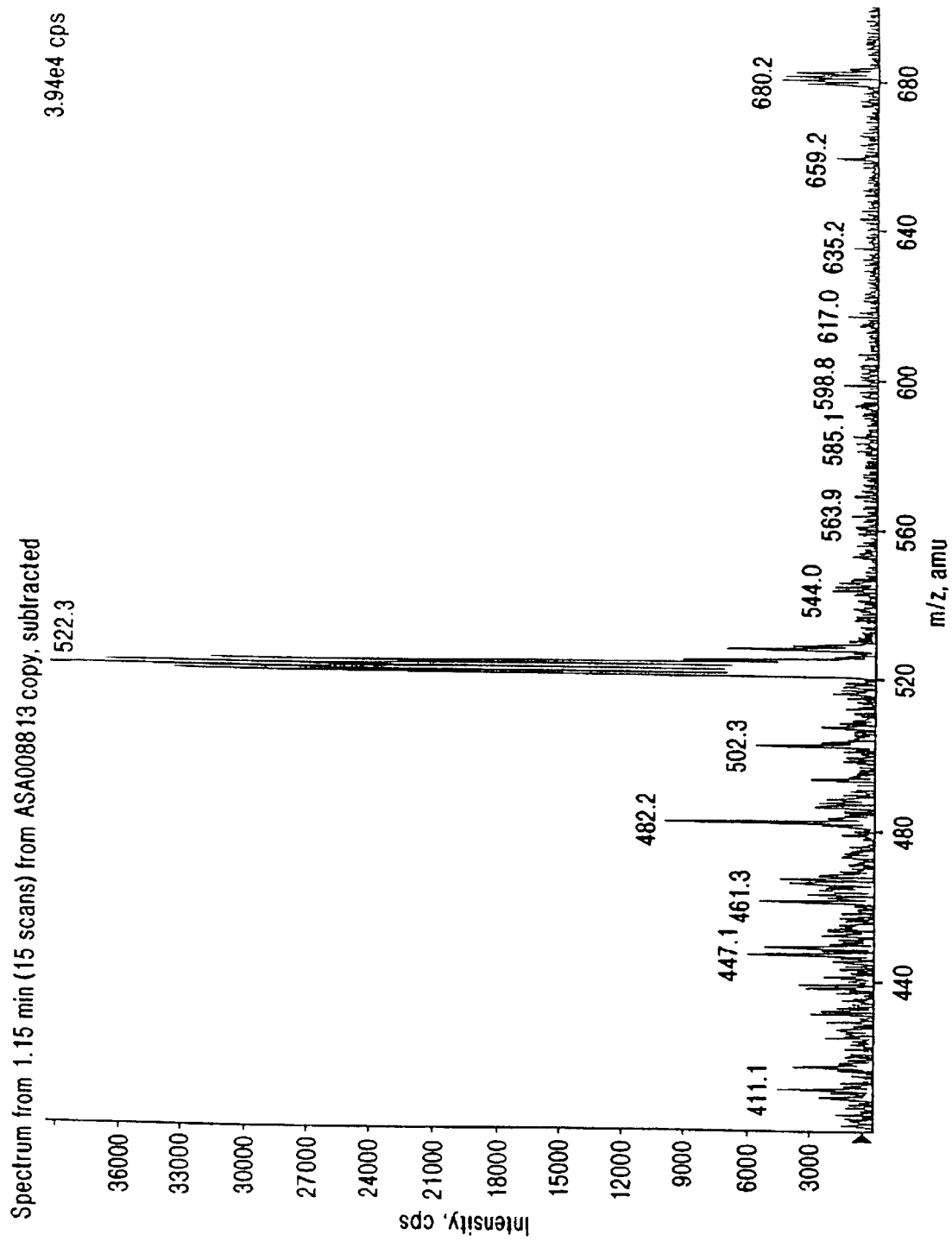
Figure 228:
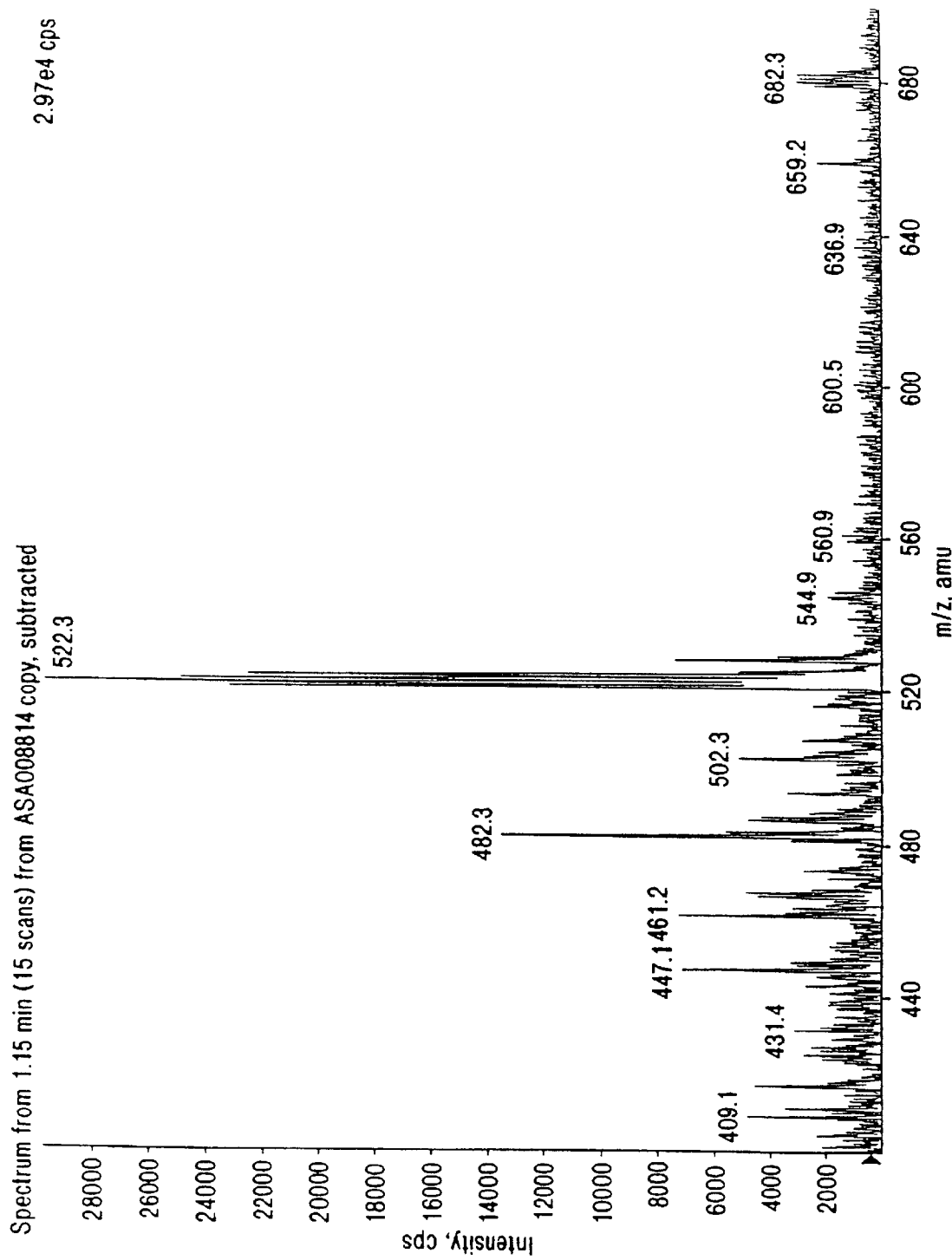
Figure 229:
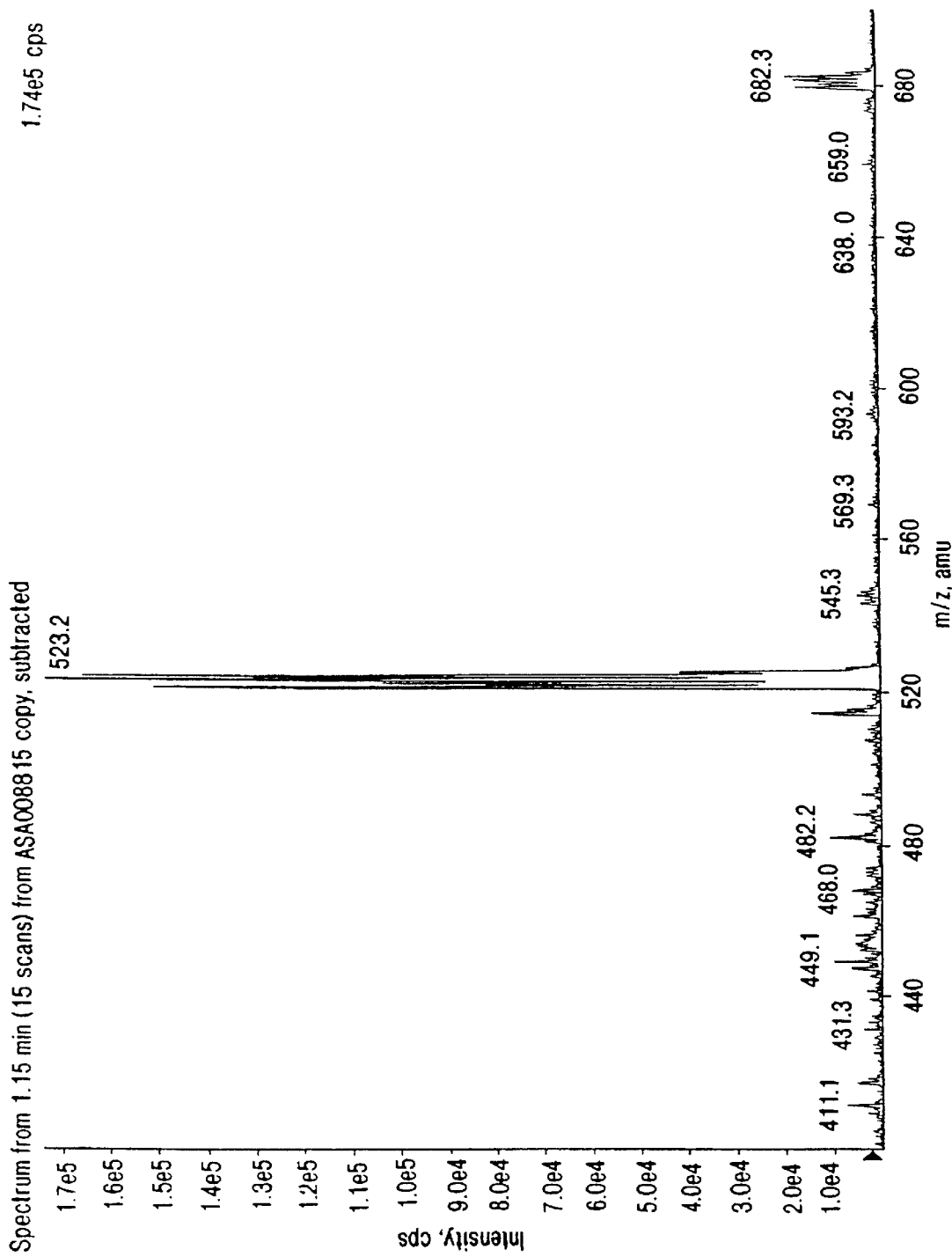
Figure 230:
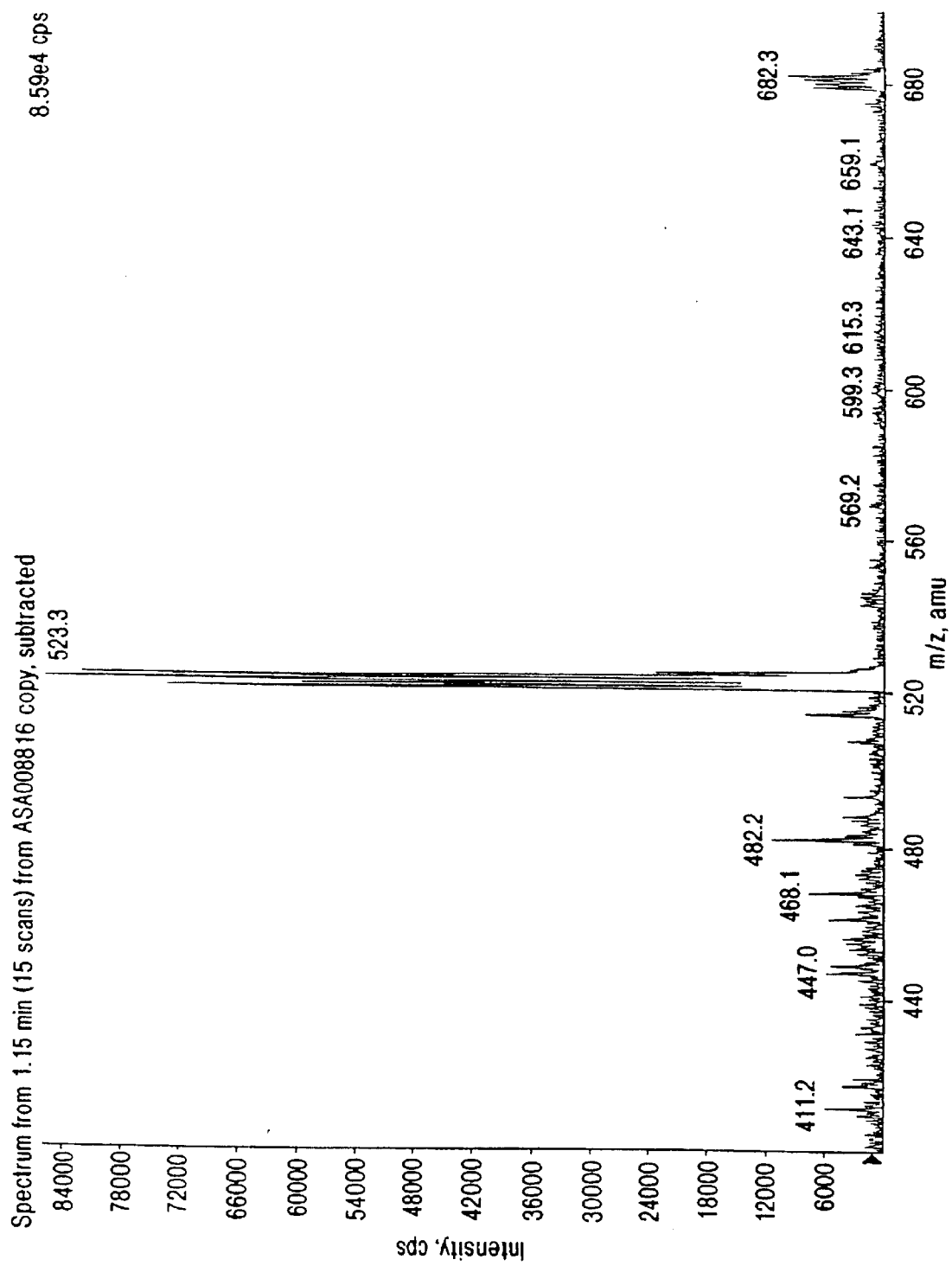
Figure 231:
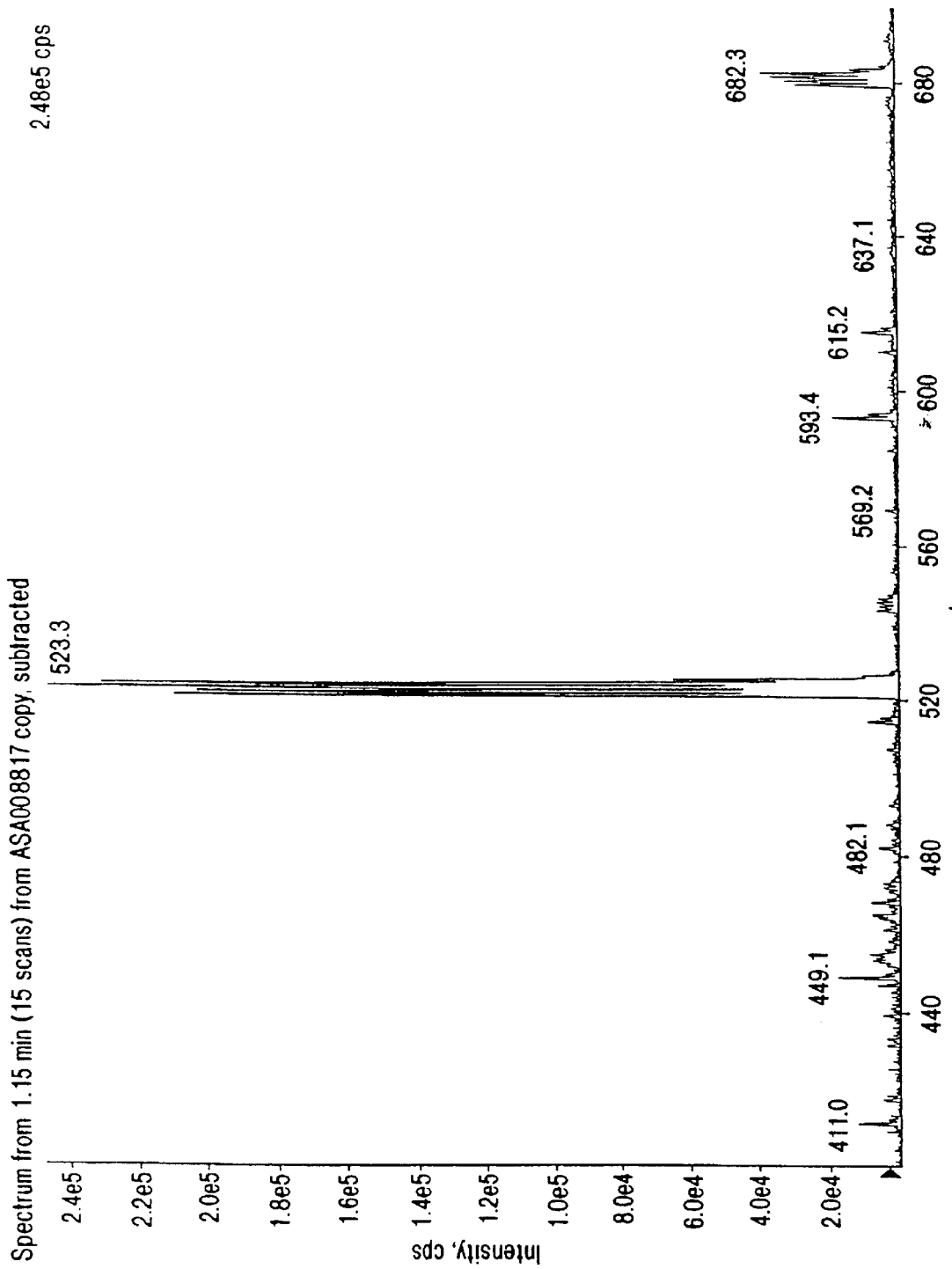
Figure 232:
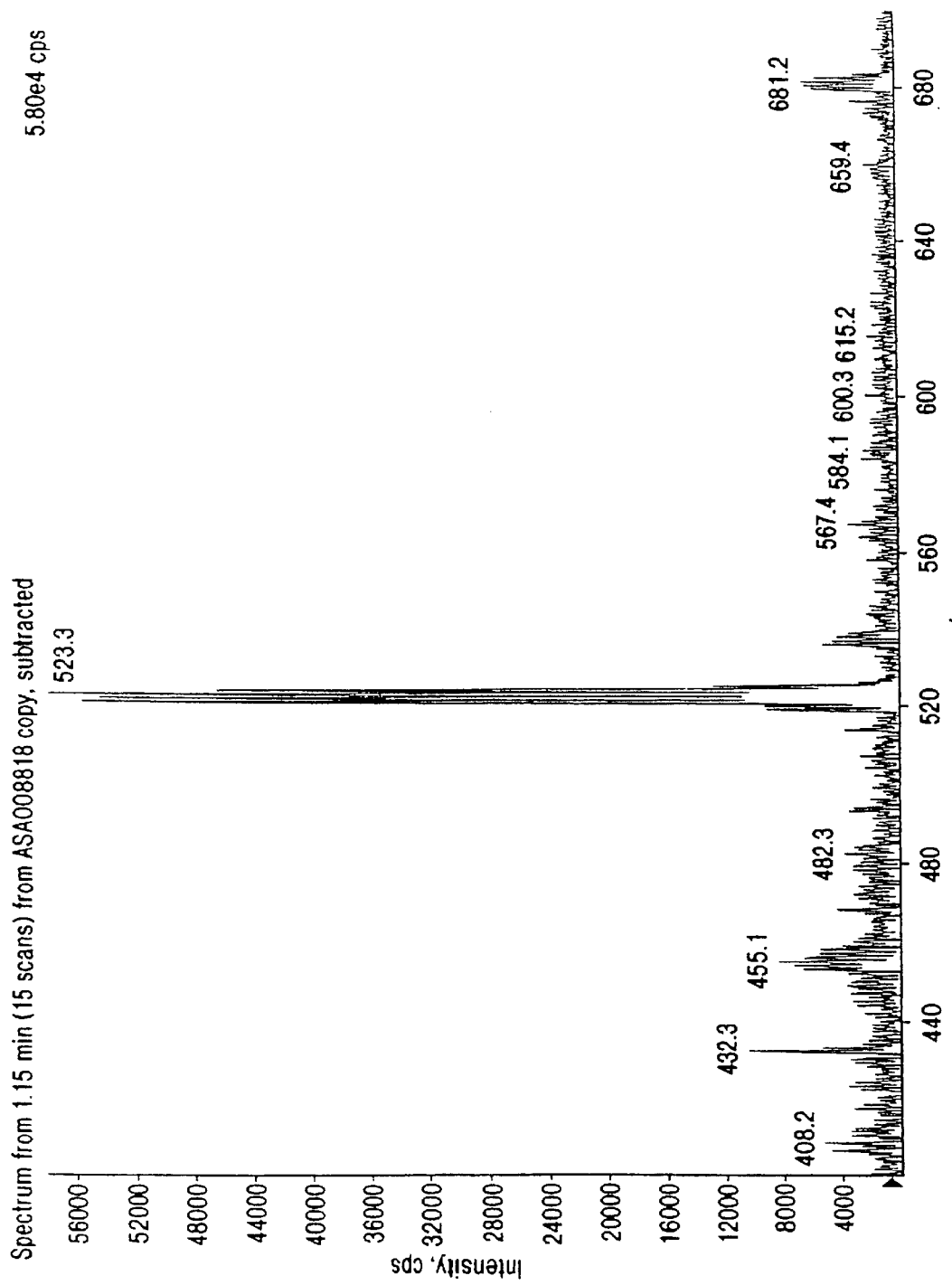
Figure 233:
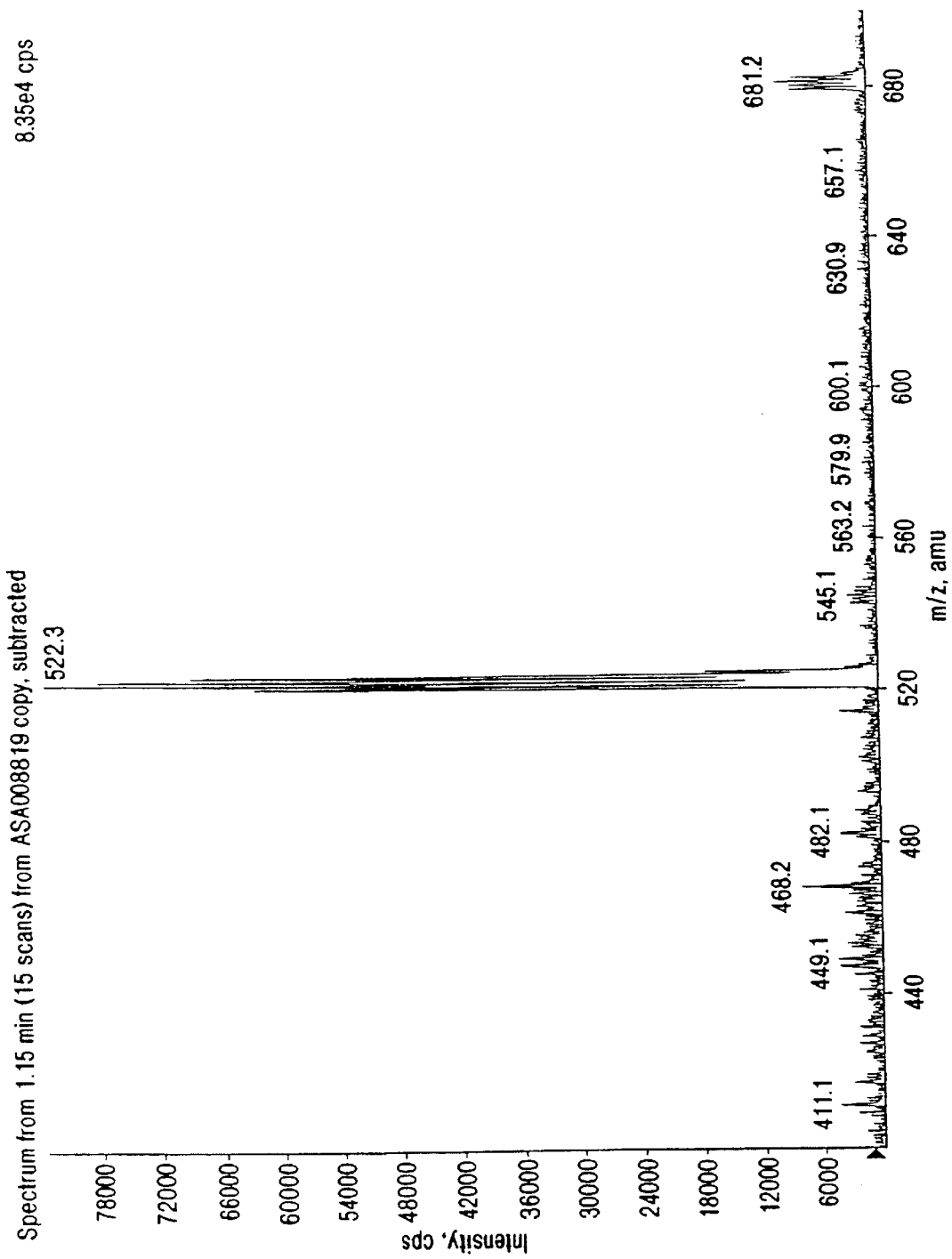
Figure 234:
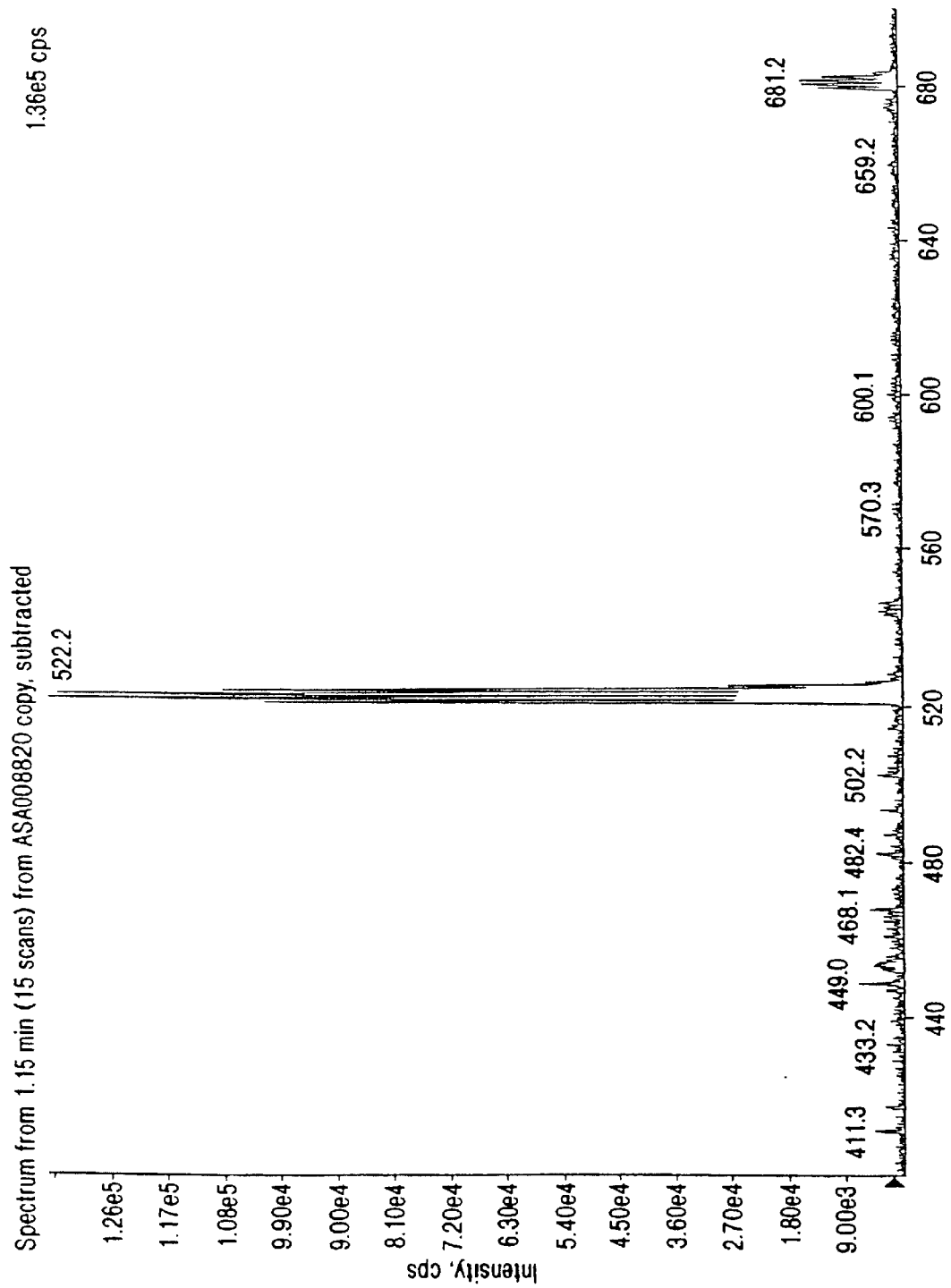
Figure 235:
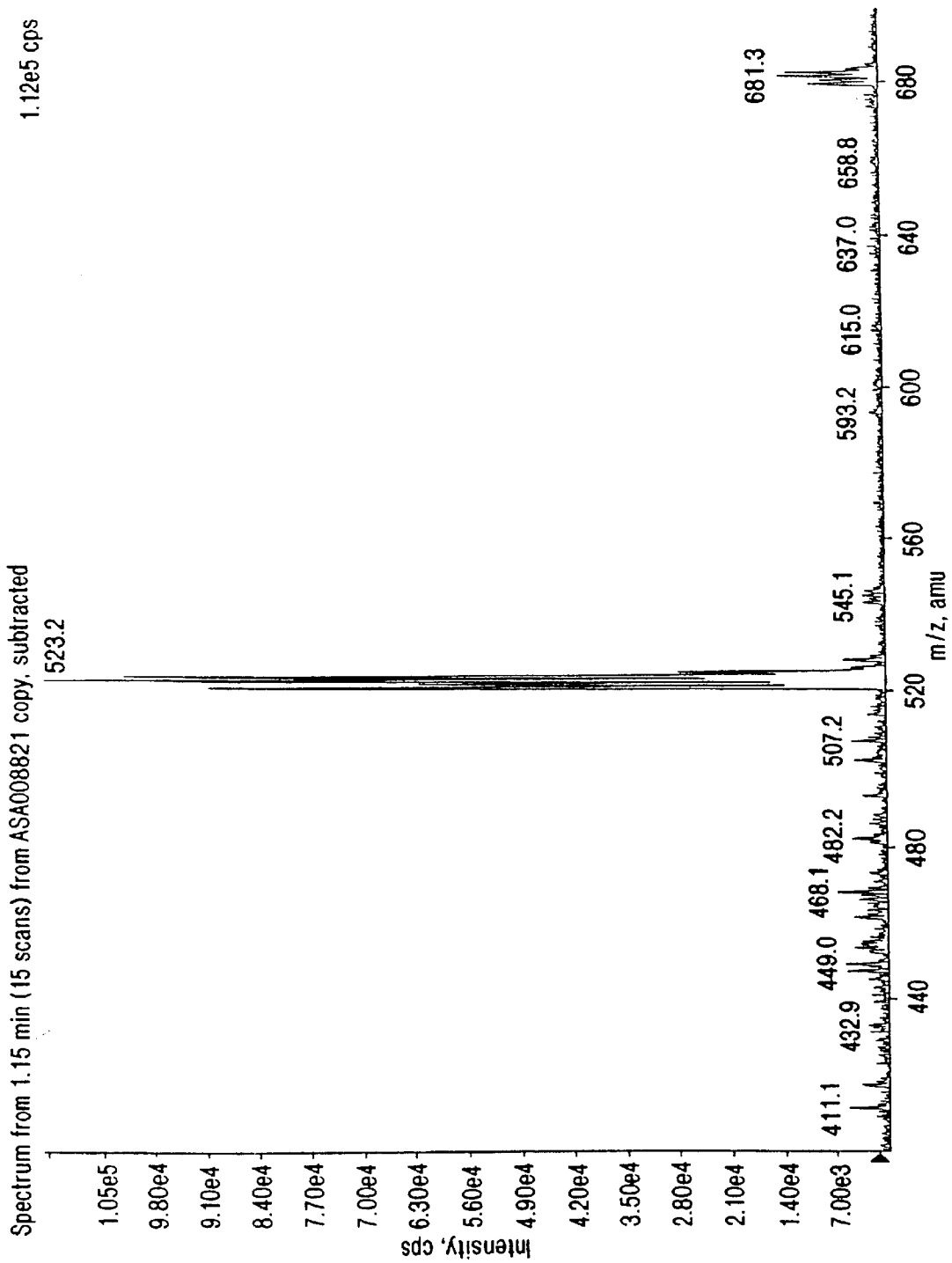
Figure 236:
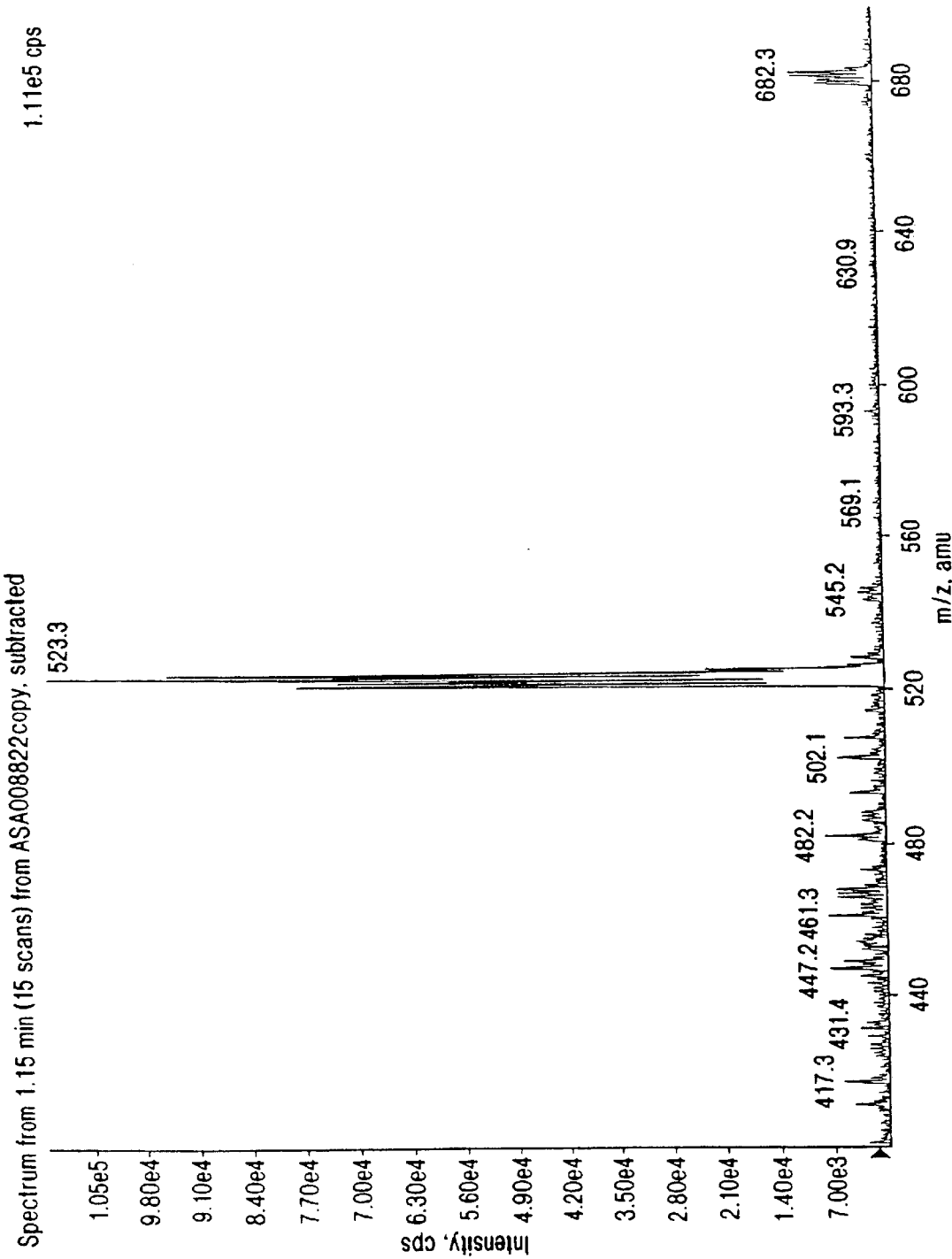
Figure 237:
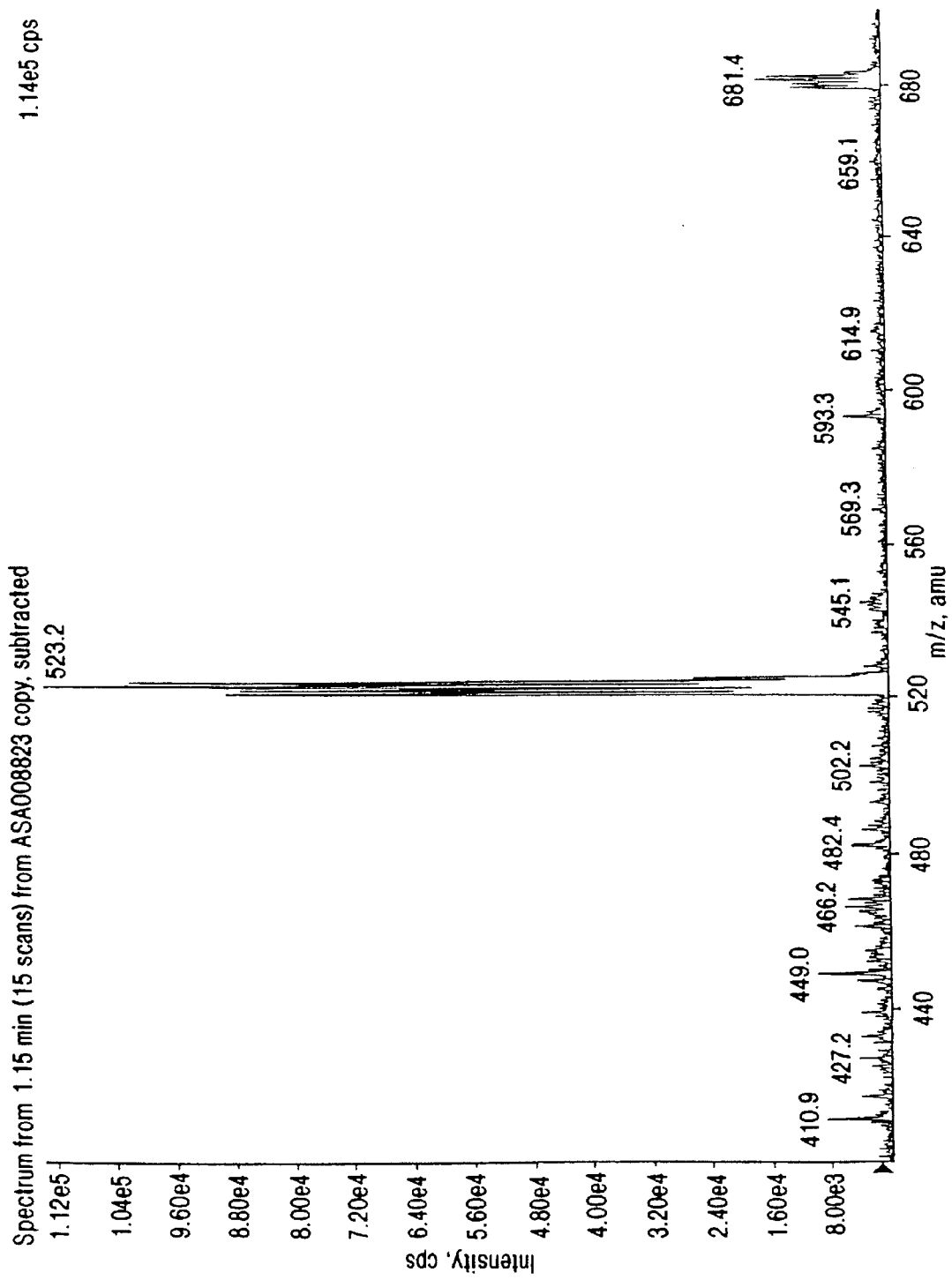
Figure 238:
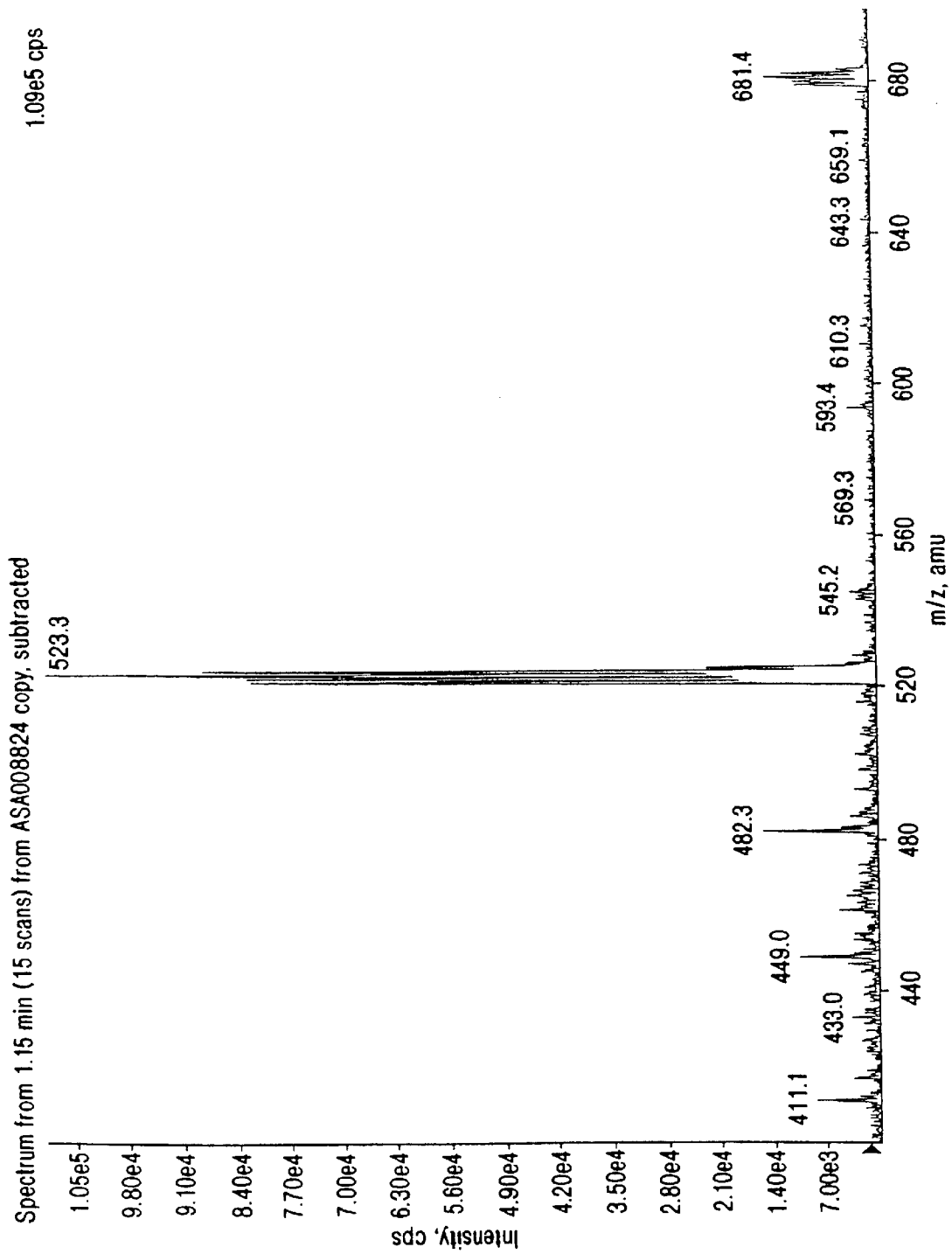
Figure 239:
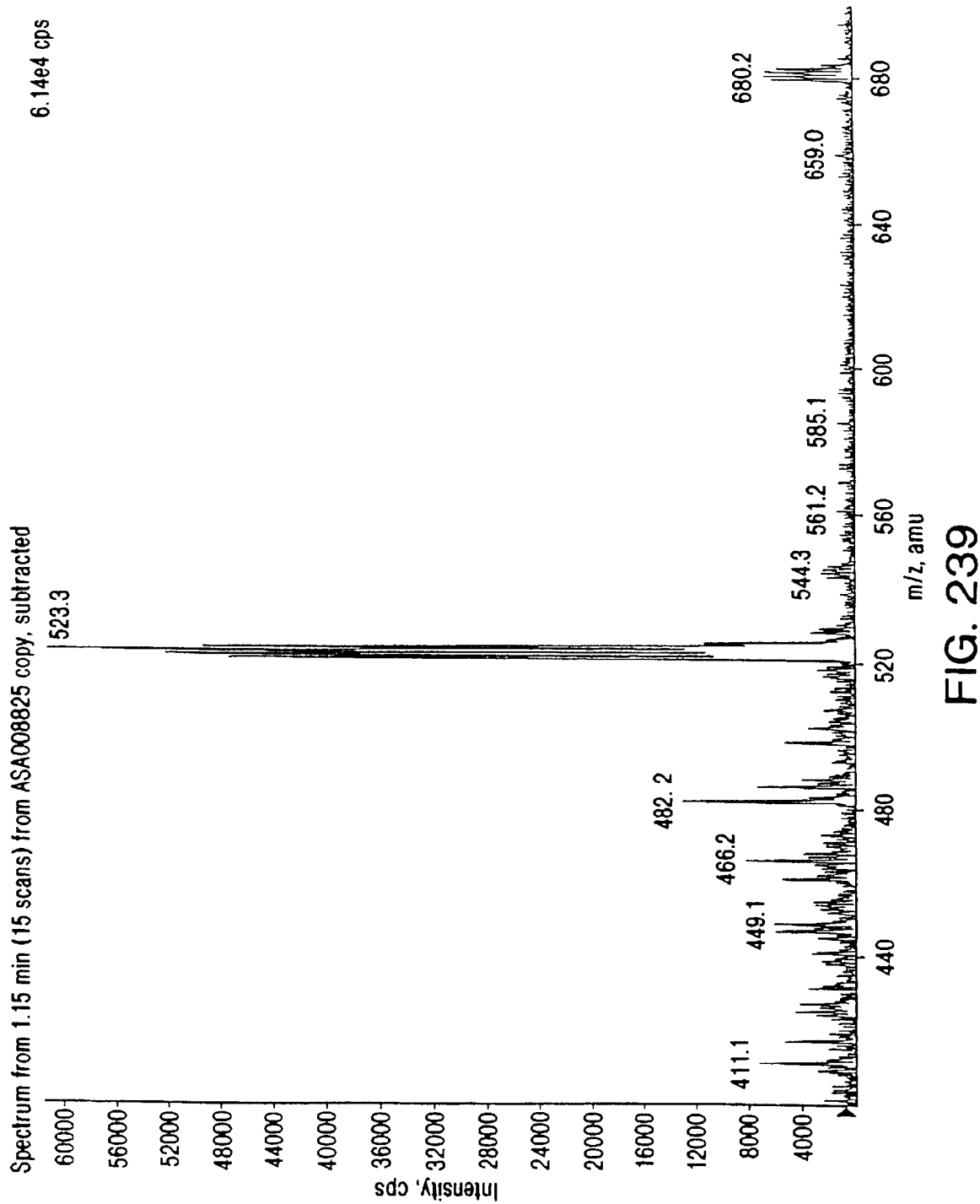
Figure 240:
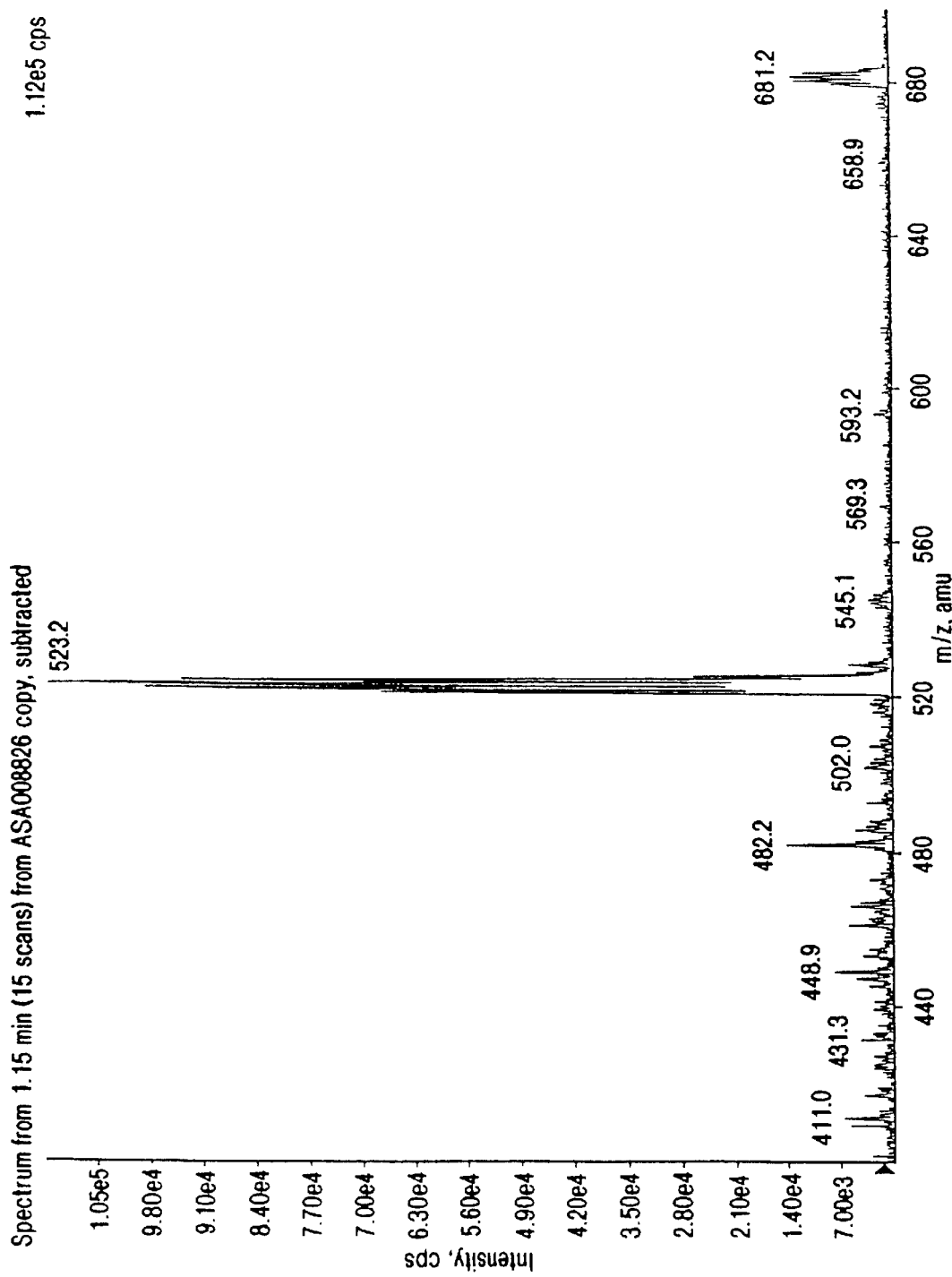
Figure 241:
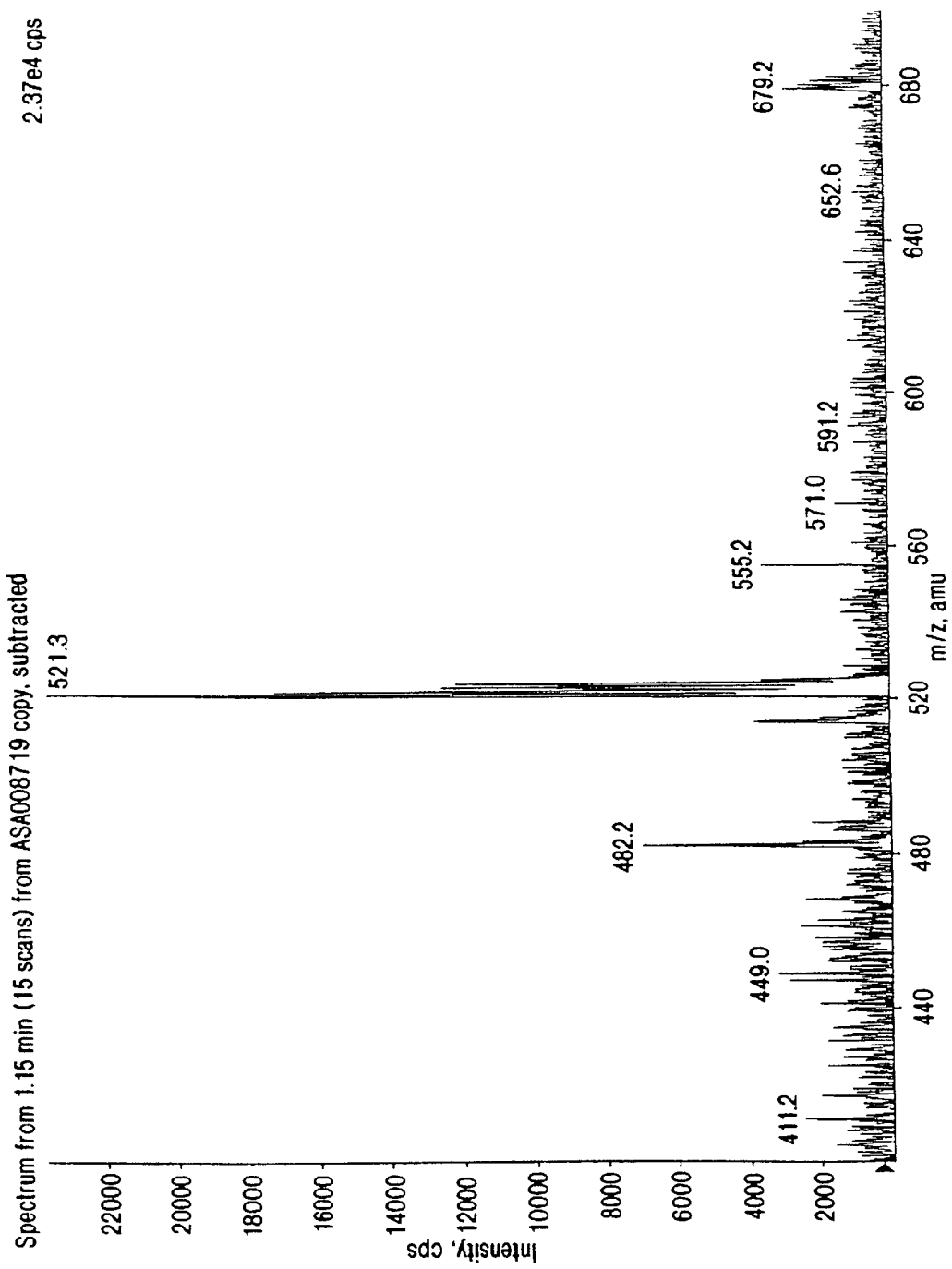
Figure 242:
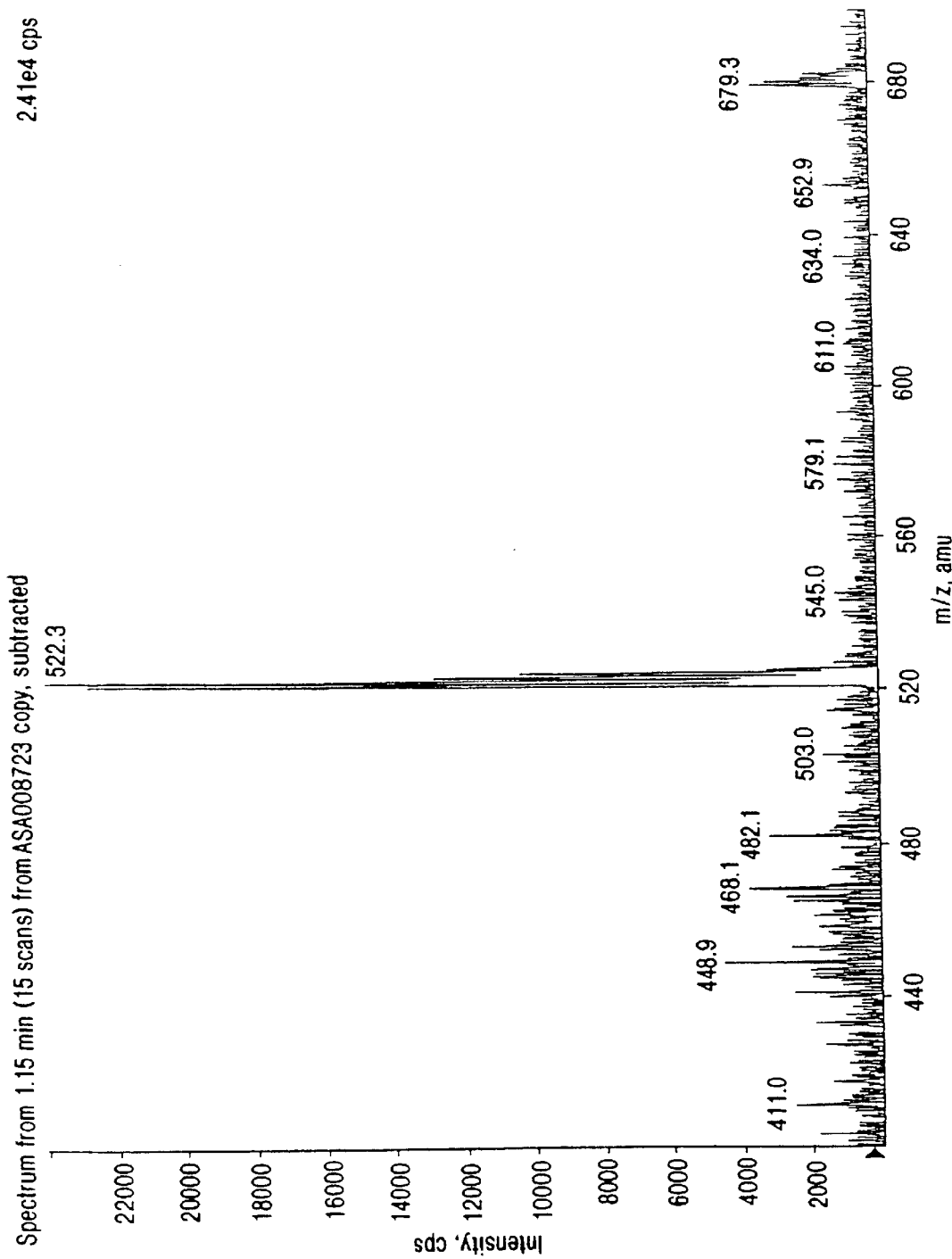
Figure 243:
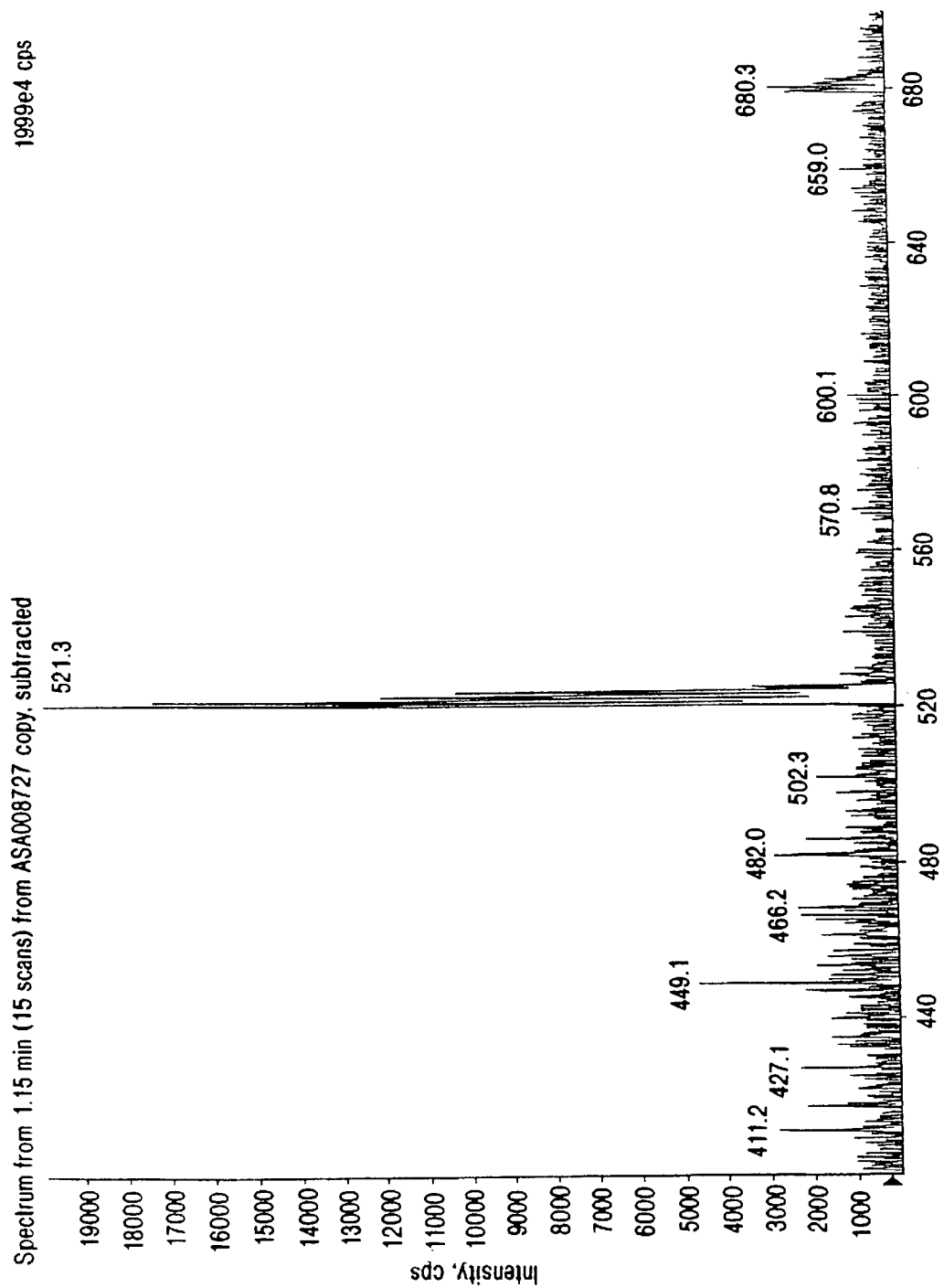
Figure 244:
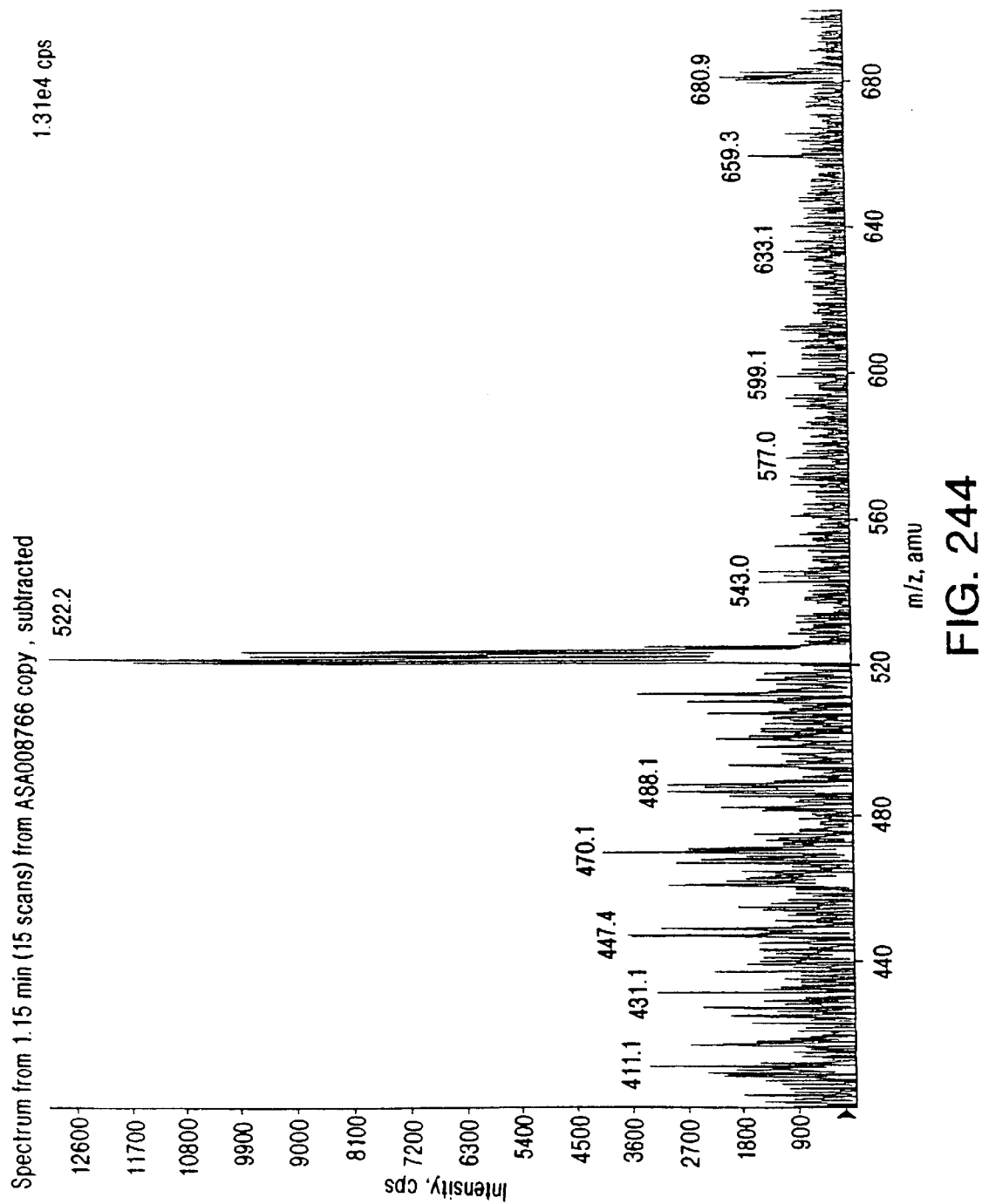
Figure 245:
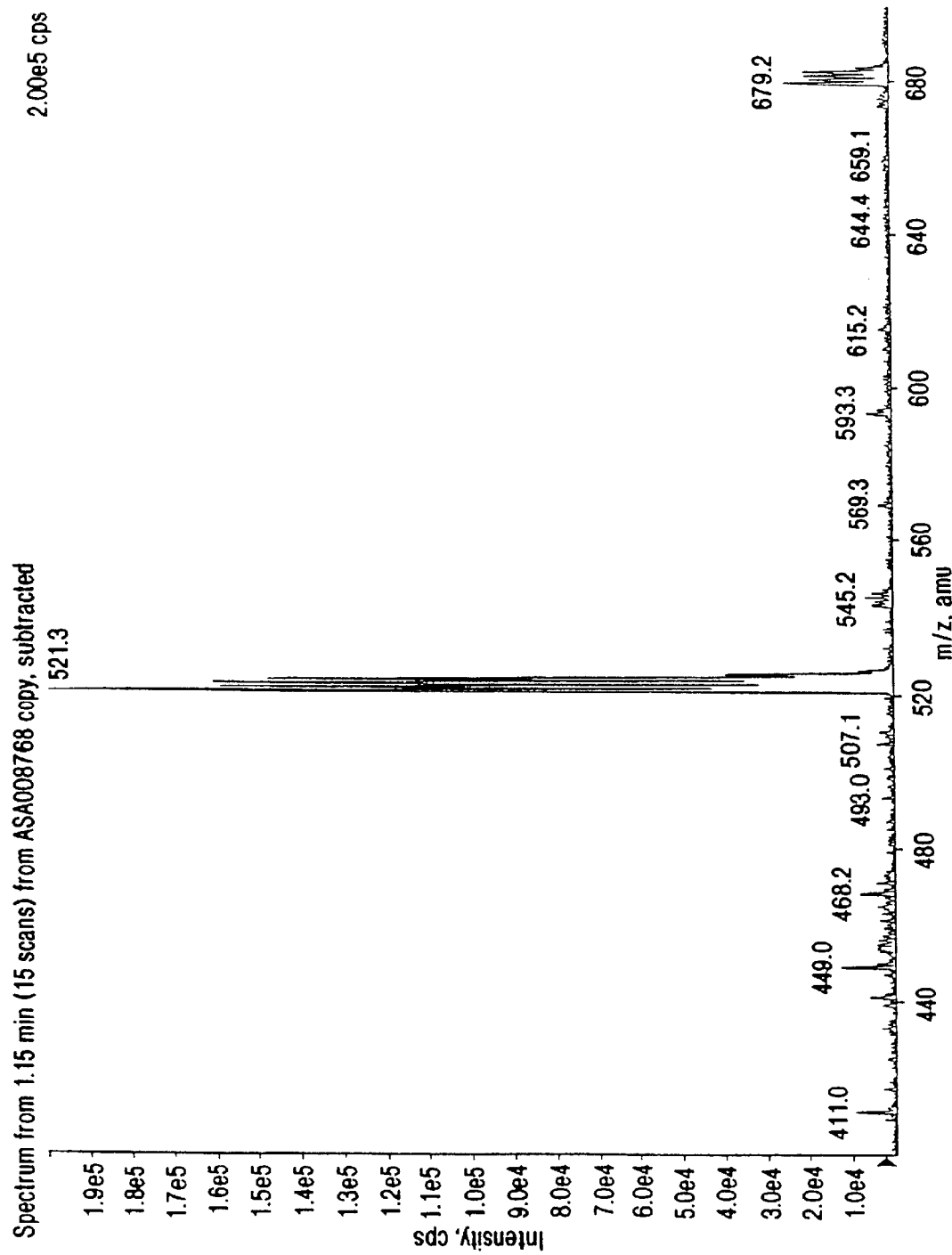
Figure 246:
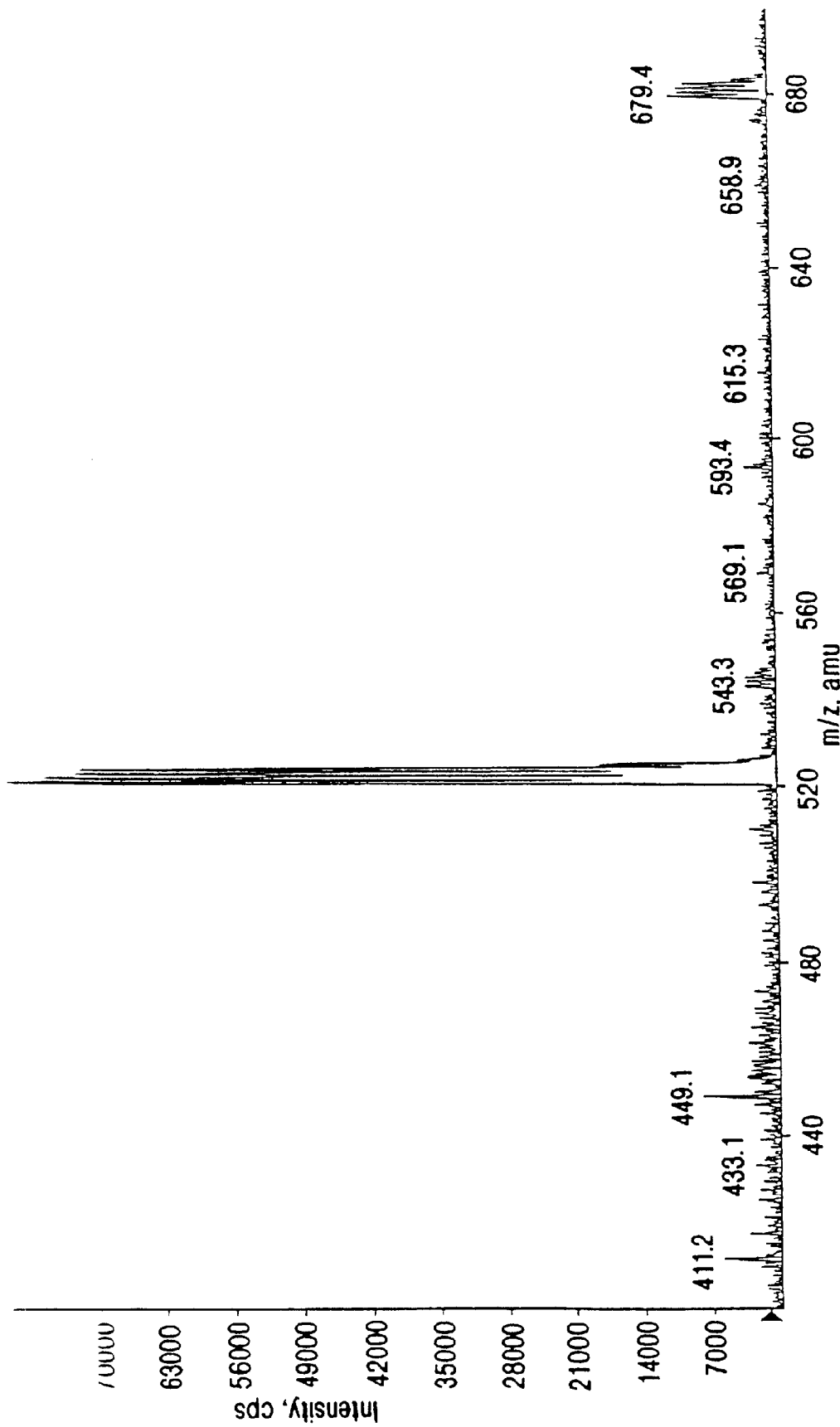
Figure 247:
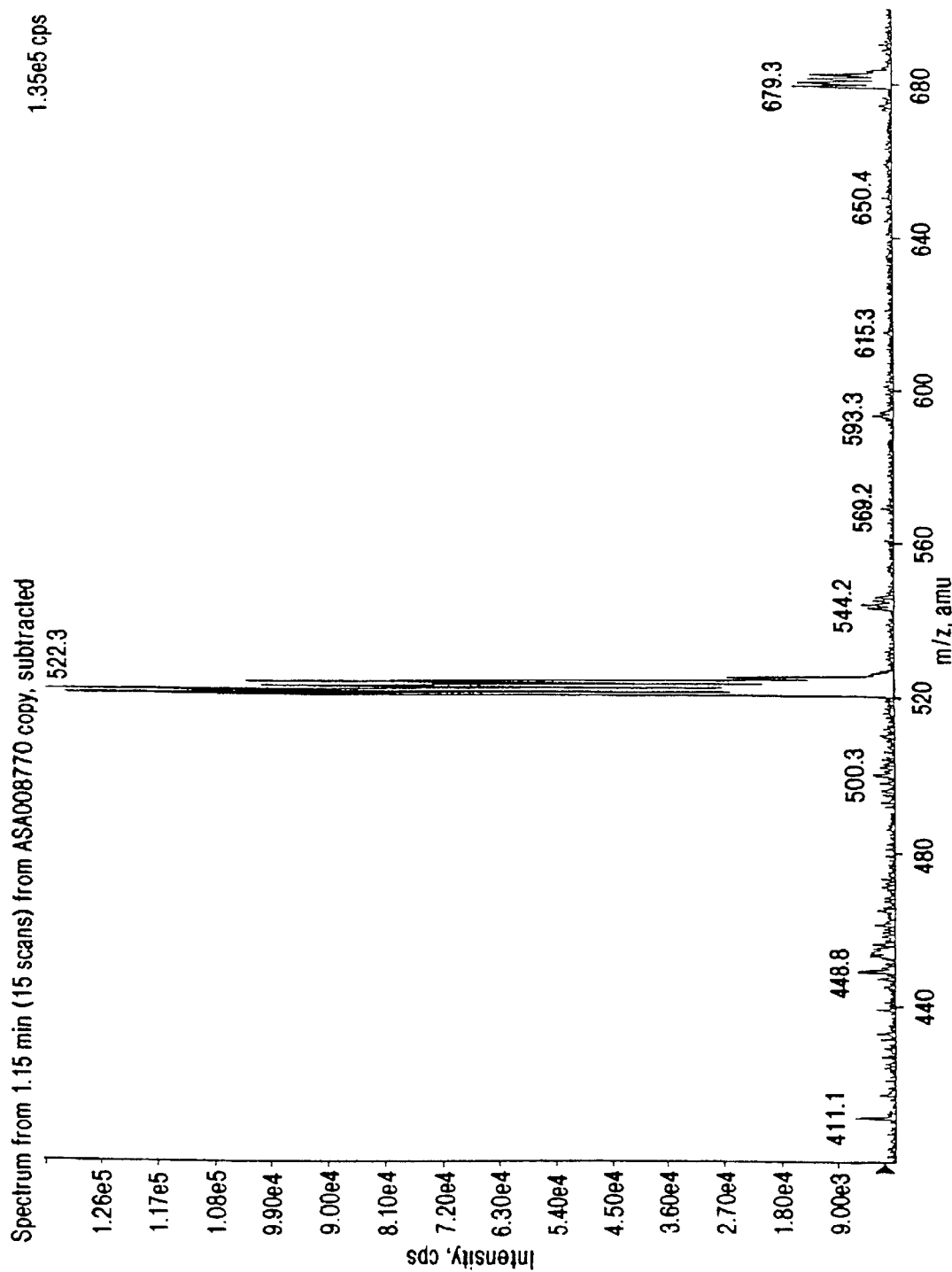
Figure 248:
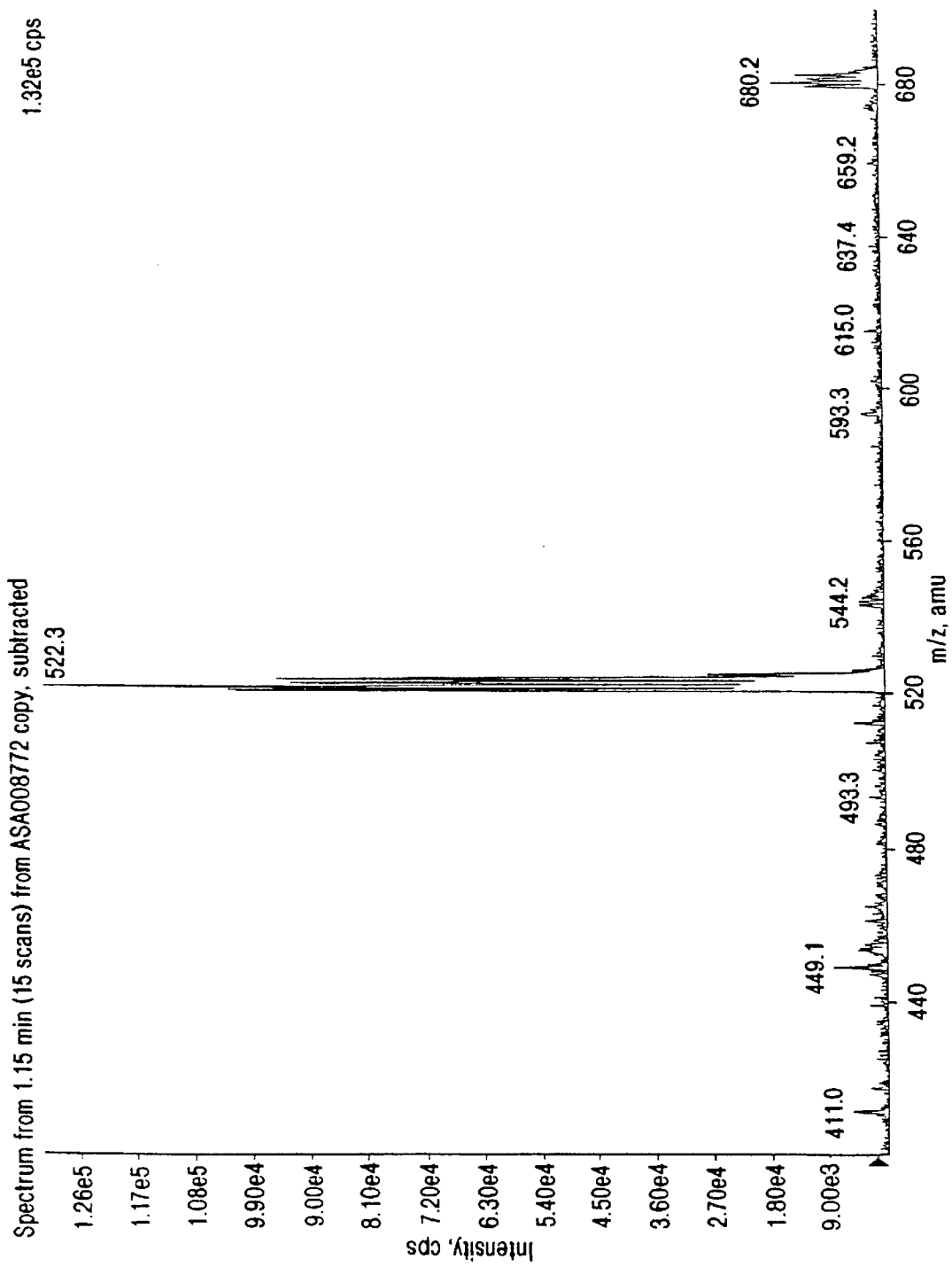
Figure 249:
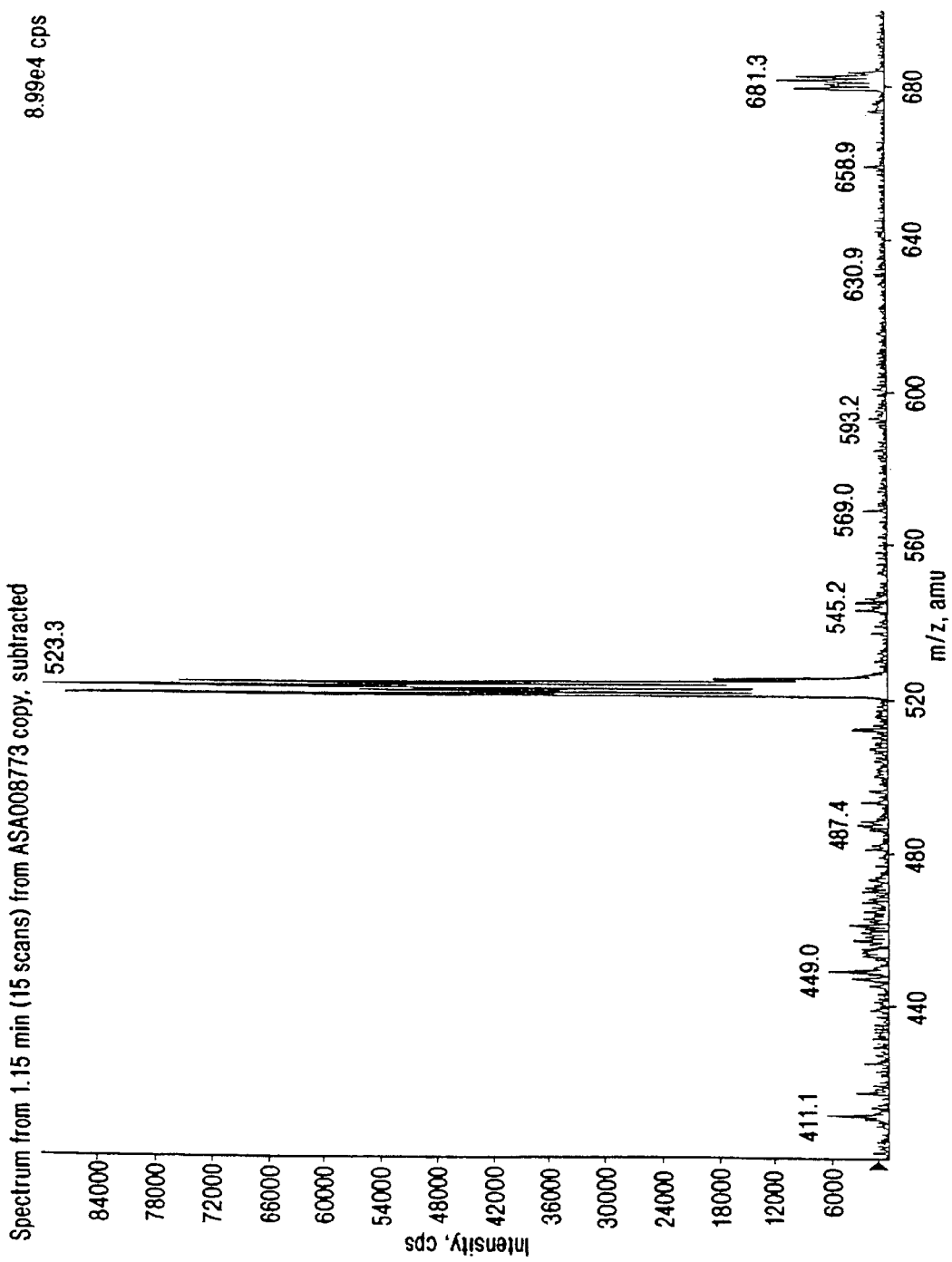
Figure 250:
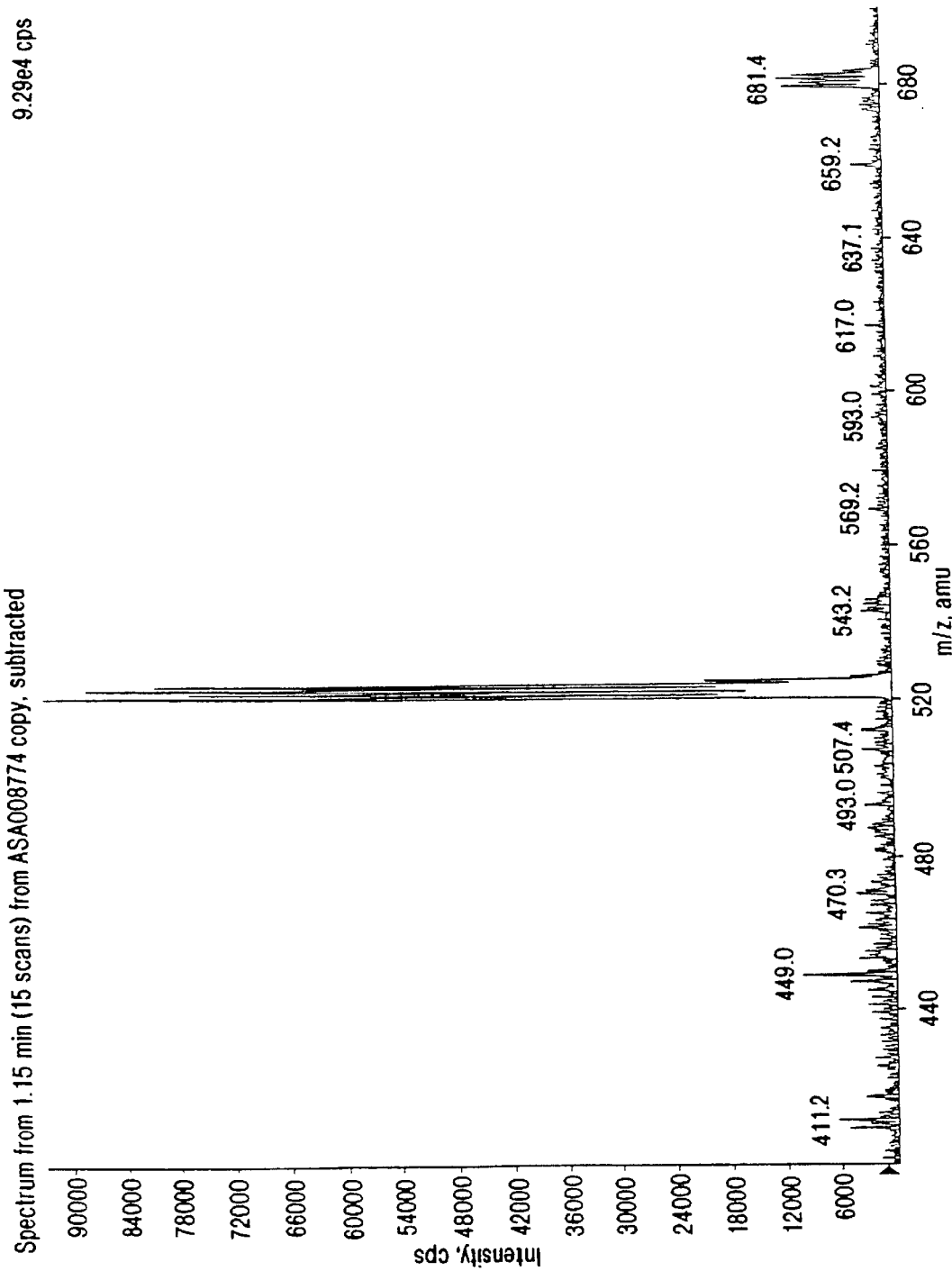
Figure 251:
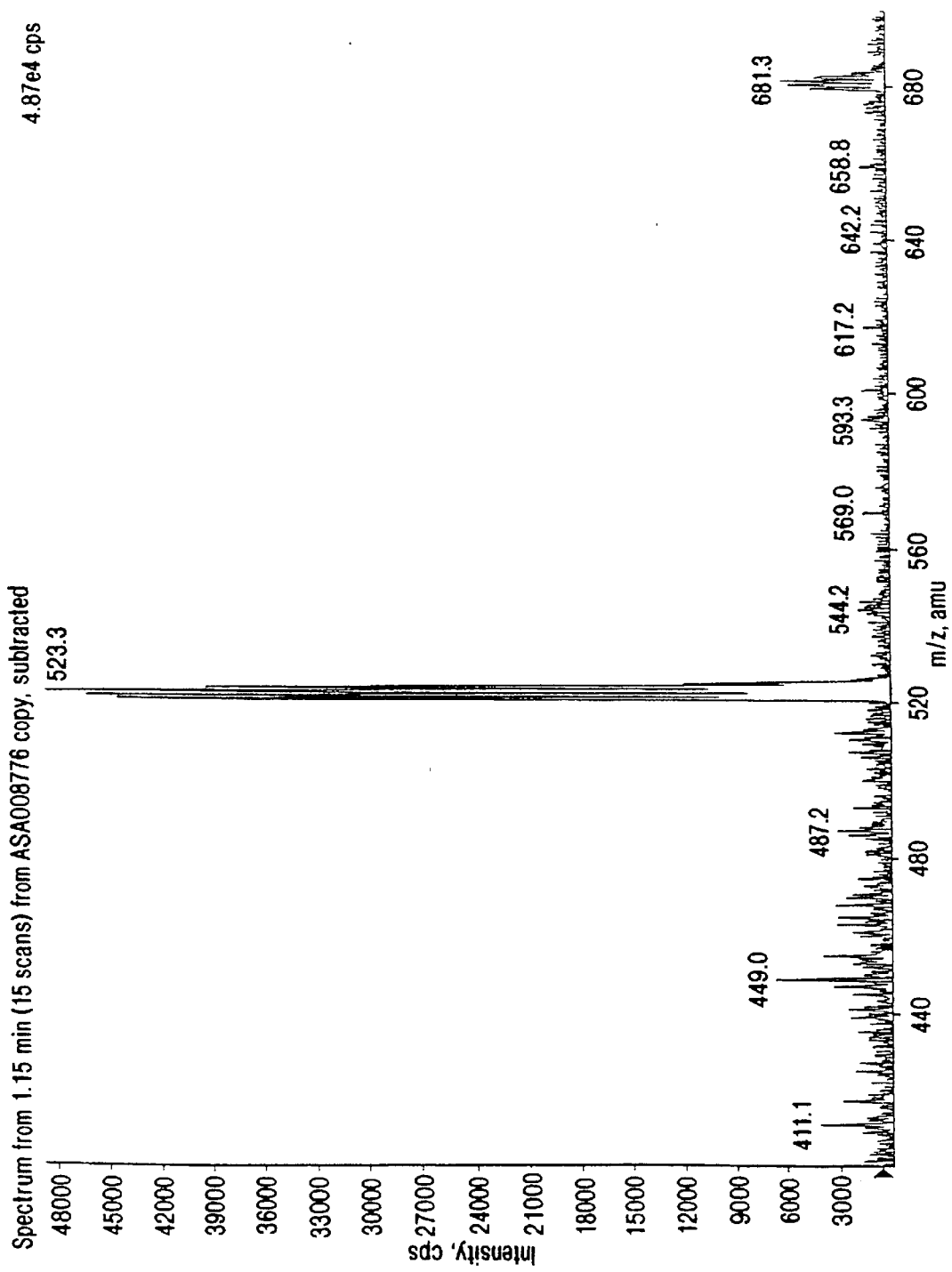
Figure 252:
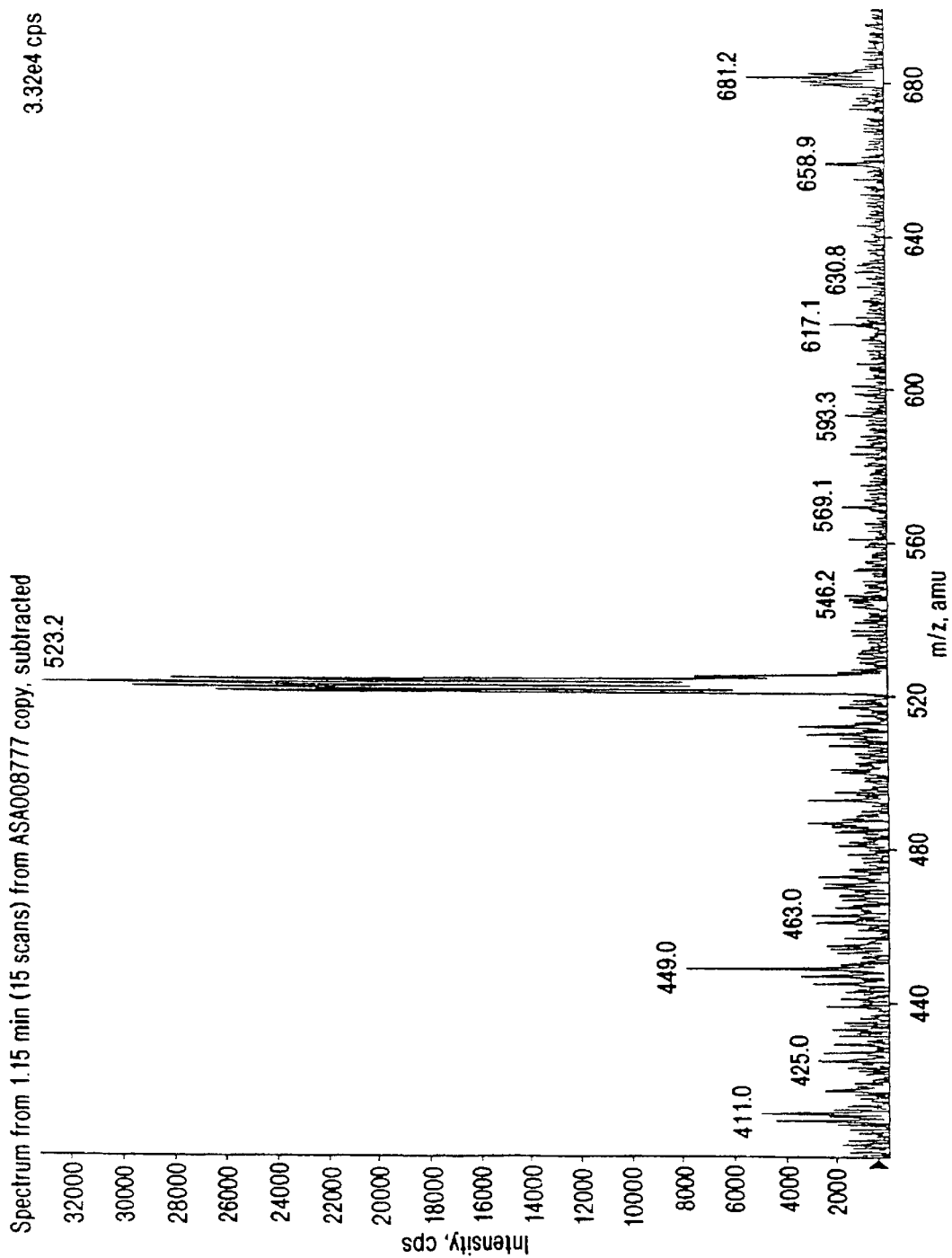
Figure 253:
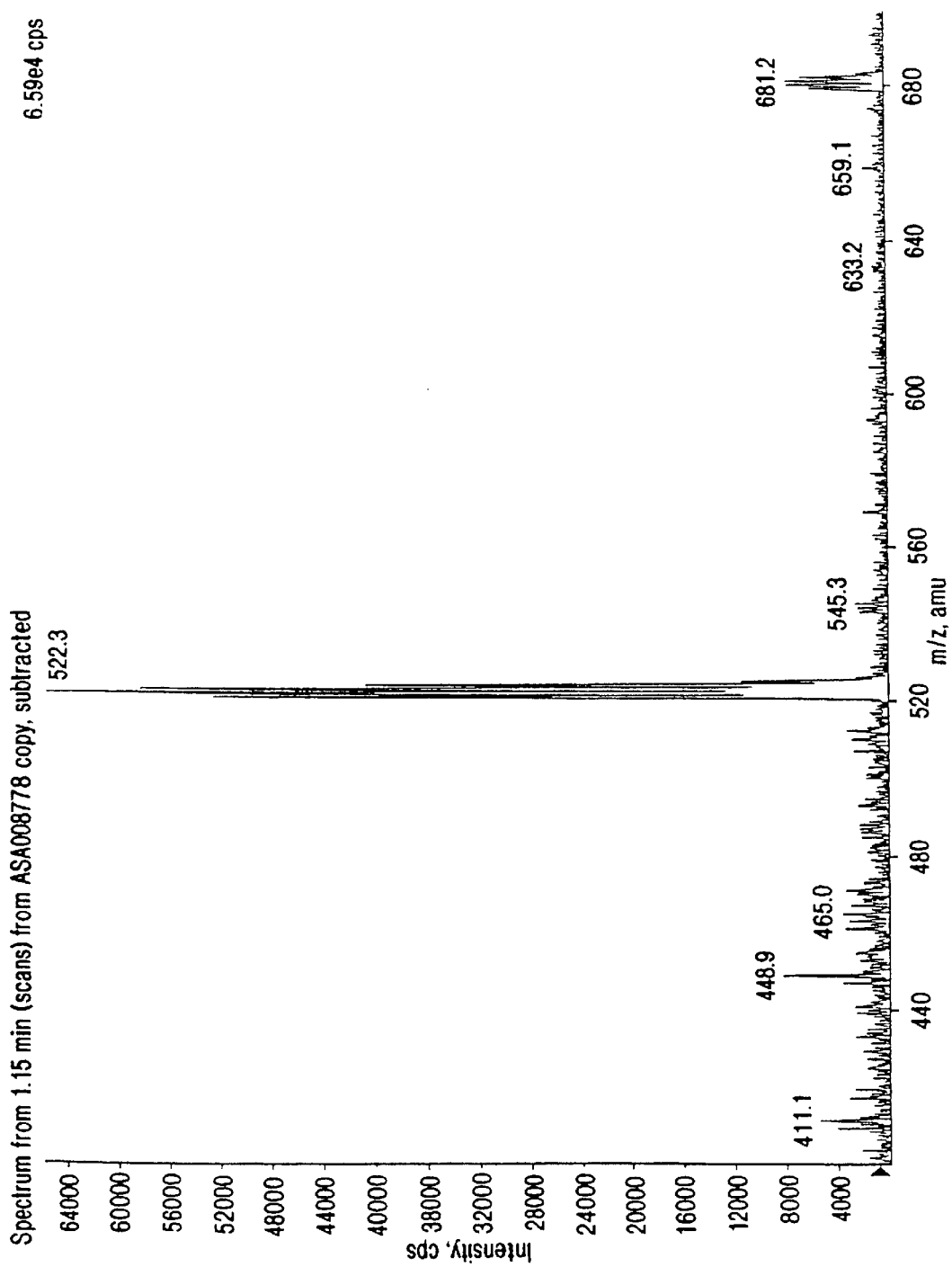
Figure 254:
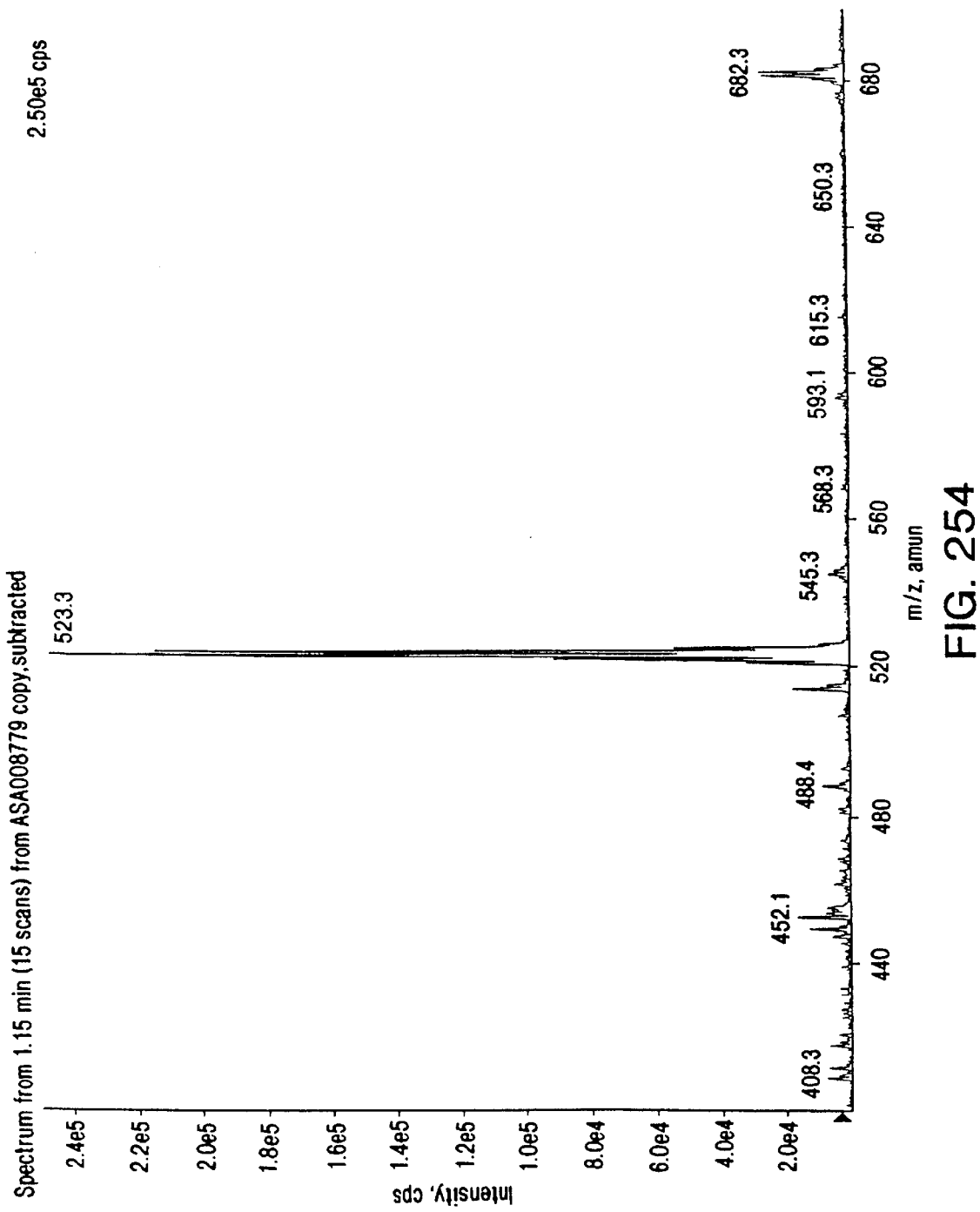
Figure 255:
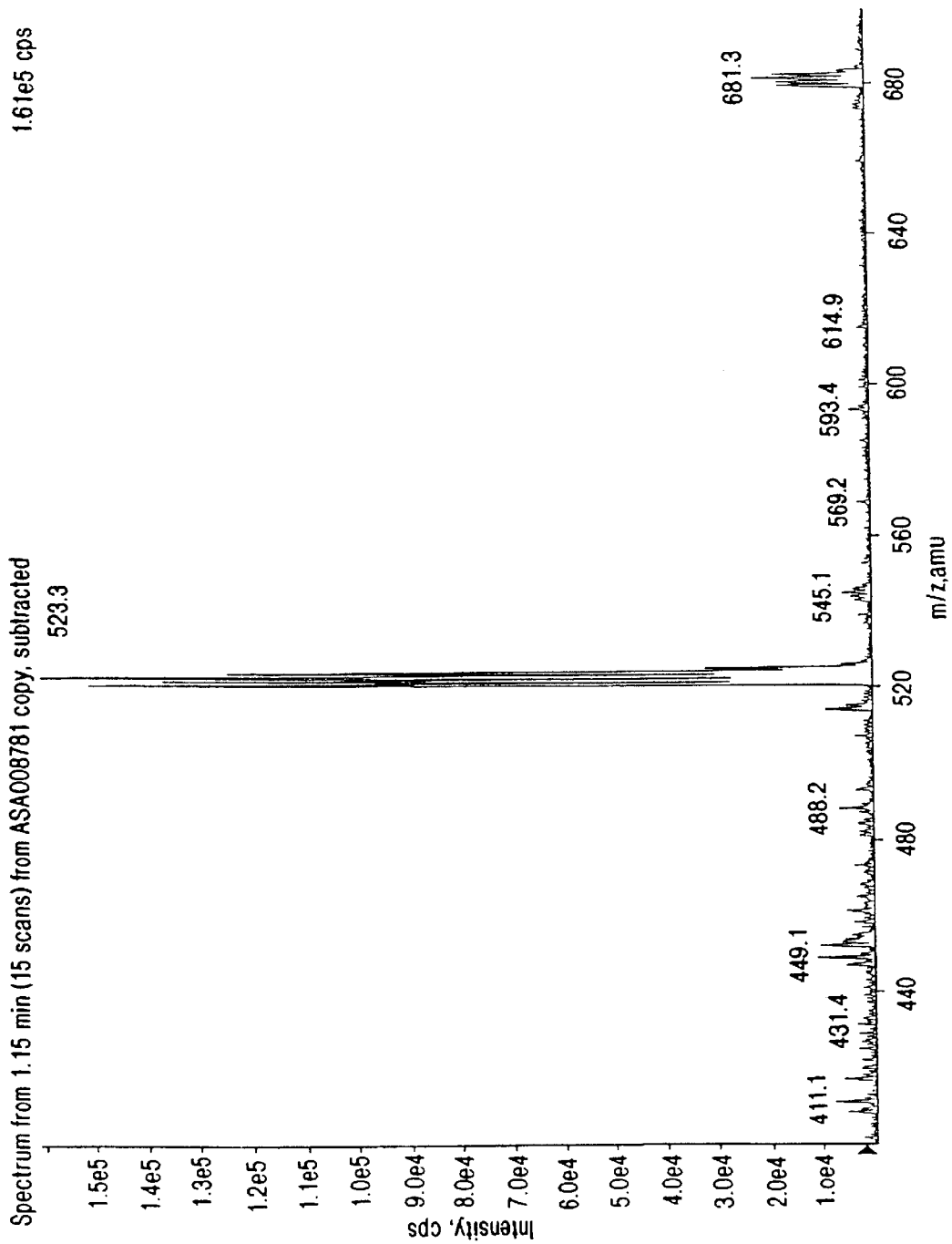
Figure 256:
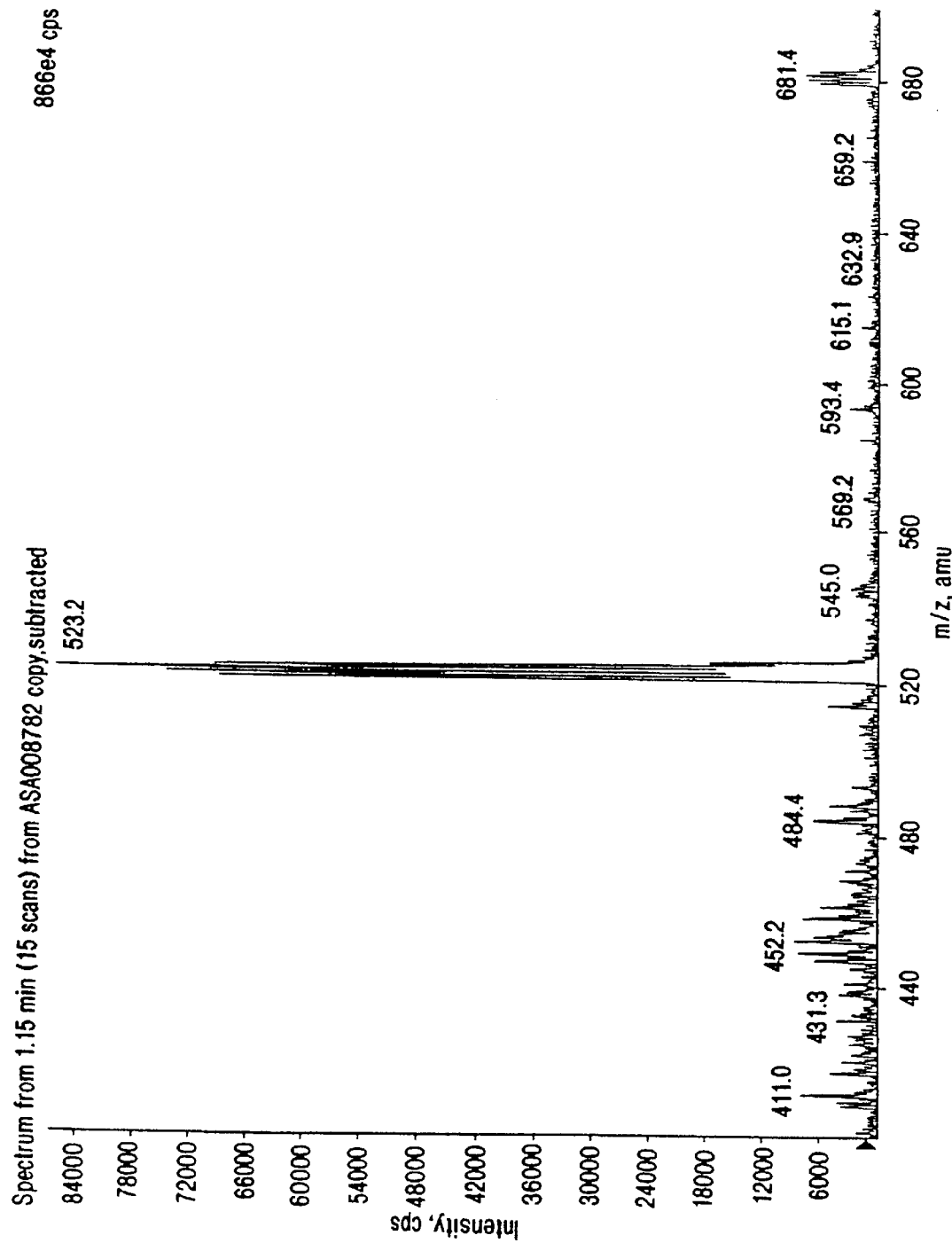
Figure 257:
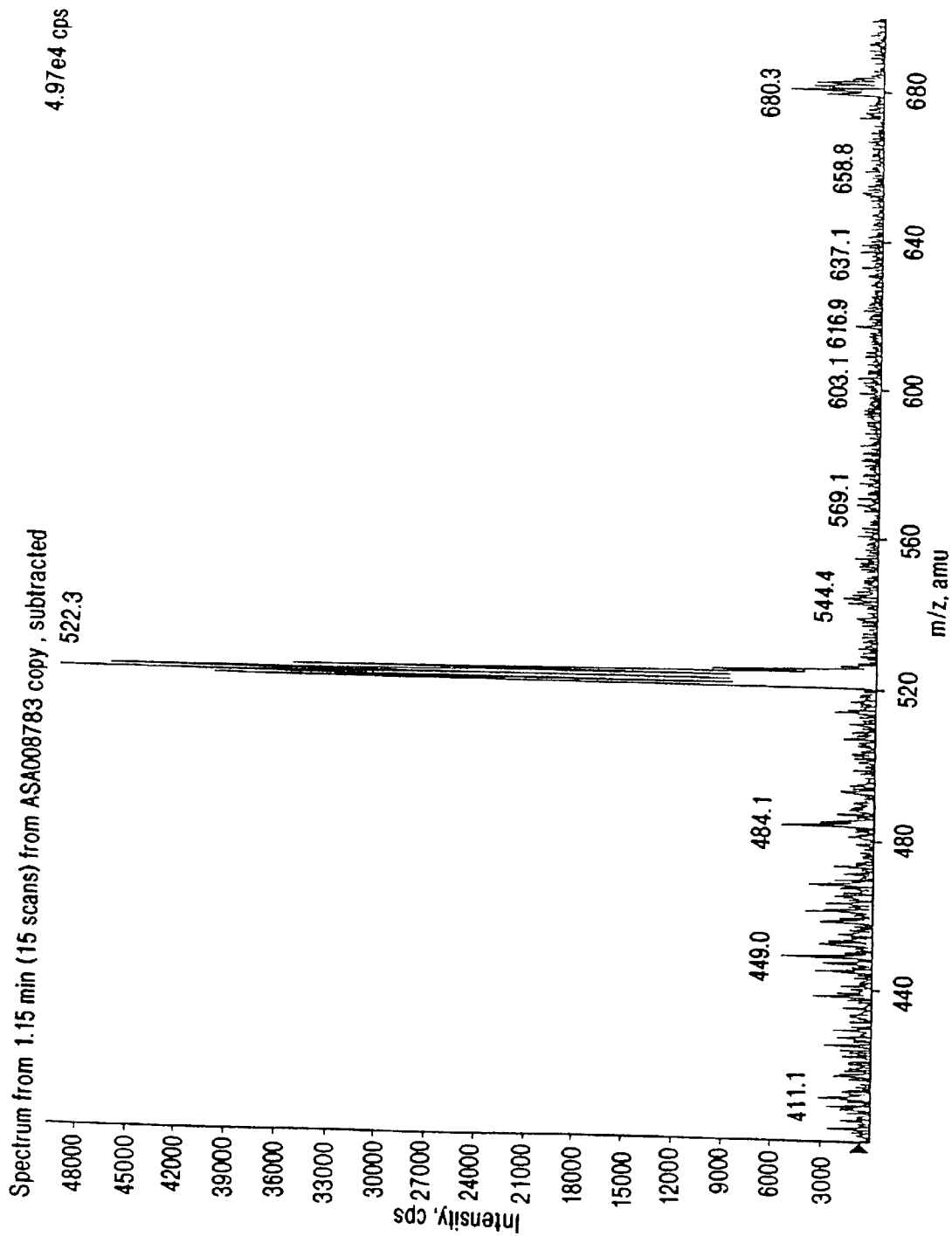
Figure 258:
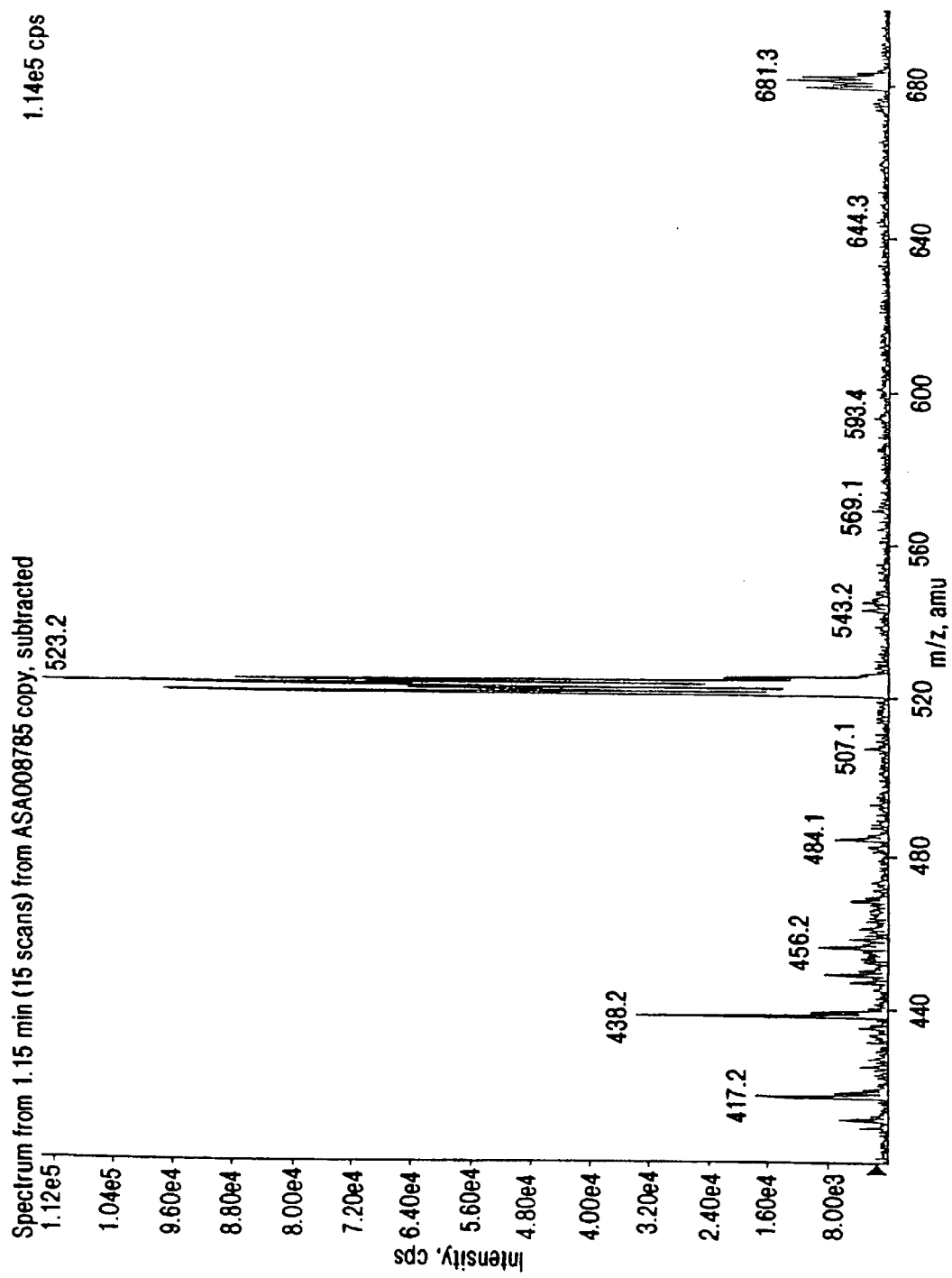
Figure 259:
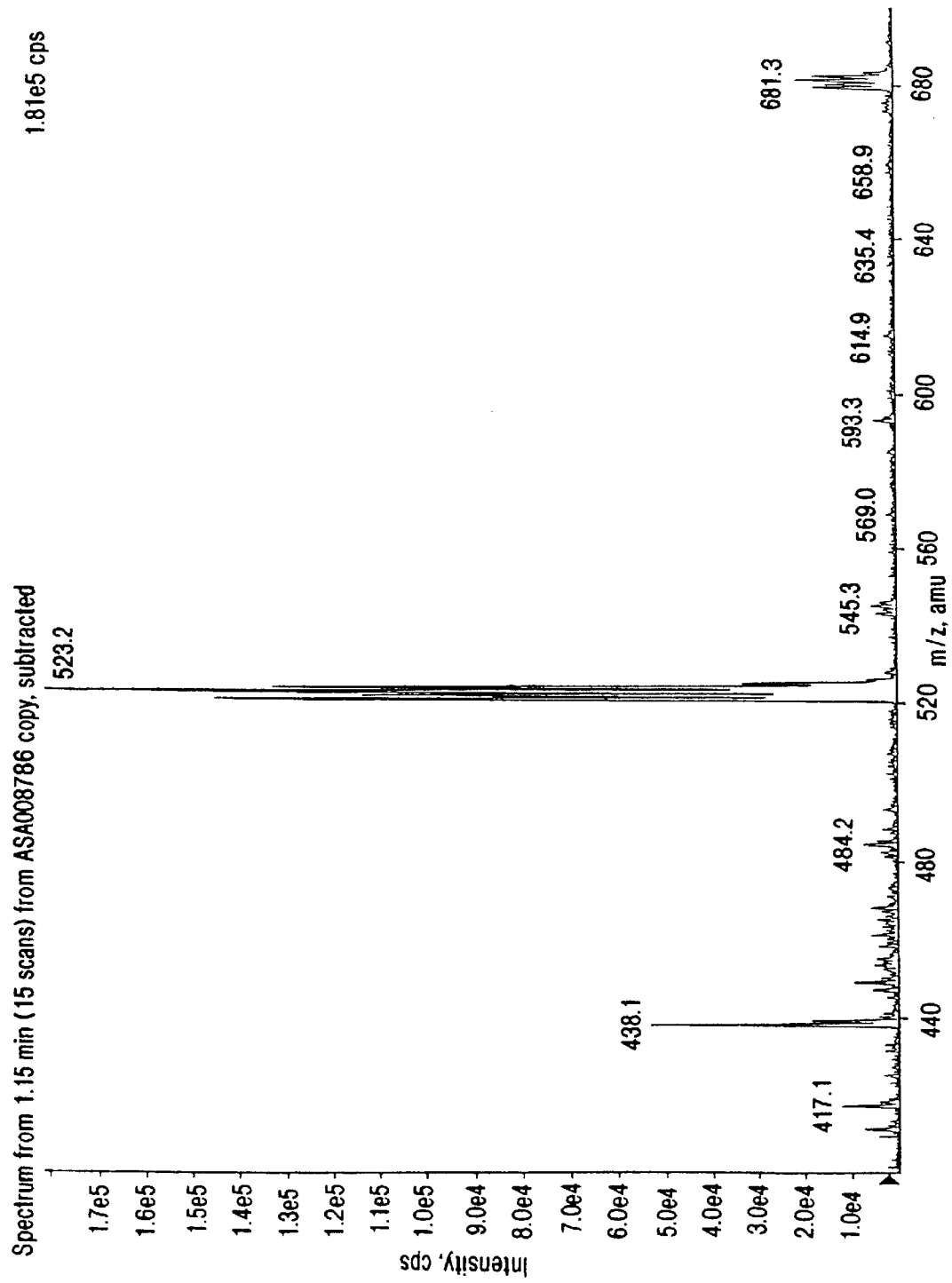
Figure 260:
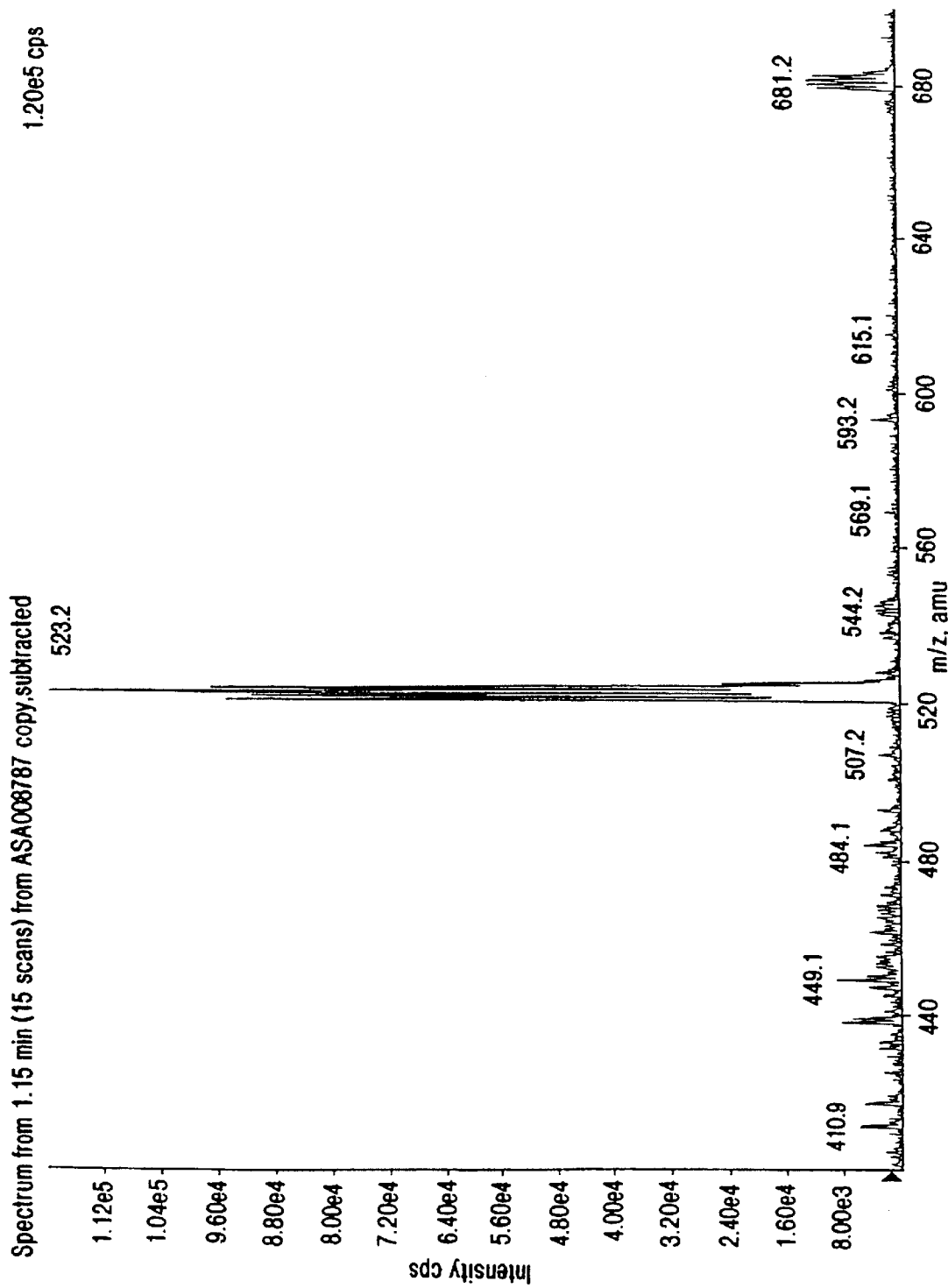
Figure 261:
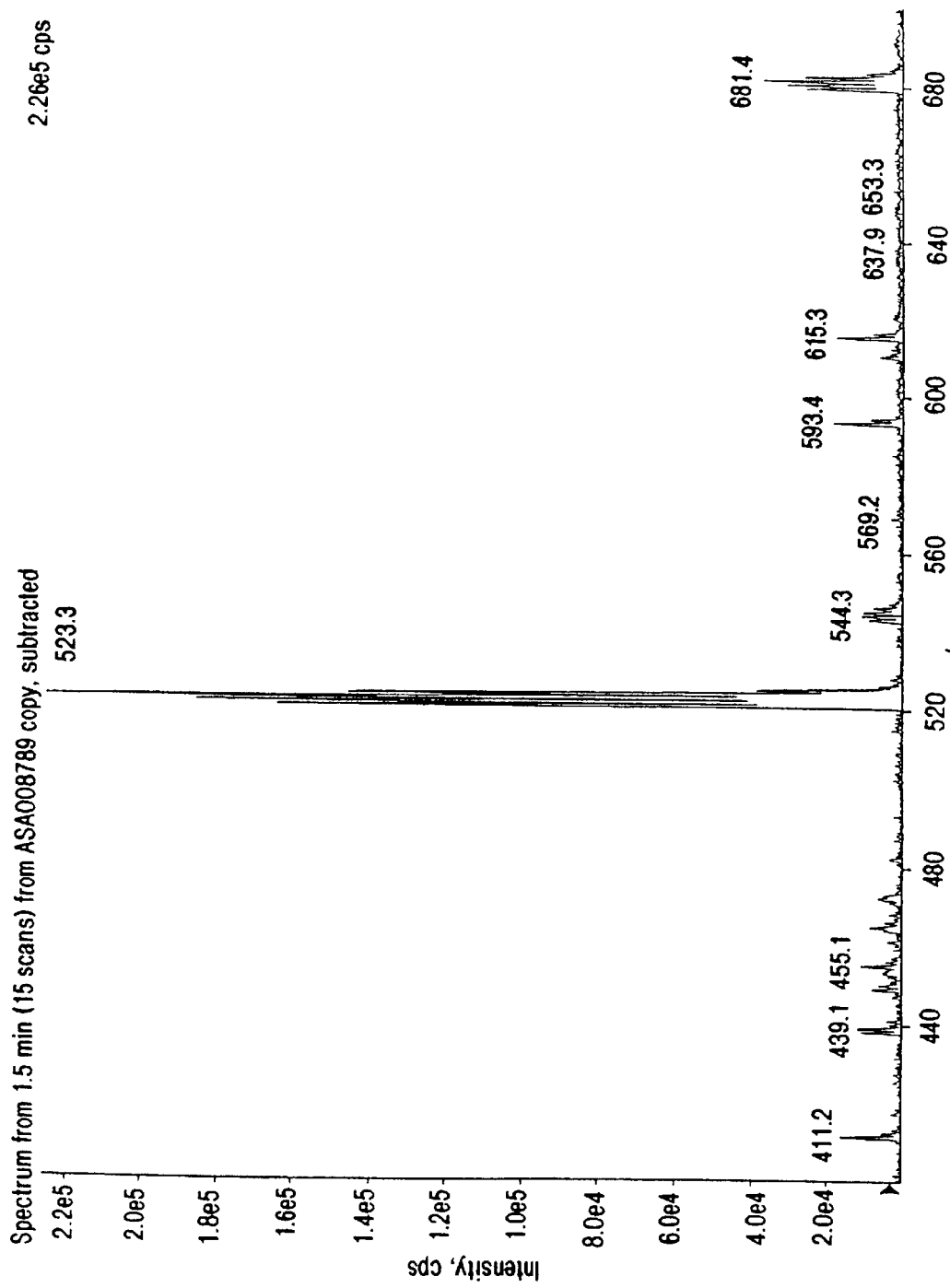
Figure 262:
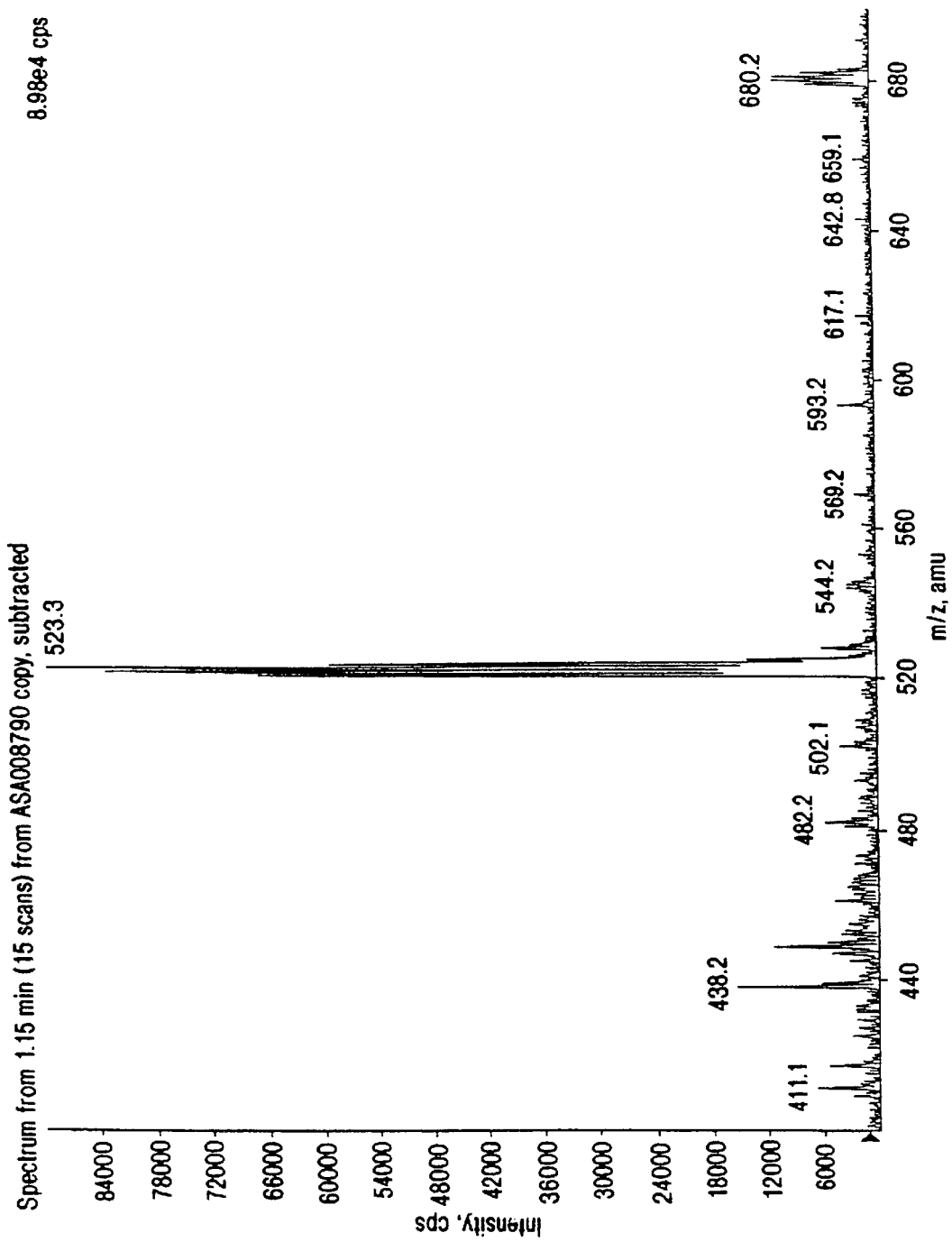
Figure 263:
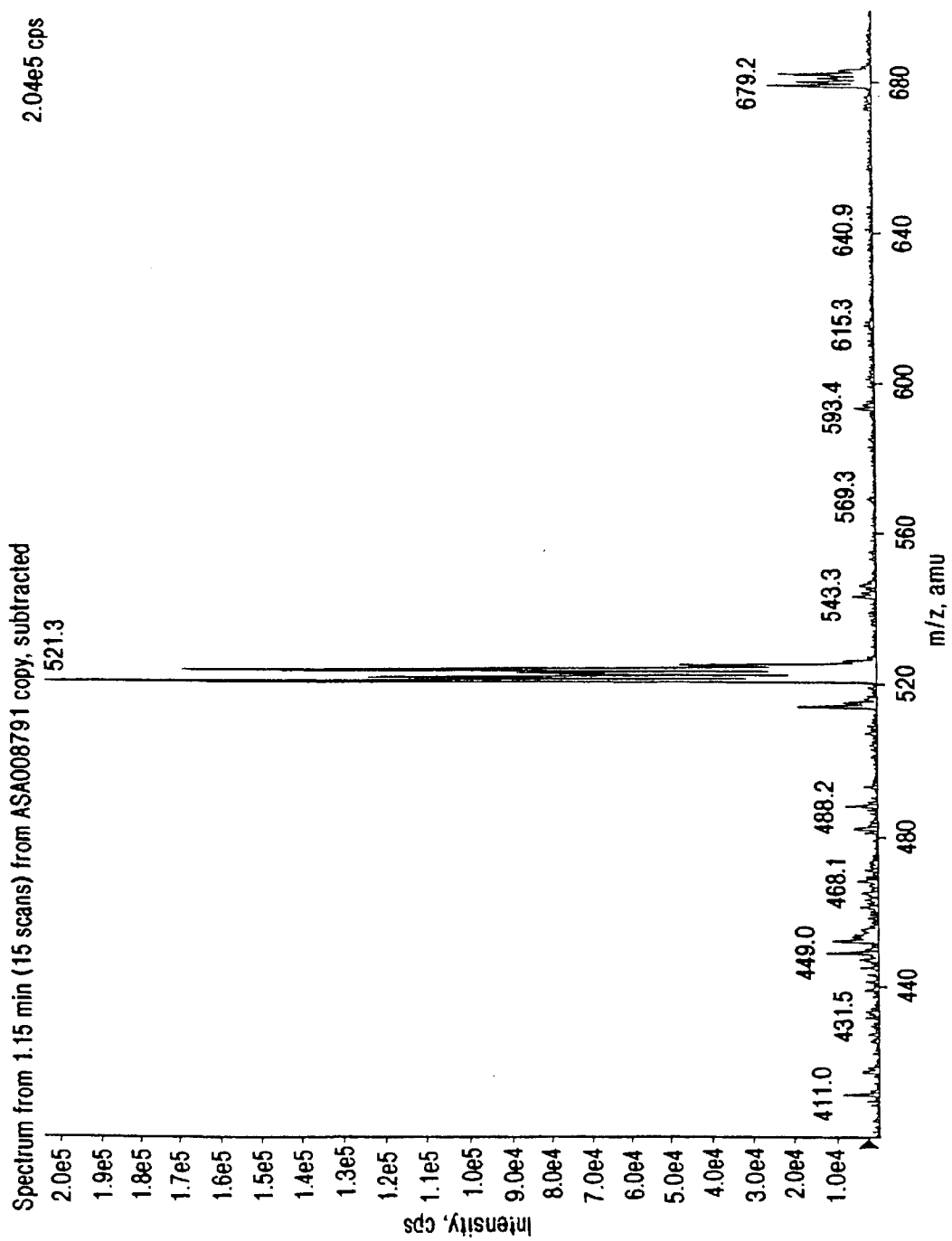
Figure 264:
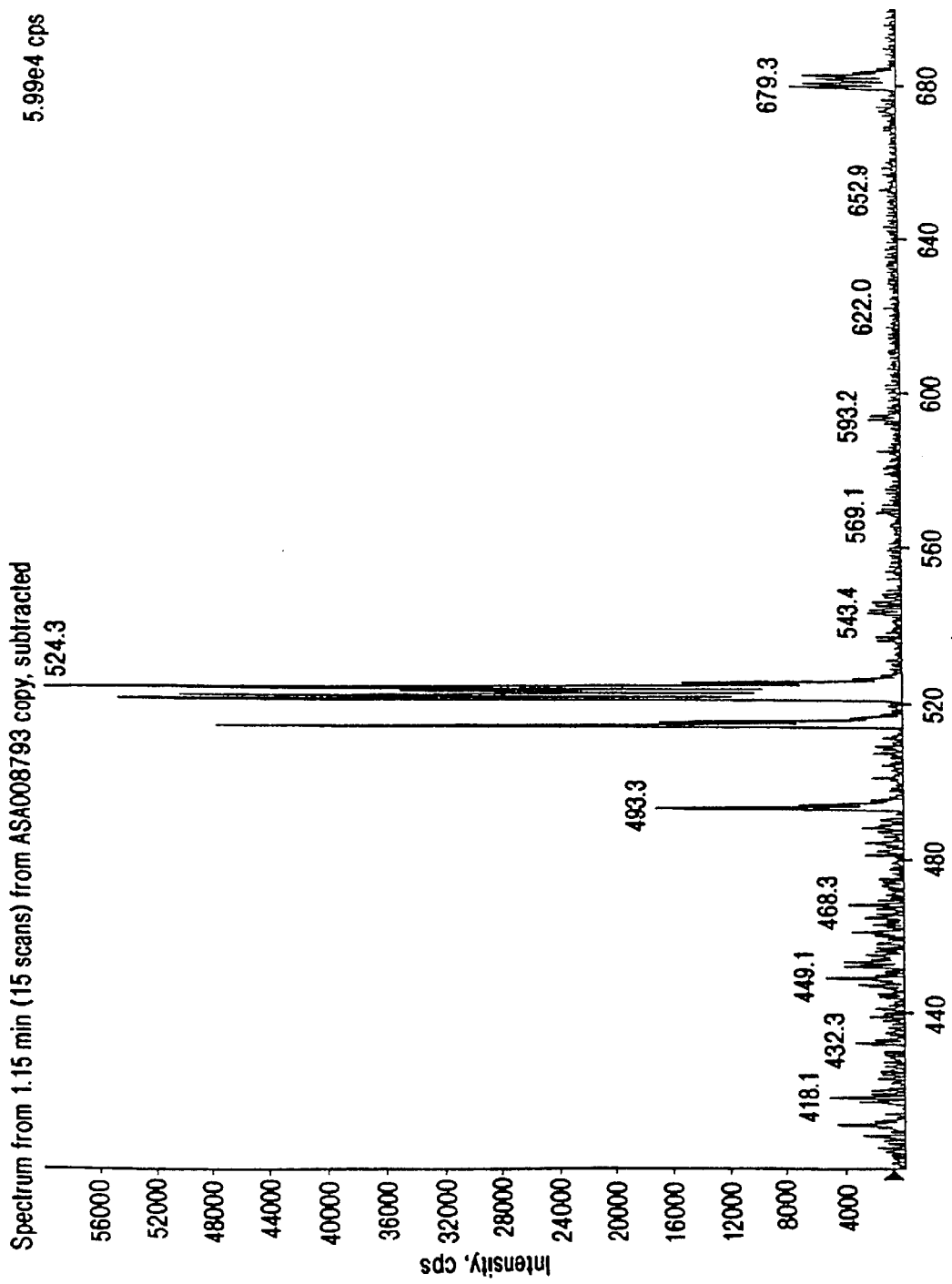
Figure 265:
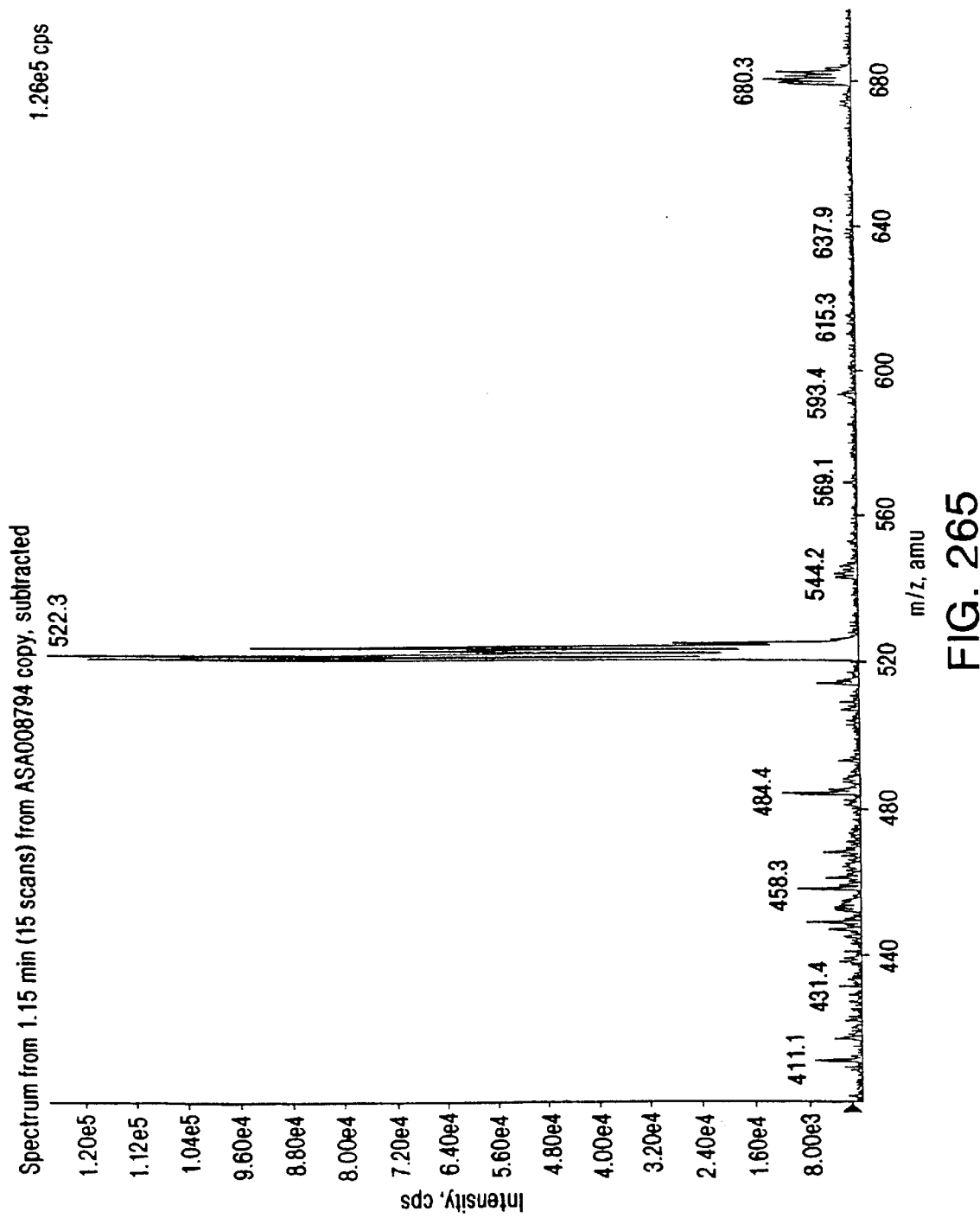
Figure 266:
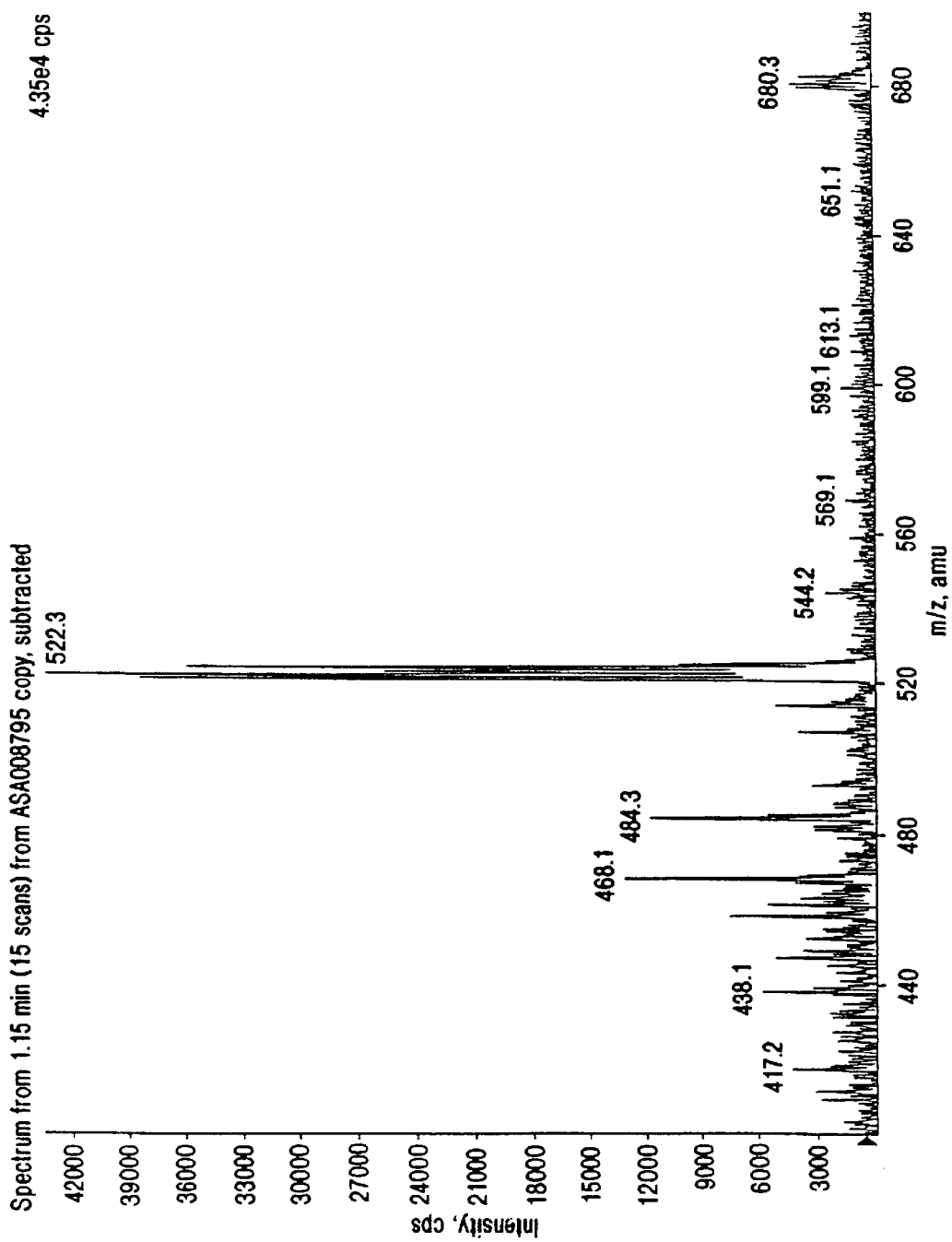
Figure 267:
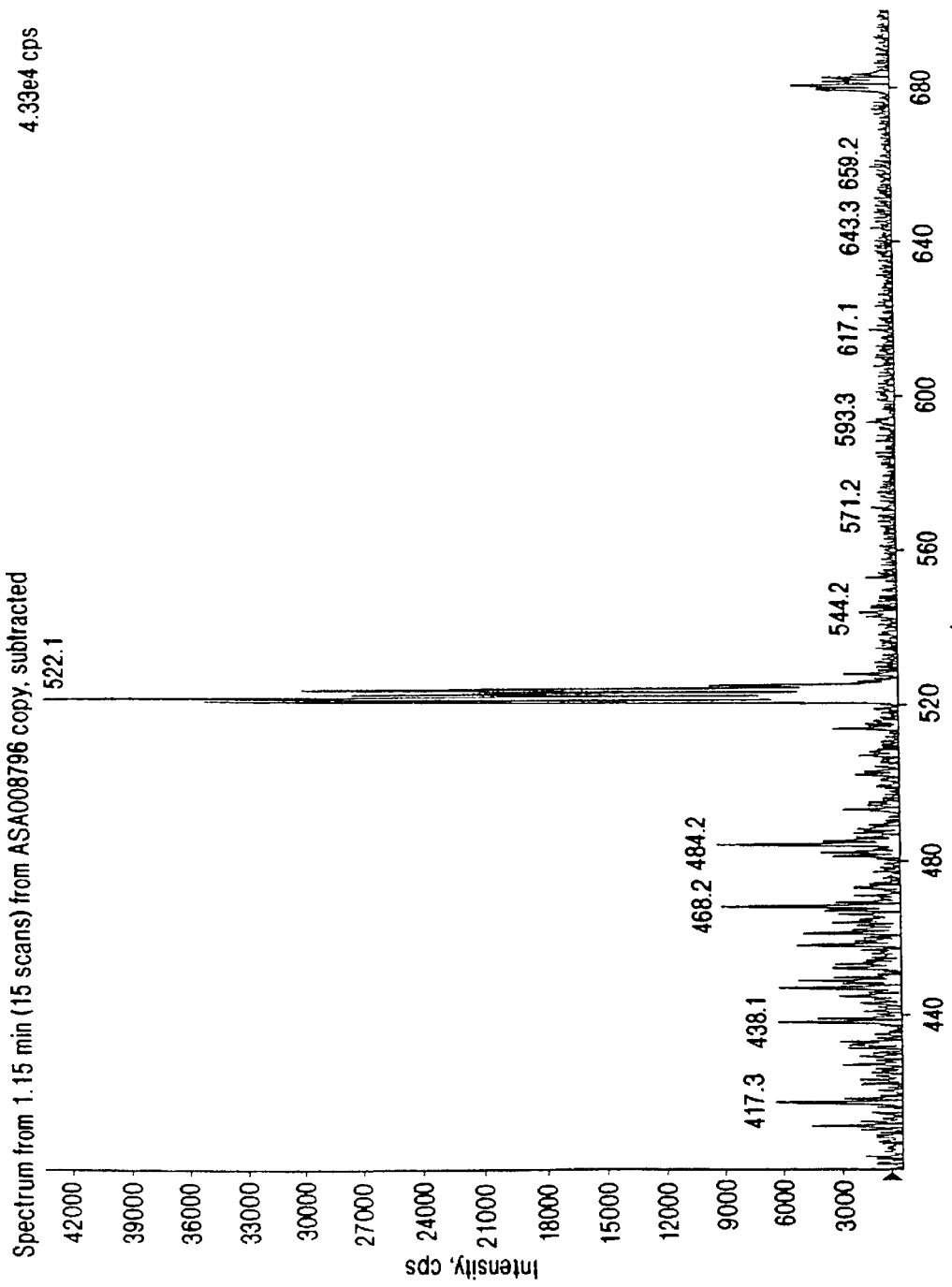
Figure 268:
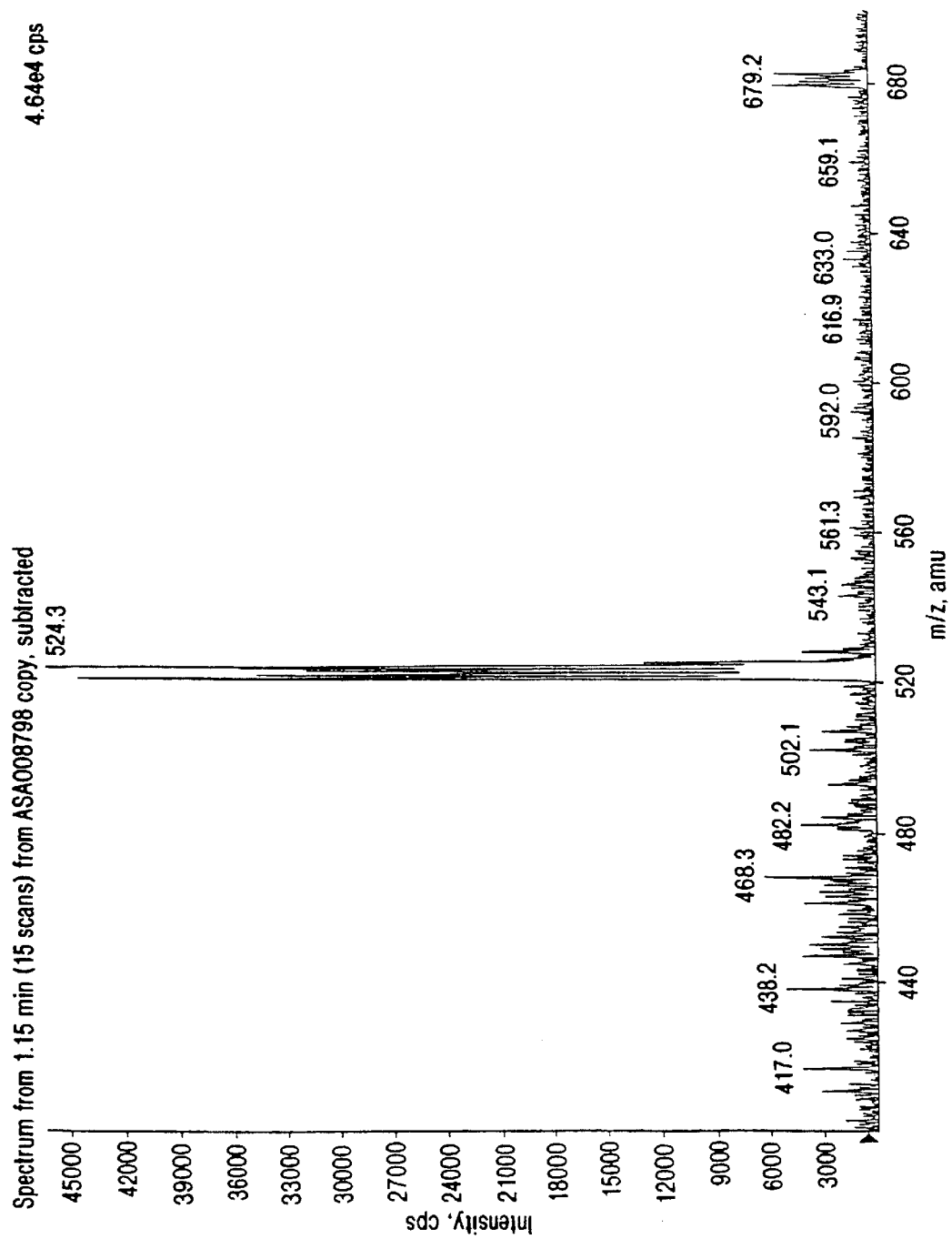
Figure 269:
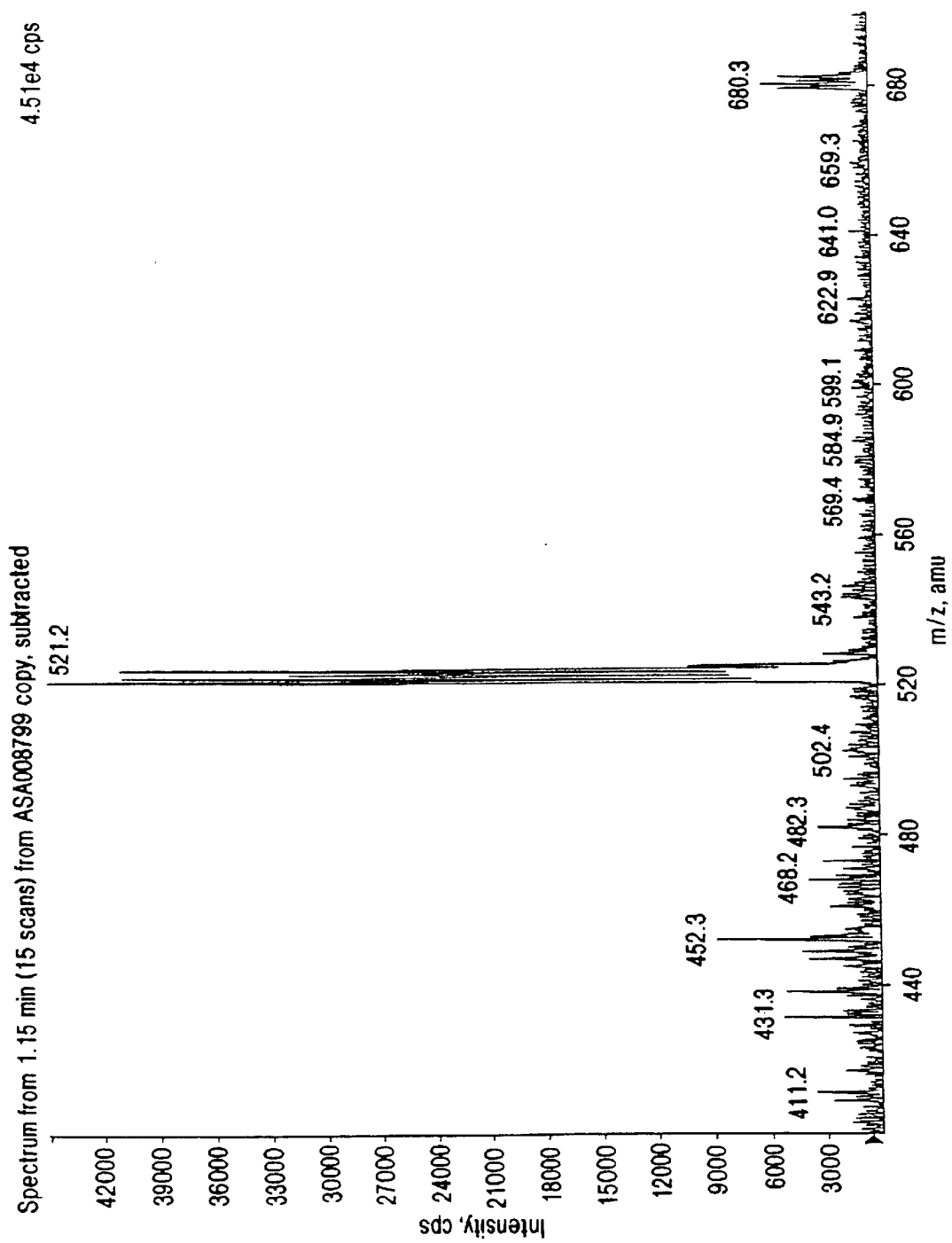
Figure 270:
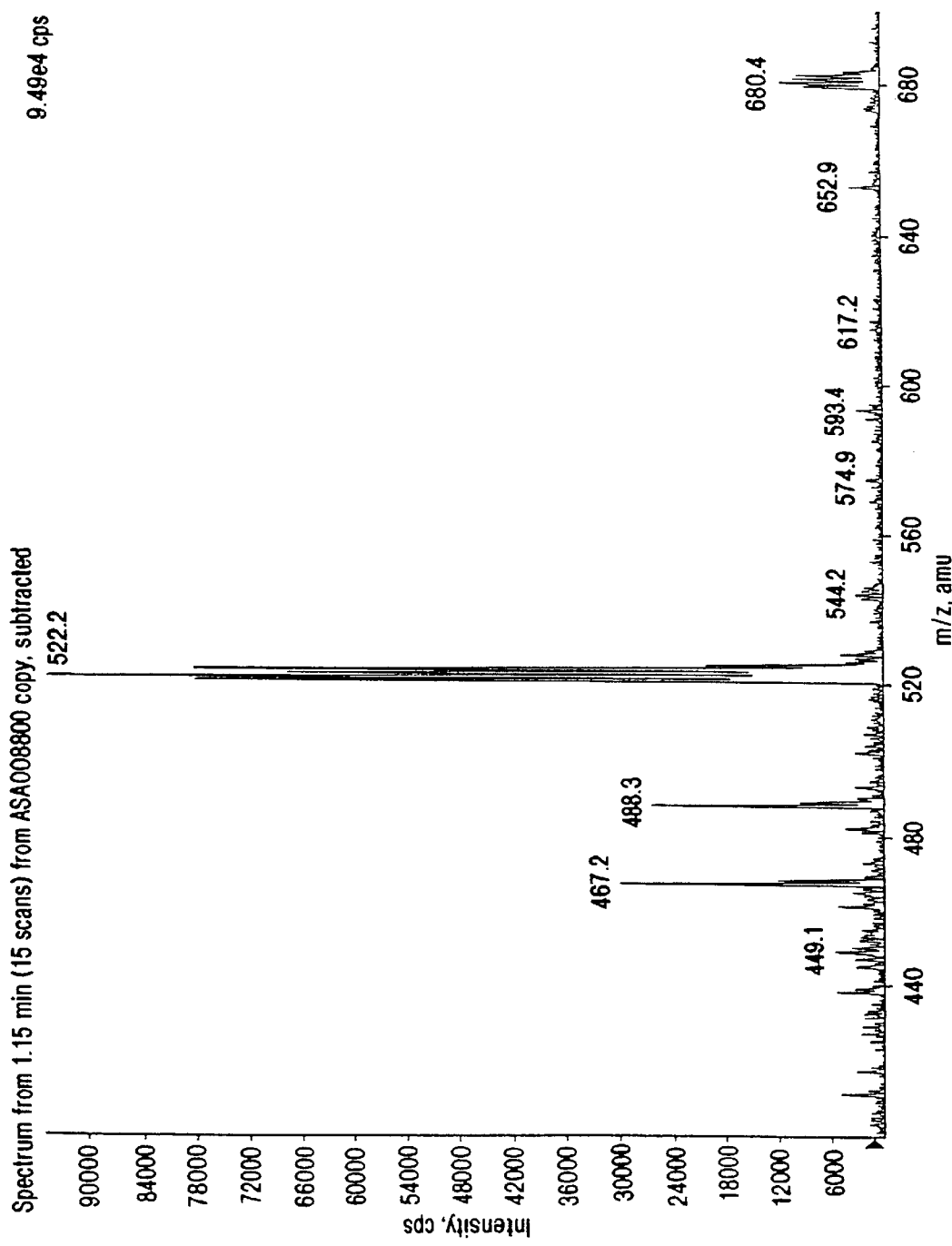
Figure 271:
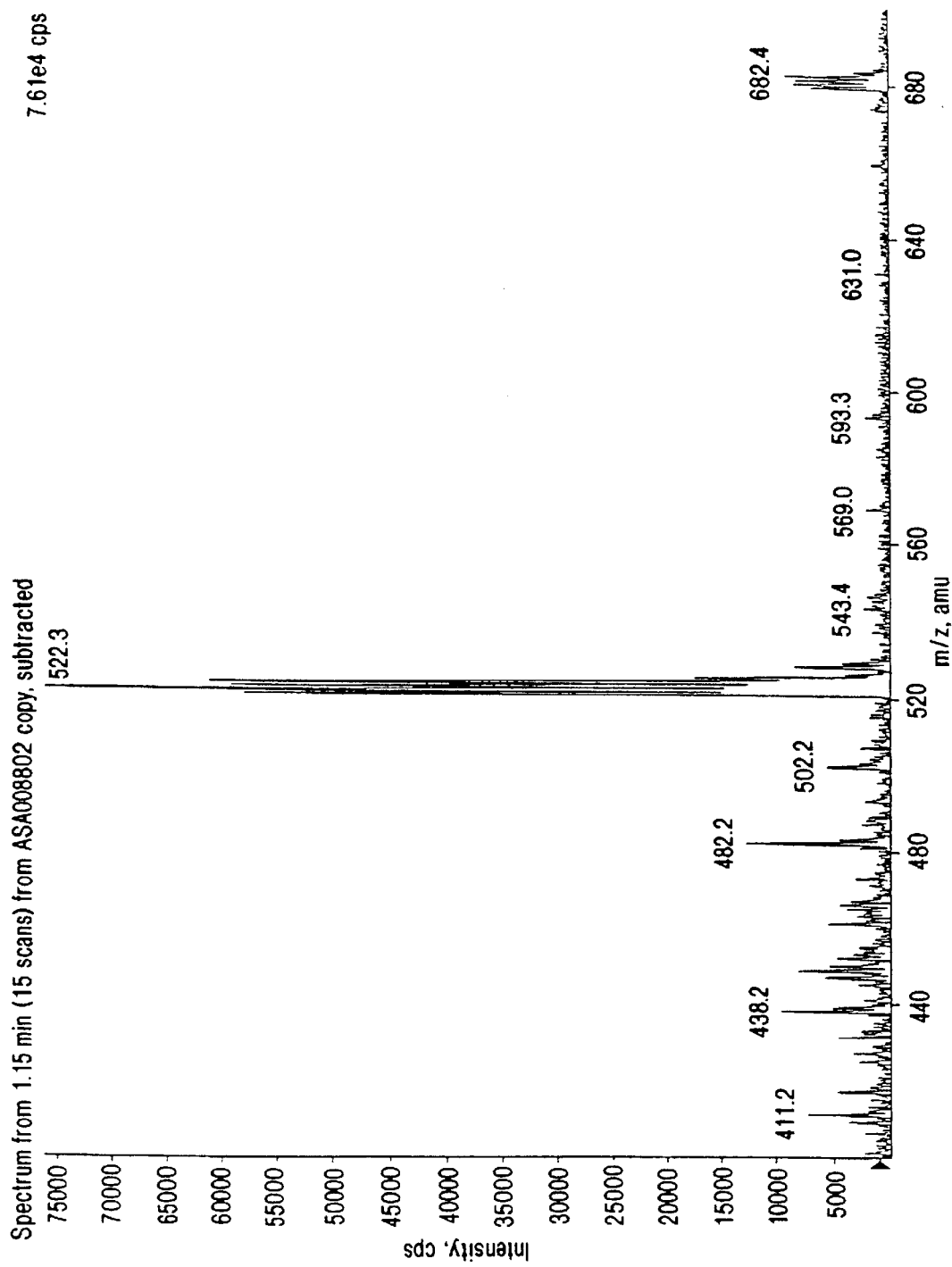
Figure 272:
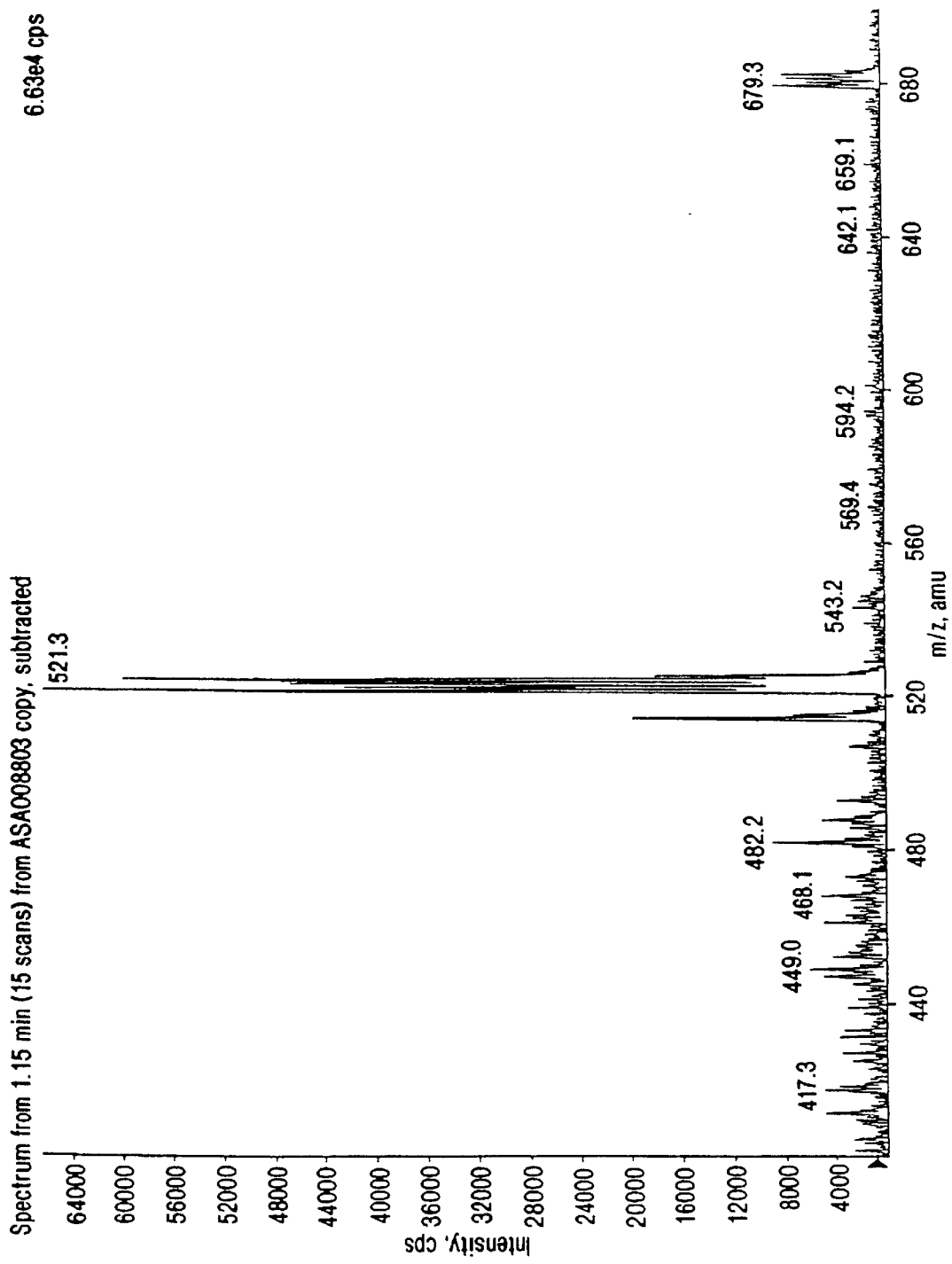
Figure 273:
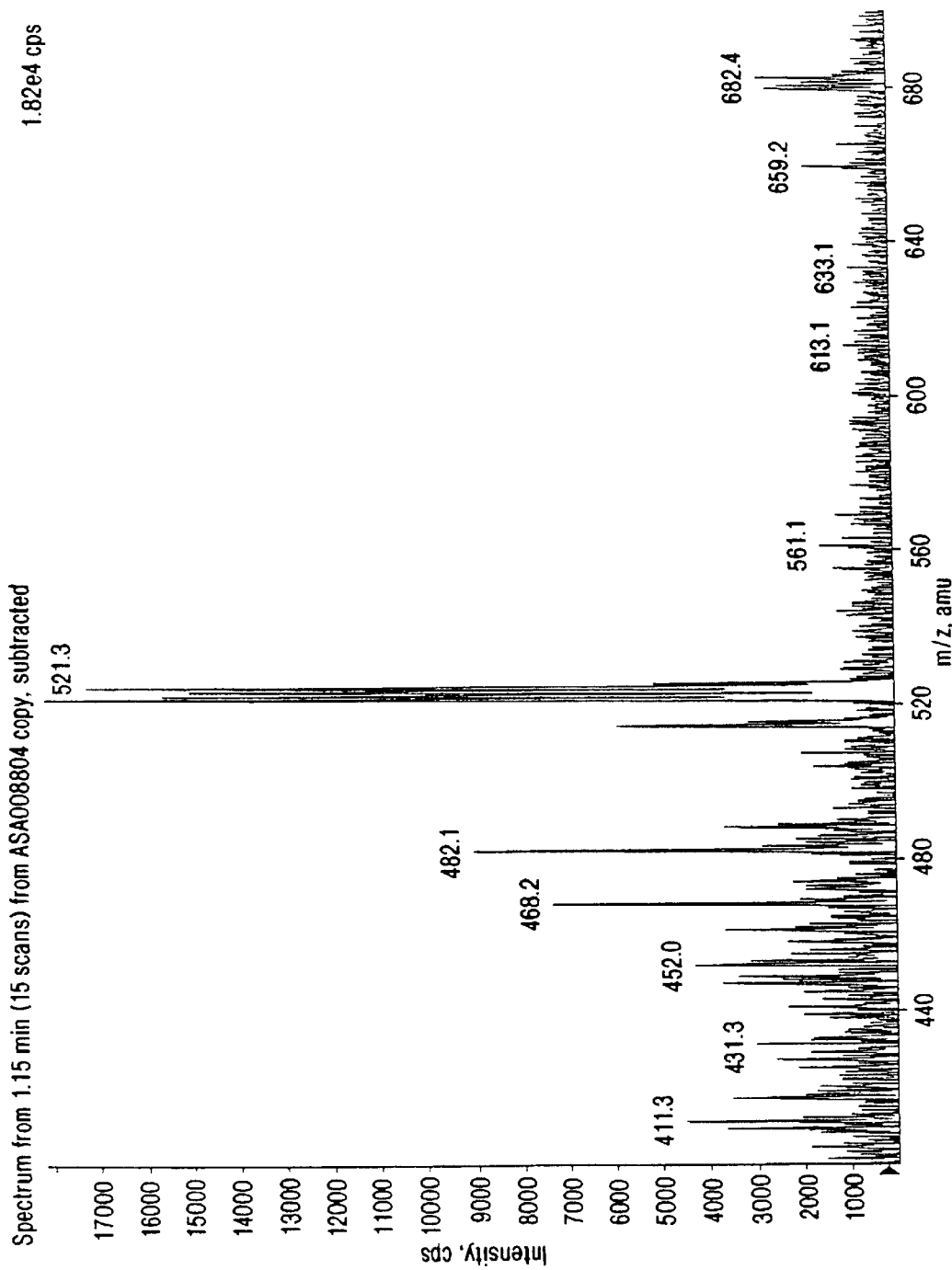
Figure 274:
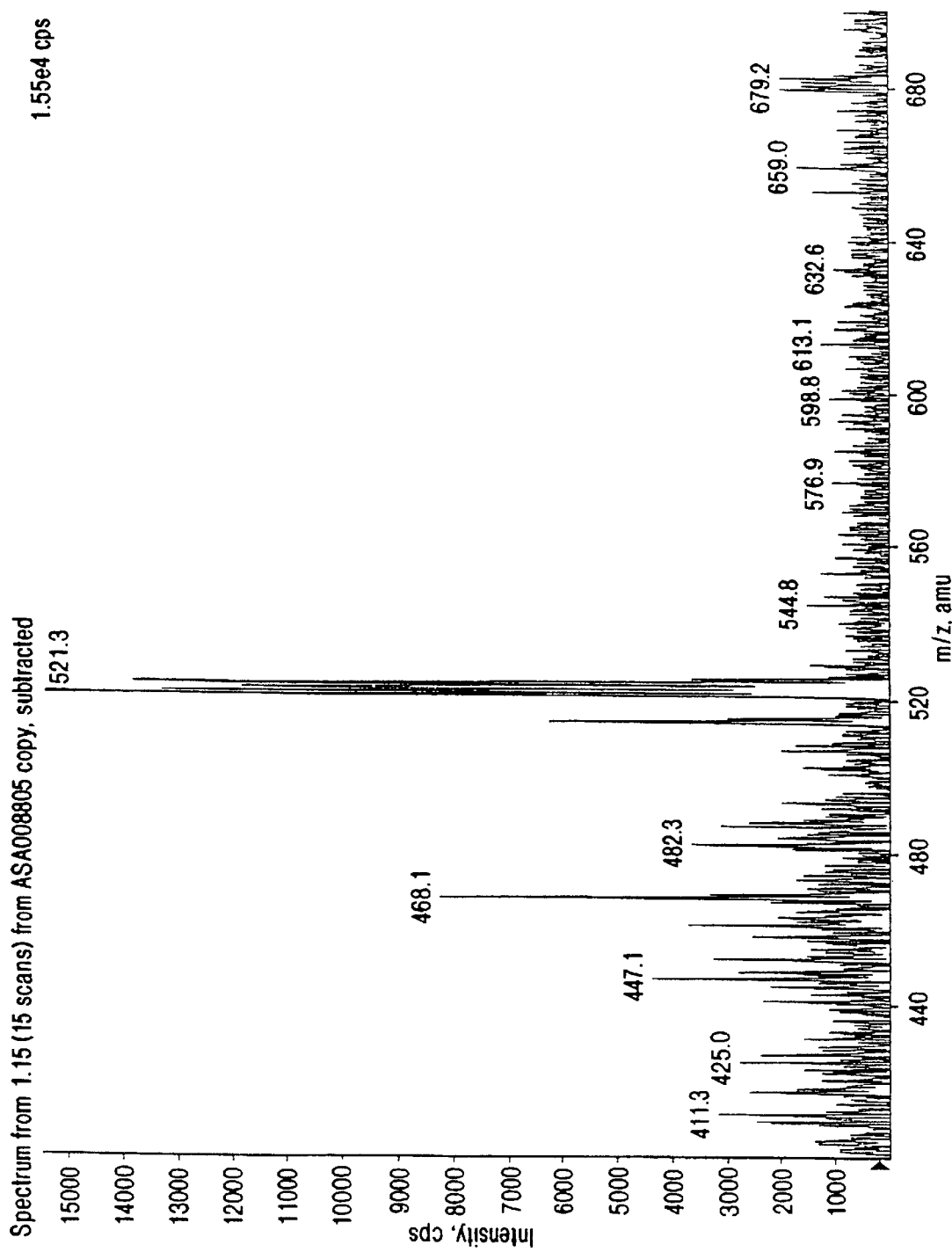
Figure 275:
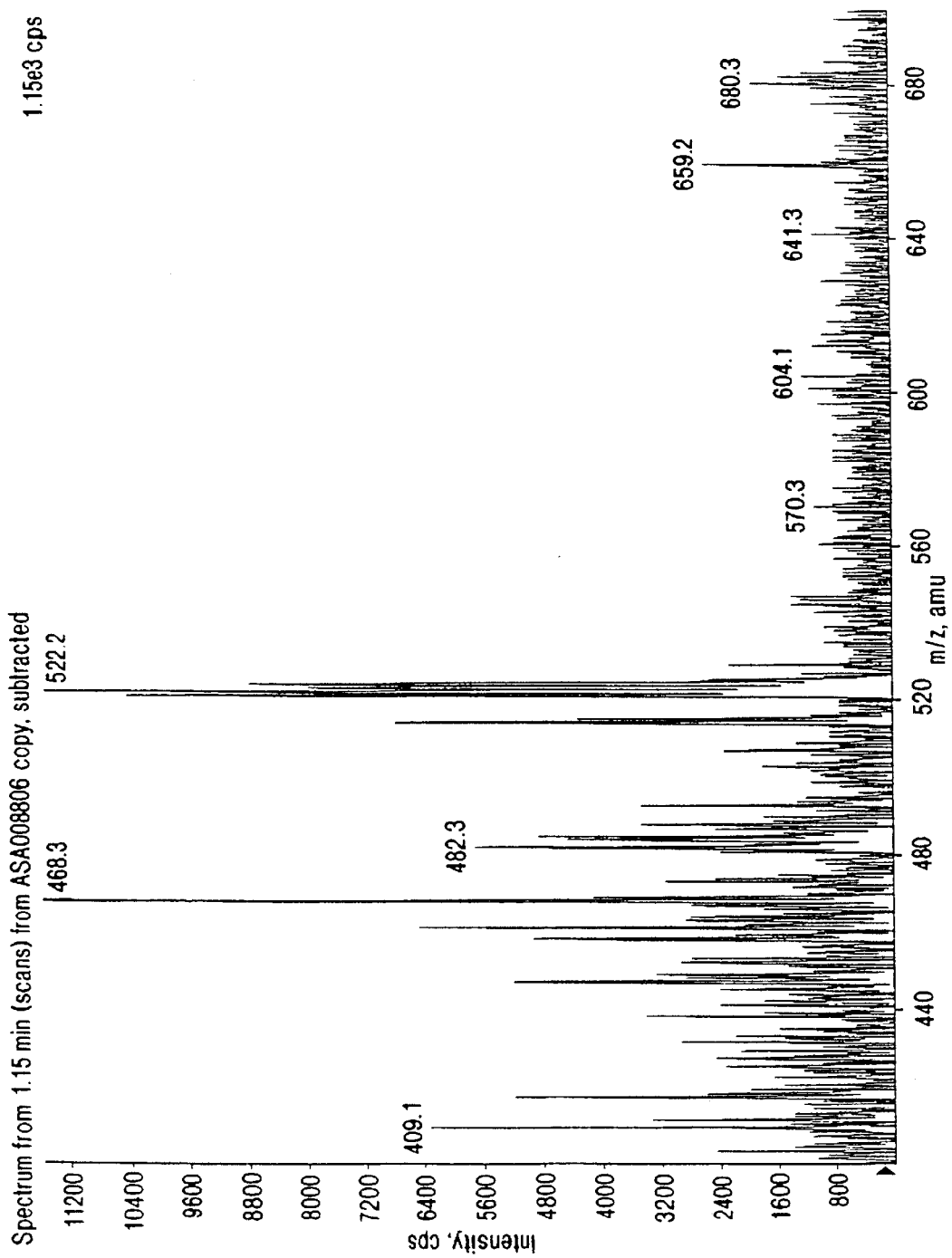
Figure 276:
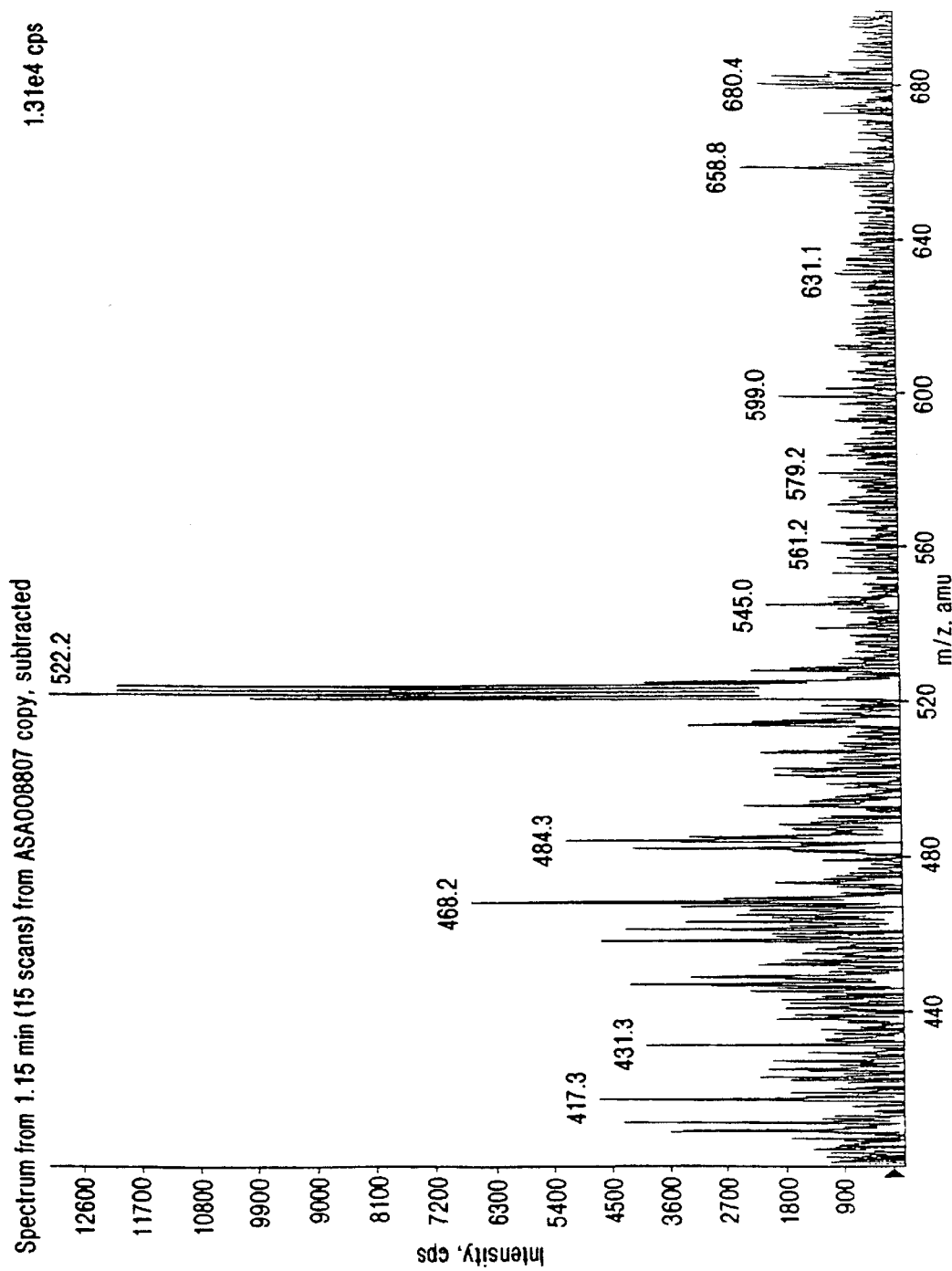
Figure 277:
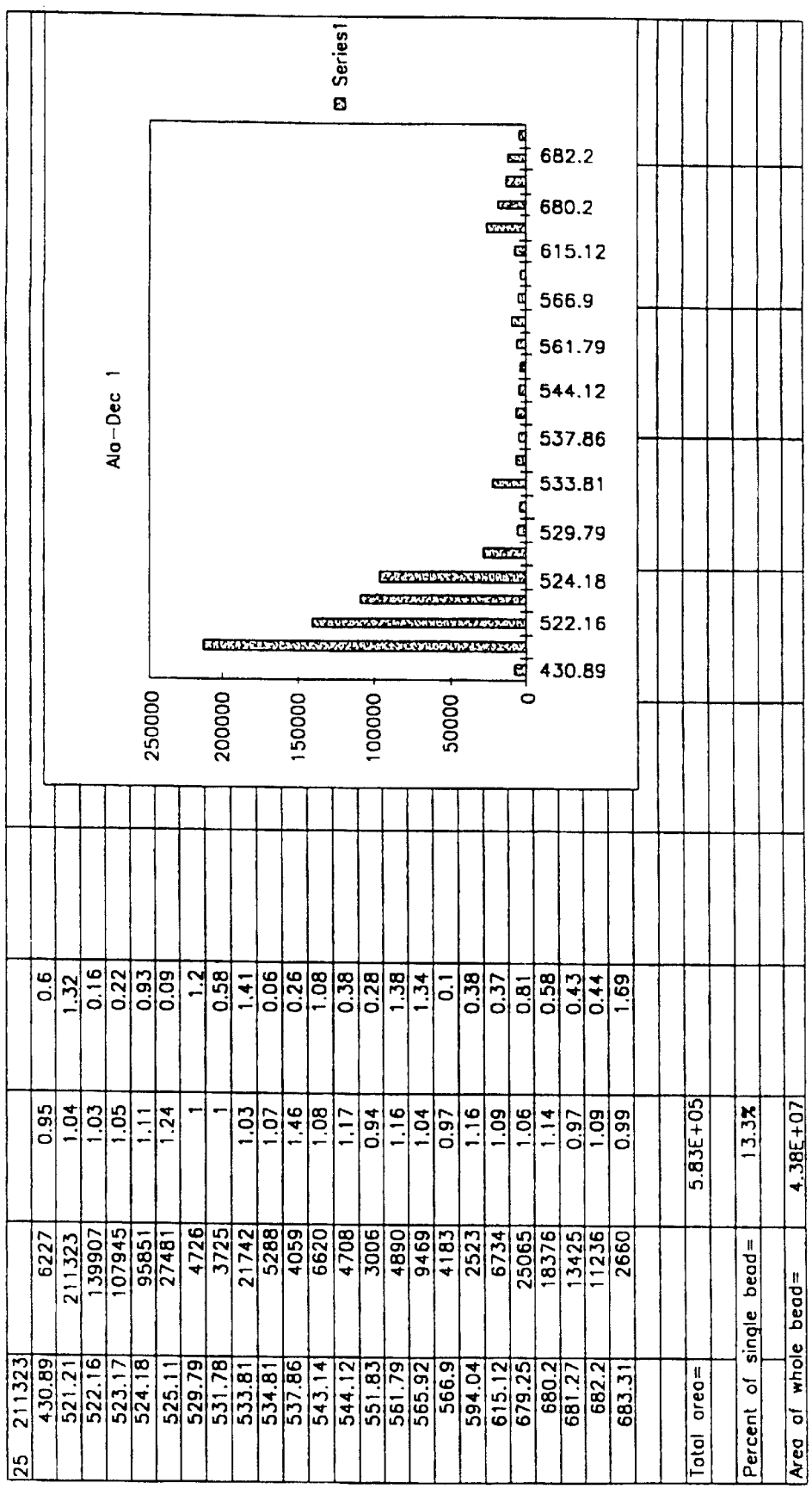
Figure 278:
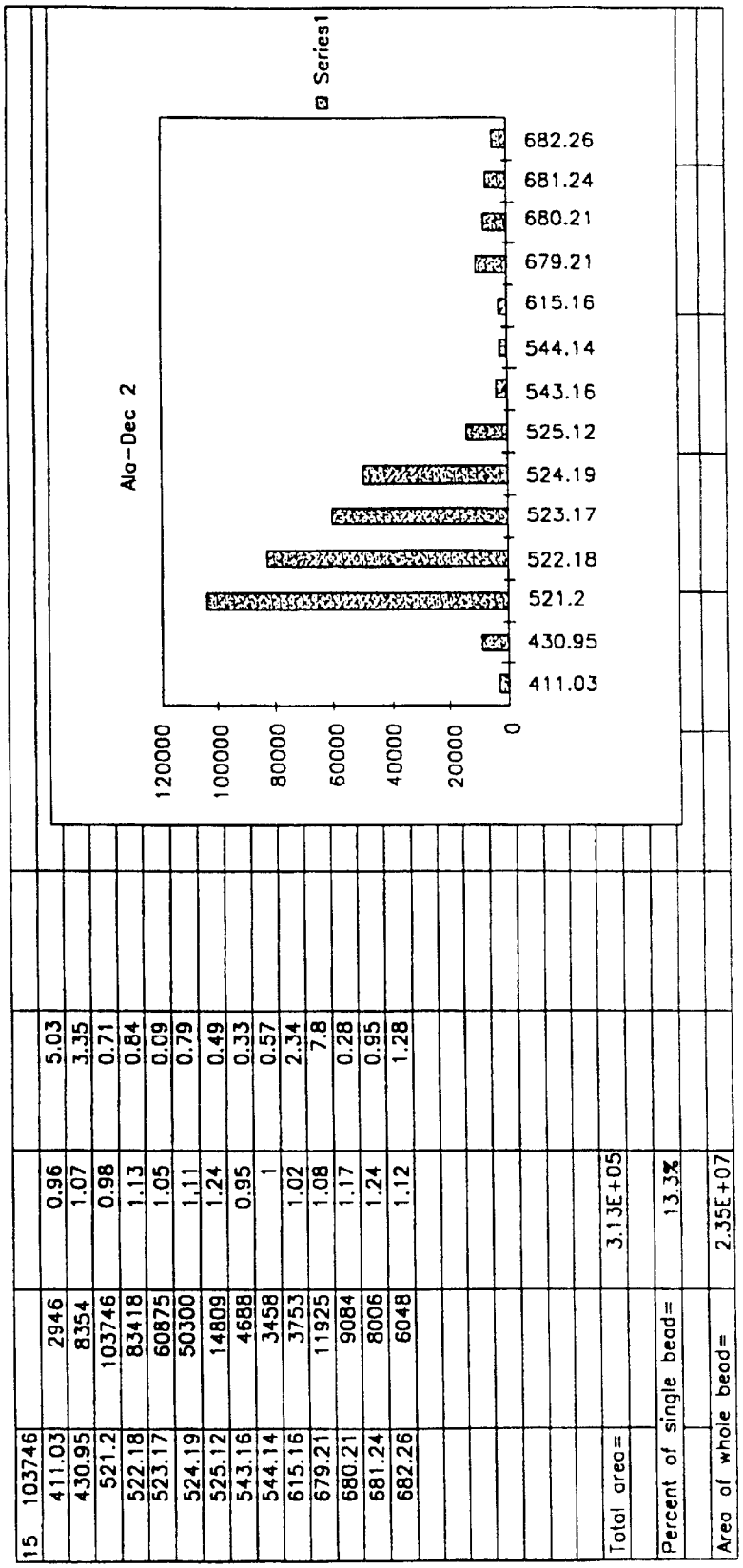
Figure 279:
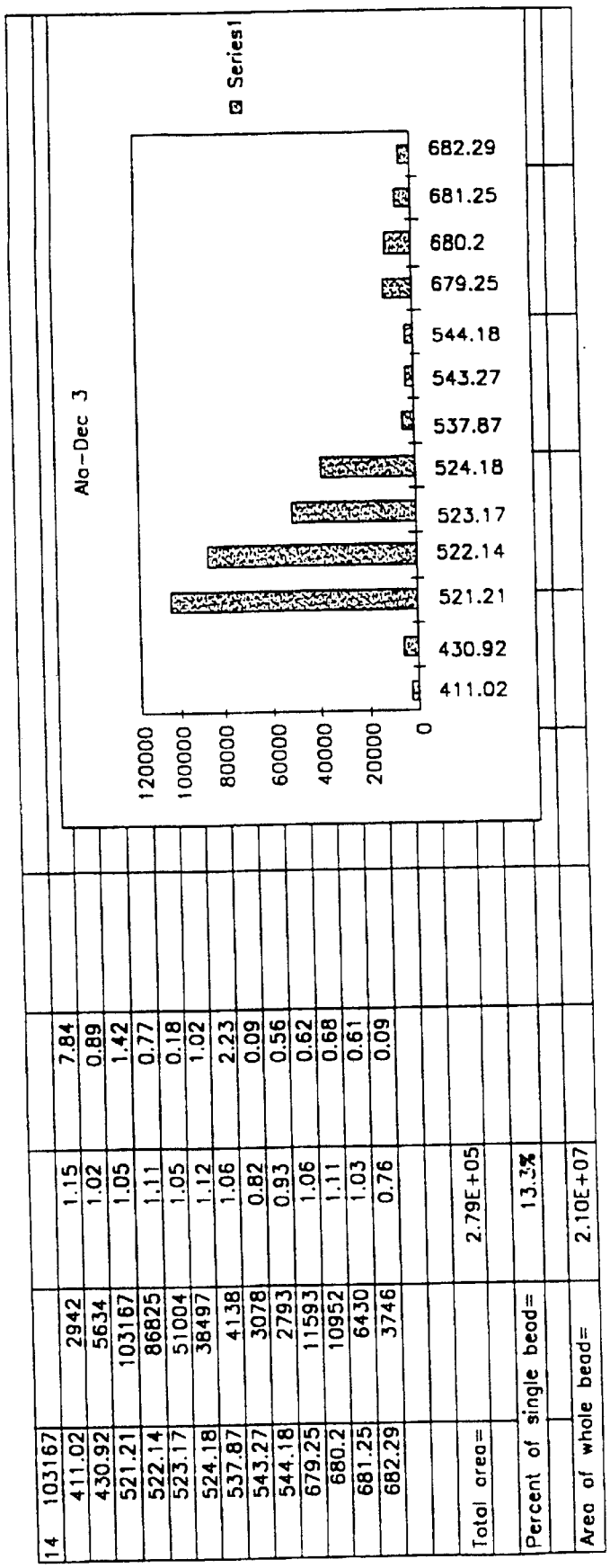
Figure 280A:
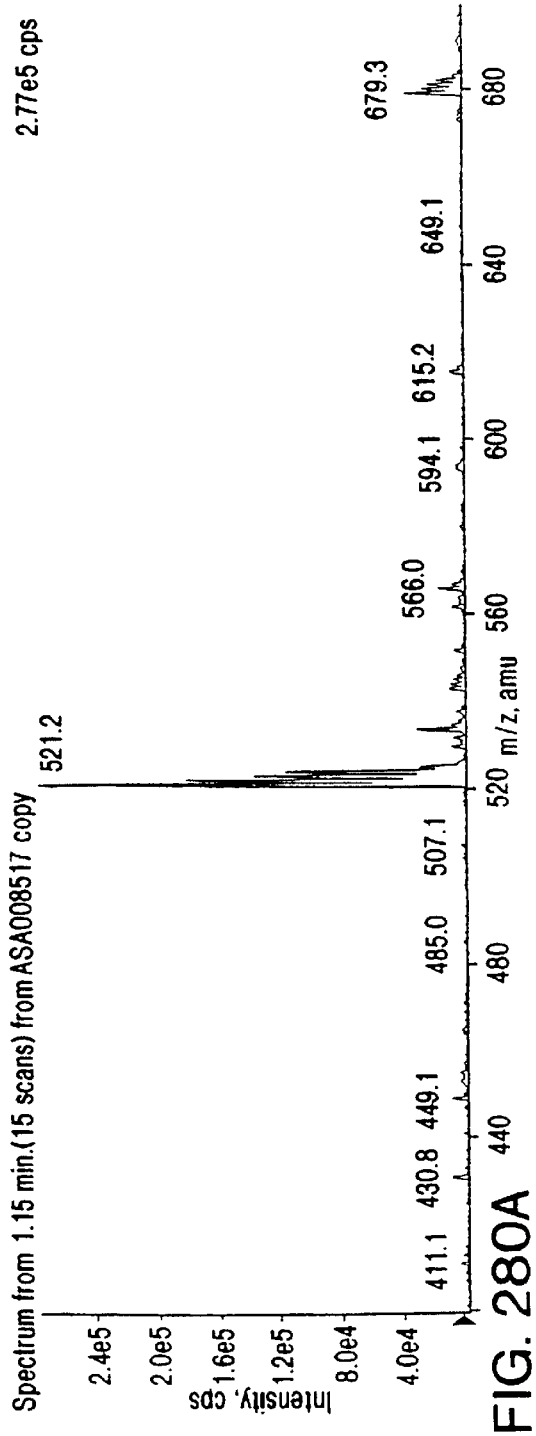
Figure 280B:
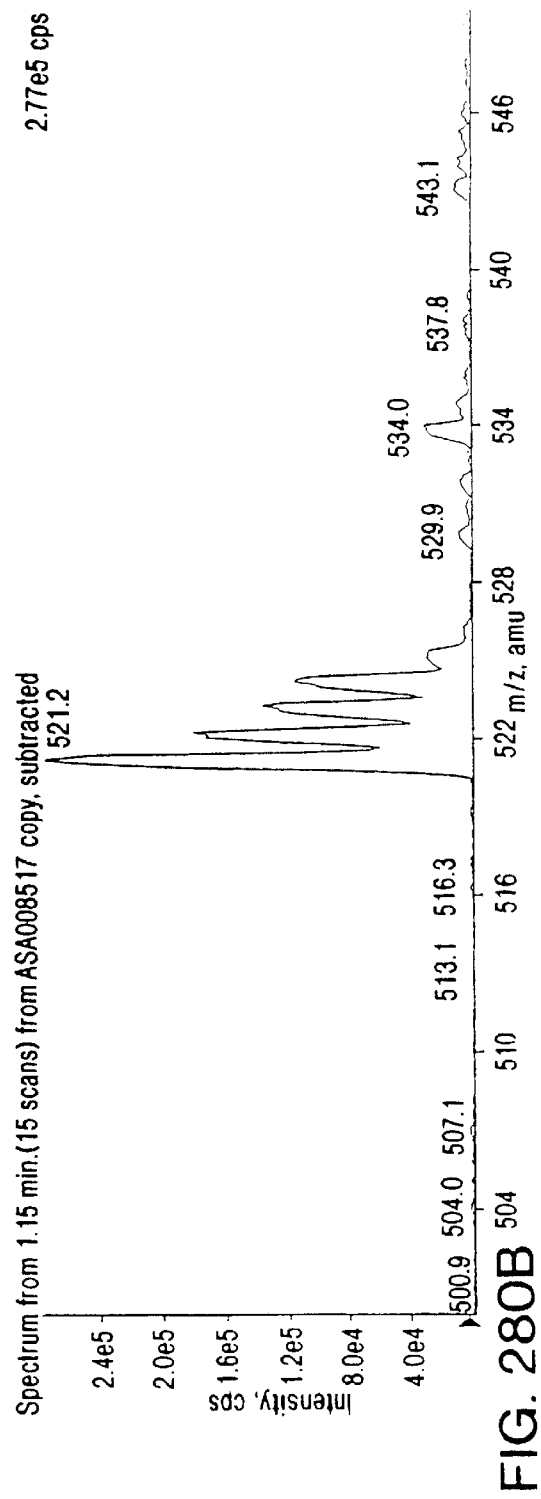
Figure 281A:
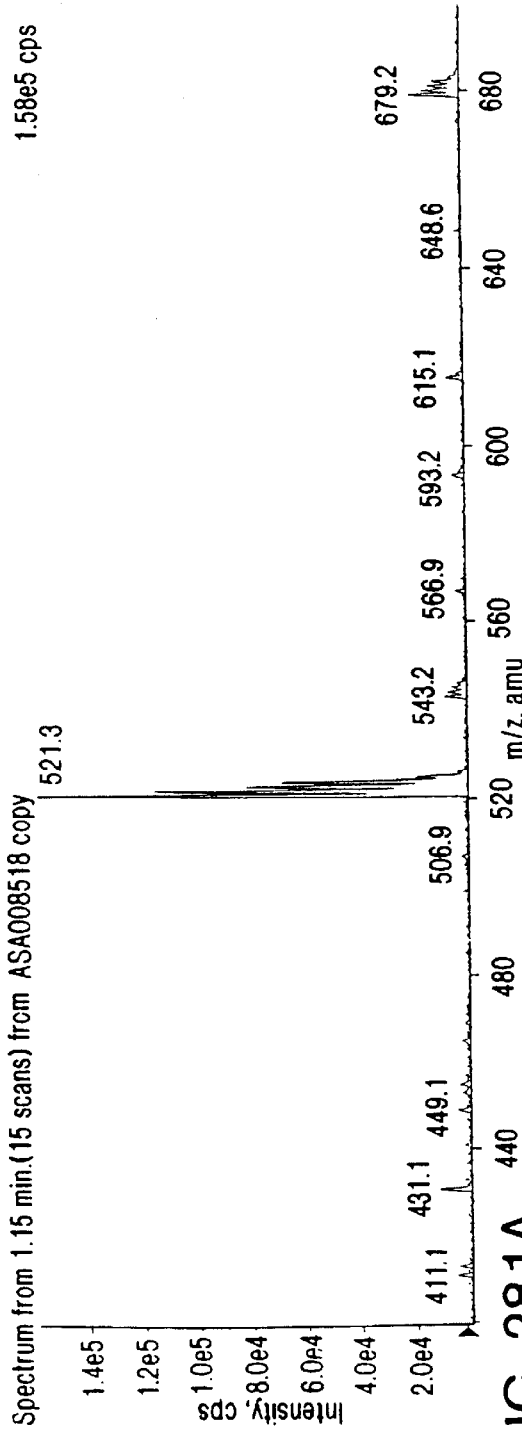
Figure 281B:
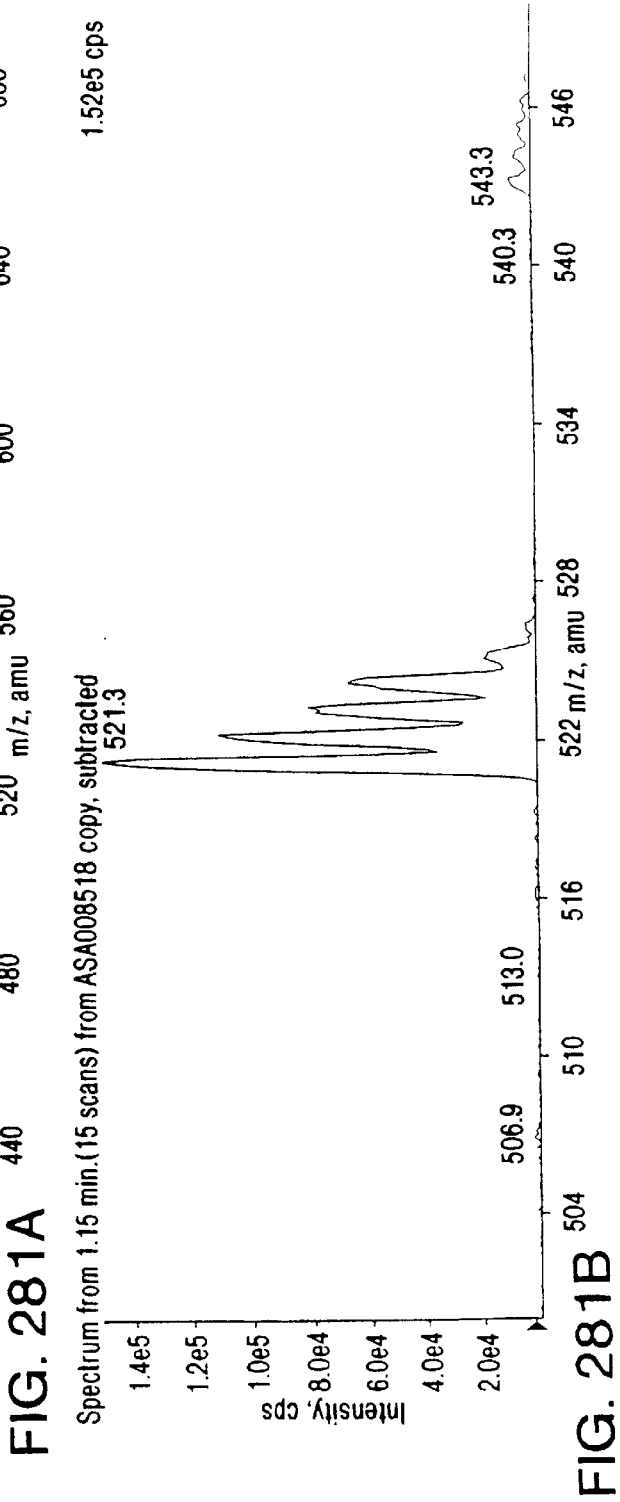
Figure 282A:
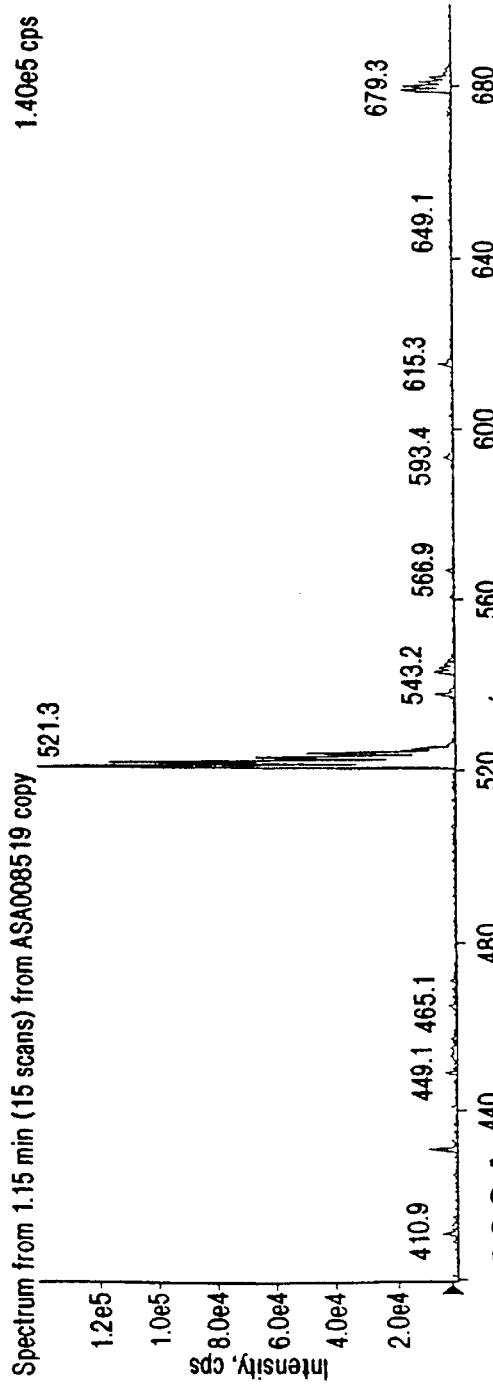
Figure 282B:
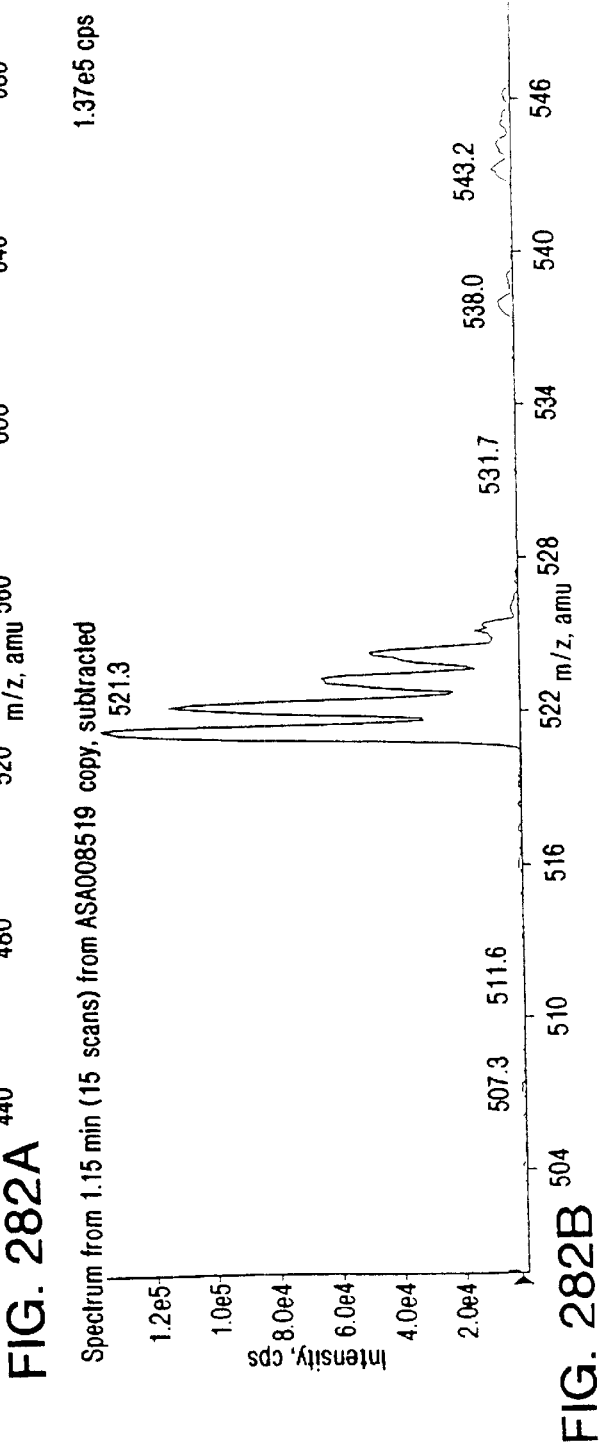
Figure 283A:
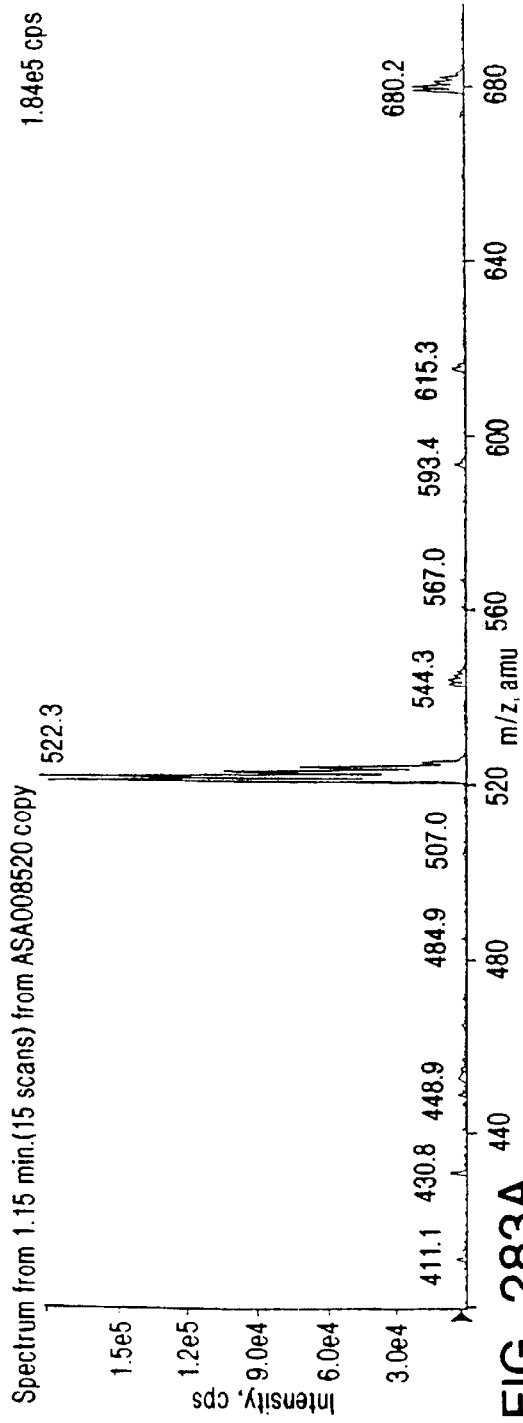
Figure 283B:
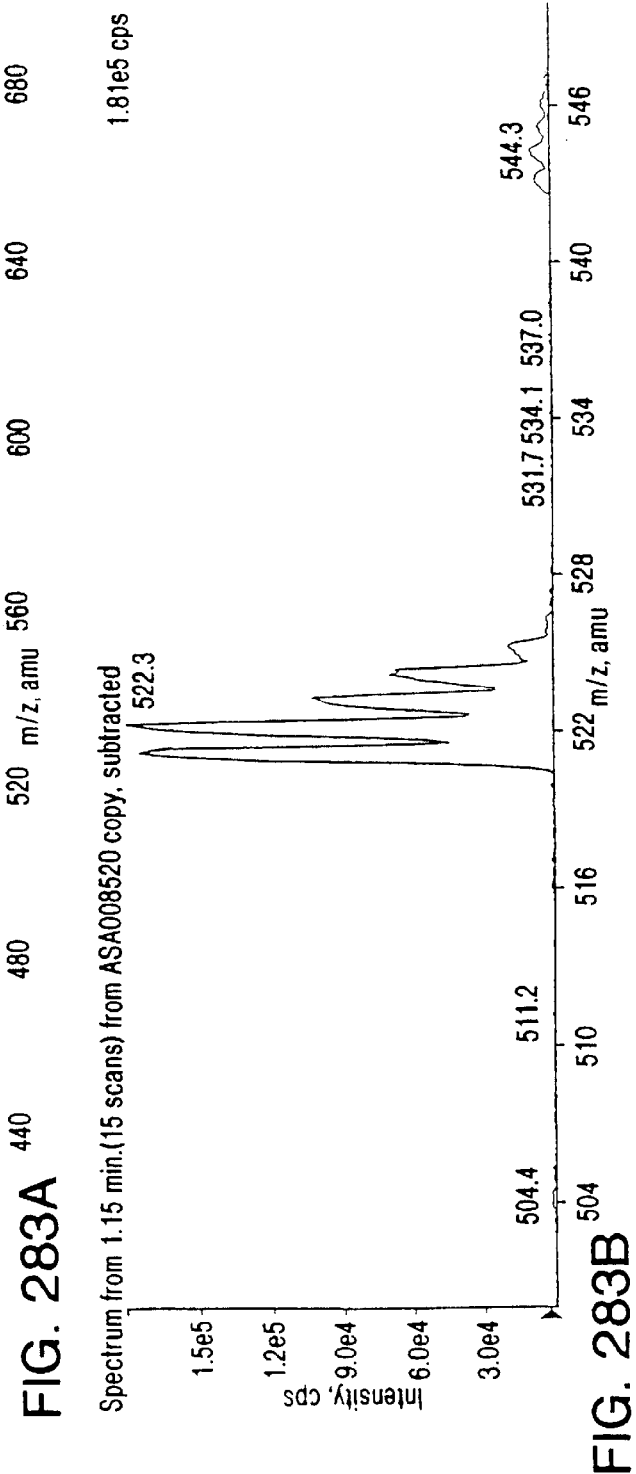
Figure 284A:
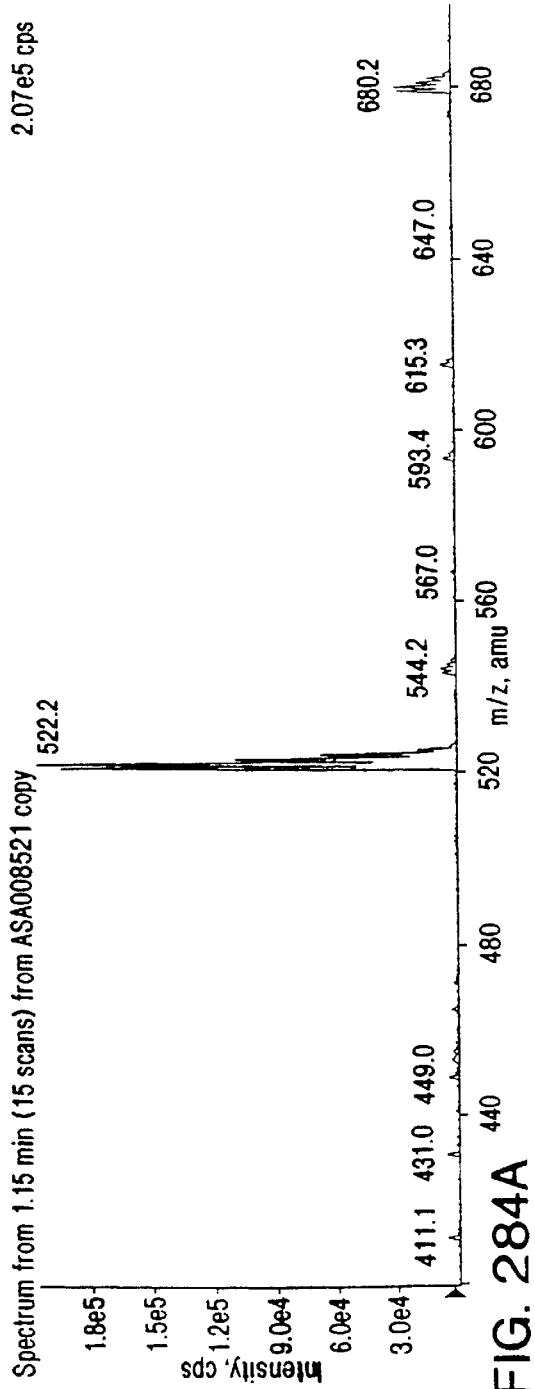
Figure 284B:
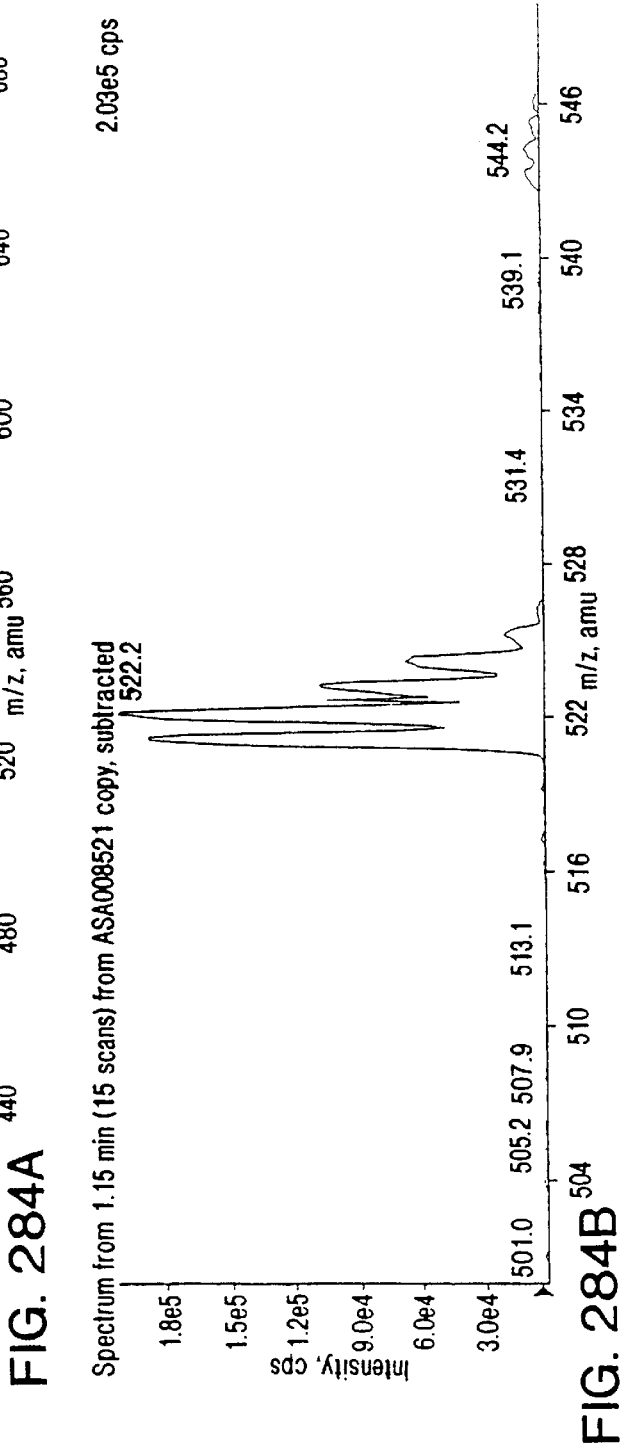
Figures 285A, 285B:
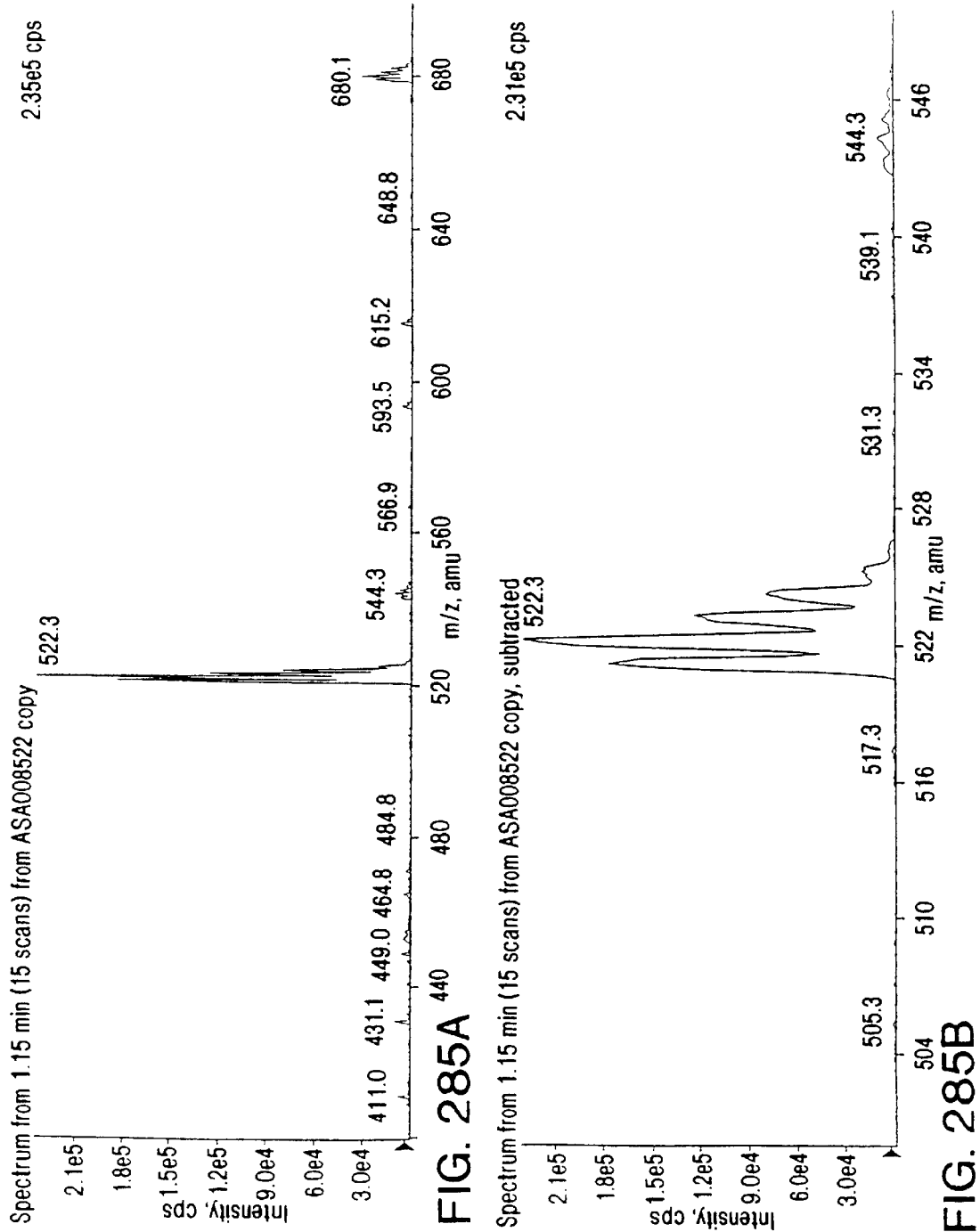
Figure 286A:
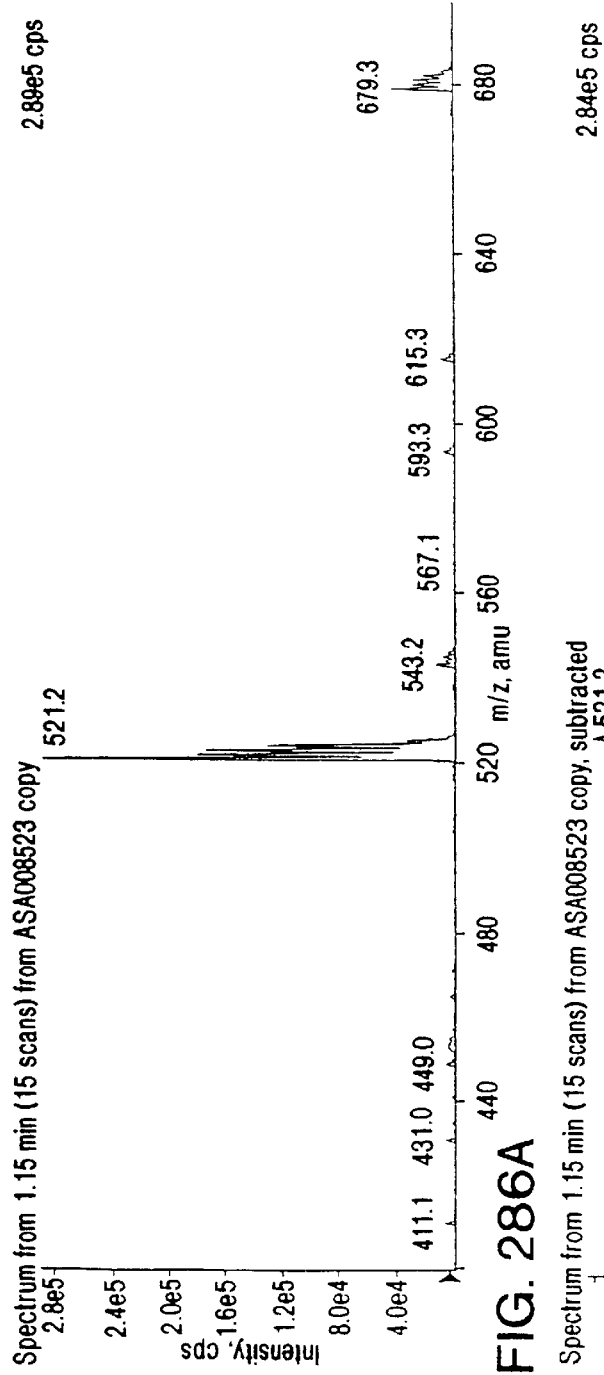
Figure 286B:
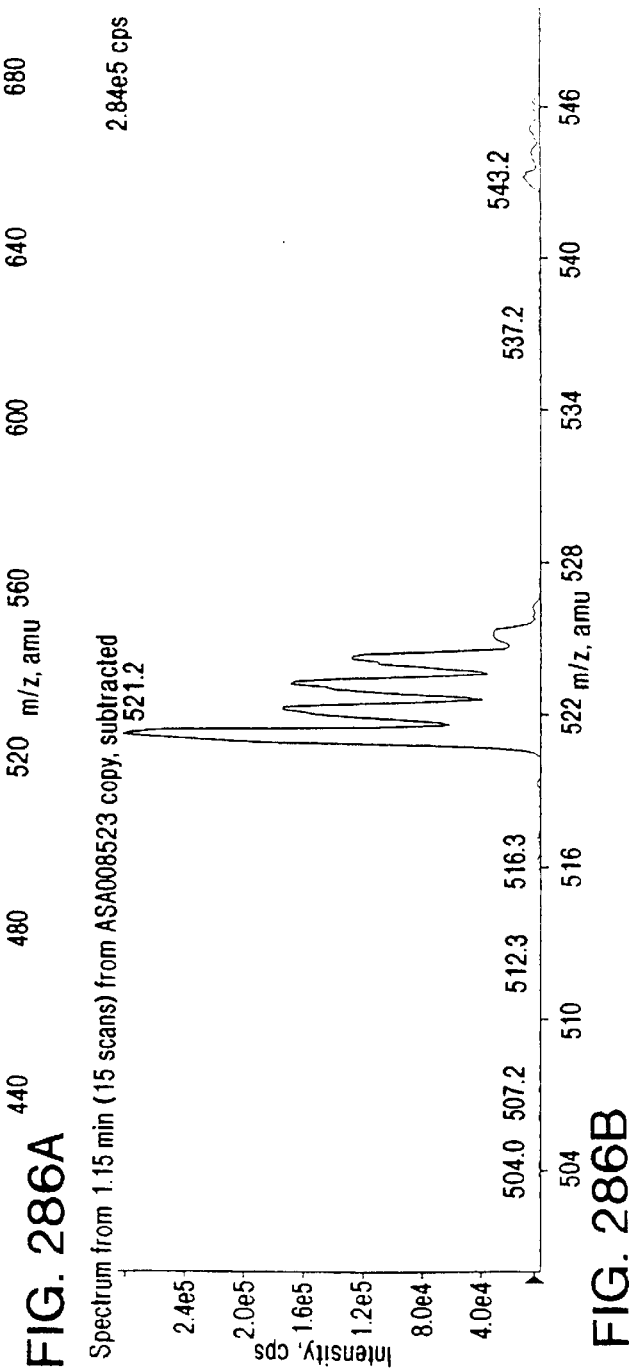
Figure 287:
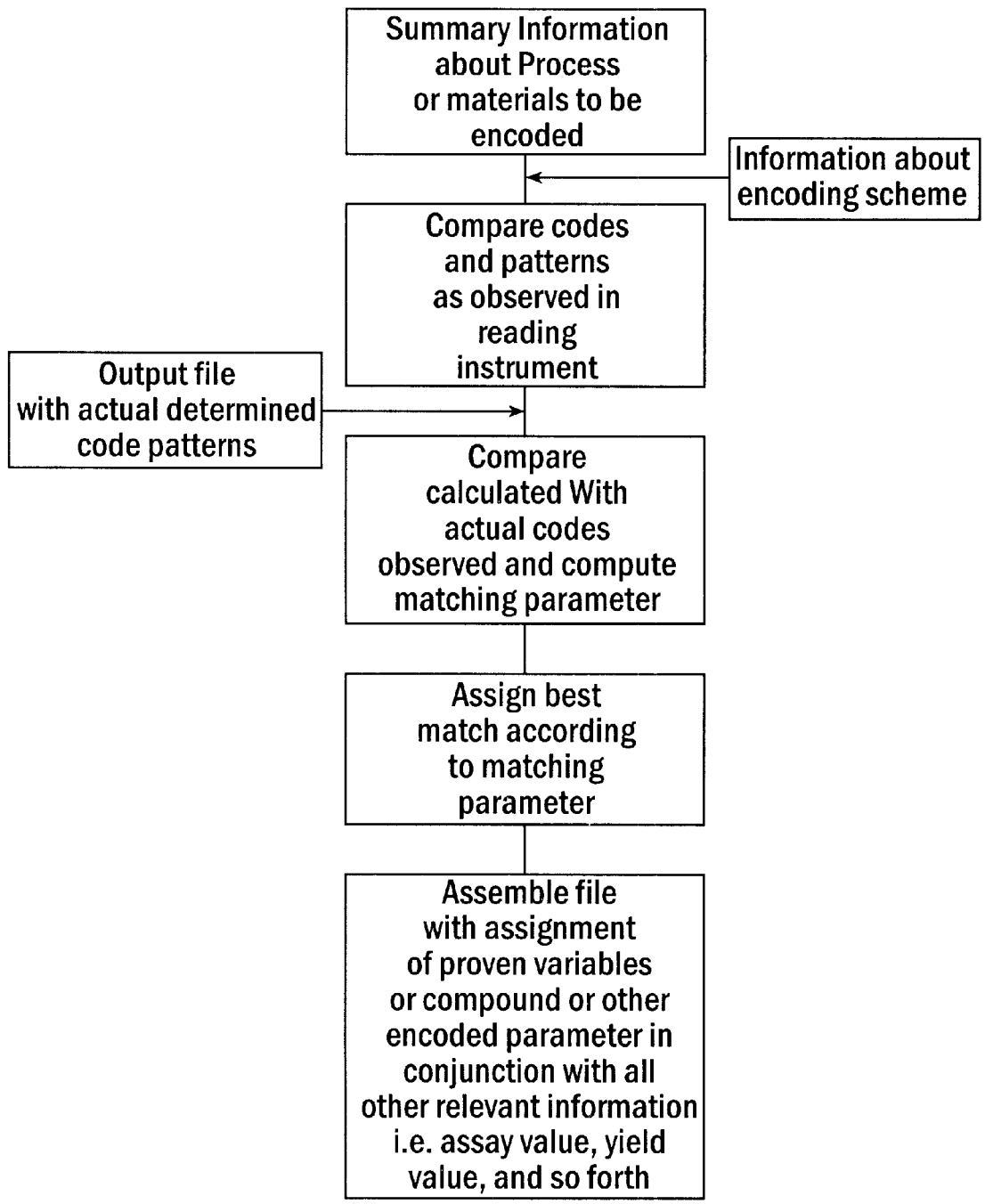

FIGS. 133 to 286 are spectra that are produced by a set of code blocks organized in a type of ratio encoding designated as four peak ratio encoding, using four isotopically distinct F-moc protected versions of alanine FIG. 287 is a flow diagram for a computer program capable of automating the decoding of a set of code blocks and their associated spectra.

SUMMARY OF THE INVENTION

In brief summary, the invention is the application of mass or isotopic encoding in the imprinting of coded information into or in conjunction with materials or processes shch that the details of the components or process steps can be easily determined by one or more of the methods of mass spectrometry, nuclear megnetic resonance spectroscopy, or infrared spectroscopy, including the technique of Ramen spectroscopy. In a preferred embodiment, the invention is a method of encoding the products of combinatorial synthesis by isotopically doping a portion of a combinatorial chemistry construct and analyzing the combinatorial reaction products by mass spectrometry, nuclear magnetic resonance spectroscopy or infrared spectroscopy.

In overview, the invention comprises several embodiments. Firstly, the invention comprises a mass-based, non-chemical method for recording the reaction of at least a portion of a reaction series on each of a plurality of unique solid supports, the method comprising: preparing a plurality of agents each having a unique defined mass; preparing a group of unique solid supports; reacting each solid support group with a different chemical reagent under a controlled reaction condition; mixing these product groups together and then dividing the mixture of unique solid supports into a plurality of groups for a second intermediate or final stage; repeating the reacting stage with a chemical reagent under a controlled reaction condition at least once to provide a plurality of final products, having different products on the different individual unique solid supports; each of the unique defined mass agents being reacted with either: each of a group of unique solid supports; each of a group of first chemical reagents in a reaction series; each of a group of second chemical reagents in a reaction series; or each of a group of subsequently added chemical reagents in a reaction series; such that each of the group of unique solid supports, group of first chemical reagents, group of second chemical reagents or group of subsequent chemical reagents has been reacted with an agent having a defined mass that is different from any other defined mass agent reacted with any other of the aforesaid groups; the unique defined mass agents being capable of being analyzed and wherein such analysis defines the choice of a first chemical reagent, reaction condition under which the first chemical reagent was added, second chemical reagent, reaction condition under which the second chemical reagent was added, subsequent chemical reagent, or reaction condition under which the subsequent chemical reagent was added. The method is particularly preferred in performing an assay or using separation techniques including column or plate chromatography or fluorescence assistance cell scanning to find reaction products having a characteristic of interest and then performing the identification analysis on such reaction products. This method is particularly preferred with respect to the determination of the first chemical reagent added to the reaction sequence. Reaction products can include a non-oligomer which is aliphatic, alicyclic, aromatic, or heterocyclic or an oligomer which is an oligopeptide, oligonucleotide, oligosaccharide, polylipid, polyester, polyamide, polyurethane, polyurea, polyether, polyphosphorus derivative where the phosporus is taken from the group consisting of phosphate, phosphonate, phosphoramide, phosphonamide, phosphite, or phosfinamide, or polysulfur derivative where the sulfur is taken from the group consisting of sulfone, sulfonate, sulfite, sulfinamide, or sulfenamide.

Preferred means of analysis are by mass spectrometry (MS), nuclear magnetic resonance (NMR) spectroscopy, and infrared or Raman spectroscopy. These means of analysis produce distinctive peak patterns used in analysis, identification, coding and decoding strategies. The mass spectrometer in particular produces unique single mass peaks, unique double mass peaks, unique pairs of single mass peaks, unique pairs of double mass peaks and other unique multiple peak patterns, which are additionally capable of being translated into machine-readable patterns, including bar codes. The NMR, IR and Raman methods also produce useful unique peak patterns that can be transformed into machine-readable patterns, including bar codes. Such patterns, including machine-readable patterns, can be assigned in encoding strategies to represent discrete chemical reagents added in a chemical reaction series, or assigned to represent discrete chemical reaction conditions under which a chemical reagent was added in a reaction series, including, but not limited to, concentrations, temperatures, pressures, catalysts, enzymes, electromagnetic energy imparted to the system (visible light conditions, irradiation, etc.), and so on. This is done by initially generating recognition patterns for unique mass defined agents which are either eye-readable or machine-readable. The patterns resulting from the analysis steps are then compared to the recognition patterns for identification and decoding, with or without the assistance of a machine. Recognition patterns and analysis patterns that are machine-readable are capable of being stored electronically in suitable computer storage and memory devices well known to those of ordinary skill in the art and such stored patterns form a readily retrievable database that also forms a claimed embodiment of the invention.

Mass agents used in these methods are preferably a molecular entity such as a solid state chemistry support resin bead linker which has had one or more of its atoms replaced by an isotope of that atom, thus altering the mass, but not the chemical properties of that chemical entity. Another alternative mass agent is to simply repeat the appearance of such a molecular entity an integral number of times in a linear chemical construct.

The method of the invention can be performed using solid state chemistry or solution chemistry. Reaction products can be cleaved off of a solid support for analysis, or the entire construct can be analyzed. Chemical reagents added to a reaction series can include one or more that can act as a substrate for the determination of binding specificity to a chemical compound of interest. Any or all of the steps of encoding, synthesis, analysis and decoding can be automated with the aid of suitable computer means and robotics means, all by methodologies well known to those of ordinary skill in the combinatorial chemistry, spectroscopy, computer science, robotics and optical scanning arts.

The invention also comprises a kit made up of a set of compounds prepared for the encoding, synthesis, analysis and decoding methods described above of chemical reagents and reaction conditions in chemical reactions of interest in a combinatorial synthesis, where the compounds in the kit have different distinguishable masses, but the same chemical properties. Such kits can comprise solid state supports attached to isotopically doped linkers, series or combinations of isotope mixtures in readily identifiable ratios, or a variety of combinations of isotopically doped chemical moieties (also called code blocks herein) with covalent bonds or or other organic moieties as links or linkers.

The invention also comprises kits of solid state supports that have been prepared so as to bear unique defined mass agents on their surface. Solid supports can be resin beads in a wide range of sizes of from 1 to 10,000 $\mu$m in dimension. The support itself can be isotopically doped by incorporating an isotope into the chemical structure of the support. This differentiates the mass of the support from like supports, but does not change its chemical properties. Such solid supports would then be used in the methods of the invention. Groups of such uniquely mass-defined supports can comprise libraries, which are also an embodiment of the invention as claimed herein.

DETAILED DESCRIPTION OF THE PREFERRED EMBODIMENTS AND BEST MODE OF THE INVENTION

The term "isotopic doping" or "isotopically doped" is used here to mean the introduction into a molecule of an isotope of one or more of the atoms normally appearing in that molecule.

A "link" is a covalent bond or a molecular moiety that is suitable for linking two portions of a construct together.

A "linker" is a moiety comprised of a code block, a first link for bonding the code block to a solid support or other moiety, and a second link for bonding the code block to a ligand or other moiety.

A "linker mix" is a mixture of two isotopically distinct but chemically identical molecules, the mix having a discrete ratio of first isotope to second isotope.

A "code block" is a molecule or series of molecules containing one or more isotopically doped atoms or having a repeating number of molecules in series, such that its mass can be discretely defined and differentiated from any other code block.

A "doped" atom, code block or moiety refers to an entity in which an atom in a molecule which has been replaced by one of its isotopes. Doped atoms as contemplated by this invention include all atoms found in organic chemistry having isotopes and in particular, hydrogen, carbon, nitrogen, fluorine and oxygen. Non-radioactive isotopes are generally preferred over radioactive ones.

The term "monomer" is used herein not only to denote subunits that make up a linear molecules such as amino acids, but also to denote starting chemical materials and chemical reagents that are chemically reacted with one another in combinatorial chemistry organic synthesis to produce molecules that are not linear, such products including so-called "small molecules" which are organic molecules of 500 Daltons or less in molecular weight.. As used herein, the terms "monomer" and "chemical reagent" are interchangeable.

A "reaction series" as used herein refers to a series of steps in a chemical synthesis in a combinatorial synthesis format.

A "solid support" is one or materials upon which combinatorial chemistry syntheses can be performed, including beads, solid surfaces. solid substrates, particles, pellets, disks, capillaries, hollow fibers, needles, solid fibers, cellulose beads, pore-glass beads, silica gels, polystyrene beads optionally crosslinked with divinylbenzene, grafted co-polybeads, poly-acrylamide beads, latex beads, dimethylacrylamide beads optionally cross-linked with N,N'-bisacryloyl ethylene diamine, glass particles coated with a hydrophobic polymer, fullerenes and soluble supports such as low molecular weight non-cross-linked polystyrene.

A "construct" is a covalently bonded entity comprising, in any combination, some type of solid support, one or more linkers, one or more code blocks, and one or more ligands.

A "ligand" is a chemical reaction product of interest. A ligand can be part of a larger construct, where the ultimate goal will be to identify and/or cleave the ligand apart from the rest of the construct.

In general, the methods of the invention make use of some variant of a construct of the non-limiting general formula:

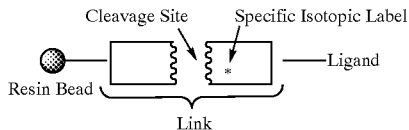

Isotopes are inserted into such constructs via doped links. That is, after the determination has been made as to what will constitute a chemically suitable link, the link is synthesized using one or more atoms of the link that has been substituted by an isotopic form of that atom. The isotopic form is chemically indistinguishable from the non-isotopic form of the link. The isotopic form is, however physically distinguishable from other isotopic forms by MS or NMR analysis. This physical difference is manifested by differently appearing MS, IR, or NMR peak patterns. A wide variety of isotopic insertion or doping strategies are available, leading to a large number of physically distinguishable chemical moieties, each having its own distinctive peak pattern. The existence of such distinctive peak patterns means that the isotopic forms can be used to create a code that can be used in various encoding strategies to readily identify different chemical entities or conditions that can be used during a combinatorial synthesis. Several of such encoding strategies are given below.

Electrospray mass spectrometry provides mass and ionic charge intensity information for a given molecular entity. In general, smaller molecules only appear in the spectrum once as singly charged species, and the effect of isotopic compositional variation results in a very predictable quantum mass shift. Thus, for example, a molecule having a molecular weight of 304 will produce a peak at 305 (M+1) on a mass spectrometer (MS) spectrum. If a nitrogen atom in such molecule having an atomic weight of 14 ($N^{14}$) is replaced (by isotopic doping, as that term is used herein) by isotope $N^{15}$, then the MS peak will shift to the right precisely one unit to 306. Furthermore, such isotopic doping will not affect the ionization or chemical reactivity of the molecule. The ability to measure both of the properties of mass and ionic intensity with reasonable accuracy (i.e. mass to about 0.1 atomic mass units and relative intensity to about 3% provides the basis for a novel encoding strategy using isotopes to isotopically, rather than chemically, encode a monomer to read a synthetic history, instead of tagging a molecule itself. Using the methods of the invention, encoding strategies are devised from the use of the mass information alone, the relative intensity information in two or more mass peaks alone or a combination of the two. The basic methodology of the invention, which is to insert different isotopes into combinatorial constructs to identify addition of monomers or chemical conditions, gives rise to several alternative embodiments for encoding and decoding, which are capable of individual implementation or in selected combinations.

Multiple preferred coding approaches using defined mass agents will be discussed. These examples are non-limiting and other coding approaches are not meant to be excluded.

EXAMPLE 1

Encoding Approaches

Encoding Example A

Ratio Coding Approach

In a most preferred embodiment of the invention, a series of isotopically doped linker mixes n is prepared, with each linker mix in the series comprising a discrete ratio of first isotope to second isotope, and with each mix in the series differing in ratio from the previous or subsequent mix in the series by an equal amount. Thus, for example, a series of 21 batches of doped monomer can be prepared, with the first batch in the series having a ratio of 100% of first isotope to 0% of second isotope, the second batch having a ratio of 95% of first isotope to 5% of second isotope, and so on until the 21st batch, which will have 0% of first isotope and 100% of second isotope. Each linker is further characterized by being capable of being cleaved such that one cleavage portion will always contain the isotopically doped molecular moiety. Each linker mix is chemically reacted with a support means on one side of the linker to yield n batches of support-linker, again each having a discrete ratio of first to second isotope. Then a reagent of interest is added to each batch to yield n batches of support-linker-molecule, each likewise having the discrete ratios ot two isotopes. If, now for example, a split synthesis method is being pursued, then the n batches are combined into a single mixing vessel and the resulting mix is then divided into n aliquots, and to each aliquot is added a second reagent of interest, and the resultant reactions are allowed to proceed. The previous step of combining all aliquots and then splitting them out into n aliquots is repeated, and a third reagent of interest can be added. If all possible reactions have proceeded to completion, then there are now $n^3$ products. The linkers can be cleaved so that the isotopically labeled fragment stays with the chemical product, and the resulting isotope label-chemical product construct is analyzed by a mass spectrometer. The resulting mass spectrogram will display a peak pattern that mirrors the ratio of first isotope to second isotope present in the linker fragment, thus identifying what the first chemical reagent was that was added to that particular reaction well. Thus, for example, if the isotope ratio is 100% for first isotope to 0% for second isotope, then one relatively tall peak will appear on the spectrogram at the position on the spectrum occupied by the discrete atomic mass that that moiety has (as will be appreciated by those of ordinary skill in the art, other relatively small peaks, will, of course appear, but just one prominent peak that is characteristic of the molecule as used in the identification method of the present invention appears.). If the isotope ratio is 95% of first isotope to 5% of second isotope, then there will be a first prominent peak and a second prominent peak, with the first prominent peak having about 95% of the total area under the combined prominent peaks, and the second prominent peak having the remaining approximately 5%, thus forming a distinct prominent peak pattern which serves to clearly identify the isotope ratio and therefore the chemical reagent. It is to be understood that another smaller peak not part of the patterns forming the codes of the invention will appear, by virtue of the natural abundance of $C^{13}$, and its relative size can be predicted using the following analysis. If a given moiety contains 24 carbons and nitrogen and it has been doped to a 50/50 ratio of $N^{14}/N^{15}$, then peak 1 will be calculated from the $N^{14}/C^{12}$ present as $(0.898)^{24} \times 0.5 = 0.383$; peak 2 will be calculated from the $N^{15}/C^{12}$ and $N^{14}/C^{13}$ present as $(0.989)^{24} \times 0.5 + (0.989)^{23} (0.011) \times 24 \times 0.5 = 0.485$; and the third peak will be calculated from the $N^{15}/C^{13}$ present as $(0.989)^{23} \times (0.011) \times 24 \times 0.5 = 0.102$, thus resulting in a distinctive pattern having two approximately equal prominent peaks, and the relatively small side peak. Ideally, the isotopically distinct species used should differ by two or more AMUs as this would produce well separated peaks that would not be affected by the natural presence of $^{13}C$. To achieve this with the atoms that are most commonly used in such chemistry (C,H,N,O) typically requires that more than one atom be isotopically substituted, as available stable isotopes of C, H and N differ by only one mass unit.

Subsequently, in order to identify the third component in the combinatorial construct, the third component can be identified by its reaction well number. Now, with the identity of the first component known by virtue of the mass spectrograph and the third component known by virtue of the well number, their combined molecular weights are subtracted from the total molecular weight of the construct to arrive at a residual mass which identifies the second component of the construct.

It should be appreciated that using the methods and constructs of the invention provide for an entire series of encoded linkers that provide great economic savings, since the only additional synthesis initially required is to isotopically dope a solid support linker that had to constructed in the first place. No other chemical modifications are needed to be made to the linkers that were initially chosen for the solid state combinatorial synthesis.

Encoding Example B

Dual Ratio Coding Approach

For syntheses having more than three steps, the procedure of Ratio Coding described above is followed in that a series of isotopically doped linker mixes n is prepared, with each linker mix in the series comprising a discrete ratio of first isotope to second isotope, and with each mix in the series differing in ratio from the previous or subsequent mix in the series by an equal amount. However, a second type of atom is also isotopically doped, so that there are two types of atomic isotopes present. For example a nitrogen position can be doped with a mix of $N^{14}$ and $N^{15}$, while a carbon position can be doped with a mix of $C^{12}$ and $C^{13}$. Again, this example will follow the progression of 5% increments, so that there are 21 possible nitrogen ratio combinations and 21 possible carbon ratio combinations. Furthermore, the carbon position is protected with a suitable protecting group, which can be deprotected to correlate to a reaction step in the combinatorial synthesis. Thus, the mass spectrograph peak pattern for the doped nitrogen identifies the first synthesis component, the mass spectrograph peak pattern for the doped carbon identifies the second synthesis component, an assay identifies the fourth component, and the third component is identified by subtraction of the first, second and fourth components from the total weight of the product.

Occasionally, code degeneration may arise when using more than one type of isotope, as in the case where one moiety bore a $N_{15}$—$C_{12}$ combination and another bore a $N_{14}$—$C_{13}$ combination, both of which would have the same atomic weight and therefore give indistinguishable peak patterns in a mass spectrograph. This problem can be circumvented in one of two general ways. Firstly, by selecting $C^{12}$ and $C^{14}$ as the carbon isotope pair, this type of code degeneracy is avoided. Or, if radioactivity is to be avoided, $C^{12}$ and $C^{13}$ can still be used by the technique of combining mass spectrography with fragmentation. For example, an amide moiety of the structure

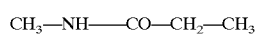

can be doped in two ways that will yield the same atomic weight as follows:

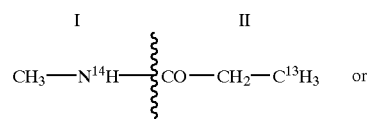

However, when they are fragmented along the indicated cleavage lines, moiety I will yield a fragment having a doped N and a normal C, while moiety II will yield a fragment having a doped C and a normal N, thereby yielding distinctive peak patterns in the MS.

The following scheme illustrates the Single Peak Positional Coding Approach

Encoding Example C

Single Peak Positional Coding

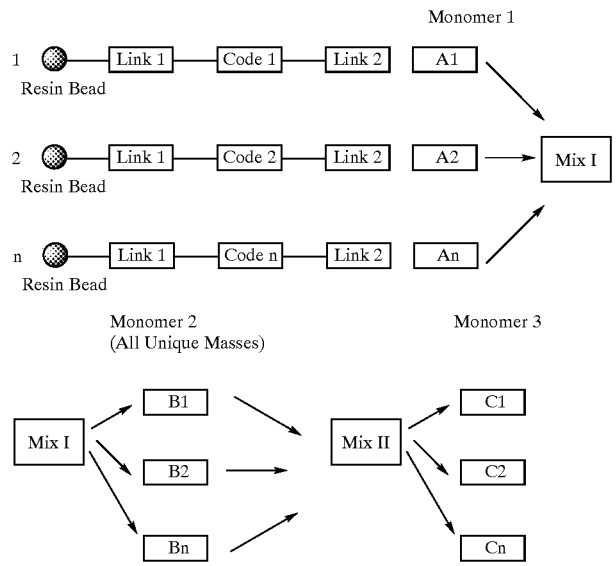

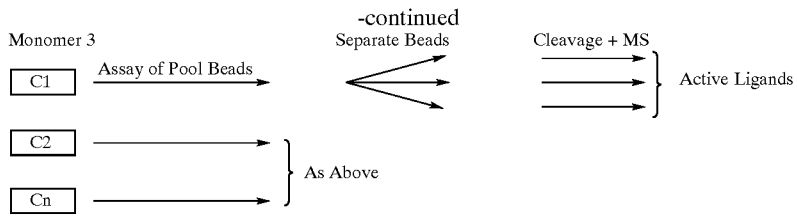

Following the process in Scheme 2, another alternative embodiment of the invention of isotopic encoding can follow a single MS peak position approach. This approach generates a MS peak. In this format, the mass of the coding block is engineered such that it appears in a convenient part of the spectrum, and it is used to represent the first monomer or building block used in the synthesis of a particular compound. After the combinatorial synthesis is complete, Link 2 is cleaved in order to determine the molecular weight of the ligand. Then Link 1 is cleaved to enable identification of the Code block, which determines the identification of the first pool monomer.

The first and second links in a linker scheme can be the same or different. The links can be the same when a direct binding assay is used, followed by removal of positive beads. When the links are different, this allows the assay to be either by direct binding or with cleaved ligand alone.

Decoding of a three monomer combinatorial library is achieved from three steps. The mass of the code block is determined, thus identifying the code, which identifies the first pool monomer. The pool number of the final monomer addition determines the final monomer, from which the mass of the final monomer is known. Then, the masses of the first and third pool monomers are subtracted from the total molecular weight of the entire construct, thus leaving the mass of the second pool monomer, from which the identity of the second pool monomer is inferred.

The Single Peak Positional encoding approach is especialy useful when active ligands are screened by use of a chromatography column, and the bound constructs are then eluted.

The following scheme illustrates the Double Peak Positional Coding Approach

Encoding Example D

Double Peak Positional Coding

Scheme 3

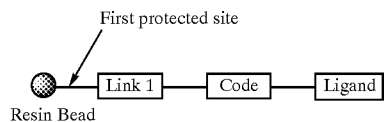

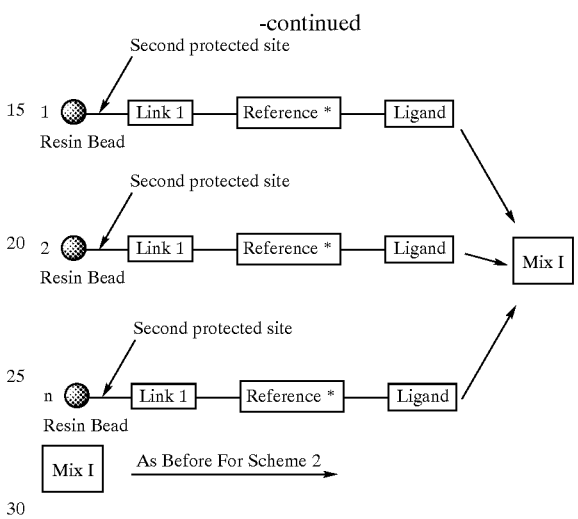

Following the process in Scheme 3, another alternative embodiment of the invention of isotopic encoding can follow a double MS peak position strategy. This approach yields two MS peaks. For example, a set of resin beads is prepared wherein the beads bear two protected sites, such as BOC and FMOC. A first protected site is de-protected. A number of isotopic code blocks n is prepared and each code is linked to a first de-protected site.

The second protected site is de-protected. A standard reference moiety having a different mass is linked to the second de- protected site. Upon MS, this will yield a peak for the standard reference and a second peak for the code, with the mass difference between the two peaks being the encoding unit. Decoding of a three monomer combinatorial library is achieved from three steps. The mass of the ligand plus code block is determined, thus identifying the code, which identifies the first pool monomer. The pool number of the final monomer addition determines the final monomer, from which the mass of the final monomer is known. Then, the masses of the first and third pool monomers are subtracted from the total molecular weight of the entire construct, thus leaving the mass of the second pool monomer, from which the identity of the second pool monomer is inferred.

In an alternative construct, the code block is prepared to contain two like species, one of which is constant and acts as a reference mass, while the other has variable mass blocks similar to those described for the single peak positional encoding scheme. After cleavage of the link to the resin, ligand is generated with an attached variable code increment. The encoded information is now determined from the difference in mass of the coding unit and the reference mass unit. The advantage of this is that the code can be left attached to the ligand and read at the same time as the mass of the whole construct is determined by MS. This strategy gives two mass peaks that represent the ligand attached to either the reference code or the variable code. The difference in mass is used to determine the identity of monomer 1, while monomer 3 known from the corresponding pool and therefore monomer 2 is inferred as described above.

The invention also makes possible an alternative embodiment that in effect creates a bar coding mechanism. Several non-limiting exemplary versions of solid state constructs are possible as follows.

Encoding Example E

The Bar Coding Approach

Version 1: Mass only:

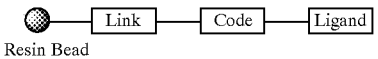

Resin Bead

Version 2: Mass and Intensity:

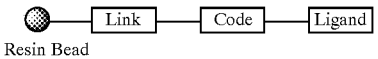

Resin Bead

Version 3: Mass only:

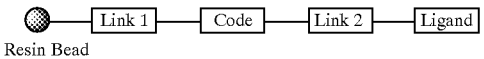

Resin Bead

Version 4: Mass and Intensity:

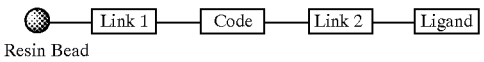

Resin Bead

In this approach and its variations, a code block most advantageously consists of a dimer, each of which unit has one, two or three discrete masses. For example a construct of the structure:

contains a code block having two mass blocks, $M_1$ and $M_2$, which in this example will be comprised of one, two or three amino acids. The amino acids are doped to give three discrete masses yielding, for example, Glycine ($G^0$), with a mass of 57, Glycine bearing $N^{15}$ ($G^1$) with a mass of 58 and Glycine bearing two Deuterium atoms ($G^2$) at carbon 2 with a mass of 59. Assembling these three moieties into 7 possible mass sets yields the following codes and their fractions of the total:

| Composition | Relative Presence |
|---|---|
| $G^0$ | 100% |
| $G^1$ | 100% |
| $G^2$ | 100% |
| $G^0G^1$ | 50% and 50% |
| $G^0G^2$ | 50% and 50% |
| $G^1G^2$ | 50% and 50% |
| $G^0G^1G^2$ | 33.3%, 33.3% and 33.3% |

It is now possible to assemble these mass sets into blocks $M_1$ and $M_2$ and to predict what the characteristic MS peak pattern will be for each code block. For this group of mass sets in Version 1 of the Bar Coding Approach, the following MS peak pattern is predicted:

| Code Sample | $M_1$ | $M_2$ | Predicted Peak Pattern, (AMU) | | | | |
|---|---|---|---|---|---|---|---|
| | | | 114 | 115 | 116 | 117 | 118 |
| 1 | 57 ($G^0$) | 57 ($G^0$) | ■ | | | | |
| 2 | 57 ($G^0$) | 57,58 ($G^0$),($G^1$) | ■ | ■ | | | |
| 3 | 57 ($G^0$) | 57,59 ($G^0$),($G^2$) | ■ | | ■ | | |
| 4 | 57 ($G^0$) | 57,58,59 ($G^0$),($G^1$),($G^2$) | ■ | ■ | ■ | | |
| 5 | 57,58 ($G^0$),($G^1$) | 57.59 ($G^0$),($G^2$) | ■ | ■ | ■ | ■ | |
| 6 | 57,59 ($G^0$),($G^2$) | 57,59 ($G^0$),($G^2$) | ■ | | ■ | | ■ |
| 7 | 57,59 ($G^0$),($G^2$) | 57,58,59 ($G^0$),($G^1$),($G^2$) | ■ | ■ | ■ | ■ | ■ |

In this table, for code sample 1 a single peak is predicted at 114, since the combined masses of each $G^0$ are 57+57=114. For code sample 2, two equal peaks are predicted at 114 and 115, since $G^0$ in $M_1$ plus $G^0$ in $M_2$ adds up to 114, and $G^0$ in $M_1$ plus $G^1$ in $M_2$ adds up to 115. In code sample 6, two single peaks are predicted at 114 and 118 and a redundancy is predicted at 116 to yield a peak approximately two times as tall as the peaks at 114 and 118.

Figure 1:
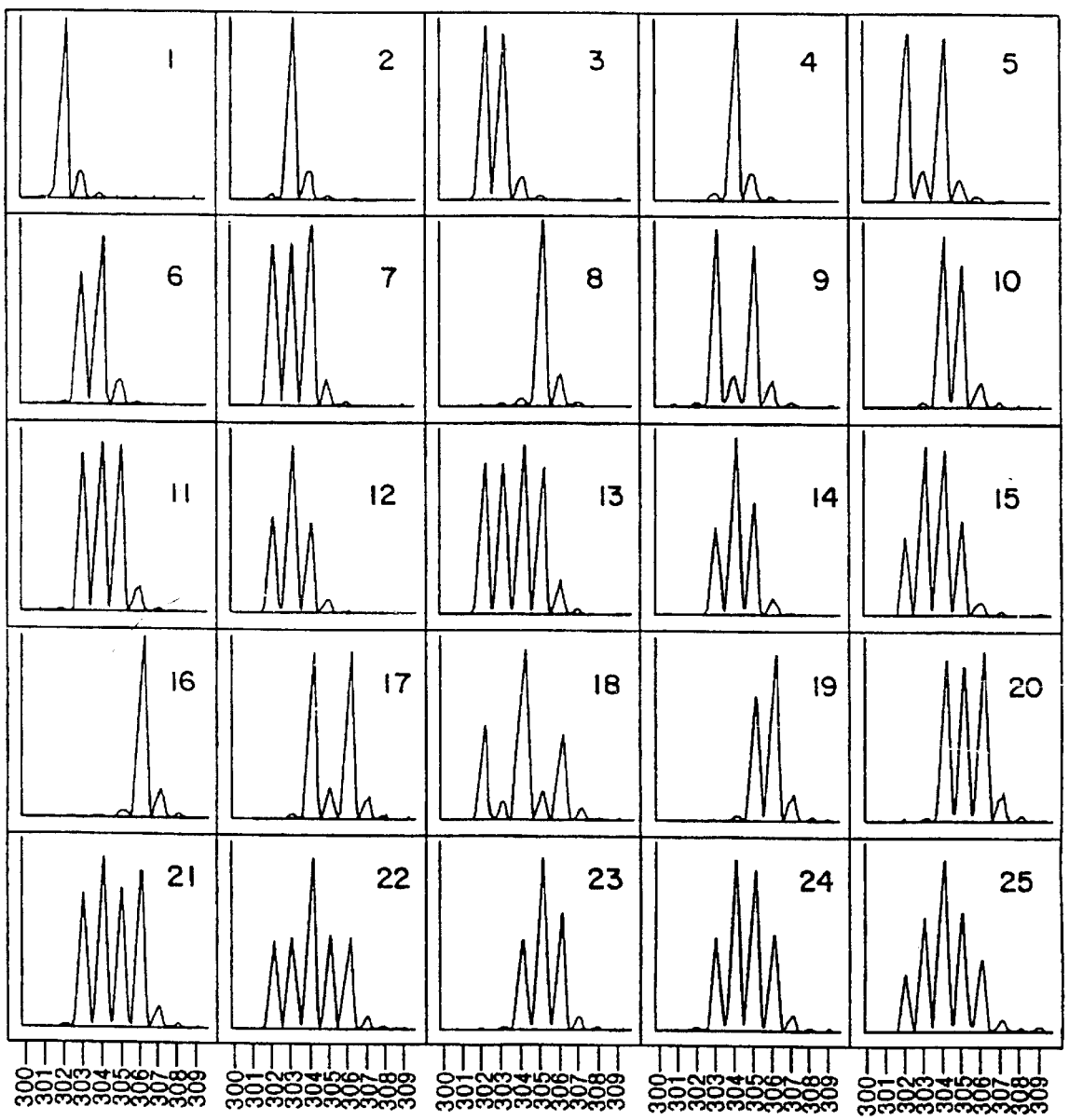
FIG. 1 is an array of MS peaks that represent the observed peak signatures for the doped glycine code blocks described in the specification below.

In the following table, predicted MS peak patterns are shown for 25 code samples. The actual MS peak patterns are shown below the predicted peak pattern table, and it can be seen that there is excellent correlation between observed and predicted peak patterns. References to $G^0$, $G^1$ and $G^2$ are omitted although the same three isotopically doped versions of Glycine described above are still being used in this table (Note that the numerical values for the MS in FIG. 1 are for the total mass of the entire construct, including a Lysine residue and the linkers, which fall into a range of 300 to 309 mass units)

| Code Sample | $M_1$ | $M_2$ | Predicted Peak Pattern, (AMU) | | | | |
|---|---|---|---|---|---|---|---|
| | | | 114 | 115 | 116 | 117 | 118 |
| 1 | 57 | 57 | ■ | | | | |
| 2 | 57 | 58 | | ■ | | | |
| 3 | 57 | 57,58 | ■ | ■ | | | |

-continued

| Code Sample | $M_1$ | $M_2$ | Predicted Peak Pattern, (AMU) | | | | |
|---|---|---|---|---|---|---|---|
| | | | 114 | 115 | 116 | 117 | 118 |
| 4 | 57 | 59 | | | ■ | | |
| 5 | 57 | 57,59 | ■ | | ■ | | |
| 6 | 57 | 58,59 | ■ | ■ | | | |
| 7 | 57 | 57,58,59 | ■ | ■ | ■ | | |
| 8 | 58 | 59 | | | | ■ | |
| 9 | 58 | 57,59 | ■ | | | ■ | |
| 10 | 59 | 57,58 | ■ | ■ | | | |
| 11 | 58 | 57,58,59 | ■ | ■ | | ■ | |
| 12 | 57,58 | 57,58 | | ■ | | | |
| 13 | 57,58 | 57,59 | ■ | ■ | ■ | ■ | |
| 14 | 57,58 | 58,59 | | | | ■ | |
| 15 | 57,58 | 57,58, 59 | ■ | ■ | ■ | ■ | ■ |
| 16 | 59 | 59 | | | | | ■ |
| 17 | 59 | 57,59 | | | ■ | | ■ |
| 18 | 57,59 | 57,59 | | ■ | | ■ | ■ |
| 19 | 59 | 58,59 | | | | ■ | ■ |
| 20 | 59 | 57,58,59 | | ■ | ■ | | ■ |
| 21 | 57,59 | 58,59 | ■ | ■ | ■ | ■ | |
| 22 | 57,59 | 57,58, 59 | | ■ | ■ | ■ | ■ |
| 23 | 58,59 | 58,59 | | | ■ | ■ | ■ |
| 24 | 58,59 | 57,58, 59 | ■ | ■ | ■ | ■ | ■ |
| 25 | 57,58,59 | 57,58, 59 | ■ | ■ | ■ | ■ | ■ |

Once the MS is run on a completed combinatorial synthesis sample, the pattern is compared to a predicted pattern, which in turn identifies the code, which in turn identifies the first pool monomer. The predicted patterns can form a type of machine readable bar code, which, using methods well known to those of ordinary skill in the optical scanning art, enables rapid data inputing, decoding and interpretation.

Other Encoding Strategies

It is possible to combine elements of one or all of the ratio, single peak, double peak or bar code methods to give code constructs. Code blocks don't have to be added into the front end of a construct-they can be added in at any point, assuming a suitable reagent is available, for example:

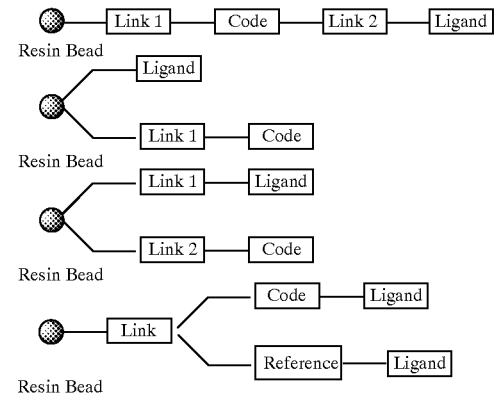

where isotope doping occurs at the bead link and attached to the end of a three monomer ligand, as indicated by the asterisk. Isotope doping could also be performed at the other end of the ligand as well.

In another alternative embodiment of the invention, since isotopes can be readily read by nuclear magnetic resonance (NMR), this can be used instead of, or in conjunction with, MS spectroscopy. NMR offers the advantages of greater accuracy (one can run ratio pools in increments of down to 1%), the bead does not have to be cleaved off of the construct prior to analysis, and that NMR, unlike MS, is non-destructive.

Other constructs can take the general non-limiting exemplary formulae:

FIGS. 133 to 286 display spectragrams associated with another variation of ratio encoding, which is a four peak ratio encoding scheme. In the following table, the first column represents the code block, the second column is an internal reference number, and the third, fourth, fifth and sixth columns represent the respective mole fractions of FMOC-protected alanines with different integral masses using isotope doping, i.e., $A^0$, $A^3$, $A^2$, and $A^1$ (A is a reference alanine, $A^3$ is alnine plus 3 atomic mass units, $A^2$ is alanine plus two atomic mass units, etc.).

1,111, 0.56, 0.16, 0.16, 0.16
2,112, 0.56, 0.16, 0.16, 0.21
3,113, 0.51, 0.11, 0.11, 0.26
4,114, 0.46, 0.11, 0.11, 0.31
5,115, 0.46, 0.11, 0.11, 0.36
6,116, 0.41, 0.11, 0.11, 0.41
7,121, 0.56, 0.16, 0.21, 0.16
8,122, 0.51, 0.11, 0.21, 0.21
9,123, 0.46, 0.11, 0.21, 0.26
10,124, 0.46, 0.11, 0.16, 0.31
11,125, 0.41, 0.11, 0.16, 0.36
12,126, 0.41, 0.11, 0.16, 0.41
13,131, 0.51, 0.11, 0.26, 0.11
14,132, 0.46, 0.11, 0.26, 0.21
15,133, 0.46, 0.11, 0.26, 0.26
16,134, 0.41, 0.11, 0.21, 0.31
17,135, 0.41, 0.11, 0.21, 0.31
18,136, 0.36, 0.11, 0.21, 0.36
19,141, 0.46, 0.11, 0.31, 0.11
20,142, 0.46, 0.11, 0.31, 0.16
21,143, 0.41, 0.11, 0.31, 0.21
22,144, 0.41, 0.11, 0.26, 0.26
23,145, 0.36, 0.11, 0.26, 0.31
24,146, 0.36, 0.11, 0.26, 0.36
25,151, 0.46, 0.11, 0.36, 0.11
26,152, 0.41, 0.11, 0.36, 0.16
27,153, 0.41, 0.11, 0.31, 0.21
28,154, 0.36, 0.11, 0.31, 0.26
29,155, 0.36, 0.11, 0.31, 0.31
30,156, 0.31, 0.11, 0.26, 0.31
31,161, 0.41, 0.11, 0.41, 0.11
32,162, 0.41, 0.11, 0.41, 0.16
33,163, 0.36, 0.11, 0.36, 0.21
34,164, 0.36, 0.11, 0.36, 0.26
35,165, 0.31, 0.11, 0.31, 0.26
36,166, 0.31, 0.11, 0.31, 0.31
37,211, 0.56, 0.21, 0.16, 0.16
38,212, 0.51, 0.21, 0.11, 0.21
39,213, 0.46, 0.21, 0.11, 0.26
40,214, 0.46, 0.16, 0.11, 0.31
41,215, 0.41, 0.16, 0.11, 0.36
42,216, 0.41, 0.16, 0.11, 0.41
43,221, 0.51, 0.21, 0.21, 0.11
44,222, 0.46, 0.21, 0.21, 0.21
45,223, 0.46, 0.16, 0.16, 0.26
46,224, 0.41, 0.16, 0.16, 0.31
47,225, 0.41, 0.16, 0.16, 0.31
48,226, 0.36, 0.16, 0.16, 0.36
49,231, 0.46, 0.21, 0.26, 0.11
50,232, 0.46, 0.16, 0.26, 0.16
51,233, 0.41, 0.16, 0.21, 0.21
52,234, 0.41, 0.16, 0.21, 0.26
53,235, 0.36, 0.16, 0.21, 0.31
54,236, 0.36, 0.16, 0.21, 0.36
55,241, 0.46, 0.16, 0.31, 0.11
56,242, 0.41, 0.16, 0.31, 0.16
57,243, 0.41, 0.16, 0.26, 0.21
58,244, 0.36, 0.16, 0.26, 0.26
59,245, 0.36, 0.16, 0.26, 0.31
60,246, 0.31, 0.16, 0.26, 0.31
61,251, 0.41, 0.16, 0.36, 0.11
62,252, 0.41, 0.16, 0.31, 0.16
63,253, 0.36, 0.16, 0.31, 0.21
64,254, 0.36, 0.16, 0.31, 0.26
65,255, 0.31, 0.16, 0.26, 0.26
66,256, 0.31, 0.11, 0.26, 0.31
67,261, 0.41, 0.16, 0.41, 0.11
68,262, 0.36, 0.16, 0.36, 0.16
69,263, 0.36, 0.16, 0.36, 0.21
70,264, 0.31, 0.16, 0.31, 0.26
71,265, 0.31, 0.11, 0.31, 0.26
72,266, 0.31, 0.11, 0.31, 0.31
73,311, 0.51, 0.26, 0.11, 0.11
74,312, 0.46, 0.26, 0.11, 0.21
75,313, 0.46, 0.26, 0.11, 0.26
76,314, 0.41, 0.21, 0.11, 0.31
77,315, 0.41, 0.21, 0.11, 0.31
78,316, 0.36, 0.21, 0.11, 0.36
79,321, 0.46, 0.26, 0.21, 0.11
80,322, 0.46, 0.26, 0.16, 0.16
81,323, 0.41, 0.21, 0.16, 0.21
82,324, 0.41, 0.21, 0.16, 0.26
83,325, 0.36, 0.21, 0.16, 0.31
84,326, 0.36, 0.21, 0.16, 0.36
85,331, 0.46, 0.26, 0.26, 0.11
86,332, 0.41, 0.21, 0.21, 0.16
87,333, 0.41, 0.21, 0.21, 0.21
88,334, 0.36, 0.21, 0.21, 0.26
89,335, 0.36, 0.21, 0.21, 0.31
90,336, 0.31, 0.21, 0.21, 0.31
91,341, 0.41, 0.21, 0.31, 0.11
92,342, 0.41, 0.21, 0.26, 0.16
93,343, 0.36, 0.21, 0.26, 0.21
94,344, 0.36, 0.21, 0.26, 0.26
95,345, 0.31, 0.21, 0.26, 0.26
96,346, 0.31, 0.16, 0.21, 0.31
97,351, 0.41, 0.21, 0.31, 0.11
98,352, 0.36, 0.21, 0.31, 0.16
99,353, 0.36, 0.21, 0.31, 0.21
100,354, 0.31, 0.21, 0.26, 0.26
101,355, 0.31, 0.16, 0.26, 0.26
102,356, 0.31, 0.16, 0.26, 0.31
103,361, 0.36, 0.21, 0.36, 0.11
104,362, 0.36, 0.21, 0.36, 0.16
105,363, 0.31, 0.21, 0.31, 0.21
106,364, 0.31, 0.16, 0.31, 0.21
107,365, 0.31, 0.16, 0.31, 0.26
108,366, 0.31, 0.16, 0.31, 0.31
109,411, 0.46, 0.31, 0.11, 0.11
110,412, 0.46, 0.31, 0.11, 0.16
111,413, 0.41, 0.31, 0.11, 0.21
112,414, 0.41, 0.26, 0.11, 0.26
113,415, 0.36, 0.26, 0.11, 0.31
114,416, 0.36, 0.26, 0.11, 0.36
115,421, 0.46, 0.31, 0.16, 0.11
116,422, 0.41, 0.31, 0.16, 0.16
117,423, 0.41, 0.26, 0.16, 0.21
118,424, 0.36, 0.26, 0.16, 0.26
119,425, 0.36, 0.26, 0.16, 0.31
120,426, 0.31, 0.26, 0.16, 0.31
121,431, 0.41, 0.31, 0.21, 0.11
122,432, 0.41, 0.26, 0.21, 0.16
123,433, 0.36, 0.26, 0.21, 0.21
124,434, 0.36, 0.26, 0.21, 0.26
125,435, 0.31, 0.26, 0.21, 0.26
126,436, 0.31, 0.21, 0.16, 0.31
127,441, 0.41, 0.26, 0.26, 0.11
128,442, 0.36, 0.26, 0.26, 0.16
129,443, 0.36, 0.26, 0.26, 0.21

130,444, 0.31, 0.26, 0.26, 0.26
131,445, 0.31, 0.21, 0.21, 0.26
132,446, 0.31, 0.21, 0.21, 0.31
133,451, 0.36, 0.26, 0.31, 0.11
134,452, 0.36, 0.26, 0.31, 0.16
135,453, 0.31, 0.26, 0.26, 0.21
136,454, 0.31, 0.21, 0.26, 0.21
137,455, 0.31, 0.21, 0.26, 0.26
138,456, 0.31, 0.21, 0.26, 0.31
139,461, 0.36, 0.26, 0.36, 0.11
140,462, 0.31, 0.26, 0.31, 0.16
141,463, 0.31, 0.21, 0.31, 0.16
142,464, 0.31, 0.21, 0.31, 0.21
143,465, 0.31, 0.21, 0.31, 0.26
144,466, 0.26, 0.21, 0.26, 0.26

In the following table, each of the enumerated code blocks listed immediately above is correlated with a spectragram number identified in the second column and shown on the face of each respective spectra in the figures.

| Code Block | Spectra Identifying Number |
|---|---|
| 1 | ASA 008683 |
| 2 | ASA 008684 |
| 3 | ASA 008685 |
| 4 | ASA 008686 |
| 5 | ASA 008687 |
| 6 | ASA 008688 |
| 7 | ASA 008689 |
| 8 | ASA 008690 |
| 9 | ASA 008691 |
| 10 | ASA 008692 |
| 11 | ASA 008693 |
| 12 | ASA 008694 |
| 13 | ASA 008695 |
| 14 | ASA 008696 |
| 15 | ASA 008697 |
| 16 | ASA 008698 |
| 17 | ASA 008699 |
| 18 | ASA 008700 |
| 19 | ASA 008701 |
| 20 | ASA 008702 |
| 21 | ASA 008703 |
| 22 | ASA 008704 |
| 23 | ASA 008705 |
| 24 | ASA 008706 |
| 25 | ASA 008707 |
| 26 | ASA 008708 |
| 27 | ASA 008709 |
| 28 | ASA 008710 |
| 29 | ASA 00871I |
| 30 | ASA 008712 |
| 31 | ASA 008713 |
| 32 | ASA 008714 |
| 33 | ASA 008715 |
| 34 | ASA 008716 |
| 35 | ASA 008717 |
| 36 | ASA 008718 |
| 37 | ASA 008719 |
| 38 | ASA 008720 |
| 39 | ASA 008721 |
| 40 | ASA 008722 |
| 41 | ASA 008723 |
| 42 | ASA 008724 |
| 43 | ASA 008725 |
| 44 | ASA 008726 |
| 45 | ASA 008727 |
| 46 | ASA 008728 |
| 47 | ASA 008729 |
| 48 | ASA 008730 |
| 49 | ASA 008731 |
| 50 | ASA 008732 |
| 51 | ASA 008733 |
| 52 | ASA 008734 |
| 53 | ASA 008735 |
| 54 | ASA 008736 |
| 55 | ASA 008737 |
| 56 | ASA 008738 |
| 57 | ASA 008739 |
| 58 | ASA 008740 |
| 59 | ASA 008741 |
| 60 | ASA 008742 |
| 61 | ASA 008743 |
| 62 | ASA 008744 |
| 63 | ASA 008745 |
| 64 | ASA 008746 |
| 65 | ASA 008747 |
| 66 | ASA 008748 |
| 67 | ASA 008749 |
| 68 | ASA 008750 |
| 69 | ASA 008751 |
| 70 | ASA 008752 |
| 71 | ASA 008753 |
| 72 | ASA 008754 |
| 73 | ASA 008755 |
| 74 | ASA 008756 |
| 75 | ASA 008757 |
| 76 | ASA 008758 |
| 77 | ASA 008759 |
| 78 | ASA 008760 |
| 79 | ASA 008761 |
| 80 | ASA 008762 |
| 81 | ASA 008763 |
| 82 | ASA 008764 |
| 83 | ASA 008765 |
| 84 | ASA 008766 |
| 85 | ASA 008767 |
| 86 | ASA 008768 |
| 87 | ASA 008769 |
| 88 | ASA 008770 |
| 89 | ASA 008771 |
| 90 | ASA 008772 |
| 91 | ASA 008773 |
| 92 | ASA 008774 |
| 93 | ASA 008775 |
| 94 | ASA 008776 |
| 95 | ASA 008777 |
| 96 | ASA 008778 |
| 97 | ASA 008779 |
| 98 | ASA 008780 |
| 99 | ASA 008781 |
| 100 | ASA 008782 |
| 101 | ASA 008783 |
| 102 | ASA 008784 |
| 103 | ASA 008785 |
| 104 | ASA 008786 |
| 105 | ASA 008787 |
| 106 | ASA 008788 |
| 107 | ASA 008789 |
| 108 | ASA 008790 |
| 109 | ASA 008791 |
| 110 | ASA 008792 |
| 111 | ASA 008793 |
| 112 | ASA 008794 |
| 113 | ASA 008795 |
| 114 | ASA 008796 |
| 115 | ASA 008797 |
| 116 | ASA 008798 |
| 117 | ASA 008799 |
| 118 | ASA 008800 |
| 119 | ASA 008801 |
| 120 | ASA 008802 |
| 121 | ASA 008803 |
| 122 | ASA 008804 |
| 123 | ASA 008805 |
| 124 | ASA 008806 |
| 125 | ASA 008807 |
| 126 | ASA 008808 |
| 127 | ASA 008809 |
| 128 | ASA 008810 |
| 129 | ASA 008811 |

| Code Block | Spectra Identifying Number |
|---|---|
| 130 | ASA 008812 |
| 131 | ASA 008813 |
| 132 | ASA 008814 |
| 133 | ASA 008815 |
| 134 | ASA 008816 |
| 135 | ASA 008817 |
| 136 | ASA 008818 |
| 137 | ASA 008819 |
| 138 | ASA 008820 |
| 139 | ASA 008821 |
| 140 | ASA 008822 |
| 141 | ASA 008823 |
| 142 | ASA 008824 |
| 143 | ASA 008825 |
| 144 | ASA 008826 |

While in principle any number of codes can be generated, the greatest utility is achieved by minimizing the size of the encoding unit, which will likewise minimize the chemical investment in it.

EXAMPLE 2

Three Commercially Available (Isotopically Doped Bromoacetic Acids Provide Three Encoding Moieties

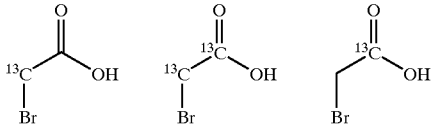

The following synthesis scheme illustrates one variant of the ratio approach. 21 Pools of bromoacetic acid, each having ratios of $C^{12}$ to $C^{13}$ that progress in 5% increments of from 0% to 100% of each are prepared, in this case with the isotope doping occuring at the number one carbon only.

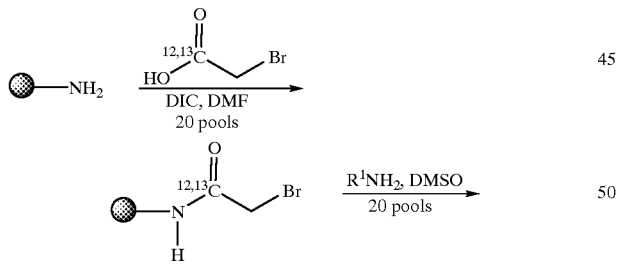

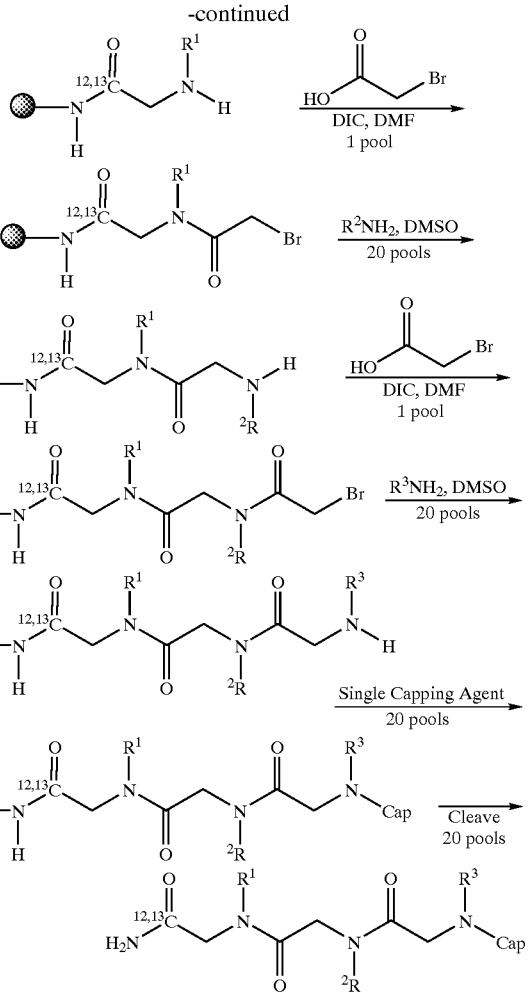

The $R^1$ moiety is encoded by the $C^{12}$ to $C^{13}$ ratio sample, the $R^3$ is encoded by the pool number from $R^3$ was taken, and the $R^2$ moiety is encoded by subtraction of the known $R^1$ and $R^3$ masses from the total construct mass.

EXAMPLE 3

Ana Example of Isotope Encoding Using the $N^{14,15}$ Isotope Ratio in the Form of a Reagent—$N^{14,}{}_{15}H_4OAc$

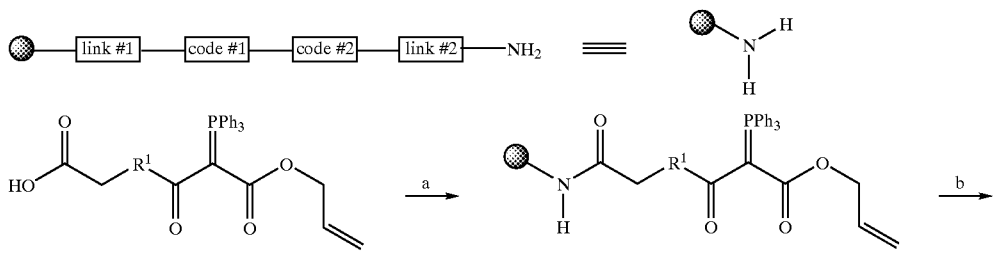

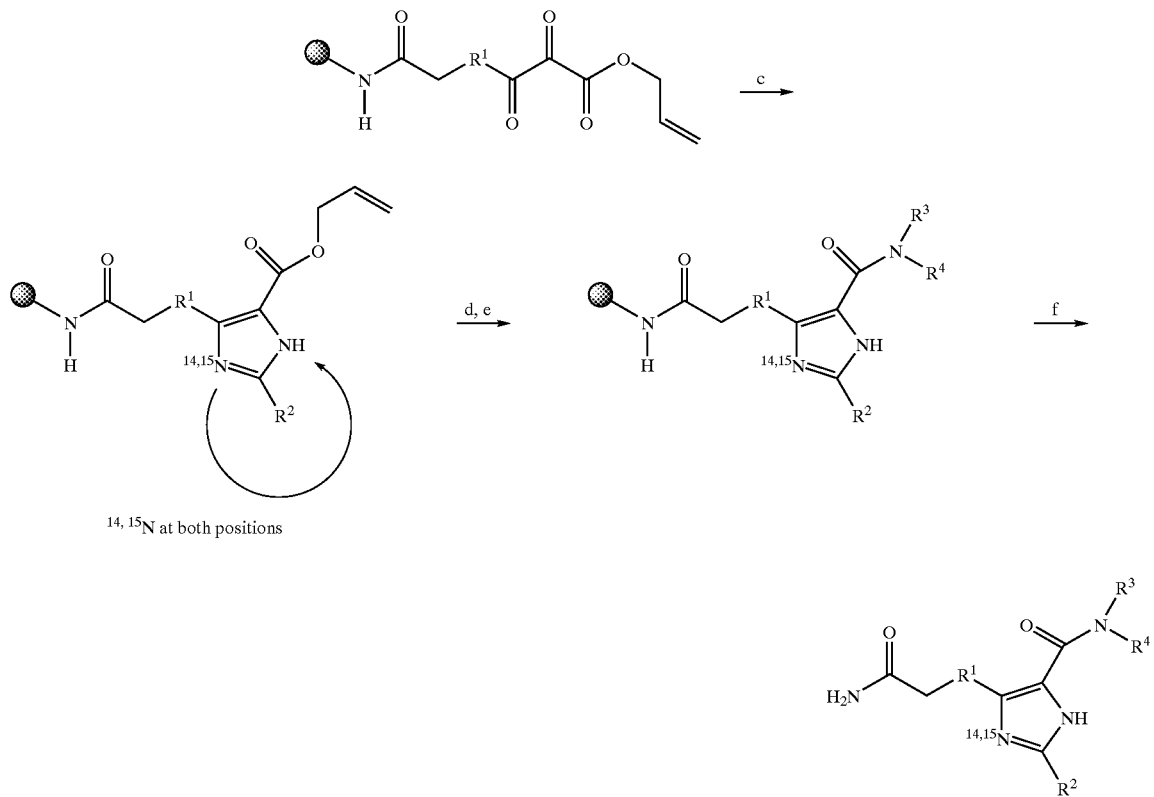

(a) Encoded resin, 1-hydroxy-7-azabenzotriazole, diisopropylcarbodiimide, DMF; (b) trans-(±)-3-phenyl-2-(phenylsulfonyl)-oxaziridine, CHCl$_3$; (c) Aldehyde, (X%:Y%) $^{14}$NH$_4$OAc: $^{15}$NH$_4$OAc, AcOH/CHCl$_3$ (50:50); (d) (i) Pd(PPh$_3$)$_4$, CHCl$_3$/4-methylmorphline/AcOH (90:5:5), (ii) sodium diethyldithiocarbamate/diisopropylethylamine/DMF (99:0.5:0.5); (e) Amine, PyBOP, diisopropylethylamine,DMF; (f) TFA/H$_2$O (95:5)

EXAMPLE 4

An Example of Isotope Encoding Using the $^{1,2}$H Isotope Ratio in the Form of a Reagent—NaCNBD$_4$ This example incorporates by reference the disclosure of Lebi, M. et al., *Drug Development and Research* 1994,33, 146–156)

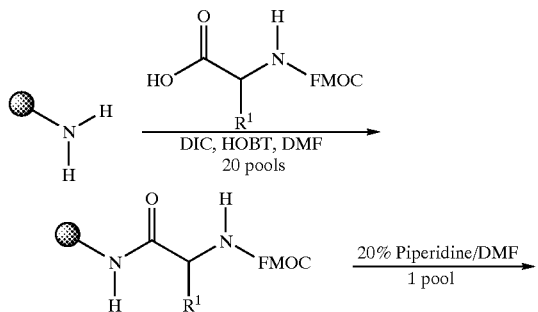

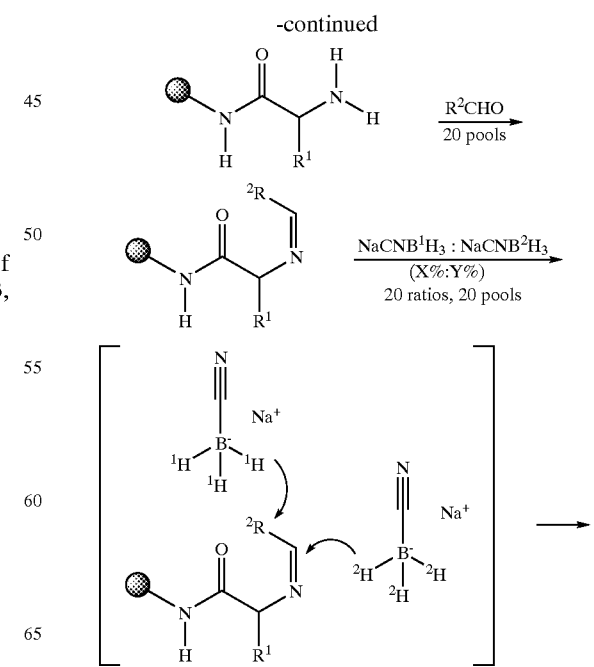

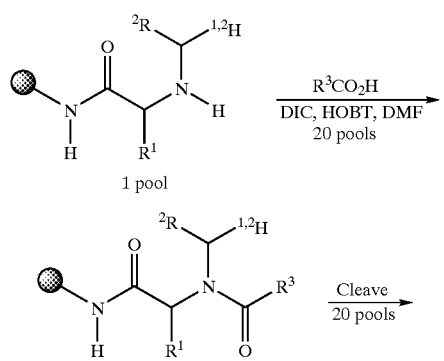
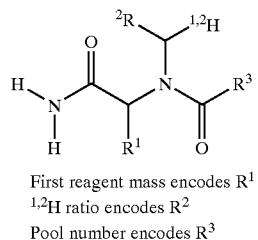
First reagent mass encodes R[1]
$^{1,2}$H ratio encodes R[2]
Pool number encodes R[3]
EXAMPLE 5
Encoding Using Four Possible Diastereomers of Link 1, Code 2, and Link 2
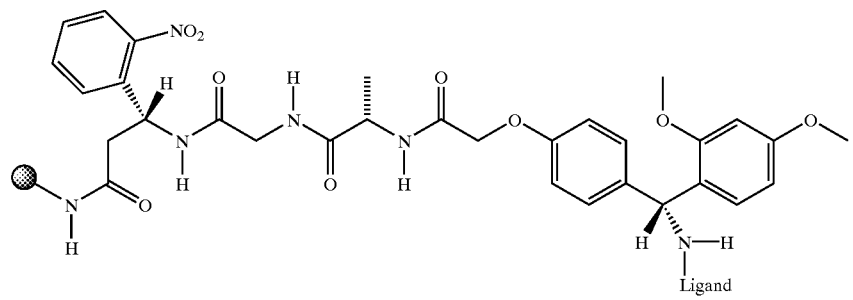
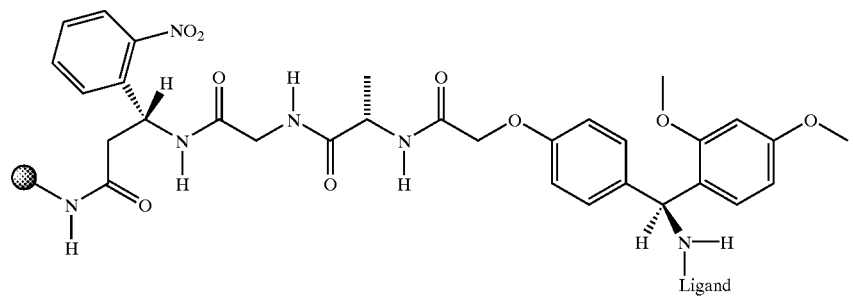
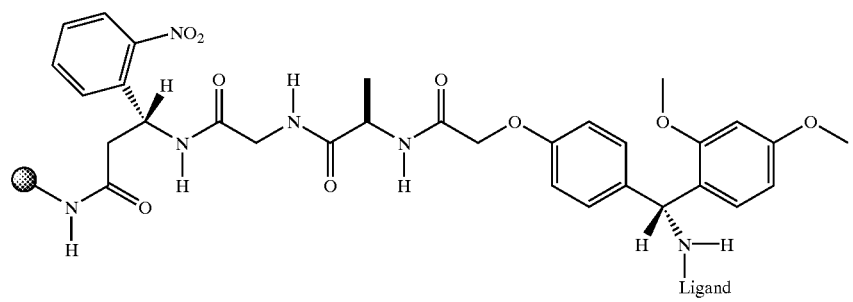
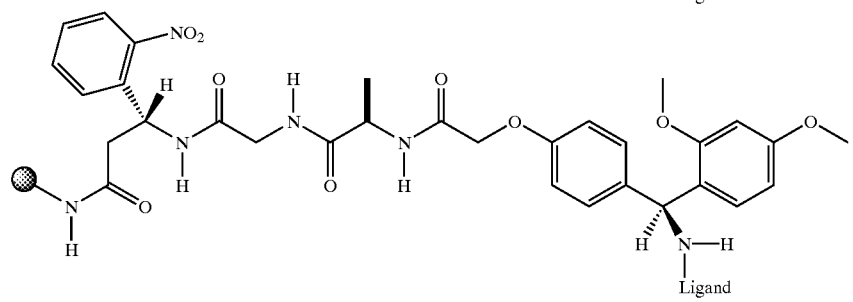

EXAMPLE 6
An Example of Isotope Encoding Using the $H^{1,2}$ Isotope Ratio in the Form of a Reagent—$NaCNBD_4$
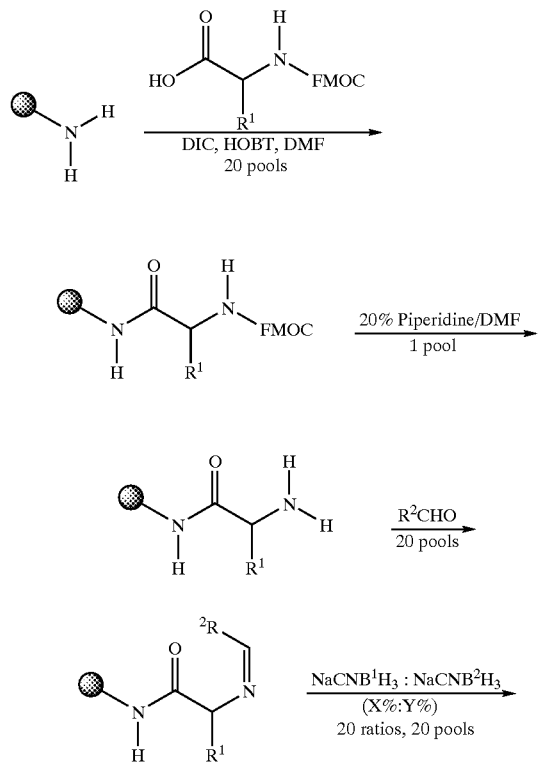
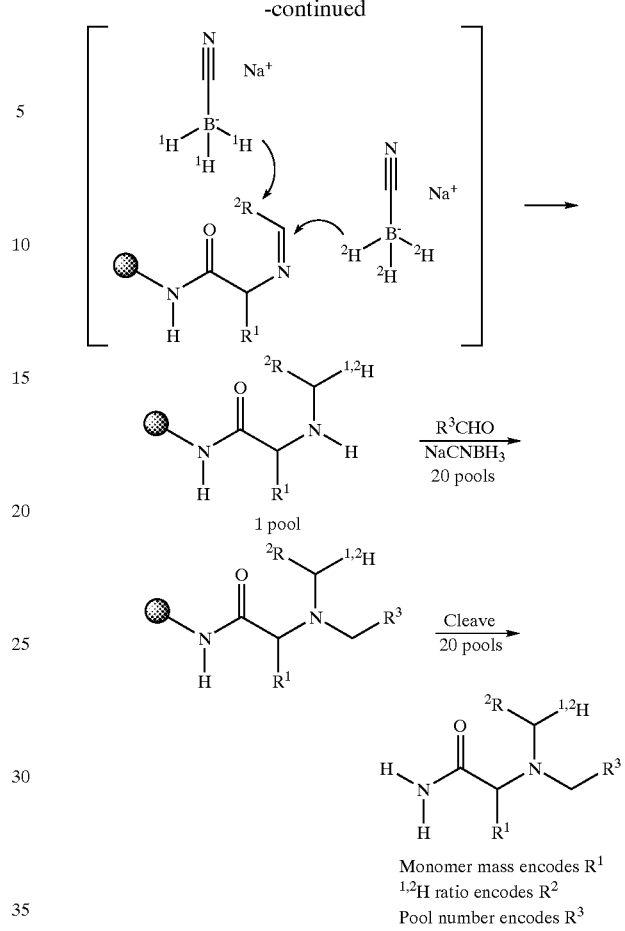
Monomer mass encodes $R^1$
$^{1,2}H$ ratio encodes $R^2$
Pool number encodes $R^3$
Scheme for Examples 7 through 13
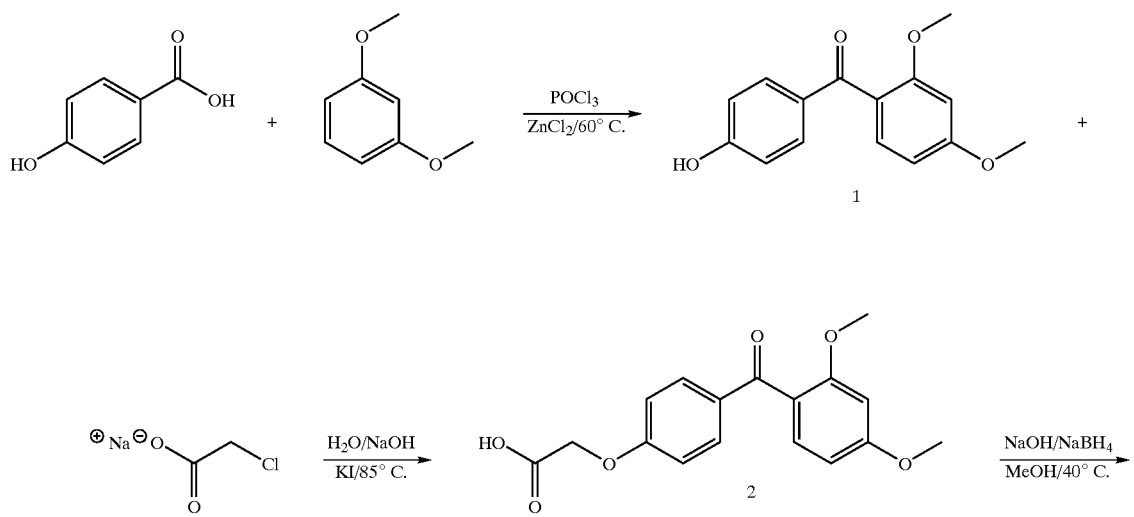

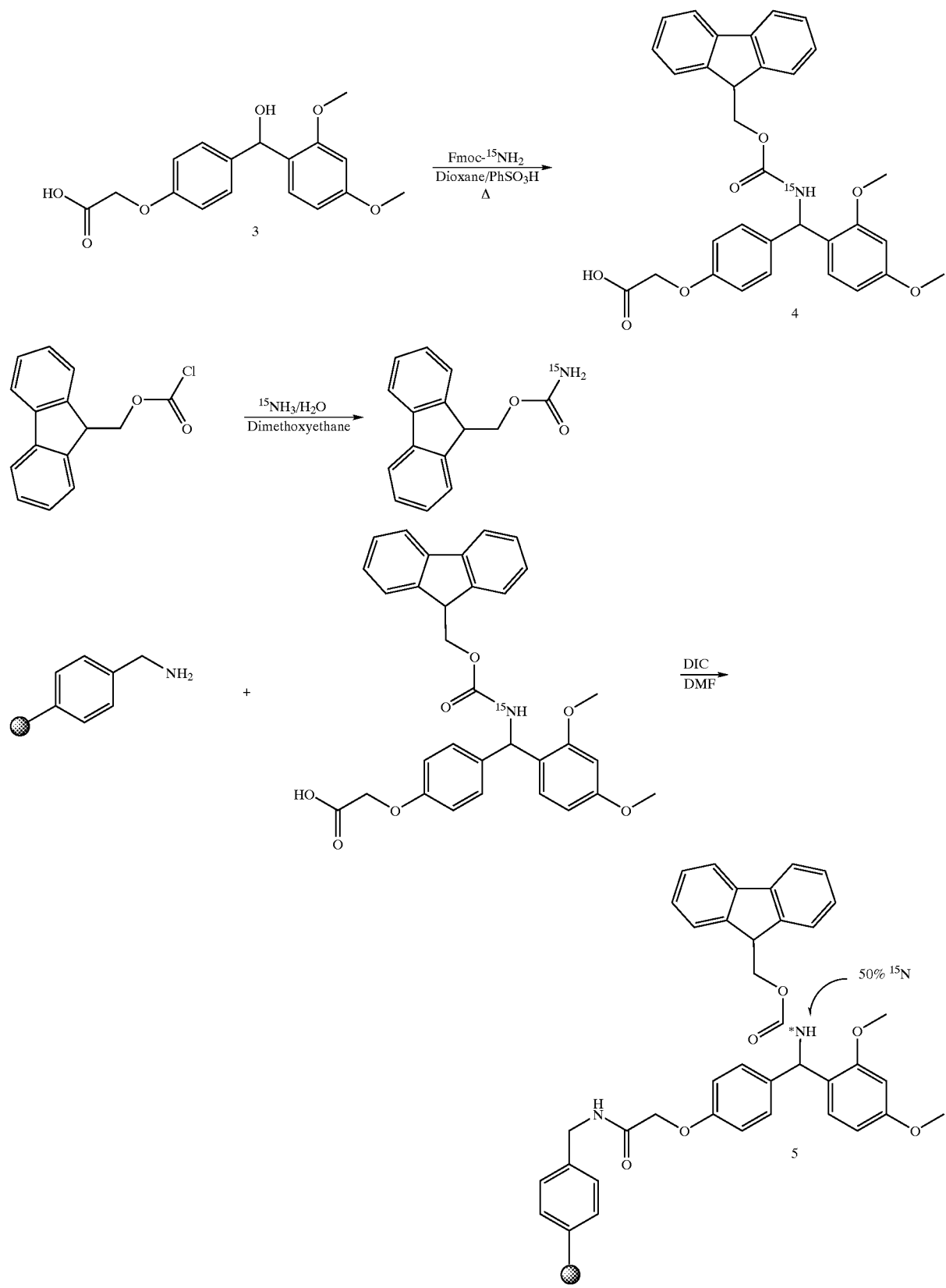

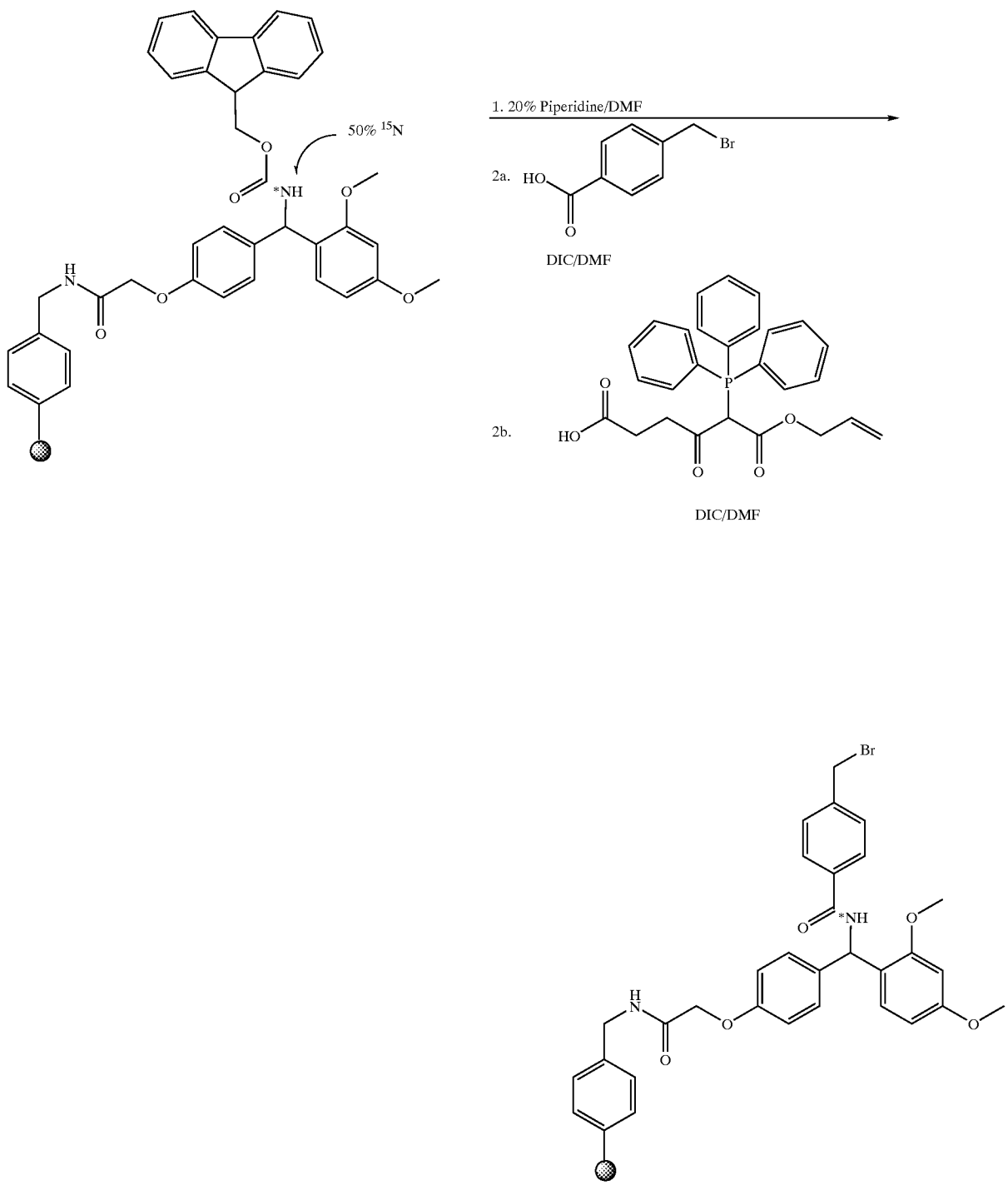

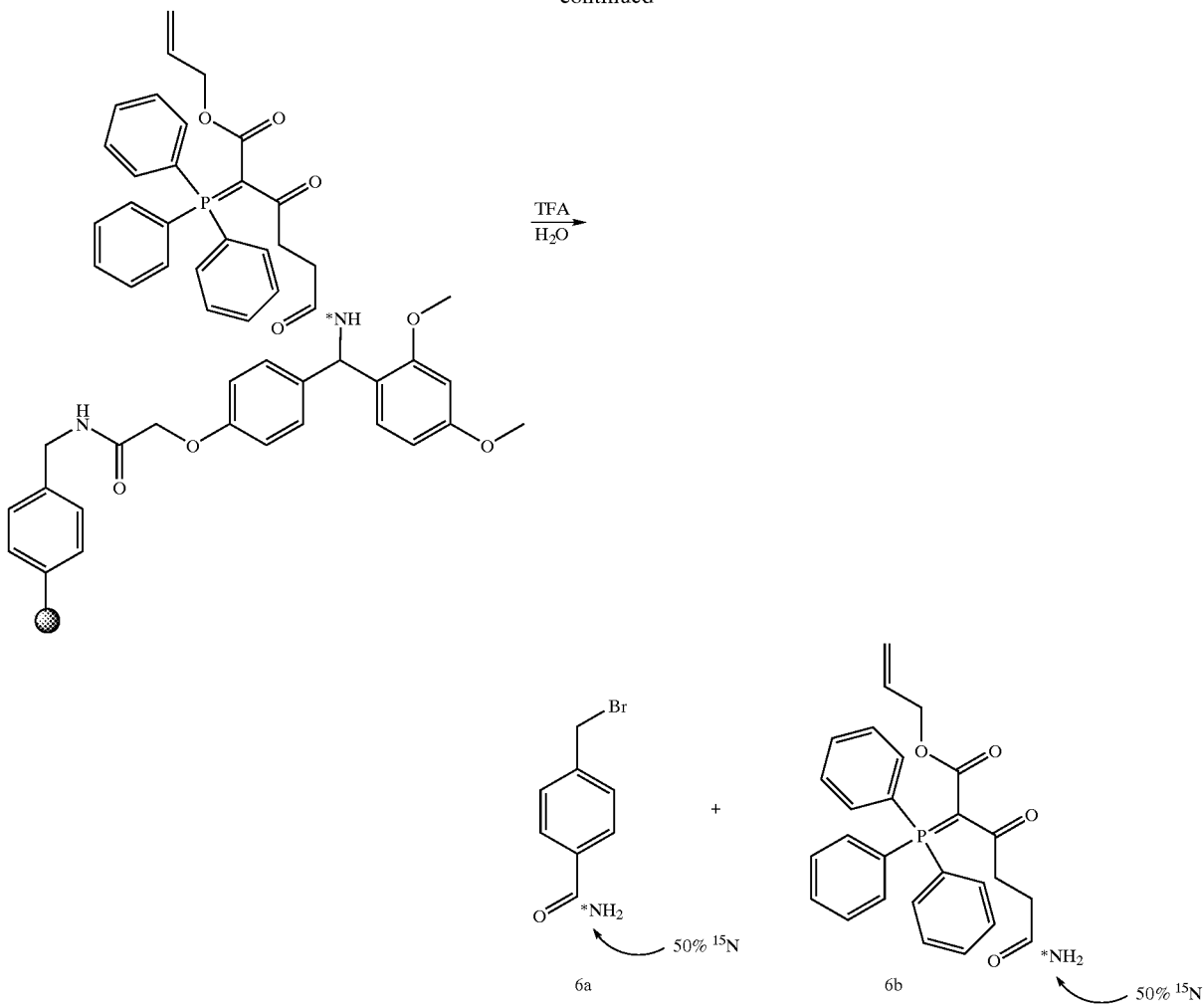

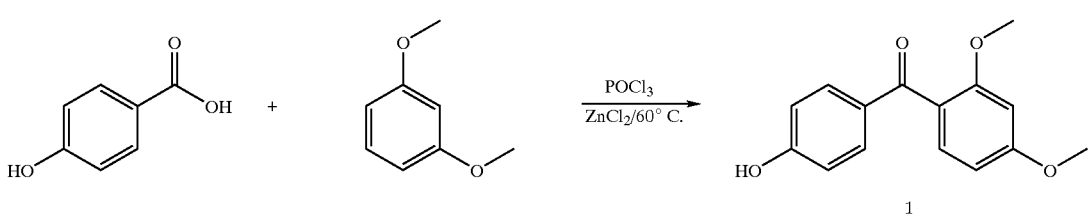

Example 7

1- In a 500 ml three-neck round-bottom flask, charged with a stir bar, fitted with a reflux condensor, and 60 ml addition funnel (under nitrogen), was placed 50.5 g 4-hydroxybenzoic acid, and 95 ml 1,3-dimethoxybenzene. 123.33 g zinc chloride was added and the mixture was heated to 60° with an oil bath. 126 ml phosphorus oxychloride was added drop-wise over approx. 30 min. After addition, the reaction ran for 90 min. at 60°. The dark red mixture was poured over 1.5 L of ice (under heavy mixing), and to this was added 276 g sodium carbonate, in small portions (significant gas evolution was observed). 400 ml ethyl acetate was added and the aqueous was extracted with another 500 ml ethyl acetate. The organics were combined and washed twice with brine and dried over mag. sulfate, filtered, and concentrated in vacuo at 40°, and further dried under vacuum to give 142.2 g of a redish-pink solid. The solid was tritrated with 400 ml hot hexane, filtered, and dried to give 63.3 g of a pink solid. Recrystalization from 75 ml hot methanol gave a first crop yield of pure 2,4-dimethoxy-4-hydroxy-benzophenone (1) as a light-pink solid (21.9%).

EXAMPLE 8

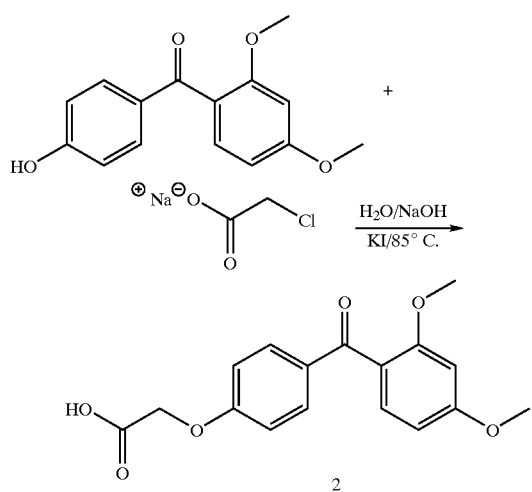

2- In a 500 ml recovery flask was added 20.043 g of 2,4-dimethoxy-4-hydroxy-benzophenone, 150 ml water, 0.75 g potassium iodide, and 82.5 g sodium chloroacetate. The mixture was then heated to 85° in an oil bath. To the mixture was added 50% NaOH (w/v) in small amounts, to maintain the pH at 11–14. The reaction was followed by TLC (2/5 methanol/methylene chloride) until the reaction was complete (3 hrs). The reaction solution was transfered to a 500 ml erlenmyer flask, while still hot, and cooled to room temp. 150 ml ethyl acetate was added and the solution was acidified to pH 2 with conc. HCl. The solution mixed overnight. The large amount of white precipitate was filtered and washed 3 x 50 ml water. The off-white solid was dried under vacuum to give a first crop yield of 16.17 g pure 2 (66%)

EXAMPLE 9

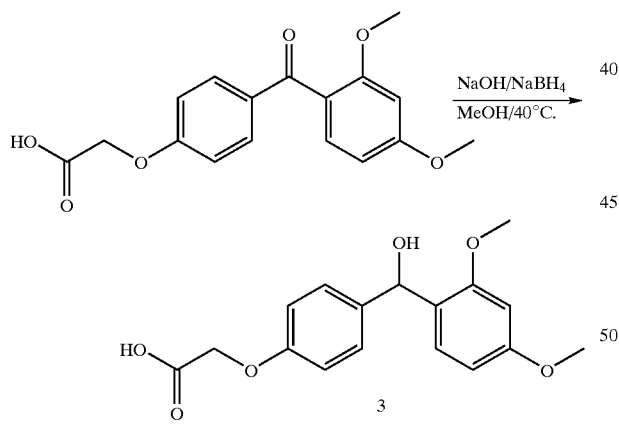

EXAMPLE 10

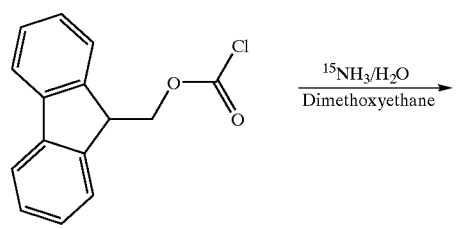

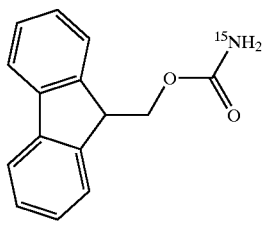

In a 200 ml recovery flask was placed 10.0 g of Fmoc-Cl, which was disolved in 100 ml of 80% dimethoxyethane. To this mixture was added approx. 35 ml of 10% $^{15}$N-ammonia in water. A white precipitate began to form. The pH of the mixture was brought to 7-9. The reaction was allowed to proceed for 30 min.

The reaction was acidified with 12N HCl and the white solid was filtered off and air dried. Further drying under vacuum gave a first crop yield of 8.072 g pure Fmoc-$^{15}$NH$_2$ as a white crystaline solid.

EXAMPLE 11

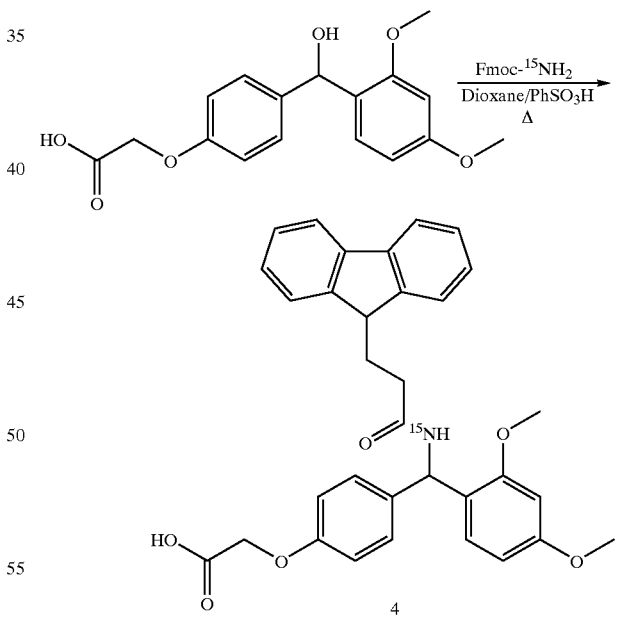

4 - In the 100 ml recovery flask used to dry 3 was added 20 ml dioxane, 0.75 g Fmoc-$^{15}$NH$_2$ and o.25 g benzenesulfonic acid. The reaction was heated to 40° C. for 18 hrs. A large amount of light gray precipitate was noted. The mixture was added to water and the light brown solid was filtered and purified by flash col. chromatography (100% ethyl acetate, then 98% ethyl acetate/acetic acid) to give 0.37 g of pure 4 as a light-brown oil.

EXAMPLE 12

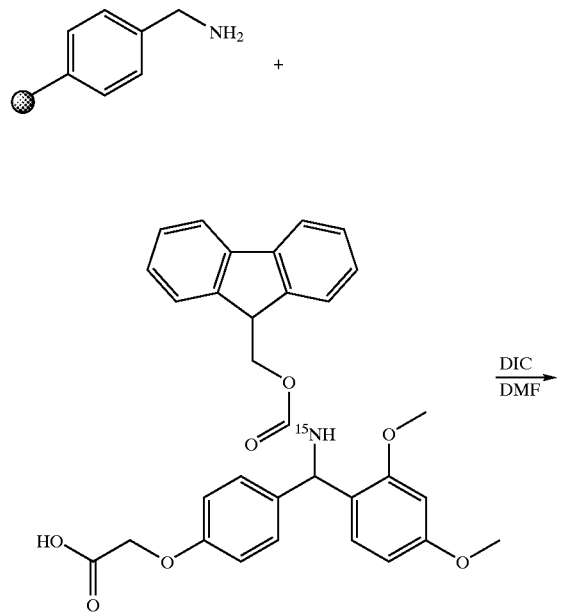

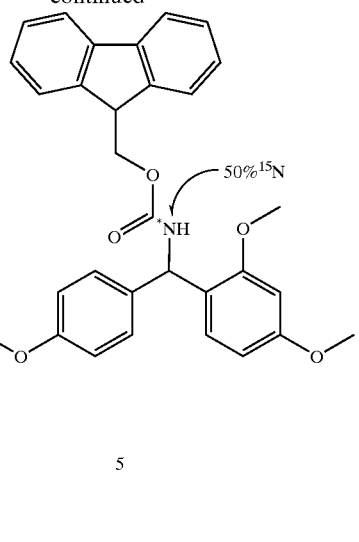

5- In a 10 ml shaker tube was placed 0.50 g of aminomethylated polystyrene (0.21 mmol/g). To the resin was added a solution of 0.1845 g 4 [15]N-Knorr linker and 0.184 g commercial [14]N-Knorr linker in 5 ml DMF, and 0.164 ml diisopropylcarbodiimide. The coupling ran on a shaker for 5 hrs. The coupling solution was filtered off, and the resin was washed with DMF and CH2Cl2, and dried under vacuum (ninhydrin negative) to provide 5.

EXAMPLE 13

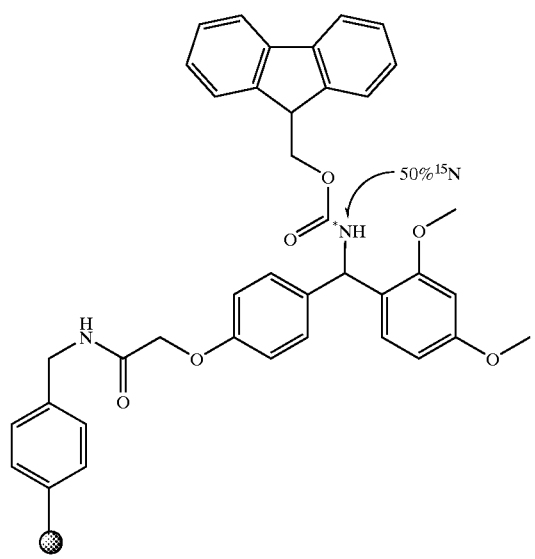

1. 20% Piperidine/DMF

2a. 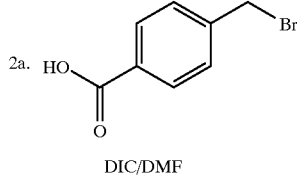
DIC/DMF

2b. 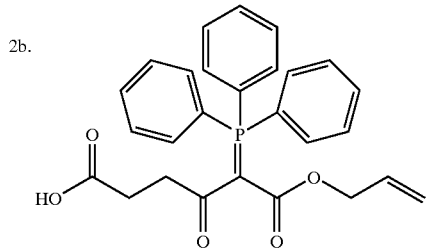
DIC/DMF

-continued

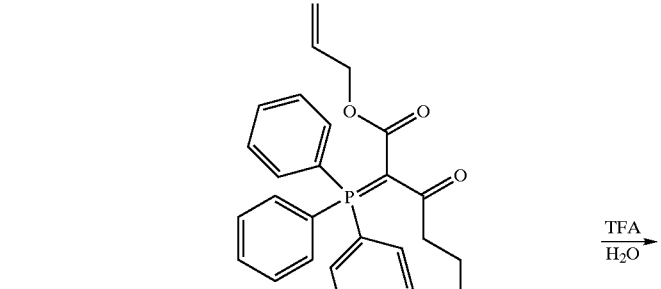

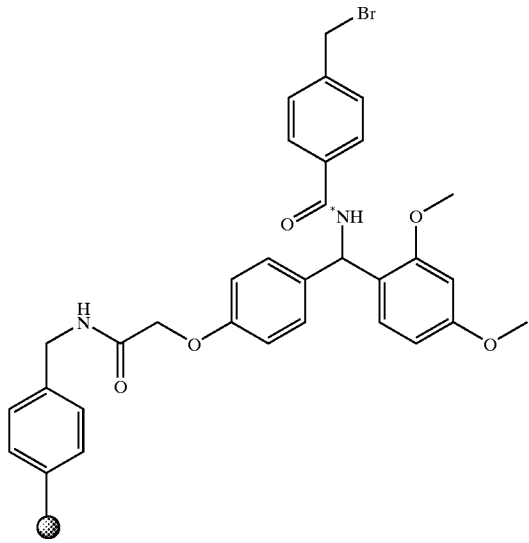

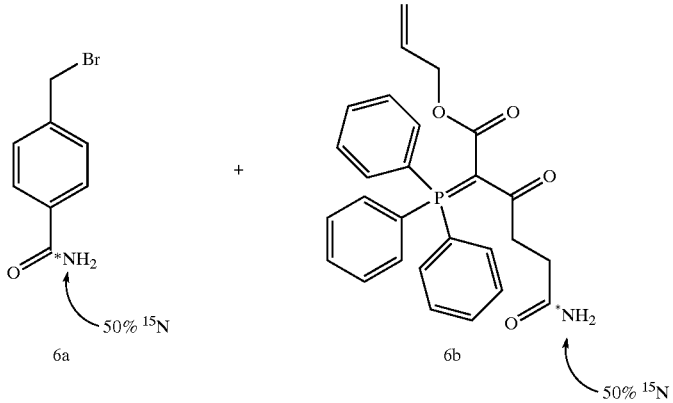

6a & 6b - In two 5 ml shaker tubes, each with approx 10 mg of resin 5, 2 x 4 ml of 20% piperidine/DMF was added to both. Both were then washed with DMF (ninhydrin pos). To the first shaker was added 0.0246 g of 4-bromomethyl benzoicacid, 0.05 ml DIC, in 1.0 ml DMF. To the second was added 0.0168 of the ylide-acid, 0.05 ml DIC, in 1.0 ml DMF. Each reaction ran on a shaker overnight. The resins were washed with DMF, methylene chloride, and dried under vacuum (ninhydrin negative). To the dry resins was added 1.0 ml of 95% TFA/water and the cleavage ran for 1 hr. Filtered the solutions and concentrated to give 6a and 6b. ESI-MS showed an approx. 46% $^{15}$N ratio.

EXAMPLE 14

Preparation of Mass-labeled Photocleavable Linkers

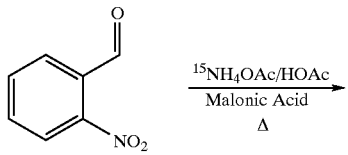

-continued

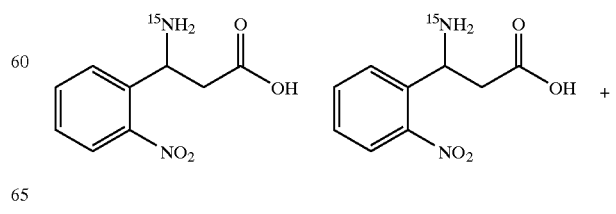

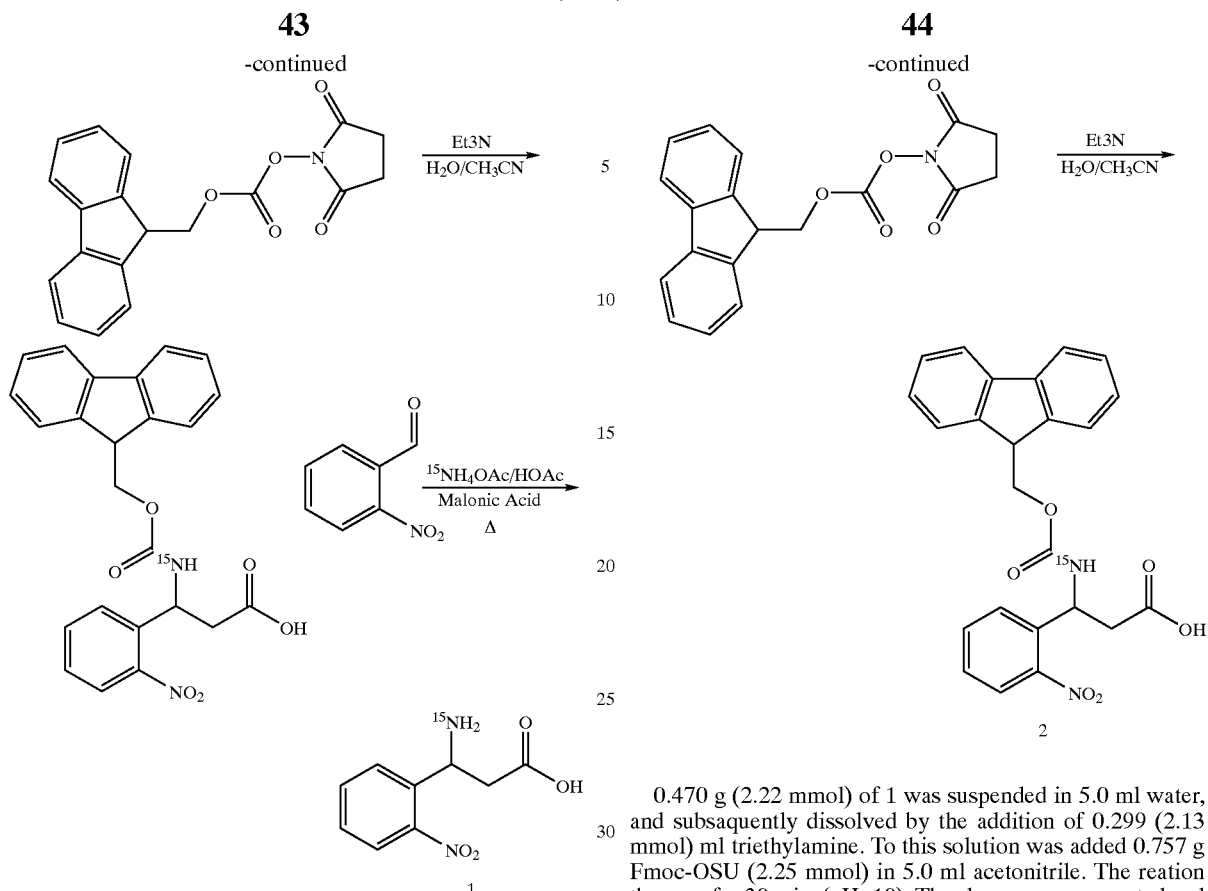

EXAMPLE 15

Ratio Codes

1—A solution of 1.511 g 2-Nitrobenzaldehyde (10.0 mmol), 1.563 g malonic acid (15.0 mmol), 2.00 g 15N (98%)-ammonium acetate (25.6 mmol), in 5.0 ml acetic acid (99.999%) was heated to 100° with an oil bath. As noted in the Oelschläger experimental, during heating there was a temporary, almost colorless precipitate (ammonium salt of the benzyliden compound). After 5 hours of heating; 8.0 ml of 25% HCl was added and heating continued for another 5 hours. To this mixture was added 12.0 ml of water and the reaction was cooled to room temperature. A light brown precipitate was filtered off and the filtrate was evaporated to almost dryness. The solution was then briefly boiled with activated carbon and filtered. The filtrate was made basic with the addition of concentrated ammonium hydroxide. 1 precipitated as a yellowish solid. The solid was then washed twice with water, once with 50% methanol in water, once with 1:1 methanol-ether, and three times with ether. The solid was then dried under vacuum to yield 0.8 g pure product 1 (38%).

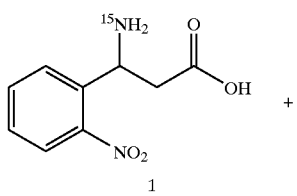

0.470 g (2.22 mmol) of 1 was suspended in 5.0 ml water, and subsaquently dissolved by the addition of 0.299 (2.13 mmol) ml triethylamine. To this solution was added 0.757 g Fmoc-OSU (2.25 mmol) in 5.0 ml acetonitrile. The reation then ran for 30 min. (pH≈10). The slurry was evaporated and diluted with 5.0 ml water and 10.0 ml ethyl acetate. The pH was adjusted to 2 with 12N HCl. A white solid precipitated. Filtered and extracted with ethyl acetate. The organics were washed with 2N HCl, H2O, and brine, dried over mag. sulfate, filtered and evaporated to give a white solid which upon tritration with ethyl acetate and hexane gave 0.36 g pure 2 (0.37%).

Well array:

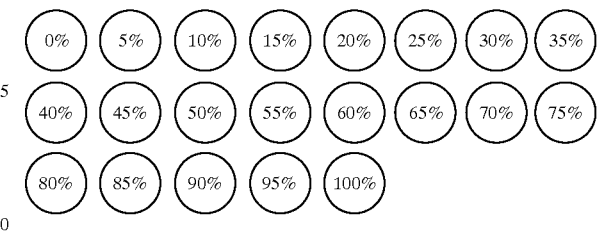

Percentage/ratio solutions of $^{14}N/^{15}N$-photolinker were generated in the following manner (from 10.5 ml stock solutions DMF of each photolinker).

0%=20×0.050 ml of 10.5 ml $^{14}N$-photolinker, and 0×0.050 ml of 10.5 ml $^{15}N$-photo 5%=19×0.050 ml of 10.5 ml $^{14}N$-photolinker, and 1×0.050 ml of 10.5 ml $^{15}N$-photo 10%=18×0.050 ml of 10.5 ml $^{14}N$-photolinker, and 2×0.050 ml of 10.5 ml $^{15}N$-photo 15%=17×0.050 ml of 10.5 ml $^{14}N$-photolinker, and 3×0.050 ml of 10.5 ml $^{15}N$-photo 20%=16×0.050 ml of 10.5 ml $^{14}N$-photolinker, and 4×0.050 ml of 10.5 ml $^{15}N$-photo 25%=15×0.050 ml of 10.5 ml $^{14}N$-photolinker, and 5×0.050 ml of 10.5 ml $^{15}N$-photo 30%=14×0.050 ml of 10.5 ml $^{14}N$-photolinker, and 6×0.050 ml of 10.5 ml $^{15}N$-photo 35%=13×0.050 ml of 10.5 ml $^{14}$N-photolinker, and 7×0.050 ml of 10.5 ml $^{15}$N-photo
40%=12×0.050 ml of 10.5 ml $^{14}$N-photolinker, and 8×0.050 ml of 10.5 ml $^{15}$N-photo
45%=11×0.050 ml of 10.5 ml $^{14}$N-photolinker, and 9×0.050 ml of 10.5 ml $^{15}$N-photo
50%=10×0.050 ml of 10.5 ml $^{14}$N-photolinker, and 10×0.050 ml of 10.5 ml $^{15}$N-photo
55%=9×0.050 ml of 10.5 ml $^{14}$N-photolinker, and 11×0.050 ml of 10.5 ml $^{15}$N-photo
60%=8×0.050 ml of 10.5 ml $^{14}$N-photolinker, and 12×0.050 ml of 10.5 ml $^{15}$N-photo
65%=7×0.050 ml of 10.5 ml $^{14}$N-photolinker, and 13×0.050 ml of 10.5 ml $^{15}$N-photo
70%=6×0.050 ml of 10.5 ml $^{14}$N-photolinker, and 14×0.050 ml of 10.5 ml $^{15}$N-photo
75%=5×0.050 ml of 10.5 ml $^{14}$N-photolinker, and 15×0.050 ml of 10.5 ml $^{15}$N-photo
80%=4×0.050 ml of 10.5 ml $^{14}$N-photolinker, and 16×0.050 ml of 10.5 ml $^{15}$N-photo
85%=3×0.050 ml of 10.5 ml $^{14}$N-photolinker, and 17×0.050 ml of 10.5 ml $^{15}$N-photo
90%=2×0.050 ml of 10.5 ml $^{14}$N-photolinker, and 18×0.050 ml of 10.5 ml $^{15}$N-photo
95%=1×0.050 ml of 10.5 ml $^{14}$N-photolinker, and 19×0.050 ml of 10.5 ml $^{15}$N-photo
100%=0×0.050 ml of 10.5 ml $^{14}$N-photolinker, and 20×0.050 ml of 10.5 ml $^{15}$N-photo

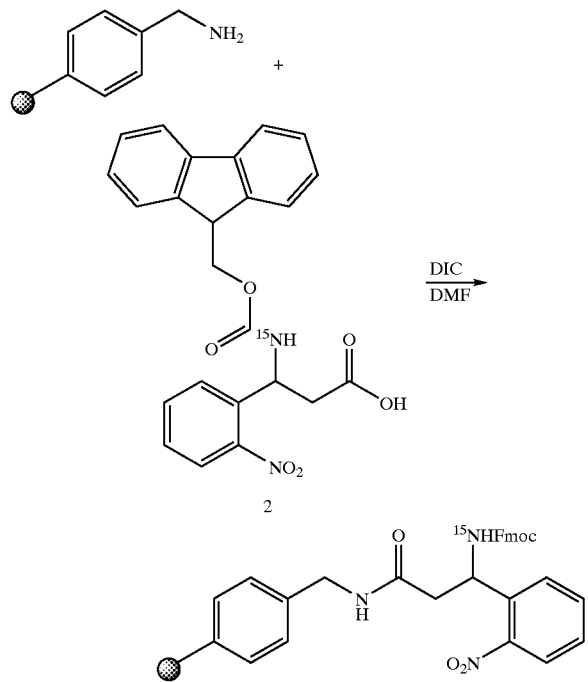

Starting with 6.3 g of aminomethyl polystyrene (0.21 mmol/g), divided into 21 equal lots of 0.300 grams each, were added the 1.0 ml solutions of varying ratios of $^{15}$N-2 and $^{14}$N-2, in 5% increments (0%, 5%, 10%, to 100% $^{15}$N-2 photolinker) (see CDW FIG. 1). These solutions were generated by disolving 0.4988 g $^{14}$N-2 photolinker and 0.500 g $^{15}$N-2 photolinker, and using 0.050 ml aloquats of each (20:0, 19:1, 18:2, to 0:20). To the mixture was then added 0.169 ml diisopropylcarbodiimide. The samples were then mixed and the coupling ran overnight (approx. 16 hours). The resins were washed 8 times with 1.5 ml DMF, and then with copious amounts of methanol.

Figure 2:
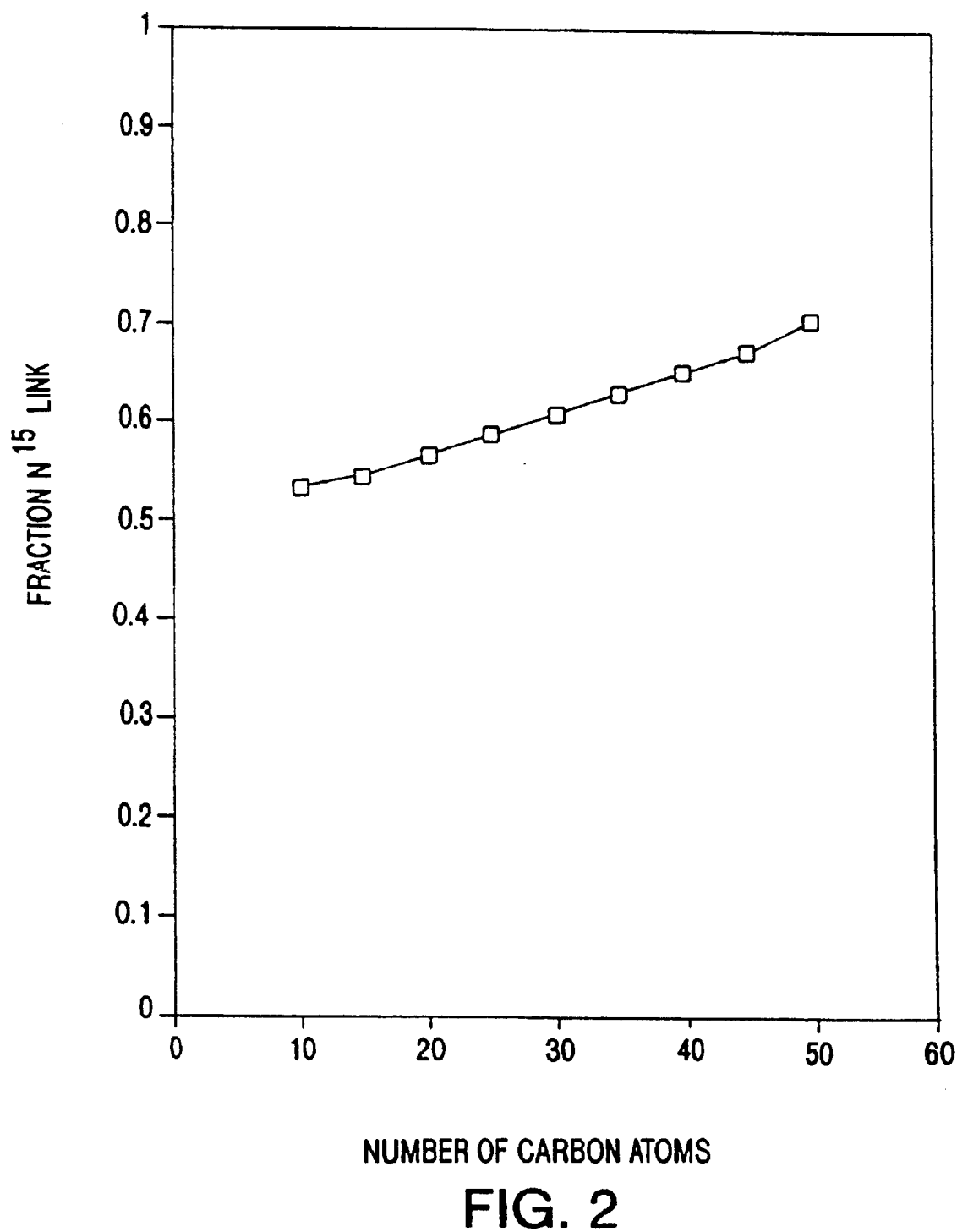
FIG. 2 is a graph that shows the observed correlation between number of carbon atoms present and the fraction of link content that has $N^{15}$ present. The chart can be used to calculate equal intensity peak signatures.
Figure 3:
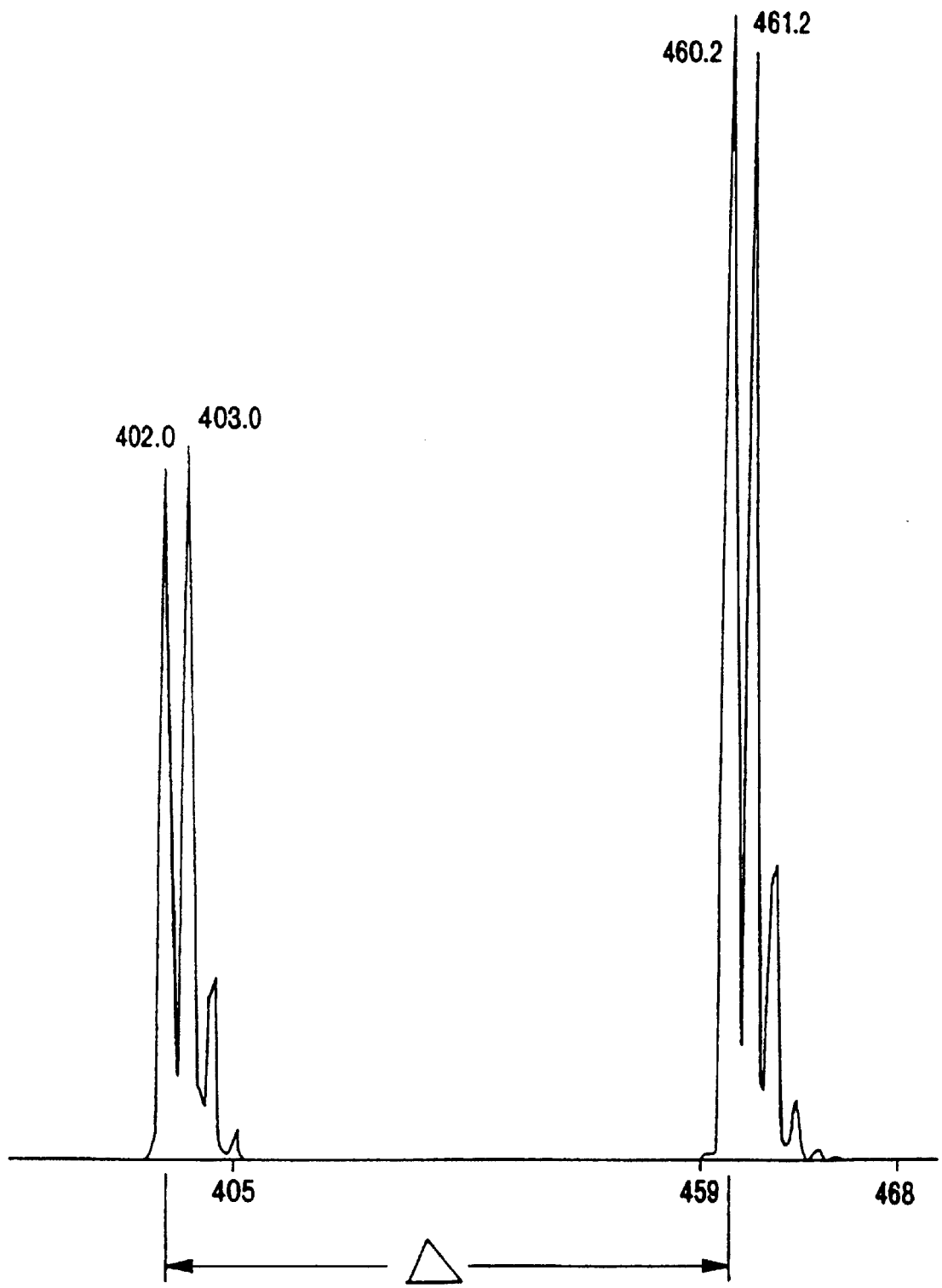
FIG. 3 illustrates a two peak positional coding strategy for a molecule, featuring splitting MS peaks into doublets to enhance code recognition.
Figure 4:
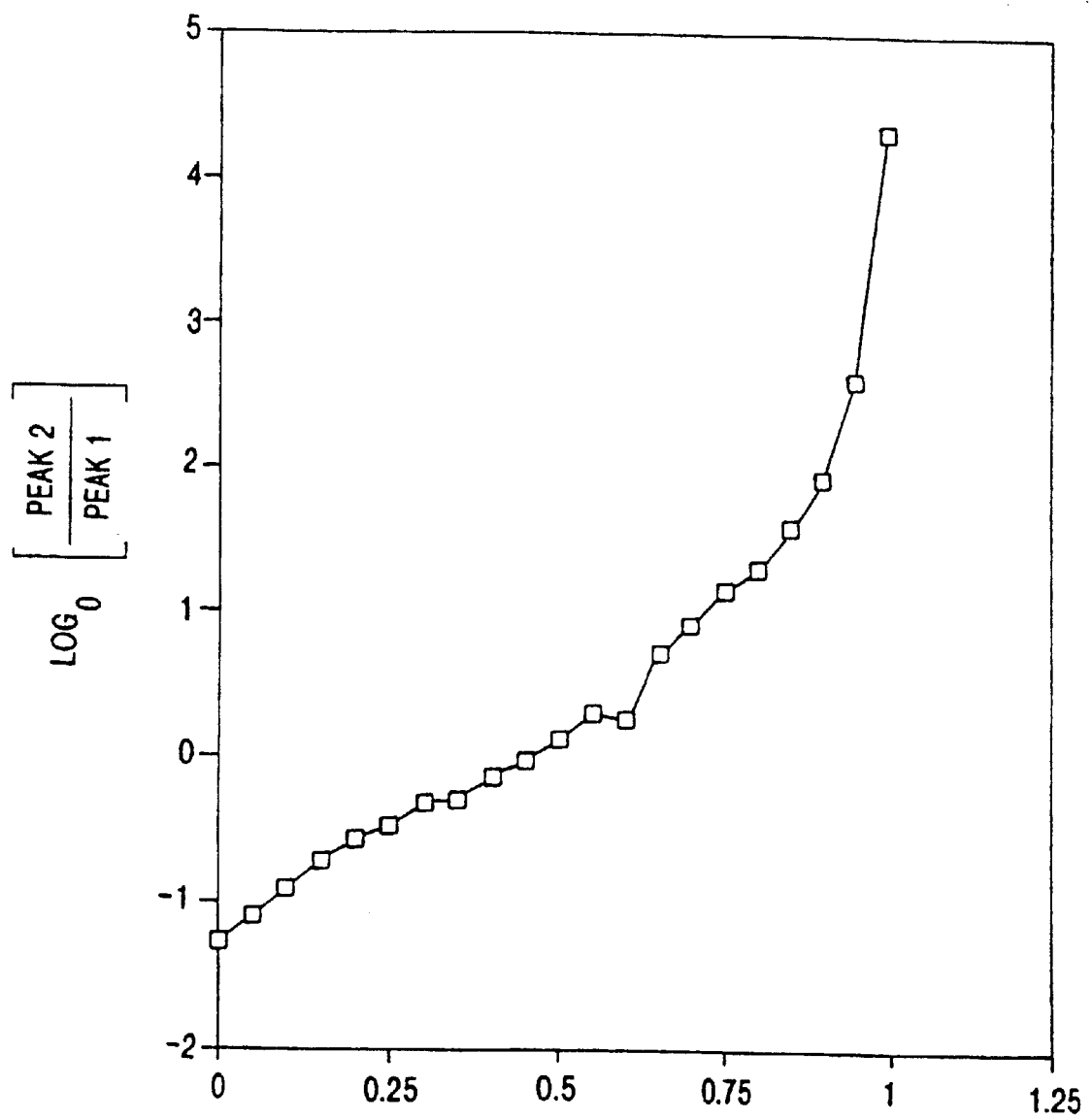
FIG. 4 illustrates the observed correlation between MS peak area and ratio of $N^{15}$ present in a code sample for a series of code samples differing in $N^{15}$ content by 5% increments.
Figure 5:
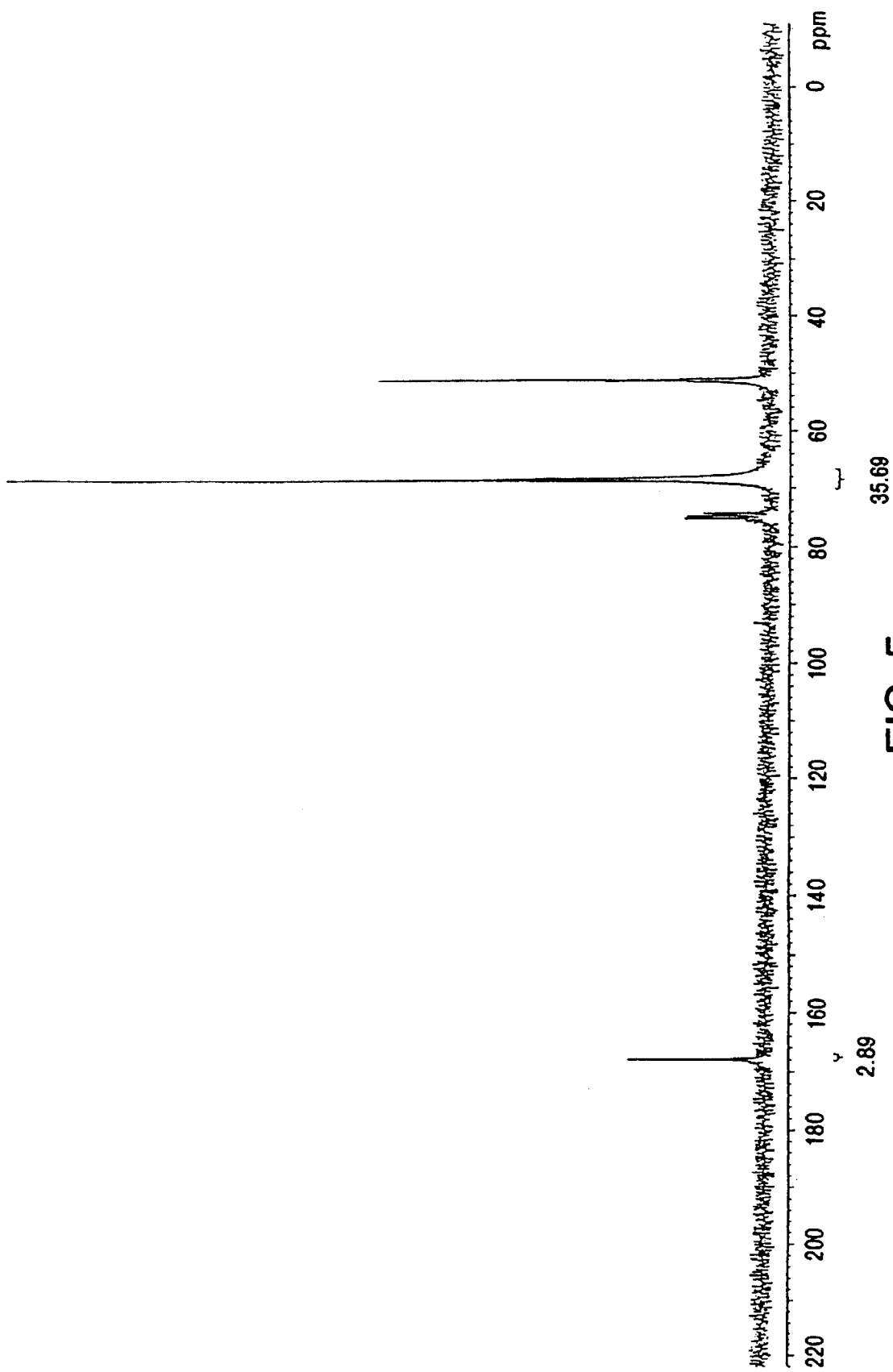
FIG. 5 is an NMR peak pattern for the compound.

Approx. 0.1 g of each lot was combined into 7 lots consisting of the following ratios per lot (see CDW FIG. 2). These 7 resin lots were used in the Tertiary Amine Library Study.

Well array:

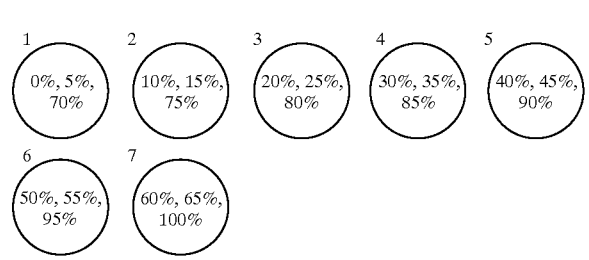

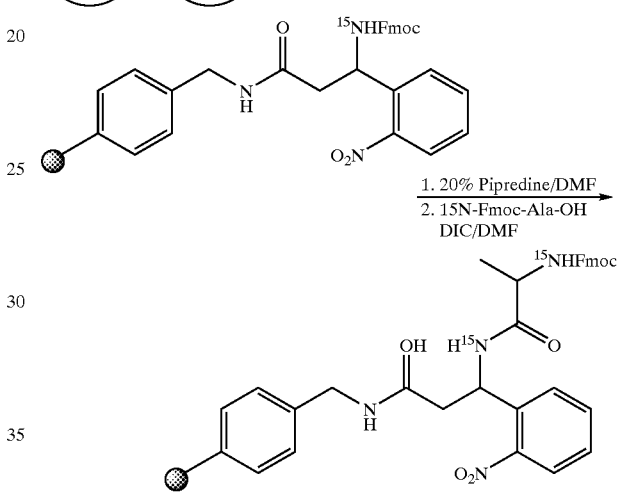

Approx. 0.1 g of each resin lot ratio was coupled with 0.50 ml of a 10.5 ml, 0.55 g 15N-Fmoc-Alanine-OH in DMF solution, followed by the addition of 0.169 ml DIC. The coupling then ran overnight. The resins were washed with copious amounts of methanol and dried under vacuum (ninhydrin negative).

A small amount of each resin lot, approx 0.01 g, was photo-cleaved for 4 hrs in 0.200 ml 3:1 water/THF. MS was subsequently performed.

EXAMPLE 16

Preparation of Mass-based Codes Distinguishable by NMR

Novabiochem TGR resin coupled with $^{13}$C$_2$-Fmoc-gly-OH. Both the carbonyl carbon and methylene carbon of glycine were evident by $^{13}$C NMR of the resin in CDCl$_3$. Additionally, these carbons could be integrated against the standard PEG signal that would remain constant throughout & the Ratios of $^{13}$C linker/ligand could be varied and subsequently determined (ligand resolution) by this non-destructive method.

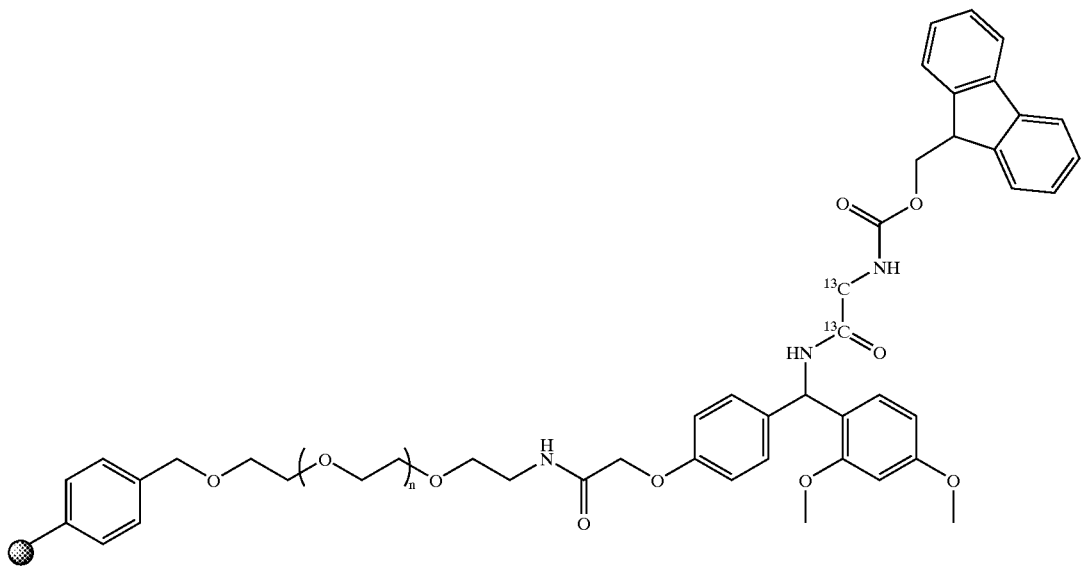

NOVABIOCHEM TG resin coupled with $^{13}C_2$-Fmoc-gly-OH

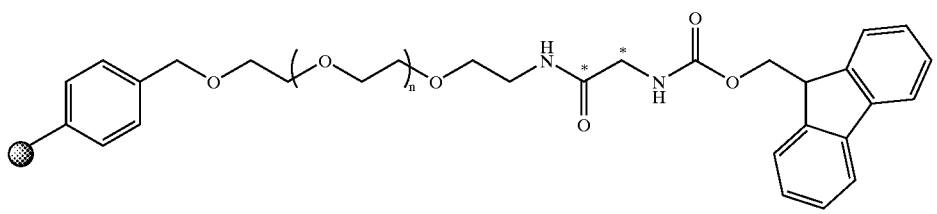

Novabiochem TG resin coupled with $^{13}C$, $^{15}N$-Photolinker. This linker could have a hard ratio $^{13}C$ to $^{13}C$ tag, as well as a cleavable $^{15}N$ tag.

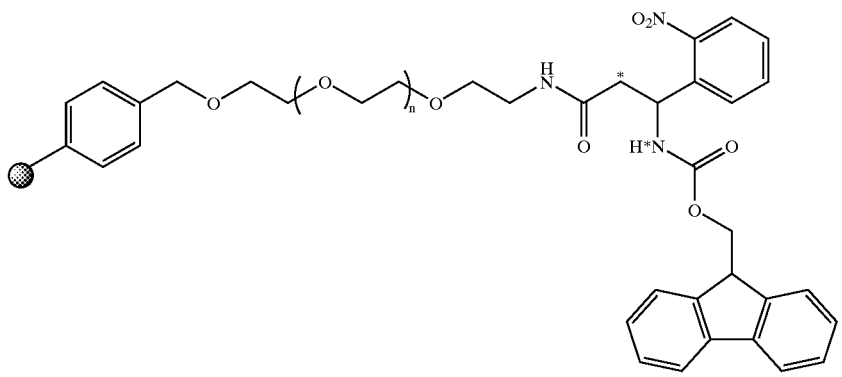

EXAMPLE 17

NMR Ratio Coding Approach $^{13}C$ NMR quantitation study on a ratio of $^{13}C$ labeled acetic acid to non-labeled acetic acid bound to TENTAGEL-NH$_2$ resin. The $^{13}C$ acetic acid carbonyl can be integrated against naturally occurring $^{13}C$ in the PEG portion of the TG-NH$_2$ resin. A differentiation of 5% increments is observed.

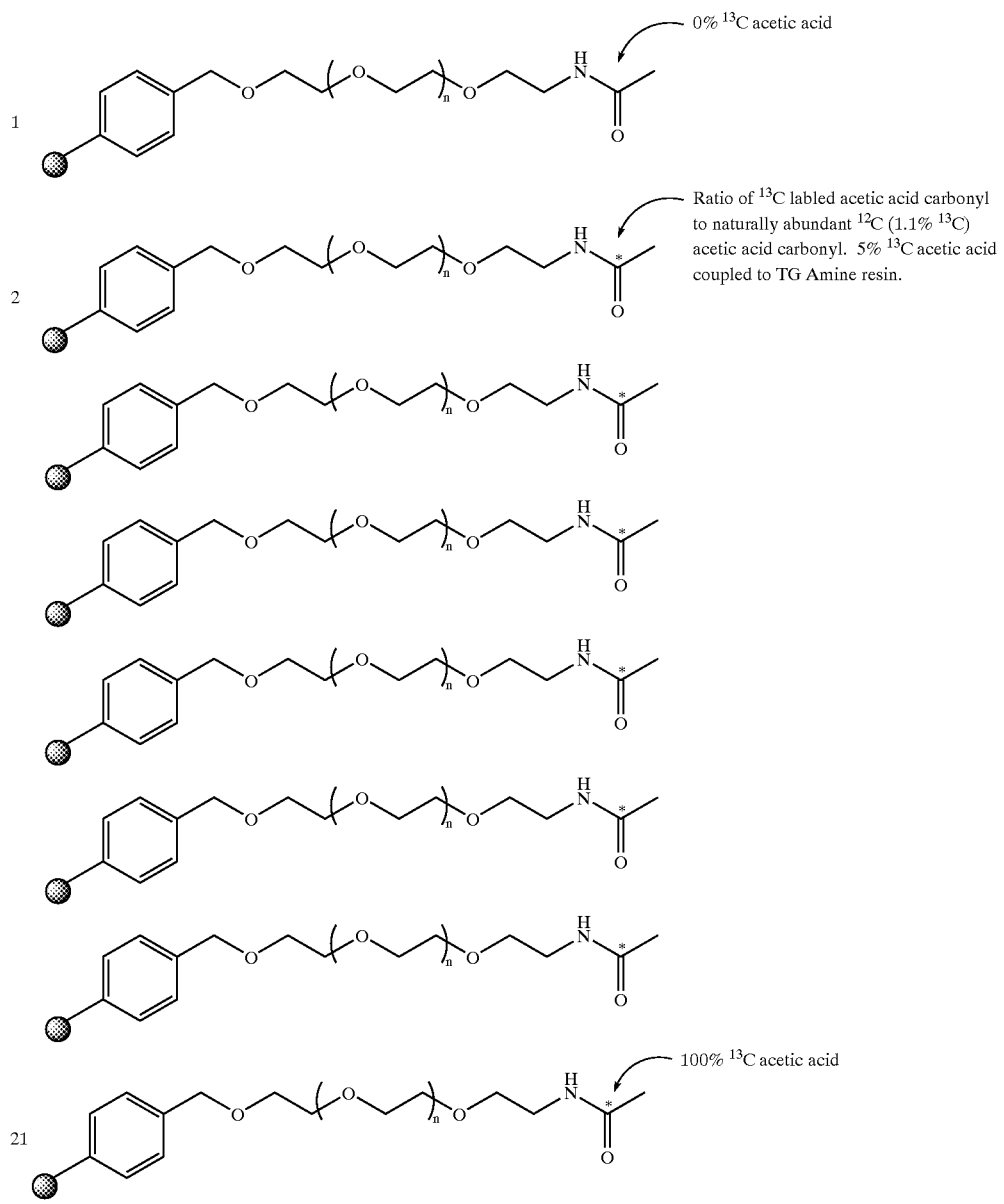
EXAMPLE 18
Preparation of FMOC-protected Isotopically Doped Code Blocks
Isotope Labeled Glycine from Cambridge Isotope Laboratories
Isotope Labeled Alanine from Cambridge Isotope Laboratories
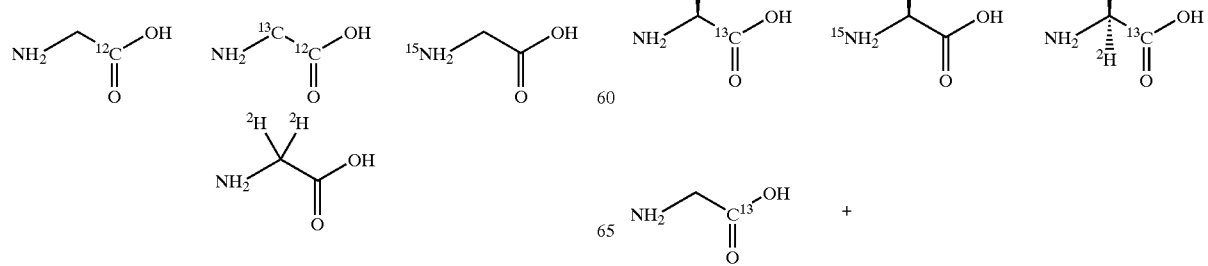

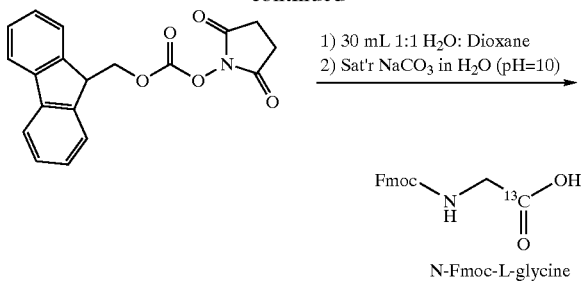

1 g of each isotope labeled glycine (13.3 mmol) were dissolved in 15 mL of purified water and 1.4 g of sodium carbonate (see Figure GP1). 15 mL of 1,4-Dioxane was added slowly to each and stirred. Over the period of two hours, 4.5 g of Fmoc-OSu (9-Fluorenylmethyl-N-hydroxysuccinimide) was added to each (see Figure GP3 for scheme). Additional saturated sodium carbonate in water was added to maintain a pH=10. Solutions were allowed to stir overnight. 6M HCl was slowly added to the solution until the pH was approximately 2. Extraction of the compound was completed using 50 mL of ethyl acetate, washing four times with 50 mL of acidified/purified water. Aqueous portions were washed with 50 mL of ethyl acetate. Both portions of ethyl acetate were combined. Magnesium sulfate was added to remove any excess water. Samples were filtered and concentrated using a RotoVap until the final volume was approximately one-third the original volume. Crystallization was completed using Hexane. Hexane was decanted and compound allowed to dry.

N-Fmoc-L-alanine 1 g of each isotope labeled alanine (11.2 mmol) were dissolved in 15 mL of purified water and 1.2 g of sodium carbonate (see Figure GP2). 15 mL of 1,4-Dioxane was added slowly to each and stirred. Over the period of two and a half hours, 3.8 g of Fmoc-OSu (9-Fluorenylmethyl-N-hydroxysuccinimide) was added to each (see Figure GP3 for scheme). Additional saturated sodium carbonate in water was added to maintain a pH=10. Solutions were allowed to stir overnight. 6M HCl was slowly added to the solution until the pH was approximately 2. Extraction of the compound was completed using two times 150 mL of ethyl acetate, washing four times with 300 mL of acidified/purified water. Magnesium sulfate was added to remove any excess water. Samples were filtered and concentrated using a RotoVap until the final volume was approximately one-third the original volume. Crystallization was completed using Hexane. Hexane was decanted and compound allowed to dry.

EXAMPLE 18

Synthesis of Isotopically Labeled Peptides for Mass Spectral Analysis Showing Their Use in Four Encoding Approaches Fmoc-protected alanine, serine and lysine were purchased from Bachem Bioscience. Fmoc-glycine was purchased from Novabiochem. Isotopically labeled amino acids were purchased from Cambridge Isotope Laboratories and were Fmoc protected in house (GP). Fmoc Knorr linker was purchased from Novabiochem. Fmoc-3-(2-nitrophenyl)-3-aminopropionic acid (a photolabile linkage agent) was purchased from Universal Organics. Aminomethyl polystyrene resin (0.81 mmol/gram) was purchased from Advanced ChemTech.

Linkers were attached to solid support manually in reaction shakers (CM). Resin was split to 85 reaction vessels on an Advanced ChemTech ACT496 MBS. Resin was deprotected with 25% piperidine/dimethylformamide twice for 10 minutes, then washed thoroughly with dimethylformamide. The first amino acids were coupled as 0.142 M solutions in N-methyl-pyrolidone, with PyBOP/Diisopropylethylamine in situ activation for 1.5 hours at room temperature. Boc deprotection was performed with 25% trifluoroacetic acid in dichloromethane for 30 minutes. Acetylations were performed with 33% acetic anhydride in dimethyl formamide for 30 minutes. All couplings were verified by ninhydrin color tests. Cleavage from the knorr linker was accomplished in 90% trifluoroacetic acid, 3% each water, phenol and thioanisole for 1.5 hours. Samples were dried under a nitrogen stream, then dissolved in water and lyophilized twice. Photocleavage was performed in 2:1 water:tetrahydrofuran under uv lamp for 12 hours. Samples were lyophiliized once.

Single Peak Positional Code

This array was designed to produce 20 samples with singlet, unique molecular weights for positive identification by mass spectroscopy. The samples were assembled in duplicate, one set of twenty on a chemically cleavable solid support, and the second set of twenty on a photocleavable support. By using a combination of one or two amino acids, a "coding region" was generated before addition of the synthetic ligand (in this case Acetyl-lysine). The twenty codes were constructed from the following amino acids:
Glycine
Glycine (15N)
Glycine (2,2-D2)
Alanine
Alanine (I 5N)
Alanine (1-13C)
Serine After the coding region had been assembled, lysine was coupled as a test ligand as well as to generate a free amino side chain for ease of observation by mass spectroscopy. The a-amino group of the lysine was then acetylated.

The codes and ligand were assembled on polystyrene resin functionalized with either Fmoc-Knorr or Fmoc-3-(2-nitrophenyl)-3-aminopropionic acid linkers.

The array for the single peak positional code is shown below:

FIG. 1

|   | Position 1 | Position 2 | Position 3 | Total MW |
|---|---|---|---|---|
| 1 | Ac-Lys- | X | X | 187 |
| 2 | Ac-Lys- | X | -Gly0- | 244 |
| 3 | Ac-Lys- | X | -Gly1- | 245 |
| 4 | Ac-Lys- | X | -Gly2- | 246 |
| 5 | Ac-Lys- | X | -Ala0- | 258 |
| 6 | Ac-Lys- | X | -Ala1- | 259 |
| 7 | Ac-Lys- | X | -Ala4- | 262 |
| 8 | Ac-Lys- | X | -Ser- | 274 |

-continued

| | Position 1 | Position 2 | Position 3 | Total MW |
|---|---|---|---|---|
| 9 | Ac-Lys- | -Gly0- | -Gly0- | 301 |
| 10 | Ac-Lys- | -Gly0- | -Gly1- | 302 |
| 11 | Ac-Lys- | -Gly1- | -Gly1- | 303 |
| 12 | Ac-Lys- | -Gly2- | -Gly1- | 304 |
| 13 | Ac-Lys- | -Gly2- | -Gly2- | 305 |
| 14 | Ac-Lys- | -Ala0- | -Gly0- | 315 |
| 15 | Ac-Lys- | -Ala1- | -Gly0- | 316 |
| 16 | Ac-Lys- | -Ala0- | -Gly2- | 317 |
| 17 | Ac-Lys- | -Ala1- | -Gly2- | 318 |
| 18 | Ac-Lys- | -Ala4- | -Gly2- | 321 |
| 19 | Ac-Lys- | -Ser- | -Gly0- | 331 |
| 20 | Ac-Lys- | -Ser- | -Gly1- | 332 |

Double Peak Positional Code

This array was designed to produce 20 samples with doublet peaks by mass spectroscopy; one peak arising from the ligand attached to a unique code, with a second peak resulting from a simultaneously assembled reference peak (ligand plus a fixed residue). As described in the SPPC above, by using a combination of one and two amino acids, a "coding region" was generated before addition of the synthetic ligand (in this case Acetyl-lysine). The twenty codes were also constructed from the following amino acids:
Glycine
Glycine (1 5N)
Glycine (2,2-D2)
Alanine
Alanine (15N)
Alanine (1-13C)
Serine The codes and ligand were assembled on polystyrene resin functionalized with Fmoc-Knorr of Fmoc-3-(2-nitrophenyl)-3-aminopropionic acid linkers.

The array for the double peak positional code is shown below:

FIG. 2

| | Position 1 | Position 2 | Position 3 | Mwt |
|---|---|---|---|---|
| 1 | Ac-Lys- | X | X | 187 |
| 2 | Ac-Lys- | X | -Gly0- | 244 |
| 3 | Ac-Lys- | X | -Gly1- | 245 |
| 4 | Ac-Lys- | X | -Gly2- | 246 |
| 5 | Ac-Lys- | X | -Ala0- | 258 |
| 6 | Ac-Lys- | X | -Ala1- | 259 |

-continued

| | Position 1 | Position 2 | Position 3 | Mwt |
|---|---|---|---|---|
| 7 | Ac-Lys- | X | -Ala4- | 262 |
| 8 | Ac-Lys- | X | -Ser- | 274 |
| 9 | Ac-Lys- | -Gly0- | -Gly0- | 301 |
| 10 | Ac-Lys- | -Gly0- | -Gly1- | 302 |
| 11 | Ac-Lys- | -Gly1- | -Gly1- | 303 |
| 12 | Ac-Lys- | -Gly2- | -Gly1- | 304 |
| 13 | Ac-Lys- | -Gly2- | -Gly2- | 305 |
| 14 | Ac-Lys- | -Ala0- | -Gly0- | 315 |
| 15 | Ac-Lys- | -Ala1- | -Gly0- | 316 |
| 16 | Ac-Lys- | -Ala0- | -Gly2- | 317 |
| 17 | Ac-Lys- | -Ala1- | -Gly2- | 318 |
| 18 | Ac-Lys- | -Ala4- | -Gly2- | 321 |
| 19 | Ac-Lys- | -Ser- | -Gly0- | 331 |
| 20 | Ac-Lys- | -Ser- | -Gly1- | 332 |

In each of the samples produced in this experiment, the peptide molecular weight shown above will appear superimposed with the reference peak generated by Ac-Lys-Gly-NH$_2$. This is to demonstrate the ability to identify both the first pooling lot and the molecular ion generated by the unknown ligand.

To produce samples displaying the coded double peak, an orthogonal protection scheme was used. The first Fmoc-protected amino acid of the coding region was coupled simultaneously with an equimolar amount of Boc-glycine. The coding region was assembled using Fmoc chemistry, then the Boc protecting group was removed with trifluoroacetic acid. After a final removal of the code Fmoc protecting group with piperidine (which concommittentley neutralized TFA salts on the exposed amine of glycine), the ligand (acetyl llysine) was coupled. Upon photocleavage, two compounds were liberated in equimolar amounts: the ligand linked to a reference amino acid (glycine) and the ligand linked to a unique code. The mass difference between the two peaks indicates the identity of the code, and hence the identity of the first monomer of the ligand coupled.

Mass Spectral Barcode

This array will produce twenty five samples, each dislying a unique molecular ion or peak pattern by mass spectroscopy. By using only combinations of isotopically labeled glycine at only two positions, twenty five unique "barcodes" are produced. In this manner the first pooled lot of any single bead derived from a split-combine library can be readily identified.

In this experiment Fmoc-protected amino acids were coupled either as discretes or equimolar mixtures of two or three amino acids.

The array for the mass spectral barcode is shown below:

FIG. 3

| | Position 1 | Position 2 | Position 3 | Peak Pattern |
|---|---|---|---|---|
| 1 | Ac-Lys- | -G0- | -G0- | 1 |
| 2 | Ac-Lys- | -G1- | -G0- | 1 |
| 3 | Ac-Lys- | -G0/G1- | -G0- | 1:1 |
| 4 | Ac-Lys- | -G2- | -G0- | 1 |
| 5 | Ac-Lys- | -G0/G2- | -G0- | 1:1 |
| 6 | Ac-Lys- | -G1/G2- | -G0- | 1:1 |
| 7 | Ac-Lys- | G0/G1/G2- | -G0- | 1:1:1 |
| 8 | Ac-Lys- | -G2- | -G1- | 1 |
| 9 | Ac-Lys- | -G0/G2- | -G1- | 1:1 |
| 10 | Ac-Lys- | -G0/G1- | -G2- | 1:1 |
| 11 | Ac-Lys- | G0/G1/G2- | -G1- | 1:1:1 |
| 12 | Ac-Lys- | -G0/G1- | -G0/G1- | 1:2:1 |
| 13 | Ac-Lys- | -G0/G2- | -G0/GI- | 1:1:1 |
| 14 | Ac-Lys- | -G1/G2- | -G0/G1- | 1:2:1 |
| 15 | Ac-Lys- | G0/G1/G2- | -G0/G1- | 1:2:2:1 |
| 16 | Ac-Lys- | -G2- | -G2- | 1 |
| 17 | Ac-Lys- | -G0/G2- | -G2- | 1:1 |
| 18 | Ac-Lys- | -G0/G2- | -G0/G2- | 1:2:1 |
| 19 | Ac-Lys- | G1/G2- | -G2- | 1:1 |
| 20 | Ac-Lys- | G0/G1/G2- | -G2- | 1:1:1 |
| 21 | Ac-Lys- | -G1/G2- | -G0/G2- | 1:1:1:1 |
| 22 | Ac-Lys- | G0/G1/G2- | -G0/G2- | 1:1:2:1 |
| 23 | Ac-Lys- | -G1/G2- | -G1/G2- | 1:2:1 |
| 24 | Ac-Lys- | — | -G1/G2- | 1:2:2:1 |
| | | G0/G1/G2- | | |
| 25 | Ac-Lys- | — | — | 1:2:3:2:1 |
| | | G0/G1/G2- | G0/G1/G2- | |

EXAMPLE 19

4 g of aminomethylated polystyrene (0.81 mmol/g) was put into each of 2–250 mL shakers. The resin was swelled with dimethylformamide (DMF) and drained. The resin was then washed with 20% piperidine/DMF for ~3 minutes and drained. The resin was washed three times with DMF, once with dichloromethane (DCM):DMF 1:1, and twice more with DMF.

To the first shaker was added 3.5 equivalents of Knorr linker (6.12 g, 11.34 mmol) and 3.5 equivalents of PyBop (5.9 g, 11.34 mmol). Enough DMF was added to cover the resin bed. The solution was then activated with 10.5 equivalents of DIEA (5.93 mL, 34.02 mmol). The reaction ran for 1 hour with manual shaking every 5–10 min.

To the second shaker was added 3.5 equivalents of photo linker (4.89 g, 11.34 mmol) and 3.5 equivalents of PyBop (5.9 g, 11.34 mmol). Enough DMF was added to cover the resin bed. The solution was then activated with 10.5 equivalents of DIEA (5.93 mL, 34.02 mmol). The reaction ran for 1 hour with manual shaking every 5–10 min.

After 1 hour both shakers were drained. Ninhydrin tests indicated complete coupling for both linkers. The resin was washed four times with DMF, once with dichloromethane (DCM):DMF 1:1, and two more times with DMF.

The resin was split to a 96 well ACT 496 Teflon reaction block.

EXAMPLE 20

Double Peak Positional Code

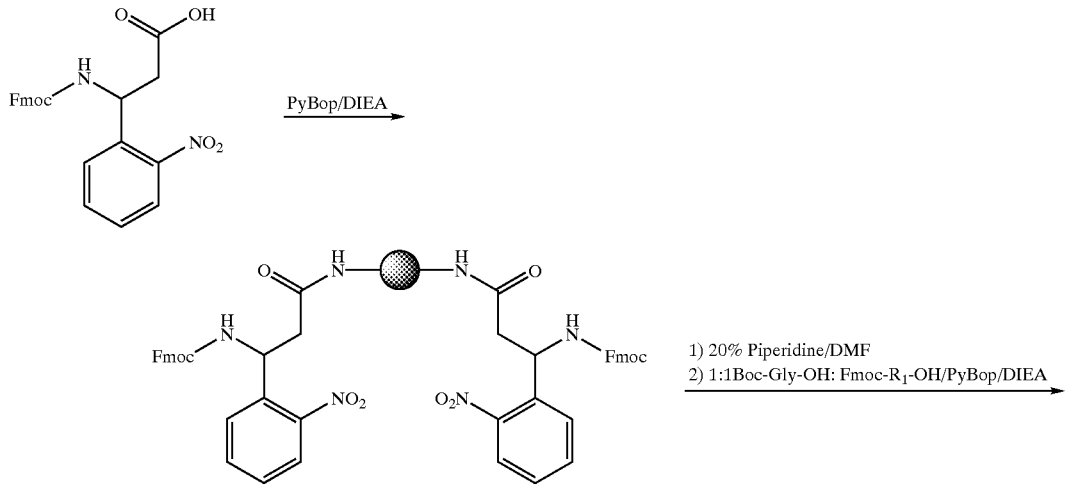

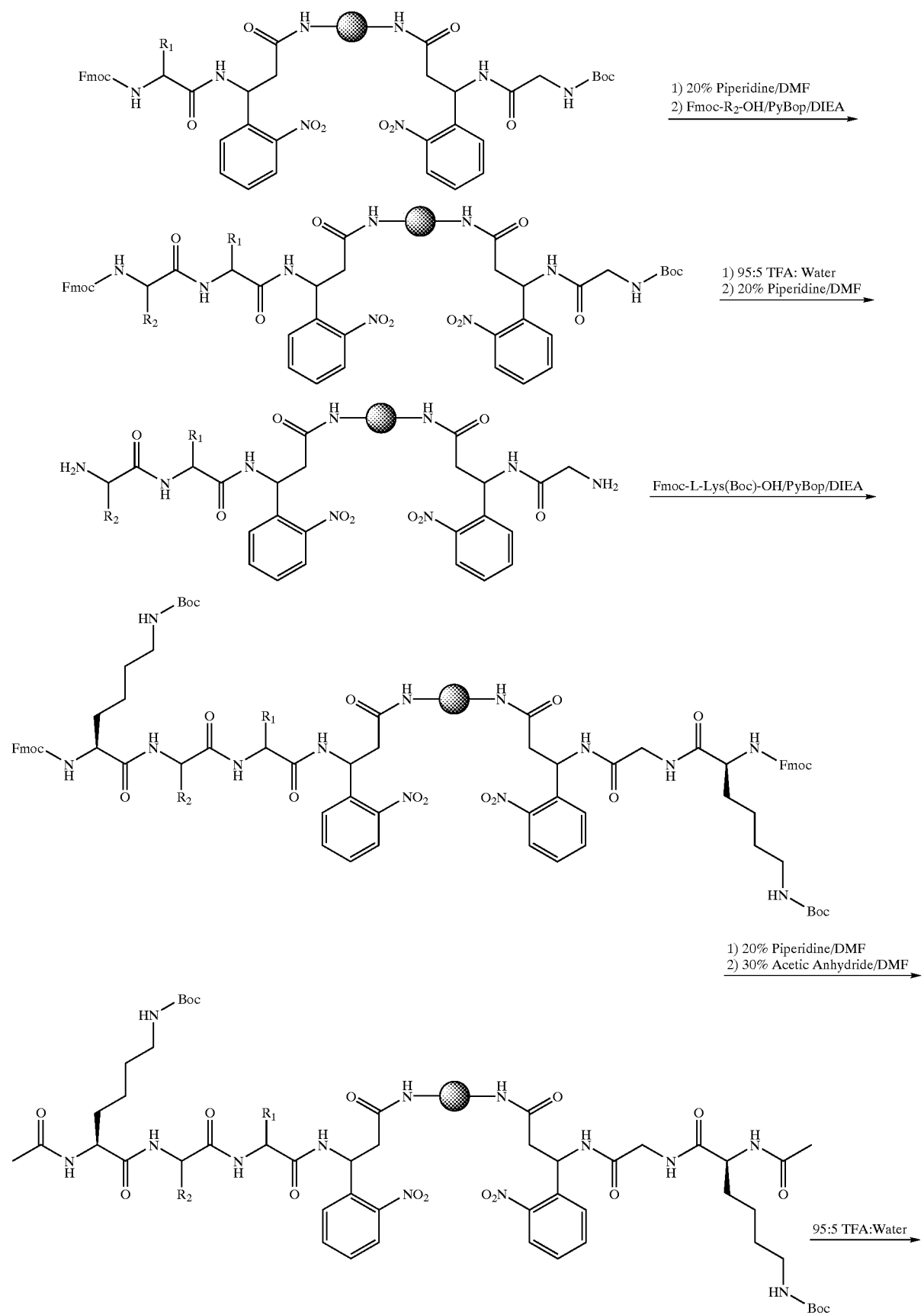

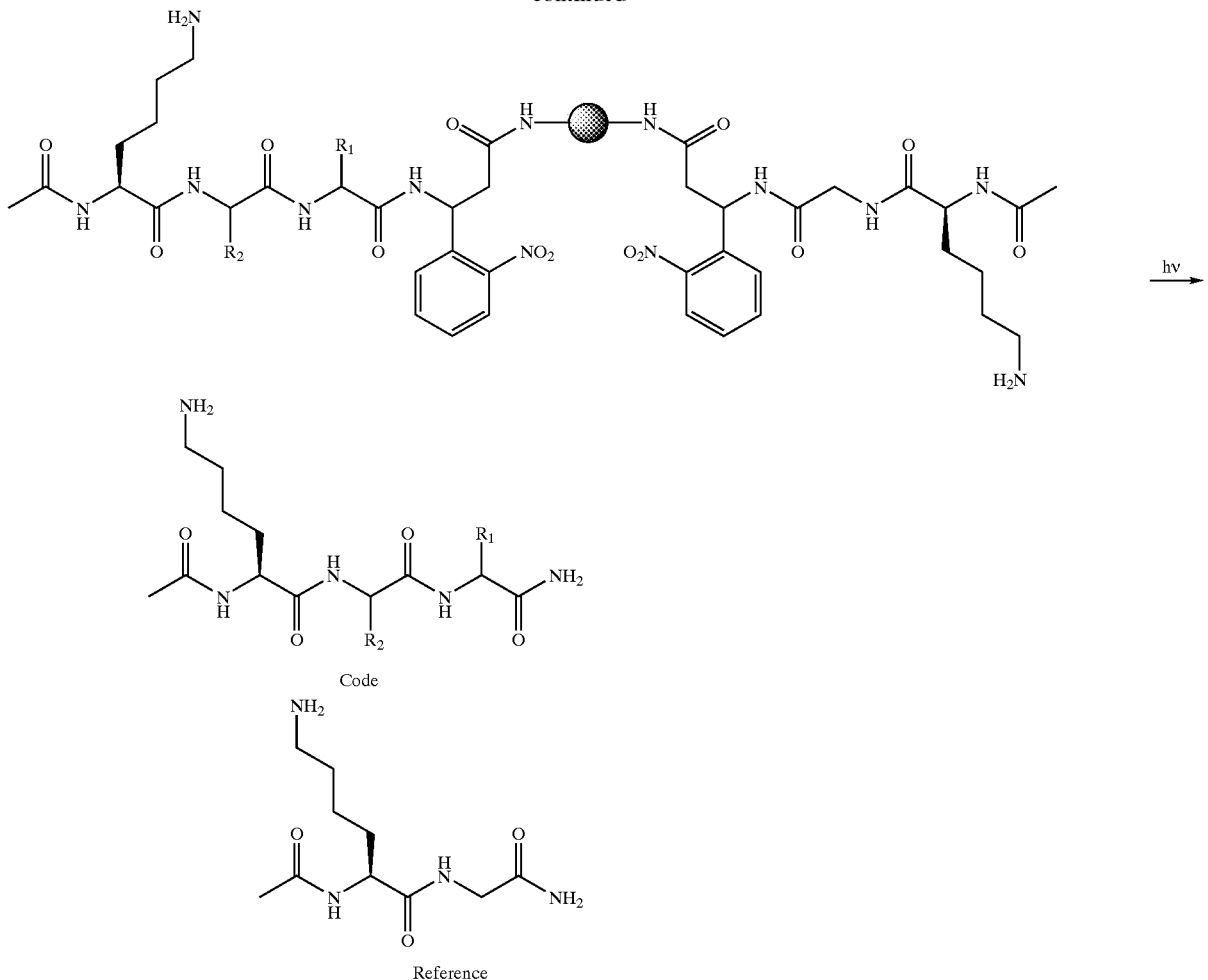

Code

Reference

EXAMPLE 21

Ratio Code Using Tertiary Amine

The seven lots of resin (CDW FIG. 2) were transferred to 10 mL shakers using dimethylformamide (DMF). The shakers were then covered with aluminum foil. The linker was Fmoc deprotected twice for 5 minutes each using 20% piperidine/DMF. The resin was washed four times with DMF, once with dichloromethane (DCM):DMF 1: 1, and twice with DMF.

0.315 mmol of each of seven halo acids were weighed in separate vials and an equimolar amount of PyB op was added to each. The halo acids were then dissolved in 2 mL of DMF. Each solution was then added to the respective lot of resin and activated with 165 μL of diisopropylethylamine (DIEA). The coupling ran for 1 hour. After coupling the resins were drained and washed four times with DMF, once with DCM:DMF 1:1, and twice with DCM to dry the resin.

0.315 mmol of each of seven halo acids were weighed in separate vials and an equimolar amount of HBTU was added to each. The halo acids were then dissolved in 2 mL of DMF. Each solution was then added to the respective lot of resin and activated with 165 μL of DIEA. The coupling ran for 1 hour. After coupling the resins were drained and washed four times with DMF, once with DCM:DMF 1:1, and twice with DMF. Coupling was complete by ninhydrin.

The resin lots were combined and split to 24 wells of a 96 well ACT 396 polypropylene reaction block. The resin was washed twice with DCM and dried.

The resin was swelled with DMF and drained. 1 mL of 1.0 M amine solution in dimethylsulfoxide (DMSO) was added to each well. The reaction ran overnight. The resin was drained and washed twice with DMF, once with DMF:methanol:water (1:1:1), and washed three more times with DMF. The 24 lots of resin were then combined and split back to 24 wells.

350 μL of aldehyde solution (3.0 M / DMF) was added to each well and mixed for 2 minutes. An additional 250 μL of trimethylorthoformate was added to each well and mixed for 1 minute followed by 100 μL of 3% acetic acid in DMF. The reaction mixed for 15 minutes before a final addition of 1 mL of 1.5 M NaBH$_3$CN. The reductive amination reaction ran for 3 hours. The resin was drained and washed twice with DMF.

A second reductive amination was run using sodium triacetoxyborohydride. 350 μL of aldehyde solution (3.0 M/DMF) was added to each well and mixed for 2 minutes. An additional 250 μL of trimethylorthoformate was added to each well and mixed for 1 minute followed by 100 μL of 3% acetic acid in DMF. The reaction mixed for 15 minutes before a final addition of mL of 1.5 M NaBH(O$_2$CCH$_3$). The reaction ran overnight. The resin was drained and washed twice with DMF, three times with DMF:methanol:water, three times with DCM, and three final times with methanol.

EXAMPLE 22
Single Peak Positional Code With Photolabile Cleavage
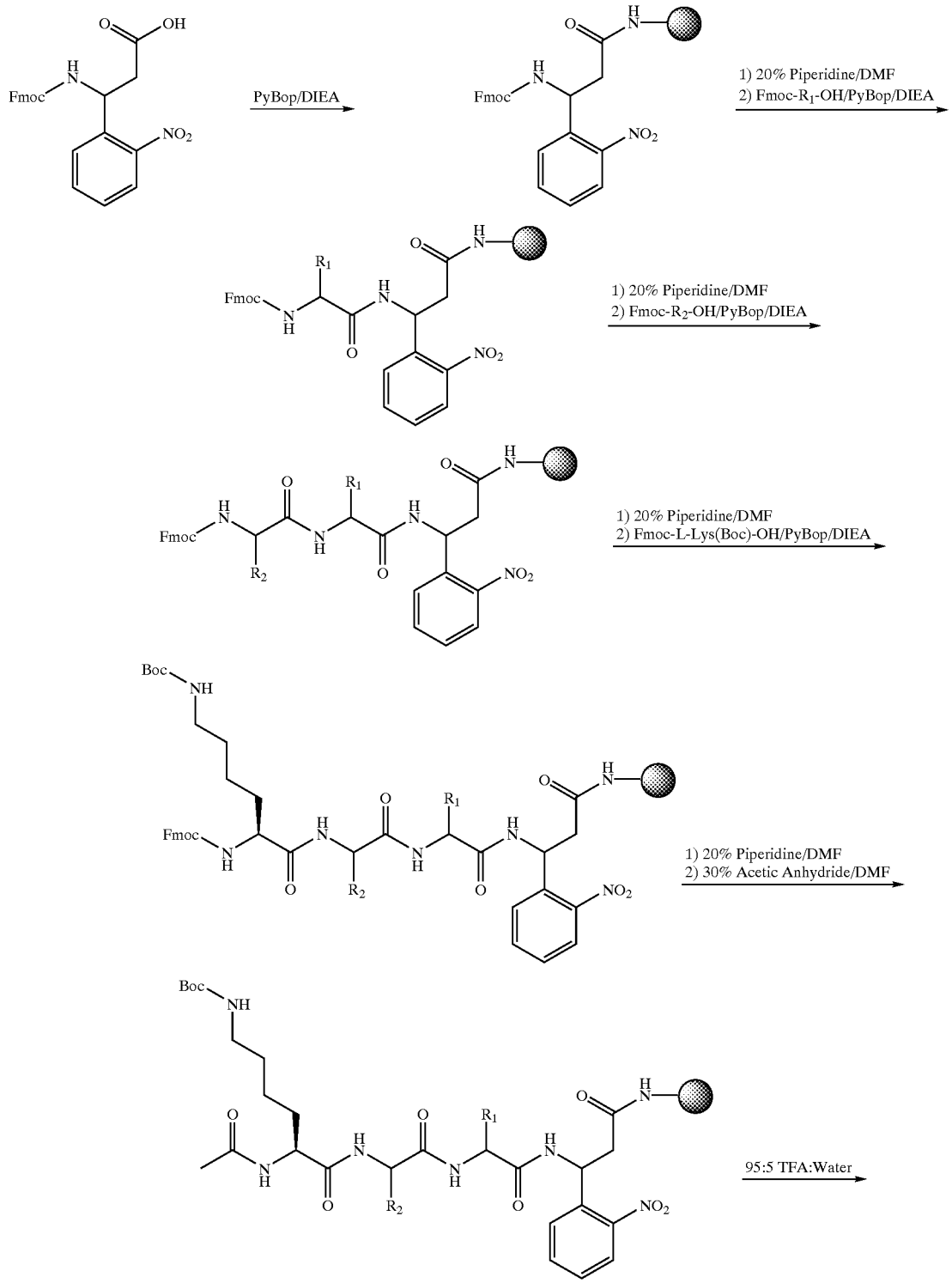

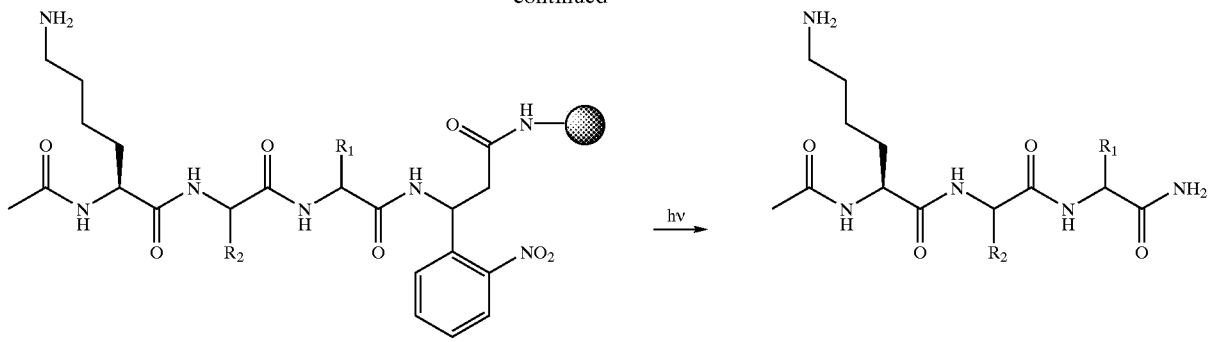

EXAMPLE 23

Reaction Screening

The synthesis of a set of serially encoded resins contained 192 combinations of of isotopically labeled amino acids (glycine $G^0, G^1, G^2, G^3$ and alanine: $A^0, A^1, A^2$, and $A^3$) and were separated by Knorr linkers as shown below:

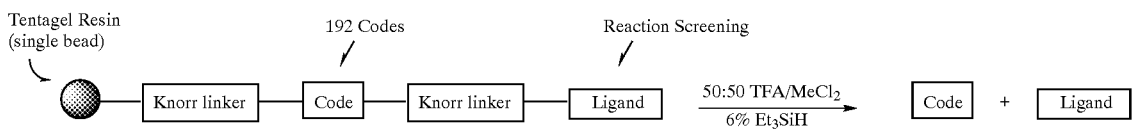

The reaction screening is performed on the ligand portion of the molecule where 3 different monomers were used for the coupling of primary amines to allylic bromides as well as 4 different reaction conditions to give a total of 12 combinations. The acylation of secondary amines with carboxylic acids involved 4 different acids and 4 different reaction conditions to give another 16 combinations. The resin was pooled and treated with 36 different conditions for the final intramolecular Heck reaction to give over 6900 potential compounds that contains different monomers and reaction conditions. Upon single bead cleavage with TFA/$MeCl_2$ and 6% triethylene both the encoded portion and the ligand are liberated as outlined above. The ligand is also encoded by the incorporation of glycine(0) and glycine(2) to help identify the ligand peaks in the mass spectrum.

The mass spectra that are shown in FIGS. 10 through 12 contain both the code (544–562) and the ligand (462 and 464), (504 and 506), (478 and 480). The monomers and conditions that were run for that particular mass spectrum are listed on the spectrum.

From these results one can use the combinatorial approach to look at various reaction conditions and monomers on a single bead and read both the code and the ligand when the material is cleaved off of the bead.

EXAMPLE 24

Ratio Code: IR. NMR and MS Analysis

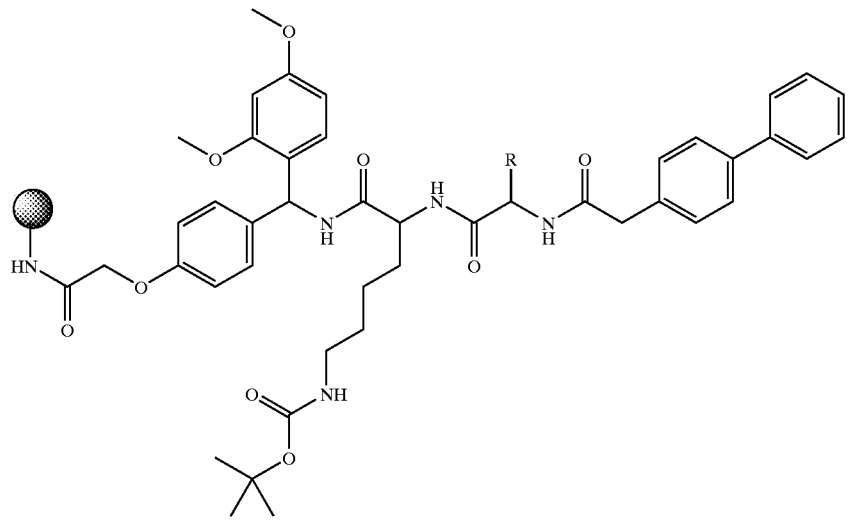

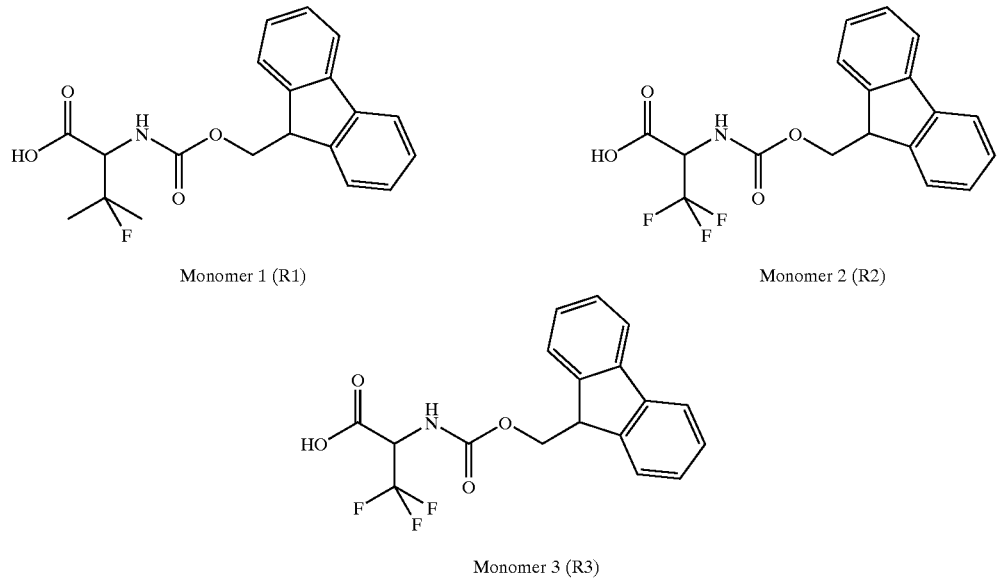

Monomer 1 (R1)

Monomer 2 (R2)

Monomer 3 (R3)

16 resin samples were synthesized where R was defined by a simultaneous coupling of monomers 1 through 3 in different ratio patterns (ratios noted below). These resing could then be analysed by several analytical techniques to elucidate their ratio identity. The beads were analysed by IR, mass spec, NMR, and Amino Acid analysis. The ratios generated for the simultaneous coupling are defined R1:R2:R3 and were as follows for the 16 samples: #1—1:1:5; Sample #2—1:2:5; Sample #3—1:3:5; Sample #4—1:4:5; Sample #5—2:5; Sample #6—2:2:5; Sample #7—2:3:5; Sample #8—2:4:5; Sample #9—3:1:5; Sample #10—3:2:5; Sample #11—3:3:5; Sample #12—3:4:5- Sample #13—4:1:5; Sample #14—4:2:5; Sample #15—4:3:5; Sample #16—4:4:5. Spectra for these ratios is shown in the accompanying FIGS. 18 through 51 as follows:

| Sample | IR Spectra Number | Mass Spec. Number |
|---|---|---|
| 1 | u7125-86-1 | CW-001 |
| 2 | u7125-86-2 | CW-002 |
| 3 | u7125-86-3 | CW-003 |
| 4 | u7125-86-4 | CW-004 |
| 5 | u7125-86-5 | CW-005 |
| 6 | u7125-86-6 | CW-006 |
| 7 | u7125-86-7 | CW-007 |
| 8 | u7125-86-8 | CW-008 |
| 9 | u7125-86-9 | CW-009 |
| 10 | u7125-86-10 | CW-0010 |
| 11 | u7125-86-11 | CW-0011 |
| 12 | u7125-86-12 | CW-0012 |
| 13 | u7125-86-13 | CW-0013 |
| 14 | u7125-86-14 | CW-0014 |
| 15 | u7125-86-15 | CW-0015 |
| 16 | u7125-86-16 | CW-0016 |

EXAMPLE 25

Encoding Styrene

The beads themselves generally used as solid supports in solid state synthesis can be isotopically doped. Styrene beads comprised of styrene can readily by doped with $C^{13}$, $F^{20}$ or $H^2$. Additionally, it is possible to combine isotopically doped constructs with beads that have themselves been coded or tagged with one or more of a series of monomers.

Styrene ($M_s$), 2-Fluorostyrene ($M_1$), 3-Fluorosytrene, ($M_2$) and 4-Fluorostyrene ($M_3$) were deinhibited prior to polymerization by passing through an alumina adsorption column.

The initiator 2,2-azobisisobutyronitrile (AIBN) was purified by crystallization from methanol Specral grade toluene was used as solvent in a free radical polymerization without further purification.

| Run | $M_1$ (%) | $M_2$ (%) | $M_3$ (%) | $M_s$ (%) |
|---|---|---|---|---|
| YL4001 | 100 | 0 | 0 | 0 |
| YL4002 | 0 | 100 | 0 | 0 |
| YL4003 | 0 | 0 | 100 | 0 |
| YL4004 | 0 | 0 | 0 | 100 |
| YL4005 | 0 | 0 | 50 | 50 |
| YL4006 | 0 | 10 | 40 | 50 |
| YL4007 | 0 | 20 | 30 | 50 |
| YL4008 | 0 | 20 | 30 | 50 |
| YL4009 | 0 | 40 | 10 | 50 |
| YL4010 | 0 | 50 | 0 | 50 |
| YL4011 | 50 | 0 | 0 | 50 |
| YL4012 | 40 | 10 | 0 | 50 |
| YL4013 | 30 | 20 | 0 | 50 |
| YL4014 | 20 | 30 | 0 | 50 |
| YL4015 | 10 | 40 | 0 | 50 |
| YL4016 | 40 | 0 | 10 | 50 |
| YL4017 | 30 | 0 | 20 | 50 |
| YL4018 | 20 | 0 | 30 | 50 |
| YL4019 | 10 | 0 | 40 | 50 |

Copolymerization of Styrene and F-Styrene

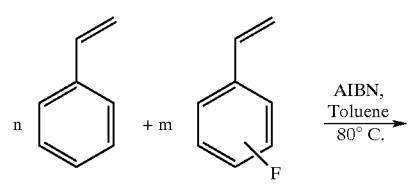

-continued

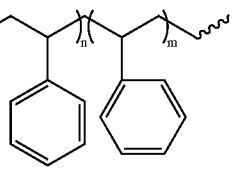

EXAMPLE 26

Encoding a Peptoid Library

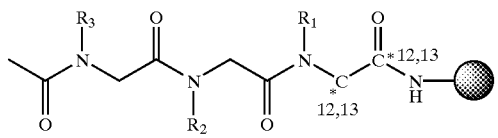

A 1000 component library consisting of three monomer positions was designed to demonstrate the utility of the encoding strategy. The library was synthesized using the split-mix methodology to create a 10×10×10 library. Since the split mix method yields one compound per bead and the beads are mixed twice during the synthesis, the chemistry or monomer addition at each step must be recorded on the bead in order to decode the compound.

The first position is encoded by controlling the ratio of $^{12}C:^{13}C_2$ incorporated with bromoacetic acid in the first synthetic step. Ten unique ratios were employed with nine percent increments ranging from 9:91 to 90:10. The use of nine percent increments avoided the endpoints of either 0:100 or 100:0 while allowing a total of ten codes. The third monomer was alreacy known because the library was not recombined after addition of the final monomer (only one monomer from set three was present in each pool.) This position was therefore pool or spatially encoded.

The second position was encoded by the molecular S weight of the compound. Since monomer one is known by the isotopic reaction and monomer three by the final pool, monomer two can be calculated using the molecular weight determined by the mass spectrometer. This imposes one constraint for any library: the monomers in the second position must have different molecular weights. The other monomers have no restrictions. For this test example, the final pools were composed of compounds having unique molecular weights in order to facilitate decoding.

Twenty single beads from each of the 10 pools were individually cleaved. The compounds were then analyzed by mass spectrometry and identified by the isotope ratio and molecular weight of the analyzed peaks. The peak resulting from the protonated monoisotopic ion was designated $M_0H^+$ while that resulting from the diisotopic ion $(M_0H+2)^+$ was designated $M_2H^+$. The deliberate doping with $^{13}C_2$ controlled the intensity of the $M_2H^+$ peak relative to the $M_0H^+$ peak.

Mass spectral data from a single bead in pool 3 showed that $M_0H^+$ and $M_2H^+$ were 552 and 554, respectively. The $M_0H^+:M_2H^+$ ratio was calculated to be 10:90, which was quite close to the actual ratio for ion 552, which was 9:91. Using $M_0H^+$ as 550 and $M_2H^+$ as 552, the calculated $M_0H^+$ to $M_2H^+$ ratio was 56:44. The compound having a $M_0R^+$ ion in pool 2 had a theoretical of 54:46, again in very close agreement to the calculated ratio. In some cases, side-reactions involved in the addition of monomers may complicate the spectra. Spectra 2C below shows the mass spectrum of a single bead from pool 1. The most intense ion in the spectrum is at m/z 586. However, the calculated $M_0H^+:M_2H^+$ ratio (65:35) does no agree with known ration for the compound in pool 1 with $M_0H^+$ of 586. This apparent discrepancy is due to the addition of the third monomer for pool 1, a nitrile. It is known that under acidic conditions (cleavage conditions) nitrites can be hydrated to an amide. With the addition of water, the peaks for the $M_0H^+$ ion at 586 shift to 586 ($M_0H^++18$). Thus, the $M_0H^+:M_2H^+$ ratio for the peaks at 586 and 588 verifies the encode for the ion at 568 (which has its own, weaker set of peaks having the same ratio.). The known ration for the compound in pool 1 with a $M_0H^+$ ion of 568 is 63:37, which corresponds to the calculated value. This particular hydration reaction was observed for all compounds in pool 1. This example demonstrates the ability to decode compounds and determine side reactions, a powerful enhancement over other encoding methodologies which would be very useful during solid phase chemistry development.

EXAMPLE 27

Pseudo-Code Program Listing for Computer-Assisted Detection of Isotope Encoded Compounds in a Mass Spectrum 1. input the molecular formula and isotope ratios of an encoded compound.
2. Calculate the monoisotopic molecular weight from step 1.
3. Calculate the theoretical isotope distribution from step 1.
4. Open the mass spectrum output file.
5. Locate the monoisotopic molecular weight in the mass spectrum output file to within +/−0.3 amu and check for corresponding isotope peaks.
6. If step 5 was successful compare the theoretical distribution from step 3 with the measured values in the mass spectrum using a Chi-Square test. The outcome of the Chi-Square determines the presence or absence of the encoded compound.

Copyright 1996, Glaxo Wellcome, Inc. All rights reserved.

This invention is executable on a MacIntosh computer or an IBM-PC compatible computer, running the Windows 95, Windows NT or MACINTOSH OS Operating system, which includes a CPU, main storage, I/O resources, and a user interface including a manually operated keyboard and mouse.

While the invention has been described and illustrated with reference to certain alternative embodiments thereof, those skilled in the art will appreciate that various changes, modifications and substitutions can be made therein without departing from the spirit and scope of the invention. It is intended, therefore, that the invention be limited only by the scope of the claims which follow, and that such claims be interpreted as broadly as possible.

What is claimed is:

1. A method for labeling a plurality of solid supports, said method comprising;
    dividing a batch of solid supports that each have a first link having a first cleavage site into two or more groups of solid supports;
    preparing a mixture of chemical moieties that are distinguishable from each other by mass to produce a set of machine readable codes;
    chemically labeling each solid support group with one of the codes of the set under controlled reaction conditions such that each solid support group is labeled with a different code that is attached to the first link;

linking a second link having a second cleavage site and a synthesis site to each code on the solid support to provide a set of constructs that each have a connecting group comprising in series the first cleavage site, the machine-readable code, the second cleavage site, and the synthesis site, wherein the formula of the connecting group is: $L_1$-C-$L_2$ where $L_1$ is the first cleavage site, C is the code and $L_2$ is the second cleavage site;

selecting at least some of the solid supports having the connecting group $L_1$-C-$L_2$ from the batch; and reading the machine readable code of the selected solid supports.

2. The method as claimed in claim 1, wherein said machine readable codes comprise defined mass agents that are capable of being analyzed by mass spectroscopy.

3. The method as claimed in claim 2, wherein said defined mass agents are selected to generate a unique single mass peak when analyzed by mass spectroscopy.

4. The method as claimed in claim 2, wherein said defined mass agents are selected to generate a unique double mass peak when analyzed by mass spectroscopy.

5. The method as claimed in claim 2, wherein said defined mass agents are selected to generate a unique pair of single mass peaks when analyzed by mass spectroscopy.

6. The method as claimed in claim 2, wherein said defined mass agents are selected to generate a unique pair of double mass peaks when analyzed by mass spectroscopy.

7. The method as claimed in claim 2, wherein said defined mass agents are selected to generate a unique pattern of one or more mass peaks.

8. The method as claimed in claim 7, wherein said unique pattern for of said defined mass agents is expressible as a machine-readable pattern.

9. The method as claimed in claim 8, wherein said machine readable pattern comprises a bar code.

10. The method as claimed in claim 3, wherein said defined mass agents are selected to independently generate a unique mass spectrometry mass peak pattern selected from the group consisting of unique single mass peaks, unique double mass peaks, unique pairs of single mass peaks, unique pairs of double mass peaks, and unique peak patterns that are capable of being expressed as machine-readable patterns.

11. The method as claimed in claim 2, wherein said mass spectroscopy analysis provides mass peaks capable of being recognized as representing encoded reagents.

12. The method as claimed in claim 11, wherein additional mass peaks are generated that serve as signature peaks for positive identification of relevant mass peaks.

13. The method as claimed in claim 1, wherein said machine readable codes comprise a plurality of defined mass agents that are chemical moieties that differ from one another by having at least one of their atoms substituted by a different isotope of that atom, provided that the chemical structural formula of said defined mass agents is the same.

14. Deviously Once Amended) The method as claimed in claim 13, wherein said plurality of defined mass agents are chemical moieties that differ from one another by having at least one isotopic substitution at different atomic positions within the molecule provided that the chemical structural formula of said defined mass agents is the same.

15. The method as claimed in claim 1, wherein said machine readable codes comprise a plurality of defied mass agents that are regularly repeating molecular entities that differ from one another by an integral number of said repeating molecular entities.

16. The method as claimed in claim 1, wherein at least two groups of said solid supports are employed in each said reacting.

17. The method as claimed in clam 1, wherein said reading step is automated.

18. The method as claimed in claim 1, wherein labeling and linking steps are automated.

19. The method as claimed in claim 1, wherein the chemical moieties are isotopically doped.

20. The method as claimed in claim 1, wherein the code is sequentially assembled in two units, wherein at least one of the units is prepared by reacting the mixture of chemical moieties.

21. The method as claimed in claim 1, wherein the chemical moieties are mixed with one another in a plurality of discrete ratios.

22. A method for labeling a plurality of solid supports to determine chemical reagents synthesized to the solid supports, said method comprising:

dividing a batch of solid supports that each have a first link having a first cleavage site into two more groups of solid supports;

preparing a mixture of chemical moieties that are distinguishable from each other by mass to produce a set of machine readable codes;

chemically labeling each solid support group with one of the codes of the set under controlled reaction conditions such that each solid support group is labeled with a different code that is attached to the first link;

linking a second link having a second cleavage site and a synthesis site to each code on the solid support to provide a set of constructs that each have a connecting group comprising in jenies the first cleavage site, the machine-readable code, the second cleavage site, and the synthesis site, wherein the formula of the connecting group is; $L_1$-C-$L_2$ where $L_1$ is the first cleavage site, C is the code and $L_2$ is the second cleavage site, wherein the chemical moieties are isotropically doped and are mixed with one another in a plurality of discrete ratios;

subjecting the solid supports having the connecting group $L_1$-C-$L_2$ of each solid support group of the batch to a first chemical reagent;

optionally combining two or more of the groups of the solid supports having the connecting group $L_1$-C-$L_2$ into a combined group of solid supports and then subjecting the combined group of solid supports to a second chemical reagent;

selecting at least some of the solid supports from the combined group of solid supports; and reading the machine readable code of the selected solid supports to determine the first chemical reagent to which the solid supports were subjected.

* * * * *